(12) United States Patent
Rescourio et al.

(10) Patent No.: US 11,274,105 B2
(45) Date of Patent: Mar. 15, 2022

(54) ALPHA-HYDROXY PHENYLACETIC ACID PHARMACOPHORE OR BIOISOSTERE MCL-1 PROTEIN ANTAGONISTS

(71) Applicant: AMGEN INC., Thousand Oaks, CA (US)

(72) Inventors: Gwenaella Rescourio, Cambridge, MA (US); Ana Gonzalez Buenrostro, San Mateo, CA (US); Sean P. Brown, Half Moon Bay, CA (US); Mike Lizarzaburu, Pacifica, CA (US); Julio Medina, San Carlos, CA (US); Salman Yojiro Jabri, Aptos, CA (US); Daqing Sun, Foster City, CA (US); Scott Preston Simonovich, Walnut Creek, CA (US); Xuelei Yan, Foster City, CA (US); Yihong Li, Millbrae, CA (US); Yosup Rew, Foster City, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 16/977,527

(22) PCT Filed: Mar. 4, 2019

(86) PCT No.: PCT/US2019/020492
§ 371 (c)(1),
(2) Date: Sep. 2, 2020

(87) PCT Pub. No.: WO2019/173181
PCT Pub. Date: Sep. 12, 2019

(65) Prior Publication Data
US 2021/0047344 A1 Feb. 18, 2021

Related U.S. Application Data

(60) Provisional application No. 62/638,846, filed on Mar. 5, 2018.

(51) Int. Cl.
| | |
|---|---|
| C07D 498/22 | (2006.01) |
| C07D 498/10 | (2006.01) |
| C07D 498/20 | (2006.01) |
| C07D 519/00 | (2006.01) |
| A61K 31/635 | (2006.01) |
| A61K 31/7068 | (2006.01) |
| A61K 38/07 | (2006.01) |

(52) U.S. Cl.
CPC ......... *C07D 498/10* (2013.01); *C07D 498/20* (2013.01); *C07D 519/00* (2013.01); *A61K 31/635* (2013.01); *A61K 31/7068* (2013.01); *A61K 38/07* (2013.01)

(58) Field of Classification Search
CPC ........................... C07D 498/22; A61K 31/553
USPC ..................... 540/453; 514/211.09
See application file for complete search history.

(56) References Cited

U.S. PATENT DOCUMENTS

| | | |
|---|---|---|
| 4,522,811 A | 6/1985 | Eppstein et al. |
| 6,468,798 B1 | 10/2002 | Deb et al. |
| 6,471,996 B1 | 10/2002 | Sokoll et al. |
| 6,472,375 B1 | 10/2002 | Hoon et al. |
| 9,562,061 B2 | 2/2017 | Brown et al. |
| 10,100,063 B2 | 10/2018 | Brown et al. |
| 10,300,075 B2 | 5/2019 | Brown et al. |
| 10,494,381 B2 | 12/2019 | Brown et al. |
| 10,500,213 B2 | 12/2019 | Brown et al. |
| 10,632,128 B2 | 4/2020 | Harrington et al. |
| 2009/0054402 A1 | 2/2009 | Wang et al. |
| 2014/0051683 A1 | 2/2014 | Wang et al. |
| 2015/0045357 A1 | 2/2015 | Nikolovska-Coleska et al. |

(Continued)

FOREIGN PATENT DOCUMENTS

| | | |
|---|---|---|
| WO | 2008/131000 A2 | 10/2008 |
| WO | 2011/094708 A2 | 8/2011 |

(Continued)

OTHER PUBLICATIONS

Beroukhim,R., et al., "The landscape of somatic copy-number alteration across human cancers," Nature 463, 899-905 (2010).
Lessene, G., et al., "BCL-2 family antagonists for cancer therapy," Nat. Rev. Drug. Discov., vol. 7, 989-1000 (2008).

(Continued)

*Primary Examiner* — Jeffrey H Murray
(74) *Attorney, Agent, or Firm* — Bernard P. Friedrichsen

(57) ABSTRACT

Provided herein are myeloid cell leukemia 1 protein (Mcl-1) inhibitors, methods of their preparation, related pharmaceutical compositions, and methods of using the same. For example, provided herein are compounds of Formula I, or a stereoisomer thereof; and pharmaceutically acceptable salts thereof and pharmaceutical compositions containing the compounds. The compounds and compositions provided herein may be used, for example, in the treatment of diseases or conditions, such as cancer.

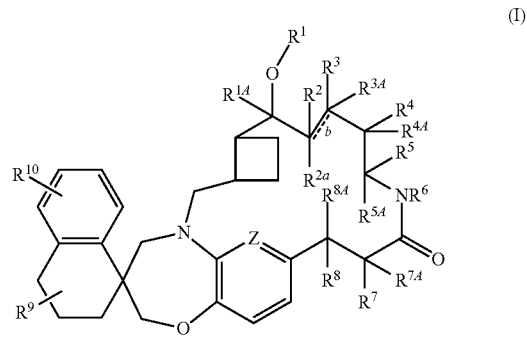

15 Claims, No Drawings

(56) References Cited

U.S. PATENT DOCUMENTS

| | | |
|---|---|---|
| 2015/0284328 A1 | 10/2015 | Wang et al. |
| 2017/0088560 A1 | 3/2017 | Brown et al. |
| 2019/0023720 A1 | 1/2019 | Brown et al. |
| 2020/0062780 A1 | 2/2020 | Brown et al. |

FOREIGN PATENT DOCUMENTS

| | | |
|---|---|---|
| WO | 2013/052943 A2 | 4/2013 |
| WO | 2013/149124 A1 | 10/2013 |
| WO | 2016/033486 A1 | 3/2016 |
| WO | 2017/147410 A1 | 8/2017 |
| WO | 2018/183418 A1 | 10/2018 |
| WO | 2019/036575 A1 | 2/2019 |
| WO | 2019/046150 A1 | 3/2019 |

OTHER PUBLICATIONS

Akgul, C., "Mcl-1 is a potential therapeutic target in multiple types of cancer," Cell. Mol. Life Sci. vol. 66 1326-1336 (2009).

Mandelin II, A. M. et al., "Myeloid cell leukemia-1 as a therapeutic target," Expert Opin. Ther. Targets, 11(3):363-373 (2007).

Rowe, R. C., et al., Handbook of Pharmaceutical Excipients, $5^{th}$ Edition (2005).

Berge, S. M. et al. "Pharmaceutical Salts", J. Pharm. Sci. 66: 1-19 (1977).

Hamajima, K. et al., "Intranasal Administration of HIV-DNA Vaccine Formulated with a Polymer, Carboxymethylcellulose, Augments Mucosal Antibody Production and Cell-Mediated Immune Response," Clin. Immunol. Immunopathol., 88(2), 205-210 (1998).

Higuchi, T. et al., "Pro-drugs as Novel Delivery Systems," vol. 14 of the A.C.S. Symposium Series (1975).

Roche, E.B., "Bioreversible Carriers in Drug Design", ed. Edward B. Roche, American Pharmaceutical Association and Pergamon Press, (1987).

Brubaker, J. D., et al., "A Practical, Enantioselective Synthetic Route to a Key Precursor to the Tetracycline Antibiotics," Org. Lett., 9, 3523-3525 (2007).

Krasovskiy, A et al., "Convenient Titration Method for Organometallic Zinc, Magnesium, and Lanthanide Reagents," Synthesis, 890-891 (2006).

Sigman, M. S. et al., "Palladium-Catalyzed Allylic Cross-Coupling Reactions of Primary and Secondary Homoallylic Electrophiles," J. Am. Chem. Soc., 134(28), 11408-11411 (2012).

International Search Report and Written Opinion for analogous PCT Application No. PCT/US2019/020492, dated May 10, 2019.

Farrell, R. P. "Breaking Symmetry Towards Development and Scale Up of a Complex Drug Candidate," American Chemical Society Meeting Presentation, Philadelphia, PA, Aug. 22, 2016.

Brown, B. "Interdiction at a Protein-Protein Interface: Structure-Based Design of Mcl-1 Inhibitors," American Chemical Society Meeting Presentation, Philadelphia, PA, Aug. 22, 2016.

Brown, S. "Interdiction at a Protein-Protein Interface: Structure-Based Design of Mcl-1 Inhibitors," Presentation at Caltech, Pasadena, CA, Jun. 1, 2016.

Brown, S. "Interdiction at a Protein-Protein Interface: Structure-Based Design of Mcl-1 Inhibitors," American Chemical Society Meeting Presentation, San Francisco, CA, Apr. 5, 2017.

Caenepeel, S. R. et al. "Preclinical Evaluation of AMG 176, A Novel, Potent and Selective Mcl-1 Inhibitor with Robust Anti-tumor Activity in Mcl-1 Dependent Cancer Models," Poster Presentation at American Association for Cancer Research Meeting, Washington DC, Apr. 1-5, 2017.

Hata, A. N. et al., "Combined targeting of MEK and MCL-1 induces apoptosis and tumor regression of KRAS mutant NSCLC," Poster Presentation at American Association for Cancer Research Meeting, Washington DC, Apr. 1-5, 2017.

Hata, A. N. et al., untitled structure slide, Poster Presentation at American Association for Cancer Research Meeting, Washington DC, Apr. 1-5, 2017.

Caenepeel, S. et al. "Preclinical Evaluation of AMG 176, A Novel, Potent and Selective Mcl-1 Inhibitor with Robust Anti-tumor Activity in Mcl-1 Dependent Cancer Models," Poster Presentation at American Association for Cancer Research Meeting, Chicago, IL, Apr. 14-18, 2018.

Caenepeel, S. et al. "Combined Inhibition of MCL1 and BCL-2 With AMG 176 and Venetoclax Induces Anti-tumor Effects in Acute Myeloid Leukemia," Poster Presentation at American Association for Cancer Research Meeting, Chicago, IL, Apr. 14-18, 2018.

Belmontes, B., "The Utilization of a Human MCL1 Knock-In Mouse Suggests that Reductions in B Cells and Monocytes may Serve as Clinically Relevant Pharmacodynamic markers of MCL1 Inhibition," Poster Presentation at American Association for Cancer Research Meeting, Chicago, IL, Apr. 14-18, 2018.

Brown, S. "Interdiction at a Protein-Protein Interface: Structure-Based Design of the Mcl-1 Inhibitor AMG 176," American Chemical Society Meeting Presentation, New Orleans, LA, Mar. 19, 2018.

Hughes, P. "The Discovery and Preclinical Characterization of AMG 176: A First-In-Class MCL-1 Inhibitor in Clinical Development for Multiple Myeloma," Poster Presentation at American Association for Cancer Research Meeting, Chicago, IL, Apr. 14-18, 2018.

ALPHA-HYDROXY PHENYLACETIC ACID PHARMACOPHORE OR BIOISOSTERE MCL-1 PROTEIN ANTAGONISTS

CROSS REFERENCES TO RELATED APPLICATIONS

This application claims the benefit of U.S. Provisional Application No. 62/638,846, filed on Mar. 5, 2018, which is hereby incorporated by reference in its entirety and for all purposes as if fully set forth herein.

FIELD OF THE INVENTION

The present invention relates to compounds that inhibit myeloid cell leukemia 1 protein (Mel-1, also abbreviated as MCl-1, MCL-1 or MCL1); methods of treating diseases or conditions, such as cancer, using the compounds; and pharmaceutical compositions containing the compounds.

BACKGROUND OF THE INVENTION

One common characteristic of human cancer is overexpression of Mcl-1. Mcl-1 overexpression prevents cancer cells from undergoing programmed cell death (apoptosis), allowing the cells to survive despite widespread genetic damage.

Mcl-1 is a member of the Bcl-2 family of proteins. The Bcl-2 family includes pro-apoptotic members (such as BAX and BAK) which, upon activation, form a homo-oligomer in the outer mitochondrial membrane that leads to pore formation and the escape of mitochondrial contents, a step in triggering apoptosis. Antiapoptotic members of the Bcl-2 family (such as Bcl-2, Bcl-XL, and Mcl-1) block the activity of BAX and BAK. Other proteins (such as BID, BIM, BIK, and BAD) exhibit additional regulatory functions.

Research has shown that Mcl-1 inhibitors can be useful for the treatment of cancers. MCl-1 is overexpressed in numerous cancers. See Beroukhim et al. (2010) Nature 463, 899-90. Cancer cells containing amplifications surrounding the Mcl-1 and Bcl-2-1-1 anti-apoptotic genes depend on the expression of these genes for survival. Beroukhim et al. Mcl-1 is a relevant target for the re-iniation of apoptosis in numerous cancer cells. See G. Lessene, P. Czabotar and P. Colman, Nat. Rev. Drug. Discov., 2008, 7, 989-1000; C. Akgul Cell. Mol. Life Sci. Vol. 66, 2009; and Arthur M. Mandelin II, Richard M. Pope, Expert Opin. Ther. Targets (2007) 11(3):363-373.

New compositions and methods for preparing and formulating Mcl-1 inhibitors would be useful.

SUMMARY OF THE INVENTION

In a first embodiment, the invention provides a compound of Formula I:

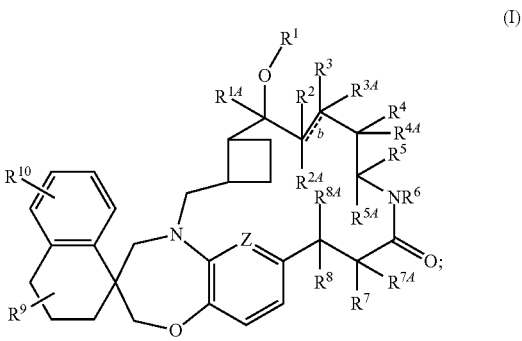

a stereoisomer thereof, a pharmaceutically acceptable salt thereof, or a pharmaceutically acceptable salt of the stereoisomer thereof, wherein:

b, represented by the symbol ====== is a single or double chemical bond which may be cis or trans, Z is selected from C or N;

$R^1$ is independently selected from H, —$C_{1-6}$haloalkyl, —$C_{1-6}$alkyl, —$C_{2-6}$alkenyl, —$C_{2-6}$alkynyl, —($CH_2$j$CH_2O)_nR^a$, —C(=O)$R^a$, —C(=O)O$R^a$, —C(=O)N$R^aR^b$, —$C_{1-6}$alkyl-O—$C_{1-6}$alkyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

$R^{1A}$ is independently selected from H, $C_{1-6}$haloalkyl, $C_{1-6}$alkyl, —$C_{2-6}$alkenyl, —$C_{2-6}$alkynyl, —($CH_2$ $CH_2O)_nR^a$, —$SO_2R^a$, —C(=O)$R^a$, —C(=O)O$R^a$, —C(=O)N$R^aR^b$, —N$R^aR^b$, —N=N=N, —$C_{1-6}$alkyl-O—$C_{1-6}$alkyl, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

each of $R^2$, $R^3$, $R^4$, $R^5$, $R^6$, $R^7$, $R^8$, $R^9$, $R^{10}$, $R^{2A}$, $R^{3A}$, $R^{4A}$, $R^{5A}$, $R^{7A}$ and $R^{8A}$ is independently selected from H, halo, —$C_{1-6}$haloalkyl, —$C_{1-6}$alkyl, —O—$C_{1-6}$alkyl, —$C_{2-6}$alkenyl, —$C_{1-6}$alkyl-O—$C_{1-6}$alkyl, —$(CH_2CH_2O)_nR^a$, —$SO_2R^a$, —$C(=O)R^a$, —$C(=O)OR^a$, —$OC(=O)R^a$, —$C(=O)NR^aR^b$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

when b is a double bond, $R^{2A}$ and $R^{3A}$ are absent;

wherein the aryl, heteroaryl, cycloalkyl, heterocycloalkyl, spirocycloalkyl and spiroheterocycloalkyl groups of the $R^1$ or $R^{1A}$ substituent can be unsubstituted or substituted with 1, 2, 3 or 4 $R^{11}$ substituents independently selected from OH, halo, —$NR^cR^d$, —$C_{1-6}$alkyl, —$C_2$-$C_6$ alkenyl, —$C_2$-$C_6$alkynyl, —$OC_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —$SO_2R^c$, —CN, —$C(=O)NR^cR^d$, —$C(=O)R^c$, —$OC(=O)R^a$, —$C(=O)OR^c$, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 0, 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

wherein the —$C_{1-6}$alkyl of any of the $R^1$, $R^2$, $R^3$, $R^4$, $R^5$, $R^6$, $R^7$, $R^8$, $R^9$, $R^{10}$, $R^{11}$, $R^{1A}$, $R^{2A}$, $R^{3A}$, $R^{4A}$, $R^{5A}$, $R^{7A}$, and $R^{8A}$ substituents is unsubstituted or substituted by 1, 2 or 3 $R^{11}$ substituents independently selected from OH, —$OC_{1-6}$alkyl, —$C_{1-6}$alkyl-O—$C_{1-6}$alkyl, halo, —O-halo$C_{1-6}$alkyl, —CN, —$NR^aR^b$, —$(NR^aR^bR^c)_n$, —$SO_2R^a$, —$(CH_2CH_2O)_nCH_3$, (=O), —$C(=O)R^a$, —$OC(=O)R^a$, —$C(=O)OR^a$, —$C(=O)NR^aR^b$, —O—$SiR^aR^bR^c$, —O-(3- to 12-membered heterocycloalkyl), phenyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

wherein the aryl, heteroaryl, cycloalkyl, heterocycloalkyl, spirocycloalkyl and spiroheterocycloalkyl groups of any of the $R^2$, $R^4$, $R^5$, $R^6$, $R^7$, $R^8$, $R^9$, $R^{10}$, $R^{11}$ and $R^{12}$ substituents can be unsubstituted or substituted with 1, 2, 3 or 4 $R^{13}$ substituents independently selected from OH, halo, —$C_{1-6}$alkyl, —$OC_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —$SO_2R^c$, —$NR^cR^d$, —CN, —$C(=O)NR^cR^d$, —$C(=O)R^a$, —$OC(=O)R^a$, —$C(=O)OR^c$, —$B(OH)_2$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

wherein each $R^a$, $R^b$, $R^c$, and $R^d$ is independently H, OH, —$C_{1-6}$alkyl, —$C_{1-6}$alkenyl, —$C_{2-6}$alkynyl, —$C_{1-6}$alkyl-$NR^{14}R^{14}$, $NR^{14}R^{14}$, —$SO_2R^{14}$, —$(CH_2CH_2O)_nCH_3$, —$C(=O)R^{14}$, —$OC(=O)R^{14}$, —$C(=O)OR^{14}$, —$C(=O)NR^{14}R^{14}$, —$C_{1-6}$haloalkyl, —O-halo$C_{1-6}$alkyl, —$C_{1-6}$alkyl-O—$C_{1-6}$alkyl, —$C_{1-6}$alkyl-OH, benzyl, phenyl, a —$C_{1-6}$alkyl-3- to 12-membered heterocycloalkyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups and the heterocycloalkyl group of the —$C_{1-6}$alkyl-heterocycloalkyl group have 1, 2, 3, or 4 heteroatoms independently selected from O, N or S, wherein the cycloalkyl, spirocycloalkyl, spiroheterocycloalkyl, heterocycloalkyl, and the heterocycloalkyl groups of the —$C_{1-6}$alkyl-heterocycloalkyl group may include a C=O group, and further wherein the spiroheterocycloalkyl and heterocycloalkyl groups may include a S=O or $SO_2$;

wherein $R^{14}$ substituents are independently selected from H, —OH, halo, —$C_{1-6}$alkyl, —$OC_{1-6}$alkyl, —$C_{1-6}$alkyl-$OC_{1-6}$alkyl, —$C_{1-6}$haloalkyl, —O-halo$C_{1-6}$alkyl, phenyl, tolyl, —$C(O)C_{1-6}$alkyl, —$C(O)OCH_3$, —$SO_2$-phenyl, —$SO_2$—$N(CH_3)_2$, —N=N=N, —$NH_2$, —$N(C_{1-6}alkyl)_2$, —$NR^{15}C_{1-6}$alkyl, —$NR^{15}C_{1-6}$alkyl-O—$C_{1-6}$alkyl, —$N(C_{1-6}alkyl)C_{1-6}$alkyl-O—$C_{1-6}$alkyl, —$NR^{15}$—$C_{1-6}$alkyl-3- to 12-membered heterocycloalkyl, a $NR^{15}$-6- to 12-membered aryl or heteroaryl, a $NR^{15}$-3- to 12-membered cycloalkenyl, a $NR^{15}$-3- to 12-membered monocyclic or bicyclic cycloalkyl, or a $NR^{15}$-3- to 12-membered monocyclic or bicyclic heterocycloalkyl group, a —$C_{1-6}$alkyl-3- to 12-membered heterocycloalkyl, a 6- to 12-membered aryl or heteroaryl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, and heterocycloalkyl groups and the heterocycloalkyl group of the —$C_{1-6}$alkyl-heterocycloalkyl group have 1, 2, 3, or 4 heteroatoms independently selected from O, N or S, wherein the cycloalkyl, heterocycloalkyl, and the heterocycloalkyl groups of the —$C_{1-6}$alkyl-heterocycloalkyl group may include a C=O group, and further wherein the heterocycloalkyl groups may include a S=O or $SO_2$;

the alkyl, aryl, heteroaryl, cycloalkyl, heterocycloalkyl and the heterocycloalkyl groups of the —$C_{1-6}$alkyl-heterocycloalkyl groups of $R^{14}$ can be unsubstituted or substituted with 1, 2, 3, or 4 $R^{15}$ substituents independently selected from H, —OH, —N=N=N, halo, —$C_{1-6}$alkyl, —$OC_{1-6}$alkyl, $C_{1-6}$haloalkyl, —O-halo$C_{1-6}$alkyl, phenyl, tolyl, —C(O)$C_{1-6}$alkyl, —C(O)$OCH_3$, $SO_2$-phenyl, —$SO_2$—$NH_2$, or —$SO_2$—$N(CH_3)_2$; and n is independently, in each instance, an integer of 1, 2, 3 or 4.

In another embodiment, the invention provides the compound of embodiment 1, wherein the compound of Formula I has the Formula Ia:

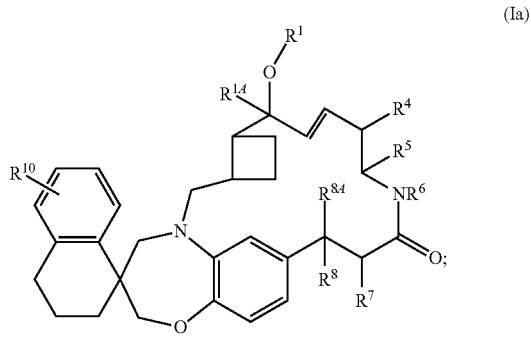

(Ia)

a stereoisomer thereof, a pharmaceutically acceptable salt thereof, or a pharmaceutically acceptable salt of the stereoisomer thereof,
wherein:

$R^1$ is independently selected from H, —$C_{1-6}$haloalkyl, —$C_{1-6}$alkyl, —$C_{2-6}$alkenyl, —$C_{2-6}$alkynyl, —($CH_2CH_2O)_nR^a$, —C(=O)$R^a$, —C(=O)$OR^a$, —C(=O)$NR^aR^b$, —$C_{1-6}$alkyl-O—$C_{1-6}$alkyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

$R^{14}$ is independently selected from H, $C_{1-6}$haloalkyl, $C_{1-6}$alkyl, —$C_{2-6}$alkenyl, —$C_{2-6}$alkynyl, —($CH_2CH_2O)_nR^a$, —$SO_2R^a$, —C(=O)$R^a$, —C(=O)$OR^a$, —C(=O)$NR^aR^b$, —$NR^aR^b$, —N=N=N, —$C_{1-6}$alkyl-O—$C_{1-6}$alkyl, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

$R^4$ is independently selected from H, —$C_{1-6}$alkyl;
$R^5$ is independently selected from H, —$C_{1-6}$alkyl;
$R^6$ is independently selected from H or —$C_{1-6}$alkyl;
alternatively R and $R^6$ together with the atoms to which they are bonded may form a 5- to 12-membered ring;
$R^7$ is independently selected from H, —$C_{1-6}$alkyl;
$R^8$ is selected from —$C_{1-6}$haloalkyl, —$C_{1-6}$alkyl, —O—$C_{1-6}$alkyl, —$C_{2-6}$alkenyl, —$C_{1-6}$alkyl-O—$C_{1-6}$alkyl, —($CH_2CH_2O)_nR^a$, —$SO_2R^a$, —C(=O)$R^a$, —C(=O)$OR^a$, —OC(=O)$R^a$, or —C(=O)$NR^aR^b$; $R^{8A}$ is selected from H, OH, halo, —$C_{1-6}$haloalkyl, —$C_{1-6}$alkyl, —O—$C_{1-6}$alkyl, —$C_{2-6}$alkenyl, —$C_{1-6}$alkyl-O—$C_{1-6}$alkyl, —($CH_2CH_2O)R^a$, —$SO_2R^c$, —C(=O)$R^a$, —C(=O)$OR^a$, —OC(=O)$R^a$, or —C(=O)$NR^aR^b$;

$R^{10}$ is independently selected from H, halo, $C_{1-6}$alkylhalo, $C_{1-6}$alkyl;

wherein the aryl, heteroaryl, cycloalkyl, heterocycloalkyl, spirocycloalkyl and spiroheterocycloalkyl groups of the $R^1$ or $R^{14}$ substituent can be unsubstituted or substituted with 1, 2, 3 or 4 $R^{11}$ substituents independently selected from OH, halo, —$NR^cR^d$, —$C_{1-6}$alkyl, —$C_2$-$C_6$ alkenyl, —$C_2$-$C_6$alkynyl, —$OC_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —$SO_2R^c$, —CN, —C(=O)$NR^cR^d$, —C(=O)$R^a$, —OC(=O)$R^a$, —C(=O)$OR^c$, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 0, 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

wherein the —$C_{1-6}$alkyl of any of the $R^1$, $R^4$, $R^5$, $R^6$, $R^7$, $R^8$, $R^{10}$, $R^{11}$, $R^{14}$, and $R^{8A}$ substituents is unsubstituted or substituted by 1, 2 or 3 $R^{12}$ substituents independently selected from OH, —$OC_{1-6}$alkyl, —$C_{1-6}$alkyl-O—$C_{1-6}$alkyl, halo, —O-halo$C_{1-6}$alkyl, —CN, —$NR^aR^b$, —($NR^aR^bR^c)_n$, —$SO_2R^c$, —($CH_2CH_2O)_nCH_3$, (=O), —C(=O)$R^a$, —OC(=O)$R^a$, —C(=O)$OR^a$, —C(=O)$NR^aR^b$, —O—$SiR^aR^bR^c$, —O-(3- to 12-membered heterocycloakyl), phenyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

wherein the aryl, heteroaryl, cycloalkyl, heterocycloalkyl, spirocycloalkyl and spiroheterocycloalkyl groups of any of the $R^4$, $R^5$, $R^6$, $R^7$, $R^8$, $R^{10}$, $R^{11}$ and $R^{12}$ substituents can be unsubstituted or substituted with 1, 2, 3 or 4 $R^{13}$ substituents independently selected from OH, halo, —$C_{1-6}$alkyl, —$OC_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —$SO_2R^c$, —$NR^cR^d$, —CN, —C(=O)$NR^cR^d$, —C(=O)$R^a$, —OC(=O)$R^a$, —C(=O)$OR^c$, —$B(OH)_2$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

wherein each $R^a$, $R^b$, R, and $R^d$ is independently H, OH, —$C_{1-6}$alkyl, —$C_{1-6}$alkenyl, —$C_{2-6}$alkynyl, —$C_{1-6}$alkyl-$NR^{14}R^{14}$, $NR^{14}R^{14}$, —$SO_2R^{14}$, —$(CH_2CH_2O)_nCH_3$, (=O), —C(=O)$R^{14}$, —OC(=O)$R^{14}$, —C(=O)$OR^{14}$, —C(=O)$NR^{14}R^{14}$, $C_{1-6}$haloalkyl, —O-halo$C_{1-6}$alkyl, —$C_{1-6}$alkyl-O—$C_{1-6}$alkyl, —$C_{1-6}$alkyl-OH, benzyl, phenyl, a —$C_{1-6}$alkyl-3- to 12-membered heterocycloalkyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups and the heterocycloalkyl group of the —$C_{1-6}$alkyl-heterocycloalkyl group have 1, 2, 3, or 4 heteroatoms independently selected from O, N or S, wherein the cycloalkyl, spirocycloalkyl, spiroheterocycloalkyl, heterocycloalkyl, and the heterocycloalkyl groups of the —$C_{1-6}$alkyl-heterocycloalkyl group may include a C=O group, and further wherein the spiroheterocycloalkyl and heterocycloalkyl groups may include a S=O or $SO_2$;

wherein $R^{11}$ substituents are independently selected from H, —OH, halo, —$C_{1-6}$alkyl, —$OC_{1-6}$alkyl, —$C_{1-6}$alkyl-$OC_{1-6}$alkyl, —$C_{1-6}$haloalkyl, —O-halo$C_{1-6}$alkyl, phenyl, tolyl, —C(O)$C_{1-6}$alkyl, —C(O)$OCH_3$, —$SO_2$— phenyl, —$SO_2$—$N(CH_3)_2$, —N=N=N, —$NH_2$, —$N(C_{1-6}alkyl)_2$, —$NR^{15}C_{1-6}$alkyl, —$NR^{15}C_{1-6}$alkyl-O—$C_{1-6}$alkyl, —$N(C_{1-6}alkyl)C_{1-6}$alkyl-O—$C_{1-6}$alkyl, —$NR^1$—$C_{1-6}$alky- 3- to 12-membered heterocycloalkyl, a $NR^{15}$-6- to 12-membered aryl or heteroaryl, a $NR^{15}$-3- to 12-membered cycloalkenyl, a $NR^{15}$-3- to 12-membered monocyclic or bicyclic cycloalkyl, or a $NR^{15}$-3- to 12-membered monocyclic or bicyclic heterocycloalkyl group, a —$C_{1-6}$alkyl-3- to 12-membered heterocycloalkyl, a 6- to 12-membered aryl or heteroaryl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, and heterocycloalkyl groups and the heterocycloalkyl group of the —$C_{1-6}$alkyl-heterocycloalkyl group have 1, 2, 3, or 4 heteroatoms independently selected from O, N or S, wherein the cycloalkyl, heterocycloalkyl, and the heterocycloalkyl groups of the —$C_{1-6}$alkyl-heterocycloalkyl group may include a C=O group, and further wherein the heterocycloalkyl groups may include a S=O or $SO_2$;

the alkyl, aryl, heteroaryl, cycloalkyl, heterocycloalkyl and the heterocycloalkyl groups of the —$C_{1-6}$alkyl-heterocycloalkyl groups of $R^{11}$ can be unsubstituted or substituted with 1, 2, 3, or 4 $R^5$ substituents independently selected from H, —OH, —N=N=N, halo, —$C_{1-6}$alkyl, —$OC_{1-6}$alkyl, $C_{1-6}$haloalkyl, —O-halo$C_{1-6}$alkyl, phenyl, tolyl, —C(O)$C_{1-6}$alkyl, —C(O)$OCH_3$, $SO_2$-phenyl, —$SO_2$—$NH_2$, or —$SO_2$—$N(CH_3)_2$; and n is independently, in each instance, an integer of 1, 2, 3 or 4.

3. In another embodiment, the invention provides the compound of embodiment 1, wherein $R^1$ is Cl.

4. In another embodiment, the invention provides the compound of embodiment 1, wherein $R^1$ is selected from H, —$C_1$-$C_6$ alkyl, or

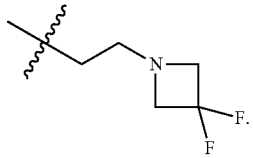

5. In another embodiment, the invention provides the compound of embodiment 4, wherein $R^1$ is H.

6. In another embodiment, the invention provides the compound of embodiment 5, wherein $R^{14}$ is H.

7. In another embodiment, the invention provides the compound of embodiment 1, wherein $R^4$ is H.

8. In another embodiment, the invention provides the compound of embodiment 1, wherein $R^5$ is H.

9. In another embodiment, the invention provides the compound of embodiment 1, wherein $R^6$ is H.

10. In another embodiment, the invention provides the compound of embodiment 1, wherein $R^7$ is H.

11. In another embodiment, the invention provides the compound of embodiment 1, wherein $R^{11}$ is independently selected from —OH, —COOH, or

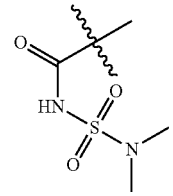

12. In another embodiment, the invention provides the compound of embodiment 1, wherein $R^8$ is —COOH.

13. In another embodiment, the invention provides the compound of embodiment 1, wherein $R^8$ is —OH.

14. In another embodiment, the invention provides the compound of embodiment 1, wherein $R^{8a}$ is —OH.

15. Another embodiment of the present invention provides a compound having the Formula II:

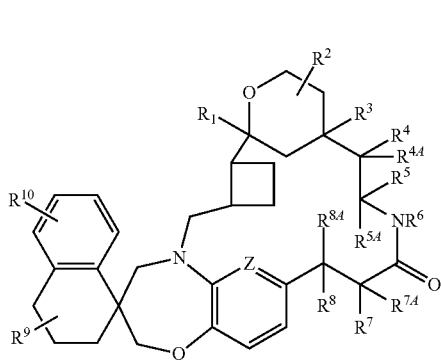

(II)

a stereoisomer thereof, a pharmaceutically acceptable salt thereof, or a pharmaceutically acceptable salt of the stereoisomer thereof,
wherein:

Z is selected from C or N;

$R^1$ is independently selected from H, —$C_{1-6}$haloalkyl, —$C_{1-6}$alkyl, —$C_{2-6}$alkenyl, —$C_{2-6}$alkynyl, —$(CH_2CH_2O)_nR^a$, —C(=O)$R^a$, —C(=O)O$R^a$, —C(=O)N$R^aR^b$, —$C_{1-6}$alkyl-O—$C_{1-6}$alkyl, each of $R^2$, $R^3$, $R^4$, $R^5$, $R^6$, $R^7$, $R^8$, $R^9$, $R^{10}$, $R^{4A}$, $R^{1A}$, $R^{7A}$, and $R^{8A}$ is independently selected from H, halo, —$C_{1-6}$haloalkyl, —$C_{1-6}$alkyl, —O—$C_{1-6}$alkyl, —$C_{2-6}$alkenyl, —$C_{1-6}$alkyl-O—$C_{1-6}$alkyl, —$(CH_2CH_2O)R^a$, —$SO_2R^c$, —C(=O)$R^a$, —C(=O)O$R^a$, —OC(=O)$R^a$, —C(=O)N$R^aR^b$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

wherein the —$C_{1-6}$alkyl of any of the R, $R^2$, $R^3$, $R^4$, $R^5$, $R^6$, $R^7$, $R^8$, $R^9$, $R^{10}$, $R^{11}$, $R^{4A}$, $R^{5A}$, $R^{7A}$, and $R^{8A}$ substituents is unsubstituted or substituted by 1, 2 or 3 $R^{11}$ substituents independently selected from OH, —O$C_{1-6}$alkyl, —$C_{1-6}$alkyl-O—$C_{1-6}$alkyl, halo, —O-halo$C_{1-6}$alkyl, —CN, —N$R^aR^b$, —(N$R^aR^bR^c$)$_n$, —$SO_2R^a$, —$(CH_2CH_2O)_nCH_3$, (=O), —C(=O)$R^a$, —OC(=O)$R^a$, —C(=O)O$R^a$, —C(=O)N$R^aR^b$, —O—Si$R^aR^bR^c$, —O-(3- to 12-membered heterocycloakyl), phenyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

wherein the aryl, heteroaryl, cycloalkyl, heterocycloalkyl, spirocycloalkyl and spiroheterocycloalkyl groups of any of the $R^2$, $R^4$, $R^5$, $R^6$, $R^7$, $R^8$, $R^9$, $R^{10}$, $R^{11}$ and $R^{12}$ substituents can be unsubstituted or substituted with 1, 2, 3 or 4 $R^{13}$ substituents independently selected from OH, halo, —$C_{1-6}$alkyl, —O$C_{1-6}$alkyl, —$C_{1-6}$alkyl-OH, —$C_{1-6}$alkyl-O—$C_{1-6}$alkyl, $C_{1-6}$haloalkyl, —O-halo$C_{1-6}$alkyl, —$SO_2R^c$, —N$R^cR^d$, —CN, —C(=O)N$R^cR^d$, —C(=O)$R^a$, —OC(=O)$R^a$, —C(=O)O$R^c$, —B(OH)$_2$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

wherein each $R^a$, $R^b$, $R^c$, and $R^d$ is independently H, OH, —$C_{1-6}$alkyl, —$C_{2-6}$alkenyl, —$C_{2-6}$alkynyl, —$C_{1-6}$alkyl-N$R^{14}R^{14}$, N$R^{14}R^{14}$, —$SO_2R^{14}$, —$(CH_2CH_2O)_nCH_3$, —C(=O)$R^{14}$, —OC(=O)$R^{14}$, —C(=O)O$R^{14}$, —C(=O)N$R^{14}R^{14}$, —$C_{1-6}$haloalkyl, —O-halo$C_{1-6}$alkyl, —$C_{1-6}$alkyl-O—$C_{1-6}$alkyl, —$C_{1-6}$alkyl-OH, benzyl, phenyl, a —$C_{1-6}$alkyl-3- to 12-membered heterocycloalkyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups and the heterocycloalkyl group of the —$C_{1-6}$alkyl-heterocycloalkyl group have 1, 2, 3, or 4 heteroatoms independently selected from O, N or S, wherein the cycloalkyl, spirocycloalkyl, spiroheterocycloalkyl, heterocycloalkyl, and the heterocycloalkyl groups of the —$C_{1-6}$alkyl-heterocycloalkyl group may include a C=O group, and further wherein the spiroheterocycloalkyl and heterocycloalkyl groups may include a S=O or $SO_2$;

wherein $R^{14}$ substituents are independently selected from H, —OH, halo, —$C_{1-6}$alkyl, —O$C_{1-6}$alkyl, —$C_{1-6}$alkyl-O$C_{1-6}$alkyl, —$C_{1-6}$haloalkyl, —O-halo$C_{1-6}$alkyl, phenyl, tolyl, —C(O)$C_{1-6}$alkyl, —C(O)OCH$_3$, —$SO_2$-phenyl, —$SO_2$—N(CH$_3$)$_2$, —N=N=N, —NH$_2$, —N(C$_{1-6}$alkyl)$_2$, —NR$^{15}$C$_{1-6}$alkyl, —NR$^{15}$C$_{1-6}$alkyl-O—C$_{1-6}$alkyl, —N(C$_{1-6}$alkyl)C$_{1-6}$alkyl-O—C$_{1-6}$alkyl, —NR$^{15}$—C$_{1-6}$alkyl-3- to 12-membered heterocycloalkyl, a NR$^{15}$-6- to 12-membered aryl or heteroaryl, a NR$^{15}$-3- to 12-membered cycloalkenyl, a NR$^{15}$-3- to 12-membered monocyclic or bicyclic cycloalkyl, or a NR$^{15}$-3- to 12-membered monocyclic or bicyclic heterocycloalkyl group, a —C$_{1-6}$alkyl-3- to 12-membered heterocycloalkyl, a 6- to 12-membered aryl or heteroaryl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, and heterocycloalkyl groups and the heterocycloalkyl group of the —C$_{1-6}$alkyl-heterocycloalkyl group have 1, 2, 3, or 4 heteroatoms independently selected from O, N or S, wherein the cycloalkyl, heterocycloalkyl, and the heterocycloalkyl groups of the —C$_{1-6}$alkyl-heterocycloalkyl group may include a C=O group, and further wherein the heterocycloalkyl groups may include a S=O or $SO_2$;

the alkyl, aryl, heteroaryl, cycloalkyl, heterocycloalkyl and the heterocycloalkyl groups of the —C$_{1-6}$alkyl-heterocycloalkyl groups of R$^{14}$ can be unsubstituted or substituted with 1, 2, 3, or 4 R$^5$ substituents independently selected from H, —OH, —N=N=N, halo, —C$_{1-6}$alkyl, —OC$_{1-6}$alkyl, $C_{1-6}$haloalkyl, —O-halo$C_{1-6}$alkyl, phenyl, tolyl, —C(O)$C_{1-6}$alkyl, —C(O)OCH$_3$, SO$_2$-phenyl, —SO$_2$—NH$_2$, or —SO$_2$—N(CH$_3$)$_2$; and n is independently, in each instance, an integer of 1, 2, 3 or 4.

16. In another embodiment, the invention provides the compound of embodiment 15, wherein the compound of Formula II has the Formula IIa:

(IIa)

[Chemical structure]

a stereoisomer thereof, a pharmaceutically acceptable salt thereof, or a pharmaceutically acceptable salt of the stereoisomer thereof, wherein:

each of $R^4$, $R^5$, $R^6$, $R^7$, $R^8$, and $R^{8A}$ is independently selected from H, halo, —C$_{1-6}$haloalkyl, —C$_{1-6}$alkyl, —O—C$_{1-6}$alkyl, —C$_{2-6}$alkenyl, —C$_{1-6}$alkyl-O—C$_{1-6}$alkyl, —(CH$_2$CH$_2$O)R$^a$, —SO$_2$R$^a$, —C(=O)R$^a$, —C(=O)OR$^a$, —OC(=O)R$^a$, —C(=O)NR$^a$R$^b$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or SO$_2$;

wherein the —C$_{1-6}$alkyl of any of the R, $R^5$, $R^6$, $R^7$, $R^8$, and $R^{8A}$ substituents is unsubstituted or substituted by 1, 2 or 3 $R^{11}$ substituents independently selected from OH, —OC$_{1-6}$alkyl, —C$_{1-6}$alkyl-O—C$_{1-6}$alkyl, halo, —O-haloC$_{1-6}$alkyl, —CN, —NR$^a$R$^b$, —(NR$^a$R$^b$R$^c$)$_n$, —SO$_2$R$^a$, —(CH$_2$CH$_2$O)$_n$CH$_3$, (=O), —C(=O)R$^a$, —OC(=O)R$^a$, —C(=O)OR$^a$, —C(=O)NR$^a$R$^b$, —O—SiR$^a$R$^b$R$^c$, —O-(3- to 12-membered heterocycloakyl), phenyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or SO$_2$;

wherein the aryl, heteroaryl, cycloalkyl, heterocycloalkyl, spirocycloalkyl and spiroheterocycloalkyl groups of any of the $R^4$, $R^5$, $R^6$, $R^7$, $R^8$, and $R^{11}$ substituents can be unsubstituted or substituted with 1, 2, 3 or 4 $R^{13}$ substituents independently selected from OH, halo, —C$_{1-6}$alkyl, —OC$_{1-6}$alkyl, —C$_{1-6}$alkyl-OH, —C$_{1-6}$alkyl-O—C$_{1-6}$alkyl, C$_{1-6}$haloalkyl, —O-haloC$_{1-6}$alkyl, —SO$_2$R$^c$, —NR$^c$R$^d$, —CN, —C(=O)NR$^c$R$^d$, —C(=O)R$^a$, —OC(=O)R$^a$, —C(=O)OR$^c$, —B(OH)$_2$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or SO$_2$;

wherein each R$^a$, R$^b$, R$^c$, and R$^d$ is independently H, OH, —C$_{1-6}$alkyl, —C$_{1-6}$alkenyl, —C$_{2-6}$alkynyl, —C$_{1-6}$alkyl-NR$^{14}$R$^{14}$, NR$^{14}$R$^{14}$, —SO$_2$R$^{14}$, —(CH$_2$CH$_2$O)$_n$CH$_3$, —C(=O)R$^{14}$, —OC(=O)R$^{14}$, —C(=O)OR$^{14}$, —C(=O)NR$^{14}$R$^{14}$, —C$_{1-6}$haloalkyl, —O-haloC$_{1-6}$alkyl, —C$_{1-6}$alkyl-O—C$_{1-6}$alkyl, —C$_{1-6}$alkyl-OH, benzyl, phenyl, a —C$_{1-6}$alkyl-3- to 12-membered heterocycloalkyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups and the heterocycloalkyl group of the —C$_{1-6}$alkyl-heterocycloalkyl group have 1, 2, 3, or 4 heteroatoms independently selected from O, N or S, wherein the cycloalkyl, spirocycloalkyl, spiroheterocycloalkyl, heterocycloalkyl, and the heterocycloalkyl groups of the —C$_{1-6}$alkyl-heterocycloalkyl group may include a C=O group, and further wherein the spiroheterocycloalkyl and heterocycloalkyl groups may include a S=O or SO$_2$;

wherein R$^{14}$ substituents are independently selected from H, —OH, halo, —C$_{1-6}$alkyl, —OC$_{1-6}$alkyl, —C$_{1-6}$alkyl-OC$_{1-6}$alkyl, —C$_{1-6}$haloalkyl, —O-haloC$_{1-6}$alkyl, phenyl, tolyl, —C(O)C$_{1-6}$alkyl, —C(O)OCH$_3$, —SO$_2$-phenyl, —SO$_2$—N(CH$_3$)$_2$, —N=N=N, —NH$_2$, —N(C$_{1-6}$alkyl)$_2$, —NR$^{15}$C$_{1-6}$alkyl, —NR$^{15}$C$_{1-6}$alkyl-O—C$_{1-6}$alkyl, —N(C$_{1-6}$alkyl)C$_{1-6}$alkyl-O—C$_{1-6}$alkyl, —NR$^{15}$—C$_{1-6}$alkyl-3- to 12-membered heterocycloalkyl, a NR$^{15}$-6- to 12-membered aryl or heteroaryl, a NR$^{15}$-3- to 12-membered cycloalkenyl, a NR$^{15}$-3- to 12-membered monocyclic or bicyclic cycloalkyl, or a NR$^{15}$-3- to 12-membered monocyclic or bicyclic heterocycloalkyl group, a —C$_{1-6}$alkyl-3- to 12-membered heterocycloalkyl, a 6- to 12-membered aryl or heteroaryl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, and heterocycloalkyl groups and the heterocycloalkyl group of the —C$_{1-6}$alkyl-heterocycloalkyl group have 1, 2, 3, or 4 heteroatoms independently selected from O, N or S, wherein the cycloalkyl, heterocycloalkyl, and the heterocycloalkyl groups of the —C$_{1-6}$alkyl-heterocycloalkyl group may include a C=O group, and further wherein the heterocycloalkyl groups may include a S=O or SO$_2$;

the alkyl, aryl, heteroaryl, cycloalkyl, heterocycloalkyl and the heterocycloalkyl groups of the —C$_{1-6}$alkyl-heterocycloalkyl groups of R$^{14}$ can be unsubstituted or substituted with 1, 2, 3, or 4 R$^{11}$ substituents independently selected from H, —OH, —N=N=N, halo, —C$_{1-6}$alkyl, —OC$_{1-6}$alkyl, C$_{1-6}$haloalkyl, —O-haloC$_{1-6}$alkyl, phenyl, tolyl, —C(O)C$_{1-6}$alkyl, —C(O)OCH$_3$, SO$_2$-phenyl, —SO$_2$—NH$_2$, or —SO$_2$—N(CH$_3$)$_2$; and n is independently, in each instance, an integer of 1, 2, 3 or 4.

17. In another embodiment, the invention provides the compound of embodiment 16, wherein R$^a$ is CH$_3$.

18. In another embodiment, the invention provides the compound of embodiment 16, wherein R$^4$ is H.

19. In another embodiment, the invention provides the compound of embodiment 16, wherein R$^5$ is H.

20. In another embodiment, the invention provides the compound of embodiment 16, wherein R$^6$ is H.

21. In another embodiment, the invention provides the compound of embodiment 16, wherein R$^7$ is H.

22. In another embodiment, the invention provides the compound of embodiment 16, wherein R$^8$ is independently selected from —OH, —COOH, or

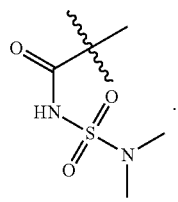

23. In another embodiment, the invention provides the compound of embodiment 22, wherein R$^8$ is —COOH.

24. In another embodiment, the invention provides the compound of embodiment 16, wherein R$^{8A}$ is —OH.

25. In another embodiment, the invention provides a compound, wherein the compound is selected from:

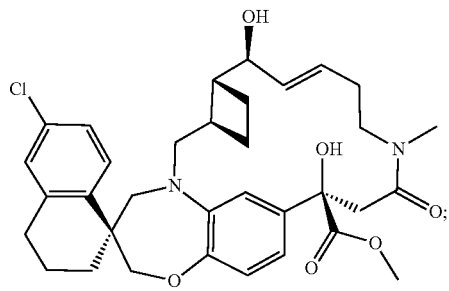

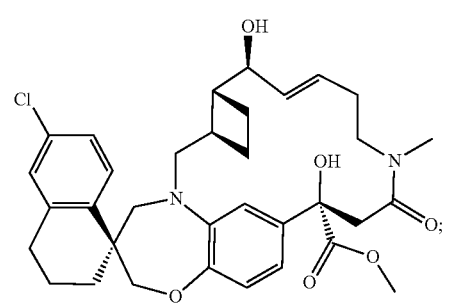

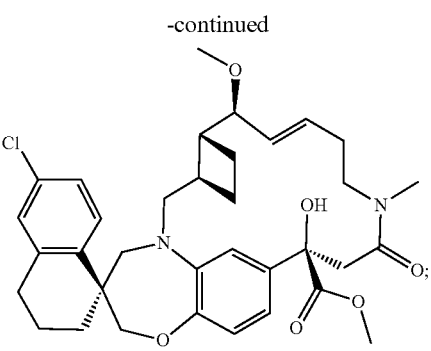

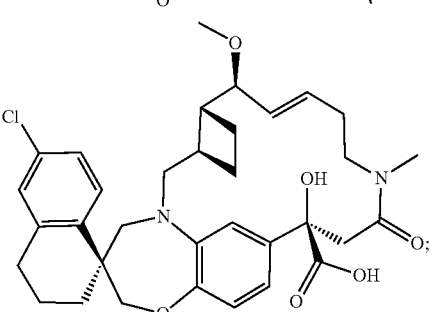

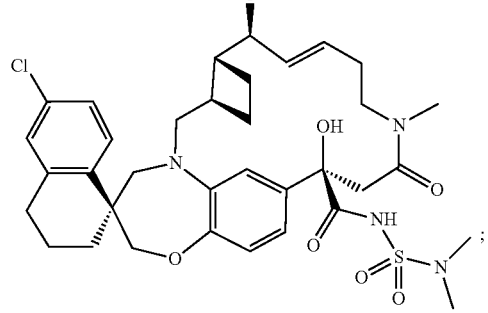

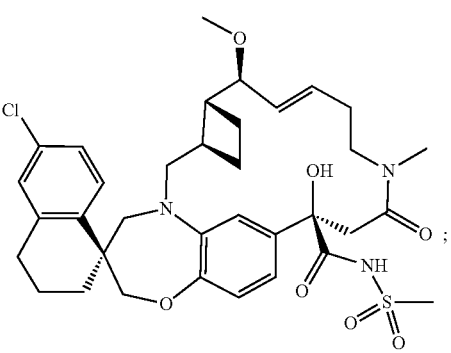

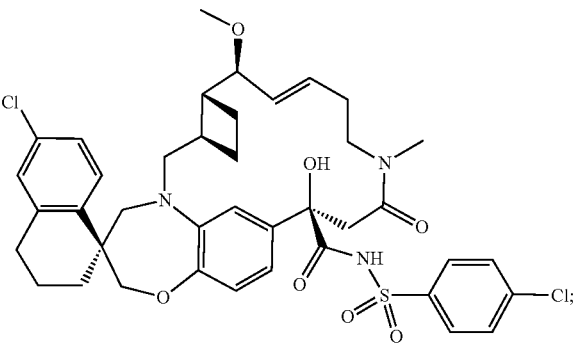

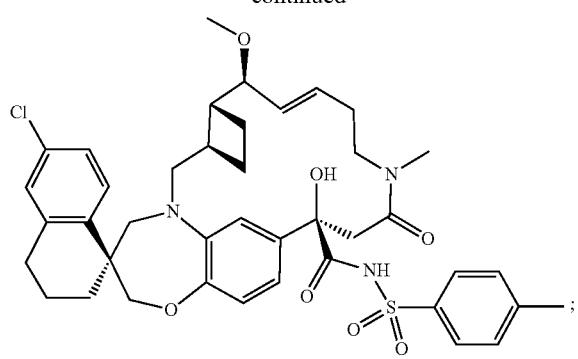
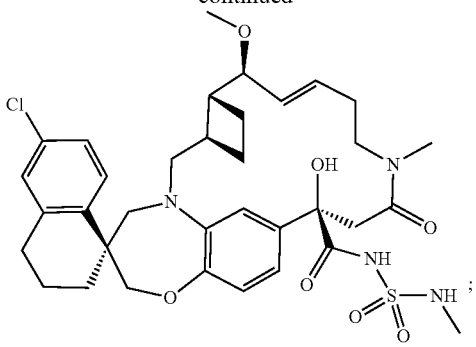
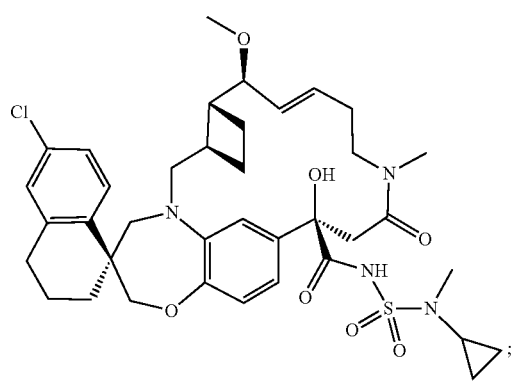
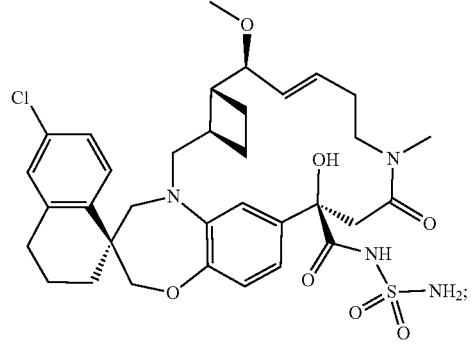
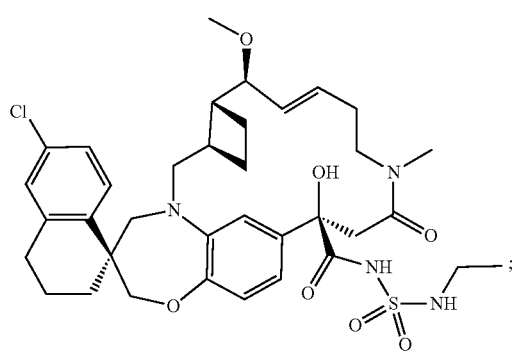
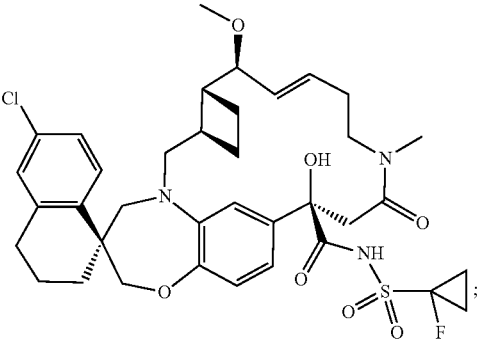
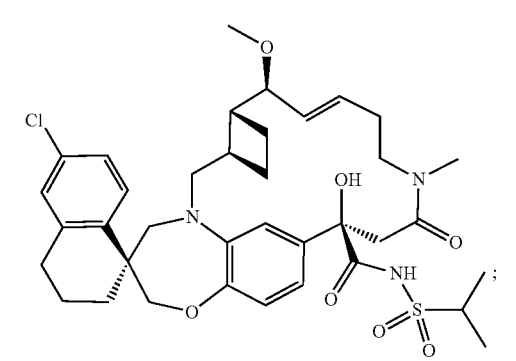
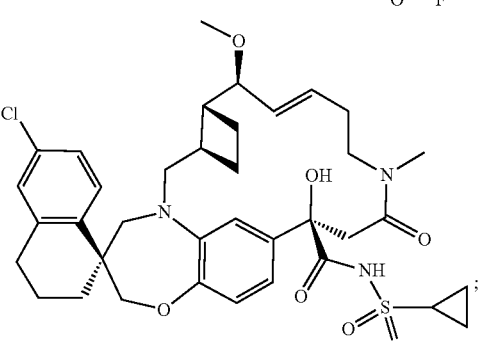
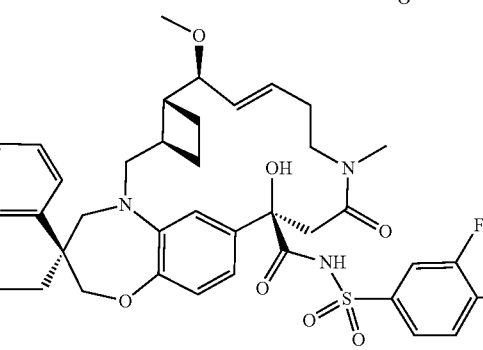

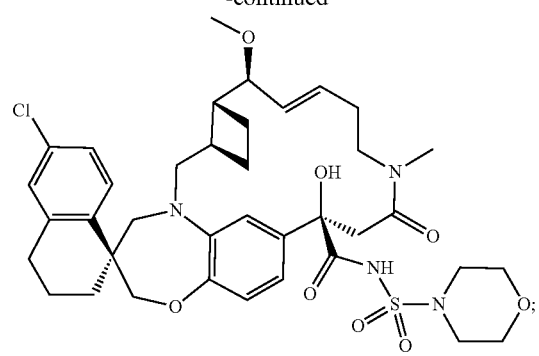
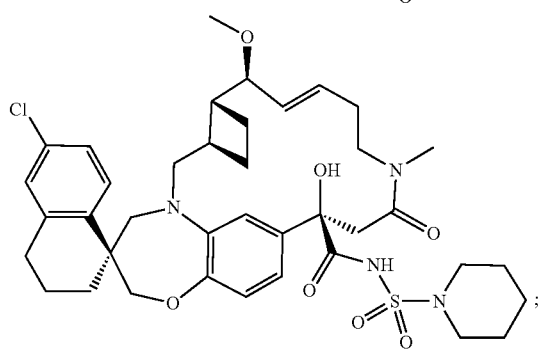
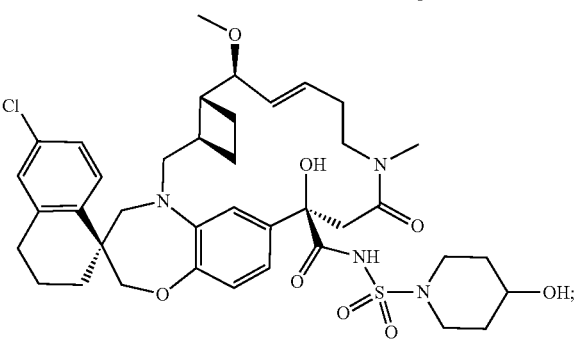
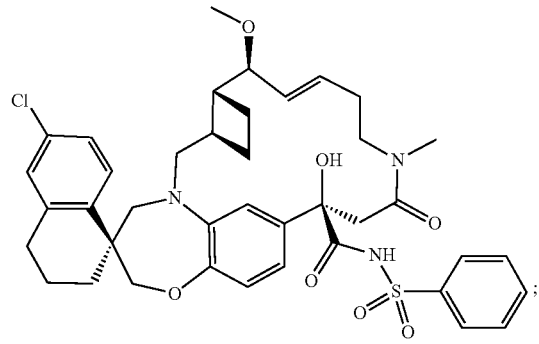
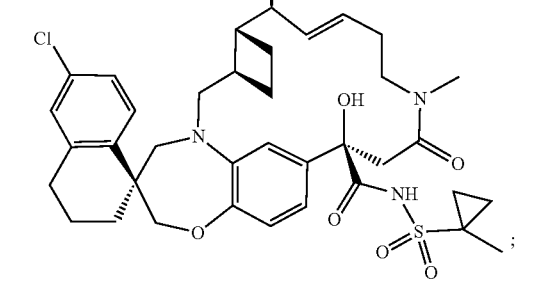
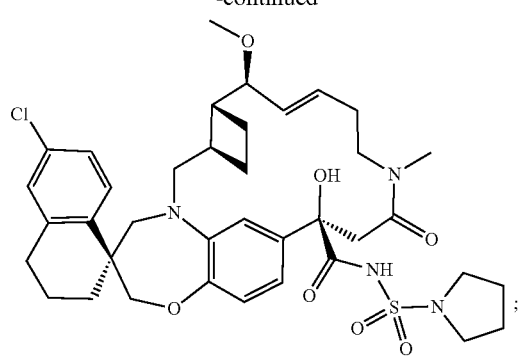
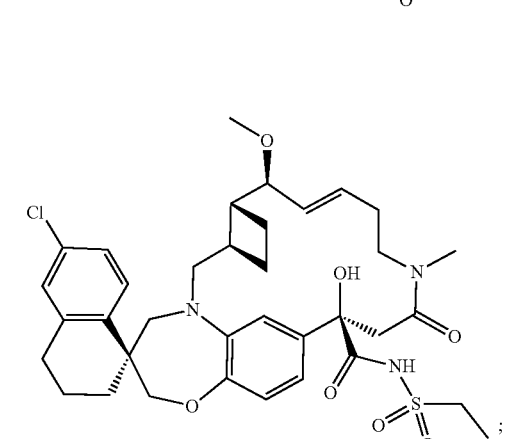
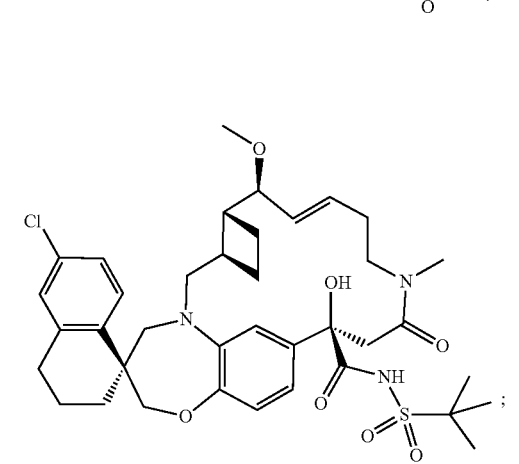
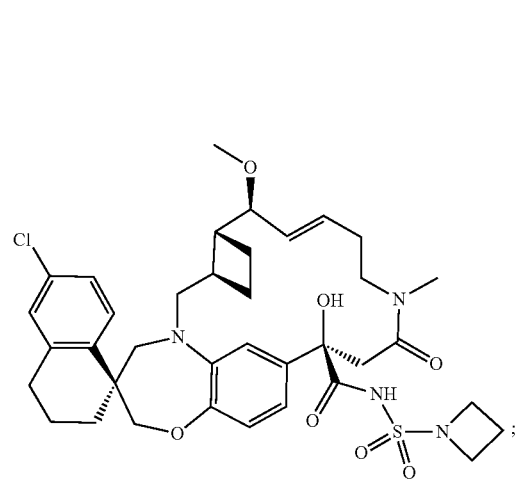

19
-continued
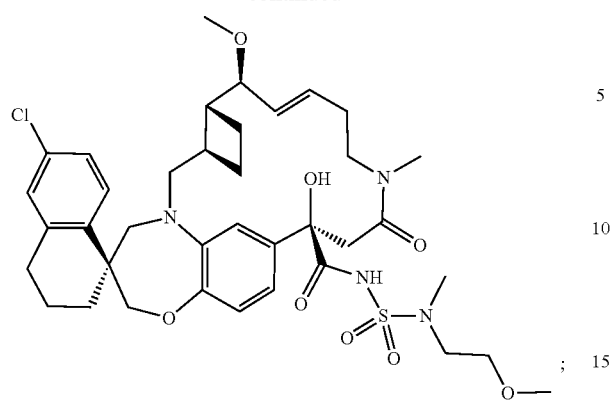
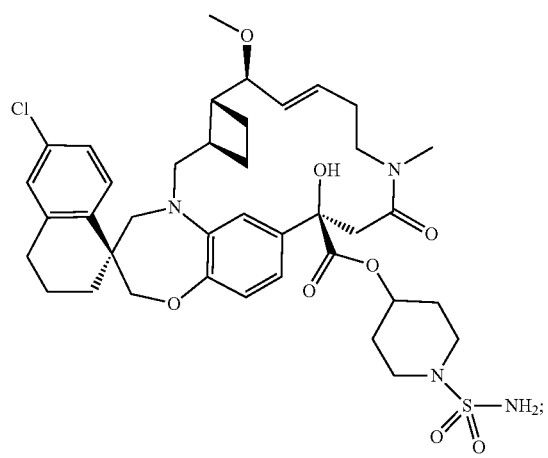
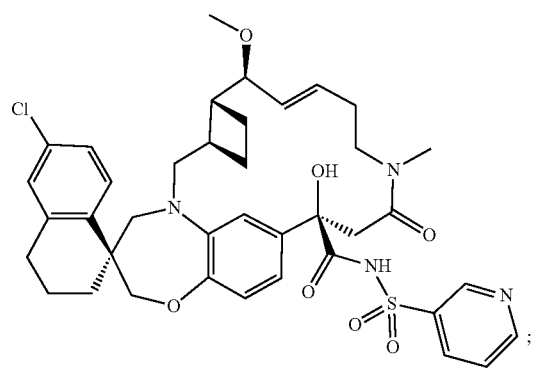
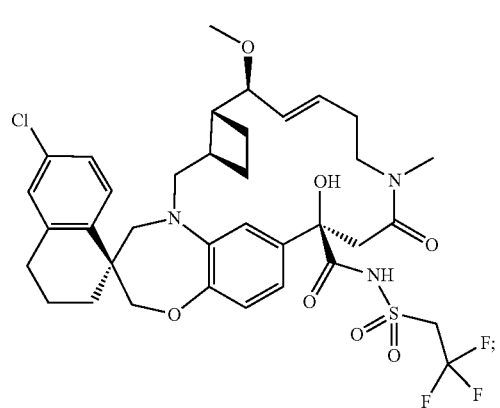
20
-continued
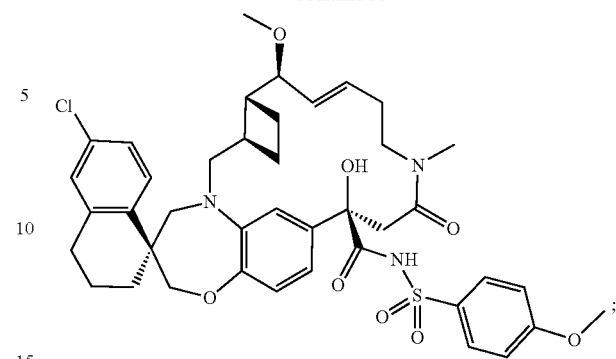
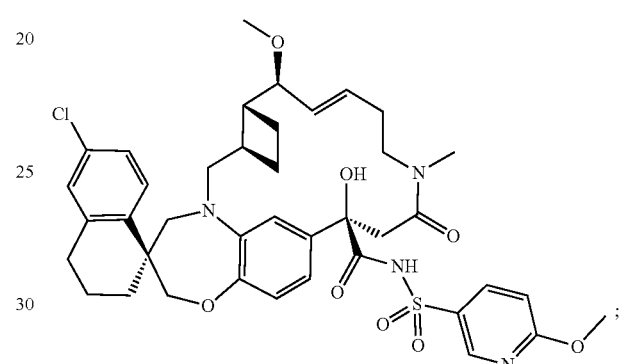
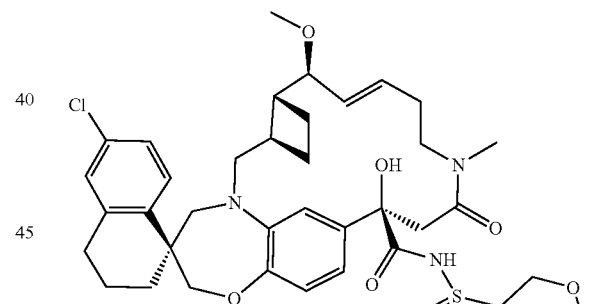
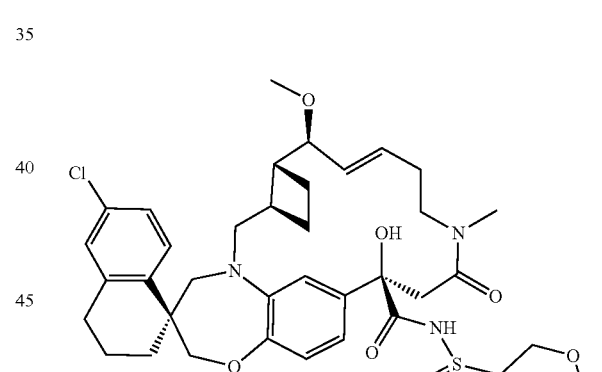
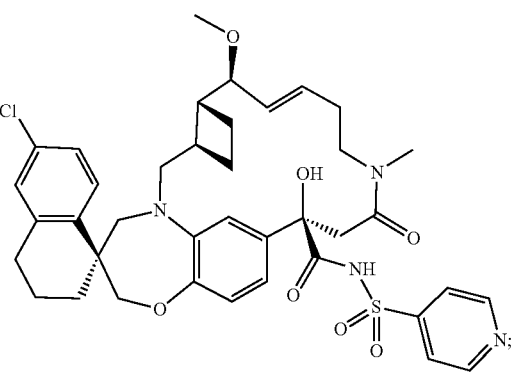
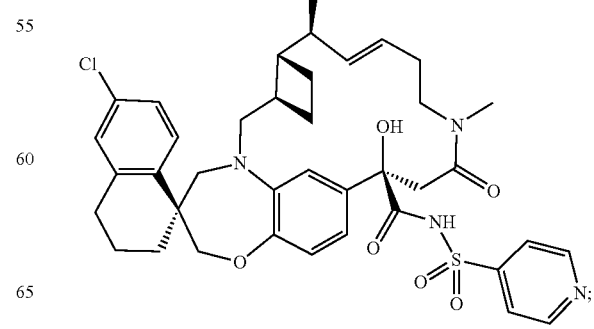

21
-continued
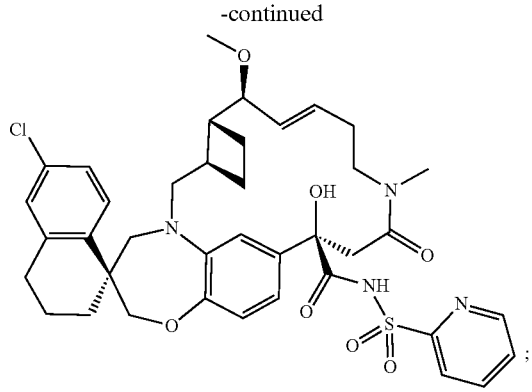
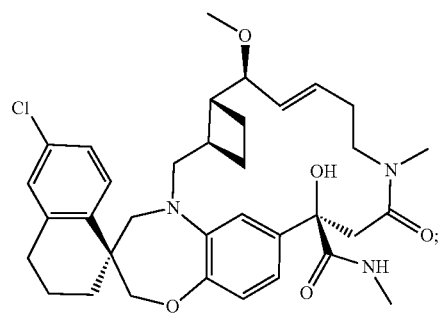
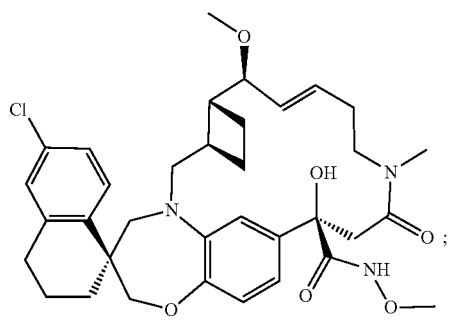
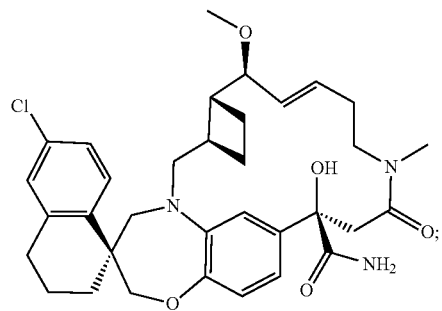
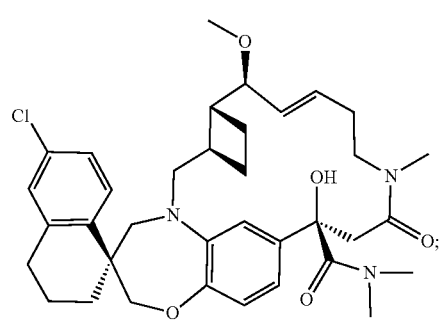
22
-continued
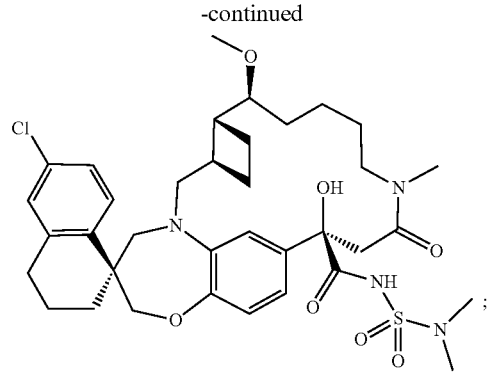
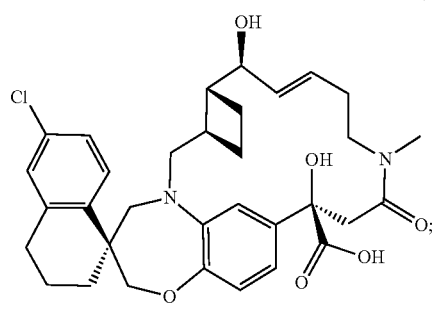
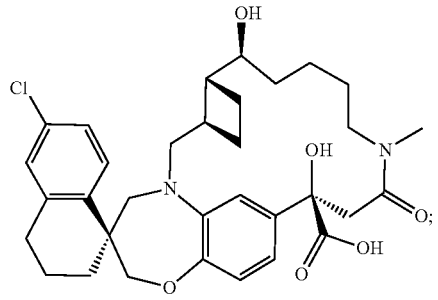
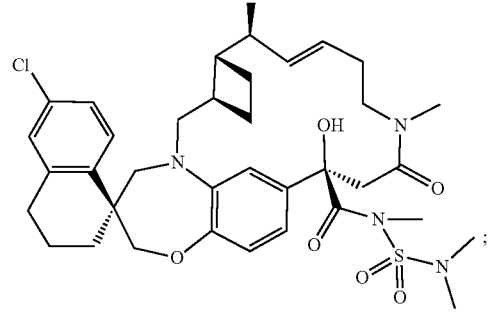
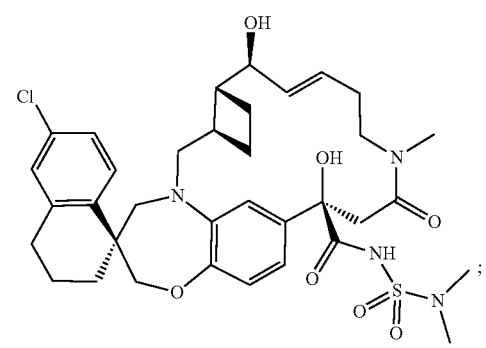

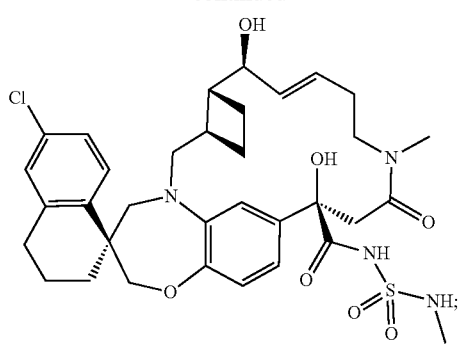
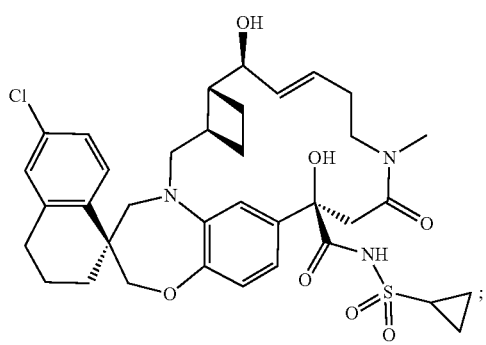
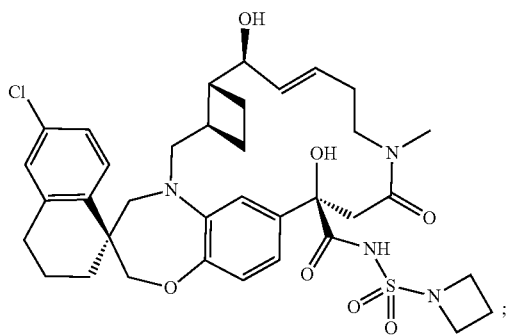
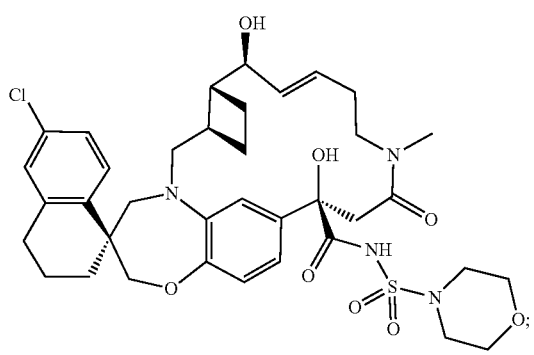
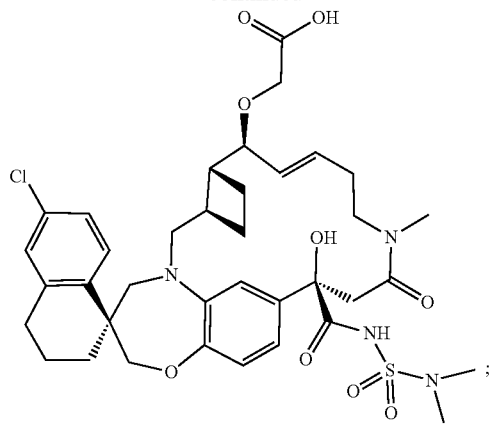
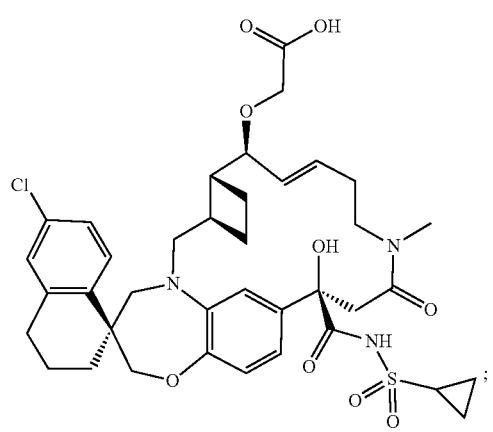
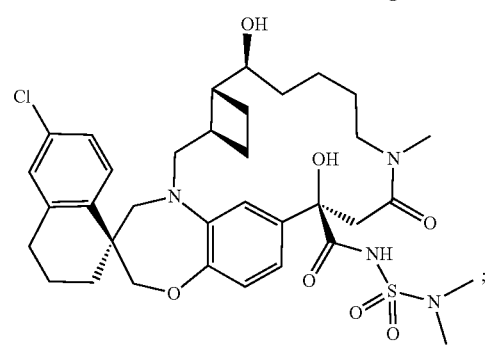
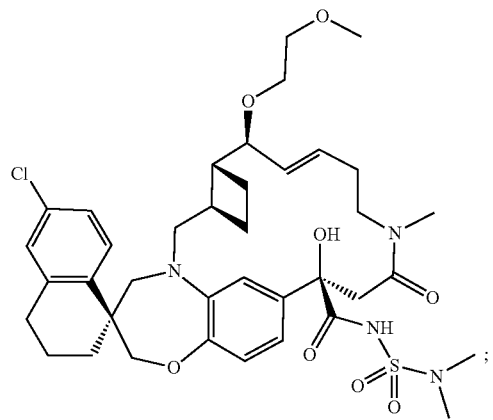

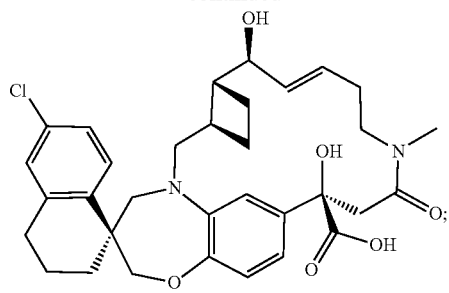
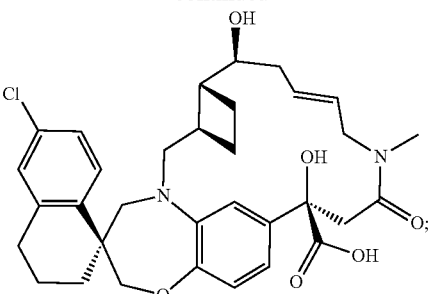
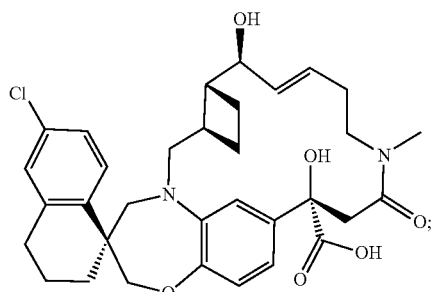
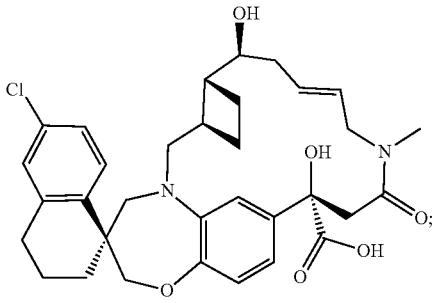
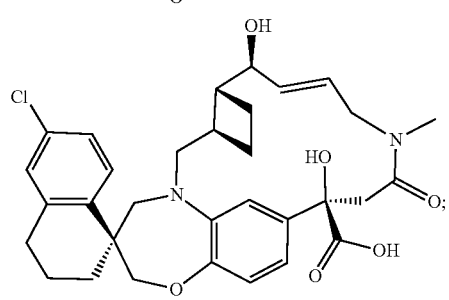
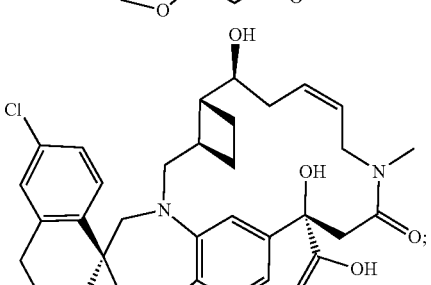
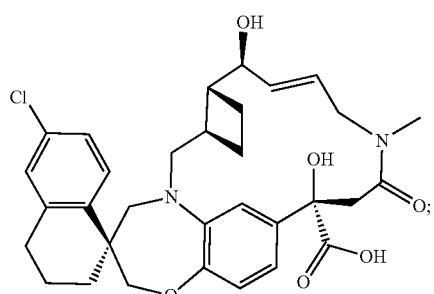
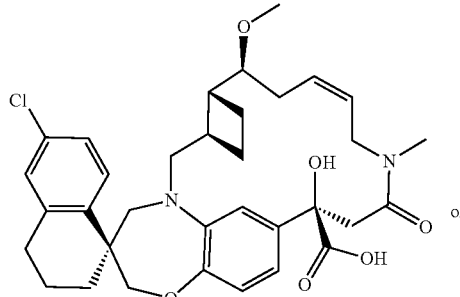 or
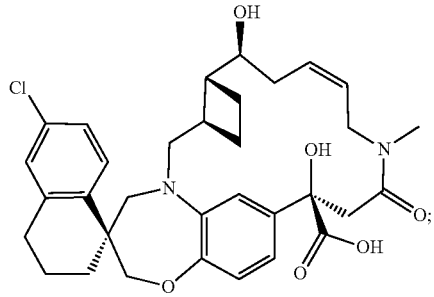
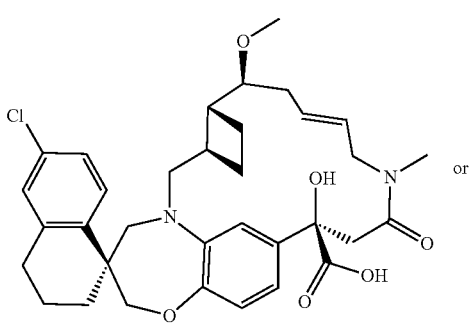 or -continued
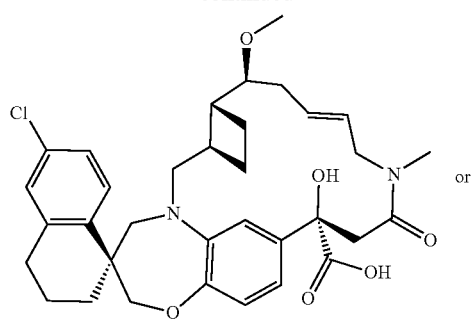
or
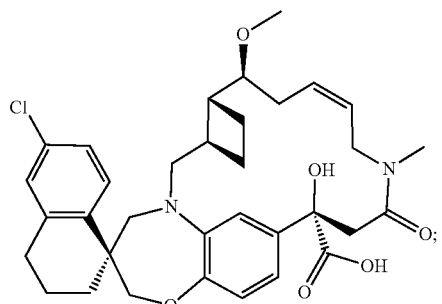
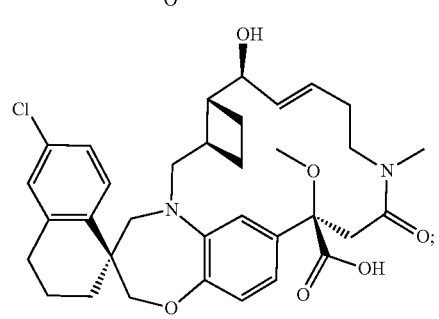
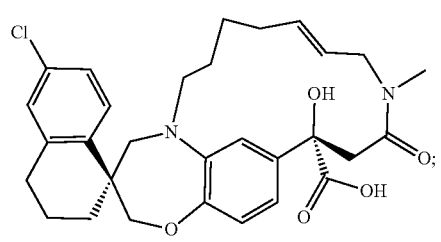
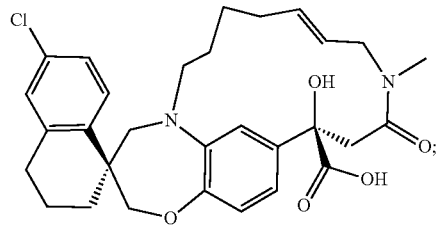
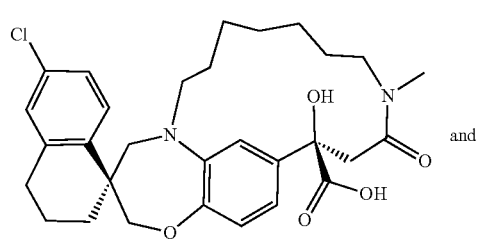
and
-continued
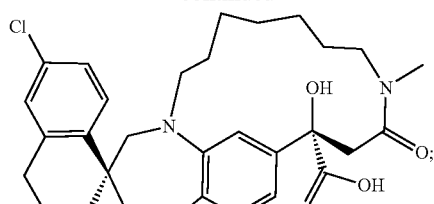
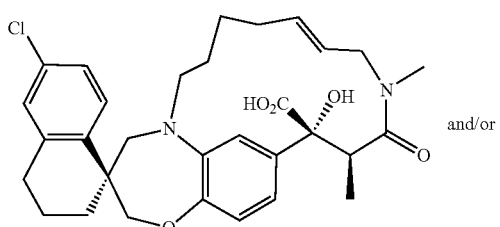
and/or

and/or;
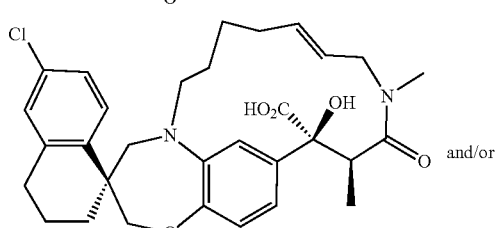
and/or
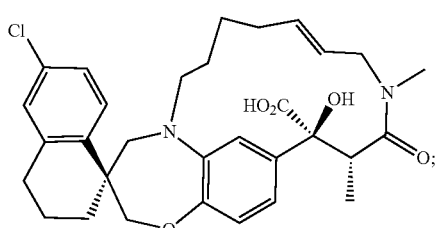
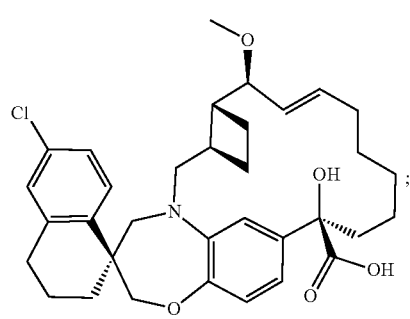

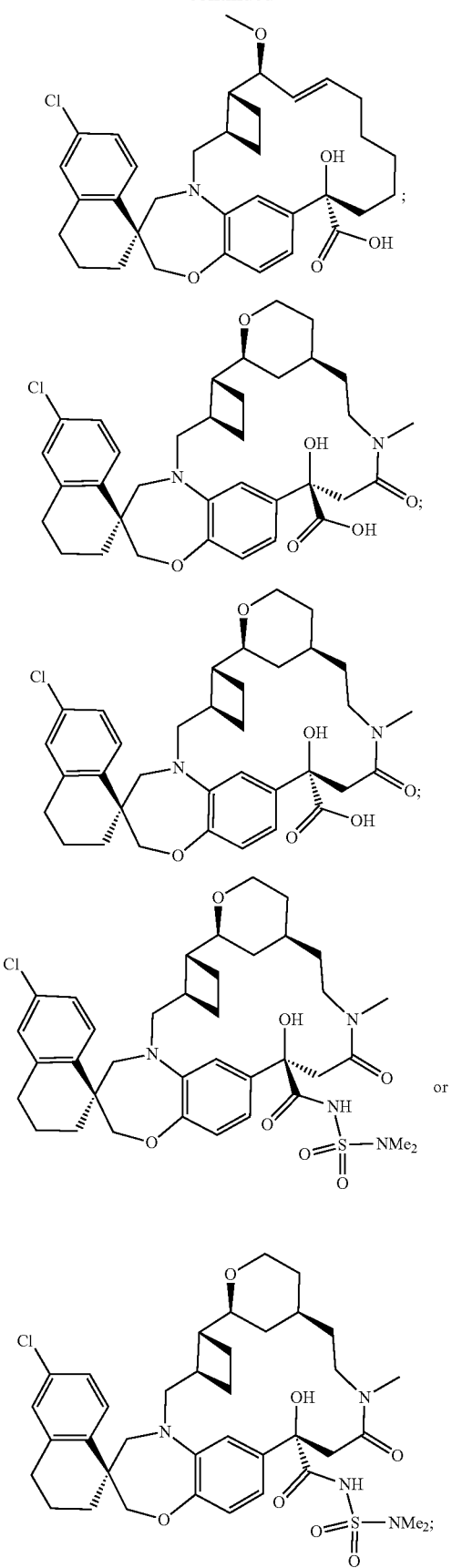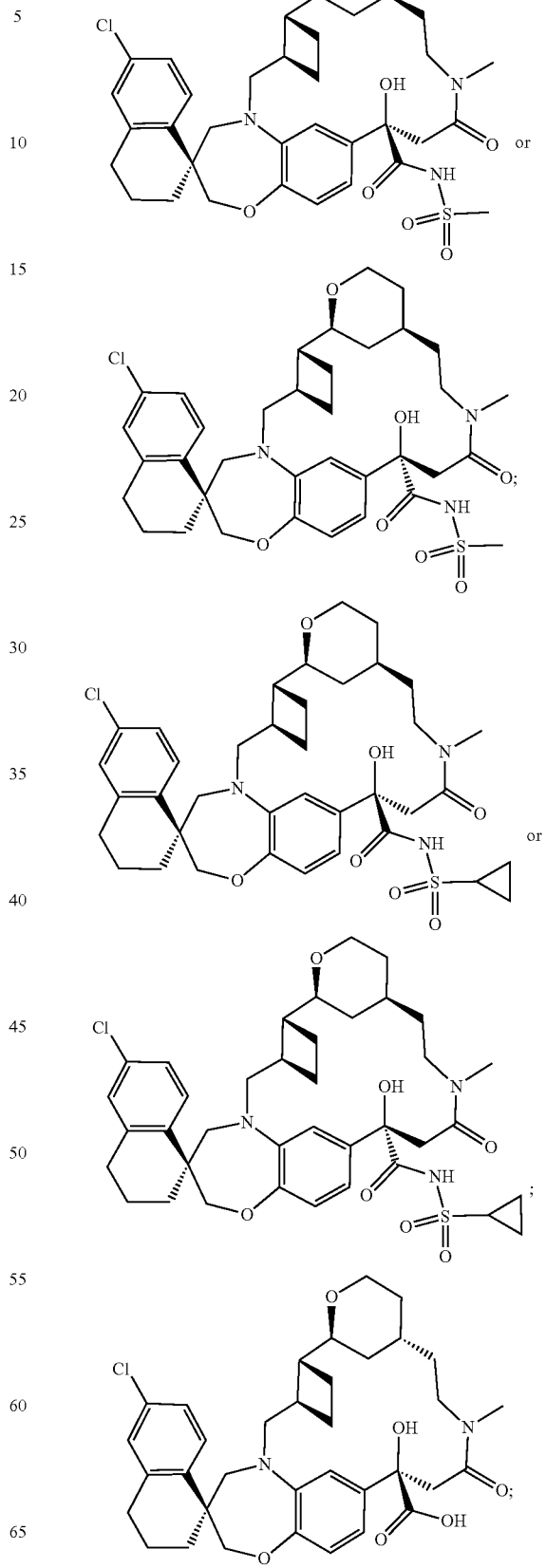

31
-continued
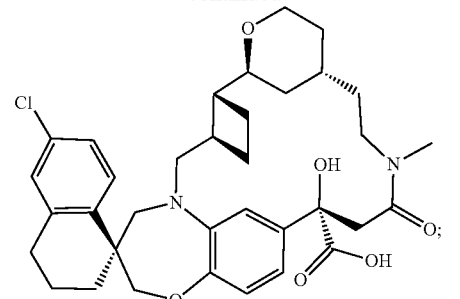
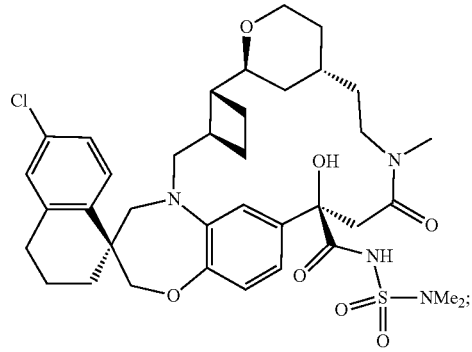
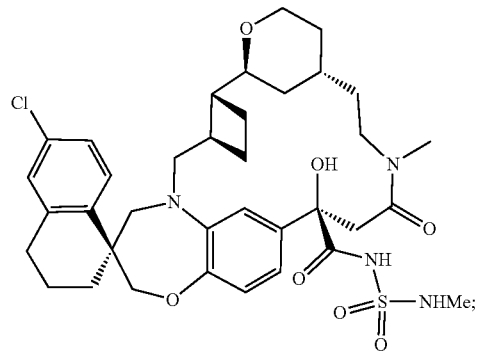
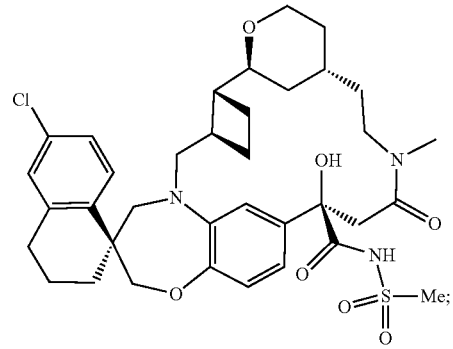
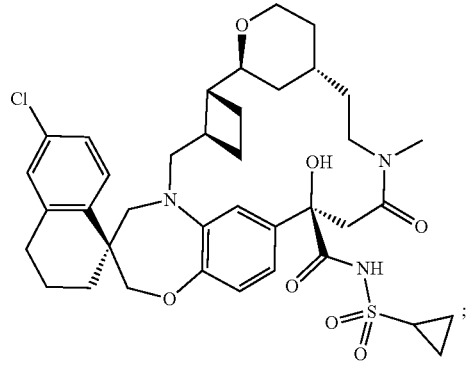
32
-continued
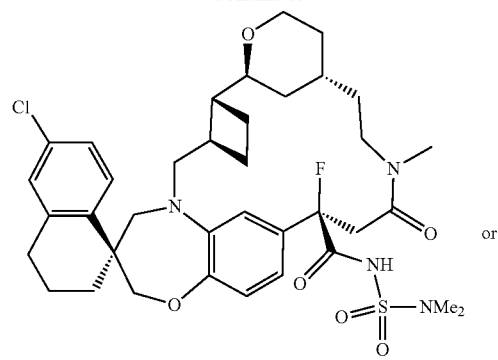
or
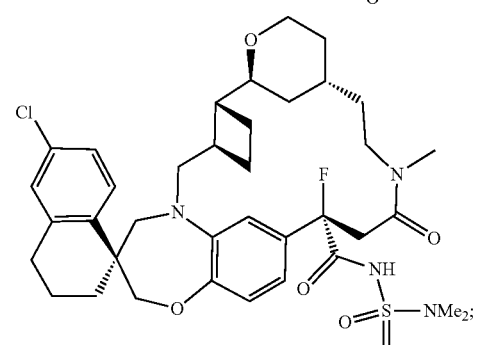
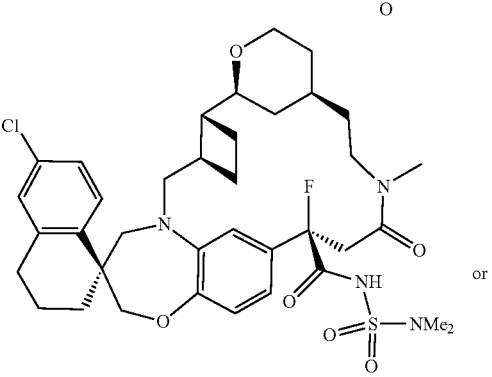
or
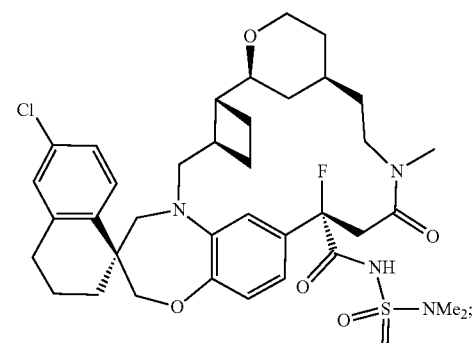
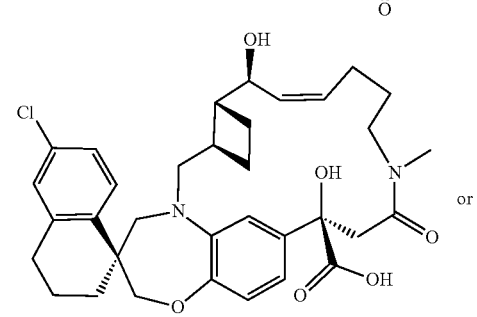
or 33
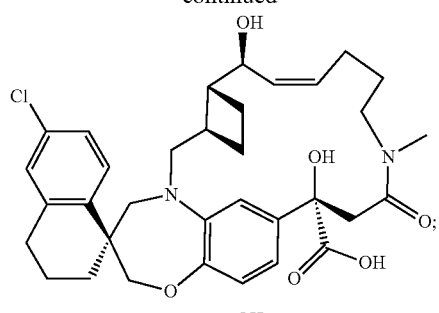
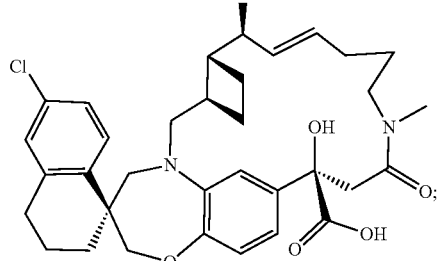
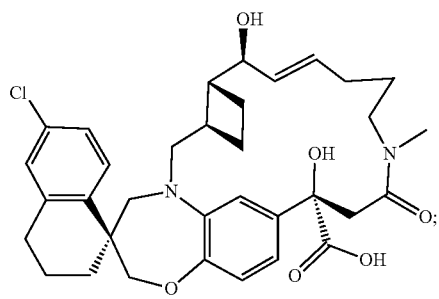
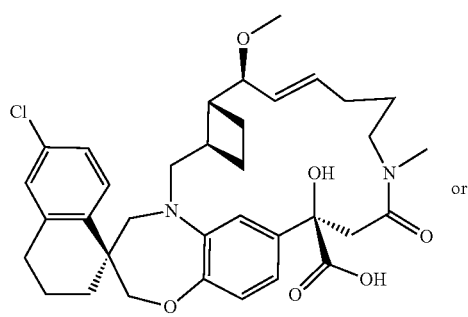
or
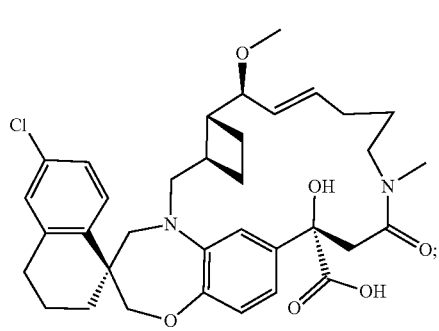
34
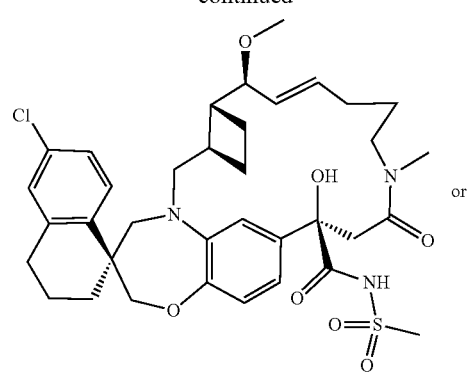
or
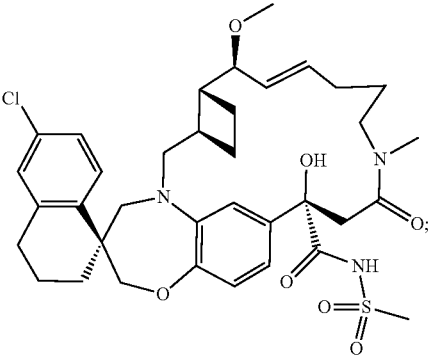
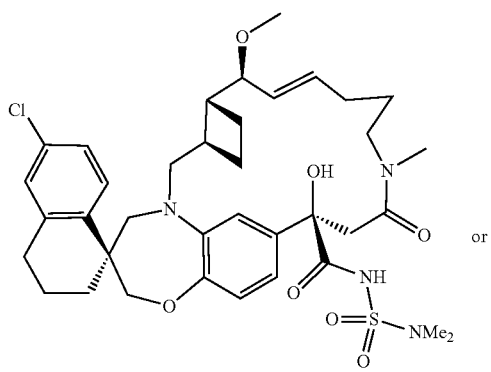
or
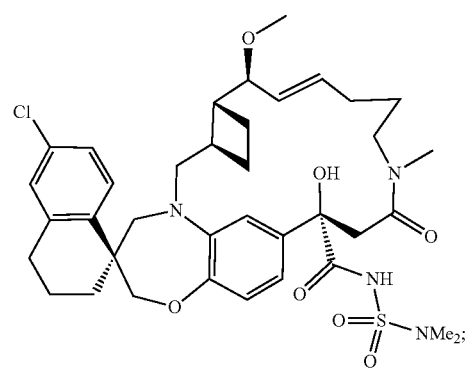

35
-continued
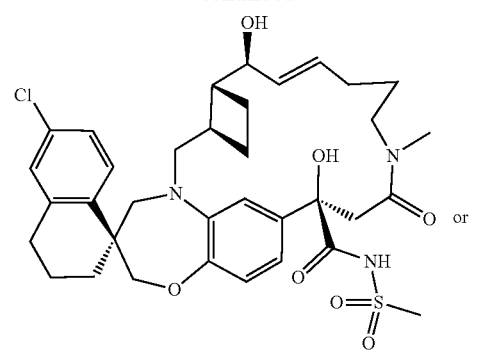
or
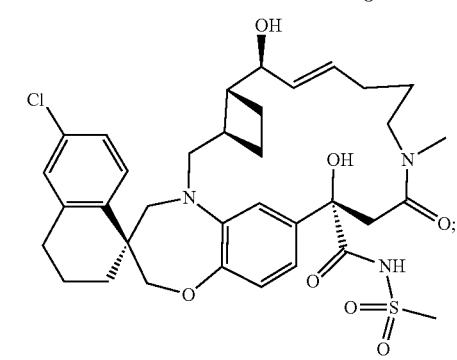
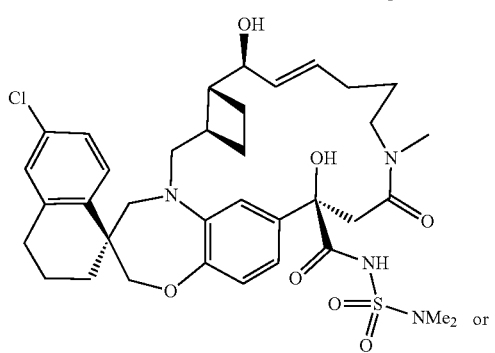
or
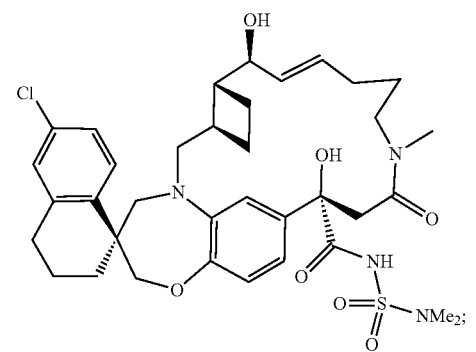
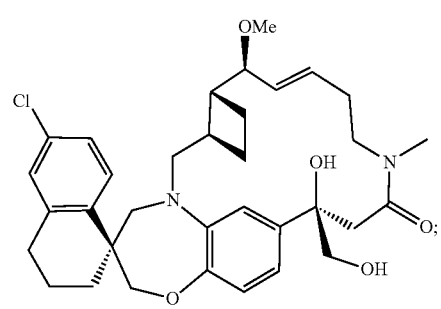
36
-continued
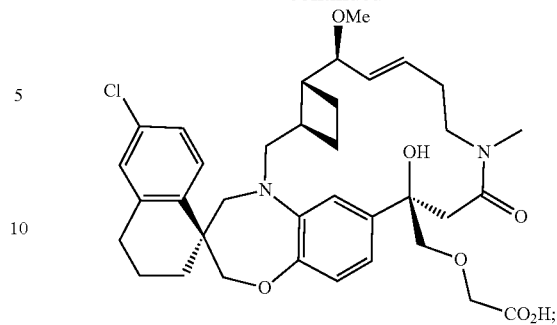
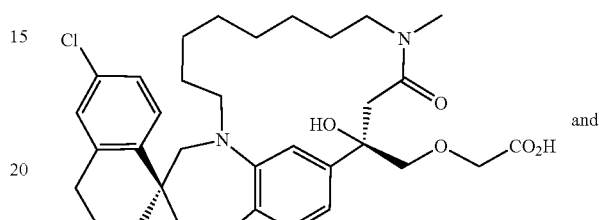
and
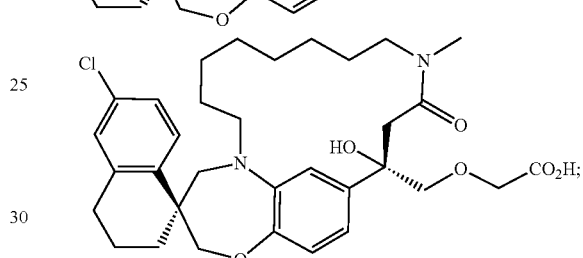
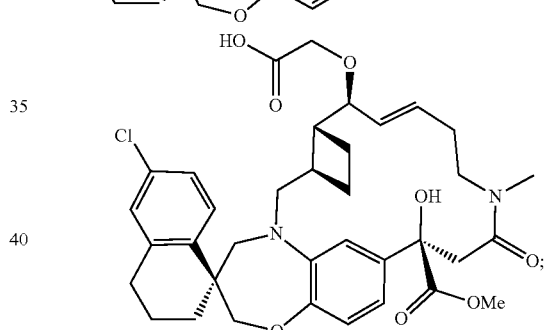
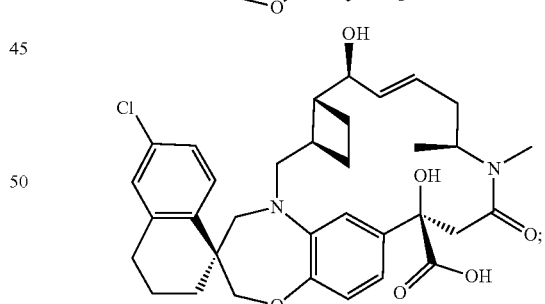
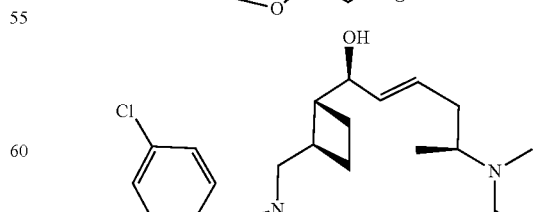
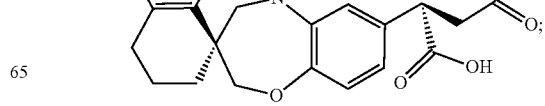

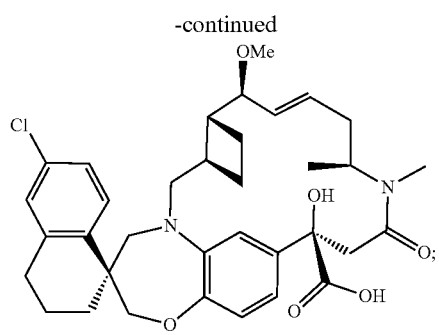
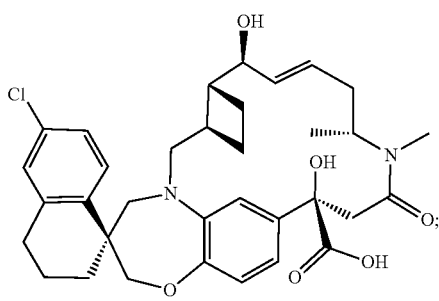
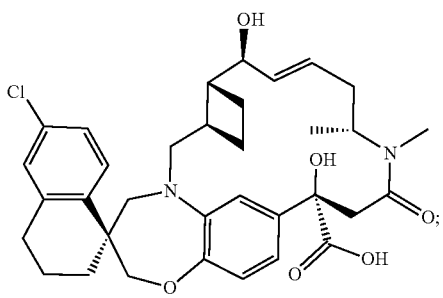
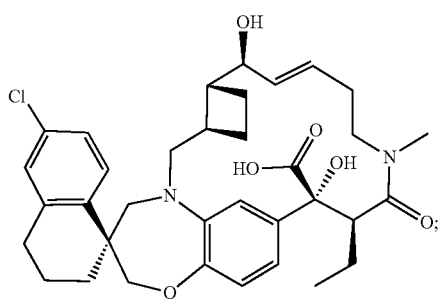
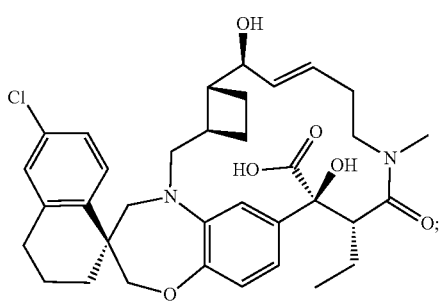
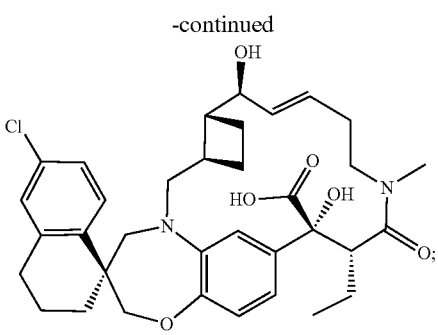
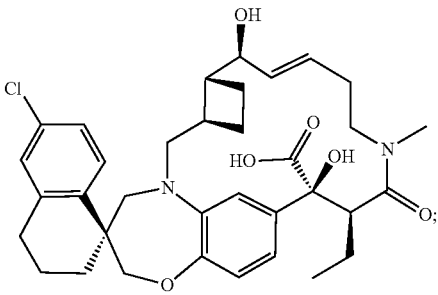
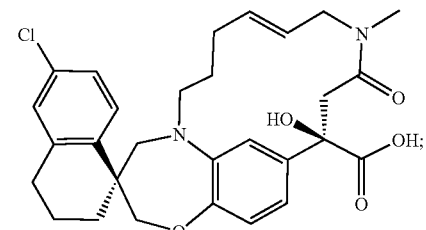
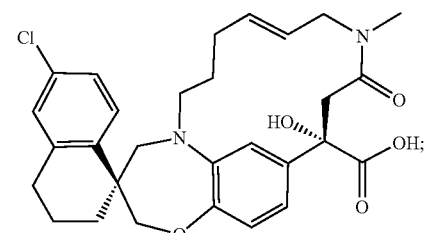
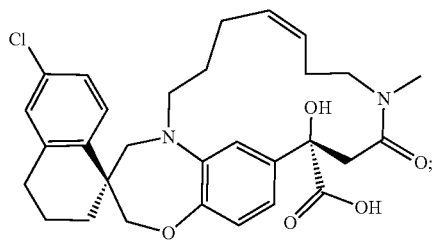
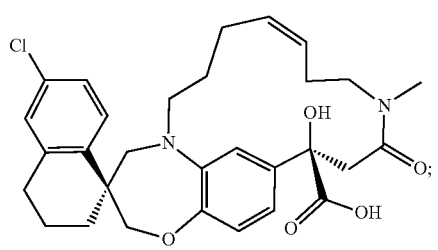

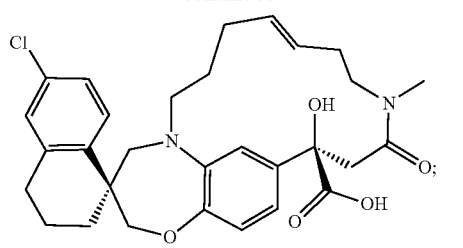
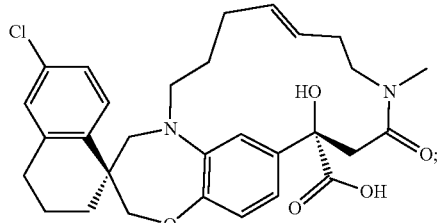
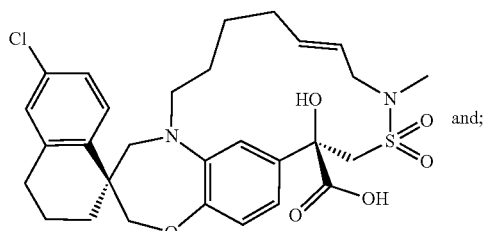 and;
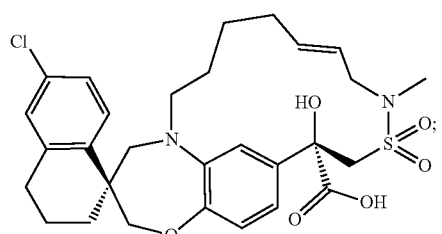
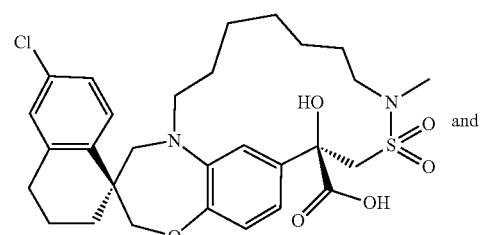 and
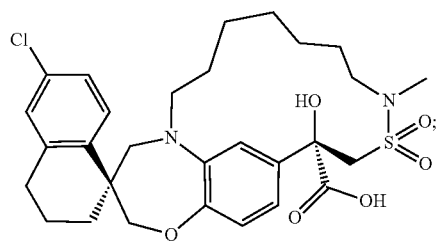
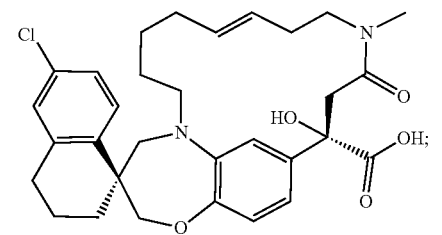
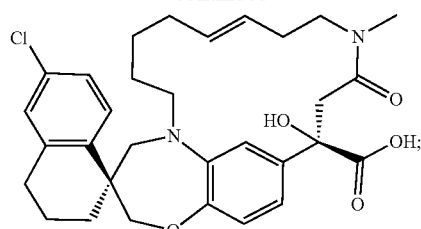
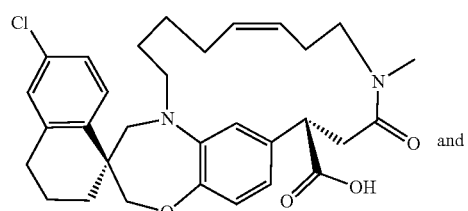 and
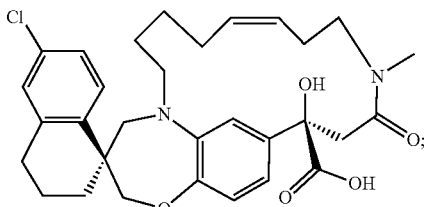
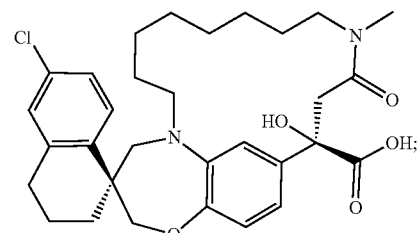
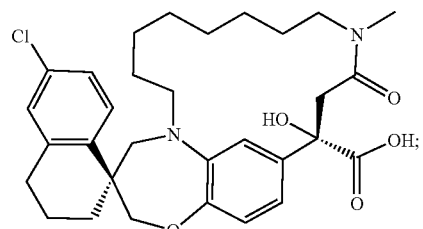
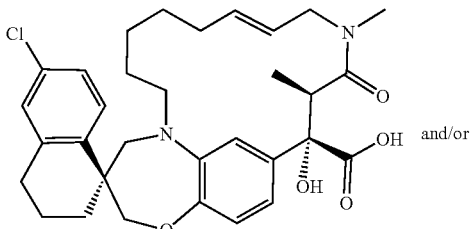 and/or
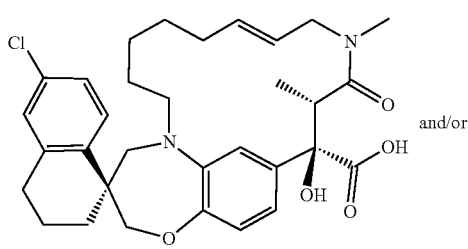 and/or

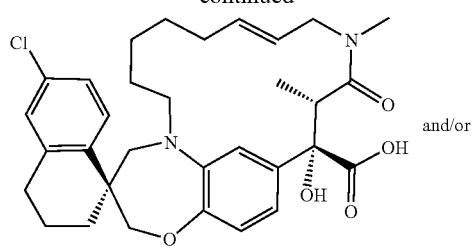
and/or
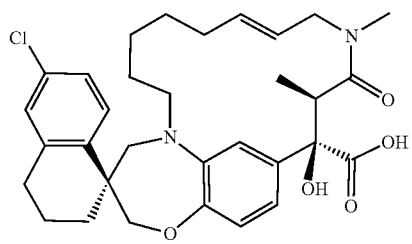
and/or
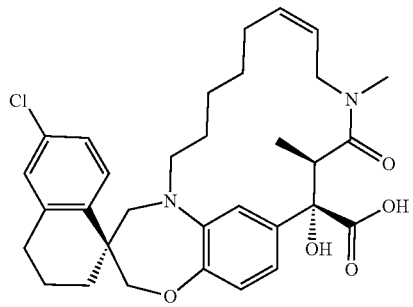
and/or
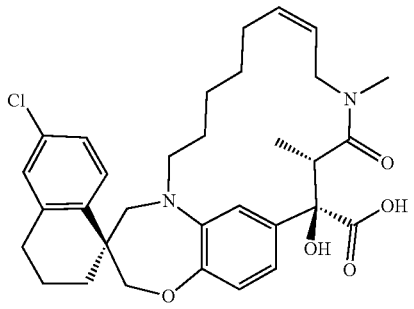
and/or
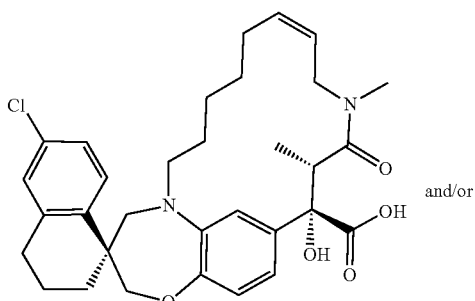
and/or
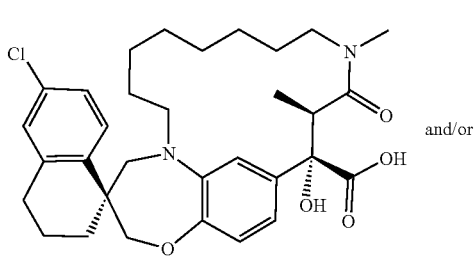
and/or
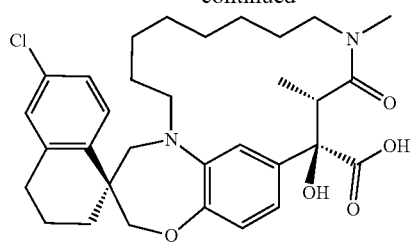
and/or
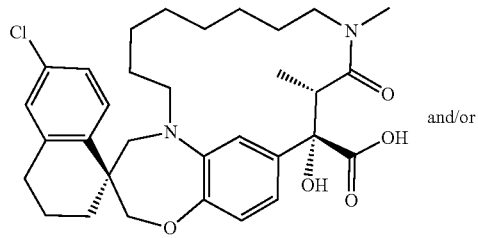
and/or
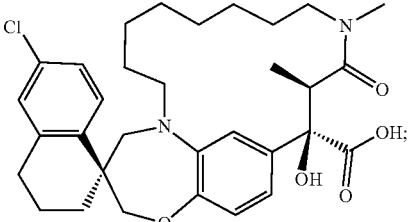
;
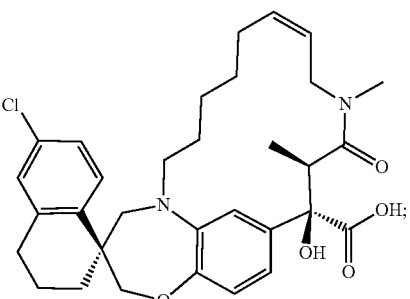
;
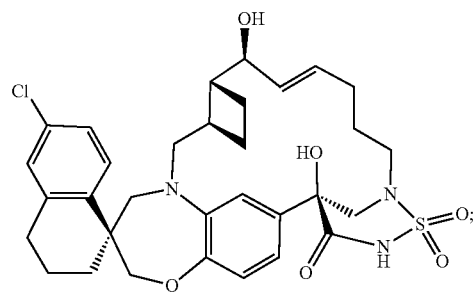
;
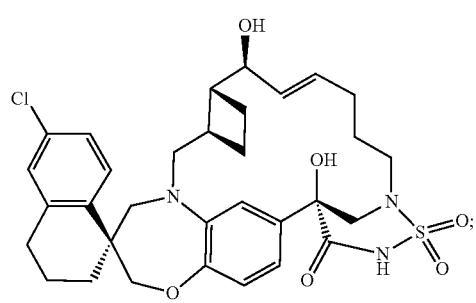
;

43
-continued
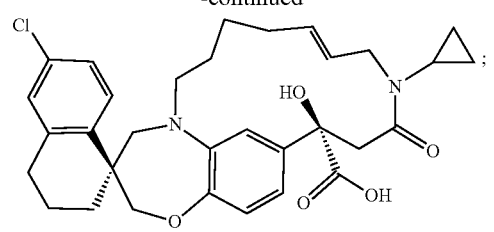
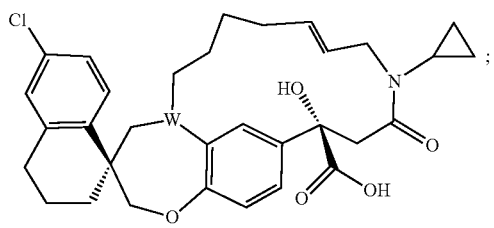
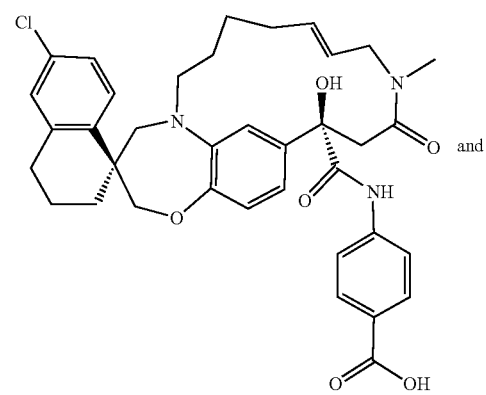
and
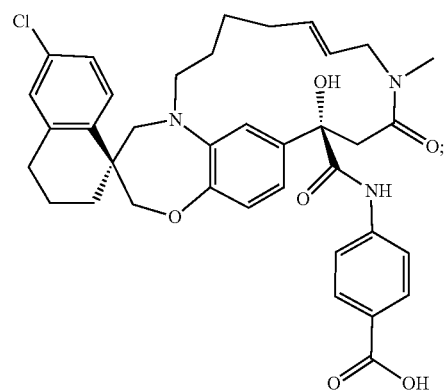
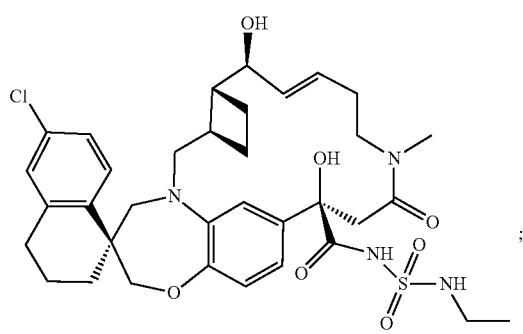
44
-continued
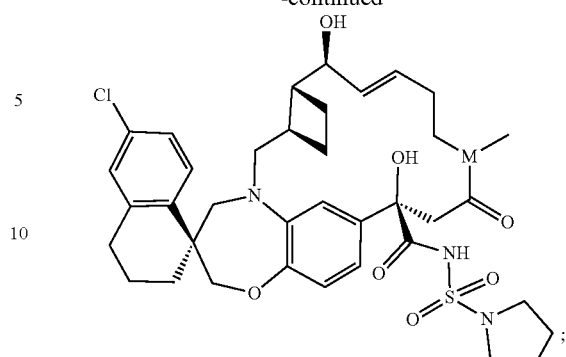
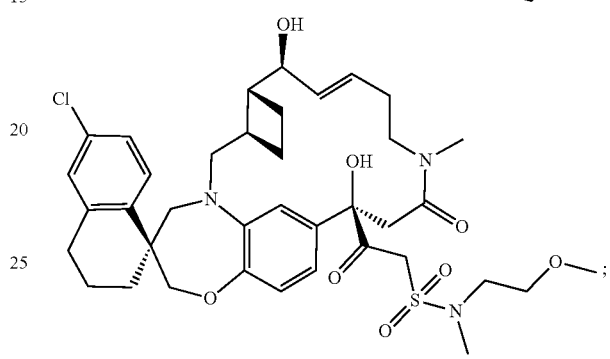
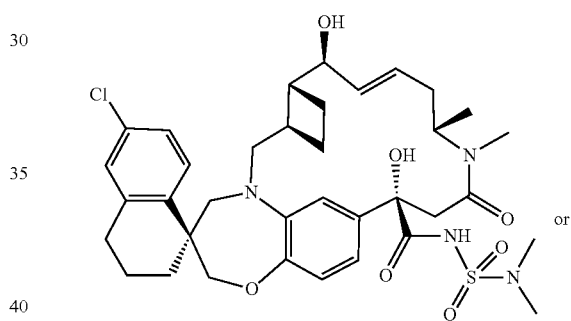
or
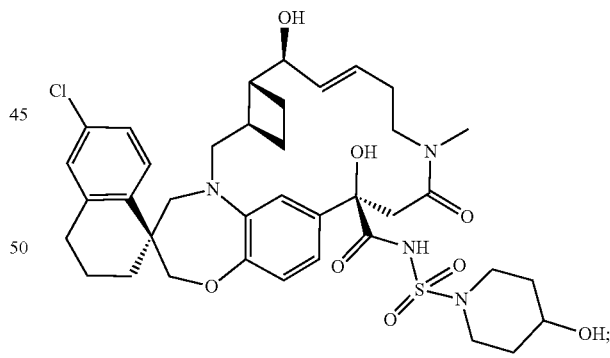
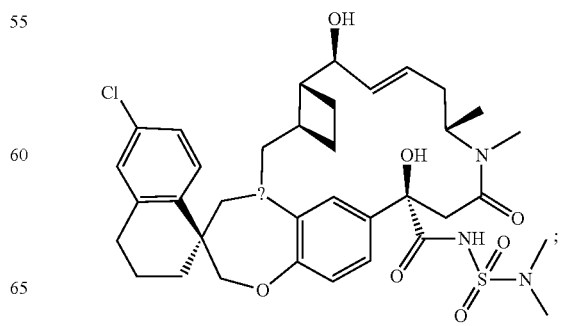

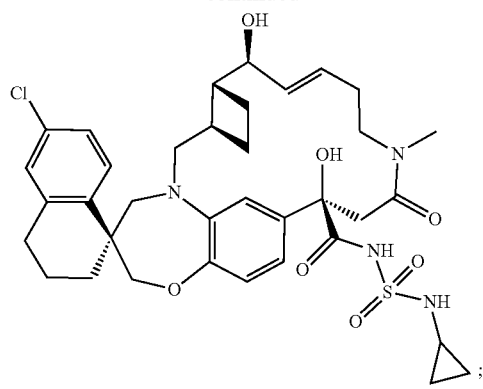
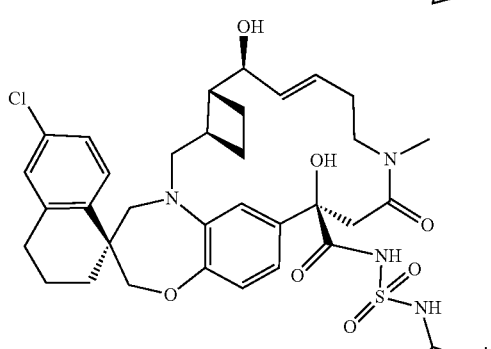
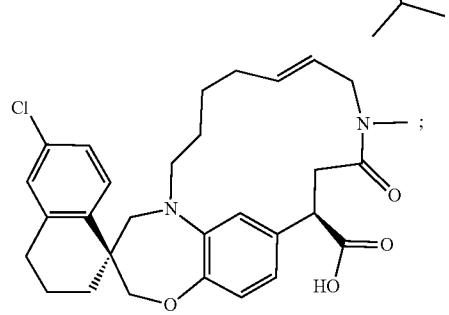
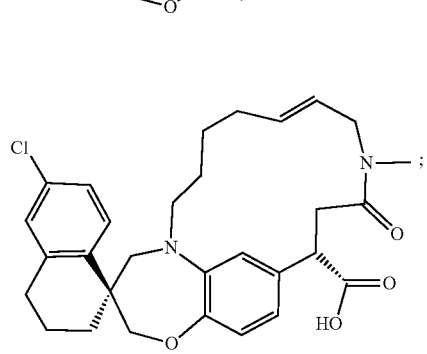

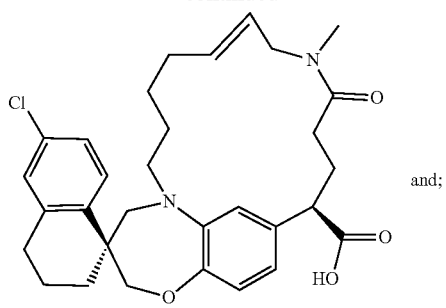
and;
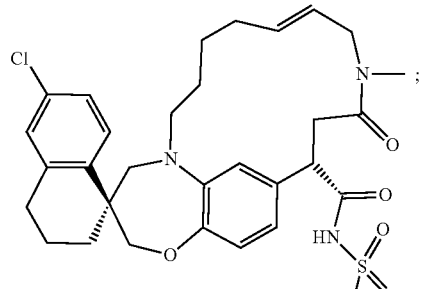
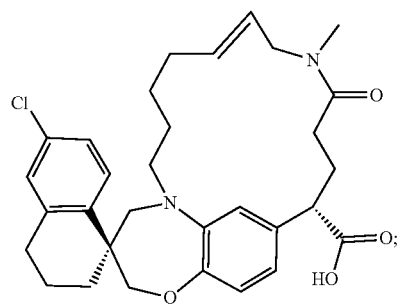
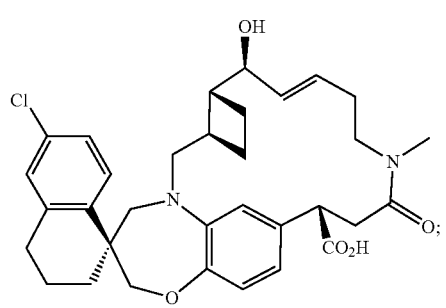
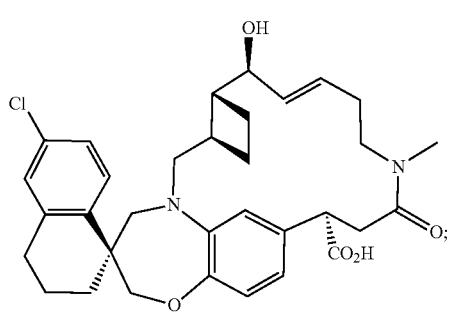
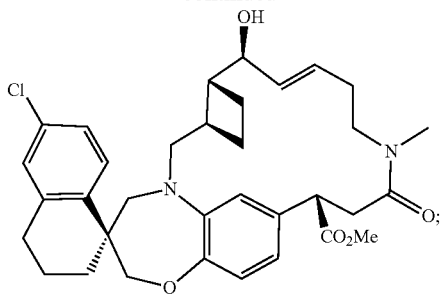
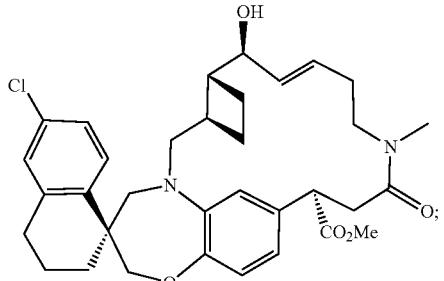
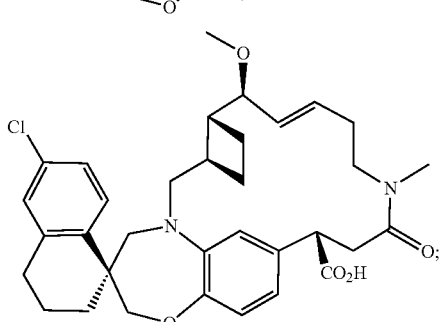
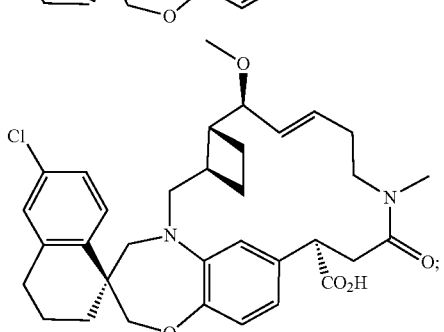
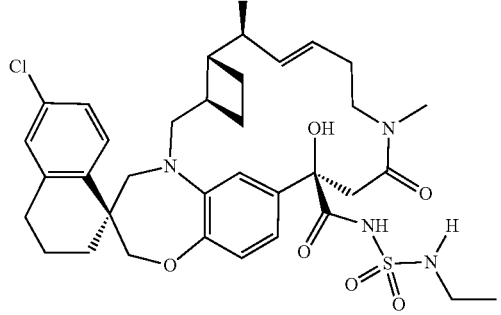

49
-continued
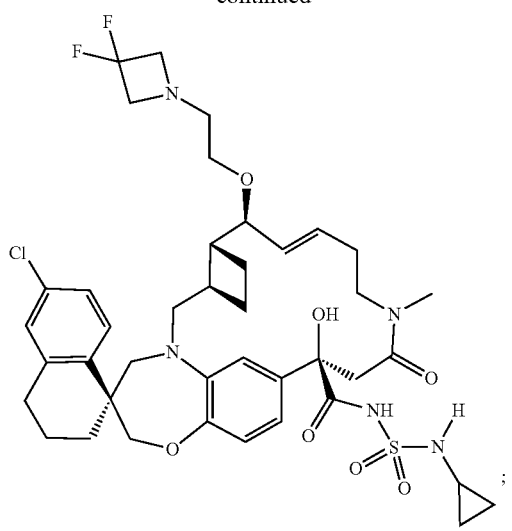
;
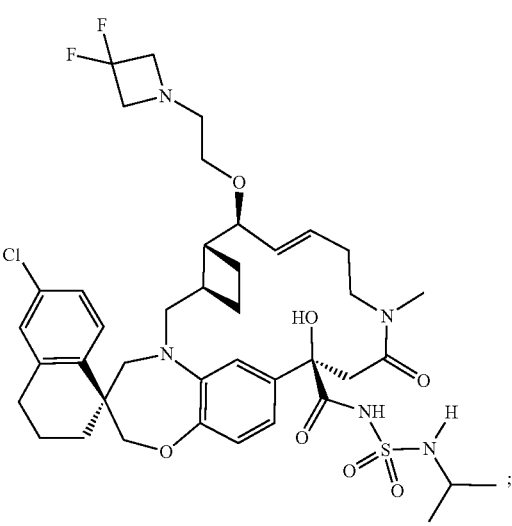
;
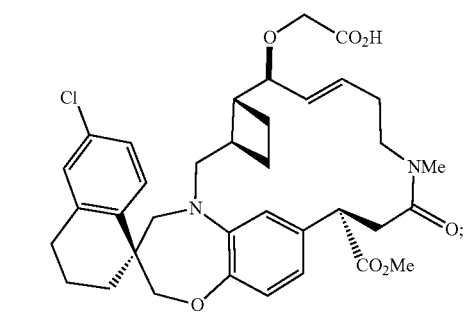
;
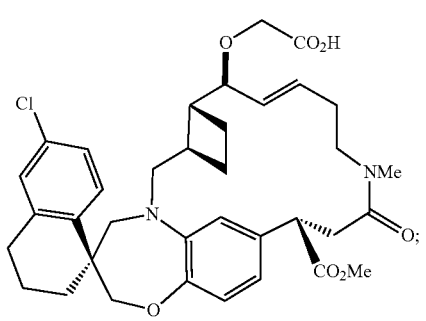
;
50
-continued
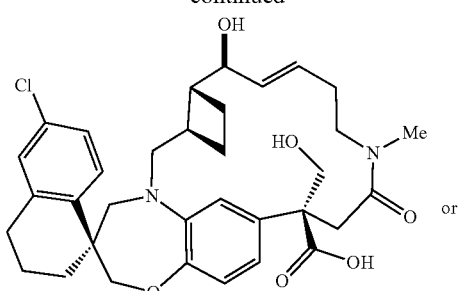
or
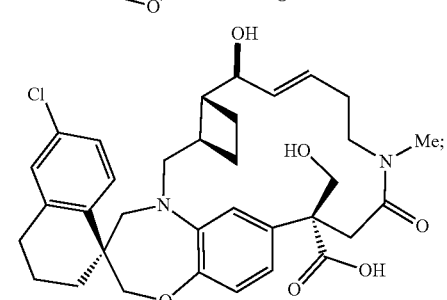
;
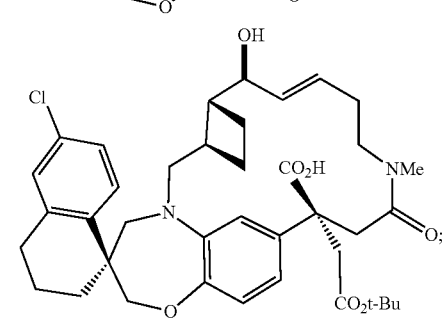
;
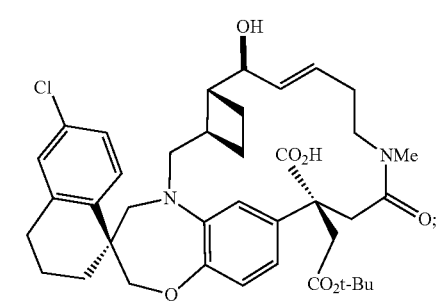
;
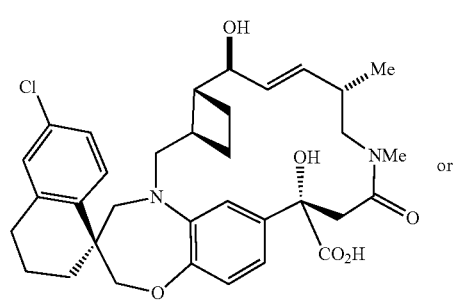
or 51
-continued
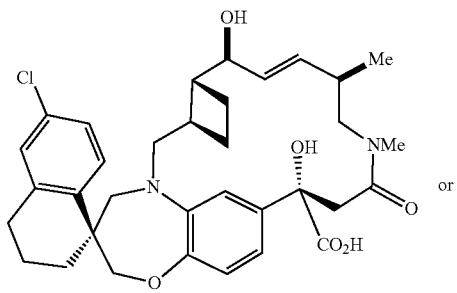
or
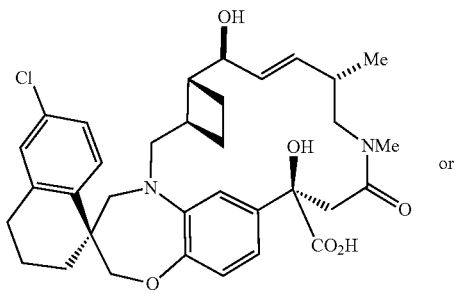
or
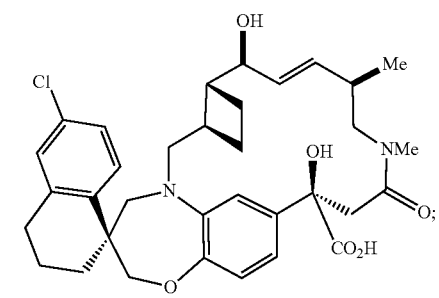
;
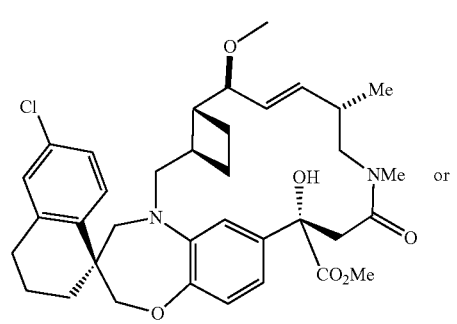
or
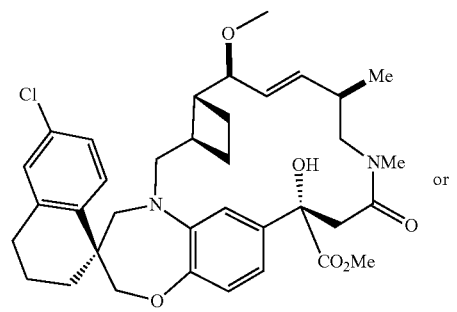
or
52
-continued
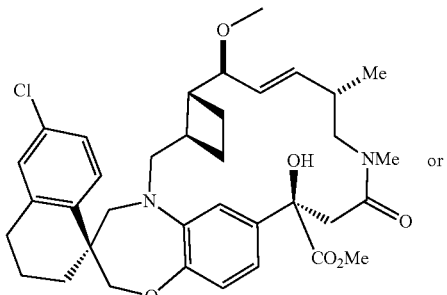
or
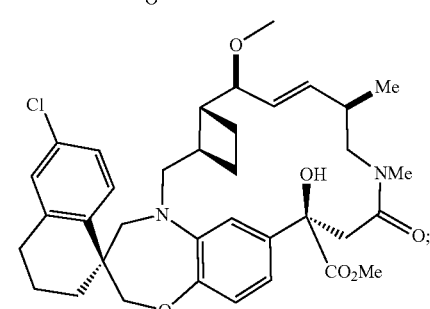
;
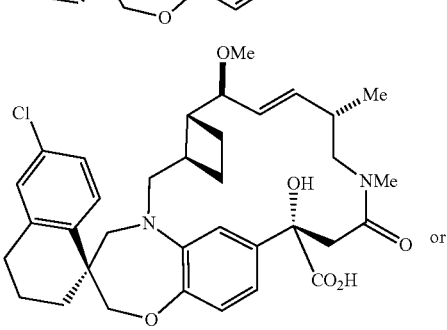
or
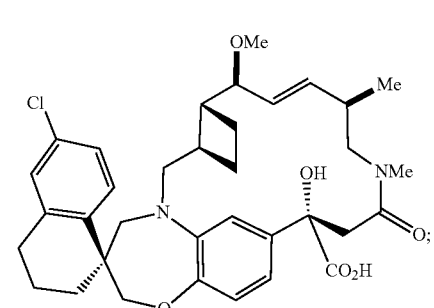
;
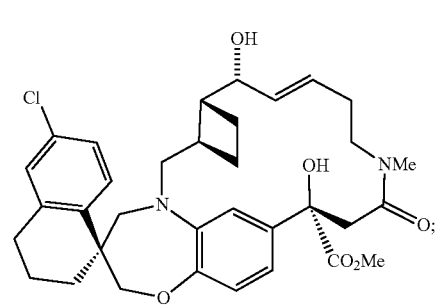
;

53
-continued
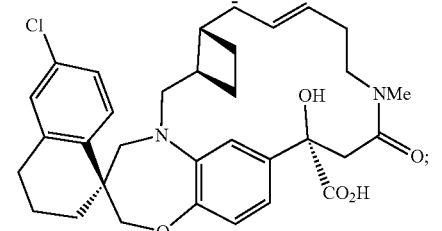
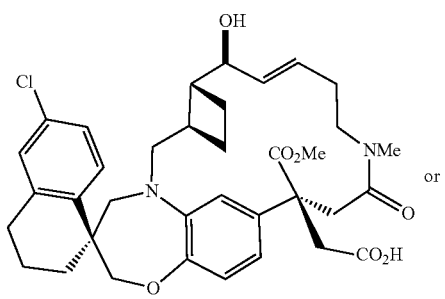
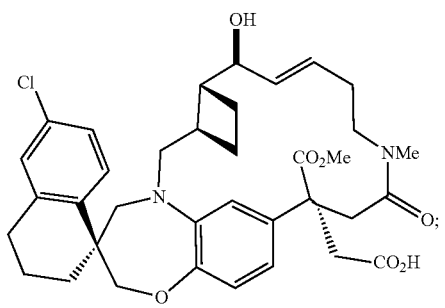
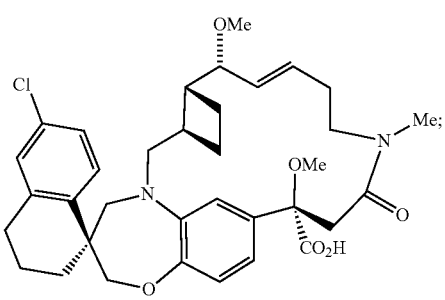
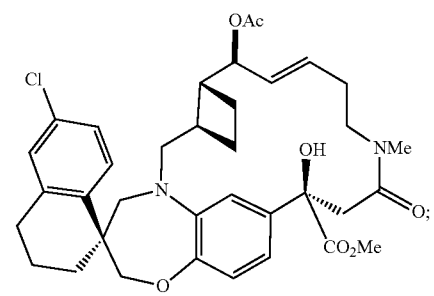
54
-continued
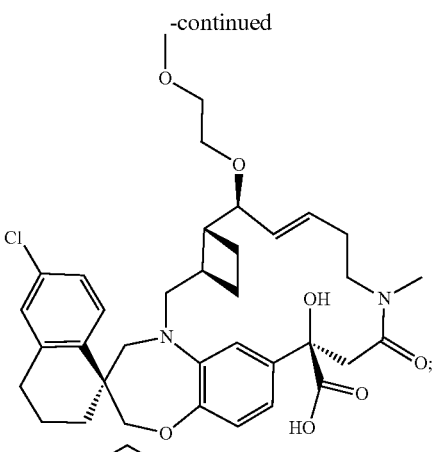
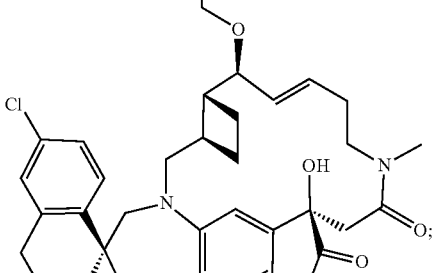
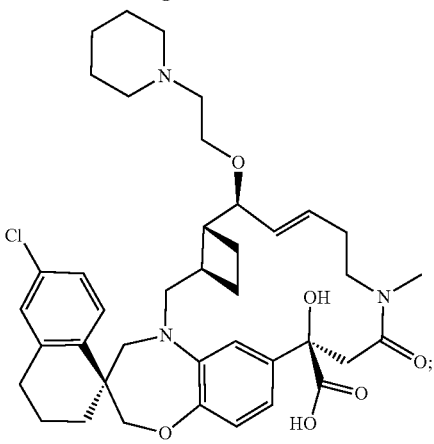
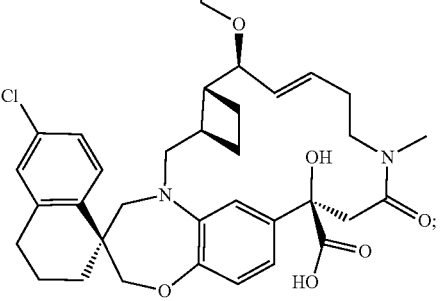

55
-continued
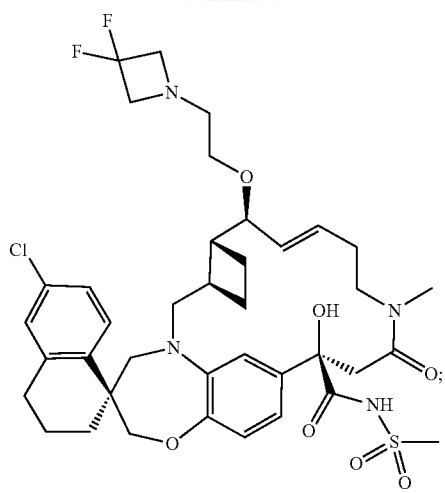
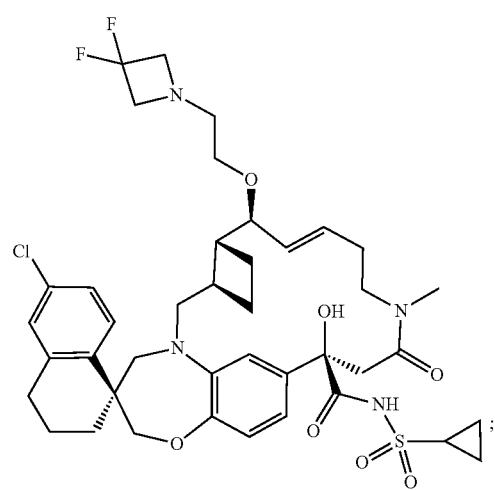
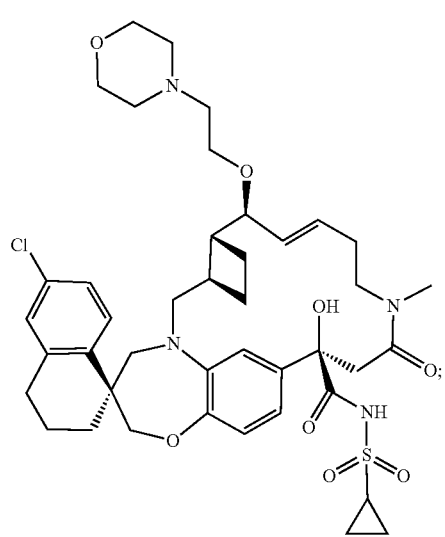
56
-continued
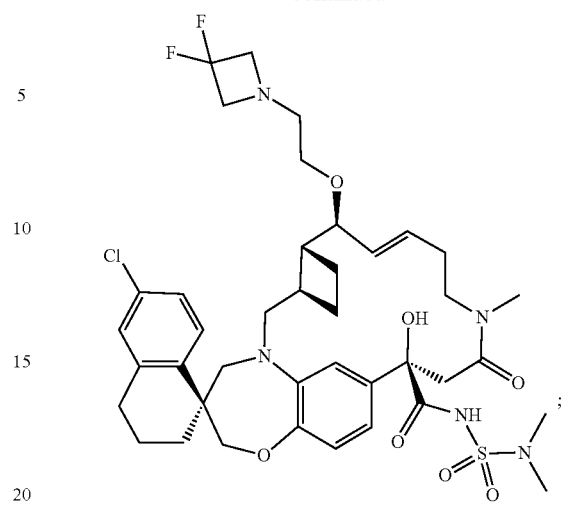
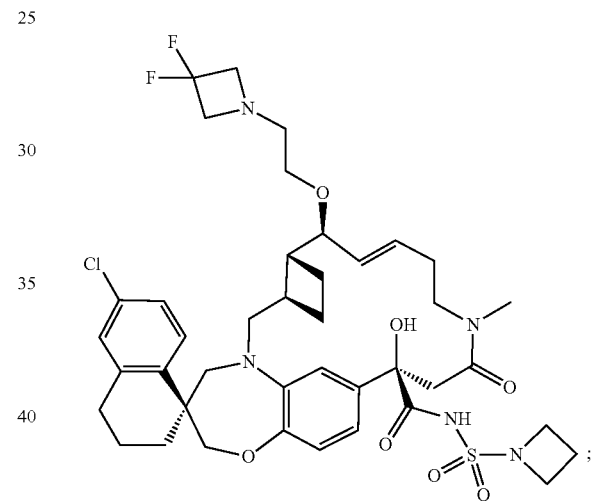
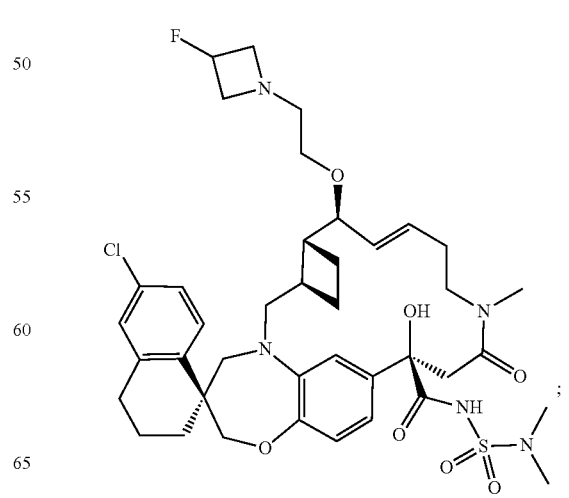

57
-continued
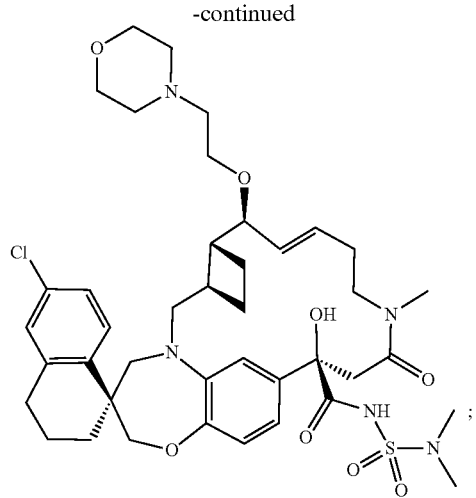
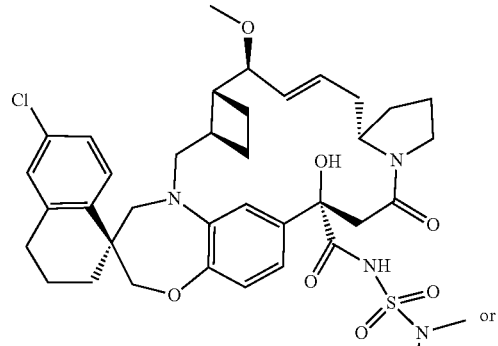
or
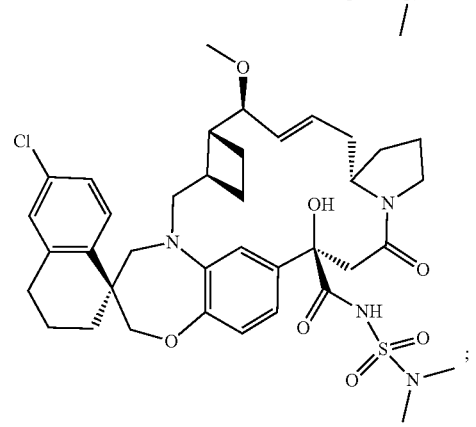
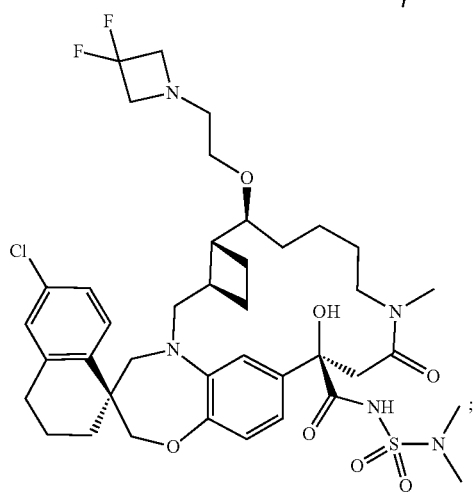
58
-continued
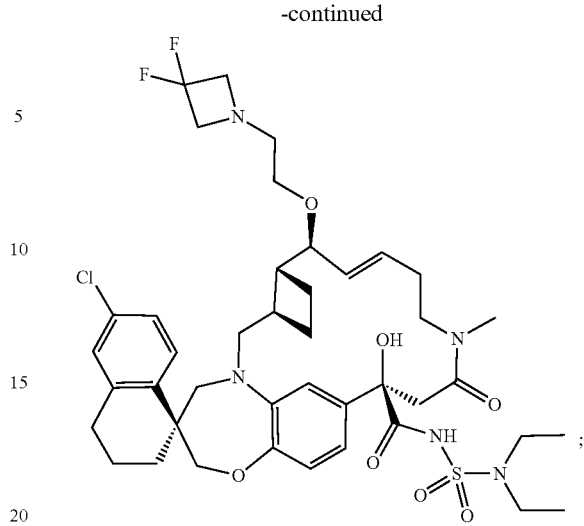
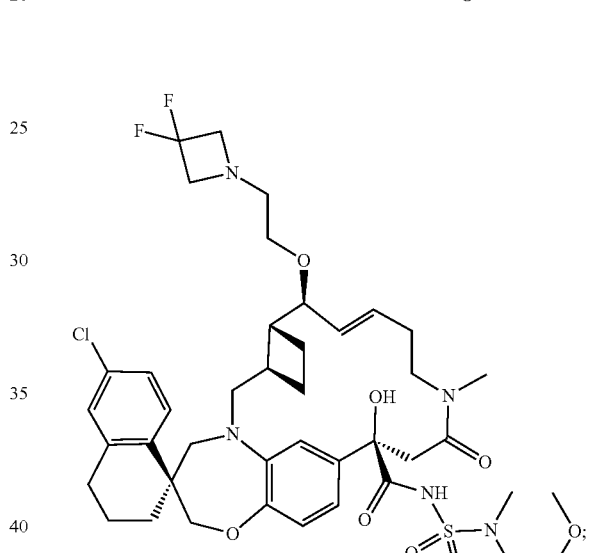
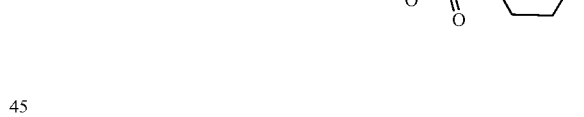
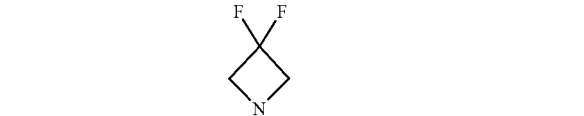
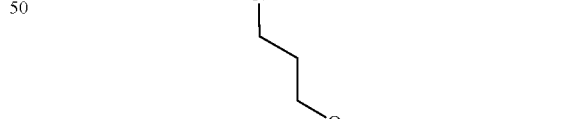
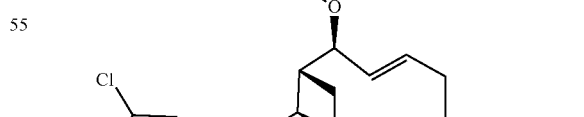
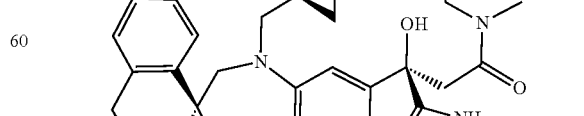
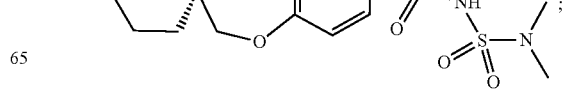

59
-continued
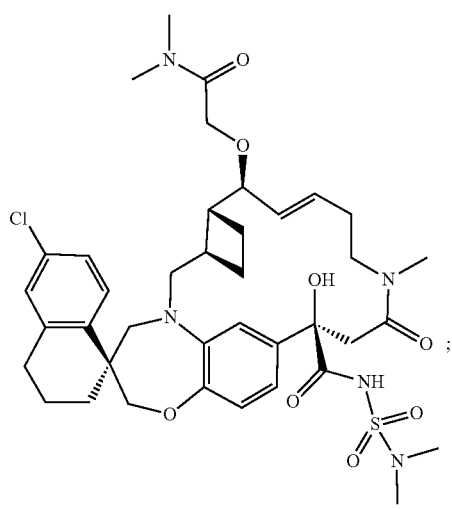
60
-continued
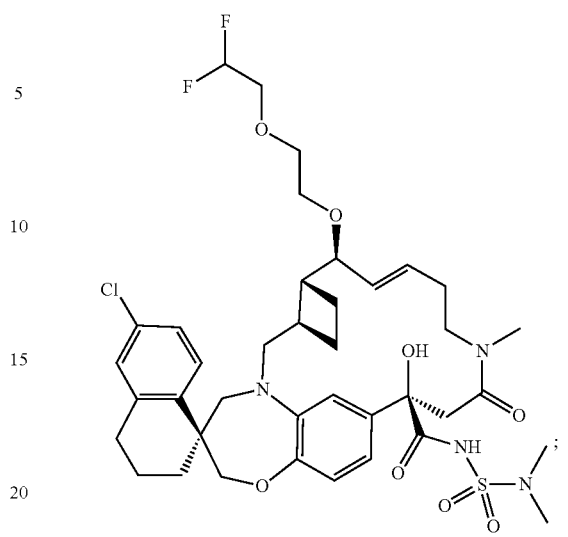
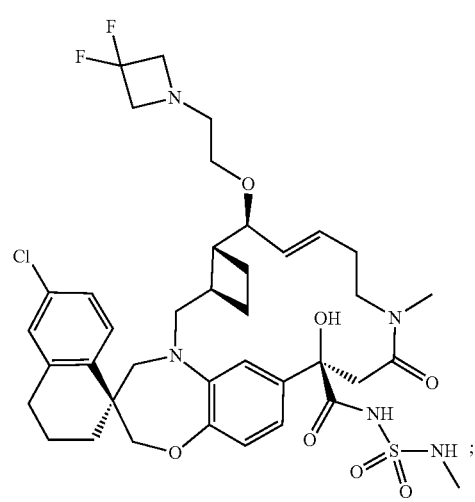
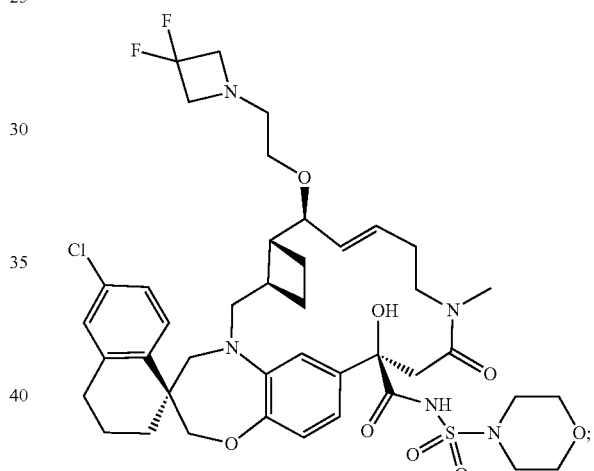
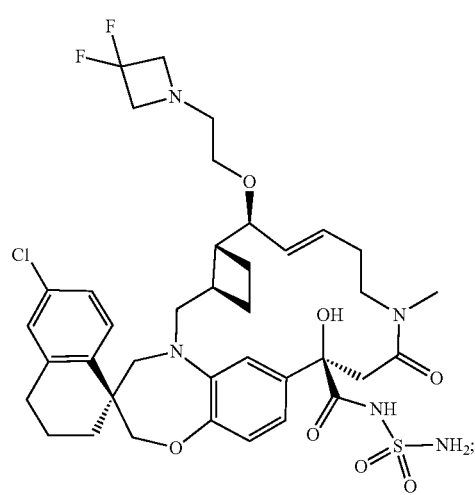
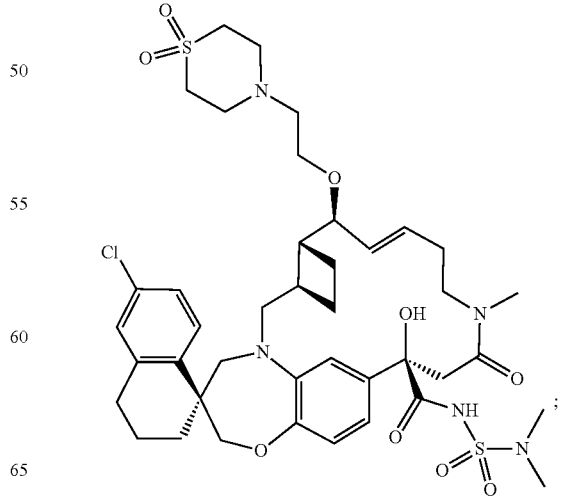

61
-continued
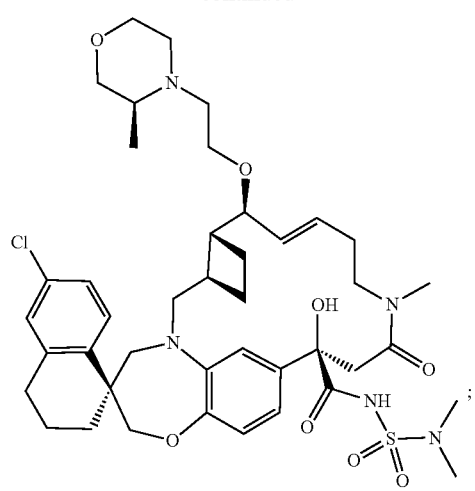
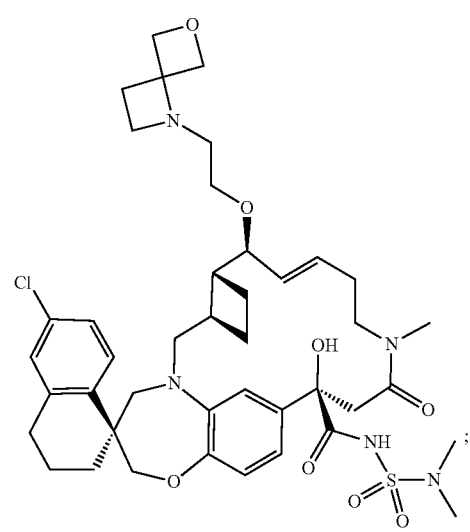
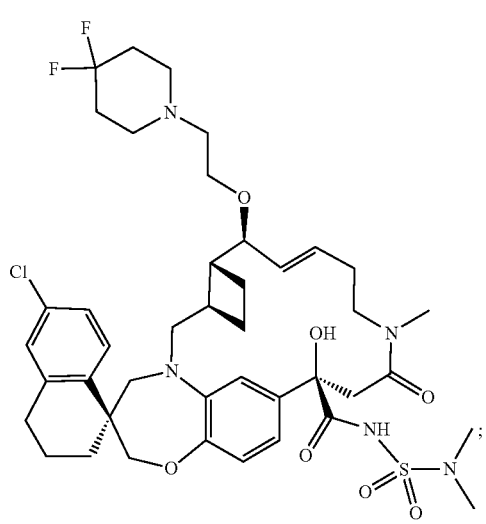
62
-continued
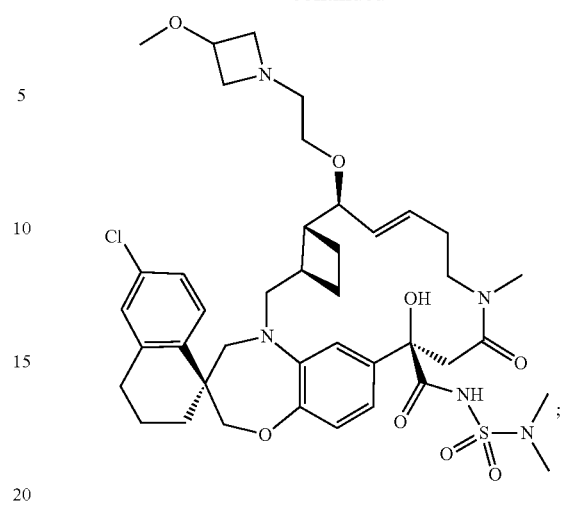
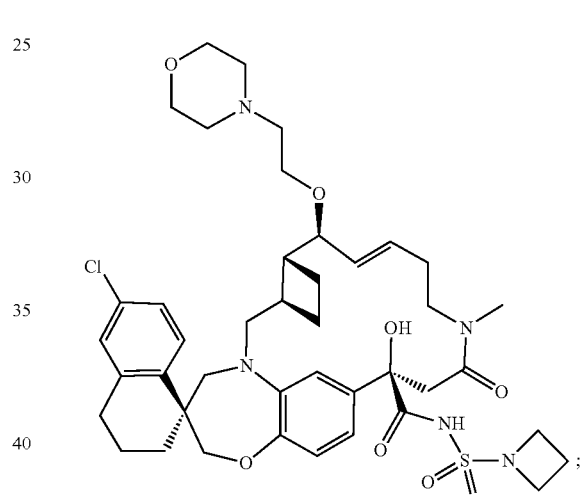
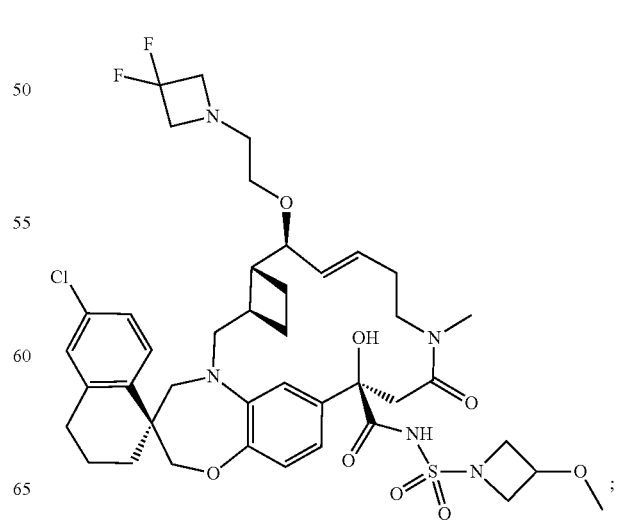

63
-continued
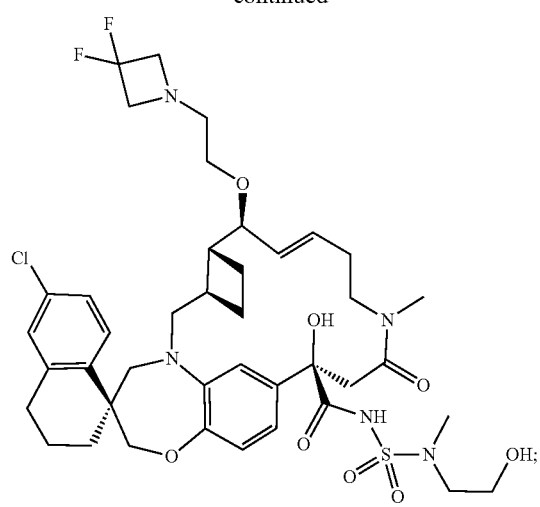
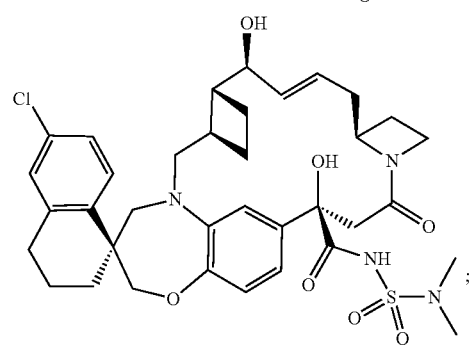
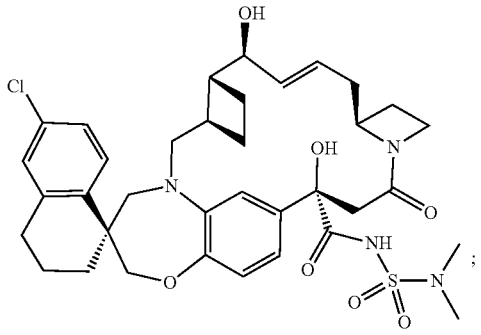
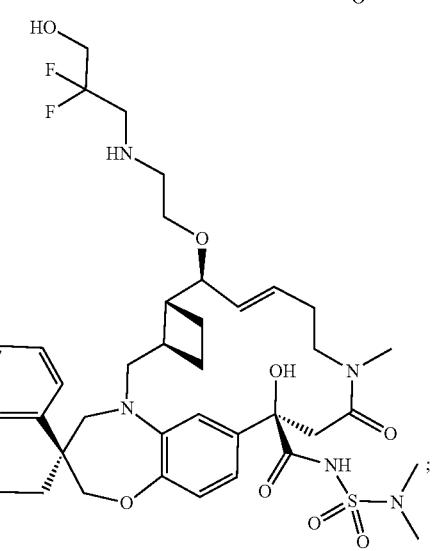
64
-continued
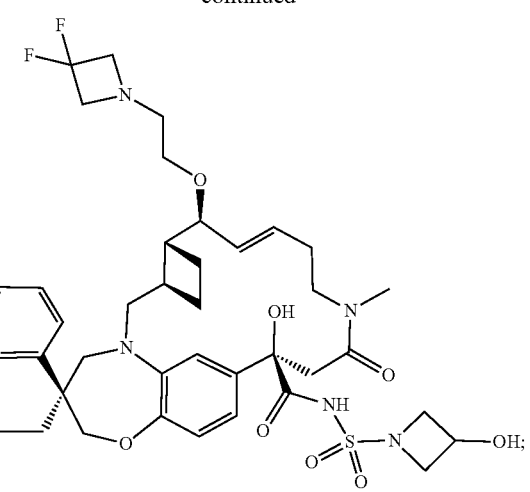
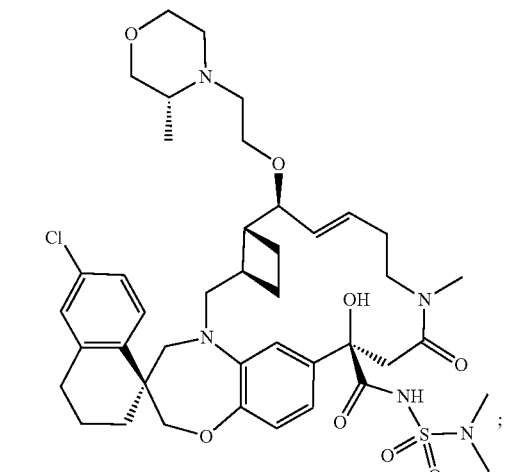
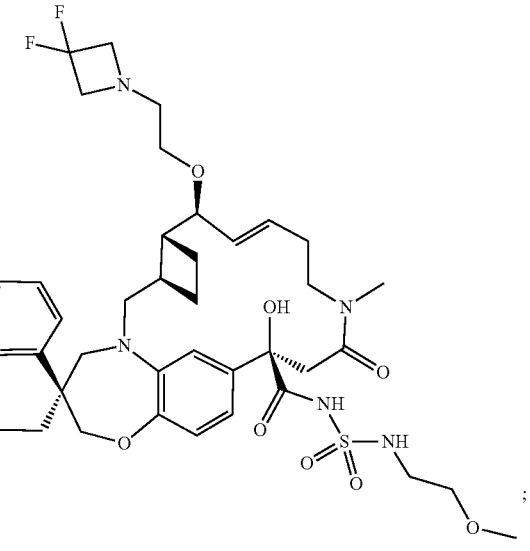

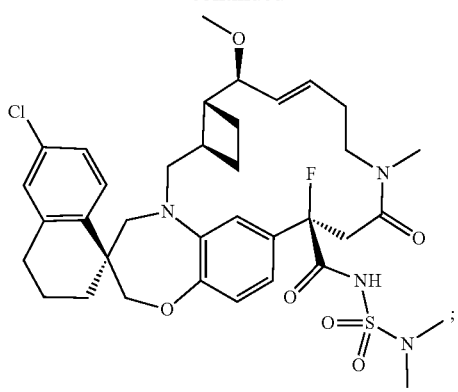
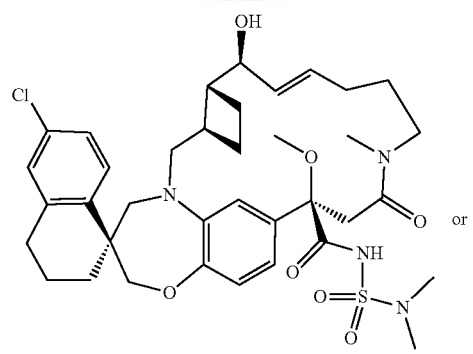
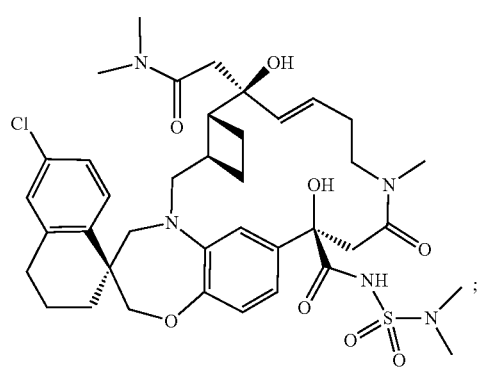
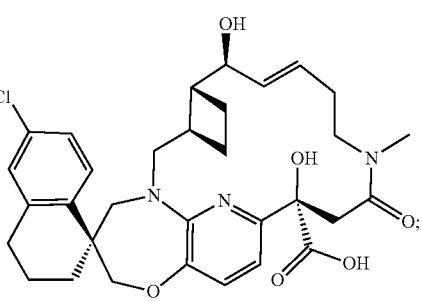
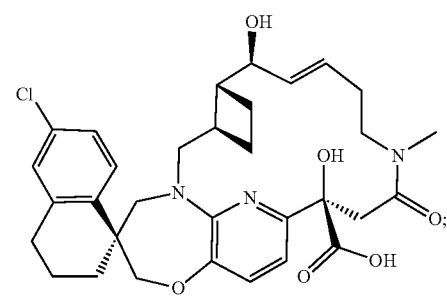

67
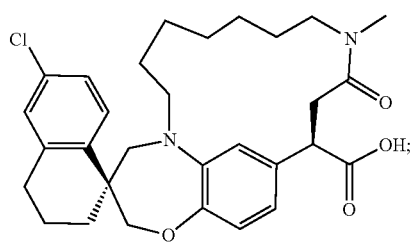
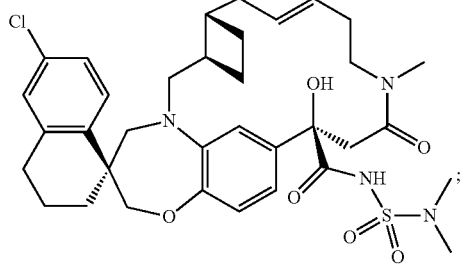
or a stereoisomer thereof, a pharmaceutically acceptable salt thereof, or a pharmaceutically acceptable salt of the stereoisomer thereof.
26. In another embodiment, the invention provides a compound, wherein the compound is selected from:
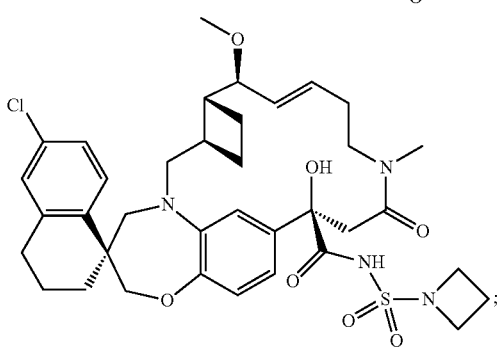
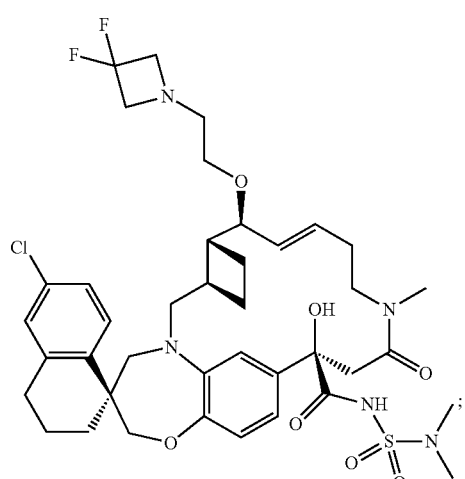
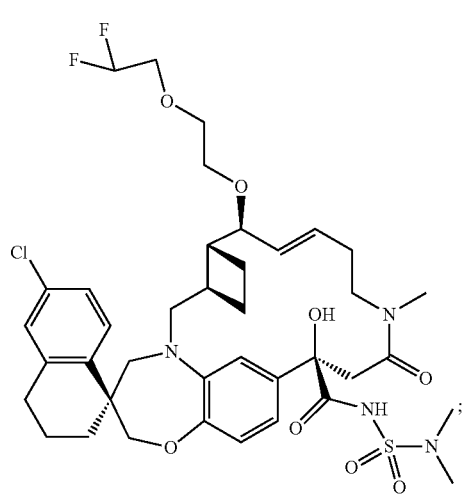
68
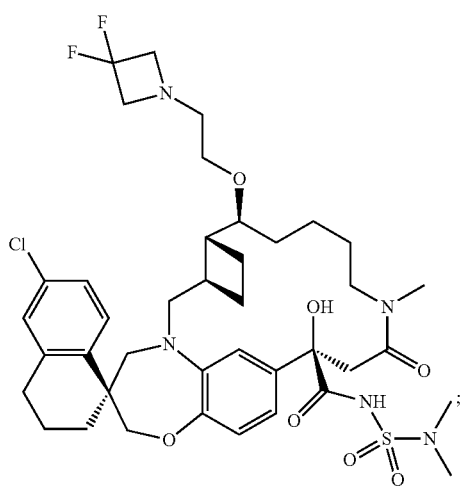
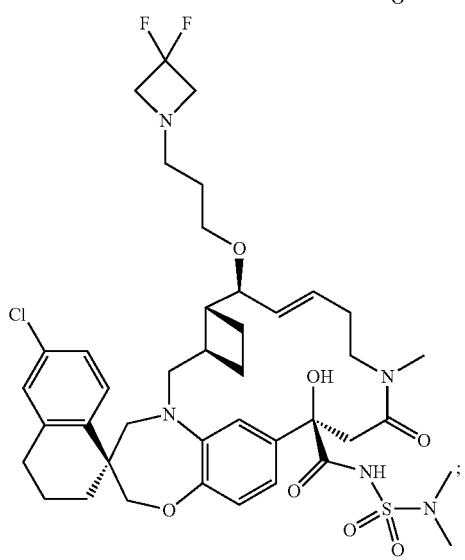

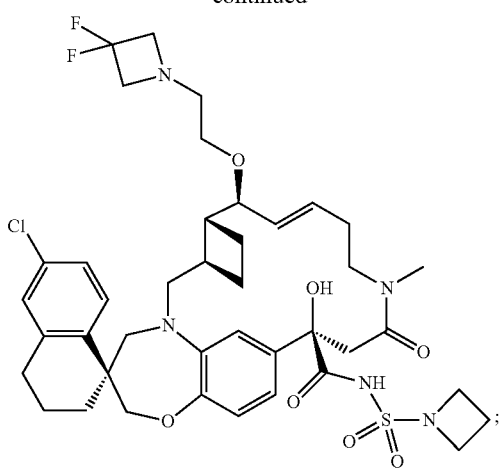

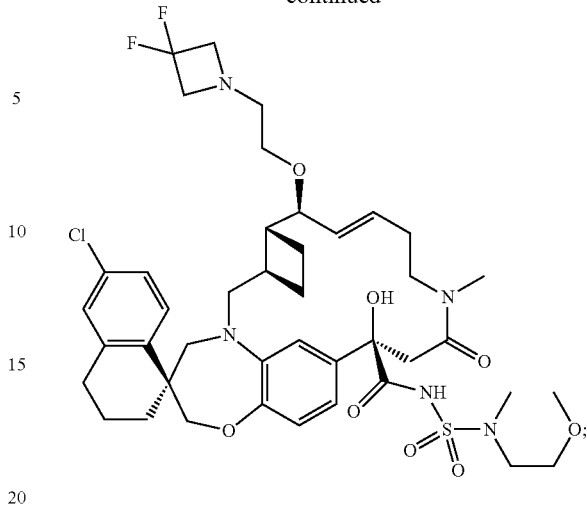

or a stereoisomer thereof, a pharmaceutically acceptable salt thereof, or a pharmaceutically acceptable salt of the stereoisomer thereof.

27. Another embodiment of the present invention provides a pharmaceutical composition comprising the compound of any one of embodiments 1, 15, 25, or 26, or the pharmaceutically acceptable salt thereof, and a pharmaceutically acceptable carrier or diluent.

28. Another embodiment of the present invention provides a method of treating cancer, the method comprising administering to a patient in need thereof a therapeutically effective amount of the compound of any of embodiments 1-27 or the pharmaceutically acceptable salt thereof.

29. In another embodiment, the invention provides the method of embodiment 28, wherein the cancer is a hematologic malignancy.

30. In another embodiment, the invention provides the method of embodiment 28, wherein the cancer is selected from the group consisting of breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia.

31. In another embodiment, the invention provides the method of embodiment 30, wherein the cancer is lung cancer.

32. In another embodiment, the invention provides the method of embodiment 30, wherein the cancer is multiple myeloma.

33. In another embodiment, the invention provides the method of embodiment 28, further comprising administering to the patient in need thereof a therapeutically effective amount of an additional pharmaceutically active compound.

34. In another embodiment, the invention provides the method of embodiment 33, wherein the additional pharmaceutically active compound is carfilzomib.

35. In another embodiment, the invention provides the method of embodiment 33, wherein the additional pharmaceutically active compound is venetoclax.

36. In another embodiment, the invention provides the method of embodiment 33, wherein the additional pharmaceutically active compound is cytarabine.

37. In another embodiment, the invention provides the use of a compound according to any one of embodiments 1-28 for treating cancer in a subject.

38. In another embodiment, the invention provides the use of a compound according to any one of embodiments 1-28 in the preparation of a medicament for treating cancer.

39. In another embodiment, the invention provides the use of a compound according to embodiment 38, wherein the cancer is a hematologic malignancy.

40. In another embodiment, the invention provides the use of a compound according to embodiment 38, wherein the cancer is selected from the group consisting of breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia.

41. In another embodiment, the invention provides the use of a compound according to embodiment 38, wherein the cancer is multiple myeloma.

42. In another embodiment, the invention provides the use of a compound according to embodiment 38, wherein the cancer is acute myelogenous leukemia.

43. In another embodiment, the invention provides the use of a compound according to embodiment 38, wherein the cancer is non-Hodgkin's lymphoma.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the Claims.

DETAILED DESCRIPTION

The symbol "—" represents a covalent bond and can also be used in a radical group to indicate the point of attachment to another group. In chemical structures, the symbol — is commonly used to represent a methyl group in a molecule.

As used herein chemical structures which contain one or more stereocenters depicted with dashed and bold bonds (i.e., ⋯⋯ and ▬ ) are meant to indicate absolute stereochemistry of the stereocenter(s) present in the chemical structure. As used herein, bonds symbolized by a simple line do not indicate a stereo-preference. Unless otherwise indicated to the contrary, chemical structures that include one or more stereocenters which are illustrated herein without indicating absolute or relative stereochemistry encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers.

As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$ alkyl.

The term "compound", as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g., hydrates and solvates).

The term "cycloalkyl" means a cyclic, nonaromatic hydrocarbon. Representative examples of cycloalkyl groups include cyclopropyl, cyclobutyl, cyclopentyl, cyclohexyl and cycloheptyl. A cycloalkyl group can contain one or more double bonds. Representative examples of cycloalkyl groups that contain double bonds include cyclopentenyl, cyclohexenyl, cyclohexadienyl and cyclobutadienyl. Common cycloalkyl groups are $C_{3-8}$ cycloalkyl groups.

The term "excipient", as used herein, means any pharmaceutically acceptable additive, carrier, diluent, adjuvant or other ingredient, other than the active pharmaceutical ingredient (API), which is typically included for formulation and/or administration to a patient. Handbook of Pharmaceutical Excipients, 5$^{th}$ Edition, R. C. Rowe, P. J. Sheskey, and S. C. Owen, editors, Pharmaceutical Press, 2005, Hardback, 928, 0853696187.

For the terms "for example" and "such as" and grammatical equivalences thereof, the phrase "and without limitation" is understood to follow unless explicitly stated otherwise.

The term "halogen" or "halo" means F, Cl, Br or I.

The term "patient" means subjects including animals, such as dogs, cats, cows, horses, sheep and humans. Particular patients are mammals. The term patient includes males and females.

The term "patient in need" means a patient having, or at risk of having, one or more diseases or conditions where the Mcl-1 protein is involved, such as cancers. Identifying a patient in need can be in the judgment of a subject or a health care professional and can be subjective (e.g., opinion) or objective (e.g., measurable by a test or diagnostic method).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The term "pharmaceutically acceptable" is employed herein to refer to those ligands, materials, compositions, and/or dosage forms which are, within the scope of sound medical judgment, suitable for administration to a patient, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain Claims, pharmaceutical compositions provided herein are non-pyrogenic, i.e., do not induce significant temperature elevations when administered to a patient.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed.

Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J Pharm. Sci. 66: 1-19.)

The phrases "systemic administration", "administered systemically", "peripheral administration", and "administered peripherally" as used herein mean the administration of a ligand, drug, or other material via route other than directly into the central nervous system, such that it enters the patient's system and thus, is subject to metabolism and other like processes, for example, subcutaneous administration.

The term "therapeutically effective amount" means an amount of a compound that ameliorates, attenuates or eliminates one or more symptom of a particular disease or condition, or prevents or delays the onset of one of more symptom of a particular disease or condition.

The terms "treating", "treat" or "treatment" and the like include preventative (e.g., prophylactic) and palliative treatment.

The methods provided herein include the manufacture and use of pharmaceutical compositions, which include one or more of the compounds provided herein. Also included are the pharmaceutical compositions themselves.

In some Claims, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

A pharmaceutical composition may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin.

In some cases, in order to prolong the effect of one or more compounds provided herein, it is desirable to slow the absorption of the compound from subcutaneous or intramuscular injection. For example, delayed absorption of a parenterally administered compound can be accomplished by dissolving or suspending the compound in an oil vehicle.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. The dose of the compound or composition can be varied over time. All combinations, delivery methods and administration sequences are contemplated.

The compounds of the present invention and in some Claims, other additional pharmaceutically active compounds, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent.

Formulations suitable for oral administration may be in the form of capsules (e.g., gelatin capsules), cachets, pills, tablets, lozenges (using a flavored basis, usually sucrose and acacia or tragacanth), powders, troches, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of a compound provided herein as an active ingredient. A composition may also be administered as a bolus, electuary, or paste. Oral compositions generally include an inert diluent or an edible carrier.

Pharmaceutically compatible binding agents, and/or adjuvant materials can be included as part of an oral composition. In solid dosage forms for oral administration (capsules, tablets, pills, dragees, powders, granules, and the like), the active ingredient can be mixed with one or more pharmaceutically acceptable carriers, such as sodium citrate or dicalcium phosphate, and/or any of the following: (1) fillers or extenders, such as starches, cyclodextrins, lactose, sucrose, saccharin, glucose, mannitol, and/or silicic acid; (2) binders, such as, for example, carboxymethylcellulose, microcrystalline cellulose, gum tragacanth, alginates, gelatin, polyvinyl pyrrolidone, sucrose, and/or acacia; (3) humectants, such as glycerol; (4) disintegrating agents, such as agar-agar, calcium carbonate, potato, corn, or tapioca starch, alginic acid, Primogel, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, Sterotes, solid polyethylene glycols, sodium lauryl sulfate, and mixtures thereof; (10) a glidant, such as colloidal silicon dioxide; (11) coloring agents; and (12) a flavoring agent such as peppermint, methyl salicylate, or orange flavoring. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of a powdered compound moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, microspheres, and/or nanoparticles. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions suitable for parenteral administration can include one or more compounds provided herein in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In one Claim, the IV formulation consists of a composition containing hydroxypropyl beta cyclodextrin within a pH range between 8-10 as a buffered or unbuffered solution. The IV formulation can be formulated as a sterile solution ready for injection, a sterile solution ready for dilution into an IV admixture or a sterile solid for reconstituion. The API in the IV formulation may exist as a free acid/base or an in situ salt.

Examples of suitable aqueous and nonaqueous carriers which may be employed in the pharmaceutical compositions provided herein include water for injection (e.g., sterile water for injection), bacteriostatic water, ethanol, polyols (such as glycerol, propylene glycol, polyethylene glycol such as liquid polyethylene glycol, and the like), sterile buffer (such as citrate buffer), and suitable mixtures thereof, vegetable oils, such as olive oil, injectable organic esters, such as ethyl oleate, and Cremophor EL™ (BASF, Parsippany, N.J.). In all cases, the composition must be sterile and should be fluid to the extent that easy syringability exists. Proper fluidity can be maintained, for example, by the use of coating materials, such as lecithin, by the maintenance of the required particle size in the case of dispersions, and by the use of surfactants.

The composition should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the methods of preparation are freeze-drying (lyophilization), which yields a powder of the active ingredient plus any additional desired ingredient from a previously sterile-filtered solution thereof.

Injectable depot forms can be made by forming microencapsule or nanoencapsule matrices of a compound provided herein in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes, microemulsions or nanoemulsions, which are compatible with body tissue.

For administration by inhalation, the compounds can be delivered in the form of an aerosol spray from a pressured container or dispenser that contains a suitable propellant (e.g., a gas such as carbon dioxide) or a nebulizer. Such methods include those described in U.S. Pat. No. 6,468,798. Additionally, intranasal delivery can be accomplished, as described in, inter alia, Hamajima et al., *Clin. Immunol. Immunopathol.*, 88(2), 205-10 (1998). Liposomes (e.g., as described in U.S. Pat. No. 6,472,375, which is incorporated herein by reference in its entirety), microencapsulation and nanoencapsulation can also be used. Biodegradable targetable microparticle delivery systems or biodegradable targetable nanoparticle delivery systems can also be used (e.g., as described in U.S. Pat. No. 6,471,996, which is incorporated herein by reference in its entirety).

Systemic administration of a therapeutic compound as described herein can also be by transmucosal or transdermal means. Dosage forms for the topical or transdermal administration of a compound provided herein include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The ointments, pastes, creams, and gels may contain, in addition to one or more compounds provided herein, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound provided herein, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

A compound provided herein can be administered by aerosol. This is accomplished by preparing an aqueous aerosol, liposomal preparation, or solid particles containing a compound or composition provided herein. A nonaqueous (e.g., fluorocarbon propellant) suspension could be used. In some Claims, sonic nebulizers are used because they minimize exposing the agent to shear, which can result in degradation of the compound.

Ordinarily, an aqueous aerosol can be made by formulating an aqueous solution or suspension of the agent together with conventional pharmaceutically acceptable carriers and stabilizers. The carriers and stabilizers vary with the requirements of the particular composition, but typically include nonionic surfactants (TWEEN® (polysorbates), PLURONIC® (poloxamers), sorbitan esters, lecithin, CREMOPHOR® (polyethoxylates)), pharmaceutically acceptable co-solvents such as polyethylene glycol, innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of a compound provided herein to the body. Such dosage forms can be made by dissolving or dispersing the agent in the proper medium. Absorption enhancers can also be used to increase the flux of the compound across the skin. The rate of such flux can be controlled by either providing a rate controlling membrane or dispersing the compound in a polymer matrix or gel.

The pharmaceutical compositions can also be prepared in the form of suppositories or retention enemas for rectal and/or vaginal delivery. Formulations presented as a suppository can be prepared by mixing one or more compounds provided herein with one or more suitable nonirritating excipients or carriers comprising, for example, cocoa butter, glycerides, polyethylene glycol, a suppository wax or a salicylate, which is solid at room temperature, but liquid at body temperature and, therefore, will melt in the rectum or vaginal cavity and release the active agent. Formulations which are suitable for vaginal administration also include pessaries, tampons, creams, gels, pastes, foams, or spray formulations containing such carriers as are known in the art to be appropriate.

In one Claim, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially (e.g., from Alza Corporation and Nova Pharmaceuticals, Inc). Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811, which is incorporated herein by reference in its entirety for all purposes.

The compounds of the present invention are used in the treatment of diseases, disorders or symptoms mediated by Mcl-1 inhibition. Examples of diseases, disorders or symptoms mediated by Mcl-1 inhibition include, but are not limited to, cancers. Non-limiting examples of cancers include breast cancer, colorectal cancer, skin cancer, melanoma, gynecologic cancer, ovarian cancer, endometrial cancer, kidney cancer, lung cancer, non-small cell lung cancer, lymphoma, non-Hodgkin's lymphoma, myeloma, multiple myeloma, leukemia, and acute myelogenous leukemia.

The cancers can include carcinomas (originating in the outer layer of cells of the skin and internal membranes, e.g., breasts, kidneys, lungs, skin); sarcomas (arising from connective tissue such as bone, muscle, cartilage, and blood vessels), and hematologic malignancies (e.g., lymphomas and leukemias, which arise in the blood or blood-forming organs such as the spleen, lymph nodes, and bone marrow). Cancer cells can include, for example, tumor cells, neoplastic cells, malignant cells, metastatic cells, and hyperplastic cells.

In an Claim, the disease, disorder or symptom is a hyperproliferative disorder, e.g., a lymphoma, leukemia, carcinoma (e.g., renal, breast, lung, skin), multiple myeloma, or a sarcoma. In one Claim, the leukemia is acute myeloid leukemia. In one Claim, the hyperproliferative disorder is a relapsed or refractory cancer.

Actual dosage levels of the active ingredients in the pharmaceutical compositions provided herein may be varied so as to obtain an amount of the active ingredient which is effective to achieve the desired therapeutic response for a particular patient, composition, and mode of administration, without being toxic to the patient.

The specific dosage and dosage range depends on a number of factors, including the requirements of the patient, the severity of the condition or disease being treated, the pharmacokinetic characteristics of the compound(s) employed, and the route of administration. In some Claims, the compositions provided herein can be provided in an aqueous solution containing about 0.1-10% w/v of a compound disclosed herein, among other substances, for parenteral administration. Typical dose ranges can include from about 0.01 to about 50 mg/kg of body weight per day, given in 1-4 divided doses. Each divided dose may contain the same or different compounds. The dosage will be a therapeutically effective amount depending on several factors including the overall health of a patient, and the formulation and route of administration of the selected compound(s).

Dosage forms or compositions containing a compound as described herein in the range of 0.005% to 100% with the balance made up from non-toxic carrier may be prepared. Methods for preparation of these compositions are known to those skilled in the art. The contemplated compositions may contain about 0.001%-100% active ingredient, in one Claim from about 0.1 to about 95%, in another Claim from about 75 to about 85%. Although the dosage will vary depending on the symptoms, age and body weight of the patient, the nature and severity of the disorder to be treated or prevented, the route of administration and the form of the drug, in general, a daily dosage of from about 0.01 to about 3,000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the Claimed compositions.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the patient and adjusting the dosage and/or timing The compounds of the present invention can be administered alone, in combination with other compounds of the present invention, or with other pharmaceutically active compounds or agents. The other pharmaceutically active compounds/agents can be intended to treat the same disease or condition as the compounds of the present invention or a different disease or condition. If the patient is to receive or is receiving multiple pharmaceutically active compounds or agents, the compounds can be administered simultaneously, or sequentially.

The compounds of the present invention, or pharmaceutically acceptable salts thereof, may be used in combination with one or more additional pharmaceutically active compounds/agents.

One or more additional pharmaceutically active compounds or agents may be administered separately, as part of a multiple dose regimen, from the compound of Formula I (e.g., sequentially, e.g., on different overlapping schedules with the administration of one or more compounds of Formula I (including any subgenera or specific compounds thereof). In other Claims, the one or more additional compounds/agents may be part of a single dosage form, mixed together with the compound of Formula I in a single composition. In still another Claim, the one or more additional compounds/agents can be given as a separate dose that is administered at about the same time that one or more compounds of Formula I are administered (e.g., simultaneously with the administration of one or more compounds of Formula I (including any subgenera or specific compounds thereof). Both the compound of Formula I and the one or more additional compounds/agents can be present at dosage levels of between about 1 to 100%, and more preferably between about 5 to 95% of the dosage normally administered in a monotherapy regimen.

In a particular embodiment, the additional pharmaceutically active compound/agent is a compound or agent that can be used to treat a cancer. For example, the additional pharmaceutically active compound/agent can be selected from antineoplastic agents, anti-angiogenic agents, chemotherapeutic agents, and peptidal cancer therapy agents. In another Claim, the antineoplastic agents are selected from antibiotic-type agents, alkylating agents, antimetabolite agents, hormonal agents, immunological agents, interferon-type agents, kinase inhibitors, proteasome inhibitors, and combinations thereof. It is noted that the additional pharmaceutically active compound/agent may be a traditional small organic chemical molecule or can be a macromolecule such as a protein, antibody, peptibody, DNA, RNA or a fragment of such macromolecules.

Examples of additional pharmaceutically active compounds/agents that can be used in the treatment of cancers and that can be used in combination with one or more compounds of the present invention include: acemannan; aclarubicin; aldesleukin; alitretinoin; amifostine; amrubicin; amsacrine; anagrelide; arglabin; arsenic trioxide; BAM 002 (Novelos); bicalutamide; broxuridine; celmoleukin; cetrorelix; cladribine; clotrimazole; cytarabine; DA 3030 (Dong-A); daclizumab; denileukin diftitox; deslorelin; dilazep; docosanol; doxercalciferol; doxifluridine; bromocriptine; cytarabine; HIT diclofenac; interferon alfa; tretinoin; edelfosine; edrecolomab; eflornithine; emitefur; epirubicin; epoetin beta; etoposide phosphate; exisulind; fadrozole; finasteride; fludarabine phosphate; formestane; fotemustine; gallium nitrate; gemtuzumab zogamicin; gimeracil/oteracil/tegafur combination; glycopine; goserelin; heptaplatin; human chorionic gonadotropin; human fetal alpha fetoprotein; ibandronic acid; interferon alfa; interferon alfa natural; interferon alfa-2; interferon alfa-2a; interferon alfa-2b; interferon alfa-N1; interferon alfa-n3; interferon alfacon-1; interferon alpha natural; interferon beta; interferon beta-1a; interferon beta-1b; interferon gamma natural; interferon gamma-1a; interferon gamma-1b; interleukin-1 beta; iobenguane; irsogladine; lanreotide; LC 9018 (Yakult); leflunomide; lenograstim; lentinan sulfate; letrozole; leukocyte alpha interferon; leuprorelin; levamisole+fluorouracil; liarozole; lobaplatin; lonidamine; lovastatin; masoprocol; melarsoprol; metoclopramide; mifepristone; miltefosine; mirimostim; mismatched double stranded RNA; mitoguazone; mitolactol; mitoxantrone; molgramostim; nafarelin; naloxone+pentazocine; nartograstim; nedaplatin; nilutamide; noscapine; novel erythropoiesis stimulating protein; NSC 631570 octreotide; oprelvekin; osaterone; paclitaxel; pamidronic acid; peginterferon alfa-2b; trimethyl polysulfate sodium; pentostatin; picibanil; pirarubicin; rabbit anti-thymocyte polyclonal antibody; polyethylene glycol interferon alfa-2a; porfimer sodium; raltitrexed; rasburicase; rhenium Re 186 etidronate; RII retinamide; romurtide; samarium (153 Sm) lexidronam; sargramostim; sizofuran; sobuzoxane; sonermin; strontium-89 chloride; suramin; tasonermin; tazarotene; tegafur; temoporfin; teniposide; tetrachlorodecaoxide; thymalfasin; thyrotropin alfa; toremifene; tositumomab-iodine 131; treosulfan; tretinoin; trilostane; trimetrexate; triptorelin; trametinib; tumor necrosis factor alpha natural; ubenimex; bladder cancer vaccine; Maruyama vaccine; melanoma lysate vaccine; valrubicin; venetoclax; verteporfin; virulizin; zinostatin stimalamer; abarelix; AE 941 (Aeterna); ambamustine; antisense oligo-nucleotide; bcl-2 (Genta); APC 8015 (Dendreon); dexaminoglutethimide; diaziquone; EL 532 (Elan); EM 800 (Endorecherche); eniluracil; etanidazole; fenretinide; galocitabine; gastrin 17 immunogen; HLA-B7 gene therapy (Vical); granulocyte macrophage colony stimulating factor; histamine dihydrochloride; ibritumomab tiuxetan; ilomastat; IM 862 (Cytran); interleukin-2; iproxifene; LDI 200 (Milkhaus); leridistim; lintuzumab; CA 125 monoclonal antibody (Mab) (Biomira); cancer Mab (Japan Pharmaceutical Development); HER-2 and Fc Mab (Medarex); idiotypic 105AD7 Mab (CRC Technology); idiotypic CEA Mab (Trilex); LYM-1-iodine 131 Mab (Techniclone); polymorphic epithelial mucin-yttrium 90 Mab (Antisoma); marimastat; menogaril; mitumomab; motexafin gadolinium; MX 6 (Galderma); nolatrexed; P 30 protein; pegvisomant; porfiromycin; prinomastat; RL 0903 (Shire); rubitecan; satraplatin; sodium phenylacetate; sparfosic acid; SRL 172 (SR Pharma); SU 5416 (SUGEN); TA 077 (Tanabe); tetrathiomolybdate; thaliblastine; thrombopoietin; tin ethyl etiopurpurin; tirapazamine; cancer vaccine (Biomira); melanoma vaccine; melanoma oncolysate vaccine; viral melanoma cell lysates vaccine; valspodarl; fluorouracil; 5-fluorouracil; imatinib; altretamine; cladibrine; cyclophosphamine; decarazine; irinotecan; mitosmycin; mitoxane; topotecan; vinorelbine; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; oprozomib; vorinostat; capecitabine; zoledronic acid; anastrozole; sunitinib; aprepitant and nelarabine, or a pharmaceutically acceptable salt thereof.

Additional pharmaceutically active compounds/agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 386; AMG 479; AMG 655; AMG 745; AMG 951; and AMG 706, or a pharmaceutically acceptable salt thereof.

In certain Claims, a composition provided herein is conjointly administered with a chemotherapeutic agent. Suitable chemotherapeutic agents may include, natural products such as vinca alkaloids (e.g., vinblastine, vincristine, and vinorelbine), paclitaxel, epipidopodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirolimus), KSP (Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163 L), aurora kinase inhibitors (e.g., MLN8237), cell surface monoclonal antibodies (e.g., anti-CD38 (HUMAX-CD38), anti-CS1 (e.g., elotuzumab), inhibitors of KRAS including covalent inhibitors of KRAS G12C, MEK inhibitor, including trametinib, HSP90 inhibitors (e.g., 17 AAG and KOS 953), P13K/Akt inhibitors (e.g., perifosine), Akt inhibitor (e.g., GSK-2141795), PKC inhibitors (e.g., enzastaurin), FTIs (e.g., Zarnestra™), anti-CD138 (e.g., BT062), Torcl/2 specific kinase inhibitor (e.g., INK128), kinase inhibitor (e.g., GS-1101), ER/UPRtargeting agent (e.g., MKC-3946), cFMS inhibitor (e.g., ARRY-382), JAK1/2 inhibitor (e.g., CYT387), PARP inhibitor (e.g., olaparib and veliparib (ABT-888)), BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

The compounds of the present invention may also be used in combination with radiation therapy, hormone therapy, surgery and immunotherapy, which therapies are well known to those skilled in the art. In certain Claims, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof. In a particular Claim, the compounds of the present invention can also be used in combination with additional pharmaceutically active agents that treat nausea. Examples of agents that can be used to treat nausea include: dronabinol; granisetron; metoclopramide; ondansetron; and prochlorperazine; or a pharmaceutically acceptable salt thereof.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, and bags. In some Claims, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, ethylamine, and the like. See, for example, S. M. Berge, et al., "Pharmaceutical Salts," J Pharm Sci, 66: 1-19 (1977).

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$) alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as Z and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diastereomeric mixture by reaction with an appropriate optically active compound (e.g., an alcohol), separating the diastereomers and converting (e.g., hydrolyzing) the individual diastereomers to the corresponding pure enantiomers.

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The compounds of the present invention may exist in various solid states including crystalline states and as an amorphous state. The different crystalline states, also called polymorphs, and the amorphous states of the present compounds are contemplated as part of this invention.

EXAMPLES

The examples presented below illustrate specific Claims of the present invention. These examples are meant to be representative and are not intended to limit the scope of the Claims in any manner.

The following abbreviations may be used herein:
~ about
Ac acetate
$Ac_2O$ acetic anhydride
AcOH or HOAc acetic acid
$Al_2O_3$ aluminum oxide
Br broad
Boc tert-butyloxycarbonyl
Calcd calculated
CDI 1,1'-carbonyldiimidazole
$CO_2$ carbon dioxide
CSA 10-camphorsulfonic acid
d day or doublet
DBU 1,8-diazabicyclo[5.4.0]undec-7-ene
DCE Dichloroethane
DCM Dichloromethane
DEA Diethylamine
Dess-Martin periodinane; 1,1,1-triacetoxy-1,1-dihydro-1,2-benziodoxol-3-(1H)-one
DIEA or DIPEA Diisopropylethylamine
DMA N,N-dimethylacetamide
DMAP 4-dimethylaminopyridine
DMF N,N-dimethylformamide
DMSO dimethyl sulfoxide
EDC N-ethyl-N'-(3-dimethylaminopropyl) carbodiimide
ee or e.e. enantiomeric excess
ELISA enzyme-linked immunosorbent assay
Eq Equivalent
ESI or ES electrospray ionization
Et Ethyl
$Et_2O$ diethyl ether
EtOAc ethyl acetate
$Et_3N$ triethylamine
EtOH ethyl alcohol
G gram(s)
GC gas chromatography
h hour(s)
$^1$H NMR proton nuclear magnetic resonance spectroscopy
$H_2$ hydrogen gas
$H_2O$ Water
$H_2SO_4$ sulfuric acid
HATU 1-[Bis(dimethylamino)methylene]-1H-1,2,3-triazolo[4,5-b]pyridinium 3-oxid hexafluorophosphate
HCl hydrochloric acid
Hex hexane(s)

HPLC high performance liquid chromatography
Hz Hertz
IP intraperitoneal
IPA isopropyl alcohol
IPAc isopropyl acetate
$K_2CO_3$ potassium carbonate
KI potassium iodide
$K_3PO_4$ potassium phosphate
KF Karl Fischer titration
KHMDS potassium hexamethyldisilazide
KOAc potassium acetate
KOH potassium hydroxide
KOtBu Potassium tert-butoxide
L liter(s)
LAH lithium aluminium hydride
LCMS, LC-MS or LC/MS liquid chromatography mass spectrometry
LiHMDS lithium hexamethyldisilazide
LiOH lithium hydroxide
m multiplet
M molar (mol $L^{-1}$)
Me methyl
MeCN acetonitrile
MHz megahertz
MeI iodomethane
MeOH methyl alcohol
MeTHF methyltetrahydrofiran
Mg milligram(s)
$MgSO_4$ magnesium sulphate
min minute(s)
μm micrometer
μm microliter
mL milliliter(s)
mm millimeter
mol mole
MS mass spectrometry
MSA methanesulfonic acid
MsCl methanesulfonyl chloride
MTBE methyl tert-butyl ether
m/z mass-to-charge ratio
N Normality (Eq/L)
$N_2$ nitrogen gas
nBuLi n-butyllithium
NaCl sodium chloride
$Na_2CO_3$ sodium carbonate
$NaHCO_3$ sodium bicarbonate
$NaH_2PO_4$ sodium dihydrogen phosphate
NaHMDS sodium bis(trimethylsilyl)amide
$NaNO_2$ sodium nitrite
NaOH sodium hydroxide
NaOtBu sodium tert-butoxide
$Na_2SO_4$ sodium sulfate
$Na_2S_2O_3$ sodium thiosulfate
$NH_3$ ammonia, azane
$NH_4Cl$ ammonium chloride
$NH_4OH$ ammonium hydroxide
NMP 1-methyl-2-pyrrolidinone
NMR nuclear magnetic resonance spectroscopy
OMe methoxy
PO per oral
$POCl_3$ phosphoryl chloride
+ve positive
Ph phenyl
PhMe toluene
PMB p-methoxybenzyl
Ppm parts per million
prep preparative
psi pounds per square inch
q quartet
QD once daily
QNMR quantitative NMR
RBF round-bottomed flask
RT or rt or r.t. room temperature
s singlet
sat. or sat'd or satd Saturated
SFC supercritical fluid chromatography
$SiO_2$ silicon dioxide, silica
$SOCl_2$ thionyl chloride
T Triplet
TBAF tetra-n-butylammonium fluoride
TBDPS tert-butyldiphenylsilyl
TBS tert-butyldimethylsilyl
tBu tert-butyl
t-BuOH tert-butanol
TEA Triethylamine
TEMPO (2,2,6,6-tetramethylpiperidin-1-yl)oxidanyl
TFA triflouroacetic acid
THF Tetrahydrofuran
TLC thin layer chromatography
TsOH toluene sulfonic acid
UV Ultraviolet
v/v Volume per volume
wt % Weight percent It is noted that when a percent (%) is used with regard to a liquid, it is a percent by volume with respect to the solution. When used with a solid, it is the percent with regard to the solid composition. The following synthetic methods show generally how to make intermediates and compounds of the present invention.

General Synthetic Schemes

Unless otherwise stated, starting materials and reagents used in preparing these compounds are either available from commercial suppliers such as Aldrich Chemical Co., (Milwaukee, Wis.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989).

The starting materials for the following synthetic methods can be found in the General Methods and General Synthesis for Intermediates. The synthesis of some of the starting materials and the intermediates are disclosed in U.S. Pat. No. 9,562,061 and PCT/US17/19336, respectively, herein incorporated by reference in their entireties for all purposes. These synthetic methods are merely illustrative of some methods by which the compounds of this invention can be synthesized, and various modifications to these methods can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 22° C.

IUPAC names were generated using either ACD/Name v2015 or ChemBioDraw Ultra 12.

Intermediate AA11A (S)-6'-CHLORO-5-(((1R,2R)-2-((S)-1-HYDROXY-ALLYL)CYCLOBUTYL)METHYL)-3',4,4',5-TET-RAHYDRO-2H,2'H-SPIRO[BENZO[B][1,4]OXAZEPINE-3,1'-NAPHTHALENE]-7-CARBOXYLIC ACID

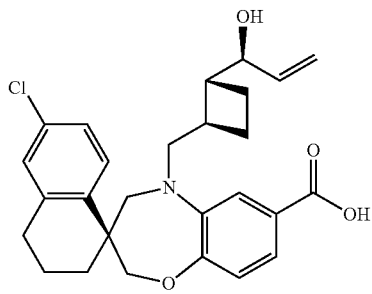 [SMILES: C=C[C@H](O)[C@@H]1CC[C@H]1CN1C[C@@]2(CCCc3cc(Cl)ccc32)COc2ccc(C(=O)O)cc21]

STEP 1: (R)-6-CHLORO-3,4-DIHYDRO-2H-SPIRO[NAPHTHALENE-1,2'-OXIRANE] AND (S)-6-CHLORO-3,4-DIHYDRO-2H-SPIRO[NAPH-THALENE-1,2'-OXIRANE]

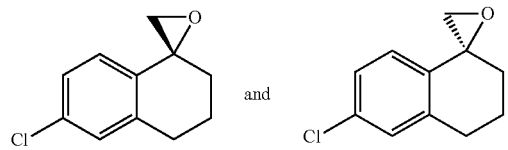 [SMILES: Clc1ccc2c(c1)CCC[C@]21CO1 ; Clc1ccc2c(c1)CCC[C@@]21CO1]

A 2 L 4-necked-RBF was charged with 6-chloro-3,4-dihydro-1(2H)-naphthalenone (123 g, 681 mmol), trimethylsulfonium iodide (143 g, 701 mmol), and DMSO (1100 mL). KOH (76 g, 1362 mmol) (pellets) was added. The suspension was stirred at ambient temperature for 2 days, after which time crude $^1$H NMR showed no remaining starting material. The solution was poured into 800 g of crushed ice, rinsed with MTBE (200 mL), and an additional portion of MTBE (700 mL) was added. The resulting mixture was stirred for 5 min and after partition, the bottom aqueous layer was extracted with MTBE twice (500 mL, 300 mL), and combined with the main MTBE extract. The combined organic stream was washed with brine (2×600 mL) and 330 g of Al$_2$O$_3$ (neutral) was added. The resulting suspension was stirred for 5 min at 22° C., filtered, and washed with MTBE (400 mL). The filtrate was concentrated to give the product as a red viscous oil (125 g, 94%).

STEP 2: (S)-6-CHLORO-1,2,3,4-TETRAHY-DRONAPHTHALENE-1-CARBALDEHYDE AND (R)-6-CHLORO-1,2,3,4-TETRAHYDRONAPH-THALENE-1-CARBALDEHYDE

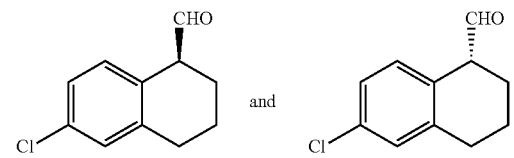 [SMILES: O=C[C@H]1CCCc2cc(Cl)ccc21 ; O=C[C@@H]1CCCc2cc(Cl)ccc21]

A 3 L 3-necked-RBF was charged with racemic 6-chloro-3,4-dihydro-2H-spiro[naphthalene-1,2'-oxirane] (160 g, 822 mmol) and THF (1760 mL). After the batch was cooled to −8° C. with a dry ice/IPA bath, boron trifluoride diethyl etherate (5.07 mL, 41.1 mmol) was added over 3 min. An exotherm raised the batch temp to 10° C. instantly. The batch was stirred at −5 to 0° C. for 5 min, and LC/MS analysis of a sample (quenched into cold NaHCO$_3$ solution) showed complete conversion. The reaction was quenched by the addition of sat. NaHCO$_3$ (300 mL) at −5° C. followed by MTBE (400 mL) and the mixture was transferred to a separatory funnel and rinsed with MTBE (240 mL). After partition, the aqueous layer was discarded along with some white solid (likely boric acid or borax). The organic layer was washed with brine (350 mL) and concentrated under reduced pressure to give a red oil. The crude material was used directly in Step 3.

STEP 3: (6-CHLORO-1,2,3,4-TETRAHY-DRONAPHTHALENE-1,1-DIYL)DIMETHANOL

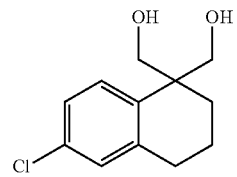

Racemic 6-chloro-1,2,3,4-tetrahydro-1-naphthalenecarb-aldehyde was charged onto a 3 L 3-necked-RBF and rinsed with diethylene glycol (1000 mL). Formaldehyde (37% solution in H$_2$O; 652 mL, 8757 mmol) was added and the resulting biphasic emulsion was cooled to 5° C. with a dry ice/IPA bath. KOH (45% aqueous solution, 652 mL, 11.9 mol) was added over ∼30 min, maintaining the temperature below 20° C. After complete addition, the batch (20° C.) was slowly heated to 45° C. (Caution: exothermic reaction) and aged for 1 h. HPLC showed complete conversion. Some viscous insoluble tar was formed, which was removed prior to aqueous workup. To the batch was added brine (500 mL) and the mixture was extracted with DCM until the product content in the aqueous phase was less than 5%. The combined DCM extract was concentrated to 750 mL as a red oil, washed with H$_2$O (500 mL), and the product began to crystallize out. Upon separation, the clear top aqueous layer was discarded and the bottom layer was stirred in ice/H$_2$O bath for 30 min, filtered, and washed with DCM (100 mL) and H$_2$O (100 mL). The product was dried under dry air/vacuum to give a first crop (113 g, 498 mmol, 57% yield). The DCM layer from the resulting mother liquor was separated and concentrated to 200-300 g (KF=0.5%), seeded, and stirred in ice/H₂O bath for 30 min. The product was filtered, washed with DCM (50 mL), and dried in dry air/vacuum to give a second crop (14.3 g, 63.1 mmol, 7% yield) for a combined total yield of 6-chloro-1,2,3,4-tetrahydronaphthalene-1,1-diyl)dimethanol of 127 g (64%).

STEP 4: (S)-(6-CHLORO-1-(HYDROXYMETHYL)-1,2,3,4-TETRAHYDRONAPHTHALEN-1-YL)METHYL 4-BROMOBENZOATE

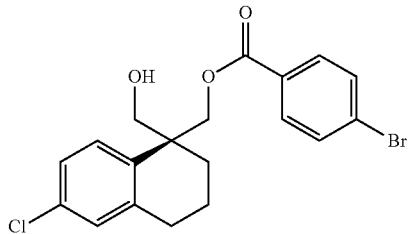 [SMILES: O=C(OC[C@@]1(CO)CCCc2cc(Cl)ccc21)c1ccc(Br)cc1]

To a solution of 2,6-bis((R)-5,5-dibutyl-4-phenyl-4,5-dihydrooxazol-2-yl)pyridine (R,R-Kang Catalyst) (1.57 g, 2.64 mmol) in dry DCM (450 mL), copper(II) chloride (0.355 g, 2.64 mmol) was added and the resulting green colored solution was stirred at rt for 1 h. This solution was added via cannula to a solution of (6-chloro-1,2,3,4-tetrahydronaphthalene-1,1-diyl)dimethanol (30 g, 132.73 mmol) in dry DCM (800 mL). The resulting mixture was cooled to −78° C. and a light green colored precipitation was observed. A solution of 4-bromobenzoyl chloride (34.77 g, 158.79 mmol) in DCM (500 mL) was then slowly added, followed by the dropwise addition of N,N-diisopropylamine (20 g, 154 mmol). The resulting reaction mixture was stirred at −78° C. for 3 h, then it was quenched with pH 3 phosphate buffer (1 L) and warmed to ambient temperature with vigorous stirring. The mixture was then diluted with DCM (2 L) and the layers were separated. The organic phase was washed with pH 3 buffer (1 L), sat. NaHCO₃ (1 L), and brine (2 L) then it was dried over Na₂SO₄, filtered, and concentrated. The crude material was purified by column chromatography over SiO₂ gel (100-200 mesh, 80% DCM in Hex) to afford pure (S)-(6-chloro-1-(hydroxymethyl)-1,2,3,4-tetrahydronaphthalen-1-yl)methyl 4-bromobenzoate (45 g, 84%; e.r=91.4:8.6). ChiralCel® OD-H (250 mm×4.6 mm); Mobile Phase: n-Hexane:IPA: 90:10; Run Time: 20 min; flow rate: 1 mL/min; sample preparation: IPA. Retention time (major peak)-9.32 min; Retention time (minor peak)-11.46 min).

STEP 5: (R)-(6-CHLORO-1-FORMYL-1,2,3,4-TETRAHYDRONAPHTHALEN-1-YL)METHYL 4-BROMOBENZOATE

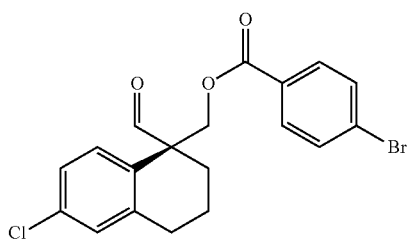 [SMILES: O=C[C@]1(COC(=O)c2ccc(Br)cc2)CCCc2cc(Cl)ccc21]

To a stirred solution of (S)-(6-chloro-1-(hydroxymethyl)-1,2,3,4-tetrahydronaphthalen-1-yl)methyl 4-bromobenzoate (100 g, 244.5 mmol) in DCM (2.5 L), Dess-Martin periodinane (121.4 g, 293.3 mmol) was added at 10° C. The cooling bath was removed after addition and the reaction mixture was stirred for 30 min at ambient temperature. H₂O (9 mL) was then added and the resulting biphasic mixture was stirred at ambient temperature for 30 min. The reaction mixture was cooled to 0° C. and quenched with 2 L of a 1:1 mixture of 10% Na₂S₂O₃/sat. NaHCO₃ solution. The reaction mixture was stirred further at ambient temperature for 10 min, then the layers were separated and the aqueous layer was extracted with EtOAc (2×1.5 L). The combined organic layer was washed with 1 L of 10% Na₂S₂O/sat. NaHCO₃ solution and 1 L of brine, then it was dried over Na₂SO₄, filtered, and concentrated. Purification of the residue by column chromatography over SiO₂ gel (100-200 mesh, 5% EtOAc/Hex) provided (R)-(6-chloro-1-formyl-1,2,3,4-tetrahydronaphthalen-1-yl)methyl 4-bromobenzoate (80 g, 81%).

The enantiomeric purity of the title compound could be improved by the following procedure: (R)-(6-chloro-1-formyl-1,2,3,4-tetrahydronaphthalen-1-yl)methyl 4-bromobenzoate (190 g) was added in toluene (950 mL) and heated to 50° C. to complete dissolution. The homogeneous solution was cooled to ambient temperature and seeded with racemic compound. The solution was cooled to −25° C. and aged overnight. The mother liquor was then decanted and concentrated to afford 160 g of enantiomerically enriched (R)-(6-chloro-1-formyl-1,2,3,4-tetrahydronaphthalen-1-yl) methyl 4-bromobenzoate (94% ee as determined by chiral HPLC). Chiral HPLC conditions: Column: ChiralCel® OD-H (250 mm×4.6 mm); Mobile Phase: n-Hexane:IPA: 90:10. Run Time: 20 min. Flow rate: 1 mL/min. Sample preparation: ethanol. Retention time (major peak): 8.488 min (96.97%); Retention time (minor peak): 9.592 min (3.03%).

STEP 6: (R)-(6-CHLORO-1-(DIMETHOXYMETHYL)-1,2,3,4-TETRAHYDRONAPHTHALEN-1-YL)METHANOL

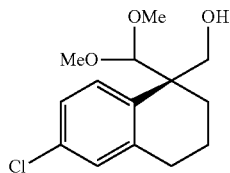 [SMILES: COC(OC)[C@]1(CO)CCCc2cc(Cl)ccc21]

To a solution of (R)-(6-chloro-1-formyl-1,2,3,4-tetrahydronaphthalen-1-yl)methyl 4-bromobenzoate (75 g, 183.8 mmol) in anhydrous MeOH (1 L), p-TsOH (1 g, 9.2 mmol) and trimethyl orthoformate (58.4 mL, 551 mmol) were added and the reaction mixture was refluxed until the starting material was completely consumed (~4 h). The reaction mass was concentrated to 50% volume and diluted with THF (1 L) and 1N NaOH (1 L, 1 mol). The resulting reaction mixture was stirred at 40° C. overnight and then concentrated under reduced pressure. The residue was diluted with EtOAc (1.5 L). The aqueous layer was separated and extracted with EtOAc (2×500 mL) and the combined organic layers were washed with 1N NaOH (1 L) and brine (1 L), dried over Na₂SO₄ and concentrated under reduced pressure. The crude material was purified by column chromatography over 100-200 mesh size SiO$_2$ gel (10% EtOAc/Hex) to give pure (R)-(6-chloro-1-(dimethoxymethyl)-1,2,3,4-tetrahydronaphthalen-1-yl)methanol as a light brown thick oil (44 g, 89%).

STEP 7: TERT-BUTYL-4-FLUORO-3-NITROBENZOATE

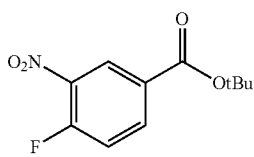 [SMILES: CC(C)(C)OC(=O)c1ccc(F)c([N+](=O)[O-])c1]

To a solution of 4-fluoro-3-nitrobenzoic acid (100 g, 540.2 mmol) in t-butanol (2.5 L), DMAP (13.18 g, 108.04 mmol) and di tert-butyl dicarbonate (248 mL, 1080.4 mmol) were added and the reaction mixture was heated at 40° C. overnight. Upon completion, the reaction mixture was diluted with H$_2$O and the aqueous phase was extracted with EtOAc (3×1.5 L). The combined organic layer was washed further with H$_2$O (1×1 L), brine (1×1 L), and dried over Na$_2$SO$_4$. The solvent was removed under reduced pressure and the crude material thus obtained was purified by column chromatography (100-200 mesh size SiO$_2$ gel, eluting with a gradient of 100% Hex to 5% EtOAc in Hex) affording pure tert-butyl-4-fluoro-3-nitrobenzoate (70 g, 54%) as light yellow solid.

STEP 8: (R)-TERT-BUTYL 4-((6-CHLORO-1-(DIMETHOXYMETHYL)-1,2,3,4-TETRAHYDRONAPHTHALEN-1-YL)METHOXY)-3-NITROBENZOATE

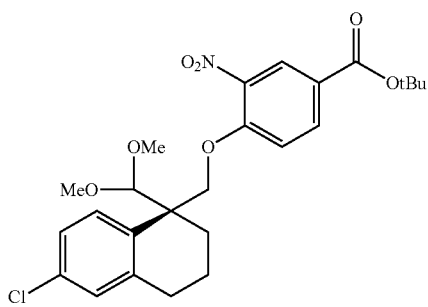 [SMILES: COC(OC)[C@]1(COc2ccc(C(=O)OC(C)(C)C)cc2[N+](=O)[O-])CCCc2cc(Cl)ccc21]

A solution of (R)-(6-chloro-1-(dimethoxymethyl)-1,2,3,4-tetrahydronaphthalen-1-yl)methanol (70 g, 259.2 mmol) in dry THF (3.5 L) was cooled to 0° C. and LiHMDS (1 M in THF; 363 mL, 363 mmol) was added dropwise. After 5 min, a solution of tert-butyl 4-fluoro-3-nitrobenzoate (74.9 g, 311 mmol) in THF (500 mL) was added dropwise via dropping funnel and the resulting mixture was warmed to ambient temperature. Upon completion (1 h), the mixture was cooled to 0° C., quenched with sat. NH$_4$Cl solution (1 L) and extracted with EtOAc (3×1 L). The combined organic layers were washed with NH$_4$Cl (1 L) and brine (1 L), dried over Na$_2$SO$_4$ and concentrated under reduced pressure. The crude material thus obtained was purified by column chromatography using 100-200 mesh size SiO$_2$ gel (5% EtOAc/hexane) to afford (R)-tert-butyl 4-((6-chloro-1-(dimethoxymethyl)-1,2,3,4-tetrahydronaphthalen-1-yl)methoxy)-3-nitrobenzoate as yellow thick oil (110 g, 87% yield).

STEP 9A: (R)-4-((6-CHLORO-1-FORMYL-1,2,3,4-TETRAHYDRONAPHTHALEN-1-YL)METHOXY)-3-NITROBENZOIC ACID

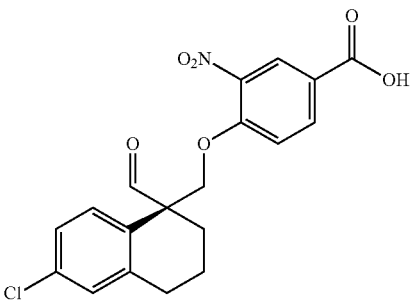 [SMILES: O=C[C@]1(COc2ccc(C(=O)O)cc2[N+](=O)[O-])CCCc2cc(Cl)ccc21]

To a solution of (R)-tert-butyl 4-((6-chloro-1-(dimethoxymethyl)-1,2,3,4-tetrahydronaphthalen-1-yl)methoxy)-3-nitrobenzoate (35 g, 71.25 mmol) in MeCN (1 L), erbium triflate (4.3 g, 7.1 mmol) and H$_2$O (13 mL) were added. The resulting mixture was heated to 80° C. overnight. The solvent was then removed under reduced pressure and the residue was dissolved in Et$_2$O (1.5 L) and washed with 1N HCl (500 mL) and brine (500 mL). The organic layer was dried over Na$_2$SO$_4$, filtered, and concentrated to afford (R)-4-((6-chloro-1-formyl-1,2,3,4-tetrahydronaphthalen-1-yl)methoxy)-3-nitrobenzoic acid (30 g), which was used without further purification.

Alternatively, (R)-4-((6-chloro-1-formyl-1,2,3,4-tetrahydronaphthalen-1-yl)methoxy)-3-nitrobenzoic acid may be prepared from (6-chloro-1,2,3,4-tetrahydronaphthalene-1,1-diyl)dimethanol (Step 4) as follows:

A 250 mL 3-necked-RBF was charged with copper (II) chloride (0.095 g, 0.02 eq), 2,6-bis((R)-5,5-dibutyl-4-phenyl-4,5-dihydrooxazol-2-yl)pyridine (0.42 g, 0.02 eq) and THF (28.5 g, 4V). After inertion with N$_2$, the batch was stirred at 20° C. for 0.5 h. To the homogenous green solution was added (6-chloro-1,2,3,4-tetrahydronaphthalene-1,1-diyl)dimethanol (8.0 g, 1.00 eq) followed by THF (14.2 g, 2V) and 4-methylmorpholine (3.75 g, 1.05 eq). The reaction mixture was cooled to −20° C., and a solution of 1-napthoyl chloride (7.06 g, 1.05 eq) in THF (21.3 g, 3 V) was added to the batch over 0.5 h maintaining the temperature below −15° C. After aging at −20° C. for 20 h, an aliquot of the reaction slurry was sampled and assayed by HPLC. The slurry was directly filtered through a glass-fritted funnel while maintaining the temperature at −20° C. The filter cake was washed with two portions of cold (<−10° C.) THF (2×14.2 g, 2V) rinsed through the reaction vessel. The filter cake (4-methylmorpholine-HCl) was transferred to a labeled container. The mother liquor and washes were concentrated to a minimum volume and distillative solvent swap by charging toluene until the batch volume is 6V and toluene/THF ratio is >98:2 (v/v) as measured by QNMR. To the batch at 20° C. was added heptane (11 g, 2V) and the slurry was heated to 85° C. (dissolution observed). The solution was cooled to 75° C. and charged with seed (0.27 g, 0.02 eq). The slurry was cooled to 20° C. over 3 h and aged for >1 h. The batch was filtered through a glass-fritted filter and the cake was washed with toluene/heptane (3:1 v/v) (11 g, 2V) then toluene/heptane (1:1 v/v) (11 g, 2V). The cake was dried under N$_2$ for 12 h at ambient temperature and the cake was assayed dry by QNMR (<1 wt % toluene and heptane). The product was obtained as an off-white solid (8.75 g, 63% after wt adjustment).

A 60 L jacketed reactor vented with a bleach scrubber was charged with (S)-(6-chloro-1-(hydroxymethyl)-1,2,3,4-tetrahydronaphthalen-1-yl)methyl 1-naphthoate (2.693 Kg, 88.6 wt %, 6.3 mol) followed by DCM (17.9 Kg, 5 vol) and EtNiPr$_2$ (2.84 Kg, 3.5 eq). After N$_2$ inertion, the batch was agitated and cooled to 0° C. To the alcohol slurry mixture in the reactor was added a solution of freshly prepared sulfur trioxide pyridine (2.10 Kg, 2.5 eq of sulfur trioxide pyridine in 7.43 Kg, 3 vol. DMSO) over 30 min while maintaining the batch temperature below 15° C. After addition, HPLC assay showed >99% conversion. The batch was quenched by the addition of H$_2$O (14 L, 5 vol) over ~20 min. maintaining the batch temperature below 15° C. and then toluene (16.8 L, 6 vol) was added. After partition, the organic layer was treated with H$_2$O (14 L, 5 vol) and toluene (16.8 L, 6 vol). The top organic layer was washed with 2 N HCl twice (14 L each, 5 vol) and brine (14 L, 5 vol). The organic layer was drained to a clean container, assayed by HPLC and then transferred back to the clean 60 L reactor through an inline filter. The batch was concentrated to a minimal volume and solvent switched to MeOH until the batch volume was 28 L (10 vol) and MeOH/toluene ratio was 3:1 (v/v) as measured by QNMR. The batch was then transferred to a 30 L jacketed reactor through an inline filter. After adjustment of the batch temperature to 30° C., the batch was seeded with the aldehyde (51 g, 0.02 eq) as a slurry in MeOH (400 mL). After the slurry was aged for 30 min at 30° C., the batch was solvent switched by distillation with MeOH until the batch volume is 11 L (4 vol) and MeOH/toluene ratio is ≥99:1 (v/v). The batch was then cooled to 5° C. and MeOH/H$_2$O mixture (3.70 Kg MeOH+1.34 Kg H$_2$O) was added over 1.5 h to bring the total solvent volume to approximately 5.5 vol and final MeOH/H$_2$O to 90/10 (v/v).

The batch was heated to 65° C. over 30 min, and cooled to 20° C. over ~2 h and aged for 2 h. The batch was filtered through an Aurora® filter fitted with ≤25 μm filter cloth. The cake was washed with MeOH/H$_2$O (10:1) (1×2 vol), then MeOH/H$_2$O (2:1) (1×2 vol). The cake was dried under N$_2$ at ambient temperature for ≥4 h until dry to give the product as an off-white solid (1.99 Kg, 72% after wt % adjustment).

A 3-necked 250 mL RBF was charged with (R)-(6-chloro-1-formyl-1,2,3,4-tetrahydronaphthalen-1-yl)methyl 1-naphthoate (10 g, 94.4 wt %, 95.3% LCAP, >99% ee), methanol (100 mL), trimethyl orthoformate (7 mL), and TsOH.H$_2$O (0.24 g). The RBF was inerted with N$_2$, and agitation was initiated. The batch was heated to 60° C. and aged for 2 h. HPLC assay showed ≥98% conversion.

The batch was concentrated under vacuum (~150-190 torr, external temp ~40° C.) to minimal volume using a rotoevaporator. The batch was turned over to THF by charging THF three times (50 mL each time) and distilling under vacuum (~165 torr, external temp ~40° C.). After each of the first two THF charges, the batch was concentrated down to a minimal volume, and after the last THF charge and distillation QNMR analysis of a sample showed the target ratio of >20/1 THF/MeOH (v/v). LiOH.H$_2$O (10.46 g, 10 eq) and H$_2$O (50 mL) were charged to the 3-necked 250 mL RBF. The reaction mixture was heated to 65° C. and aged for 18 h. HPLC assay showed >99% conversion. The batch was cooled to 20° C. and transferred to a 500-mL separatory funnel. MTBE (106 mL) was charged to the separatory funnel and the funnel was shaken well. After settling for 5 min, the bottom aqueous layer was drained. The top organic layer was washed with 20% K$_2$CO$_3$ twice (32 mL and 11 mL). The batch was transferred to a 250 mL RBF. Assay by HPLC showed <2% naphthanoic acid by-product. The batch was concentrated to a minimal volume at reduced pressure on the rotoevaporator (300 mbar, external temp ~40° C.). The batch was turned over to THF using a rotoevaporator (~250 mbar, external temp ~40° C.) by adding and distilling THF (~50 mL, ~50 mL). After each THF charge, the batch was distilled down to a minimal volume. THF (50 mL) was charged to the 250 mL RBF. KF of a sample showed 0% H$_2$O (≤0.1% acceptable). The batch was polish filtered (60 mL medium-frit funnel) into a clean and dry 250 mL 3-necked-RBF using THF (50 mL) for rinsing and volume adjusting. To the batch was added 4-fluoro-3-nitrobenzoic acid (4.61 g, 1.0 eq), the mixture was cooled to −20° C., and 20% potassium tert-butoxide THF solution (40 mL) was added over 1.5 h, maintaining the batch temperature at −20±10° C. (exothermic). After complete addition, the batch was aged at −20° C. and an aliquot assayed by HPLC after 1.5 h showed 98% conversion. To the batch in the flask was added sat. NH$_4$Cl solution (10 mL), maintaining the temperature at −20±10° C., followed by addition of H$_2$O (20 mL) and MeTHF (34 mL) at −20±20° C. The mixture was warmed to 20° C. and agitated for 13 h. The batch was transferred to a separatory funnel, allowed to settle for ~5 min, and the bottom aqueous layer was removed keeping the rag with the organic stream. The top organic stream was washed with sat. NH$_4$Cl solution (10 mL) and H$_2$O (20 mL) at 20° C. After ~5 min of settling, the aqueous layer was separated. To the total crude organic stream (KF=14%) was added MSA (4 mL) in a 250 mL 3-necked-RBF. The batch was heated to reflux (65° C.) for 25 h and LC assay showed full conversion (≥97%).

The batch was cooled to <20° C. and K$_3$PO$_4$.H$_2$O (4.5 g) and H$_2$O (7 mL) were added. The batch was transferred to a separatory funnel and the bottom aqueous layer was drained to give the aldehyde product crude solution. The combined organic crude stream was concentrated to minimum volume using a rotary evaporator. To the batch in a 500 mL RBF was charged AcOH (~50 mL, ~50 mL) and distilled using a rotary evaporator at reduced pressure (30 mbar, external temp ~40° C.). The THF level was measured by QNMR and none was observed. The mixture was transferred to a 250 mL 3-necked RBF and AcOH was added to adjust the total volume to ~40 mL, when crystallization occurred. To the batch was added H$_2$O (12 mL) over ~1 h. After aging for >1 h, LC assay of supernatant concentration was 9 mg/mL. If concentration is >10 mg/mL then a small portion of H$_2$O (0.2 vol) can be added; after checking by LC, repeat if necessary. The batch was filtered, washed with 20% H$_2$O/AcOH (23 mL) and dried under N$_2$/vacuum for 3.25 h to give the title compound (8.22 g) as an off-white solid (82% yield corrected for purity).

STEP 9B: (R)-TERT BUTYL 4-((6-CHLORO-1-FORMYL-1,2,3,4-TETRAHYDRONAPHTHALEN-1-YL)METHOXY)-3-NITROBENZOATE

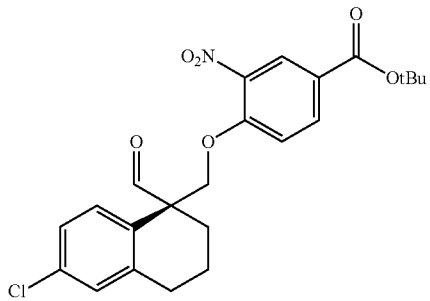 [SMILES: CC(C)(C)OC(=O)c1ccc(OC[C@@]2(C=O)CCCc3cc(Cl)ccc32)c([N+](=O)[O-])c1]

To a solution of (R)-tert-butyl 4-((6-chloro-1-(dimethoxymethyl)-1,2,3,4-tetrahydronaphthalen-1-yl)methoxy)-3-nitrobenzoate (1 g, 2.033 mmol) in anhydrous acetone (41 mL) was added Amberlyst®-15 (1 g, 2.033 mmol; pre-washed with 2×10 mL dry acetone). The mixture was heated to 50° C. for 3.5 h, then filtered and rinsed with DCM. The filtrate was concentrated and dried under high vacuum overnight (it turned a dark red color). LC/MS and NMR analysis suggested 10% of corresponding carboxylic acid was present as well as 0.5 eq mesityl oxide. The mixture was advanced to Step 11 without further purification.

STEP 10: (S)-6'-CHLORO-3',4,4',5-TETRAHYDRO-2H,2'H-SPIRO[BENZO[B][1,4]OXAZEPINE-3,1'-NAPHTHALENE]-7-CARBOXYLIC ACID

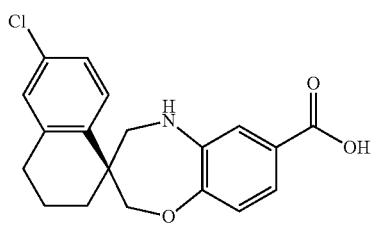 [SMILES: O=C(O)c1ccc2c(c1)NC[C@@]1(CCCc3cc(Cl)ccc31)CO2]

A solution of crude (R)-4-((6-chloro-1-formyl-1,2,3,4-tetrahydronaphthalen-1-yl)methoxy)-3-nitrobenzoic acid (30 g, 77.10 mmol) in AcOH (1 L) was heated to 70° C. and iron powder (28 g, 500 mmol) was added. The resulting mixture was heated for ~4 h at 70° C. AcOH was then removed under reduced pressure and the residue was dissolved in DCE (1 L). Sodium triacetoxy borohydride (46.5 g, 740 mmol) was added portion-wise and the reaction mixture was stirred at ambient temperature for 1 h. The reaction was then quenched with $H_2O$ followed by 10% aqueous citric acid (500 mL). The aqueous phase was extracted with DCM (2×1 L) and the combined organic layer was washed with brine (500 mL), dried over $Na_2SO_4$ and concentrated under reduced pressure. The residue was purified by column chromatography using 100-200 mesh size $SiO_2$ gel (40% EtOAc/Hex) to afford pure (S)-6'-chloro-3',4,4',5-tetrahydro-2H,2'H-spiro[benzo[b][1,4]oxazepine-3,1'-naphthalene]-7-carboxylic acid as white solid (24 g, 99% after two steps).

Alternatively, (S)-6'-chloro-3',4,4',5-tetrahydro-2H,2'H-spiro[benzo[b][1,4]oxazepine-3,1'-naphthalene]-7-carboxylic acid with ((1S,4R)-7,7-dimethyl-2-oxobicyclo[2.2.1]heptan-1-yl)methanesulfonic acid (1:1) may be prepared as follows:

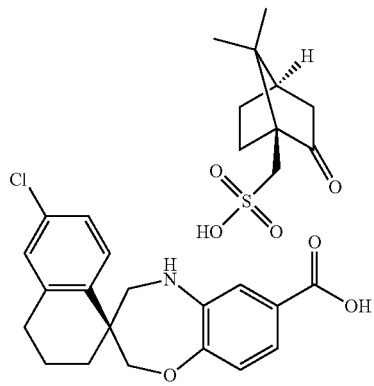

A pressure reactor was charged with (R)-4-((6-chloro-1-formyl-1,2,3,4-tetrahydronaphthalen-1-yl)methoxy)-3-nitrobenzoic acid (20 g, 94 wt %), 5% Pt/S/C wet (2.2 g), THF (400 mL) and titanium isopropoxide (0.5 mL). The reactor was sealed, purged with inert gas (3 cycles, at least once with stirring), and then purged with $H_2$ (1 cycle). The reactor was pressurized with $H_2$ to 70 psig, stirring (950 rpm) was initiated, and the temperature was increased to 90° C. maintaining the $H_2$ pressure in the reactor (70 psig at 22-30° C., 80 psig at 50-60° C. and 90 psig at 88-91C). After 16 h, the reactor was cooled to ambient temperature and purged with inert gas (3 cycles). HPLC analysis of the reaction confirmed >98% conversion.

The reaction mixture was filtered through a Celite® pad (2 inch) using additional THF for rinses, and the filtrate was concentrated under reduced pressure at 40° C. To the residue was added IPA (60 mL) and 24% aqueous MeOH (10 mL). The mixture was stirred for 10 min and then it was filtered through a Celite® pad (2 inch). MeOH was evaporated under reduced pressure at 40° C. and to the concentrated IPA solution cooled to ambient temperature was added a solution of +CSA (56.0 g) in IPA (200 mL) dropwise over 2 h. After 10% of the CSA solution has been added, the mixture was seeded with crystals of the title compound (10-15 mg) followed by the addition of the remaining CSA solution. After stirring at ambient temperature overnight, the mixture was filtered, and the filter cake was washed with 100 mL of IPA and dried under vacuum/$N_2$ at ambient temperature. The product is isolated as a white solid: (S)-6'-chloro-3',4,4',5-tetrahydro-2H,2'H-spiro[benzo[b][1,4]oxazepine-3,1'-naphthalene]-7-carboxylic acid with ((1S,4R)-7,7-dimethyl-2-oxobicyclo[2.2.1]heptan-1-yl)methanesulfonic acid (1:1) (85-88% yield, >99.5% ee).

STEP 11A: (S)-METHYL 6'-CHLORO-3',4,4',5-TETRAHYDRO-2H,2'H-SPIRO[BENZO[B][1,4]OXAZEPINE-3,1'-NAPHTHALENE]-7-CARBOXYLATE

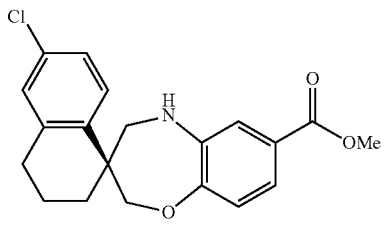 [SMILES: COC(=O)c1ccc2c(c1)NC[C@@]1(CCCc3cc(Cl)ccc31)CO2]

To a solution of (S)-6'-chloro-3',4,4',5-tetrahydro-2H,2'H-spiro[benzo[b][1,4]oxazepine-3,1'-naphthalene]-7-carboxylic acid (130 g, 379 mmol) in methanol (6 L) was added Amberlyst®-15 (130 g, pre-washed with anhydrous methanol) and heated to reflux for 10 h. Amberlyst® was then removed by filtration and rinsed with methanol (3×300 mL). The combined filtrate was concentrated and the residue was purified by column chromatography to give pure (S)-methyl 6'-chloro-3',4,4',5-tetrahydro-2H,2'H-spiro[benzo[b][1,4]oxazepine-3,1'-naphthalene]-7-carboxylate as a white solid (105 g, 77%). Chiral HPLC conditions: Column: ChiralCel® OD-H (250 mm×4.6 mm, 5 ▫m); Mobile Phase: n-Hexane:EtOH: 95:05. Run Time: 25 min. Flow rate: 1 mL/min. Retention time (minor peak): 10.162 min (1.98%); Retention time (major peak): 12.292 min (98.02%).

STEP 11B: (S)-TERTBUTYL 6'-CHLORO-3',4,4',5-TETRAHYDRO-2H,2'H-SPIRO[BENZO[B][1,4]OXAZEPINE-3,1'-NAPHTHALENE]-7-CARBOXYLATE

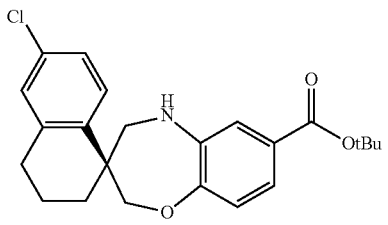 [SMILES: CC(C)(C)OC(=O)c1ccc2c(c1)NC[C@@]1(CCCc3cc(Cl)ccc31)CO2]

To a solution of (R)-tert-butyl 4-((6-chloro-1-formyl-1,2,3,4-tetrahydronaphthalen-1-yl)methoxy)-3-nitrobenzoate (0.9 g, 2.018 mmol) in AcOH (20.22 mL, 353 mmol) at 70° C. was added iron (0.676 g, 12.11 mmol). The mixture was stirred vigorously for 4 h, then concentrated, and the residue was diluted with 20 mL 1,2-DCE. Sodium triacetoxyhydroborate (1.711 g, 8.07 mmol) was added and the mixture was stirred at ambient temperature for 20 min. Upon quenching by addition of 20 mL H₂O, a thick slurry was formed. 20 mL 10% citric acid solution was added and the mixture became lighter in color. The layers were separated and the aqueous layer was extracted with 2×20 mL DCM. The combined organics were washed with 10 mL 10% citric acid and 10 mL brine, dried over MgSO₄, filtered, and concentrated. The residue was deposited on 3 g SiO₂ gel and purified using 5-10% EtOAc in Hex to give (S)-tert-butyl 6'-chloro-3',4,4',5-tetrahydro-2H,2'H-spiro[benzo[b][1,4]oxazepine-3,1'-naphthalene]-7-carboxylate (557 mg, 1.393 mmol, 69.0% yield). Further elution with 30% EtOAc in Hex provided (S)-6'-chloro-3',4,4',5-tetrahydro-2H,2'H-spiro[benzo[b][1,4]oxazepine-3,1'-naphthalene]-7-carboxylic acid (132 mg, 0.384 mmol, 19.02% yield).

STEP 12: (1R,2S)-1,2-CYCLOBUTANEDIYLDIMETHANOL

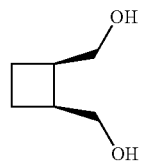

To a rapidly stirred solution of LAH (1.0 M solution in THF, 1000 mL, 1000 mmol) at ambient temperature in a 3000 mL 3-necked RBF under a stream of argon, solid (1R,5S)-3-oxabicyclo[3.2.0]heptane-2,4-dione (40 g, 317 mmol) was gradually added over 2 h, maintaining the internal temperature of the reaction mixture below 50° C. The reaction was stirred overnight at ambient temperature under argon. After 16 h, the reaction mixture was cooled by an ice bath to 10° C., and, under a fast stream of argon, a solution of 36 mL H₂O was added drop wise by addition funnel at a rate that maintained the temperature between 12-15° C., approximately 1 mL/min, with vigorous stirring (500 rpm). The mixture was then vigorously stirred (500 rpm) in the ice-bath for 1 h, then removed from the bath and stirred to rt for 1 h before cooling again with an ice bath to 5-10° C. To the mixture was added 36 mL of a 15% NaOH aqueous solution over a period of 45 min, maintaining the temperature between 10-20° C. To the mixture was added 108 mL H₂O drop wise by addition funnel, maintaining the temperature between 10-20° C., over ~1 h. Upon completed addition of the H₂O, the flask was removed from the ice bath, equilibrated to rt and left to stir vigorously under argon overnight. After stirring for 16 h, the mixture was filtered and the filtrate concentrated under reduced pressure to afford a colorless, slightly opaque oil. The oil was taken up in Et₂O and stirred over anhydrous MgSO₄ and filtered through a pad of Celite®. The filtrate concentrated under reduced pressure to afford 32.8 g of a colorless oil, which was used in the next step without further purification (89% yield).

STEP 13: CIS-CYCLOBUTANE-1,2-DIYLBIS(METHYLENE) DIACETATE

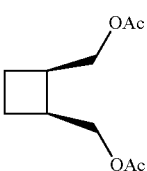

Ac₂O (2.59 mL; 3.0 eq) was added to the CIS-1,2-cyclobutanediyldimethanol (1.06 g, 9.15 mmol) and the resulting solution was heated to 50° C. After stirring overnight, the mixture was assayed by GC and showed complete conversion. The mixture was then diluted with 15 mL of heptane and concentrated under vacuum to give a clear oil.

The oil was dissolved in 15 mL heptane and concentrated back down to an oil (azeotropic removal of Ac₂O) to give the title compound as an oil (1.827 g, 88% yield, 88.3% purity by QNMR using benzyl benzoate as an internal standard).

STEP 14:
((1R,2S)-2-(HYDROXYMETHYL)CYCLOBUTYL) METHYL ACETATE

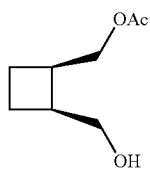 [SMILES: CC(=O)OC[C@H]1CC[C@H]1COC(C)=O]

A 12 L 3-neck-RBF equipped with mechanical stirrer was charged with a 1M sodium citrate solution (prepared by mixing sodium citrate tribasic dihydrate; 682 g, 2320 mmol) and H₂O to reach total volume ~2.3 L) and 3.48 L H₂O (~25° C.). The mixture was cooled using an ice/H₂O bath to ~20.2° C. pH~8.46 (measured with pH probe). Amano Lipase from *Pseudomonas fluorescens* (41.8 g, 1547 mmol) was then added in one charge (pH~8.12) and the mixture was vigorously stirred at ambient temperature for ~5 min. (1R,2S)-cyclobutane-1,2-diylbis(methylene) diacetate (348 g, 1547 mmol) was added in one charge and the resulting mixture was stirred vigorously at ambient temperature monitoring internal temperature and pH. After stirring the mixture overnight (~20.9° C. and pH~5.45) an aliquot was collected, extracted with IPAc, diluted with MeCN and analyzed by GC and the reaction was deemed complete (1.21% SM leftover, 0.17% of enantiomer, 1.8% of diol). Celite® (70 g) was added to the reaction mixture and the slurry was filtered through a Celite® pad on a medium porosity glass filter (fast filtration, 15-20 min), rinsing with 2.5 L IPA. The biphasic mixture was transferred into a 12 L-extractor and stirred for 1 min. The aqueous layer was separated and extracted with IPAc (1×4 L), and the combined organic extract was concentrated in vacuo obtaining 337.28 g (99.6% ee; 50-60 mol % of residual IPA by ¹HNMR; QNMR: 37.63 mg+benzyl benzoate (Aldrich catalog #B6630, lot #MKBG9990V, 61.27 mg; Result: 65 wt %; corrected yield 89%). The crude product was used as such for the next step.

STEP 15:
((1R,2R)-2-FORMYLCYCLOBUTYL)METHYL ACETATE

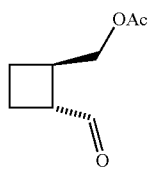 [SMILES: CC(=O)OC[C@@H]1CC[C@H]1C=O]

A 2-L Atlas reactor was charged with ((1R,2S)-2-(hydroxymethyl)cyclobutyl)methyl acetate (126.39 g, 79.6 wt % by QNMR; 636 mmol) and 1 L of DCM and the jacket temperature was set to 20° C. Iodobenzene diacetate (225 g, 700 mmol) was added as a solid (endothermic addition: the temperature decreased to 15° C.). TEMPO (3.97 g, 25.4 mmol) was added as a solid in one portion resulting in a cloudy orange solution, which became clear over the course of 20 min. After stirring at 20° C. overnight, an aliquot was collected, diluted with MeOH, and analyzed by GC. An Additional kicker charge of iodobenzene diacetate and TEMPO can be used to push the reaction to completion if necessary. The reaction mixture was then cooled to 1.8° C. (internal temperature, ice/dry ice/H₂O bath) and DIPEA (194 mL, 1113 mol) was added drop-wise via addition funnel over 65 min keeping internal temperature <5° C. The cooling bath was removed and the mixture was allowed to warm to ambient temperature with stirring. After 48 h an aliquot was collected, diluted with methanol, and analyzed by GC showing a 12:1 ratio of trans:cis isomers. The reaction mixture was then cooled to <5° C. (ice/H₂O bath) and H₂O (230 mL) was added over ~10 min (internal temperature reached 14° C.). The organic layer was separated, washed with H₂O (125 mL) and 1M aqueous NaH₂PO₄ (90 mL) and concentrated in vacuo to afford 273.4 g of ((1R,2R)-2-formylcyclobutyl)methyl acetate (QNMR: 68.85 mg+benzyl benzoate (Aldrich catalog #B6630, Lot #MKBG9990V, 72.36 mg). The crude product was used as such for next step.

STEP 16: ((1R,2R)-2-((R)-(1H-BENZO[D][1,2,3]TRIAZOL-1-YL)(HYDROXY)METHYL)CYCLOBUTYL)METHYL ACETATE

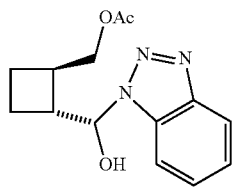 [SMILES: CC(=O)OC[C@@H]1CC[C@H]1C(O)n1nnc2ccccc21]

To a solution of crude ((1R,2R)-2-formylcyclobutyl)methyl acetate (5 g, 10.27 mmol) in 8 mL MTBE was added benzotriazole (1.296 g, 10.00 mmol) as a solid (slightly exothermic). The clear solution became increasingly cloudy and a precipitate formed. The mixture was allowed to equilibrate overnight at ambient temperature then heptane was added (6 mL). After aging for 6 h the mixture was filtered at ambient temperature and washed with 10 mL of 1:1 MTBE/heptane. The white solid was air dried on the frit under vacuum obtaining 2.48 g of ((1R,2R)-2-((R)-(1H-benzo[d][1,2,3]triazol-1-yl)(hydroxy)methyl)cyclobutyl) methyl acetate.

STEP 17: (S)-METHYL 5-(((1S,2R)-2-ACETOXY-CYCLOBUTYL)METHYL)-6'-CHLORO-3',4,4',5-TETRAHYDRO-2H,2'H-SPIRO[BENZO[B][1,4]OXAZEPINE-3,1'-NAPHTHALENE]-7-CARBOXYLATE

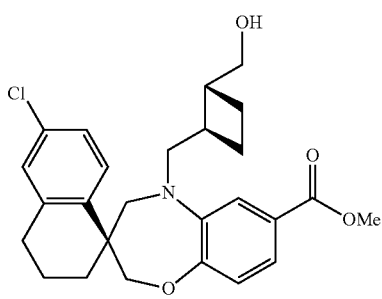 [SMILES: COC(=O)c1ccc2c(c1)N(C[C@@H]1CC[C@H]1CO)C[C@@]1(CCCc3cc(Cl)ccc31)CO2]

(((1R,2R)-2-Formylcyclobutyl)methyl acetate (from Step 15; 4.36 g, 27.9 mmol) was added to a solution of (S)-methyl 6'-chloro-3',4,4',5-tetrahydro-2H,2'H-spiro[benzo[b][1,4]oxazepine-3,1'-naphthalene]-7-carboxylate (from Intermediate 11A1 Step 11A, 5.0 g, 13.97 mmol) in DCM (78 mL) and AcOH (38.8 mL). The solution was stirred at ambient temperature for 10 min, then cooled to 0° C., and sodium cyanoborohydride (1.463 mL, 27.9 mmol) was added slowly over 1 h. The mixture was stirred at 0° C. for 10 min, then poured slowly into cold NaOH solution, and extracted with EtOAc (120 mL). The organic phase was washed with brine, dried over anhydrous $Na_2SO_4$, and concentrated. The residue was loaded to a 220 g ISCO gold column and eluted with 0% to 10% EtOAc/Hex to provide the title compound 6.0 g of the title compound as a white solid. m/z (ESI+ve ion) 498.1 (M+H)+.

STEP 18A: (S)-METHYL 6'-CHLORO-5-(((1R,2R)-2-(HYDROXYMETHYL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

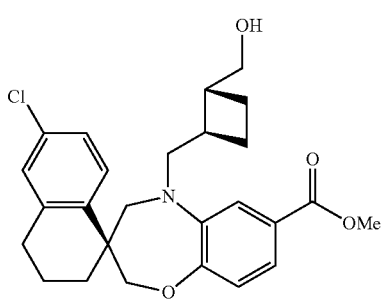 [SMILES: COC(=O)c1ccc2c(c1)N(C[C@@H]1CC[C@H]1CO)C[C@@]1(CCCc3cc(Cl)ccc31)CO2]

KOH (0.278 mL, 10.14 mmol) was added to a solution of (S)-methyl 5-(((1R,2S)-2-(acetoxymethyl)cyclobutyl)methyl)-6'-chloro-3',4,4',5-tetrahydro-2H,2'H-spiro[benzo[b][1,4]oxazepine-3,1'-naphthalene]-7-carboxylate (from Step 17; 1.530 g, 3.07 mmol) in MeOH (99 mL). The mixture was stirred at ambient temperature for 4 h, then neutralized with 1N HCl to pH=7, and concentrated under reduced pressure. The aqueous residue was extracted with EtOAc (400 mL) and the organic extract was washed with brine, dried over anhydrous $Na_2SO_4$, and filtered through a short plug of $SiO_2$ gel to afford the title compound as a white solid. (1.354 g was obtained. m/z (ESI, +ve ion) 456.2 $(M+H)^+$)

Alternatively, (S)-methyl 6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate may be prepared as follows:

To a slurry of (S)-6'-chloro-3',4,4',5-tetrahydro-2H,2'H-spiro[benzo[b][1,4]oxazepine-3,1'-naphthalene]-7-carboxylic acid with ((1S,4R)-7,7-dimethyl-2-oxobicyclo[2.2.1]heptan-1-yl)methanesulfonic acid (1:1) (Step 10) (32.22 g, 52.5 mmol) and ((1R,2R)-2-((R)-(1H-benzo[d][1,2,3]triazol-1-yl)(hydroxy)methyl)cyclobutyl)methyl acetate (Step 16) (15.89 g, 57.7 mmol) in DCM (226 mL, 7 mL/g) was added sodium triacetoxylborohydride (13.90 g, 65.6 mmol) in 4 portions over 30 min. Additional ((1R,2R)-2-((R)-(1H-benzo[d][1,2,3]triazol-1-yl)(hydroxy)methyl)cyclobutyl)methyl acetate (2.89 g, 10.50 mmol) and sodium triacetoxyborohydride (2.78 g, 13.12 mmol) were added to drive the reaction to completion (determined by HPLC assay). 80 mL of $H_2O$ was then added and the resulting mixture was agitated for 5 min. The layers were separated, the organic phase was washed with 60 mL $H_2O$ and 20 mL of brine, and then concentrated to an oil under reduced pressure. The residue was dissolved in 50 mL of MeOH and 40 mL of 5N NaOH were then added at ambient temperature (exothermic). Upon reaction completion (determined by HPLC assay), the reaction mixture was partitioned between 133 mL of MTBE and 35 mL of 1.5 M citric acid. The organic phase was transferred to a RBF and the solvent was exchanged to MeCN via atmospheric distillation. This solution was seeded at 62° C. (a slurry developed), was allowed to reach ambient temperature, and then aged overnight. The slurry was filtered at 20.5° C. through a coarse frit glass sinter funnel and the filter cake was washed using 60 mL of MeCN, then dried in a vacuum oven at 40° C. to constant weight. Final mass: 21.87 g (96.4 w t % by HPLC).

A 100 mL 3-necked-RBF was charged with (S)-6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylic acid (4.53 g, 1.0 eq), MeOH (45 mL, 10 vol), and then a prepared solution of $SOCl_2$ (11.28 mL, 1.0M in MeCN, 1.1 eq). Under an atmosphere of $N_2$, the batch was heated to 55° C. and stirred for 18 h (or until >99% conversion as determined by HPLC). The reaction mixture was then allowed to cool to 20° C. over 2 h. To the resulting white slurry was added Hunig's base (3.94 mL, 2.2 eq) and after aging for 0.5 h, $H_2O$ (9.0 mL, 2 V) was added as antisolvent over 1 h. The white slurry was aged for >2 h and the batch was filtered through a glass-fritted filter and the cake was washed with MeOH/$H_2O$ (5:1 v/v) (9.0 mL, 2V) then MeOH/$H_2O$ (2:1 v/v) (9.0 mL, 2V). The cake was dried under $N_2$ with vacuum for 12 h at ambient temperature. The product was obtained as a white solid (4.36 g, 92% yield).

STEP 18B: (S)-TERTBUTYL 6'-CHLORO-5-(((1R,2R)-2-(HYDROXYMETHYL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

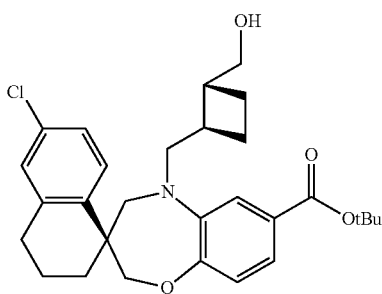 [SMILES: CC(C)(C)OC(=O)c1ccc2c(c1)N(C[C@@H]1CC[C@H]1CO)C[C@@]1(CCCc3cc(Cl)ccc31)CO2]

The title compound was synthesized from (S)-tertbutyl 6'-chloro-3',4,4',5-tetrahydro-2H,2'H-spiro[benzo[b][1,4]oxazepine-3,1'-naphthalene]-7-carboxylate (Step 11B) following the procedures described for Intermediate AA11A, Steps 17-18A.

STEP 19A: (S)-METHYL 6'-CHLORO-5-(((1R,2R)-2-FORMYLCYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

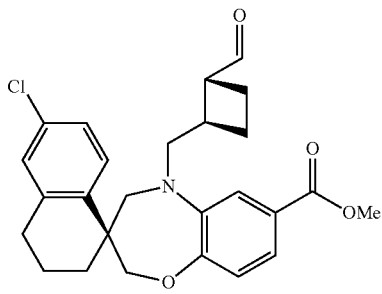 [SMILES: COC(=O)c1ccc2c(c1)N(C[C@@H]1CC[C@H]1C=O)C[C@@]1(CCCc3cc(Cl)ccc31)CO2]

To a cooled (−70° C.) solution of DMSO (7.12 mL, 2.5 eq) and DCM (183 mL, 10 vol) in a 1 L 3-necked-RBF inerted with $N_2$ was added oxalyl chloride (26.1 mL, 1.0M in DCM, 1.3 eq) at a rate to maintain temperature below −70° C. The batch was aged below −70° C. for 30 min and then a prepared solution of (S)-methyl 6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate (from Step 18A; 18.3 g, 1.0 eq) in DCM (183 mL, 10 vol) was added at a rate to maintain reaction temperature <−70° C. The batch was aged for 1.5 h and then $Et_3N$ (22.4 mL, 4.0 eq) was added at a rate to maintain batch temperature <−70° C. After aging for 1 h, the batch was allowed to warm to −20° C. and $H_2O$ (366 mL, 20 vol) was added. The batch was agitated at 20° C. and the phases separated. The organic layer was washed with 2×1N HCl (183 mL, 10 vol) and brine (183 mL, 10 vol). The organic layer was polish filtered and concentrated in vacuo to afford (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (19.91 g, 94% yield corrected for wt %) as a tan foam.

STEP 19B: (S)-TERTBUTYL 6'-CHLORO-5-(((1R,2R)-2-FORMYLCYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

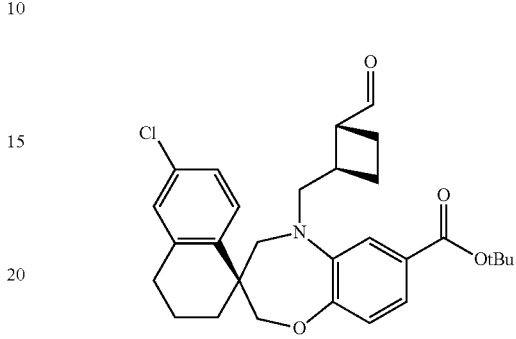

The title compound was synthesized from (S)-tertbutyl 6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate (from Step 18B) following the procedure described for Intermediate AA11A, step 19A.

STEP 20: (S)-METHYL 6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

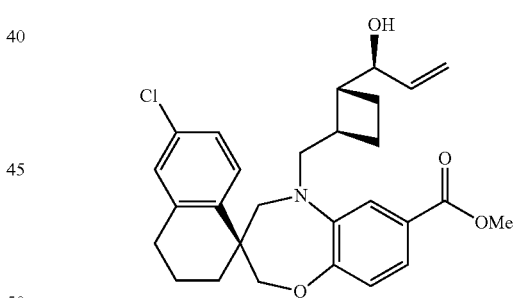

An oven dried 3-necked-RBF equipped with a pressure-equalizing addition funnel, thermocouple, and magnetic stirbar was cooled to ambient temperature under a purge of argon gas. The flask was charged with (1R,2S)-2-morpholino-1-phenylpropan-1-ol (40.2 g, 182 mmol; prepared according to the literature procedure by Brubaker, J. D.; Myers, A. G. Org. Lett. 2007, 9, 3523-3525) against a positive pressure of argon. The addition funnel was charged with toluene (450 mL), which was dropped into the reactor. The solution was cooled in an ethyleneglycol-$CO_2$ bath (~−12° C.) and treated with butyllithium solution (2.5 M in Hex, 72.6 mL, 182 mmol), causing a white solid to precipitate that gradually went into solution as it was stirred over 30 min. Divinylzinc solution (605 mL, 182 mmol; prepared according to Brubaker, J. D.; Myers, A. G. Org. Lett. 2007, 9, 3523-3525. The concentration of divinylzinc solution was determined by titrating against iodine (Krasovskiy, A.; Knochel, P. Synthesis 2006, 890-891; concentration was generally ~0.25M) was added, and the solution was aged with stirring in the cold bath for 1 h; the internal temperature was −15° C. (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (from Step 19A; 48.5 g, 107 mmol) (azeotroped thrice with toluene) was added as a solution in toluene (200 mL, 150 mL+2×25 mL cannula/vial rinse) via cannula (16 G), over 20 min. The internal temperature rose to −10° C. The mixture was stirred for 90 min while maintaining the internal reaction temperature below −5° C. The addition funnel was charged with 30% w/w aqueous citric acid (450 mL), then the reaction was quenched by adding the solution to the reaction mixture. The reactor was removed from the bath and permitted to stir at ambient temperature. The solution was transferred to a separatory funnel and the flask was rinsed with toluene and 30% aqueous citric acid (50 mL each). The layers were mixed and then separated. The organic layer was washed with H$_2$O (250 mL), then brine (250 mL), and finally dried with MgSO$_4$. The solution was filtered and concentrated to yield a yellow oil, ~90 g after vacuum overnight, 20:1 dr. This was split into 3 batches and purified by column chromatography 10 to 20% EtOAc/Hex 1.5 kg SiO$_2$, to provide (S)-methyl-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylate (43.3 g, 84%). The aqueous layer and washings were placed in an ice/H$_2$O bath and basified to pH>13 by addition of 8N aqueous NaOH. This solution was then extracted with toluene (3×250 mL). The combined organic extracts were washed with H$_2$O (250 mL) and brine (250 mL), then dried with MgSO$_4$. The solution was filtered and concentrated to recover the ligand in >95% yield.

STEP 21: (S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID

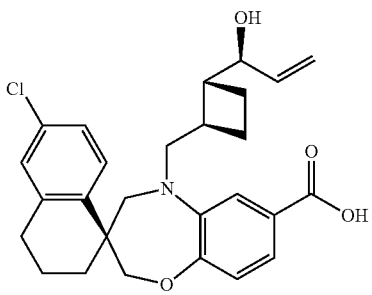 [SMILES: C=C[C@H](O)[C@@H]1CC[C@H]1CN1C[C@@]2(CCCc3cc(Cl)ccc32)COc2ccc(C(=O)O)cc21]

To a solution of (S)-methyl 6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylate (from Step 20; 4.59 g, 9.52 mmol) in a mixture of THF (18 mL), MeOH (6.00 mL) and H$_2$O (6.00 mL) was added LiOH.H$_2$O (0.799 g, 19.05 mmol) and the reaction was stirred at 50° C. for 4 h. The reaction mixture was concentrated to 15 mL, cooled to 0° C. and acidified with 2N HCl to pH=3. The resulting viscous oil was diluted with 20 mL of H$_2$O and 50 mL of EtOAc and a clear two-layer mixture was obtained. More EtOAc (ca. 200 mL) was added and the organic layer was separated, washed with brine, dried with MgSO$_4$, filtered and concentrated under reduced pressure. The crude material was loaded onto a column (220 g), and purified with EtOAc in Hex using the following gradient: 0-2.5 min 0% of EtOAc, 2.5 min-6 min 0-20% EtOAc, 6 min-35 min 20-60% EtOAc, 35 min-40 min 70% EtOAc to give (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (4.22 g, 9.02 mmol, 95% yield) as a white solid.

Intermediate AA13A (S)-6'-CHLORO-5-(((1R,2R)-2-((S)-1-HYDROXYBUT-3-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID

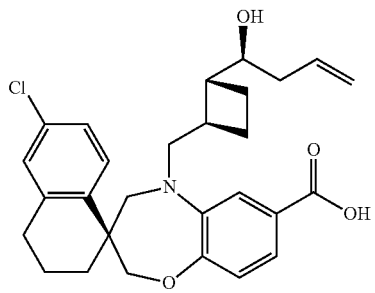 [SMILES: C=CC[C@H](O)[C@@H]1CC[C@H]1CN1C[C@@]2(CCCc3cc(Cl)ccc32)COc2ccc(C(=O)O)cc21]

STEP 1A: (S)-METHYL 6'-CHLORO-5-(((1R,2R)-2-((S)-1-HYDROXYBUT-3-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

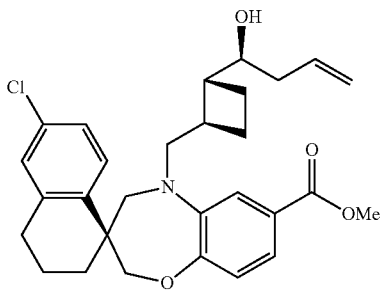 [SMILES: C=CC[C@H](O)[C@@H]1CC[C@H]1CN1C[C@@]2(CCCc3cc(Cl)ccc32)COc2ccc(C(=O)OC)cc21]

An oven-dried 200-mL flask charged with a suspension of (1R,2R)—N-methyl-1-phenyl-1-(((1S,5S,10R)-10-(trimethylsilyl)-9-borabicyclo[3.3.2]decan-9-yl)oxy)propan-2-amine (5.40 g, 14.54 mmol) in Et$_2$O (73 mL) under argon was cooled to −78° C. and treated with allylmagnesium bromide (13.22 mL, 13.22 mmol) solution, dropwise. The mixture was allowed to warm to ambient temperature and stirred for 1 h. The solution (0.17 M; solution A) was then recooled to −78° C.

A separate 200 mL flask charged with ((S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7. carboxylate (Intermediate AA1A, Step 19A, 2.0 g, 4.41 mmol) in Et$_2$O (22.03 mL) under argon was cooled to −78° C. To this solution was added 40 mL of the above-referenced solution A and the resulting mixture was stirred at −78° C. for 40 min. 4-methylmorpholine 4-oxide (3.10 g, 26.4 mmol) was then added and the mixture was allowed to warm to ambient temperature for 10 min. Methanol (10 mL) was added and the volatile organics were evaporated under reduced pressure at ambient temperature. Additional methanol (100 mL) was added and after stirring at ambient temperature for 1 h the mixture was concentrated. The residue was diluted with EtOAc (450 mL), washed with 1N HCl (15 mL), Na$_2$CO$_3$ solution (10 mL), and brine (6 mL), dried over anhydrous Na$_2$SO$_4$ and concentrated. The residue was loaded to a 220 g ISCO gold column and eluted with 0% to 5% EtOAc/Hex, to provide 1.88 g of the title compound as a white solid. m/z (ESI, +ve ion) 496.0 (M+H)+.

STEP 1B: (S)-TERTBUTYL 6'-CHLORO-5-(((1R,2R)-2-((S)-1-HYDROXYBUT-3-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

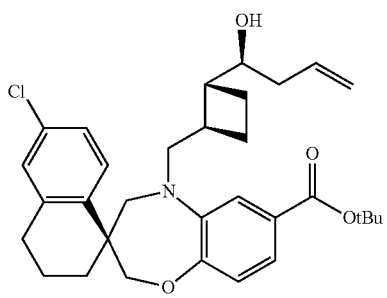 [SMILES: C=CC[C@H](O)[C@@H]1CC[C@H]1CN1C[C@@]2(CCCc3cc(Cl)ccc32)COc2ccc(C(=O)OC(C)(C)C)cc21]

The title compound was synthesized from (S)-tert-butyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 19B; 3.0 g) following the procedure described for Intermediate AA13A, Step 1A. The crude material was purified on a 220 g SiO$_2$ gel column eluting with 5% EtOAc in Hex over 60 min to provide (S)-tert-butyl 6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate (2.19 g).

STEP 2: (S)-6'-CHLORO-5-(((1R,2R)-2-((S)-1-HYDROXYBUT-3-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID

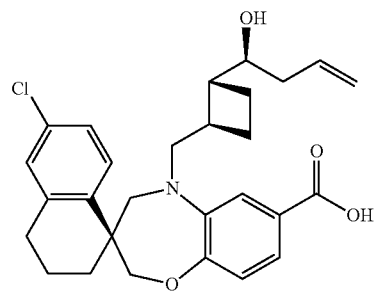 [SMILES: C=CC[C@H](O)[C@@H]1CC[C@H]1CN1C[C@@]2(CCCc3cc(Cl)ccc32)COc2ccc(C(=O)O)cc21]

A mixture of (S)-methyl 6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate (from Intermediate AA13A, Step 1A; 1.88 g, 3.79 mmol) and LiOH solution (1M) (34.1 mL, 34.1 mmol) in MeOH (34 mL) and THF (50 mL) was stirred at 65° C. for 50 min. After cooling to ambient temperature, the mixture was acidified with 1N HCl to pH 2 to 3, extracted with EtOAc (350 mL), dried over anhydrous Na$_2$SO$_4$ and concentrated to provide 1.82 g of the title compound as a white solid. m/z (ESI, +ve ion) 482.0 (M+H)+.

Alternatively, the title compound may be synthesized as follows:

To a solution of (S)-tert-butyl 6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate (Intermediate AA13A, Step 1B; 250 mg, 0.465 mmol) in DCM (3.717 mL) at ambient temperature, TFA (0.929 mL) was added and the reaction mixture was stirred for 4 h. The crude reaction mixture was then concentrated, the residue was taken up in EtOAc, washed once with sat. NaHCO$_3$, dried over MgSO$_4$, filtered and concentrated to give a white foam. The crude material was used as such, without further purification.

Example 1

METHYL (1S,3'R,6'R,7'S,8'E,15'R)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE

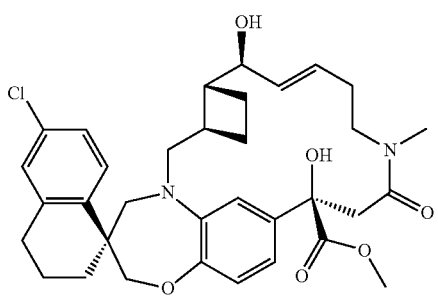 [SMILES: COC(=O)[C@@]1(O)CC(=O)N(C)CC/C=C/[C@H](O)[C@@H]2CC[C@H]2CN2C[C@@]3(CCCc4cc(Cl)ccc43)COc3ccc1cc32]

Step 1. Sulfur ylide. Reference: Lippert, A. R. *JACS*, 133(11), 3776-3779.

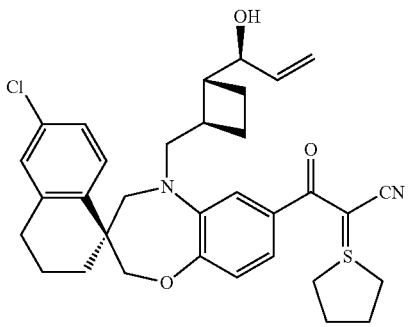 [SMILES: C=C[C@H](O)[C@@H]1CC[C@H]1CN1C[C@@]2(CCCc3cc(Cl)ccc32)COc2ccc(C(=O)C(C#N)=S3CCCC3)cc21]

(S)-6'-chloro-5-(((1R,2R)-2-((S)-1-hydroxyallyl)cyclobutyl)methyl)-3',4',5-tetrahydro-2H,2'H-spiro[benzo[b][1,4]oxazepine-3,1'-naphthalene]-7-carboxylic acid (synthesis described in Intermediate AA11A) (300 mg, 0.641 mmol) was diluted in DCM (9.953 mL). O-(benzotriazol-1-yl)-N,N,N,N-tetramethyluronium hexafluorophosphate, HBTU (365 mg, 0.962 mmol), 1-(cyanomethyl)tetrahydro-1H-thiophen-1-ium bromide (173 mg, 0.833 mmol) and N,N-diisopropylethylamine solution (0.335 mL, 1.923 mmol) were added and the reaction was stirred at room temperature overnight. The crude was concentrated and absorbed onto a plug of silica gel and purified by chromatography through a Redi-Sep pre-packed silica gel column (40 g), eluting with a gradient of 0% to 10% MeOH in DCM, to provide the above compound (366 mg, 99% yield). $^1$H NMR (500 MHz, CD$_2$Cl$_2$) δ 7.80-7.65 (m, 1H), 7.40 (s, 1H), 7.32 (d, J=8.07 Hz, 1H), 7.16 (d, J=8.56 Hz, 1H), 7.08 (s, 1H), 6.86 (dd, J=2.32, 8.19 Hz, 1H), 5.92-5.75 (m, 1H), 5.23 (d, J=17.12 Hz, 1H), 5.04 (d, J=10.51 Hz, 1H), 4.15-3.96 (m, 4H), 3.77 (d, J=14.92 Hz, 1H), 3.63 (d, J=14.18 Hz, 1H), 3.53-3.3 (m, 4H), 3.25 (d, J=14.18 Hz, 1H), 3.18-3.05 (m, 1H), 2.45-2.63 (m, 3H), 2.10 (d, J=3.67 Hz, 2H), 1.94-1.75 (m, 3H), 1.70-1.54 (m, 3H), 1.51-1.34 (m, 3H), 1.23 (dt, J=2.45, 7.21 Hz, 2H). LRMS: (ESI, +ve ion) m/z 577.2 (M+H)$^+$.

Step 2. 2-((S)-6'-CHLORO-5-(((1R,2R)-2-((S)-1-HYDROXYALLYL)CYCLOBUTYL)METHYL)-3',4',5-TETRAHYDRO-2H,2'H-SPIRO[BENZO[B][1,4]OXAZEPINE-3,1'-NAPHTHALEN]-7-YL)-2-OXOACETIC ACID (Reference: Lippert, A. R. *JACS*, 133(11),3776-3779)

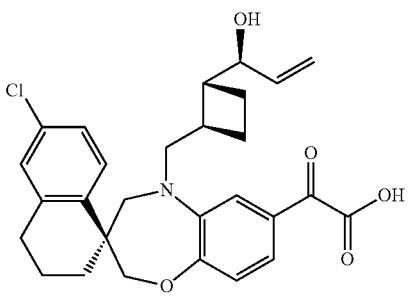 [SMILES: C=C[C@H](O)[C@@H]1CC[C@H]1CN1C[C@@]2(CCCc3cc(Cl)ccc32)COc2ccc(C(=O)C(=O)O)cc21]

The sulfur ylide from Step 1 (365 mg, 0.632 mmol) was dissolved in THF (4.216 mL) and water (2.108 mL). Oxone, monopersulfate compound (1166 mg, 1.897 mmol) was added and the suspension was stirred for 30 minutes. After this period the reaction mixture was poured into water (90 mL) and diethyl ether (90 mL) and the fractions were separated. The aqueous phase was washed twice with diethyl ether (2×90 mL). The combined organic layer were dried over magnesium sulfate, filtered and concentrated. 10 ml of toluene was added to the crude and concentrated under vacuo to give the title product. The latter was taken to the next step without further purification assuming 100% yield. $^1$H NMR (400 MHz, CDCl$_3$) δ 7.73-7.62 (m, 3H), 7.17 (dd, J=2.35, 8.41 Hz, 1H), 7.09 (d, J=2.35 Hz, 1H), 7.02-6.92 (m, 1H), 5.83 (ddd, J=6.06, 10.71, 17.07 Hz, 1H), 5.25 (td, J=1.44, 17.26 Hz, 1H), 5.10 (td, J=1.34, 10.42 Hz, 1H), 4.20-4.02 (m, 3H), 3.77 (d, J=13.30 Hz, 1H), 3.64 (d, J=14.28 Hz, 1H), 3.30 (d, J=14.28 Hz, 1H), 3.14 (dd, J=9.68, 15.16 Hz, 1H), 3.03-2.92 (m, 1H), 2.68-2.80 (m, 2H), 2.54 (t, J=8.90 Hz, 1H), 2.22-2.16 (m, 1H), 1.78-2.11 (m, 5H), 1.74-1.54 (m, 2H), 1.50-1.41 (m, 1H). LRMS: (ESI, +ve ion) m/z 496.2 (M+H)$^+$.

Step 3. METHYL 2-((S)-6'-CHLORO-5-(((1R,2R)-2-((S)-1-HYDROXYALLYL)CYCLOBUTYL)METHYL)-3',4',5-TETRAHYDRO-2H,2'H-SPIRO[BENZO[B][1,4]OXAZEPINE-3,1'-NAPHTHALEN]-7-YL)-2-OXOACETATE

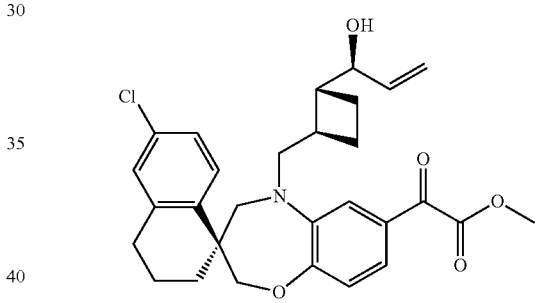

To a solution of 2-((S)-6'-chloro-5-(((1R,2R)-2-((S)-1-hydroxyallyl)cyclobutyl)methyl)-3',4',5-tetrahydro-2H,2'H-spiro[benzo[b][1,4]oxazepine-3,1'-naphthalen]-7-yl)-2-oxoacetic acid (1.060 g, 2.137 mmol) (from Step 2) and triethylamine (0.297 mL, 2.137 mmol) in DCM (8.55 mL) at 23° C. was added methyl chloroformate (0.165 mL, 2.137 mmol). After 1 h, the reaction was diluted with EtOAc and washed with water, then brine. The combined organic layer were dried over sodium sulfate, filtered and concentrated in vacuo. The crude material was absorbed onto a plug of silica gel and purified by chromatography through a Redi-Sep pre-packed silica gel column (80 g), eluting with a gradient of 0% to 100% EtOAc in hexane to provide methyl 2-((S)-6'-chloro-5-(((1R,2R)-2-((S)-1-hydroxyallyl)cyclobutyl)methyl)-3',4',5-tetrahydro-2H,2'H-spiro[benzo[b][1,4]oxazepine-3,1'-naphthalen]-7-yl)-2-oxoacetate (1.0 g, 1.961 mmol, 92% yield) as colorless solid/film. $^1$H NMR (400 MHz, CD$_2$Cl$_2$) δ 7.71 (d, J=8.41 Hz, 1H), 7.60 (d, J=1.96 Hz, 1H), 7.29 (dd, J=2.15, 8.22 Hz, 1H), 7.27-7.21 (m, 1H), 7.20-7.15 (m, 2H), 7.10 (d, J=2.15 Hz, 1H), 6.96 (d, J=8.22 Hz, 1H), 5.83 (ddd, J=5.97, 10.47, 17.21 Hz, 1H), 5.24 (td, J=1.47, 17.22 Hz, 1H), 5.07 (td, J=1.64, 10.22 Hz, 1H), 4.23-4.08-(m, 2H), 4.08-4.00 (m, 1H), 3.80 (dd, J=2.64, 14.97 Hz, 1H), 3.65 (d, J=14.28 Hz, 1H), 3.31 (d, J=14.28 Hz, 1H), 3.18 (dd, J=9.19, 15.06 Hz, 1H), 2.84-2.69 (m, 2H), 2.56 (d, J=4.69 Hz, 1H), 2.54-2.48 (m, 1H), 2.34 (s, 1H), 2.11-1.99 (m, 3H), 1.96-1.78 (m, 3H), 1.73-1.55 (m, 2H), 1.52-1.43 (m, 1H). LRMS: (ESI, +ve ion) m/z 510.2 (M+H).

Step 4. 4-TERT-BUTYL 1-METHYL 2-(6'-CHLORO-5-((2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXYSUCCINATE

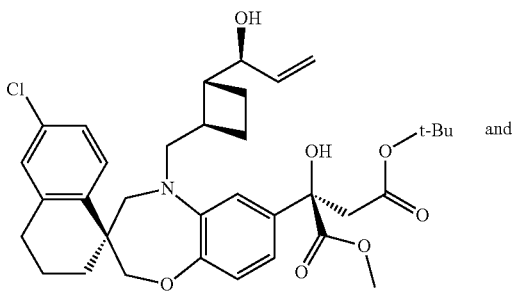

and

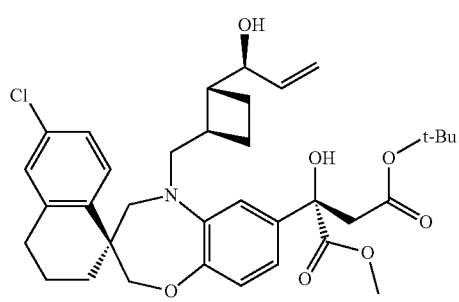

Step 5. 3-((S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-3-HYDROXY-4-METHOXY-4-OXOBUTANOIC ACID

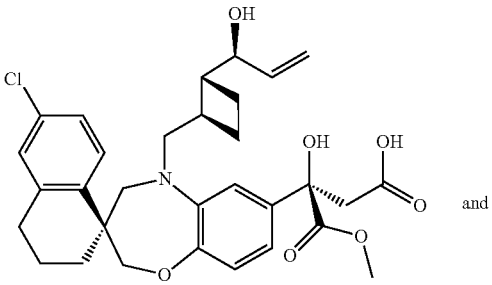

and

Under Argon, to a solution of methyl 2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-oxoacetate (Step 3, 310 mg, 0.608 mmol) in THF (1.2 mL) was added 2-tert-butoxy-2-oxoethylzinc chloride (0.5 M in diethyl ether) (3.65 mL, 1.823 mmol). The reaction mixture was stirred at room temperature for 1 h and was then quenched with water. Sodium bicarbonate was added and the aqueous layer was extracted with diethyl ether. The combined organic layer was dried over magnesium sulfate, filtered, concentrated and taken into the next step without further purification, quantitive yield. The product was isolated as a 2:1 mixture of isomers. NMR of the mixture: ¹H NMR (400 MHz, CD₂Cl₂) δ 7.77-7.60 (m, 1H), 7.15 (dd, J=2.25, 8.51 Hz, 1H), 7.11-7.03 (m, 2H), 6.85-6.82 (m, 1H), 5.92-5.78 (m, 1H), 5.30-5.19 (m, 1H), 5.13-5.02 (m, 1H), 4.16-3.94 (m, 4H), 3.77-3.73 (m, 3H), 3.65 (d, J=14.08 Hz, 1H), 3.46-3.31 (m, 1H), 3.30-3.08 (m, 2H), 2.93-2.68 (m, 4H), 2.57-2.41 (m, 1H), 2.12-2.01 (m, 3H), 1.96-1.78 (m, 3H), 1.72-1.53 (m, 2H), 1.46-1.41-(m, 9H), 1.24 (t, J=7.14 Hz, 1H). LRMS: (ESI, +ve ion) m/z 626.2 (M+H)⁺.

To a flask containing 4-tert-butyl 1-methyl 2-(('S)-6'-chloro-5-((2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxysuccinate (2:1 mixture of isomers from Step 4, 218 mg, 0.348 mmol) was added trifluoroacetic acid (1.0 mL, 13.46 mmol) (neat). The reaction mixture was stirred at 23° C. for 1 h, then diluted with toluene (10 mL) and concentrated in vacuo. This sequence was repeated twice, which provided 3-((1'S)-6'-chloro-5-((2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-3-hydroxy-4-methoxy-4-oxobutanoic acid (195 mg, 0.342 mmol, 98% yield) as an off-white solid in sufficient purity to carry forward with no purification. NMR of the epimeric mixture: ¹H NMR (400 MHz, CD₂Cl₂) δ 7.72 (dd, J=2.35, 8.41 Hz, 1H), 7.23-7.03 (m, 3H), 6.92-6.69 (m, 2H), 5.84 (ddd, J=6.06, 10.61, 16.97 Hz, 1H), 5.29-5.19 (m, 1H), 5.11 (d, J=10.37 Hz, 1H), 4.20-3.97 (m, 6H), 3.88-3.73 (m, 4H), 3.68 (d, J=14.09 Hz, 1H), 3.54 (d, J=16.82 Hz, 1H), 3.33-3.07 (m, 2H), 3.04-2.91 (m, 1H), 2.86-2.68 (m, 2H), 2.63-2.43 (m, 1H), 2.15-2.07 (m, 2H), 1.87 (dd, J=5.09, 14.28 Hz, 3H), 1.74-1.41 (m, 3H). LRMS: (ESI, +ve ion) m/z 626.2 (M+H)⁺.

Step 6. METHYL 4-(BUT-3-EN-1-YL(METHYL)AMINO)-2-((S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXY-4-OXOBUTANOATE

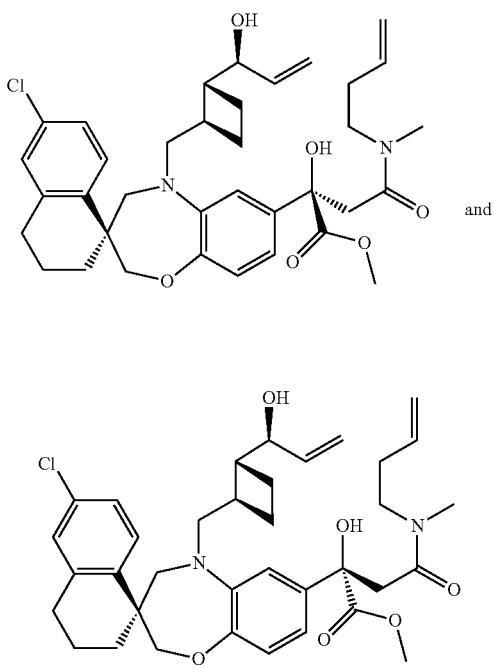 [SMILES: C=CCCN(C)C(=O)C[C@](O)(C(=O)OC)c1ccc2c(c1)N(C[C@@H]1CC[C@H]1[C@@H](O)C=C)C[C@@]1(CCCc3cc(Cl)ccc31)CO2 ; C=CCCN(C)C(=O)C[C@@](O)(C(=O)OC)c1ccc2c(c1)N(C[C@@H]1CC[C@H]1[C@@H](O)C=C)C[C@@]1(CCCc3cc(Cl)ccc31)CO2]

and

To a solution of 3-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-3-hydroxy-4-methoxy-4-oxobutanoic acid (From Step 5, a 2:1 mixture of isomers, 400 mg, 0.702 mmol) in DCM (1.4 mL) was added O-(-7-azabenzotriazol-1-yl)-N,N,N',N'-tetramethyluroniumhexafluorophosphate (400 mg, 1.052 mmol), N,N-diisopropylethylamine (366 µL, 2.105 mmol) and N-methylbut-3-en-1-amine (90 mg, 1.052 mmol). The reaction mixture was stirred at room temperature for 30 minutes and was then diluted with saturated NH$_4$Cl (10 mL) and extracted with Et$_2$O (3×30 mL). The organic extract was dried over MgSO$_4$. The solution was filtered and concentrated in vacuo to give the crude material as a light-yellow oil. The crude material was then absorbed onto a plug of silica gel and purified by chromatography through a Redi-Sep pre-packed silica gel column (40 g), eluting with a gradient of 0% to 100% acetone in heptanes, to provide methyl 4-(but-3-en-1-yl(methyl)amino)-2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-4-oxobutanoate (403 mg, 0.632 mmol, 90% yield) as light-yellow solid and a 2:1 mixture of isomers. NMR of the mixture: $^1$H NMR (400 MHz, CD$_2$Cl$_2$) δ 7.79-7.66 (m, 1H), 7.21-7.03 (m, 3H), 6.85-6.70 (m, 2H), 6.01-5.62 (m, 3H), 5.27-5.00 (m, 4H), 4.04-3.99 (m, 2H), 3.87-3.76 (m, 3H), 3.72-3.69 (m, 3H), 3.69-3.63 (m, 1H), 3.57-3.33 (m, 4H), 3.29-3.19 (m, 1H), 3.17-3.07 (m, 1H), 3.02-2.89 (m, 3H), 2.80-2.65 (m, 3H), 2.53-2.22 (m, 3H), 2.10-2.01 (m, 3H), 1.94-1.77 (m, 3H), 1.71-1.47 (m, 3H). LRMS: (ESI, +ve ion) m/z 637.2 (M+H)$^+$.

Step 7. METHYL (1S,3'R,6'R,7'S,8'E,15'R)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE

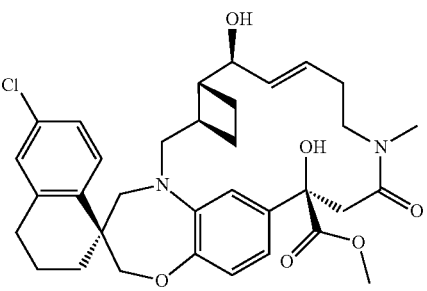 [SMILES: COC(=O)[C@@]1(O)CC(=O)N(C)CC/C=C/[C@H](O)[C@@H]2CC[C@H]2CN2C[C@@]3(CCCc4cc(Cl)ccc43)COc3ccc1cc32]

A solution of methyl 4-(but-3-en-1-yl(methyl)amino)-2-(6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-4-oxobutanoate (From Step 6, a 2:1 mixture of epimers, 0.204 g, 0.320 mmol) in 1,2-dichloroethane (160 mL) was purged with argon for 30 minutes. Then, (1,3-dimesitylimidazolidin-2-ylidene)(2-isopropoxybenzylidene)ruthenium(VI) chloride (0.040 g, 0.064 mmol) was quickly added and the reaction mixture was stirred overnight at 50° C. under argon. The reaction mixture was cooled and concentrated. The crude material was absorbed onto a plug of silica gel and purified by chromatography through a Redi-Sep pre-packed silica gel column (24 g), eluting with a gradient of 20% to 100% acetone in heptanes, to provide first methyl (1S,3'R,6'R,7'S,8'E,15'S)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate as a beige solid (Example 2, 50 mg, 26%) and then methyl (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate, the title compound as a beige solid (Example 1, 101 mg, 54%). Characterization of the slowest eluting isomer: $^1$H NMR (400 MHz, CD$_2$Cl$_2$) δ 7.72 (d, J=8.61 Hz, 1H), 7.15 (dd, J=2.25, 8.51 Hz, 1H), 7.08 (d, J=2.15 Hz, 1H), 6.96 (dd, J=1.76, 8.22 Hz, 1H), 6.83 (d, J=8.22 Hz, 1H), 6.53 (br. s., 1H), 6.19 (br. s., 1H), 5.88 (dd, J=7.73, 14.77 Hz, 1H), 5.47 (br. s., 1H), 4.22 (d, J=7.43 Hz, 1H), 4.01 (s, 2H), 3.74 (s, 3H), 3.72-3.65 (m, 1H), 3.64-3.48 (m, 2H), 3.44 (d, J=16.82 Hz, 1H), 3.35 (d, J=14.28 Hz, 1H), 3.17 (d, J=14.28 Hz, 1H), 2.94 (s, 3H), 2.83-2.71 (m, 2H), 2.64-2.48 (m, 2H), 2.44-2.22 (m, 3H), 2.07-1.98 (m, 2H), 1.96-1.70 (m, 5H), 0.97-0.80 (m, 3H). LRMS: (ESI, +ve ion) m/z 637.2 (M+H)$^+$.

Example 2

METHYL (1S,3'R,6'R,7'S,8'E,15'S)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE

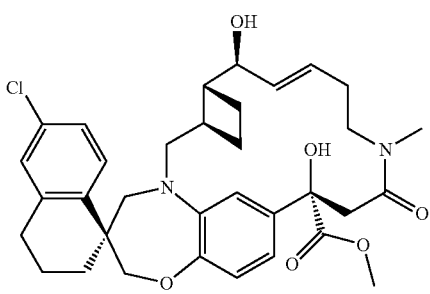 [SMILES: COC(=O)[C@]1(O)CC(=O)N(C)CC/C=C/[C@H](O)[C@@H]2CC[C@H]2CN2C[C@@]3(CCCc4cc(Cl)ccc43)COc3ccc1cc32]

The title compound was isolated as the fastest eluting isomer from Example 1, Step 7. $^1$H NMR (400 MHz, CD$_2$Cl$_2$) δ 7.73 (d, J=8.41 Hz, 1H), 7.16 (dd, J=2.35, 8.41 Hz, 1H), 7.08 (d, J=2.15 Hz, 1H), 6.96 (dd, J=2.15, 8.22 Hz, 1H), 6.82 (d, J=8.22 Hz, 1H), 6.51 (d, J=1.96 Hz, 1H), 6.08-5.93 (m, 1H), 5.76 (d, J=15.65 Hz, 1H), 4.14-3.86 (m, 3H), 3.75 (s, 3H), 3.74-3.55 (m, 4H), 3.33 (d, J=14.28 Hz, 1H), 3.20-3.02 (m, 2H), 2.95 (s, 3H), 2.80-2.72 (m, 2H), 2.71-2.58 (m, 2H), 2.53 (d, J=16.63 Hz, 1H), 2.34-2.16 (m, 2H), 2.07-1.89 (m, 4H), 1.80-1.61 (m, 2H), 1.52 (br. s., 2H), 1.39 (t, J=12.72 Hz, 1H), 0.96-0.80 (m, 1H). LRMS: (ESI, +ve ion) m/z 637.2 (M+H)$^+$.

Example 3

METHYL (1S,3'R,6'R,7'S,8'E,15'R)-6-CHLORO-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE

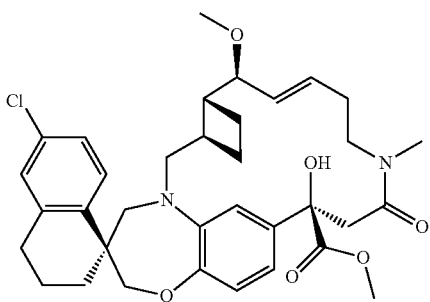 [SMILES: COC(=O)[C@@]1(O)CC(=O)N(C)CC/C=C/[C@H](OC)[C@@H]2CC[C@H]2CN2C[C@@]3(CCCc4cc(Cl)ccc43)COc3ccc1cc32]

To a solution of methyl (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 1, 142 mg, 0.233 mmol) in THF (1 mL) was added sodium bis(trimethylsilyl)amide (1.0 M solution in THF) (0.932 mL, 0.932 mmol) and then iodomethane (0.145 mL, 2.331 mmol). The reaction was stirred at room temperature for 20 minutes. The reaction mixture was diluted with saturated aqueous NH$_4$Cl (10 mL) and extracted with Et$_2$O (3×30 mL). The organic extract was dried over MgSO$_4$. The solution was filtered and concentrated in vacuo to give the crude material as a light-yellow oil. The crude material was absorbed onto a plug of silica gel and purified by chromatography through a Redi-Sep prepacked silica gel column (40 g), eluting with a gradient of 0% to 100% acetone in heptanes, to provide the title compound (76 mg, 0.122 mmol, 52% yield). $^1$H NMR (400 MHz, CD$_2$Cl$_2$) δ 7.73 (d, J=8.61 Hz, 1H), 7.16 (dd, J=2.35, 8.61 Hz, 1H), 7.08 (d, J=2.35 Hz, 1H), 7.00 (dd, J=2.15, 8.22 Hz, 1H), 6.84 (d, J=8.22 Hz, 1H), 6.48 (d, J=1.96 Hz, 1H), 6.27-6.14 (m, 1H), 5.66 (ddd, J=1.76, 9.49, 15.16 Hz, 1H), 4.07-3.93 (m, 2H), 3.73 (s, 3H), 3.67-3.55 (m, 3H), 3.51 (d, J=16.63 Hz, 1H), 3.33 (d, J=14.28 Hz, 1H), 3.19 (s, 3H), 3.17-3.03 (m, 2H), 2.96 (s, 3H), 2.83-2.60 (m, 3H), 2.55 (d, J=16.63 Hz, 1H), 2.46-2.36 (m, 2H), 2.35-2.24 (m, 1H), 2.05-1.69 (m, 7H). LRMS: (ESI, +ve ion) m/z 623.2 (M+H)$^+$.

Example 4

(1S,3'R,6'R,7'S,8'E,15'S)-6-CHLORO-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

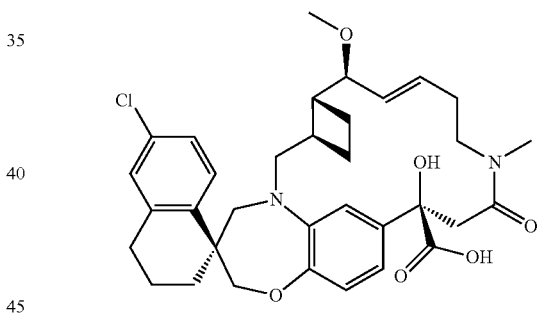

To a solution of methyl (1S,3'R,6'R,7'S,8'E,15'R)-6-chloro-15'-hydroxy-7'-methoxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 3, 8 mg, 0.013 mmol) in THF (1 mL) was added LiOH (2 M, 1 mL). The reaction mixture was stirred at room temperature overnight. After this period, the reaction mixture was quenched with 1 N HCl (2 mL). The crude was transferred to an extraction funnel containing 15 mL of water and was extracted with diethyl ether (3×20 mL). The combined organic layer was dried over MgSO$_4$, filtered and concentrated. The crude mixture was purified via prep HPLC (Phenomenex Gemini column, 10 micron, C18, 100 Å, 150×30 mm) eluting with a gradient of 50% to 90% acetonitrile in water (both solvents containing 0.1% TFA) over a period of 27 minutes. The title product was dried on the lyophilizer overnight. $^1$H NMR (400 MHz, (CD$_3$)$_2$SO) δ 7.67 (d, J=8.61 Hz, 1H), 7.26 (dd, J=2.25, 8.51 Hz, 1H), 7.17 (d, J=2.35 Hz, 1H), 6.92 (dd, J=1.86, 8.31 Hz, 1H), 6.82 (d, J=8.22 Hz, 1H), 6.59 (d, J=1.76 Hz, 1H), 6.20-6.04 (m, 1H), 5.66 (dd, J=8.12, 15.16 Hz, 1H), 4.13-3.85 (m, 2H), 3.73-

3.49 (m, 5H), 3.34-3.24 (m, 3H), 3.18-3.10 (m, 2H), 3.08 (s, 3H), 2.89 (s, 3H), 2.81-2.59 (m, 3H), 2.44-2.22 (m, 4H), 2.06-1.83 (m, 5H). LRMS: (ESI, +ve ion) m/z 609.2 (M+H)⁺.

Example 5

(1S,3'R,6'R,7'S,8'E,15'R)-6-CHLORO-N-(DIMETHYLSULFAMOYL)-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXAMIDE

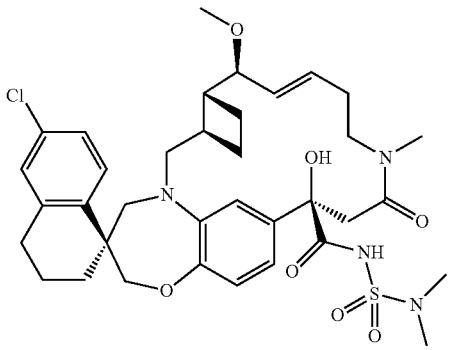 [SMILES: CO[C@H]1/C=C/CCN(C)C(=O)C[C@](O)(C(=O)NS(=O)(=O)N(C)C)c2ccc3c(c2)N(C[C@@H]2CC[C@H]21)C[C@@]1(CCCc2cc(Cl)ccc21)CO3]

To a solution of (1S,3'R,6'R,7'S,8'E,15'S)-6-chloro-15'-hydroxy-7'-methoxy-12'-methyl-13'-oxo-3,4-dihydro-2H-spiro[naphthalene-1,22'-[20]oxa[1,12]diazatetracyclo[14.7.2.0³,⁶.0¹⁹,²⁴]pentacosa[8,16,18,24]tetraene]-15'-carboxylic acid (Example 4, 32 mg, 0.053 mmol) in DCM (2 mL) was added 1,1'-carbonyldiimidazole (10.22 mg, 0.063 mmol). The reaction mixture was stirred at room temperature for 2 hours. N,N-dimethylsulfamide (19.57 mg, 0.158 mmol) and 1,8-diazabicyclo[5.4.0]undec-7-ene (23.99 µL, 0.158 mmol) were then added and the reaction mixture was stirred overnight. After this time, the reaction mixture was diluted with water (10 mL) and extracted with CH₂Cl₂ (3×10 mL). The organic extract was dried over MgSO₄, filtered and concentrated in vacuo to give the crude material as a light-yellow oil. The crude material was absorbed onto a plug of silica gel and purified by chromatography through a Redi-Sep pre-packed silica gel column (12 g), eluting with a gradient of 0% to 100% acetone in hexanes, to provide the title compound (27 mg, 0.038 mmol, 72% yield) as white solid. ¹H NMR (300 MHz, CDCl₃) δ 8.90 (br. s., 1H), 7.73 (d, J=8.48 Hz, 1H), 7.17 (dd, J=2.19, 8.33 Hz, 1H), 7.08 (d, J=1.90 Hz, 1H), 7.01 (dd, J=1.90, 8.18 Hz, 1H), 6.94-6.86 (m, 1H), 6.54 (d, J=14.91 Hz, 2H), 6.49-6.34 (m, 1H), 5.76-5.61 (m, 1H), 4.03 (d, J=3.07 Hz, 2H), 3.83-3.53 (m, 7H), 3.30 (d, J=14.47 Hz, 2H), 3.22 (s, 3H), 3.10-3.01 (m, 2H), 2.99 (s, 3H), 2.93 (s, 6H), 2.85-2.75 (m, 3H), 2.64 (s, 1H), 2.52 (d, J=16.52 Hz, 1H), 2.44-2.13 (m, 5H). LRMS: (ESI, +ve ion) m/z 715.0 (M+H)⁺.

Example 6

(1S,3'R,6'R,7'S,8'E,15'R)-6-CHLORO-15'-HYDROXY-7'-METHOXY-12'-METHYL-N-(METHYLSULFONYL)-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXAMIDE

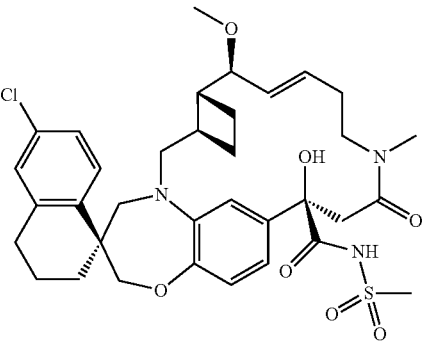 [SMILES: CO[C@H]1/C=C/CCN(C)C(=O)C[C@](O)(C(=O)NS(C)(=O)=O)c2ccc3c(c2)N(C[C@@H]2CC[C@H]21)C[C@@]1(CCCc2cc(Cl)ccc21)CO3]

The title compound (4 mg, 47%) was synthesized from Example 4 through a procedure similar to that used for the synthesis of Example 5. ¹H NMR (400 MHz, CD₂Cl₂) δ 9.00 (s, 1H), 7.72 (d, J=8.61 Hz, 1H), 7.16 (dd, J=2.35, 8.41 Hz, 1H), 7.08 (d, J=2.35 Hz, 1H), 7.02-6.92 (m, 2H), 6.86 (d, J=8.41 Hz, 1H), 6.49 (d, J=1.76 Hz, 1H), 6.29 (t, J=12.42 Hz, 1H), 5.77-5.58 (m, 1H), 4.02 (s, 2H), 3.80-3.66 (m, 2H), 3.64-3.52 (m, 3H), 3.33 (d, J=14.48 Hz, 1H), 3.21 (d, J=4.30 Hz, 6H), 2.97 (s, 3H), 2.81-2.53 (m, 4H), 2.47-2.26 (m, 3H), 1.98-1.80 (m, 10H). LRMS: (ESI, +ve ion) m/z 686.2 (M+H)⁺.

Example 7

(1S,3'R,6'R,7'S,8'E,15'R)-6-CHLORO-N-((4-CHLOROPHENYL)SULFONYL)-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXAMIDE

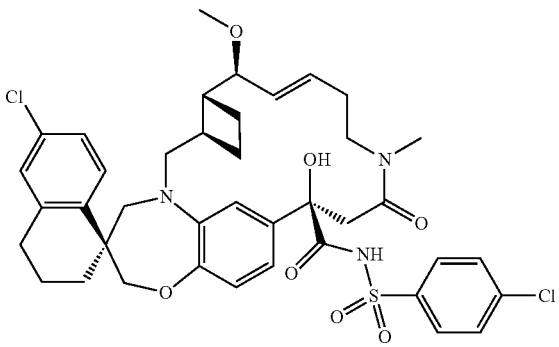 [SMILES: CO[C@H]1/C=C/CCN(C)C(=O)C[C@](O)(C(=O)NS(=O)(=O)c2ccc(Cl)cc2)c2ccc3c(c2)N(C[C@@H]2CC[C@H]21)C[C@@]1(CCCc2cc(Cl)ccc21)CO3]

The title compound (21 mg, 55%) was synthesized from Example 4 through a procedure similar to that used for the synthesis of Example 5. $^1$H NMR (300 MHz, CD$_2$Cl$_2$) δ 9.17 (br. s., 1H), 7.85-7.77 (m, 2H), 7.73 (d, J=8.51 Hz, 1H), 7.53-7.43 (m, 2H), 7.18 (dd, J=2.23, 8.44 Hz, 1H), 7.12 (d, J=2.05 Hz, 1H), 6.97 (d, J=7.31 Hz, 1H), 6.92-6.82 (m, 1H), 7.02-6.82 (m, 1H), 6.36 (t, J=11.95 Hz, 1H), 5.90 (br. s., 1H), 5.65 (ddd, J=1.42, 9.57, 15.09 Hz, 1H), 4.20-4.02 (m, 1H), 4.02-3.89 (m, 1H), 3.76-3.49 (m, 3H), 3.38 (d, J=16.81 Hz, 1H), 3.32 (s, 3H), 3.10-3.21 (m, 1H), 2.97 (s, 4H), 2.88-2.77 (m, 3H), 2.47 (d, J=16.70 Hz, 1H), 2.42-1.80 (m, 10H), 1.78-1.65 (m, 1H), 1.56-1.42 (m, 1H). LRMS: (ESI, +ve ion) m/z 781.1 (M+H)$^+$.

Example 8

(1S,3'R,6'R,7'S,8'E,15'R)-6-CHLORO-15'-HYDROXY-7'-METHOXY-12'-METHYL-N-((4-METHYLPHENYL)SULFONYL)-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$] PENTACOSA[8,16,18,24]TETRAENE]-15'-CARBOXAMIDE

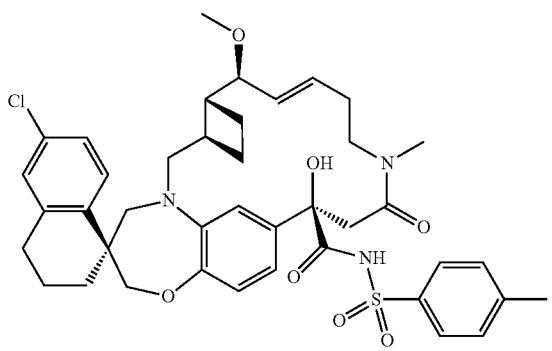 [SMILES: CO[C@H]1/C=C/CCN(C)C(=O)C[C@](O)(C(=O)NS(=O)(=O)c2ccc(C)cc2)c2ccc3c(c2)N(C[C@@H]2CC[C@H]21)C[C@@]1(CCCc2cc(Cl)ccc21)CO3]

The title compound (22 mg, 59%) was synthesized from Example 4 through a procedure similar to that used for the synthesis of Example 5. $^1$H NMR (300 MHz, CD$_2$Cl$_2$) δ 9.09 (br. s., 1H), 7.84-7.65 (m, 3H), 7.31 (d, J=8.15 Hz, 2H), 7.18 (dd, J=2.23, 8.48 Hz, 1H), 7.12 (d, J=2.12 Hz, 1H), 7.05-6.83 (m, 2H), 6.41 (t, J=12.13 Hz, 1H), 5.64 (ddd, J=1.44, 9.54, 15.11 Hz, 1H), 4.15-4.02 (m, 1H), 4.02-3.86 (m, 1H), 3.73-3.46 (m, 3H), 3.42-3.31 (m, 4H), 3.30-3.22 (m, 1H), 3.21-3.11 (m, 1H), 2.96 (s, 3H), 2.90-2.77 (m, 4H), 2.74-2.59 (m, 1H), 2.51 (s, 3H), 2.46 (d, J=16.99 Hz, 1H), 2.38-2.16 (m, 3H), 2.09-1.78 (m, 7H), 1.76-1.62 (m, 1H), 1.58-1.42 (m, 1H). LRMS: (ESI, +ve ion) m/z 762.0 (M+H)$^+$.

Example 9

(1S,3'R,6'R,7'S,8'E,15'R)-6-CHLORO-N-(CYCLOPROPYL(METHYL)SULFAMOYL)-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$] PENTACOSA[8,16,18,24]TETRAENE]-15'-CARBOXAMIDE

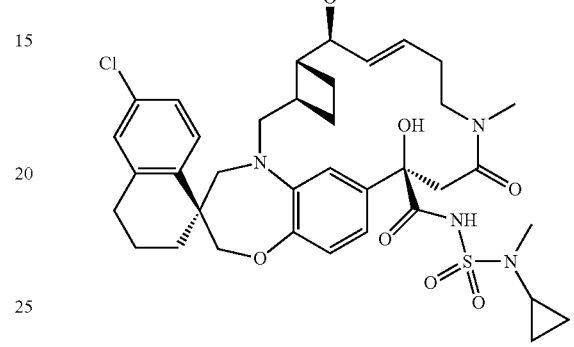

The title compound (15 mg, 62%) was synthesized from Example 4 through a procedure similar to that used for the synthesis of Example 5. $^1$H NMR (300 MHz, CD$_2$Cl$_2$) δ 8.99 (s, 1H), 7.72 (d, J=8.48 Hz, 1H), 7.16 (dd, J=2.34, 8.48 Hz, 1H), 7.08 (d, J=2.19 Hz, 1H), 7.03-6.96 (m, 1H), 6.86 (d, J=8.18 Hz, 1H), 6.51 (s, 1H), 6.40 (t, J=12.06 Hz, 1H), 5.66 (ddd, J=1.75, 9.57, 15.27 Hz, 1H), 4.13-3.89 (m, 2H), 3.81-3.50 (m, 5H), 3.32 (d, J=14.47 Hz, 1H), 3.19 (s, 3H), 3.15-3.12 (m, 1H), 2.97 (s, 3H), 2.94 (s, 3H), 2.83-2.61 (m, 4H), 2.52 (d, J=16.66 Hz, 1H), 2.46-2.25 (m, 4H), 2.11-1.66 (m, 8H), 1.39 (t, J=11.62 Hz, 1H), 0.77-0.52 (m, 4H). LRMS: (ESI, +ve ion) m/z 741.0 (M+H)$^+$.

Example 10

(1S,3'R,6'R,7'S,8'E,15'R)-6-CHLORO-N-(ETHYLSULFAMOYL)-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$] PENTACOSA[8,16,18,24]TETRAENE]-15'-CARBOXAMIDE

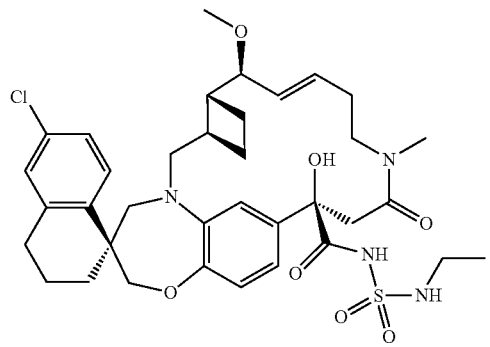 [SMILES: CCNS(=O)(=O)NC(=O)[C@@]1(O)CC(=O)N(C)CC/C=C/[C@H](OC)[C@@H]2CC[C@H]2CN2C[C@@]3(CCCc4cc(Cl)ccc43)COc3ccc1cc32]

The title compound (15 mg, 43%) was synthesized from Example 4 through a procedure similar to that used for the synthesis of Example 5. $^1$H NMR (500 MHz, CD$_2$Cl$_2$) δ 9.09 (s, 1H), 7.72 (d, J=8.31 Hz, 1H), 7.16 (dd, J=2.20, 8.56 Hz, 1H), 7.08 (d, J=2.20 Hz, 1H), 6.99 (dd, J=1.47, 8.31 Hz, 1H), 6.86 (d, J=8.31 Hz, 1H), 6.49 (s, 1H), 6.31 (t, J=12.47 Hz, 1H), 5.68 (ddd, J=1.47, 9.60, 15.10 Hz, 1H), 5.15 (t, J=5.50 Hz, 1H), 4.08-3.90 (m, 2H), 3.84-3.67 (m, 2H), 3.64-3.53 (m, 3H), 3.33 (d, J=14.43 Hz, 1H), 3.24 (s, 3H), 3.20-3.13 (m, 1H), 3.12-2.98 (m, 2H), 2.97 (s, 3H), 2.84-2.62 (m, 5H), 2.58 (d, J=16.87 Hz, 1H), 2.50-2.37 (m, 2H), 2.37-2.27 (m, 1H), 2.02-1.90 (m, 4H), 1.87-1.70 (m, 3H), 1.37 (t, J=12.72 Hz, 1H), 1.06 (t, J=7.34 Hz, 3H). LRMS: (ESI, +ve ion) m/z 715.2 (M+H)$^+$.

Example 11

(1S,3'R,6'R,7'S,8'E,15'R)-6-CHLORO-15'-HYDROXY-7'-METHOXY-12'-METHYL-N-((1-METHYLETHYL)SULFONYL)-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$] PENTACOSA[8,16,18,24]TETRAENE]-15'-CARBOXAMIDE

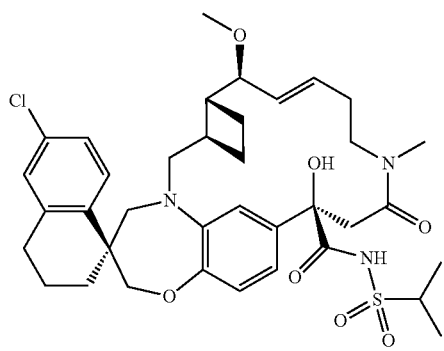 [SMILES: CO[C@H]1/C=C/CCN(C)C(=O)C[C@](O)(C(=O)NS(=O)(=O)C(C)C)c2ccc3c(c2)N(C[C@@H]2CC[C@H]21)C[C@@]1(CCCc2cc(Cl)ccc21)CO3]

The title compound (8 mg, 40%) was synthesized from Example 4 through a procedure similar to that used for the synthesis of Example 5. $^1$H NMR (400 MHz, CD$_2$Cl$_2$) δ 8.79 (s, 1H), 7.73 (d, J=8.41 Hz, 1H), 7.16 (dd, J=2.35, 8.61 Hz, 1H), 7.08 (d, J=2.15 Hz, 1H), 6.99 (dd, J=2.15, 8.22 Hz, 1H), 6.86 (d, J=8.22 Hz, 1H), 6.47 (d, J=1.76 Hz, 1H), 6.30 (t, J=12.72 Hz, 1H), 5.66 (ddd, J=1.56, 9.54, 15.11 Hz, 1H), 4.07-3.93 (m, 2H), 3.55 (s, 6H), 3.33 (d, J=14.48 Hz, 1H), 3.21 (s, 3H), 3.19-3.12 (m, 1H), 3.07 (dd, J=10.07, 15.36 Hz, 1H), 2.97 (s, 3H), 2.83-2.73 (m, 2H), 2.67 (t, J=12.81 Hz, 1H), 2.55 (d, J=16.82 Hz, 1H), 2.47-2.38 (m, 2H), 2.36-2.26 (m, 2H), 2.08-1.69 (m, 8H), 1.40 (d, J=6.85 Hz, 3H), 1.20 (d, J=6.85 Hz, 3H). LRMS: (ESI, +ve ion) m/z 714.2 (M+H)$^+$.

Example 12

(1S,3'R,6'R,7'S,8'E,15'R)-6-CHLORO-15'-HYDROXY-7'-METHOXY-12'-METHYL-N-(METHYLSULFAMOYL)-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$] PENTACOSA[8,16,18,24]TETRAENE]-15'-CARBOXAMIDE

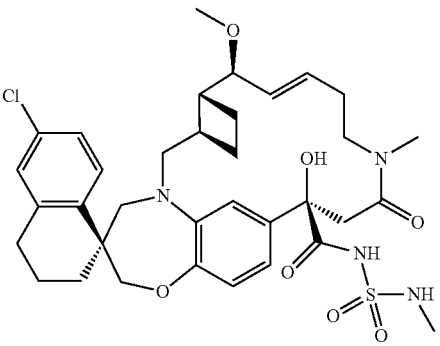 [SMILES: CNS(=O)(=O)NC(=O)[C@@]1(O)CC(=O)N(C)CC/C=C/[C@H](OC)[C@@H]2CC[C@H]2CN2C[C@@]3(CCCc4cc(Cl)ccc43)COc3ccc1cc32]

The title compound (18 mg, 52%) was synthesized from Example 4 through a procedure similar to that used for the synthesis of Example 5. $^1$H NMR (300 MHz, CD$_2$Cl$_2$) δ ppm 9.05 (s, 1H), 7.72 (d, J=8.62 Hz, 1H), 7.16 (dd, J=8.48, 2.34 Hz, 1H), 7.08 (d, J=2.19 Hz, 1H), 7.00 (dd, J=8.18, 2.05 Hz, 1H), 6.86 (d, J=8.33 Hz, 1H), 6.48 (d, J=1.75 Hz, 1H), 6.32 (t, J=12.20 Hz, 1H), 5.76-5.62 (m, 1H), 5.16 (d, J=5.12 Hz, 1H), 4.10-3.93 (m, 2H), 3.85-3.66 (m, 2H), 3.65-3.50 (m, 3H), 3.33 (d, J=14.32 Hz, 2H), 3.24 (s, 3H), 3.21-3.01 (m, 3H), 2.97 (s, 3H), 2.82-2.65 (m, 3H), 2.61 (d, J=4.82 Hz, 3H), 2.49-2.26 (m, 3H), 2.08-1.69 (m, 7H), 1.38 (t, J=11.62 Hz, 1H). LRMS: (ESI, +ve ion) m/z 701.0 (M+H)$^+$.

Example 13

(1S,3'R,6'R,7'S,8'E,15'R)-6-CHLORO-15'-HYDROXY-7'-METHOXY-12'-METHYL-13'-OXO-N-SULFAMOYL-3,4-DIHYDRO-2H-SPIRO[NAPHTHALENE-1,22'-[20]OXA[1,12]DIAZATETRACYCLO[14.7.2.0$^{3,6}$.0$^{19,24}$] PENTACOSA[8,16,18,24]TETRAENE]-15'-CARBOXAMIDE

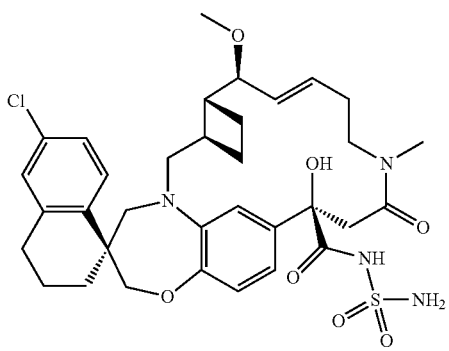 [SMILES: CO[C@H]1/C=C/CCN(C)C(=O)C[C@](O)(C(=O)NS(N)(=O)=O)c2ccc3c(c2)N(C[C@@H]2CC[C@H]21)C[C@@]1(CCCc2cc(Cl)ccc21)CO3]

The title compound (17 mg, 50%) was synthesized from Example 4 through a procedure similar to that used for the synthesis of Example 5. $^1$H NMR (300 MHz, CD$_2$Cl$_2$) δ 9.37 (s, 1H), 7.76 (d, J=8.48 Hz, 1H), 7.19 (dd, J=2.34, 8.48 Hz, 1H), 7.11 (d, J=2.34 Hz, 1H), 7.01 (dd, J=1.97, 8.11 Hz, 1H), 6.96.8-(m, 1H), 6.54 (s, 1H), 6.32 (t, J=11.84 Hz, 1H), 5.79-5.66 (m, 1H), 5.44 (br. s., 2H), 4.05 (s, 2H), 3.86-3.56 (m, 5H), 3.37 (d, J=14.47 Hz, 1H), 3.26 (s, 2H), 3.05-3.24 (m, 2H), 2.99 (s, 3H), 2.58-2.83 (m, 6H), 2.52-2.29 (m, 3H), 2.15-1.72 (m, 7H), 1.42 (t, J=11.55 Hz, 1H). LRMS: (ESI, +ve ion) m/z 687.0 (M+H)$^+$.

Example 14

(1S,3'R,6'R,7'S,8'E,15'R)-6-CHLORO-N-((1-FLUOROCYCLOPROPYL)SULFONYL)-15'-HYDROXY-7-METHOXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$] PENTACOSA[8,16,18,24]TETRAENE]-15'-CARBOXAMIDE

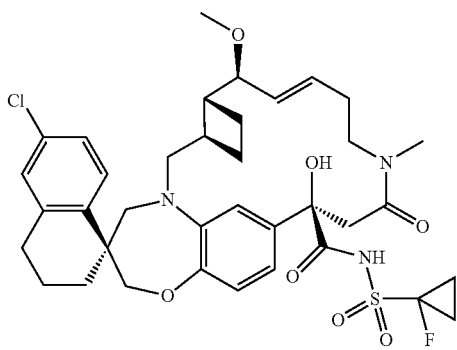 [SMILES: CO[C@H]1/C=C/CCN(C)C(=O)C[C@](O)(C(=O)NS(=O)(=O)C2(F)CC2)c2ccc3c(c2)N(C[C@@H]2CC[C@H]21)C[C@@]1(CCCc2cc(Cl)ccc21)CO3]

The title compound (17 mg, 47%) was synthesized from Example 4 through a procedure similar to that used for the synthesis of Example 5. $^1$H NMR (300 MHz, CD$_2$Cl$_2$) δ 9.11 (br. s., 1H), 7.72 (d, J=8.48 Hz, 1H), 7.16 (dd, J=2.34, 8.48 Hz, 1H), 7.08 (d, J=2.19 Hz, 1H), 7.04-6.97 (m, 1H), 6.87 (d, J=8.18 Hz, 1H), 6.45 (d, J=1.90 Hz, 1H), 6.34 (t, J=12.28 Hz, 1H), 5.68 (ddd, J=1.53, 9.57, 15.20 Hz, 1H), 4.11-3.93 (m, 2H), 3.84-3.49 (m, 5H), 3.32 (d, J=14.47 Hz, 1H), 3.26-3.02 (m, 5H), 2.98 (s, 3H), 2.81-2.52 (m, 4H), 2.49-2.20 (m, 3H), 2.13-1.70 (m, 9H), 1.52-1.27 (m, 4H). LRMS: (ESI, +ve ion) m/z 730.1 (M+H)$^+$.

Example 15

(1S,3'R,6'R,7'S,8'E,15'R)-6-CHLORO-N-(CYCLOPROPYLSULFONYL)-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

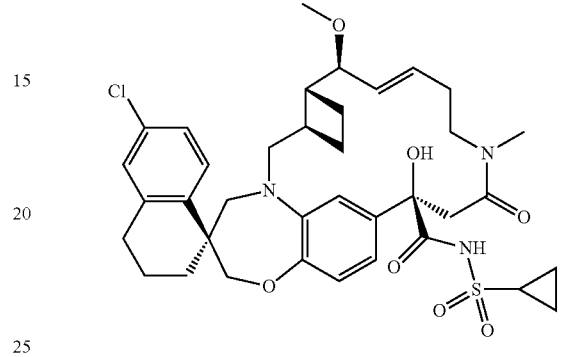

The title compound (27 mg, 51%) was synthesized from Example 4 through a procedure similar to that used for the synthesis of Example 5. $^1$H NMR (400 MHz, CD$_2$Cl$_2$) δ 8.93 (s, 1H), 7.72 (d, J=8.41 Hz, 1H), 7.16 (dd, J=2.15, 8.41 Hz, 1H), 7.08 (d, J=1.96 Hz, 1H), 6.98 (dd, J=1.96, 8.22 Hz, 1H), 6.86 (d, J=8.22 Hz, 1H), 6.50 (d, J=1.56 Hz, 1H), 6.34 (t, J=12.42 Hz, 1H), 5.65 (dd, J=10.27, 14.18 Hz, 1H), 4.14-3.92 (m, 2H), 3.83-3.67 (m, 2H), 3.63-3.52 (m, 3H), 3.33 (d, J=14.48 Hz, 1H), 3.21 (s, 3H), 3.19-3.04 (m, 2H), 2.96 (s, 3H), 2.84-2.72 (m, 3H), 2.66 (t, J=12.91 Hz, 1H), 2.54 (d, J=16.82 Hz, 1H), 2.42 (br. s., 2H), 2.36-2.25 (m, 1H), 1.88-1.66 (m, 7H), 1.46-1.37 (m, 1H), 1.37-1.25 (m, 2H), 1.25-1.15 (m, 1H), 1.13-1.01 (m, 1H), 0.99-0.88 (m, 1H). LRMS: (ESI, +ve ion) m/z 712.2 (M+H)$^+$.

Example 16

(1S,3'R,6'R,7'S,8'E,15'R)-6-CHLORO-N-((3,4-DIFLUOROPHENYL)SULFONYL)-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$] PENTACOSA[8,16,18,24]TETRAENE]-15'-CARBOXAMIDE

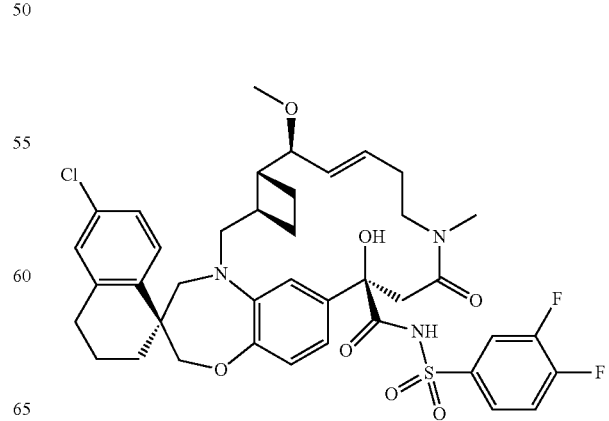

The title compound (19 mg, 59%) was synthesized from Example 4 through a procedure similar to that used for the synthesis of Example 5. $^1$H NMR (300 MHz, CD$_2$Cl$_2$) δ 9.20 (s, 1H), 7.80-7.66 (m, 3H), 7.38-7.23 (m, 1H), 7.18 (dd, J=2.30, 8.48 Hz, 1H), 7.11 (d, J=2.19 Hz, 1H), 7.00-6.91 (m, 1H), 6.89-6.81 (m, 1H), 6.28 (t, J=11.97 Hz, 1H), 6.00 (d, J=1.72 Hz, 1H), 5.72-5.57 (m, 1H), 4.13-3.88 (m, 2H), 3.71-3.50 (m, 3H), 3.50-3.30 (m, 2H), 3.27 (s, 3H), 3.19-3.09 (m, 1H), 3.00 (d, J=6.43 Hz, 2H), 2.94 (s, 3H), 2.86-2.76 (m, 2H), 2.73-2.59 (m, 1H), 2.47 (d, J=16.70 Hz, 1H), 2.41-2.20 (m, 3H), 2.12-1.67 (m, 8H). LRMS: (ESI, +ve ion) m/z 784.0 (M+H)$^+$.

Example 17

(1S,3'R,6'R,7'S,8'E,15'R)-6-CHLORO-15'-HYDROXY-7'-METHOXY-12'-METHYL-N-(4-MORPHOLINYLSULFONYL)-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$] PENTACOSA[8,16,18,24]TETRAENE]-15'-CARBOXAMIDE

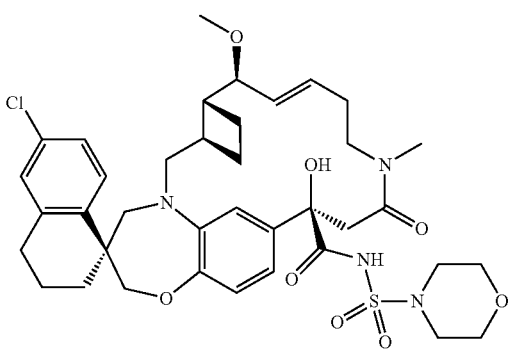 [SMILES: CO[C@H]1/C=C/CCN(C)C(=O)C[C@](O)(C(=O)NS(=O)(=O)N2CCOCC2)c2ccc3c(c2)N(C[C@@H]2CC[C@H]21)C[C@@]1(CCCc2cc(Cl)ccc21)CO3]

The title compound (25 mg, 50%) was synthesized from Example 4 through a procedure similar to that used for the synthesis of Example 5. $^1$H NMR (300 MHz, CD$_2$Cl$_2$) δ 9.04 (br. s., 1H), 7.77 (br. s., 1H), 7.23-7.08 (m, 2H), 7.05-6.81 (m, 2H), 6.58 (br. s., 2H), 6.39 (br. s., 1H), 5.70 (br. s., 1H), 4.48 (br. s., 1H), 4.04 (br. s., 2H), 3.87 (br. s., 1H), 3.76 (d, J=14.29 Hz, 4H), 3.66 (d, J=13.01 Hz, 4H), 3.34 (br. s., 3H), 3.25-3.14 (m, 6H), 3.02 (br. s., 3H), 2.87-2.31 (m, 8H), 2.06-1.75 (m, 7H). LRMS: (ESI, +ve ion) m/z 757.0 (M+H)$^+$.

Example 18

(1S,3'R,6'R,7'S,8'E,15'R)-6-CHLORO-15'-HYDROXY-7'-METHOXY-12'-METHYL-13'-OXO-N-(1-PIPERIDINYLSULFONYL)-3,4-DIHYDRO-2H-SPIRO[NAPHTHALENE-1,22'-[20]OXA[1,12]DIAZATETRACYCLO [14.7.2.0$^{3,6}$.0$^{19,24}$] PENTACOSA[8,16,18,24]TETRAENE]-15'-CARBOXAMIDE

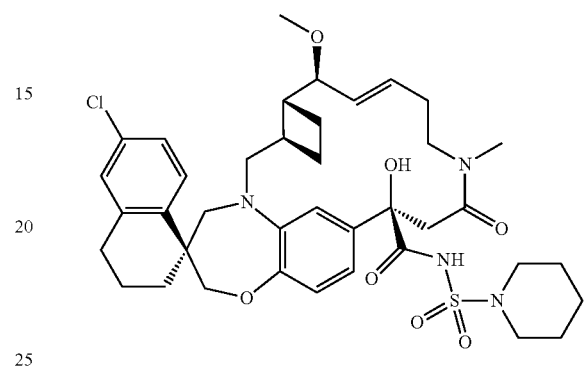

The title compound (15 mg, 40%) was synthesized from Example 4 through a procedure similar to that used for the synthesis of Example 5. $^1$H NMR (500 MHz, CD$_2$Cl$_2$) δ 8.95 (s, 1H), 7.73 (d, J=8.56 Hz, 1H), 7.16 (dd, J=2.32, 8.44 Hz, 1H), 7.08 (d, J=2.45 Hz, 1H), 6.99 (dd, J=1.59, 8.19 Hz, 1H), 6.86 (d, J=8.31 Hz, 1H), 6.52 (s, 1H), 6.40 (t, J=12.59 Hz, 1H), 5.67 (ddd, J=1.71, 9.54, 15.16 Hz, 1H), 4.08-4.00 (m, 1H), 3.93 (d, J=12.23 Hz, 1H), 3.82-3.69 (m, 2H), 3.67-3.53 (m, 3H), 3.37-3.23 (m, 3H), 3.22 (s, 3H), 3.20-3.06 (m, 4H), 2.98 (s, 3H), 2.84-2.62 (m, 3H), 2.53 (d, J=16.63 Hz, 1H), 2.47-2.38 (m, 2H), 2.37-2.27 (m, 1H), 2.06-1.90 (m, 4H), 1.89-1.69 (m, 3H), 1.61-1.52 (m, 2H), 1.51-1.42 (m, 4H), 1.37 (t, J=12.72 Hz, 1H). LRMS: (ESI, +ve ion) m/z 755.3 (M+H)$^+$.

Example 19

(1S,3'R,6'R,7'S,8'E,15'R)-6-CHLORO-15'-HYDROXY-N-((4-HYDROXY-1-PIPERIDINYL)SULFONYL)-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$] PENTACOSA[8,16,18,24]TETRAENE]-15'-CARBOXAMIDE

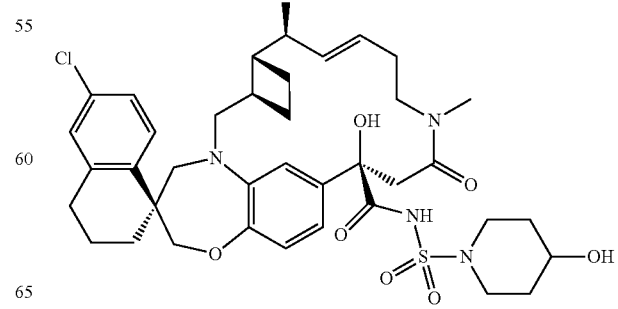

The title compound (6.1 mg, 14%) was synthesized from Example 4 through a procedure similar to that used for the synthesis of Example 5. $^1$H NMR (500 MHz, CD$_2$Cl$_2$) δ 8.99 (s, 1H), 7.73 (d, J=8.56 Hz, 1H), 7.15 (dd, J=2.32, 8.44 Hz, 1H), 7.07 (d, J=2.45 Hz, 1H), 6.97 (dd, J=2.20, 8.31 Hz, 1H), 6.85 (d, J=8.31 Hz, 1H), 6.50 (d, J=1.96 Hz, 1H), 6.37 (t, J=12.47 Hz, 1H), 5.66 (ddd, J=1.71, 9.60, 15.10 Hz, 1H), 4.05-3.94 (m, 2H), 3.79-3.53 (m, 8H), 3.33 (d, J=14.43 Hz, 1H), 3.20-3.18 (m, 3H), 3.18-3.12-(m, 2H), 3.12-3.03 (m, 2H), 2.97 (s, 3H), 2.83-2.63 (m, 3H), 2.52 (d, J=16.63 Hz, 1H), 2.44-2.37 (m, 2H), 2.35-2.26 (m, 1H), 2.05-1.90 (m, 4H), 1.88-1.77 (m, 5H), 1.65-1.57 (m, 2H), 1.48 (dtd, J=4.16, 8.62, 12.84 Hz, 1H), 1.37 (t, J=12.47 Hz, 1H). LRMS: (ESI, +ve ion) m/z 771.2 (M+H)$^+$.

Example 20

(1S,3'R,6'R,7'S,8'E,15'R)-6-CHLORO-15'-HYDROXY-7'-METHOXY-12'-METHYL-13'-OXO-N-(PHENYLSULFONYL)-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

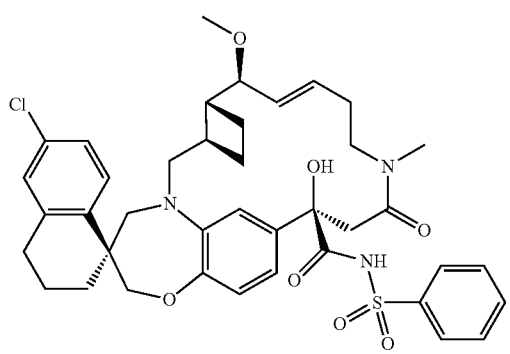 [SMILES: CO[C@H]1/C=C/CCN(C)C(=O)C[C@](O)(C(=O)NS(=O)(=O)c2ccccc2)c2ccc3c(c2)N(C[C@@H]2CC[C@H]21)C[C@@]1(CCCc2cc(Cl)ccc21)CO3]

The title compound (7 mg, 30%) was synthesized from Example 4 through a procedure similar to that used for the synthesis of Example 5. $^1$H NMR (400 MHz, CD$_2$Cl$_2$) δ 9.09 (br. s., 1H), 7.82 (dd, J=1.27, 8.51 Hz, 2H), 7.69 (d, J=8.41 Hz, 1H), 7.64-7.60 (m, 1H), 7.52-7.60 (m, 1H), 7.45 (t, J=7.59 Hz, 2H), 7.15 (dd, J=2.45, 8.51 Hz, 1H), 7.08 (d, J=2.35 Hz, 1H), 6.92 (dd, J=2.15, 8.22 Hz, 1H), 6.82 (d, J=8.22 Hz, 1H), 6.63 (s, 1H), 6.28 (t, J=12.13 Hz, 1H), 5.57 (ddd, J=1.86, 9.44, 15.11 Hz, 1H), 4.08-3.87 (m, 2H), 3.66-3.44 (m, 3H), 3.34 (d, J=16.63 Hz, 1H), 3.24-3.22 (m, 3H), 3.14-3.04 (m, 1H), 2.90 (s, 3H), 2.86-2.75 (m, 4H), 2.68-2.55 (m, 1H), 2.40 (d, J=16.63 Hz, 1H), 2.34-2.13 (m, 4H), 2.05-1.73 (m, 7H), 1.69-1.59 (m, 1H). LRMS: (ESI, +ve ion) m/z 748.2 (M+H)$^+$.

Example 21

(1S,3'R,6'R,7'S,8'E,15'R)-6-CHLORO-15'-HYDROXY-7'-METHOXY-12'-METHYL-N-((1-METHYLCYCLOPROPYL)SULFONYL)-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

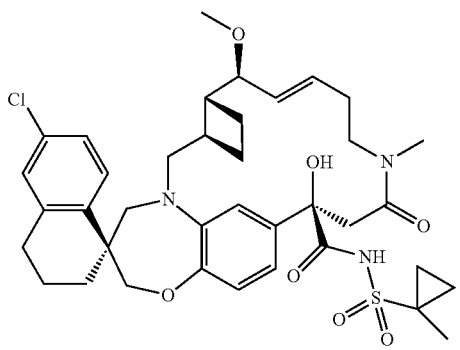 [SMILES: CO[C@H]1/C=C/CCN(C)C(=O)C[C@](O)(C(=O)NS(=O)(=O)C2(C)CC2)c2ccc3c(c2)N(C[C@@H]2CC[C@H]21)C[C@@]1(CCCc2cc(Cl)ccc21)CO3]

The title compound (12 mg, 32%) was synthesized from Example 4 through a procedure similar to that used for the synthesis of Example 5. $^1$H NMR (300 MHz, CD$_2$Cl$_2$) δ 8.86 (s, 1H), 7.76 (d, J=8.48 Hz, 1H), 7.19 (dd, J=2.06, 8.50 Hz, 1H), 7.12 (s, 1H), 7.04 (dd, J=1.88, 8.24 Hz, 1H), 6.90 (d, J=8.26 Hz, 1H), 6.72 (s, 1H), 6.55 (d, J=1.53 Hz, 1H), 6.43 (t, J=12.15 Hz, 1H), 5.69 (dd, J=9.81, 14.16 Hz, 1H), 4.50 (br. s., 3H), 4.23-3.89 (m, 2H), 3.83-3.71 (m, 3H), 3.65-3.55 (m, 3H), 3.36 (d, J=14.40 Hz, 1H), 3.27-3.22 (m, 3H), 3.19-3.06 (m, 2H), 3.00 (s, 3H), 2.89-2.70 (m, 3H), 2.55 (d, J=16.66 Hz, 1H), 2.49-2.28 (m, 4H), 1.59 (s, 3H), 0.82-0.71 (m, 6H). LRMS: (ESI, +ve ion) m/z 726.0 (M+H)$^+$.

Example 22

(1S,3'R,6'R,7'S,8'E,15'R)-6-CHLORO-15'-HYDROXY-7'-METHOXY-12'-METHYL-13'-OXO-N-(1-PYRROLIDINYLSULFONYL)-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

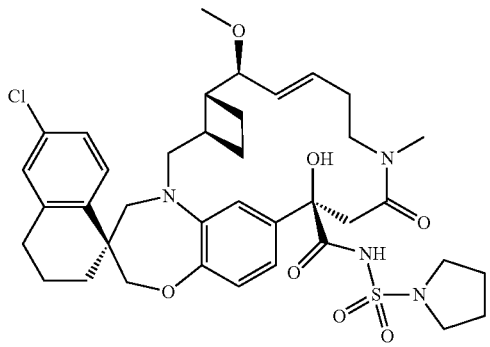 [SMILES: CO[C@H]1/C=C/CCN(C)C(=O)C[C@](O)(C(=O)NS(=O)(=O)N2CCCC2)c2ccc3c(c2)N(C[C@@H]2CC[C@H]21)C[C@@]1(CCCc2cc(Cl)ccc21)CO3]

The title compound (13 mg, 36%) was synthesized from Example 4 through a procedure similar to that used for the synthesis of Example 5. $^1$H NMR (500 MHz, CD$_2$Cl$_2$) δ 9.02 (s, 1H), 7.73 (d, J=8.56 Hz, 1H), 7.16 (dd, J=2.32, 8.44 Hz, 1H), 7.08 (d, J=2.20 Hz, 1H), 6.98 (dd, J=1.83, 8.19 Hz, 1H), 6.86 (d, J=8.07 Hz, 1H), 6.52 (d, J=1.22 Hz, 1H), 6.38 (t, J=12.59 Hz, 1H), 5.68 (ddd, J=1.71, 9.60, 15.10 Hz, 1H), 4.00 (q, J=12.23 Hz, 3H), 3.78 (dd, J=1.83, 9.66 Hz, 2H), 3.71 (d, J=14.43 Hz, 2H), 3.64-3.52 (m, 4H), 3.42 (t, J=5.38 Hz, 5H), 3.32 (d, J=14.67 Hz, 1H), 3.20 (s, 3H), 3.18-3.14 (m, 1H), 3.12-3.04 (m, 1H), 3.05-3.04 (m, 1H), 2.96 (s, 3H), 2.84-2.76 (m, 2H), 2.51 (d, J=16.63 Hz, 1H), 2.47-2.27 (m, 4H), 2.02-1.91 (m, 4H), 1.74 (d, J=8.80 Hz, 2H), 1.38 (t, J=12.59 Hz, 1H). LRMS: (ESI, +ve ion) m/z 741.2 (M+H)$^+$.

Example 23

(1S,3'R,6'R,7'S,8'E,15'R)-6-CHLORO-N-(ETHYL-SULFONYL)-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

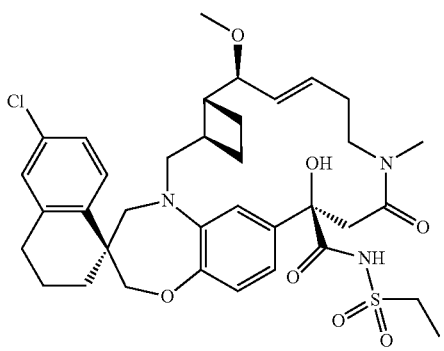 [SMILES: CCS(=O)(=O)NC(=O)[C@@]1(O)CC(=O)N(C)CC/C=C/[C@H](OC)[C@@H]2CC[C@H]2CN2C[C@@]3(CCCc4cc(Cl)ccc43)COc3ccc1cc32]

The title compound (11 mg, 48%) was synthesized from Example 4 through a procedure similar to that used for the synthesis of Example 5. $^1$H NMR (300 MHz, CDCl$_3$) δ 8.84 (br. s., 1H), 7.74 (d, J=8.48 Hz, 1H), 7.18 (dd, J=2.12, 8.40 Hz, 1H), 7.09 (d, J=2.05 Hz, 1H), 7.04-6.98 (m, 1H), 6.89 (s, 1H), 6.49 (d, J=7.75 Hz, 1H), 6.36 (t, J=11.98 Hz, 1H), 5.68 (dd, J=9.43, 14.83 Hz, 1H), 4.04 (s, 2H), 3.54-3.82 (m, 5H), 3.53-3.41 (m, 1H), 3.40-3.32 (m, 2H), 3.27 (s, 3H), 3.24-3.13 (m, 2H), 3.00 (s, 3H), 2.79 (br. s., 1H), 2.73-2.53 (m, 3H), 2.45-2.24 (m, 3H), 2.04-1.58 (m, 9H), 1.46 (t, J=7.38 Hz, 2H). LRMS: (ESI, +ve ion) m/z 700.0 (M+H)$^+$.

Example 24

(1S,3'R,6'R,7'S,8'E,15'R)—N-(TERT-BUTYLSULFONYL)-6-CHLORO-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

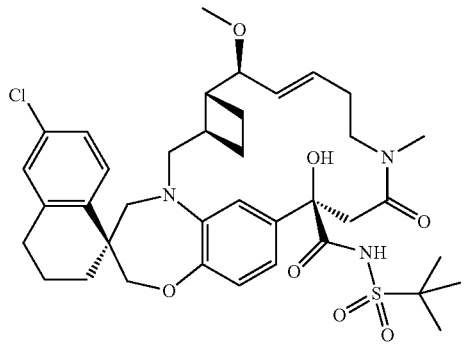 [SMILES: CO[C@H]1/C=C/CCN(C)C(=O)C[C@](O)(C(=O)NS(=O)(=O)C(C)(C)C)c2ccc3c(c2)N(C[C@@H]2CC[C@H]21)C[C@@]1(CCCc2cc(Cl)ccc21)CO3]

The title compound (15 mg, 42%) was synthesized from Example 4 through a procedure similar to that used for the synthesis of Example 5. $^1$H NMR (300 MHz, CD$_2$Cl$_2$) δ 8.70 (s, 1H), 7.73 (d, J=8.48 Hz, 1H), 7.16 (dd, J=2.27, 8.55 Hz, 1H), 7.08 (d, J=2.19 Hz, 1H), 6.99 (d, J=7.02 Hz, 1H), 6.86 (d, J=8.18 Hz, 1H), 6.49 (s, 1H), 6.33 (t, J=11.98 Hz, 1H), 5.72-5.60 (m, 1H), 4.08-3.93 (m, 2H), 3.80-3.51 (m, 5H), 3.33 (d, J=14.32 Hz, 1H), 3.21 (s, 3H), 3.13-3.20 (m, 1H), 3.11-3.01 (m, 1H), 2.97 (s, 3H), 2.83-2.60 (m, 3H), 2.55 (d, J=16.81 Hz, 1H), 2.47-2.24 (m, 3H), 2.10-1.66 (m, 8H), 1.35 (s, 9H). LRMS: (ESI, +ve ion) m/z 728.0 (M+H)$^+$.

Example 25

(1S,3'R,6'R,7'S,8'E,15'R)—N-(1-AZETIDINYLSULFONYL)-6-CHLORO-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

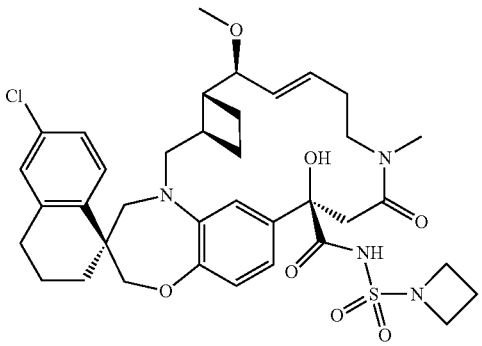 [SMILES: CO[C@H]1/C=C/CCN(C)C(=O)C[C@](O)(C(=O)NS(=O)(=O)N2CCC2)c2ccc3c(c2)N(C[C@@H]2CC[C@H]21)C[C@@]1(CCCc2cc(Cl)ccc21)CO3]

The title compound (14 mg, 52%) was synthesized from Example 4 through a procedure similar to that used for the synthesis of Example 5. ¹H NMR (300 MHz, CD₂Cl₂) δ 8.98 (s, 1H), 7.73 (d, J=8.48 Hz, 1H), 7.16 (dd, J=2.28, 8.46 Hz, 1H), 7.07 (d, J=2.19 Hz, 1H), 7.01 (dd, J=2.06, 8.24 Hz, 1H), 6.87 (d, J=8.26 Hz, 1H), 6.57 (d, J=1.97 Hz, 1H), 6.37 (t, J=11.73 Hz, 1H), 5.68 (ddd, J=1.55, 9.54, 15.15 Hz, 1H), 4.16-3.94 (m, 6H), 3.80-3.55 (m, 5H), 3.33 (d, J=14.40 Hz, 1H), 3.20 (s, 3H), 3.17-3.02 (m, 2H), 2.98 (s, 3H), 2.79-2.53 (m, 7H), 2.49-2.27 (m, 4H), 2.13 (quin, J=7.59 Hz, 2H), 2.03-1.65 (m, 7H). LRMS: (ESI, +ve ion) m/z 728.0 (M+H)⁺.

Example 26

(1S,3'R,6'R,7'S,8'E,15'R)-6-CHLORO-15'-HYDROXY-7'-METHOXY-N-((2-METHOXYETHYL)(METHYL)SULFAMOYL)-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXAMIDE

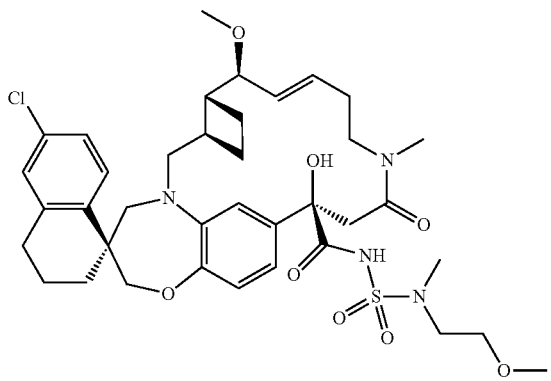 [SMILES: COCCN(C)S(=O)(=O)NC(=O)[C@@]1(O)CC(=O)N(C)CC/C=C/[C@H](OC)[C@@H]2CC[C@H]2CN2C[C@@]3(CCCc4cc(Cl)ccc43)COc3ccc1cc32]

The title compound (9 mg, 36%) was synthesized from Example 4 through a procedure similar to that used for the synthesis of Example 5. ¹H NMR (500 MHz, CD₂Cl₂) δ 9.25 (s, 1H), 7.72 (d, J=8.56 Hz, 1H), 7.15 (dd, J=2.32, 8.44 Hz, 1H), 7.08 (d, J=2.45 Hz, 1H), 6.98 (dd, J=2.20, 8.31 Hz, 1H), 6.85 (d, J=8.31 Hz, 1H), 6.52 (d, J=1.96 Hz, 1H), 6.38 (t, J=12.47 Hz, 1H), 5.65 (ddd, J=1.71, 9.54, 14.92 Hz, 1H), 4.04-3.97 (m, 2H), 3.75 (dd, J=1.96, 9.54 Hz, 1H), 3.70 (d, J=14.43 Hz, 1H), 3.63-3.56 (m, 2H), 3.57-3.44 (m, 4H), 3.41-3.37 (m, 1H), 3.36 (s, 3H), 3.32 (d, J=14.18 Hz, 1H), 3.18 (s, 3H), 3.17-3.04 (m, 2H), 2.97 (s, 3H), 2.88 (s, 3H), 2.83-2.71 (m, 2H), 2.70-2.61 (m, 1H), 2.49 (d, J=16.87 Hz, 1H), 2.45-2.38 (m, 2H), 2.33-2.26 (m, 2H), 2.07-1.98 (m, 2H), 1.98-1.89 (m, 2H), 1.89-1.78 (m, 2H), 1.78-1.69 (m, 1H), 1.37 (t, J=12.59 Hz, 1H). LRMS: (ESI, +ve ion) m/z 759.2 (M+H)⁺.

Example 27

(1-SULFAMOYL-4-PIPERIDINYL (1S,3'R,6'R,7'S,8'E,15'R)-6-CHLORO-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLATE

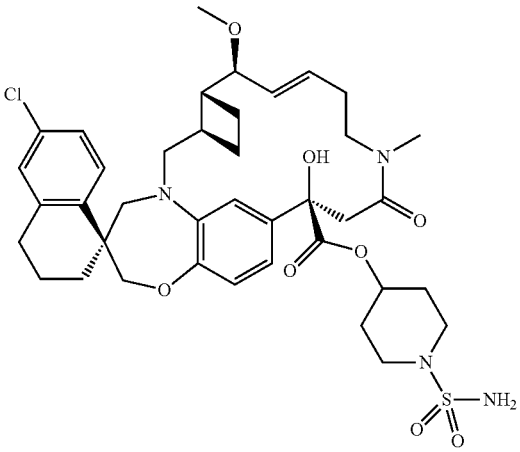 [SMILES: CO[C@H]1/C=C/CCN(C)C(=O)C[C@](O)(C(=O)OC2CCN(S(N)(=O)=O)CC2)c2ccc3c(c2)N(C[C@@H]2CC[C@H]21)C[C@@]1(CCCc2cc(Cl)ccc21)CO3]

The title compound (4 mg, 2%) was synthesized from Example 4 through a procedure similar to that used for the synthesis of Example 5. ¹H NMR (500 MHz, CD₂Cl₂) δ 7.73 (d, J=8.56 Hz, 1H), 7.16 (dd, J=2.32, 8.44 Hz, 1H), 7.08 (d, J=2.20 Hz, 1H), 7.01 (dd, J=1.96, 8.31 Hz, 1H), 6.84 (d, J=8.31 Hz, 1H), 6.49 (d, J=1.96 Hz, 1H), 6.18 (ddd, J=2.57, 11.55, 14.73 Hz, 1H), 5.66 (ddd, J=1.71, 9.35, 15.10 Hz, 1H), 4.93 (tt, J=3.55, 7.09 Hz, 1H), 4.41 (br. s., 2H), 4.07-3.92 (m, 2H), 3.76-3.64 (m, 2H), 3.63-3.55 (m, 2H), 3.49 (d, J=16.87 Hz, 1H), 3.42-3.29 (m, 2H), 3.19 (s, 3H), 3.17-3.02 (m, 5H), 2.97-2.92 (m, 3H), 2.83-2.73 (m, 2H), 2.70-2.63 (m, 1H), 2.60 (d, J=16.87 Hz, 1H), 2.47-2.37 (m, 2H), 2.30 (dd, J=12.35, 14.31 Hz, 1H), 1.69-1.89 (m, 11H), 1.45-1.34 (m, 1H). LRMS: (ESI, +ve ion) m/z 771.0 (M+H)⁺.

Example 28

(1S,3'R,6'R,7'S,8'E,15'R)-6-CHLORO-15'-HY-DROXY-7'-METHOXY-12'-METHYL-13'-OXO-N-(3-PYRIDINYLSULFONYL)-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

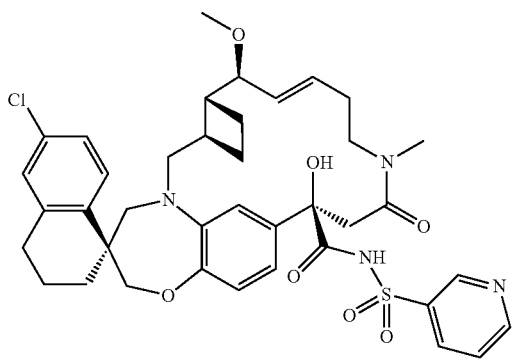 [SMILES: CO[C@H]1/C=C/CCN(C)C(=O)C[C@](O)(C(=O)NS(=O)(=O)c2cccnc2)c2ccc3c(c2)N(C[C@@H]2CC[C@H]21)C[C@@]1(CCCc2cc(Cl)ccc21)CO3]

The title compound (18 mg, 59%) was synthesized from Example 4 through a procedure similar to that used for the synthesis of Example 5. $^1$H NMR (300 MHz, CD$_2$Cl$_2$) δ 9.27 (br. s., 1H), 9.37-9.17 (m, 1H), 9.03-8.94 (m, 1H), 8.84 (d, J=4.82 Hz, 1H), 8.16 (d, J=7.89 Hz, 1H), 7.73 (d, J=8.48 Hz, 1H), 7.44 (s, 1H), 7.25-7.06 (m, 3H), 7.01-6.83 (m, 2H), 6.59 (br. s., 1H), 6.33-6.15 (m, 1H), 6.01 (br. s., 1H), 5.72-5.53 (m, 1H), 4.12-3.95 (m, 2H), 3.79-3.30 (m, 6H), 3.26 (s, 3H), 3.22-3.08 (m, 2H), 2.91 (s, 3H), 2.86-2.73 (m, 3H), 2.71-2.20 (m, 5H), 2.11-1.92 (m, 4H). LRMS: (ESI, +ve ion) m/z 749.0 (M+H)$^+$.

Example 29

(1S,3'R,6'R,7'S,8'E,15'R)-6-CHLORO-15'-HY-DROXY-7'-METHOXY-12'-METHYL-13'-OXO-N-((2,2,2-TRIFLUOROETHYL)SULFONYL)-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

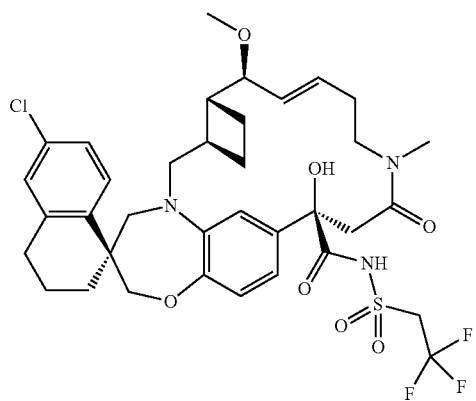 [SMILES: CO[C@H]1/C=C/CCN(C)C(=O)C[C@](O)(C(=O)NS(=O)(=O)CC(F)(F)F)c2ccc3c(c2)N(C[C@@H]2CC[C@H]21)C[C@@]1(CCCc2cc(Cl)ccc21)CO3]

The title compound (28 mg, 57%) was synthesized from Example 4 through a procedure similar to that used for the synthesis of Example 5. $^1$H NMR (300 MHz, CD$_3$OD) δ 7.71 (d, J=8.51 Hz, 1H), 7.23-7.06 (m, 4H), 6.96 (dd, J=1.83, 8.29 Hz, 1H), 6.76 (d, J=8.29 Hz, 1H), 6.43-6.23 (m, 1H), 5.65 (dd, J=9.77, 15.33 Hz, 1H), 4.20-3.90 (m, 7H), 3.82 (d, J=14.80 Hz, 1H), 3.66 (d, J=14.03 Hz, 4H), 3.24 (s, 3H), 2.99 (s, 3H), 2.84-2.75 (m, 3H), 2.54-2.28 (m, 3H), 2.14-1.74 (m, 9H). LRMS: (ESI, +ve ion) m/z 754.0 (M+H)$^+$.

Example 30

(1S,3'R,6'R,7'S,8'E,15'R)-6-CHLORO-15'-HY-DROXY-7'-METHOXY-N-((4-METHOXYPHE-NYL)SULFONYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

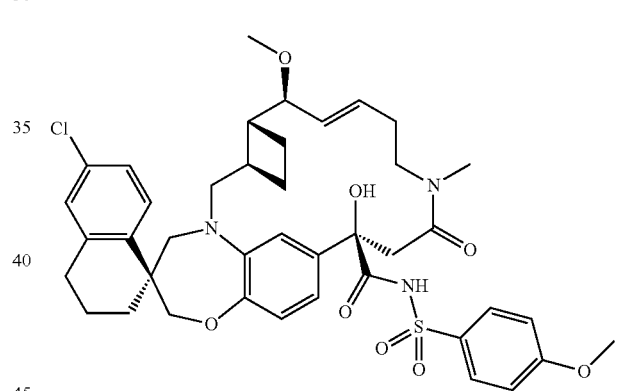

The title compound (21 mg, 55%) was synthesized from Example 4 through a procedure similar to that used for the synthesis of Example 5. $^1$H NMR (300 MHz, CD$_2$Cl$_2$) δ 9.00 (s, 1H), 7.75 (d, J=8.95 Hz, 2H), 7.69 (d, J=8.48 Hz, 1H), 7.14 (dd, J=2.10, 8.50 Hz, 1H), 7.09 (s, 1H), 6.87-6.96 (m, 3H), 6.86-6.78 (m, 1H), 6.37 (t, J=12.11 Hz, 1H), 5.87 (s, 1H), 5.59 (dd, J=8.93, 14.34 Hz, 1H), 4.08-3.99 (m, 1H), 3.93-3.89 (m, 3H), 3.96-3.86 (m, 4H), 3.66-3.44 (m, 4H), 3.33 (d, J=16.66 Hz, 1H), 3.27 (s, 3H), 3.23 (d, J=14.47 Hz, 1H), 3.22-3.15 (m, 1H), 3.15-3.06 (m, 2H), 2.93 (s, 3H), 2.82 (d, J=4.82 Hz, 5H), 2.63 (t, J=12.86 Hz, 1H), 2.39 (d, J=16.70 Hz, 1H), 2.33-2.11 (m, 3H), 2.10-1.75 (m, 7H), 1.71-1.58 (m, 1H), 1.51-1.36 (m, 1H). LRMS: (ESI, +ve ion) m/z 778.0 (M+H)$^+$.

Example 31

(1S,3'R,6'R,7'S,8'E,15'R)-6-CHLORO-15'-HYDROXY-7'-METHOXY-N-((6-METHOXY-3-PYRIDINYL)SULFONYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

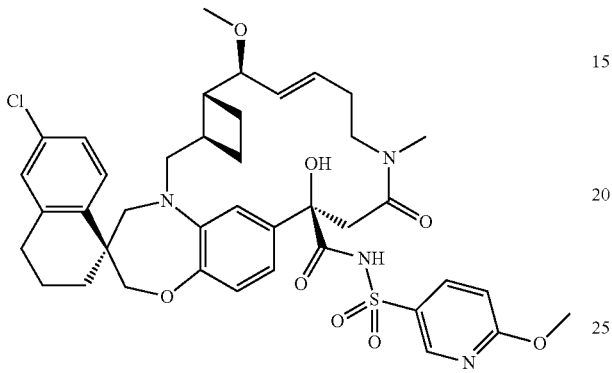

The title compound (17 mg, 44%) was synthesized from Example 4 through a procedure similar to that used for the synthesis of Example 5. $^1$H NMR (300 MHz, CD$_2$Cl$_2$) δ 9.18 (br. s., 1H), 8.78 (d, J=2.19 Hz, 1H), 7.85 (dd, J=2.41, 8.84 Hz, 1H), 7.72 (d, J=8.48 Hz, 1H), 7.23-7.10 (m, 2H), 7.02-6.81 (m, 2H), 6.75 (d, J=8.92 Hz, 1H), 6.36 (t, J=12.13 Hz, 1H), 5.99 (br. s., 1H), 5.66 (dd, J=9.43, 14.83 Hz, 1H), 4.12-4.03 (m, 4H), 4.00-3.88 (m, 1H), 3.78-3.37 (m, 5H), 3.35 (s, 3H), 3.28 (d, J=14.62 Hz, 1H), 3.20-3.11 (m, 1H), 2.95 (s, 3H), 2.84 (d, J=4.38 Hz, 2H), 2.74-2.60 (m, 1H), 2.48 (d, J=16.81 Hz, 1H), 2.43-2.21 (m, 3H), 2.16-1.64 (m, 8H), 1.55-1.39 (m, 1H). LRMS: (ESI, +ve ion) m/z 779.0 (M+H)$^+$.

Example 32

(1S,3'R,6'R,7'S,8'E,15'R)-6-CHLORO-15'-HYDROXY-7'-METHOXY-N-((2-METHOXYETHYL)SULFONYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

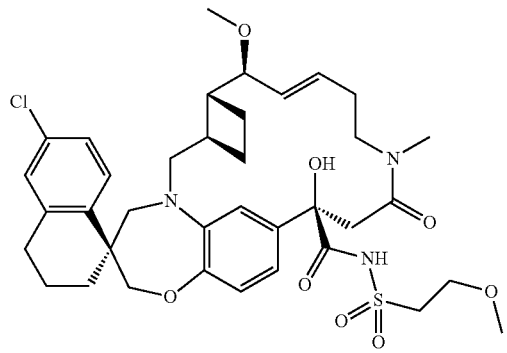 [SMILES: COCCS(=O)(=O)NC(=O)[C@@]1(O)CC(=O)N(C)CC/C=C/[C@H](OC)[C@@H]2CC[C@H]2CN2C[C@@]3(CCCc4cc(Cl)ccc43)COc3ccc1cc32]

The title compound (10 mg, 40%) was synthesized from Example 4 through a procedure similar to that used for the synthesis of Example 5. $^1$H NMR (300 MHz, CD$_2$Cl$_2$) δ 9.00 (br. s., 1H), 7.72 (d, J=8.48 Hz, 1H), 7.16 (dd, J=2.34, 8.48 Hz, 1H), 7.08 (d, J=2.19 Hz, 1H), 6.99 (dd, J=1.75, 8.18 Hz, 1H), 6.91-6.83 (m, 1H), 6.47 (s, 1H), 6.31 (t, J=12.20 Hz, 1H), 5.67 (ddd, J=1.53, 9.54, 15.09 Hz, 1H), 4.00 (d, J=2.05 Hz, 2H), 3.80-3.51 (m, 10H), 3.33 (d, J=14.32 Hz, 1H), 3.24 (s, 3H), 3.23 (s, 3H), 2.97 (s, 3H), 2.79-2.54 (m, 4H), 2.46-2.23 (m, 3H), 2.10-1.68 (m, 8H), 1.45-1.31 (m, 1H). LRMS: (ESI, +ve ion) m/z 731.0 (M+H)$^+$.

Example 33

(1S,3'R,6'R,7'S,8'E,15'R)-6-CHLORO-15'-HYDROXY-7'-METHOXY-12'-METHYL-13'-OXO-N-(4-PYRIDINYLSULFONYL)-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

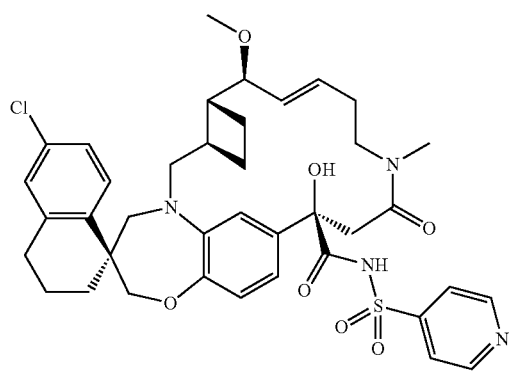 [SMILES: CO[C@H]1/C=C/CCN(C)C(=O)C[C@](O)(C(=O)NS(=O)(=O)c2ccncc2)c2ccc3c(c2)N(C[C@@H]2CC[C@H]21)C[C@@]1(CCCc2cc(Cl)ccc21)CO3]

The title compound (25 mg, 68%) was synthesized from Example 4 through a procedure similar to that used for the synthesis of Example 5. $^1$H NMR (300 MHz, CD$_2$Cl$_2$) δ 9.32 (br. s., 1H), 8.91-8.72 (m, 2H), 7.90-7.81 (m, 2H), 7.70 (d, J=8.48 Hz, 1H), 7.15 (dd, J=2.05, 8.48 Hz, 1H), 7.08 (s, 1H), 6.99-6.92 (m, 1H), 6.88-6.81 (m, 1H), 6.15 (t, J=11.77 Hz, 1H), 6.05 (s, 1H), 5.61 (dd, J=10.52, 14.03 Hz, 1H), 4.11-3.93 (m, 2H), 3.68-3.24 (m, 9H), 3.23 (s, 3H), 3.16-2.94 (m, 3H), 2.86 (s, 3H), 2.82-2.74 (m, 2H), 2.61 (t, J=12.86 Hz, 1H), 2.48 (d, J=16.95 Hz, 1H), 2.40-2.17 (m, 3H), 2.09-1.75 (m, 6H), 1.74-1.62 (m, 1H), 1.43 (t, J=13.30 Hz, 1H). LRMS: (ESI, +ve ion) m/z 749.0 (M+H)$^+$.

Example 34

(1S,3'R,6'R,7'S,8'E,15'R)-6-CHLORO-15'-HYDROXY-7'-METHOXY-12'-METHYL-13'-OXO-N-(2-PYRIDINYLSULFONYL)-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

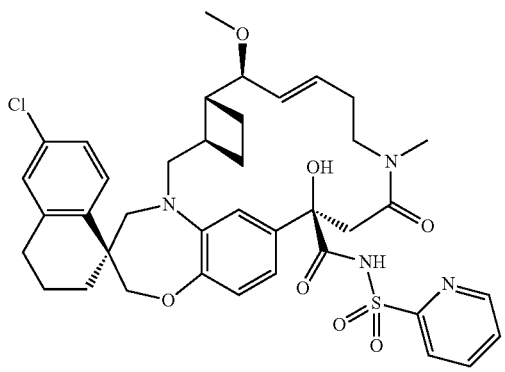 [SMILES: CO[C@H]1/C=C/CCN(C)C(=O)C[C@](O)(C(=O)NS(=O)(=O)c2ccccn2)c2ccc3c(c2)N(C[C@@H]2CC[C@H]21)C[C@@]1(CCCc2cc(Cl)ccc21)CO3]

The title compound (17 mg, 60%) was synthesized from Example 4 through a procedure similar to that used for the synthesis of Example 5. $^1$H NMR (300 MHz, CD$_2$Cl$_2$) δ 9.29 (br. s., 1H), 8.52 (td, J=0.77, 3.87 Hz, 1H), 8.14 (d, J=7.89 Hz, 1H), 7.96 (dt, J=1.68, 7.78 Hz, 1H), 7.71 (d, J=8.62 Hz, 1H), 7.54 (ddd, J=1.10, 4.71, 7.64 Hz, 1H), 7.15 (dd, J=2.34, 8.48 Hz, 1H), 7.09 (d, J=2.19 Hz, 1H), 6.98 (dd, J=1.75, 8.18 Hz, 1H), 6.90-6.83 (m, 1H), 6.26-6.09 (m, 1H), 5.98 (s, 1H), 5.57 (ddd, J=1.83, 9.50, 15.13 Hz, 1H), 4.02 (q, J=12.13 Hz, 2H), 3.64 (d, J=14.47 Hz, 1H), 3.56-3.42 (m, 2H), 3.40-3.21 (m, 3H), 3.19 (s, 3H), 3.16-3.05 (m, 2H), 2.89 (s, 4H), 2.83-2.71 (m, 3H), 2.67-2.51 (m, 2H), 2.45 (d, J=16.81 Hz, 1H), 2.36-2.14 (m, 3H), 2.07-1.58 (m, 8H), 1.49 (d, J=12.42 Hz, 1H). LRMS: (ESI, +ve ion) m/z 749.0 (M+H)$^+$.

Example 35

(1S,3'R,6'R,7'S,8'E,15'R)-6-CHLORO-15'-HYDROXY-7'-METHOXY-N,12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

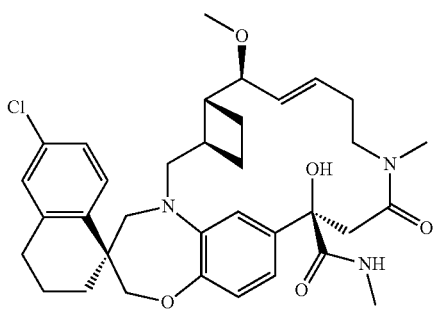 [SMILES: CNC(=O)[C@@]1(O)CC(=O)N(C)CC/C=C/[C@H](OC)[C@@H]2CC[C@H]2CN2C[C@@]3(CCCc4cc(Cl)ccc43)COc3ccc1cc32]

To a solution of (1S,3'R,6'R,7'S,8'E,15'S)-6-chloro-15'-hydroxy-7'-methoxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid (Example 4, 14 mg, 0.023 mmol) in DCM (0.5 mL) was added 1,1'-carbonyldiimidazole (4.10 mg, 0.025 mmol). The reaction mixture was stirred at room temperature for 2 hours. After this time, methylamine (2.0 M solution in THF) (46.0 µL, 0.092 mmol) was added. The reaction mixture was stirred overnight and was then diluted with water (10 mL) and extracted with CH$_2$Cl$_2$ (3×10 mL). The combined organic extract was dried over MgSO$_4$, filtered and concentrated. The crude material was purified by reverse-phase preparative HPLC using a Phenomenex Gemini column, 10 micron, C18, 100 Å, 150×30 mm, 0.1% TFA in CH$_3$CN/H$_2$O, eluting with a gradient 50% to 95% over 27 minutes to provide the title compound (8 mg, 45%) as a white solid after drying in the lyophilizer overnight. $^1$H NMR (400 MHz, CD$_2$Cl$_2$) δ 7.72 (d, J=8.61 Hz, 1H), 7.15 (dd, J=2.35, 8.41 Hz, 1H), 7.07 (d, J=2.35 Hz, 1H), 6.96 (d, J=7.83 Hz, 1H), 6.90 (d, J=4.89 Hz, 1H), 6.81 (d, J=8.22 Hz, 1H), 6.71 (br. s., 1H), 6.45 (t, J=12.62 Hz, 1H), 5.62 (ddd, J=1.76, 9.49, 15.16 Hz, 1H), 3.98 (br. s., 2H), 3.80 (d, J=9.39 Hz, 1H), 3.74-3.51 (m, 4H), 3.32 (d, J=14.28 Hz, 1H), 3.20 (s, 3H), 3.09-3.16 (m, 1H), 3.05 (dd, J=8.80, 14.48 Hz, 1H), 2.94 (s, 3H), 2.75 (d, J=4.89 Hz, 3H), 2.72-2.56 (m, 2H), 2.40 (d, J=16.24 Hz, 4H), 2.29 (dd, J=13.40, 14.97 Hz, 2H), 2.07-1.68 (m, 8H). LRMS: (ESI, +ve ion) m/z 622.2 (M+H)$^+$.

Example 36

(1S,3'R,6'R,7'S,8'E,15'R)-6-CHLORO-15'-HYDROXY-N,7'-DIMETHOXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

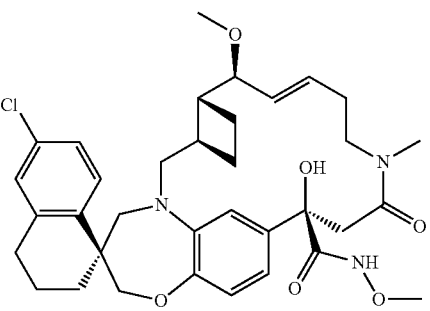 [SMILES: CONC(=O)[C@@]1(O)CC(=O)N(C)CC/C=C/[C@H](OC)[C@@H]2CC[C@H]2CN2C[C@@]3(CCCc4cc(Cl)ccc43)COc3ccc1cc32]

The title compound (8 mg, 63%) was synthesized from Example 4 through a procedure similar to that used for the synthesis of Example 35. $^1$H NMR (400 MHz, CD$_2$Cl$_2$) δ 9.17 (s, 1H), 7.15 (dd, J=2.35, 8.41 Hz, 1H), 7.07 (d, J=2.35 Hz, 1H), 6.97-6.94 (m, 1H), 6.93 (d, J=2.15 Hz, 1H), 6.82 (d, J=8.22 Hz, 1H), 6.66 (d, J=1.96 Hz, 1H), 6.44 (s, 1H), 5.62 (ddd, J=1.76, 9.54, 15.11 Hz, 1H), 3.99 (s, 2H), 3.84-3.79 (m, 1H), 3.68 (s, 3H), 3.65-3.61 (m, 1H), 3.60-3.54 (m, 1H), 3.32 (d, J=14.28 Hz, 1H), 3.21 (s, 3H), 3.17-3.01 (m, 2H), 2.95 (s, 3H), 2.83-2.59 (m, 4H), 2.49-2.22 (m, 5H), 2.11-1.67 (m, 9H). LRMS: (ESI, +ve ion) m/z 638.2 (M+H)$^+$.

Example 37

(1S,3'R,6'R,7'S,8'E,15'R)-6-CHLORO-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO [14.7.2.0$^{3,6}$.0$^{19,24}$]PENTACOSA [8,16,18,24]TETRAENE]-15'-CARBOXAMIDE

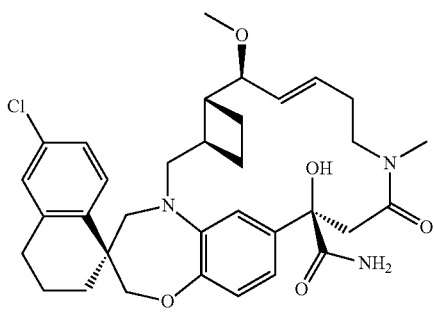 [SMILES: CO[C@H]1/C=C/CCN(C)C(=O)C[C@](O)(C(N)=O)c2ccc3c(c2)N(C[C@@H]2CC[C@H]21)C[C@@]1(CCCc2cc(Cl)ccc21)CO3]

The title compound (8 mg, 35%) was synthesized from Example 4 through a procedure similar to that used for the synthesis of Example 35. $^1$H NMR (400 MHz, CD$_2$Cl$_2$) δ 7.73 (d, J=8.41 Hz, 1H), 7.15 (dd, J=2.25, 8.51 Hz, 1H), 7.08 (d, J=1.96 Hz, 1H), 7.03-6.94 (m, 2H), 6.84 (d, J=8.22 Hz, 1H), 6.68 (br. s., 1H), 6.44 (br. s., 1H), 6.36 (t, J=12.52 Hz, 1H), 5.64 (ddd, J=1.37, 9.54, 15.11 Hz, 1H), 4.04-3.94 (m, 2H), 3.81-3.49 (m, 6H), 3.33 (d, J=14.28 Hz, 1H), 3.19 (s, 3H), 3.18-3.03 (m, 2H), 2.96 (s, 3H), 2.85-2.71 (m, 2H), 2.71-2.58 (m, 1H), 2.52-2.19 (m, 4H), 2.09-1.66 (m, 8H). LRMS: (ESI, +ve ion) m/z 608.2 (M+H)$^+$.

Example 38

(1S,3'R,6'R,7'S,8'E,15'R)-6-CHLORO-15'-HYDROXY-7'-METHOXY-N,N,12'-TRIMETHYL-13'-OXO-3,4-DIHYDRO-2H-SPIRO[NAPHTHALENE-1,22'-[20]OXA[1,12]DIAZATETRACYCLO [14.7.2.0$^{3,6}$.0$^{19,24}$]PENTACOSA[8,16,18,24]TETRAENE]-15'-CARBOXAMIDE

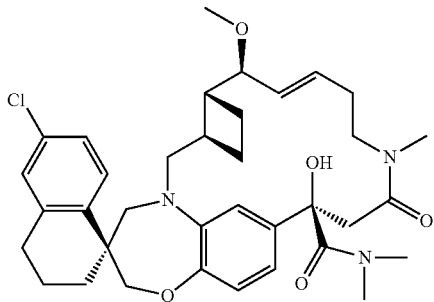 [SMILES: CO[C@H]1/C=C/CCN(C)C(=O)C[C@](O)(C(=O)N(C)C)c2ccc3c(c2)N(C[C@@H]2CC[C@H]21)C[C@@]1(CCCc2cc(Cl)ccc21)CO3]

The title compound (10 mg, 53%) was synthesized from Example 4 through a procedure similar to that used for the synthesis of Example 35. $^1$H NMR (400 MHz, CD$_2$Cl$_2$) δ 7.78 (d, J=8.61 Hz, 1H), 7.20 (dd, J=2.35, 8.61 Hz, 1H), 7.12 (d, J=2.15 Hz, 1H), 7.05 (dd, J=2.05, 8.12 Hz, 1H), 6.98 (br. s., 1H), 6.89 (d, J=8.22 Hz, 1H), 6.31 (s, 1H), 5.75-5.51 (m, 1H), 4.03 (s, 2H), 3.80-3.56 (m, 4H), 3.48 (d, J=16.24 Hz, 1H), 3.35 (d, J=14.48 Hz, 1H), 3.24 (s, 3H), 3.18-3.02 (m, 2H), 2.99 (s, 3H), 2.92 (d, J=7.04 Hz, 6H), 2.85-2.76 (m, 2H), 2.76-2.66 (m, 1H), 2.47-2.21 (m, 4H), 2.15-1.67 (m, 8H). LRMS: (ESI, +ve ion) m/z 636.2 (M+H)$^+$.

Example 39

(1S,3'R,6'R,7'S,15'R)-6-CHLORO-N-(DIMETHYLSULFAMOYL)-15'-HYDROXY-7'-METHOXY-12'-METHYL-13'-OXO-3,4-DIHYDRO-2H-SPIRO [NAPHTHALENE-1,22'-[20]OXA[1,12] DIAZATETRACYCLO[14.7.2.0$^{3,6}$.0$^{19,24}$] PENTACOSA[16,18,24]TRIENE]-15'-CARBOXAMIDE

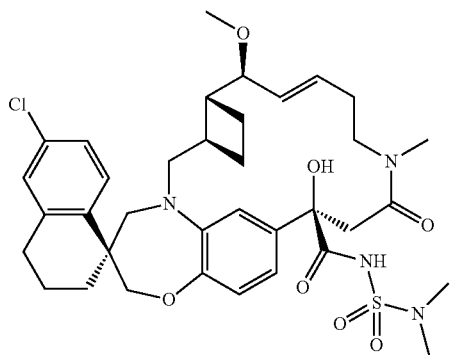 [SMILES: CO[C@H]1/C=C/CCN(C)C(=O)C[C@](O)(C(=O)NS(=O)(=O)N(C)C)c2ccc3c(c2)N(C[C@@H]2CC[C@H]21)C[C@@]1(CCCc2cc(Cl)ccc21)CO3]

A mixture of (1S,3'R,6'R,7'S,8'E,15'R)-6-chloro-N-(dimethylsulfamoyl)-15'-hydroxy-7'-methoxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide (Example 5, 30 mg, 0.042 mmol) and platinum (IV) oxide (16.42 mg, 0.072 mmol) in EtOAc (1.801 mL) were stirred under H$_2$ (balloon) at room temperature. The reaction was quenched after 1 hour. The mixture was then filtered through a syringe filter to remove solid catalyst and concentrated. The crude material was purified by reverse-phase preparative HPLC using a Phenomenex Gemini column, 10 micron, C18, 100 Å, 150×30 mm, eluting with a gradient of 35% to 95% acetonitrile in water (both solvents containing 0.1% TFA) over a period of 30 minutes to provide the title compound as a white solid after drying in the lyophilizer overnight (22 mg, 73%). $^1$H NMR (400 MHz, CD$_2$Cl$_2$) δ ppm 8.98 (s, 1H), 7.75 (d, J=8.41 Hz, 1H), 7.16 (dd, J=8.51, 2.25 Hz, 1H), 7.11-7.00 (m, 2H), 6.88 (d, J=8.41 Hz, 1H), 6.51 (d, J=1.96 Hz, 1H), 4.11-3.95-(m, 2H), 3.73 (d, J=14.09 Hz, 1H), 3.68-3.57 (m, 2H), 3.53 (d, J=16.43 Hz, 1H), 3.44 (d, J=11.15 Hz, 1H), 3.31-3.22 (m, 1H), 3.13-2.98 (m, 2H), 2.92-2.88 (m, 3H), 2.87-2.83 (m, 6H), 2.81-2.70 (m, 2H), 2.57-2.38 (m, 4H), 2.08-1.99 (m, 4H), 1.98-1.61 (m, 9H), 1.61-1.33 (m, 4H). LRMS: (ESI, +ve ion) m/z 717.0 (M+H)$^+$.

Example 40

(1S,3'R,6'R,7'S,8'E,15'S)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

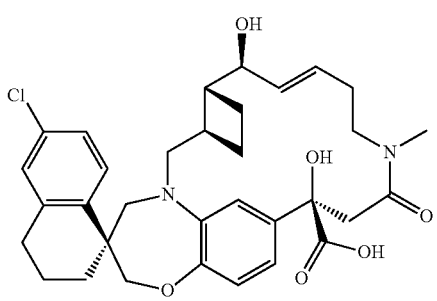 [SMILES: CN1CC/C=C/[C@H](O)[C@@H]2CC[C@H]2CN2C[C@@]3(CCCc4cc(Cl)ccc43)COc3ccc(cc32)[C@@](O)(C(=O)O)CC1=O]

The title compound (19 mg, 83%) was synthesized from Example 1 via saponification with lithium hydroxide through a procedure similar to that used for the synthesis of Example 4. $^1$H NMR (400 MHz, CD$_2$Cl$_2$) δ 7.72 (d, J=8.41 Hz, 1H), 7.14-7.13 (m, 1H), 7.16 (d, J=1.76 Hz, 1H), 7.08 (d, J=2.15 Hz, 1H), 6.99 (dd, J=2.05, 8.31 Hz, 1H), 6.85 (d, J=8.22 Hz, 1H), 6.69-6.52 (m, 1H), 6.28 (t, J=13.01 Hz, 1H), 5.88 (dd, J=8.71, 14.77 Hz, 1H), 4.38-4.25 (m, 1H), 4.00 (d, J=2.35 Hz, 2H), 3.52 (d, J=16.82 Hz, 4H), 3.39-3.27 (m, 1H), 3.22-3.05 (m, 3H), 2.77 (d, J=4.89 Hz, 3H), 2.66-2.50 (m, 2H), 2.37 (br. s., 3H), 2.05 (br. s., 7H), 1.47-1.32 (m, 1H). LRMS: (ESI, +ve ion) m/z 595.2 (M+H)$^+$.

Example 41

(1S,3'R,6'R,7'S,15'S)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO [14.7.2.0$^{3,6}$.0$^{19,24}$]PENTACOSA[16,18,24]TRIENE]-15'-CARBOXYLIC ACID

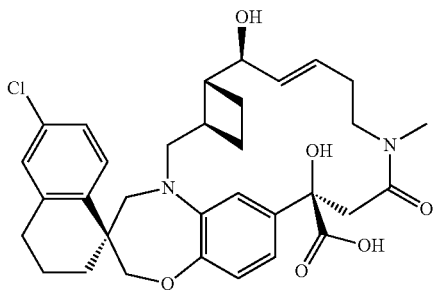 [SMILES: CN1CC/C=C/[C@H](O)[C@@H]2CC[C@H]2CN2C[C@@]3(CCCc4cc(Cl)ccc43)COc3ccc(cc32)[C@@](O)(C(=O)O)CC1=O]

The title compound (5 mg, 92%) was synthesized from Example 40 via hydrogenation with platinum (IV) oxide through a procedure similar to that used for the synthesis of Example 39. $^1$H NMR (400 MHz, CD$_2$Cl$_2$) δ 7.75 (d, J=8.61 Hz, 1H), 7.16 (dd, J=2.35, 8.61 Hz, 1H), 7.10-7.00 (m, 2H), 6.87 (d, J=8.22 Hz, 1H), 6.60 (d, J=1.96 Hz, 1H), 4.07-3.94 (m, 2H), 3.92-3.83 (m, 1H), 3.80-3.49 (m, 4H), 3.33-3.18 (m, 1H), 3.13-2.95 (m, 2H), 2.90 (s, 3H), 2.83-2.70 (m, 2H), 2.65-2.54 (m, 1H), 2.52-2.40 (m, 1H), 2.36-2.25 (m, 1H), 2.10-2.01 (m, 3H), 1.96-1.25 (m, 12H). LRMS: (ESI, +ve ion) m/z 597.2 (M+H)$^+$.

Example 42

(1S,3'R,6'R,7'S,8'E,15'R)-6-CHLORO-N-(DIMETHYLSULFAMOYL)-15'-HYDROXY-7'-METHOXY-N,12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA [8,16,18,24]TETRAENE]-15'-CARBOXAMIDE

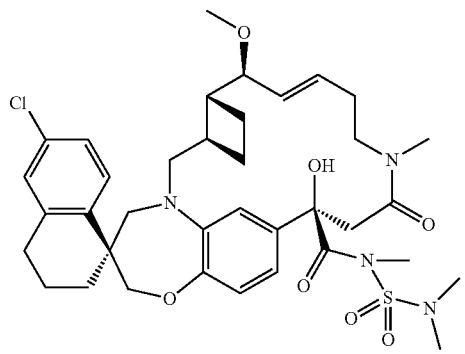 [SMILES: CO[C@H]1/C=C/CCN(C)C(=O)C[C@](O)(C(=O)N(C)S(=O)(=O)N(C)C)c2ccc3c(c2)N(C[C@@H]2CC[C@H]21)C[C@@]1(CCCc2cc(Cl)ccc21)CO3]

To a stirred solution of (1S,3'R,6'R,7'S,8'E,15'R)-6-chloro-N-(dimethylsulfamoyl)-15'-hydroxy-7'-methoxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide (Example 5, 25 mg, 0.035 mmol) and cesium carbonate (28.5 mg, 0.087 mmol) in DMF (2.5 mL) was added iodomethane (14.88 mg, 0.105 mmol). The resulting reaction mixture was stirred at room temperature for 30 minutes and then filtered and diluted with DMSO. The crude material was purified by reverse-phase preparative HPLC using a Phenomenex Gemini column, 10 micron, C18, 100 Å, 150×30 mm, eluting with a gradient of 35% to 95% acetonitrile in water (both solvents containing 0.1% TFA) over a period of 30 minutes to provide the title compound as a white solid. $^1$H NMR (300 MHz, CD$_2$Cl$_2$) δ 7.73 (d, J=8.33 Hz, 1H), 7.15 (dd, J=2.19, 8.48 Hz, 1H), 7.08 (s, 1H), 7.04-6.96 (m, 1H), 6.93-6.85 (m, 1H), 6.67 (t, J=12.28 Hz, 1H), 6.22 (s, 1H), 5.64 (dd, J=9.50, 15.20 Hz, 1H), 4.01 (s, 2H), 3.74-3.55 (m, 4H), 3.43 (d, J=16.37 Hz, 1H), 3.31 (d, J=14.47 Hz, 1H), 3.16 (d, J=0.88 Hz, 6H), 3.14-3.01 (m, 2H), 2.97 (s, 3H), 2.90 (s, 6H), 2.81-2.65 (m, 3H), 2.49-2.22 (m, 4H), 2.12-1.66 (m, 8H), 1.46-1.30 (m, 1H). LRMS: (ESI, +ve ion) m/z 729.0 (M+H)$^+$.

Example 43

(1S,3'R,6'R,7'S,8'E,15'R)-6-CHLORO-N-(DIMETHYLSULFAMOYL)-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXAMIDE

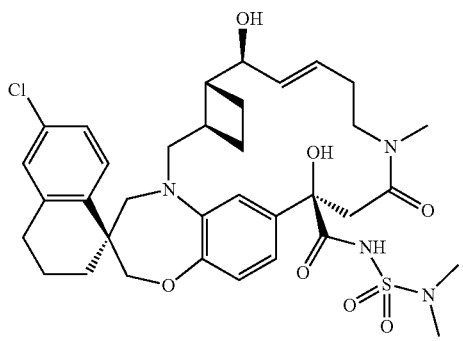 [SMILES: CN1CC/C=C/[C@H](O)[C@@H]2CC[C@H]2CN2C[C@@]3(CCCc4cc(Cl)ccc43)COc3ccc(cc32)[C@@](O)(C(=O)NS(=O)(=O)N(C)C)CC1=O]

Step 1: Methyl(1S,3'R,6'R,7'S,8'E,15'R)-6-chloro-15'-hydroxy-7'-(tert-butyldimethylsilyl)oxy-12'-methyl-13'-oxo-3,4-dihydro-2H-spiro[naphthalene-1,22'-[20]oxa[1,12]diazatetracyclo[14.7.2.0³,⁶.0¹⁹,²⁴]pentacosa[8,16,18,24]tetraene]-15'-carboxylate

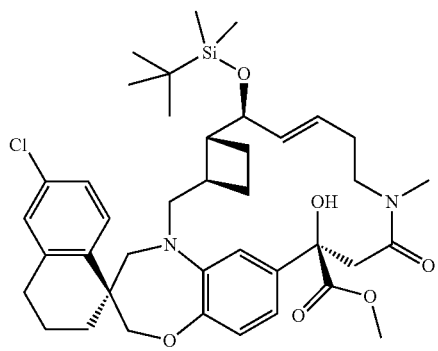 [SMILES: COC(=O)[C@@]1(O)CC(=O)N(C)CC/C=C/[C@H](O[Si](C)(C)C(C)(C)C)[C@@H]2CC[C@H]2CN2C[C@@]3(CCCc4cc(Cl)ccc43)COc3ccc1cc32]

To a solution of methyl (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12]diazatetracyclo[14.7.2.0³,⁶.0¹⁹,²⁴]pentacosa[8,16,18,24]tetraene]-15'-carboxylate (Example 1, 440 mg, 0.722 mmol) in DMF (1 mL) was added imidazole (73.8 mg, 1.083 mmol) and tert-butylchlorodimethylsilane solution (50% wt. in toluene) (0.375 mL, 1.083 mmol). The reaction mixture was stirred at room temperature for 1 hour and was then quenched with water. A saturated aqueous solution of NH₄Cl was added and the reaction mixture was extracted with EtOAc (2×30 mL). The combined organic layer was dried over sodium sulfate, filtered and concentrated under reduced pressure. The crude material was absorbed onto a plug of silica gel and purified by chromatography through a Redi-Sep pre-packed silica gel column (4 g), eluting with a gradient of 0% to 30% EtOAc in hexane, to provide the above compound (410 mg, 0.567 mmol, 78% yield). ¹H NMR (400 MHz, CD₂Cl₂) δ 7.73 (d, J=8.41 Hz, 1H), 7.16 (dd, J=2.25, 8.51 Hz, 1H), 7.08 (d, J=2.35 Hz, 1H), 6.99 (dd, J=1.96, 8.22 Hz, 1H), 6.83 (d, J=8.22 Hz, 1H), 6.51 (d, J=1.96 Hz, 1H), 6.22-6.08 (m, 1H), 5.79 (ddd, J=1.56, 9.05, 15.21 Hz, 1H), 4.27 (dd, J=2.93, 9.00 Hz, 1H), 4.04-3.91 (m, 2H), 3.72 (s, 3H), 3.65-3.53 (m, 2H), 3.50 (d, J=16.63 Hz, 1H), 3.33 (d, J=14.28 Hz, 1H), 3.16-3.01 (m, 2H), 2.94 (s, 3H), 2.82-2.71 (m, 2H), 2.62-2.49 (m, 2H), 2.42-2.17 (m, 3H), 2.08-1.79 (m, 6H), 1.76-1.65 (m, 1H), 1.54 (s, 3H), 0.90-0.84 (m, 9H), 0.11 (s, 3H), 0.07-0.02 (m, 3H). LRMS: (ESI, +ve ion) m/z 723.0 (M+H)⁺.

Step 2: (1S,3'R,6'R,7'S,8'E,15'S)-6-CHLORO-15'-HYDROXY-7'-(TERT-BUTYLDIMETHYLSILYL)OXY-12'-METHYL-13'-OXO-3,4-DIHYDRO-2H-SPIRO[NAPHTHALENE-1,22'-[20]OXA[1,12]DIAZATETRACYCLO [14.7.2.0³,⁶.0¹⁹,²⁴]PENTACOSA[8,16,18,24]TETRAENE]-15'-CARBOXYLIC ACID

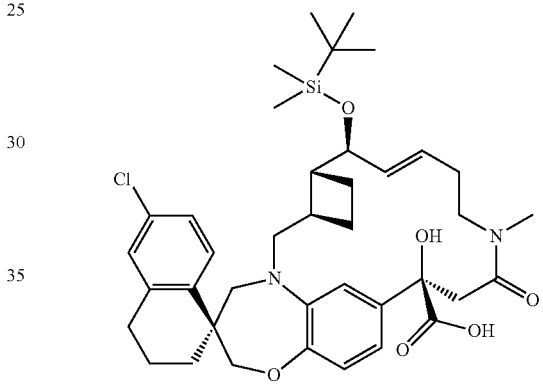

To a solution of methyl (1S,3'R,6'R,7'S,8'E,15'R)-6-chloro-15'-hydroxy-7'-(tert-butyldimethylsilyl)oxy-12'-methyl-13'-oxo-3,4-dihydro-2H-spiro[naphthalene-1,22'-[20]oxa[1,12]diazatetracyclo[14.7.2.0³,⁶.0¹⁹,²⁴]pentacosa[8,16,18,24]tetraene]-15'-carboxylate (Example 43, Step 1, 410 mg, 0.567 mmol) in THF (3 mL) and MeOH (2 mL) was added LiOH (2 M, 2 mL). The reaction mixture was stirred at room temperature for 1 h and then neutralized with HCl (1 N, 4 mL). The reaction mixture was diluted with water (10 mL) and extracted with EtOAc (3×20 mL). The combined organic extract was dried over MgSO₄, filtered and concentrated in vacuo to give the crude material as a white solid which was taken to the next step without further purification. ¹H NMR (300 MHz, CDCl₃) δ 7.73 (d, J=8.48 Hz, 1H), 7.17 (dd, J=2.27, 8.55 Hz, 1H), 7.09-7.01 (m, 2H), 6.93-6.86 (m, 2H), 6.67 (d, J=1.75 Hz, 1H), 6.28-6.14 (m, 1H), 5.76 (dd, J=8.77, 15.05 Hz, 1H), 4.33 (dd, J=2.85, 8.84 Hz, 1H), 4.08-3.94 (m, 2H), 3.80-3.51 (m, 4H), 3.32 (d, J=14.32 Hz, 1H), 3.22-3.03 (m, 2H), 3.00 (s, 3H), 2.81-2.72 (m, 2H), 2.66-2.51 (m, 2H), 2.41-2.20 (m, 3H), 2.07-1.83 (m, 6H), 1.73-1.60 (m, 1H), 1.47-1.37 (m, 1H), 1.26 (d, J=4.24 Hz, 1H), 0.89-0.86 (m, 9H), 0.12-0.09 (m, 3H), 0.05-0.02 (m, 3H). LRMS: (ESI, +ve ion) m/z 709.2 (M+H)⁺.

Step 3: (1S,3'R,6'R,7'S,8'E,15'R)-6-CHLORO-N-(DIMETHYLSULFAMOYL)-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXAMIDE

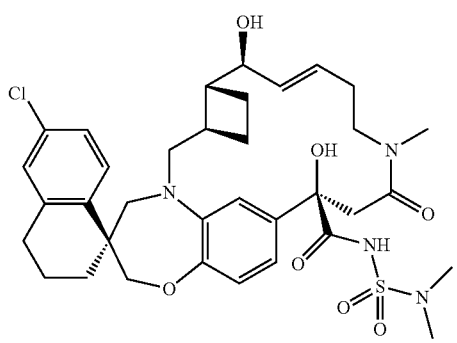 [SMILES: CN1CC/C=C/[C@H](O)[C@@H]2CC[C@H]2CN2C[C@@]3(CCCc4cc(Cl)ccc43)COc3ccc(cc32)[C@@](O)(C(=O)NS(=O)(=O)N(C)C)CC1=O]

To a solution of (1S,3'R,6'R,7'S,8'E,15'S)-6-chloro-15'-hydroxy-7'-(tert-butyldimethylsilyl)oxy-12'-methyl-13'-oxo-3,4-dihydro-2H-spiro[naphthalene-1,22'-[20]oxa[1,12]diazatetracyclo[14.7.2.0³,⁶.0¹⁹,²⁴]pentacosa[8,16,18,24]tetraene]-15'-carboxylic acid (Example 43, Step 2, 40 mg, 0.056 mmol) in DCM (2 mL) was added di(1H-imidazol-1-yl)methanone (13.71 mg, 0.085 mmol). The reaction mixture was stirred at room temperature for 2 hours. N,N-dimethylsulfamide (21.00 mg, 0.169 mmol) and 1,8-diazabicyclo(5.4.0)undec-7-ene (0.0258 mL, 0.169 mmol) were then added and the reaction was stirred overnight. After this time, the reaction mixture was diluted with saturated aqueous NH₄Cl (5 mL), then water (15 mL) and extracted with EtOAc (3×20 mL). The organic extract was dried over MgSO₄, filtered and concentrated in vacuo to give the crude material as a light-yellow oil. The crude material was absorbed onto a plug of silica gel and purified by chromatography through a Redi-Sep pre-packed silica gel column (40 g), eluting with a gradient of 0% to 100% acetone in hexanes, to provide (1S,3'R,6'R,7'S,8'E,15'R)-6-chloro-N-(dimethylsulfamoyl)-15'-hydroxy-7'-(tert-butyldimethylsilyl)oxy-12'-methyl-13'-oxo-3,4-dihydro-2H-spiro[naphthalene-1,22'-[20]oxa[1,12]diazatetracyclo[14.7.2.0³,⁶.0¹⁹,²⁴]pentacosa[8,16,18,24]tetraene]-15'-carboxamide (28 mg, 0.034 mmol, 61% yield). To the obtained solid was directly added tetrabutylammonium fluoride (1.0 M in THF) (0.169 mL, 0.169 mmol) and the reaction mixture was allowed to stir overnight. The latter was then diluted with saturated aqueous NH₄Cl (5 mL), then water (15 mL) and extracted with EtOAc (3×20 mL). The organic extract was dried over MgSO₄, filtered and concentrated in vacuo. The crude material was purified by reverse-phase preparative HPLC using a Phenomenex Gemini column, 10 micron, C18, 100 Å, 150×30 mm, eluting with a gradient of 35% to 90% acetonitrile in water (both solvents containing 0.1% TFA) over a period of 30 minutes to provide the title compound (15 mg, 0.021 mmol, 38% yield) as a white solid after drying in the lyophilizer overnight. ¹H NMR (300 MHz, CD₂Cl₂) δ 8.94 (s, 1H), 7.73 (d, J=8.48 Hz, 1H), 7.16 (dd, J=2.34, 8.48 Hz, 1H), 7.08 (d, J=2.19 Hz, 1H), 7.01-6.94 (m, 1H), 6.90-6.78 (m, 1H), 6.53 (s, 1H), 6.36 (t, J=11.84 Hz, 1H), 5.89 (dd, J=8.62, 14.91 Hz, 1H), 4.35 (d, J=8.77 Hz, 1H), 4.13-3.93 (m, 2H), 3.78-3.48 (m, 4H), 3.33 (d, J=14.18 Hz, 1H), 3.20-3.06 (m, 2H), 2.96 (s, 3H), 2.86 (s, 6H), 2.82-2.72 (m, 2H), 2.64-2.44 (m, 3H), 2.34-2.23 (m, 4H), 2.06-1.87 (m, 6H), 1.80-1.71 (m, 1H), 1.49-1.34-(m, 1H). LRMS: (ESI, +ve ion) m/z 701.0 (M+H)⁺.

Example 44

(1S,3'R,6'R,7'S,8'E,15'R)-6-CHLORO-7',15'-DIHYDROXY-12'-METHYL-N-(METHYLSULFAMOYL)-13'-OXO-3,4-DIHYDRO-2H-SPIRO[NAPHTHALENE-1,22'-[20]OXA[1,12]DIAZATETRACYCLO [14.7.2.0³,⁶.0¹⁹,²⁴]PENTACOSA [8,16,18,24]TETRAENE]-15'-CARBOXAMIDE

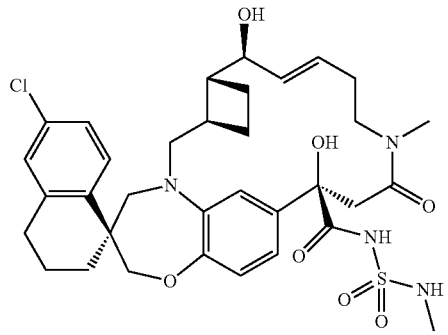 [SMILES: CNS(=O)(=O)NC(=O)[C@@]1(O)CC(=O)N(C)CC/C=C/[C@H](O)[C@@H]2CC[C@H]2CN2C[C@@]3(CCCc4cc(Cl)ccc43)COc3ccc1cc32]

The title compound (13 mg, 46%) was synthesized from Example 1 and N-methylsulfamide through a procedure similar to that used for the synthesis of Example 43. ¹H NMR (300 MHz, CD₂Cl₂) δ 9.03 (s, 1H), 7.73 (d, J=8.48 Hz, 1H), 7.16 (dd, J=2.41, 8.55 Hz, 1H), 7.08 (d, J=2.19 Hz, 1H), 6.99 (dd, J=2.05, 8.18 Hz, 1H), 6.86 (d, J=8.18 Hz, 1H), 6.52 (s, 1H), 6.42-6.28 (m, 1H), 5.89 (dd, J=8.92, 16.66 Hz, 1H), 4.35 (d, J=6.87 Hz, 1H), 4.01 (s, 1H), 3.75-3.49 (m, 3H), 3.33 (d, J=14.18 Hz, 1H), 3.15 (d, J=15.20 Hz, 2H), 2.94 (s, 3H), 2.82-2.69 (m, 2H), 2.67-2.46 (m, 4H), 2.41-2.20 (m, 3H), 2.13-1.59 (m, 10H), 1.45-1.30 (m, 2H), 0.97 (d, J=6.58 Hz, 1H). LRMS: (ESI, +ve ion) m/z 687.2 (M+H)⁺.

Example 45

(1S,3'R,6'R,7'S,8'E,15'R)-6-CHLORO-N-(CYCLO-PROPYLSULFONYL)-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24] TETRAENE]-15'-CARBOXAMIDE

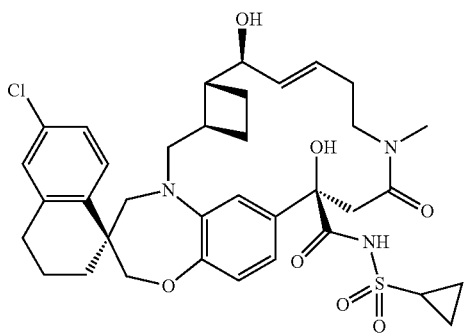 [SMILES: CN1CC/C=C/[C@H](O)[C@@H]2CC[C@H]2CN2C[C@@]3(CCCc4cc(Cl)ccc43)COc3ccc(cc32)[C@@](O)(C(=O)NS(=O)(=O)C2CC2)CC1=O]

The title compound (225 mg, 56% from Example 1) was synthesized from Example 1 and cyclopropanesulfonamide through a procedure similar to that used for the synthesis of Example 43. $^1$H NMR (300 MHz, CD$_2$Cl$_2$) δ 8.95 (s, 1H), 7.73 (d, J=8.48 Hz, 1H), 7.20-7.12 (m, 1H), 7.08 (d, J=2.19 Hz, 1H), 7.01-6.95 (m, 1H), 6.89-6.83 (m, 1H), 6.51 (s, 1H), 6.36 (br. s., 1H), 5.89 (dd, J=8.26, 14.83 Hz, 1H), 4.35 (d, J=9.06 Hz, 1H), 4.01 (s, 2H), 3.70 (d, J=14.18 Hz, 1H), 3.63-3.50 (m, 3H), 3.33 (d, J=14.62 Hz, 1H), 3.16 (d, J=14.47 Hz, 2H), 2.95 (s, 3H), 2.67-2.89 (m, 3H), 2.54 (d, J=16.81 Hz, 2H), 2.41-2.20 (m, 3H), 2.11-2.00 (m, 3H), 1.75 (d, J=10.08 Hz, 2H), 1.50-1.14 (m, 5H), 1.10-0.83 (m, 3H). LRMS: (ESI, +ve ion) m/z 698.0 (M+H)$^+$.

Example 46

(1S,3'R,6'R,7'S,8'E,15'R)—N-(1-AZETIDINYLSULFONYL)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

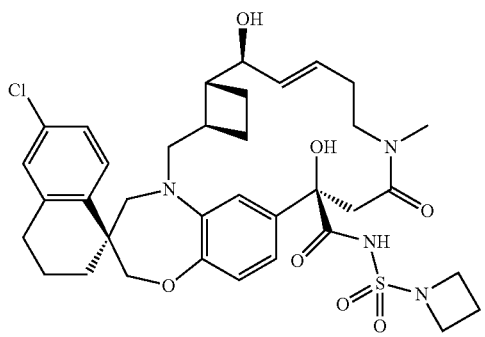 [SMILES: CN1CC/C=C/[C@H](O)[C@@H]2CC[C@H]2CN2C[C@@]3(CCCc4cc(Cl)ccc43)COc3ccc(cc32)[C@@](O)(C(=O)NS(=O)(=O)N2CCC2)CC1=O]

The title compound (10 mg, 23% from Example 1) was synthesized from Example 1 and 1-azetidinesulfonamide through a procedure similar to that used for the synthesis of Example 43. $^1$H NMR (300 MHz, CD$_2$Cl$_2$) δ 8.99 (s, 1H), 7.73 (d, J=8.62 Hz, 1H), 7.16 (dd, J=2.34, 8.48 Hz, 1H), 7.08 (d, J=2.19 Hz, 1H), 7.01 (dd, J=2.05, 8.18 Hz, 1H), 6.87 (d, J=8.18 Hz, 1H), 6.57 (d, J=1.61 Hz, 1H), 6.44-6.30 (m, 1H), 5.90 (dd, J=8.62, 14.91 Hz, 1H), 4.35 (d, J=8.62 Hz, 1H), 4.18-3.92 (m, 5H), 3.72 (d, J=14.18 Hz, 1H), 3.61 (d, J=16.52 Hz, 2H), 3.33 (d, J=14.47 Hz, 1H), 3.23-3.03 (m, 2H), 3.03-2.92 (m, 3H), 2.84-2.69 (m, 2H), 2.57 (d, J=16.81 Hz, 2H), 2.44-1.86 (m, 12H), 1.72 (d, J=8.33 Hz, 2H), 1.38 (t, J=11.62 Hz, 2H). LRMS: (ESI, +ve ion) m/z 713.0 (M+H)$^+$.

Example 47

(1S,3'R,6'R,7'S,8'E,15'R)-6-CHLORO-7',15'-DIHYDROXY-12'-METHYL-N-(4-MORPHOLINYLSULFONYL)-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

The title compound (23 mg, 45% from Example 1) was synthesized from Example 1 and 4-morpholinesulfonamide through a procedure similar to that used for the synthesis of Example 43. $^1$H NMR (300 MHz, CD$_2$Cl$_2$) δ 8.99 (s, 1H), 7.73 (d, J=8.48 Hz, 1H), 7.16 (dd, J=2.34, 8.62 Hz, 1H), 7.08 (d, J=2.19 Hz, 1H), 6.98 (dd, J=2.12, 8.26 Hz, 1H), 6.91-6.80 (m, 1H), 6.52 (d, J=1.90 Hz, 1H), 6.44-6.26 (m, 1H), 5.89 (ddd, J=1.61, 9.06, 15.05 Hz, 1H), 4.31 (d, J=9.21 Hz, 1H), 4.08-3.94 (m, 2H), 3.80-3.48 (m, 6H), 3.40-3.24 (m, 2H), 3.23-3.07 (m, 3H), 2.99-2.85 (m, 3H), 2.82-2.72 (m, 2H), 2.65-2.48 (m, 2H), 2.45-2.14 (m, 3H), 2.10-1.84 (m, 9H), 1.77-1.68 (m, 2H), 1.47-1.30 (m, 2H). LRMS: (ESI, +ve ion) m/z 743.0 (M+H)$^+$.

Example 48

(1S,3'R,6'R,7'S,8'E,15'R)-6-CHLORO-15'-((DIMETHYLSULFAMOYL)CARBAMOYL)-15'-HYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAEN]-7'-YL)OXY)ACETIC ACID

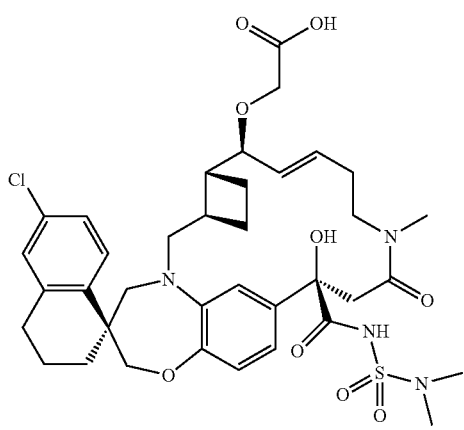 [SMILES: CN1CC/C=C/[C@H](OCC(=O)O)[C@@H]2CC[C@H]2CN2C[C@@]3(CCCc4cc(Cl)ccc43)COc3ccc(cc32)[C@@](O)(C(=O)NS(=O)(=O)N(C)C)CC1=O]

To a solution of (1S,3'R,6'R,7'S,8'E,15'R)-6-chloro-N-(dimethylsulfamoyl)-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide (Example 43, 43 mg, 0.061 mmol) in THF (5 mL) was added sodium bis(trimethylsilyl)amide (1 M solution in THF) (0.0501 mL, 0.050 mmol) followed by ethyl bromoacetate (0.068 mL, 0.613 mmol). The reaction mixture was stirred at room temperature for 1 h. The reaction mixture was then diluted with MeOH (1 mL) and LiOH (2 M, 2 mL) and stirred at room temperature for 4 hours. The reaction mixture was then neutralized with HCl (4 mL, 1 N), diluted with water (10 mL) and extracted with EtOAc (3×15 mL). The combined organic layers were dried over magnesium sulfate, filtered and concentrated. The crude material was purified by reverse-phase preparative HPLC using a Phenomenex Gemini column, 10 micron, C18, 100 Å, 150×30 mm, eluting with a gradient of 35% to 90% acetonitrile in water (both solvents containing 0.1% TFA) over a period of 30 minutes to provide the title compound (15 mg, 0.020 mmol, 32% yield) as a white solid after drying in the lyophilizer overnight. $^1$H NMR (300 MHz, CD$_2$Cl$_2$) δ 8.95 (s, 1H), 7.72 (d, J=8.48 Hz, 1H), 7.16 (dd, J=8.55, 2.27 Hz, 1H), 7.08 (d, J=2.19 Hz, 1H), 6.99 (dd, J=8.26, 1.97 Hz, 1H), 6.86 (d, J=8.18 Hz, 1H), 6.54-6.37 (m, 2H), 5.72 (dd, J=15.20, 9.79 Hz, 1H), 4.15-3.89 (m, 4H), 3.80-3.43 (m, 4H), 3.32 (d, J=14.32 Hz, 5H), 3.23-3.02 (m, 5H), 3.00-2.92 (m, 3H), 2.89-2.83 (m, 4H), 2.81-2.24 (m, 7H), 2.13-1.70 (m, 6H), 1.48-1.32 (m, 1H). LRMS: (ESI, +ve ion) m/z 759.0 (M+H)$^+$.

Example 49

(1S,3'R,6'R,7'S,8'E,15'R)-6-CHLORO-15'-((CYCLOPROPYLSULFONYL)CARBAMOYL)-15'-HYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAEN]-7'-YL)OXY)ACETIC ACID

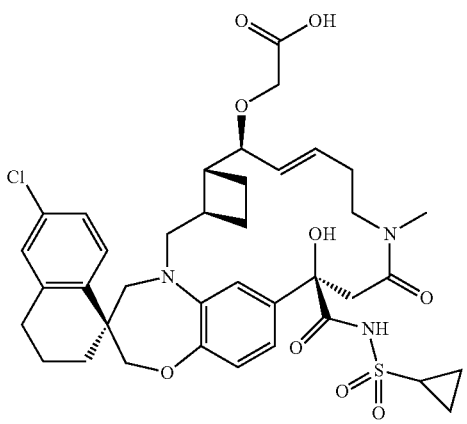 [SMILES: CN1CC/C=C/[C@H](OCC(=O)O)[C@@H]2CC[C@H]2CN2C[C@@]3(CCCc4cc(Cl)ccc43)COc3ccc(cc32)[C@@](O)(C(=O)NS(=O)(=O)C2CC2)CC1=O]

The title compound (3 mg, 40%) was synthesized from Example 45 and ethyl bromoacetate through a procedure similar to that used for the synthesis of Example 48. $^1$H NMR (300 MHz, CD$_2$Cl$_2$) δ ppm 8.95 (d, J=7.31 Hz, 1H), 7.72 (d, J=8.48 Hz, 1H), 7.16 (dd, J=8.48, 2.34 Hz, 1H), 7.08 (d, J=2.19 Hz, 1H), 6.99 (dd, J=8.18, 2.05 Hz, 1H), 6.90-6.83 (m, 1H), 6.46 (d, J=1.75 Hz, 2H), 5.72 (dd, J=14.54, 10.01 Hz, 1H), 4.22-4.11 (m, 1H), 4.08-3.99 (m, 2H), 3.71 (d, J=14.32 Hz, 1H), 3.63-3.44 (m, 2H), 3.31 (d, J=14.32 Hz, 1H), 3.20-3.03 (m, 2H), 3.00-2.84 (m, 3H), 2.82-2.73 (m, 2H), 2.68-2.42 (m, 6H), 2.43-2.26 (m, 4H), 2.07-1.70 (m, 6H), 1.41 (d, J=12.57 Hz, 1H), 1.25-0.84 (m, 5H). LRMS: (ESI, +ve ion) m/z 756.0 (M+H)$^+$.

Example 50

(1S,3'R,6'R,7'S,15'R)-6-CHLORO-N-(DIMETHYLSULFAMOYL)-7',15'-DIHYDROXY-12'-METHYL-13'-OXO-3,4-DIHYDRO-2H-SPIRO[NAPHTHALENE-1,22'-[20]OXA[1,12]DIAZATETRACYCLO [14.7.2.0$^{3,6}$.0$^{19,24}$]PENTACOSA[16,18,24]TRIENE]-15'-CARBOXAMIDE

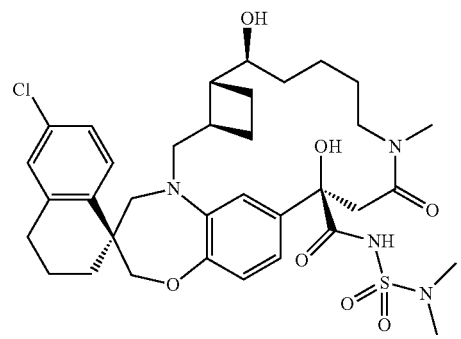 [SMILES: CN1CCCC[C@H](O)[C@@H]2CC[C@H]2CN2C[C@@]3(CCCc4cc(Cl)ccc43)COc3ccc(cc32)[C@@](O)(C(=O)NS(=O)(=O)N(C)C)CC1=O]

The title compound (3 mg, 75%) was synthesized from Example 43 via hydrogenation with platinum (IV) oxide through a procedure similar to that used for the synthesis of Example 39. $^1$H NMR (400 MHz, CD$_2$Cl$_2$) δ 8.99 (s, 1H), 7.75 (d, J=8.41 Hz, 1H), 7.70 (dd, J=3.33, 5.67 Hz, 1H), 7.16 (dd, J=2.25, 8.51 Hz, 1H), 7.08 (d, J=2.15 Hz, 1H), 7.04 (dd, J=2.15, 8.22 Hz, 1H), 6.88 (d, J=8.22 Hz, 1H), 6.52 (d, J=2.15 Hz, 1H), 4.05-3.95 (m, 2H), 3.91-3.81 (m, 1H), 3.78-3.52 (m, 4H), 3.26 (d, J=14.28 Hz, 1H), 3.15-2.97 (m, 2H), 2.83 (s, 3H), 2.81-2.73 (m, 2H), 2.62-2.41 (m, 2H), 2.37-2.22 (m, 1H), 2.09-1.97 (m, 3H), 1.94-1.87 (m, 1H), 1.85-1.57 (m, 10H), 1.41-1.35 (m, 3H), 0.87-0.78 (m, 4H). LRMS: (ESI, +ve ion) m/z 703.1 (M+H)$^+$.

Example 51

(1S,3'R,6'R,7'S,8'E,15'R)-6-CHLORO-N-(DIMETHYLSULFAMOYL)-15'-HYDROXY-7'-(2-METHOXYETHOXY)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$] PENTACOSA[8,16,18,24]TETRAENE]-15'-CARBOXAMIDE

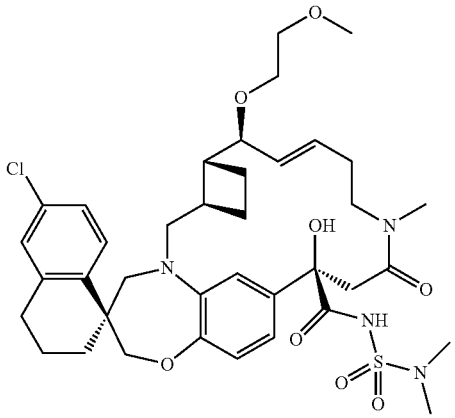 [SMILES: COCCO[C@H]1/C=C/CCN(C)C(=O)C[C@](O)(C(=O)NS(=O)(=O)N(C)C)c2ccc3c(c2)N(C[C@@H]2CC[C@H]21)C[C@@]1(CCCc2cc(Cl)ccc21)CO3]

To a solution of (1S,3'R,6'R,7'S,8'E,15'R)-6-chloro-N-(dimethylsulfamoyl)-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide (Example 43, 25 mg, 0.036 mmol) in THF (5 mL) was added sodium bis(trimethylsilyl) amide (1 M solution in THF) (0.0501 mL, 0.050 mmol) followed by 2-bromoethyl methyl ether (0.034 mL, 0.356 mmol). The reaction mixture was stirred at room temperature overnight. After this time, the reaction mixture was concentrated, diluted with DMSO and filtered. The crude material was purified by reverse-phase preparative HPLC using a Phenomenex Gemini column, 10 micron, C18, 100 Å, 150×30 mm, eluting with a gradient of 35% to 90% acetonitrile in water (both solvents containing 0.1% TFA) over a period of 30 minutes to provide the title compound (6 mg, 7.90 μmol, 22% yield) as a white solid after drying in the lyophilizer overnight. $^1$H NMR (300 MHz, CD$_2$Cl$_2$) δ ppm 8.94 (s, 1H), 7.73 (d, J=8.48 Hz, 1H), 7.16 (dd, J=8.62, 2.34 Hz, 1H), 7.08 (d, J=2.34 Hz, 1H), 6.99 (dd, J=8.11, 1.68 Hz, 1H), 6.86 (d, J=8.33 Hz, 1H), 6.53 (s, 1H), 6.36 (d, J=8.18 Hz, 1H), 5.76-5.59 (m, 1H), 4.10-3.93 (m, 2H), 3.87 (d, J=9.65 Hz, 1H), 3.91-3.44 (m, 6H), 3.39-3.27 (m, 3H), 3.18 (s, 2H), 3.16-3.03 (m, 2H), 2.97 (d, J=1.75 Hz, 3H), 2.89-2.82 (m, 6H), 2.81-2.56 (m, 5H), 2.51 (d, J=16.66 Hz, 1H), 2.46-2.23 (m, 3H), 2.10-1.67 (m, 8H). LRMS: (ESI, +ve ion) m/z 759.0 (M+H)$^+$.

Example 52

(1S,3'R,6'R,7'S,8'E,15'R)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO [14.7.2.0$^{3,6}$.0$^{19,24}$]PENTACOSA[8,16,18,24]TETRAENE]-15'-CARBOXYLIC ACID

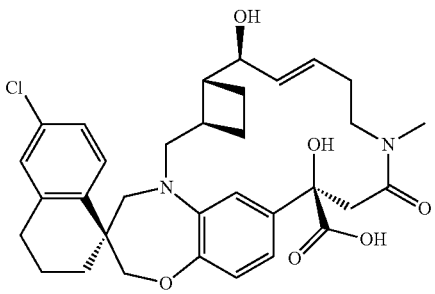 [SMILES: CN1CC/C=C/[C@H](O)[C@@H]2CC[C@H]2CN2C[C@@]3(CCCc4cc(Cl)ccc43)COc3ccc(cc32)[C@@](O)(C(=O)O)CC1=O]

The title compound (19 mg, 86% from Example 1) was synthesized from Example 1 via saponification with lithium hydroxide through a procedure similar to that used for the synthesis of Example 4. $^1$H NMR (400 MHz, CD$_2$Cl$_2$) δ 7.72 (d, J=8.41 Hz, 1H), 7.14-7.13 (m, 1H), 7.16 (d, J=1.76 Hz, 1H), 7.08 (d, J=2.15 Hz, 1H), 6.99 (dd, J=2.05, 8.31 Hz, 1H), 6.85 (d, J=8.22 Hz, 1H), 6.69-6.52 (m, 1H), 6.28 (t, J=13.01 Hz, 1H), 5.88 (dd, J=8.71, 14.77 Hz, 1H), 4.38-4.25 (m, 1H), 4.00 (d, J=2.35 Hz, 2H), 3.52 (d, J=16.82 Hz, 4H), 3.39-3.27 (m, 1H), 3.22-3.05 (m, 3H), 2.77 (d, J=4.89 Hz, 3H), 2.66-2.50 (m, 2H), 2.37 (br. s., 3H), 2.05 (br. s., 7H), 1.47-1.32 (m, 1H). LRMS: (ESI, +ve ion) m/z 595.2 (M+H)$^+$.

Example 53

(1S,3'R,6'R,7'S,8'E,15'S)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

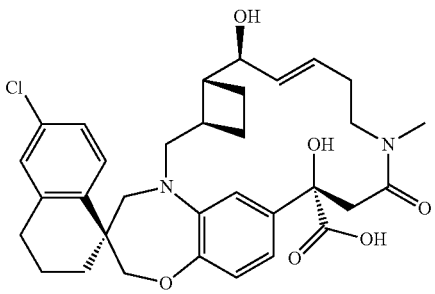 [SMILES: CN1CC/C=C/[C@H](O)[C@@H]2CC[C@H]2CN2C[C@@]3(CCCc4cc(Cl)ccc43)COc3ccc(cc32)[C@](O)(C(=O)O)CC1=O]

The title compound (6 mg, 47% from Example 2) was synthesized from Example 2 via saponification with lithium hydroxide through a procedure similar to that used for the synthesis of Example 4. $^1$H NMR (400 MHz, CD$_2$Cl$_2$) δ 7.82 (br. s., 1H), 7.35-6.79 (m, 4H), 6.69-6.50 (m, 1H), 6.06 (br. s., 1H), 5.87 (d, J=16.24 Hz, 1H), 5.43 (br. s., 7H), 4.21-3.94 (m, 2H), 3.87-3.55 (m, 3H), 3.44-3.30 (m, 1H), 3.16 (d, J=13.30 Hz, 2H), 3.09-2.96 (m, 3H), 2.85 (br. s., 3H), 2.69 (d, J=16.63 Hz, 2H), 2.33 (br. s., 2H), 2.09-1.96 (m, 3H), 1.55-1.32 (m, 2H). LRMS: (ESI, +ve ion) m/z 595.2 (M+H)$^+$.

Example 54

(1S,3'R,6'R,7'S,8'E,14'R)-6-CHLORO-7',14'-DIHYDROXY-11'-METHYL-12'-OXO-3,4-DIHYDRO-2H-SPIRO[NAPHTHALENE-1,21'-[19]OXA[1,11]DIAZATETRACYCLO[13.7.2.0$^{3,6}$.0$^{18,23}$]TETRACOSA[8,15,17,23]TETRAENE]-14'-CARBOXYLIC ACID OR (1S,3'R,6'R,7'S,8'E,14'S)-6-CHLORO-7',14'-DIHYDROXY-11'-METHYL-12'-OXO-3,4-DIHYDRO-2H-SPIRO[NAPHTHALENE-1,21'-[19]OXA[1,11]DIAZATETRACYCLO [13.7.2.0$^{3,6}$.0$^{18,23}$]TETRACOSA[8,15,17,23]TETRAENE]-14'-CARBOXYLIC ACID

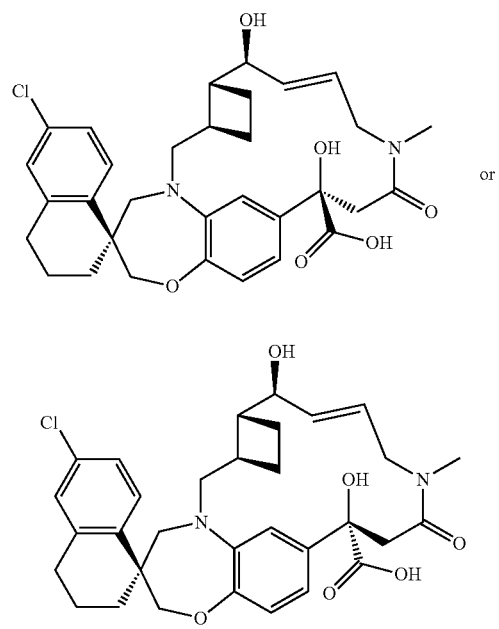

The title compound (18 mg, 65% last step) was synthesized through a procedure similar to the one used for the synthesis of Example 1 (steps 1-7), substituting N-methylbutyl-3-en-1-amine with N-methylprop-2-en-1-amine in Step 6, followed by saponification of the slow eluting isomer in Step 7 through a procedure similar to that used for the synthesis of Example 4. $^1$H NMR (400 MHz, CD$_2$Cl$_2$) δ 7.82-7.36 (m, 1H), 7.26-6.48 (m, 5H), 5.89 (dd, J=7.43, 16.04 Hz, 1H), 5.03-4.70 (m, 1H), 4.58-3.69 (m, 6H), 3.50-3.08 (m, 4H), 3.04-2.87 (m, 4H), 2.83-2.66 (m, 4H), 2.60-2.40 (m, 3H), 2.12-1.62 (m, 7H), 1.55-1.40 (m, 1H). LRMS: (ESI, +ve ion) m/z 581.1 (M+H)$^+$.

Example 55

(1S,3'R,6'R,7'S,8'E,14'S)-6-CHLORO-7',14'-DIHYDROXY-11'-METHYL-12'-OXO-3,4-DIHYDRO-2H-SPIRO[NAPHTHALENE-1,21'-[19]OXA[1,11]DIAZATETRACYCLO [13.7.2.0$^{3,6}$.0$^{18,23}$]TETRACOSA[8,15,17,23]TETRAENE]-14'-CARBOXYLIC ACID OR (1S,3'R,6'R,7'S,8'E,14'R)-6-CHLORO-7',14'-DIHYDROXY-11'-METHYL-12'-OXO-3,4-DIHYDRO-2H-SPIRO [NAPHTHALENE-1,21'-[19]OXA[1,11]DIAZATETRACYCLO [13.7.2.0$^{3,6}$.0$^{18,23}$] TETRACOSA[8,15,17,23]TETRAENE]-14-CARBOXYLIC ACID

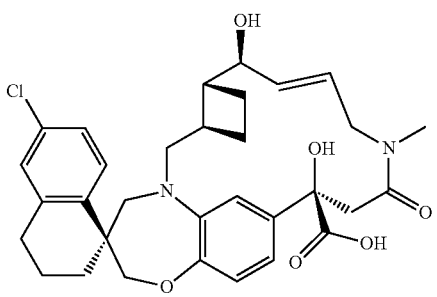

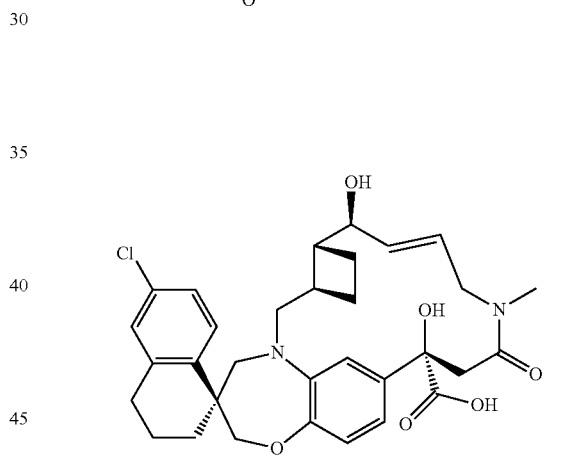

The title compound (6 mg, 51% last step) was synthesized through a procedure similar to the one used for the synthesis of Example 1 (steps 1-7), substituting N-methylbutyl-3-en-1-amine with N-methylprop-2-en-1-amine in Step 6, followed by saponification of the fast eluting isomer in Step 7 through a procedure similar to that used for the synthesis of Example 4. $^1$H NMR (400 MHz, CD$_2$Cl$_2$) δ 7.72 (d, J=8.41 Hz, 1H), 7.20-7.06 (m, 3H), 7.02-6.93 (m, 1H), 6.84 (d, J=8.22 Hz, 1H), 6.55 (d, J=1.96 Hz, 1H), 6.14-6.00 (m, 1H), 5.91 (d, J=16.04 Hz, 1H), 4.22-4.10 (m, 2H), 4.04-3.95 (m, 2H), 3.93-3.75 (m, 2H), 3.71-3.60 (m, 2H), 3.34 (d, J=14.48 Hz, 1H), 3.24 (dd, J=10.37, 15.06 Hz, 2H), 3.05 (s, 3H), 2.74-2.65 (m, 2H), 2.49 (d, J=15.65 Hz, 1H), 2.28 (dd, J=9.19, 17.80 Hz, 3H), 2.16-2.11 (m, 3H), 1.95-1.90 (m, 2H), 1.71-1.66 (m, 1H), 1.52-1.39 (m, 2H). LRMS: (ESI, +ve ion) m/z 581.1 (M+H)$^+$.

Example 56

(1S,3'R,6'R,7'S,9'Z,15'S)-6-CHLORO-7',15'-DIHY-
DROXY-12'-METHYL-13'-OXO-3,4-DIHYDRO-
2H-SPIRO[NAPHTHALENE-1,22'-[20]OXA[1,12]
DIAZATETRACYCLO[14.7.2.0$^{3,6}$.0$^{19,24}$]
PENTACOSA[9,16,18,24]TETRAENE]-15'-
CARBOXYLIC ACID or (1S,3'R,6'R,7'S,9'E,15'S)-
6-CHLORO-7',15'-DIHYDROXY-12'-METHYL-
13'-OXO-3,4-DIHYDRO-2H-SPIRO
[NAPHTHALENE-1,22'-[20]OXA[1,12]
DIAZATETRACYCLO[14.7.2.0$^{3,6}$.0$^{19,24}$]
PENTACOSA[9,16,18,24]TETRAENE]-15'-
CARBOXYLIC ACID or (1S,3'R,6'R,7'S,9'Z,15'R)-
6-CHLORO-7',15'-DIHYDROXY-12'-METHYL-
13'-OXO-3,4-DIHYDRO-2H-SPIRO
[NAPHTHALENE-1,22'-[20]OXA[1,12]
DIAZATETRACYCLO[14.7.2.0$^{3,6}$.0$^{19,24}$]
PENTACOSA[9,16,18,24]TETRAENE]-15'-
CARBOXYLIC ACID or (1S,3'R,6'R,7'S,9'E,15'R)-
6-CHLORO-7',15'-DIHYDROXY-12'-METHYL-
13'-OXO-3,4-DIHYDRO-2H-SPIRO
[NAPHTHALENE-1,22'-[20]OXA[1,12]
DIAZATETRACYCLO[14.7.2.0$^{3,6}$.0$^{19,24}$]
PENTACOSA[9,16,18,24]TETRAENE]-15'-
CARBOXYLIC ACID

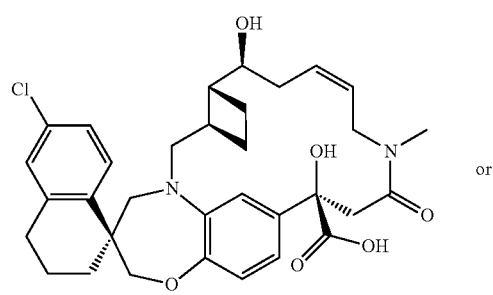 or

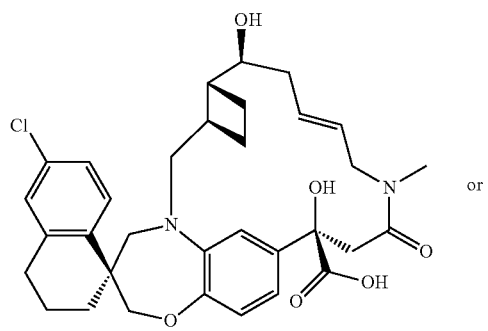 or

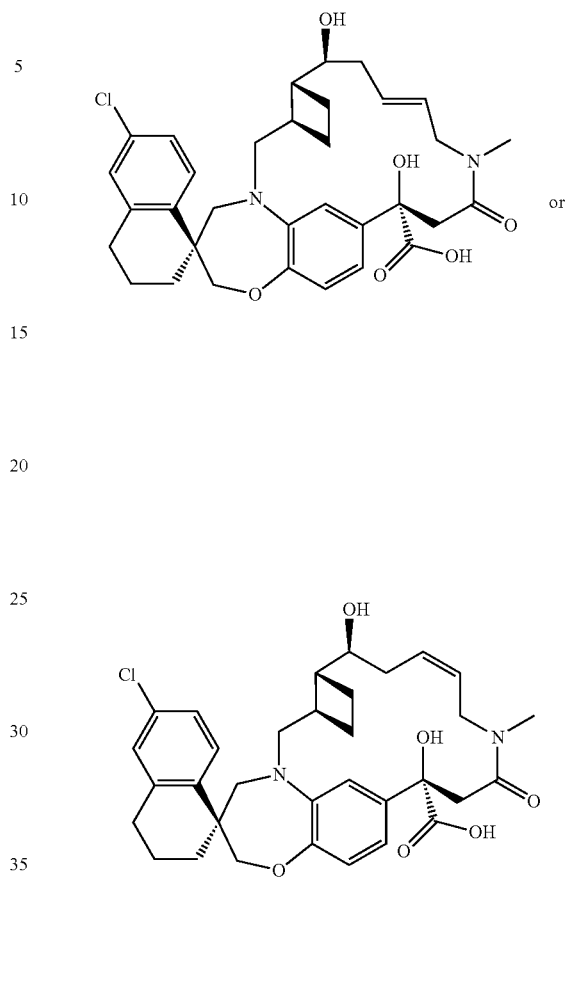

The title compound (2.0 mg) was synthesized starting from (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA13A, Step 2)) through a procedure similar to the one used for the synthesis of Example 1 (steps 1-7), substituting N-methylbutyl-3-en-1-amine with N-methylprop-2-en-1-amine in Step 6, followed by saponification of the methyl ester through a procedure similar to that used for the synthesis of Example 4. The compound was the slowest eluting isomer isolated by reverse-phase preparative HPLC using a Phenomenex Gemini column, 10 micron, C18, 100 Å, 150×30 mm, eluting with a gradient of 50% to 90% acetonitrile in water (both solvents containing 0.1% TFA) over a period of 30 minutes. $^1$H NMR (400 MHz, (CD$_3$)$_2$SO) δ 7.70 (d, J=8.41 Hz, 1H), 7.28 (d, J=7.63 Hz, 1H), 7.18 (br. s., 1H), 6.92 (d, J=8.41 Hz, 1H), 6.83 (d, J=8.22 Hz, 1H), 6.64 (br. s., 1H), 5.83-5.54 (m, 2H), 4.30 (dd, J=7.73, 15.36 Hz, 1H), 4.05-3.97 (m, 1H), 3.97-3.78 (m, 2H), 3.73 (d, J=14.48 Hz, 1H), 3.64 (d, J=14.28 Hz, 2H), 3.30 (d, J=14.28 Hz, 2H), 3.16-3.02 (m, 2H), 2.98 (br. s., 1H), 2.92 (s, 3H), 2.90-2.66 (m, 4H), 2.41-2.11 (m, 4H), 2.01 (d, J=13.11 Hz, 1H), 1.85 (d, J=13.89 Hz, 3H), 1.80-1.66 (m, 2H). LRMS: (ESI, +ve ion) m/z 595.2 (M+H)$^+$.

Example 57

(1S,3'R,6'R,7'S,9'Z,15'S)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[9,16,18,24]TETRAENE]-15'-CARBOXYLIC ACID or (1S,3'R,6'R,7'S,9'E,15'S)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[9,16,18,24]TETRAENE]-15'-CARBOXYLIC ACID or (1S,3'R,6'R,7'S,9'Z,15'R)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[9,16,18,24]TETRAENE]-15'-CARBOXYLIC ACID or (1S,3'R,6'R,7'S,9'E,15'R)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[9,16,18,24]TETRAENE]-15'-CARBOXYLIC ACID

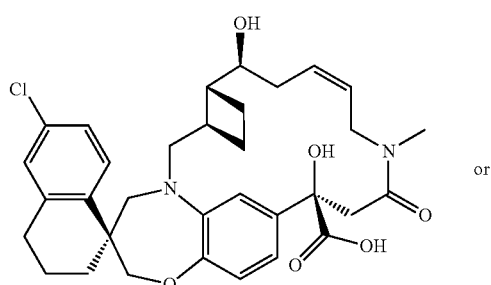 or

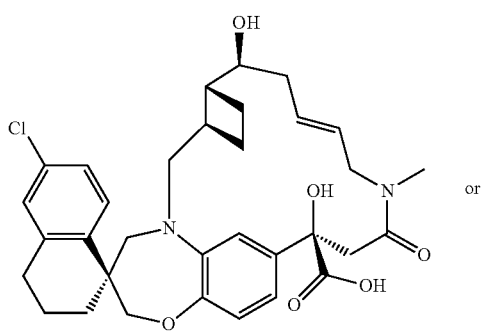 or

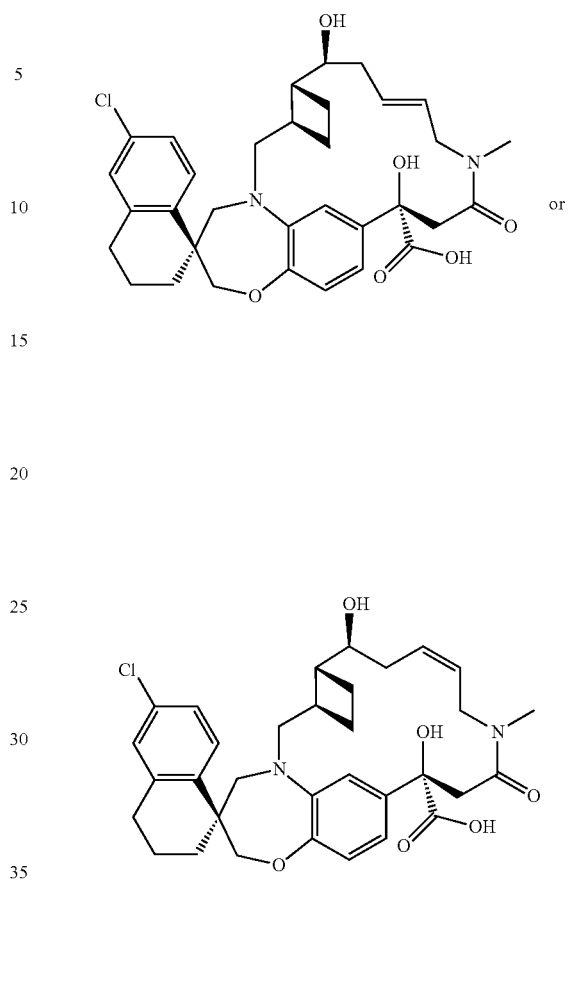

The title compound (15 mg, 61% last step) was synthesized starting from (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA13A, Step 2) through a procedure similar to the one used for the synthesis of Example 1 (steps 1-7), substituting N-methylbutyl-3-en-1-amine with N-methylprop-2-en-1-amine in Step 6, followed by saponification of the methyl ester through a procedure similar to that used for the synthesis of Example 4. The compound was the second eluting isomer isolated by reverse-phase preparative HPLC using a Phenomenex Gemini column, 10 micron, C18, 100 Å, 150×30 mm, eluting with a gradient of 50% to 90% acetonitrile in water (both solvents containing 0.1% TFA) over a period of 30 minutes. $^1$H NMR (400 MHz, (CD$_3$)$_2$SO) δ 7.69 (d, J=8.61 Hz, 1H), 7.27 (dd, J=2.45, 8.51 Hz, 1H), 7.21-7.10 (m, 2H), 6.87 (dd, J=2.15, 8.22 Hz, 1H), 6.78 (d, J=8.22 Hz, 1H), 5.69-5.37 (m, 2H), 4.10-4.00 (m, 6H), 3.80-3.53 (m, 3H), 3.45 (q, J=14.80 Hz, 2H), 3.28 (dd, J=5.87, 15.45 Hz, 1H), 3.22-3.09 (m, 1H), 2.89 (s, 3H), 2.82-2.66 (m, 3H), 2.65-2.56 (m, 1H), 2.28-2.16 (m, 3H), 2.10 (s, 1H), 1.94 (d, J=13.30 Hz, 1H), 1.88-1.79 (m, 2H), 1.57 (br. s., 1H). LRMS: (ESI, +ve ion) m/z 595.2 (M+H)$^+$.

Example 58

(1S,3'R,6'R,7'S,9'Z,15'S)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[9,16,18,24]TETRAENE]-15'-CARBOXYLIC ACID or (1S,3'R,6'R,7'S,9'E,15'S)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[9,16,18,24]TETRAENE]-15'-CARBOXYLIC ACID or (1S,3'R,6'R,7'S,9'Z,15'R)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[9,16,18,24]TETRAENE]-15'-CARBOXYLIC ACID or (1S,3'R,6'R,7'S,9'E,15'R)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[9,16,18,24]TETRAENE]-15'-CARBOXYLIC ACID

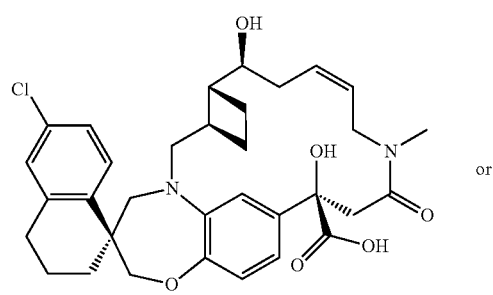 or

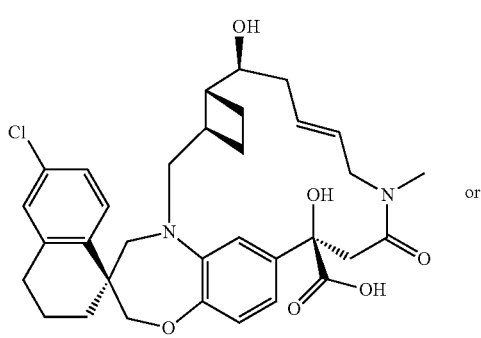 or

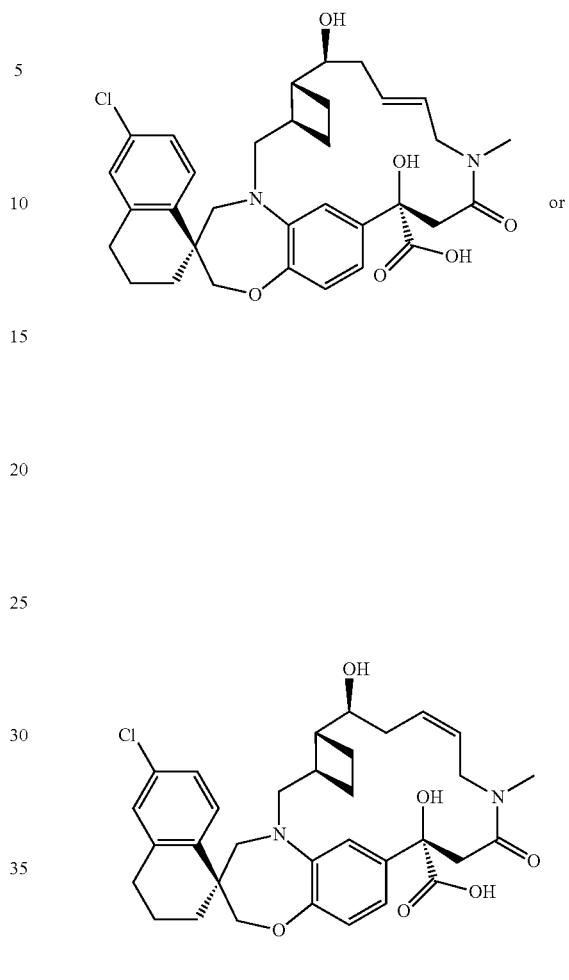

The title compound (2.6 mg) was synthesized starting from (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA13A, Step 2) through a procedure similar to the one used for the synthesis of Example 1 (steps 1-7), substituting N-methylbutyl-3-en-1-amine with N-methylprop-2-en-1-amine in Step 6, followed by saponification of the methyl ester through a procedure similar to that used for the synthesis of Example 4. The compound was the third eluting isomer isolated by reverse-phase preparative HPLC using a Phenomenex Gemini column, 10 micron, C18, 100 Å, 150×30 mm, eluting with a gradient of 50% to 90% acetonitrile in water (both solvents containing 0.1% TFA) over a period of 30 minutes. $^1$H NMR (400 MHz, (CD$_3$)$_2$SO) δ 7.64 (d, J=8.61 Hz, 1H), 7.25 (dd, J=2.25, 8.51 Hz, 1H), 7.18 (d, J=2.35 Hz, 1H), 7.16 (br. s., 1H), 7.13 (s, 1H), 6.80 (s, 1H), 6.79-6.73 (m, 1H), 6.73-6.68 (m, 1H), 6.67 (s, 1H), 5.54 (s, 1H), 5.46 (br. s., 1H), 4.05-3.96 (m, 4H), 3.41-2.95 (m, 8H), 2.95-2.80 (m, 3H), 2.84-2.66 (m, 4H), 2.22 (br. s., 4H), 1.60-1.44 (m, 3H). LRMS: (ESI, +ve ion) m/z 595.2 (M+H)$^+$.

Example 59

(1S,3'R,6'R,7'S,9'Z,15'S)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[9,16,18,24]TETRAENE]-15'-CARBOXYLIC ACID or (1S,3'R,6'R,7'S,9'E,15'S)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[9,16,18,24]TETRAENE]-15'-CARBOXYLIC ACID or (1S,3'R,6'R,7'S,9'Z,15'R)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[9,16,18,24]TETRAENE]-15'-CARBOXYLIC ACID or (1S,3'R,6'R,7'S,9'E,15'R)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[9,16,18,24]TETRAENE]-15'-CARBOXYLIC ACID

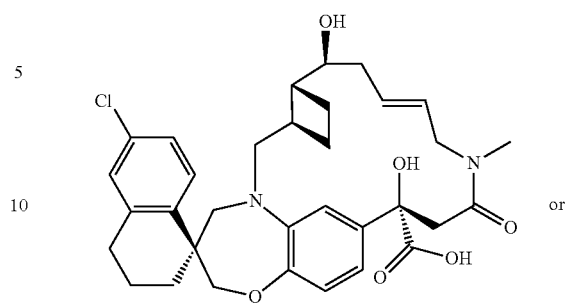

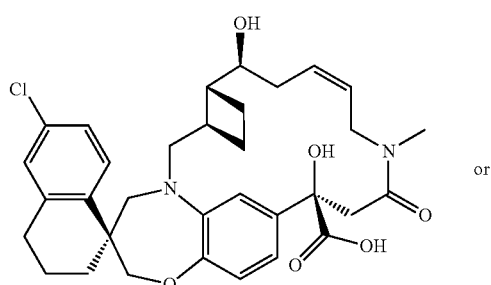

The title compound (1.0 mg) was synthesized starting from (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA13A, Step 2) through a procedure similar to the one used for the synthesis of Example 1 (steps 1-7), substituting N-methylbutyl-3-en-1-amine with N-methylprop-2-en-1-amine in Step 6, followed by saponification of the methyl ester through a procedure similar to that used for the synthesis of Example 4. The compound was the fastest eluting isomer isolated by reverse-phase preparative HPLC using a Phenomenex Gemini column, 10 micron, C18, 100 Å, 150×30 mm, eluting with a gradient of 50% to 90% acetonitrile in water (both solvents containing 0.1% TFA) over a period of 30 minutes. $^1$H NMR (400 MHz, (CD$_3$)$_2$SO) δ 7.64 (d, J=8.61 Hz, 1H), 7.25 (dd, J=2.25, 8.51 Hz, 1H), 7.18 (d, J=2.35 Hz, 1H), 7.16 (br. s., 1H), 7.13 (s, 1H), 6.80 (s, 1H), 6.79-6.73 (m, 1H), 6.73-6.68 (m, 1H), 6.67 (s, 1H), 5.54 (s, 1H), 5.46 (br. s., 1H), 4.05-3.96 (m, 4H), 3.41-2.95 (m, 8H), 2.95-2.80 (m, 3H), 2.84-2.66 (m, 4H), 2.22 (br. s., 4H), 1.60-1.44 (m, 3H). LRMS: (ESI, +ve ion) m/z 595.2 (M+H)$^+$.

Example 60

(1S,3'R,6'R,7'S,9'Z,15'S)-6-CHLORO-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0[3,6].0[19,24]]PENTACOSA[9,16,18,24]TETRAENE]-15'-CARBOXYLIC ACID or (1S,3'R,6'R,7'S,9'E,15'S)-6-CHLORO-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0[3,6].0[19,24]]PENTACOSA[9,16,18,24]TETRAENE]-15'-CARBOXYLIC ACID or (1S,3'R,6'R,7'S,9'Z,15'R)-6-CHLORO-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0[3,6].0[19,24]]PENTACOSA[9,16,18,24]TETRAENE]-15'-CARBOXYLIC ACID or (1S,3'R,6'R,7'S,9'E,15'R)-6-CHLORO-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0[3,6].0[19,24]]PENTACOSA[9,16,18,24]TETRAENE]-15'-CARBOXYLIC ACID

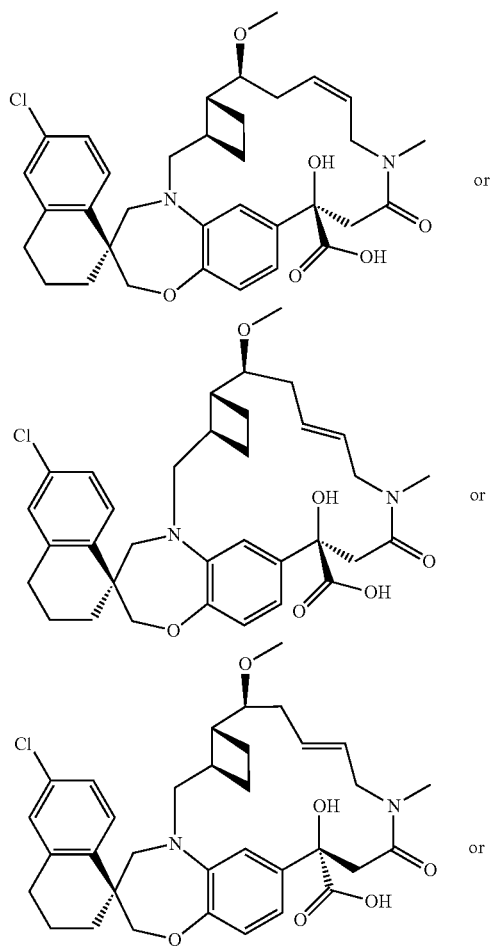

or or or

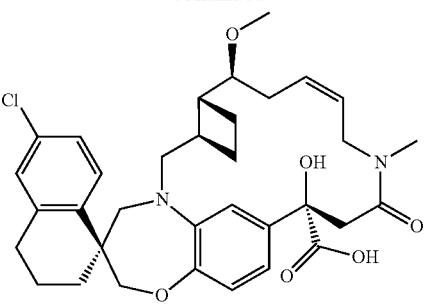

The title compound (1.2 mg, 2%) was synthesized from the methyl ester intermediate from Example 57 through a procedure similar to that used for the synthesis of Example 3, followed by saponification with lithium hydroxide through a procedure similar to that used for the synthesis of Example 4. $^1$H NMR (400 MHz, (CD$_3$)$_2$SO) δ 7.69 (d, J=8.61 Hz, 1H), 7.27 (dd, J=2.35, 8.41 Hz, 1H), 7.17 (d, J=2.35 Hz, 1H), 7.12 (s, 1H), 6.91-6.83 (m, 1H), 6.81-6.75 (m, 1H), 5.69-5.54 (m, 1H), 5.43 (dd, J=7.92, 15.55 Hz, 1H), 4.14-3.91 (m, 4H), 3.56 (s, 3H), 3.28 (dd, J=5.87, 15.06 Hz, 2H), 3.19-3.08 (m, 2H), 2.94-2.85 (m, 3H), 2.83-2.64 (m, 4H), 2.36-2.00 (m, 6H), 1.94 (d, J=13.69 Hz, 1H), 1.81 (br. s., 2H), 1.63-1.35 (m, 3H). LRMS: (ESI, +ve ion) m/z 609.2 (M+H)$^+$.

Example 61

(1S,3'R,6'R,7'S,8'E,15'S)-6-CHLORO-7'-HYDROXY-15'-METHOXY-12'-METHYL-13'-OXO-3,4-DIHYDRO-2H-SPIRO[NAPHTHALENE-1,22'-[20]OXA[1,12] DIAZATETRACYCLO [14.7.2.0[3,6].0[19,24]]PENTACOSA[8,16,18,24]TETRAENE]-15'-CARBOXYLIC ACID

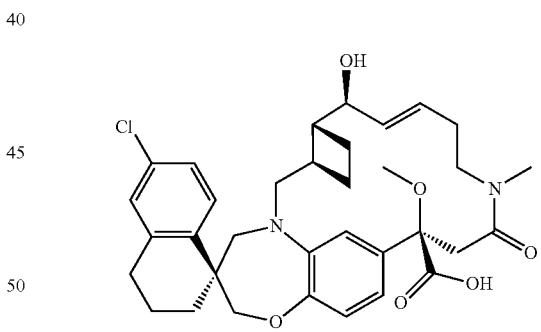

The title compound (2 mg, 14%) was obtained from methyl (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12]diazatetracyclo[14.7.2.0[3,6].0[19,24]]pentacosa[8,16,18,24]tetraene]-15'-carboxylate (Example 1) as a side product from the synthesis of Example 3, followed by saponification of the methyl ester through a procedure similar to that used for the synthesis of Example 4. $^1$H NMR (400 MHz, (CD$_3$)$_2$SO) δ 12.60 (br. s., 1H), 7.67 (d, J=8.61 Hz, 1H), 7.26 (dd, J=2.25, 8.51 Hz, 1H), 7.17 (d, J=2.15 Hz, 1H), 6.92 (dd, J=1.96, 8.22 Hz, 1H), 6.82 (d, J=8.22 Hz, 1H), 6.59 (d, J=1.76 Hz, 1H), 6.20-6.01 (m, 1H), 5.66 (dd, J=9.68, 13.99 Hz, 1H), 4.03-3.89 (m, 2H), 3.68-3.43 (m, 5H), 3.17-3.10 (m, 3H), 3.10-3.07 (m, 3H), 2.89 (s, 3H), 2.68 (td, J=1.79, 3.67 Hz, 2H), 2.63 (d, J=16.24 Hz, 2H), 2.43-2.24 (m, 5H), 2.04-1.84 (m, 5H). LRMS: (ESI, +ve ion) m/z 609.2 (M+H)+.

Example 62

(1S,6'E,12'S)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.016,21]DOCOSA[6,13,15,21]TETRAENE]-12'-CARBOXYLIC ACID

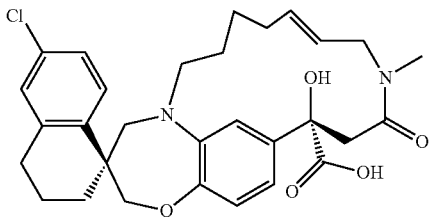 [SMILES: CN1C/C=C/CCCCN2C[C@@]3(CCCc4cc(Cl)ccc43)COc3ccc(cc32)[C@](O)(C(=O)O)CC1=O]

Step 1. METHYL (S)-6'-CHLORO-5-(HEX-5-EN-1-YL)-3',4,4',5-TETRAHYDRO-2H,2'H-SPIRO[BENZO[B][1,4]OXAZEPINE-3,1'-NAPHTHALENE]-7-CARBOXYLATE

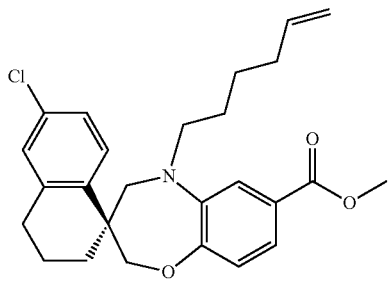 [SMILES: C=CCCCCN1C[C@@]2(CCCc3cc(Cl)ccc32)COc2ccc(C(=O)OC)cc21]

To a solution of methyl (S)-6'-chloro-3',4,4',5-tetrahydro-2H,2'H-spiro[benzo[b][1,4]oxazepine-3,1'-naphthalene]-7-carboxylate (from Intermediate AA11A Step 11A, 1500 mg, 4.19 mmol) and hex-5-enal (2.518 mL, 20.96 mmol) in DCM (4.19 mL) was added sodium triacetoxyborohydride (2665 mg, 12.58 mmol) and acetic acid (0.726 mL, 12.58 mmol). The reaction mixture was stirred overnight at room temperature. After this period, the reaction reached completion and the crude mixture was extracted with a saturated aqueous solution of sodium bicarbonate and diethyl ether. The combined organic layers were dried over magnesium sulfate, filtered and concentrated. The crude material was absorbed onto a plug of silica gel and purified by chromatography through a Redi-Sep pre-packed silica gel column (40 g), eluting with a gradient of 0% to 100% EtOAc in hexane, to provide methyl (S)-6'-chloro-5-(hex-5-en-1-yl)-3',4,4',5-tetrahydro-2H,2'H-spiro[benzo[b][1,4]oxazepine-3,1'-naphthalene]-7-carboxylate (1810 mg, 4.11 mmol, 98% yield) as light-yellow oil. MS (ESI, +ve ion) m/z 440.2 (M+H)+.

Step 2. (S)-6'-CHLORO-5-(HEX-5-EN-1-YL)-3',4,4',5-TETRAHYDRO-2H,2'H-SPIRO[BENZO[B][1,4]OXAZEPINE-3,1'-NAPHTHALENE]-7-CARBOXYLIC ACID

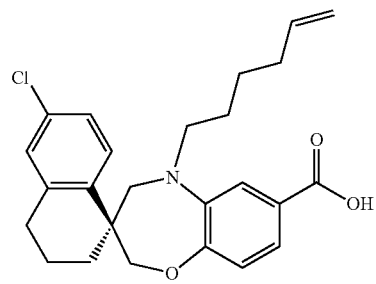 [SMILES: C=CCCCCN1C[C@@]2(CCCc3cc(Cl)ccc32)COc2ccc(C(=O)O)cc21]

To a solution of (S)-methyl 6'-chloro-5-(hex-5-en-1-yl)-3',4,4',5-tetrahydro-2H,2'H-spiro[benzo[b][1,4]oxazepine-3,1'-naphthalene]-7-carboxylate (3.52 g, 8.00 mmol) in THF (8 mL) and MeOH (4.00 mL) was added a pre-made 2M aqueous solution of lithium hydroxide monohydrate (4.00 mL, 8.00 mmol). The reaction mixture was stirred at 50° C.; the reaction progress was monitored by LCMS: addition of a second portion of LiOH was required for complete conversion. After 48 h, the reaction mixture was cooled to rt, neutralized (by the addition of 1N HCl), then extracted with ethyl acetate (2×). The combined organic layer was dried over sodium sulfate, filtered and concentrated. The crude material was absorbed onto a plug of silica gel and purified by chromatography through a Redi-Sep pre-packed silica gel column (80 g), eluting with a gradient of 0% to 60% EtOAc in hexane, to provide (S)-6'-chloro-5-(hex-5-en-1-yl)-3',4,4',5-tetrahydro-2H,2'H-spiro[benzo[b][1,4]oxazepine-3,1'-naphthalene]-7-carboxylic acid (3.0 g, 7.04 mmol, 88% yield) as a colorless foam (eluting at 20% EtOAc). MS (ESI, +ve ion) m/z 426.2 (M+H)+.

Step 3. METHYL (1S,6'E,12'S)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO [11.7.2.0$^{16,21}$]DOCOSA[6,13,15,21]TETRAENE]-12'-CARBOXYLATE and METHYL (1S,6'E,12'R)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.016,21] DOCOSA[6,13,15,21]TETRAENE]-12'-CARBOXYLATE

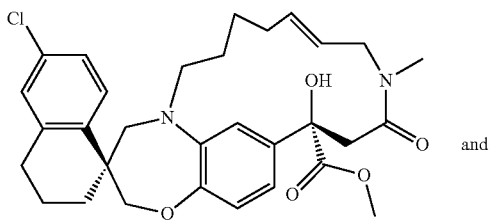

and

-continued

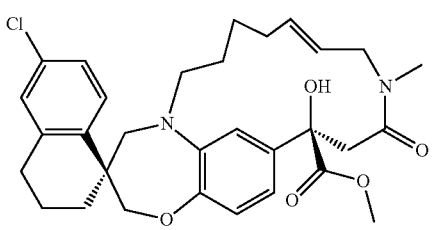

The above compounds were synthesized from (S)-6'-chloro-5-(hex-5-en-1-yl)-3',4,4',5-tetrahydro-2H,2'H-spiro[benzo[b][1,4]oxazepine-3,1'-naphthalene]-7-carboxylate (Example 62, Step 2) through a procedure similar to that used for the synthesis of Example 1, Steps 1 through 7 (100 mg, 45% combined yield from Step 1 as a mixture of epimers at C12). The isomers were separated by SFC (AS column, isopropanol 30% isocratic, 5 minutes). MS (ESI, +ve ion) m/z 553.2 (M+H)+.

Step 4. (1S,6'E,12'S)-6-chloro-12'-hydroxy-9'-methyl-10'-oxo-3,4-dihydro-2H-spiro[naphthalene-1, 19'-[17]oxa[1,9]diazatricyclo[11.7.2.0$^{16,21}$]docosa[6, 13,15,21]tetraene]-12'-carboxylic acid

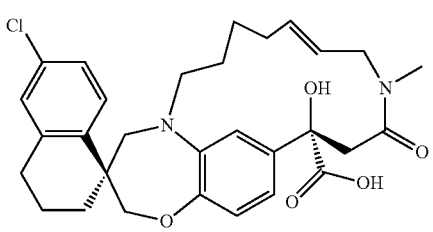 [SMILES: CN1C/C=C/CCCCN2C[C@@]3(CCCc4cc(Cl)ccc43)COc3ccc(cc32)[C@](O)(C(=O)O)CC1=O]

The title compound (7 mg, 63%) was synthesized via saponification from the fast eluting isomer from SFC separation in Step 3, though a procedure similar to that used for the synthesis of Example 4. $^1$H NMR (400 MHz, CD$_2$Cl$_2$) δ 7.75 (d, J=8.41 Hz, 1H), 7.15 (dd, J=2.35, 8.41 Hz, 1H), 7.08 (d, J=2.35 Hz, 1H), 6.91-6.85 (m, 1H), 6.84-6.80 (m, 1H), 6.61 (d, J=1.96 Hz, 1H), 5.71 (td, J=7.34, 15.06 Hz, 1H), 5.57-5.45 (m, 1H), 4.22-4.02 (m, 2H), 3.82 (d, J=5.48 Hz, 2H), 3.51 (d, J=14.48 Hz, 1H), 3.40-3.28 (m, 2H), 3.26-3.16 (m, 2H), 3.07 (d, J=17.41 Hz, 1H), 2.96 (s, 3H), 2.75 (d, J=6.26 Hz, 2H), 2.16 (br. s., 1H), 2.12-2.02 (m, 1H), 1.90-1.76 (m, 3H), 1.64 (d, J=10.17 Hz, 4H), 0.93-0.81 (m, 2H). LRMS: (ESI, +ve ion) m/z 539.2 (M+H)+.

Example 63

(1S,6'E,12'R)-6-CHLORO-12'-HYDROXY-9'-METHYL-10'-OXO-3,4-DIHYDRO-2H-SPIRO [NAPHTHALENE-1,19'-[17]OXA[1,9]DIAZATRI-CYCLO[11.7.2.0$^{16,21}$]DOCOSA[6,13,15,21] TETRAENE]-12'-CARBOXYLIC ACID

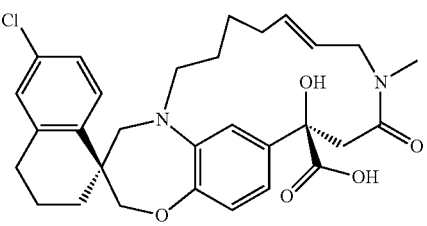 [SMILES: CN1C/C=C/CCCCN2C[C@@]3(CCCc4cc(Cl)ccc43)COc3ccc(cc32)[C@@](O)(C(=O)O)CC1=O]

The title compound (7 mg, 80%) was synthesized via saponification from the slow eluting isomer from SFC separation on Example 62, Step 3, though a procedure similar to that used for the synthesis of Example 4. $^1$H NMR (400 MHz, CD$_2$Cl$_2$) δ 7.76 (d, J=8.61 Hz, 1H), 7.16 (dd, J=2.35, 8.61 Hz, 1H), 7.08 (d, J=2.15 Hz, 1H), 6.93-6.87 (m, 1H), 6.85-6.80 (m, 1H), 6.60 (d, J=2.15 Hz, 1H), 5.78-5.65 (m, 1H), 5.56-5.45 (m, 1H), 4.13-4.02 (m, 2H), 3.82 (br. s., 2H), 3.58 (d, J=13.69 Hz, 1H), 3.40-3.18 (m, 4H), 3.05 (d, J=17.22 Hz, 1H), 2.96 (s, 3H), 2.81-2.69 (m, 2H), 2.22 (d, J=18.58 Hz, 1H), 2.10-2.00 (m, 1H), 1.97-1.77 (m, 3H), 1.68 (d, J=18.19 Hz, 2H), 1.52 (br. s., 2H), 0.94-0.81 (m, 2H). LRMS: (ESI, +ve ion) m/z 539.2 (M+H)+.

Example 64

(1S,12'R)-6-CHLORO-12'-HYDROXY-9'-METHYL-10'-OXO-3,4-DIHYDRO-2H-SPIRO [NAPHTHALENE-1,19'-[17]OXA[1,9]DIAZATRI-CYCLO [11.7.2.0$^{16,21}$]DOCOSA[13,15,21] TRIENE]-12'-CARBOXYLIC ACID and (1S,12'S)-6-CHLORO-12'-HYDROXY-9'-METHYL-10'-OXO-3,4-DIHYDRO-2H-SPIRO [NAPHTHALENE-1,19'-[17]OXA[1,9] DIAZATRICYCLO[11.7.2.0$^{16,21}$]DOCOSA[13,15, 21]TRIENE]-12'-CARBOXYLIC ACID

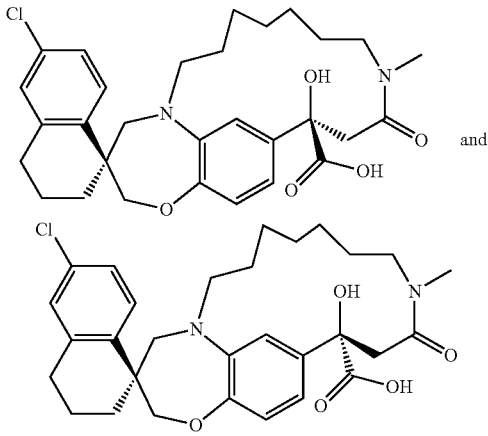

The title compounds (29 mg, 74%) were synthesized from methyl (1S,6'E,12'S)-6-chloro-12'-hydroxy-9'-methyl-10'-oxo-3,4-dihydro-2H-spiro[naphthalene-1,19'-[17]oxa[1,9]diazatricyclo[11.7.2.0$^{16,21}$]docosa[6,13,15,21]tetraene]-12'-carboxylate and methyl (1S,6'E,12'R)-6-chloro-12'-hydroxy-9'-methyl-10'-oxo-3,4-dihydro-2H-spiro[naphthalene-1,19'-[17]oxa[1,9]diazatricyclo[11.7.2.0$^{16,21}$]docosa[6,13,15,21]tetraene]-12'-carboxylate and (nearly 1:1 mixture of epimers at C$_{12}$, Example 62, Step 3) via hydrogenation through a through a procedure similar to that used for the synthesis of Example 39 followed by saponification through a procedure similar to that used for the synthesis of Example 4. NMR of the mixture: $^1$H NMR (400 MHz, CD$_2$Cl$_2$) δ 7.81-7.71 (m, 1H), 7.20-7.11 (m, 1H), 7.09 (s, 1H), 7.01-6.91 (m, 1H), 6.89-6.82 (m, 1H), 6.75-6.67 (m, 1H), 4.07 (s, 2H), 2.95-3.69 (m, 7H), 2.94 (s, 3H), 2.64-2.84 (m, 4H), 1.42-1.96 (m, 11H), 1.40-1.19 (m, 4H). LRMS: (ESI, +ve ion) m/z 541.2 (M+H)$^+$.

Example 65

(1S,6'E,11'R,12'S)-6-CHLORO-12'-HYDROXY-9',11'-DIMETHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID and/or
(1S,6'E,11'R,12'R)-6-CHLORO-12'-HYDROXY-9',11'-DIMETHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID and/or
(1S,6'E,11'S,12'S)-6-CHLORO-12'-HYDROXY-9',11'-DIMETHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID and/or
(1S,6'E,11'S,12'R)-6-CHLORO-12'-HYDROXY-9',11'-DIMETHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID

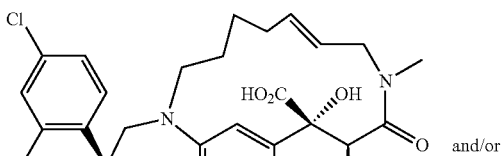 and/or

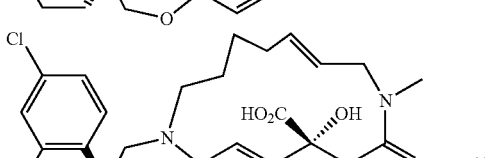 and/or

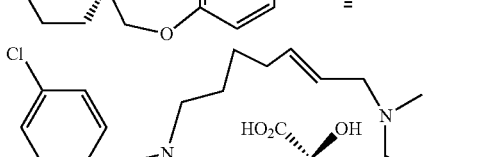 and/or

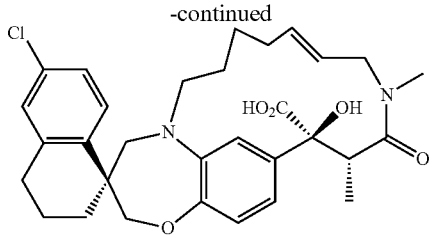

The title compounds were synthesized through a procedure similar to that described for the synthesis of Example 62 taking the slowest two isomers from Step 3 onto Step 4. The compounds were isolated as a nearly 1:1 mixture of two of the above four isomers. NMR of the mixture: $^1$H NMR (400 MHz, CD$_2$Cl$_2$) δ 7.82-7.61 (m, 1H), 7.21-7.10 (m, 1H), 7.09 (s, 1H), 7.02-6.57 (m, 3H), 5.87-5.66 (m, 1H), 5.63-5.37 (m, 1H), 4.22-3.96 (m, 2H), 3.84-3.61 (m, 1H), 3.54-3.16 (m, 3H), 3.06-2.87 (m, 3H), 2.81-2.67 (m, 2H), 2.48-2.17 (m, 5H), 1.96 (d, J=10.76 Hz, 1H), 1.88-1.58 (m, 5H), 1.54-1.34 (m, 3H), 1.04-0.84 (m, 2H). LRMS: (ESI, +ve ion) m/z 553.2 (M+H)$^+$.

Example 66

(1S,6'E,11'R,12'S)-6-CHLORO-12'-HYDROXY-9',11'-DIMETHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID and/or
(1S,6'E,11'R,12'R)-6-CHLORO-12'-HYDROXY-9',11'-DIMETHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID and/or
(1S,6'E,11'S,12'S)-6-CHLORO-12'-HYDROXY-9',11'-DIMETHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID and/or
(1S,6'E,11'S,12'R)-6-CHLORO-12'-HYDROXY-9',11'-DIMETHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID

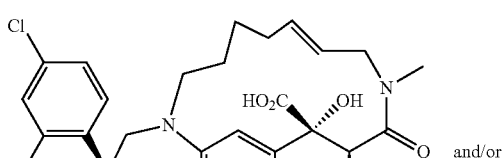 and/or

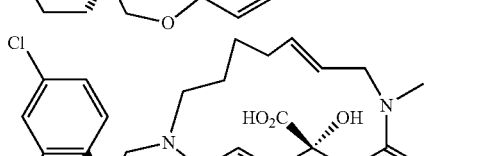 and/or

-continued

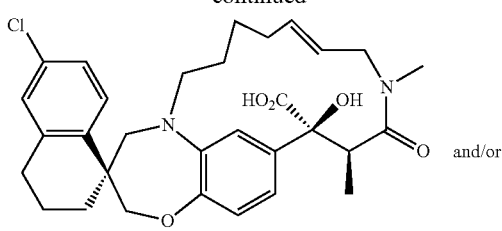

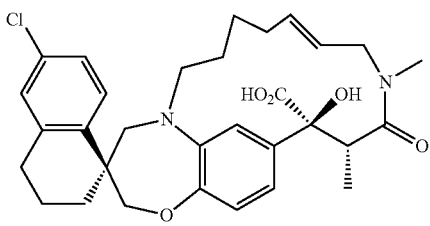

The title compounds were synthesized through a procedure similar to that described for the synthesis of Example 62 taking the slowest two isomers from Step 3 onto Step 4. The compounds were isolated as a nearly 1:1 mixture of two of the above four isomers. NMR of the mixture: $^1$H NMR (400 MHz, CD$_2$Cl$_2$) δ 7.80-7.63 (m, 1H), 7.20-6.94 (m, 3H), 6.93-6.79 (m, 1H), 6.78-6.61 (m, 1H), 5.81-5.38 (m, 2H), 4.24-4.06 (m, 2H), 4.00 (dd, J=11.93, 17.41 Hz, 1H), 3.76-3.50 (m, 3H), 3.46-2.95 (m, 5H), 2.88-2.75 (m, 3H), 2.23 (br. s., 1H), 2.09-1.43 (m, 8H), 1.41 (d, J=4.11 Hz, 3H), 1.31-1.25-(m, 1H). LRMS: (ESI, +ve ion) m/z 553.2 (M+H)$^+$.

Example 67

(1S,3'R,6'R,7'S,8'E,15'R)-6-CHLORO-15'-HYDROXY-7'-METHOXY-3,4-DIHYDRO-2H-SPIRO[NAPHTHALENE-1,22'-[20]OXA[1]AZATETRACYCLO[14.7.2.0$^{3,6}$.0$^{19,24}$]PENTACOSA[8,16,18,24]TETRAENE]-15'-CARBOXYLIC ACID or (1S,3'R,6'R,7'S,8'E,15'S)-6-CHLORO-15'-HYDROXY-7'-METHOXY-3,4-DIHYDRO-2H-SPIRO[NAPHTHALENE-1,22'-[20]OXA[1]AZATETRACYCLO[14.7.2.0$^{3,6}$.0$^{19,24}$]PENTACOSA[8,16,18,24]TETRAENE]-15'-CARBOXYLIC ACID

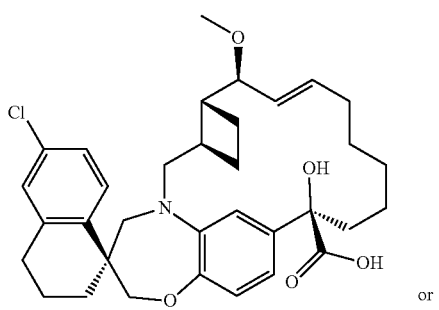

or

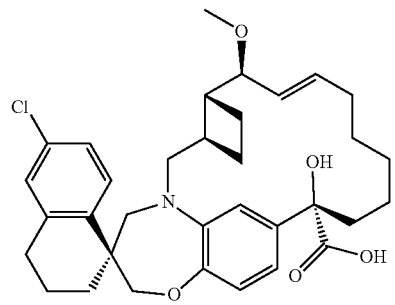

Step 1: Methyl 2-(6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxynon-8-enoate

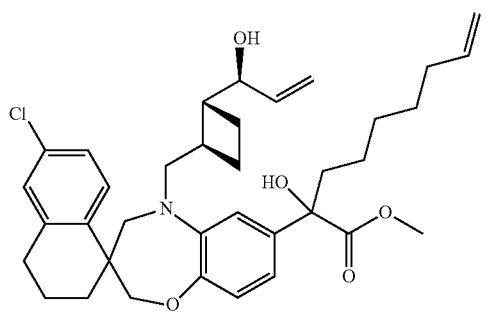 [SMILES: C=CCCCCCC(O)(C(=O)OC)c1ccc2c(c1)N(C[C@@H]1CC[C@H]1[C@@H](O)C=C)CC1(CCCc3cc(Cl)ccc31)CO2]

Under Argon, to a solution of methyl 2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-oxoacetate (from Example 1 Step 3, 80 mg, 0.157 mmol) in THF (314 μl) at −78° C. was added hept-6-en-1-ylmagnesium bromide (314 μl, 0.157 mmol). The reaction was stirred for 15 minutes. After this time, the reaction mixture was diluted with water (30 mL) and extracted with Et$_2$O (3×30 mL). The organic extract was dried over MgSO$_4$. The solution was filtered and concentrated in vacuo. The crude material (70 mg) containing methyl 2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxynon-8-enoate was used as such in the next step. LRMS: (ESI, +ve ion) m/z 608.2 (M+H)$^+$.

Step 2: Methyl(1S,3'R,6'R,7'S,8'E,15'R)-6-chloro-7',15'-dihydroxy-3,4-dihydro-2H-spiro[naphthalene-1,22'-[20]oxa[1]azatetracyclo[14.7.2.0³,⁶.0¹⁹,²⁴]pentacosa[8,16,18,24]tetraene]-15'-carboxylate and Methyl(1S,3'R,6'R,7'S,8'E,15'S)-6-chloro-7',15'-dihydroxy-3,4-dihydro-2H-spiro[naphthalene-1,22'-[20]oxa[1]azatetracyclo[14.7.2.03,6.019,24]pentacosa[8,16,18,24]tetraene]-15'-carboxylate Step 3: (1S,3'R,6'R,7'S,8'E,15'R)-6-chloro-15'-hydroxy-7'-methoxy-3,4-dihydro-2H-spiro[naphthalene-1,22'-[20]oxa[1]azatetracyclo[14.7.2.0³,⁶.0¹⁹,²⁴]pentacosa[8,16,18,24]tetraene]-15'-carboxylic Acid or (1S,3'R,6'R,7'S,8'E,15'S)-6-chloro-15'-hydroxy-7'-methoxy-3,4-dihydro-2H-spiro[naphthalene-1,22'-[20]oxa[1]azatetracyclo[14.7.2.0³,⁶.0¹⁹,²⁴]pentacosa[8,16,18,24]tetraene]-15'-carboxylic Acid

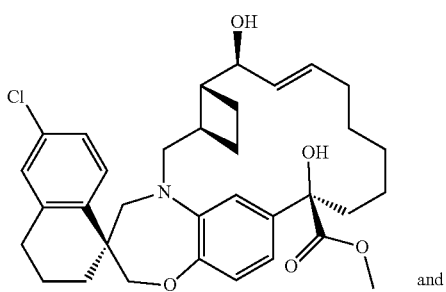

and

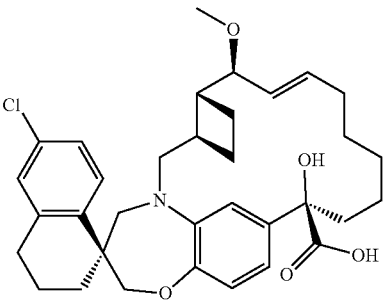

or

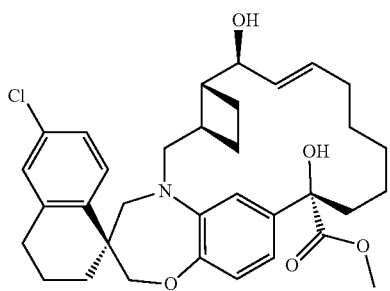

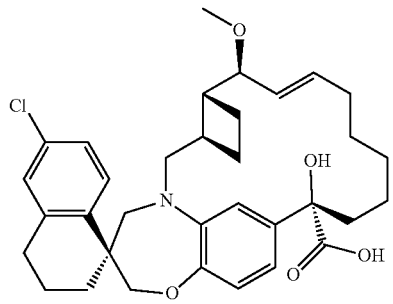

To the product from step 1 (70 mg, 0.115 mmol) in 1,1-dichloroethane (57.500 mL), was added hoveyda-grubbs catalyst 2nd generation (14.42 mg, 0.023 mmol) as a solid. The reaction was stirred overnight at 50° C. under argon. After this period, the product was observed by LCMS. The mixture was cooled and concentrated. The material thus obtained was absorbed onto a plug of silica gel and purified by chromatography through a Redi-Sep pre-packed silica gel column (40 g), eluting with a gradient of 10% to 100% acetone in heptanes, to provide the title compounds as a mixture of diastereomers (31 mg, 0.053 mmol, 46.4% yield). Under these conditions, the diastereoisomers were not separated. LRMS: (ESI, +ve ion) m/z 580.2 (M+H)⁺.

The title compound (2.1 mg, <1% yield) was synthesized from Example 67, step 2 via methylation through a procedure similar to that used for the synthesis of Example 3, followed by saponification through a procedure similar to that used for the synthesis of Example 4. The crude material was purified by reverse-phase preparative HPLC using a Phenomenex Luna column, 10 micron, C18(2), 100 Å, 250×50 mm, eluting with a gradient of 50% to 95% acetonitrile in water (both solvents containing 0.1% TFA) over a period of 27 minutes to provide the title compound (slow eluting isomer). $^1$H NMR (400 MHz, CD$_2$Cl$_2$) δ 7.66 (d, J=8.61 Hz, 1H), 7.14 (dd, J=2.35, 8.61 Hz, 1H), 7.10 (d, J=2.15 Hz, 1H), 6.88 (s, 2H), 6.63 (s, 1H), 5.60-5.51 (m, 1H), 5.41 (d, J=6.06 Hz, 1H), 4.15 (t, J=5.09 Hz, 1H), 4.10-3.98 (m, 2H), 3.54 (d, J=14.48 Hz, 1H), 3.45-3.37 (m, 1H), 3.35 (s, 3H), 3.33-3.22 (m, 2H), 2.82-2.73 (m, 2H), 2.62-2.50 (m, 1H), 2.46-2.29 (m, 3H), 2.08-2.01 (m, 4H), 1.92-1.84 (m, 6H), 1.69-1.55 (m, 6H). LRMS: (ESI, +ve ion) m/z 580.2 (M+H)⁺

Example 68

(1S,3'R,6'R,7'S,8'E,15'R)-6-CHLORO-15'-HYDROXY-7'-METHOXY-3,4-DIHYDRO-2H-SPIRO[NAPHTHALENE-1,22'-[20]OXA[1]AZATETRACYCLO[14.7.2.0$^{3,6}$.0$^{19,24}$]PENTACOSA[8,16,18,24]TETRAENE]-15'-CARBOXYLIC ACID or (1S,3'R,6'R,7'S,8'E,15'S)-6-CHLORO-15'-HYDROXY-7'-METHOXY-3,4-DIHYDRO-2H-SPIRO[NAPHTHALENE-1,22'-[20]OXA[1]AZATETRACYCLO[14.7.2.0$^{3,6}$.0$^{19,24}$]PENTACOSA[8,16,18,24]TETRAENE]-15'-CARBOXYLIC ACID

Example 69

(3R,6R,7S,11R,17R,24S)-6'-CHLORO-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXYLIC ACID OR (3R,6R,7S,11R,17S,24S)-6'-CHLORO-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXYLIC ACID

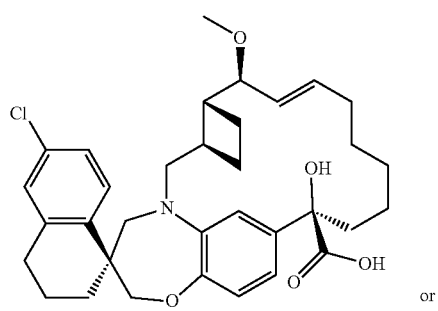

or

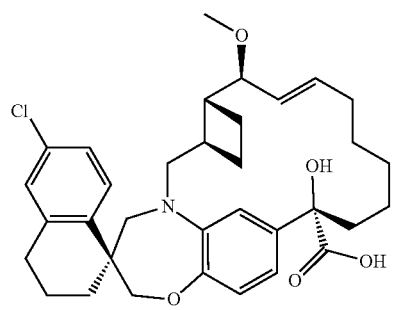

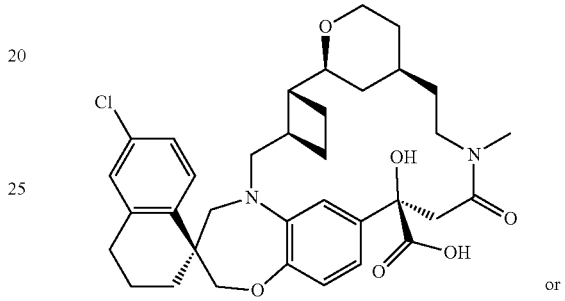

or

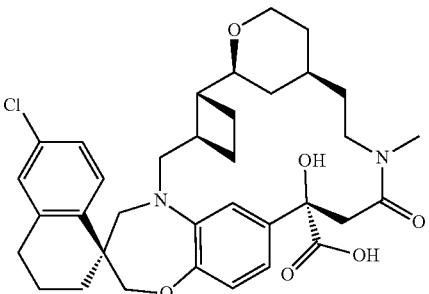

The title (1.4 mg, <1% yield) compound was synthesized from Example 67, Step 2 via methylation through a procedure similar to that used for the synthesis of Example 3, followed by saponification through a procedure similar to that used for the synthesis of Example 4. The crude material was purified by reverse-phase preparative HPLC using a Phenomenex Luna column, 10 micron, C18(2), 100 Å, 250×50 mm, eluting with a gradient of 50% to 95% acetonitrile in water (both solvents containing 0.1% TFA) over a period of 27 minutes to provide the title compound (fast eluting isomer). $^1$H NMR (400 MHz, CD$_2$Cl$_2$) δ 7.71 (d, J=8.61 Hz, 1H), 7.20-7.17 (m, 1H), 7.14 (d, J=2.15 Hz, 1H), 6.91 (d, J=8.22 Hz, 1H), 6.88 (d, J=1.96 Hz, 1H), 6.74 (dd, J=2.15, 8.22 Hz, 1H), 5.65-5.55 (m, 2H), 4.16 (t, J=4.30 Hz, 1H), 4.14-4.03 (m, 3H), 3.66 (d, J=14.28 Hz, 1H), 3.49-3.42 (m, 2H), 3.42-3.36 (m, 1H), 3.32 (s, 3H), 2.86-279 (m, 3H), 2.63 (td, J=7.87, 16.33 Hz, 2H), 2.43-2.24 (m, 8H), 1.99-1.90 (m, 4H), 1.90-1.84 (m, 3H), 1.72-1.66 (m, 2H). LRMS: (ESI, +ve ion) m/z 580.2 (M+H)$^+$.

Step 1. (1'S)-METHYL 6'-CHLORO-5-((2-((S)-4-OXO-3,4-DIHYDRO-2H-PYRAN-2-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

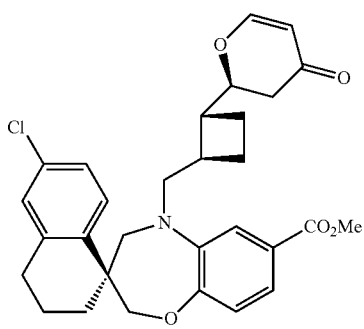 [SMILES: COC(=O)c1ccc2c(c1)N(C[C@@H]1CC[C@H]1[C@@H]1CC(=O)C=CO1)C[C@@]1(CCCc3cc(Cl)ccc31)CO2]

To a solution of (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (described in Step 19A of Intermediate AA11A) (1.92 g, 4.23 mmol) in methyl tert-butylether (42.3 mL) cooled to −78° C. was added 1-methoxy-3-trimethylsiloxy-1,3-butadiene, 95% (0.906 mL, 4.65 mmol) then boron trifluoride diethyl etherate (0.574 mL, 4.65 mmol) (as a stream down the side of the flask). The reaction mixture (color change to orange/red) was stirred at −78° C. for 7 h (TLC indicated formation of a mixture of addition products), then quenched by the sequential addition of EtOAc and saturated aqueous NaHCO$_3$ (at low temp). The layers were separated and the organic extract was washed with water (1×), brine (1×) then dried over Na$_2$SO$_4$. The solution was filtered and concentrated in vacuo to give the crude material. To a solution of the crude material in CH$_2$Cl$_2$ (20 mL) was added p-toluenesulfonic acid monohydrate (40.2 mg, 0.211 mmol). The reaction mixture was maintained at room temperature for 10 minutes (TLC indicated conversion of the tetrahydropyranone intermediate, (1'S)-methyl 6'-chloro-5-((2-(6-methoxy-4-oxotetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate to the desired dihydropyranone products, (1'S)-methyl 6'-chloro-5-((2-((S)-4-oxo-3,4-dihydro-2H-pyran-2-yl)cyclobutyl)methyl)-3',4,4',5-tetrahydro-2H,2'H-spiro[benzo[b][1,4]oxazepine-3,1'-naphthalene]-7-carboxylate and (1'S)-methyl 6'-chloro-5-((2-((R)-4-oxo-3,4-dihydro-2H-pyran-2-yl)cyclobutyl)methyl)-3',4,4',5-tetrahydro-2H,2'H-spiro[benzo[b][1,4]oxazepine-3,1'-naphthalene]-7-carboxylate), then was diluted with saturated aqueous NH$_4$Cl and extracted with EtOAc (2×). The organic extract was washed with saturated aqueous NaCl and dried over Na$_2$SO$_4$. The solution was filtered and concentrated in vacuo to give the crude residue. The residue was absorbed onto a plug of silica gel and purified by chromatography through a Redi-Sep pre-packed silica gel column (120 g), eluting with a gradient of 0% to 50% EtOAc in hexanes, to provide the dihydropyranone products as a 2.5:1 mixture of epimers. The mixture of epimeric products was submitted to slow crystallization from hot EtOAc. Two crops were collected and combined affording the above compound/major isomer (1505 mg, 68% yield, 9:1 dr) as a white crystalline solid: $^1$H NMR (400 MHz, CDCl$_3$) δ 7.71 (d, J=8.4 Hz, 1H), 7.58 (d, J=5.7 Hz, 1H), 7.46 (s, 1H), 7.40 (dd, J=2.0, 8.2 Hz, 1H), 7.18 (dd, J=2.3, 8.4 Hz, 1H), 7.10 (d, J=2.2 Hz, 1H), 6.93 (d, J=8.2 Hz, 1H), 5.46 (d, J=5.9 Hz, 1H), 4.39 (ddd, J=6.4, 9.1, 10.7 Hz, 1H), 4.14-4.05 (m, 2H), 3.86 (s, 3H), 3.79 (dd, J=2.5, 14.9 Hz, 1H), 3.67 (d, J=14.3 Hz, 1H), 3.32-3.19 (m, 2H), 2.84-2.73 (m, 2H), 2.72-2.62 (m, 1H), 2.47-2.30 (m, 3H), 2.19-2.09 (m, 1H), 2.07-1.71 (m, 5H), 1.70-1.59 (m, 1H), 1.55-1.45 (m, 1H). LRMS: m/z (ESI, +ve ion) 522.1 (M+H)$^+$. The absolute and relative configuration of the above compound was confirmed by single-crystal xray diffraction (as described below).

Step 2. (1'S)-METHYL 6'-CHLORO-5-((2-((S)-4-OXOTETRAHYDRO-2H-PYRAN-2-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

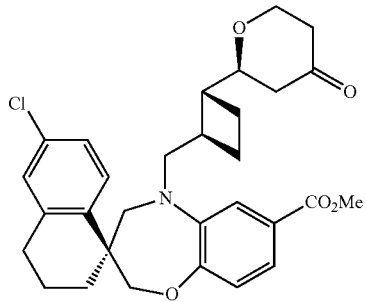 [SMILES: COC(=O)c1ccc2c(c1)N(C[C@@H]1CC[C@H]1[C@@H]1CC(=O)CCO1)C[C@@]1(CCCc3cc(Cl)ccc31)CO2]

To a solution of (1'S)-methyl 6'-chloro-5-((2-((S)-4-oxo-3,4-dihydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (from Step 1) (1.50 g, 2.87 mmol) in EtOAc (57.5 mL) in a thick-walled, high-pressure glass vessel fitted with a rubber-lined teflon screw top under an argon atmosphere was added platinum (IV) oxide (15.5 mg, 0.068 mmol). The reaction mixture was exposed to an atmosphere of H$_2$ (15 psi, by connection of the pressure vessel to a hydrogen gas tank both fitted with pressure regulators), with stirring for 4 h. Analysis by LCMS indicated consumption of the starting material and formation of a mixture of the desired product, (1'S)-methyl 6'-chloro-5-((2-((2S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate and (1'S)-methyl 6'-chloro-5-(((1R,2R)-2-((2S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (over-reduction alcohol). The hydrogen atmosphere was replaced with an argon atmosphere (via balloon with multiple cycles of vacuum evacuation/back-filling), then the reaction mixture was filtered through a pad of celite eluting with EtOAc, the mixture was concentrated under reduced pressure. To a solution of oxalyl chloride (0.281 mL, 3.16 mmol) in DCM (25 mL) cooled to −78° C. was added dimethyl sulfoxide (0.448 mL, 6.32 mmol). After 10 minutes, a solution of the crude mixture (as a solution in 8 mL of DCM) was added as a slow, steady stream down the side of the reaction vessel. After 10 minutes, triethylamine (1.80 mL, 12.9 mmol) was slowly added to the solution (as a steady stream down the side of the reaction vessel). The reaction mixture was maintained for 1 h at −78° C. and then the mixture was allowed to warm to room temperature. The reaction mixture was quenched by addition of water and EtOAc. The layers were separated and the aqueous phase was further extracted with EtOAc (2×). The combined organic layer was washed with brine then dried over Na$_2$SO$_4$, filtered and concentrated under reduced pressure. The crude material was absorbed onto a plug of silica gel and purified by chromatography through a Isco Redi-sep 80 g column, eluting with a gradient of 0% to 50% EtOAc in hexane, to provide the above compound (1.21 g, 80%) as a colorless foam: $^1$H NMR (400 MHz, CDCl$_3$) δ 7.71 (d, J=8.6 Hz, 1H), 7.45 (d, J=1.8 Hz, 1H), 7.38 (dd, J=1.9, 8.3 Hz, 1H), 7.18 (dd, J=2.3, 8.6 Hz, 1H), 7.09 (d, J=2.3 Hz, 1H), 6.91 (d, J=8.2 Hz, 1H), 4.40 (dd, J=6.6, 11.6 Hz, 1H), 4.12-4.05 (m, 2H), 3.87 (s, 3H), 3.85-3.74 (m, 2H), 3.66 (d, J=14.7 Hz, 1H), 3.57 (ddd, J=2.2, 8.4, 11.1 Hz, 1H), 3.31 (d, J=14.5 Hz, 1H), 3.20 (dd, J=9.5, 14.8 Hz, 1H), 2.84-2.73 (m, 2H), 2.72-2.57 (m, 2H), 2.40-2.30 (m, 2H), 2.24-2.09 (m, 2H), 2.09-2.00 (m, 3H), 1.97-1.80 (m, 3H), 1.76-1.65 (m, 1H), 1.64-1.57 (m, 1H), 1.54-1.44 (m, 1H). LRMS: m/z (ESI, +ve ion) 524.2 (M+H)$^+$.

Step 3. TERT-BUTYL METHYL(2-((1-PHENYL-1H-TETRAZOL-5-YL)THIO)ETHYL)CARBAMATE

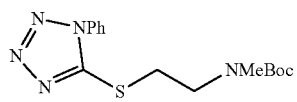

To a solution of (2-hydroxy-ethyl)-methyl-carbamic acid tert-butyl ester (1.70 mL, 9.70 mmol), 1-phenyltetrazole-5-thiol (1.90 g, 10.7 mmol) and triphenylphosphine (2.80 g, 10.7 mmol) in THF (48.5 mL) was added diethyl azodicarboxylate, 40 wt. % solution in toluene (5.30 mL, 11.6 mmol) dropwise over 10 minutes. The reaction was maintained at room temperature for 4 h, then concentrated under reduced pressure. The crude material was absorbed onto a plug of silica gel and purified by chromatography through a Redi-Sep pre-packed silica gel column (80 g), eluting with a gradient of 0% to 100% EtOAc in hexane, to provide the above compound (3.04 g, 93% yield) as a colorless oil: $^1$H NMR (300 MHz, CDCl$_3$) δ 7.62-7.51 (m, 5H), 3.68 (t, J=6.7 Hz, 2H), 3.52 (t, J=6.7 Hz, 2H), 2.93 (s, 3H), 1.42 (s, 10H). LRMS: m/z (ESI, +ve ion) 336.0 (M+H)$^+$.

Step 4. TERT-BUTYL METHYL(2-((1-PHENYL-1H-TETRAZOL-5-YL)SULFONYL)ETHYL)CARBAMATE

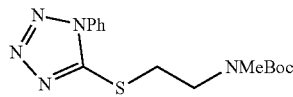

To a solution of tert-butyl methyl(2-((1-phenyl-1H-tetrazol-5-yl)thio)ethyl)carbamate (from step 3) (3.04 g, 9.06 mmol) in CH$_2$Cl$_2$ (91 mL) at 0° C. was added 3-chloroperoxybenzoic acid (70% purity) (11 g, 44.6 mmol) in a portionwise fashion (note: a slight exotherm is observed; the flask heats up by touch). The ice-water bath was removed and the resulting suspension was stirred at room temperature. After stirring overnight, the reaction mixture was diluted with CH$_2$Cl$_2$ and quenched by the addition of 1N NaOH (~100 mL). The layers were separated and the aqueous layer was extracted with CH$_2$Cl$_2$ (2x). The organic extract was washed with saturated aqueous NaCl (1x) and dried over Na$_2$SO$_4$. The solution was filtered and concentrated in vacuo to give the crude material. The crude material was purified by chromatography through a 80 g column, eluting with a gradient of 0% 70% EtOAc in hexane, to provide the above compound (3.0 g, 90% yield) as a colorless waxy solid/oil: $^1$H NMR (300 MHz, CDCl$_3$) δ 7.73-7.57 (m, 5H), 3.99 (d, J=5.7 Hz, 2H), 3.90-3.81 (m, 2H), 2.93 (s, 3H), 1.58-1.41 (m, 10H). LRMS: m/z (ESI, +ve ion) 368.0 (M+H)$^+$.

Step 5. (S)-METHYL 5-(((1R,2R)-2-((S,Z)-4-(2-((TERT-BUTOXYCARBONYL)(METHYL)AMINO)ETHYLIDENE)TETRAHYDRO-2H-PYRAN-2-YL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALENE]-7-CARBOXYLATE AND (S)-METHYL 5-(((1R,2R)-2-((S,E)-4-(2-((TERT-BUTOXYCARBONYL)(METHYL)AMINO)ETHYLIDENE)TETRAHYDRO-2H-PYRAN-2-YL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALENE]-7-CARBOXYLATE

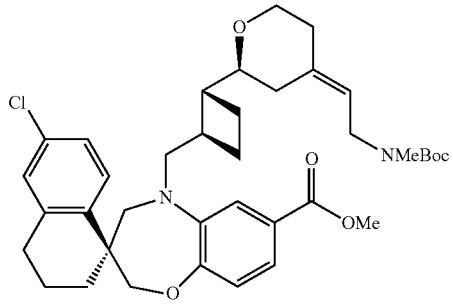

and

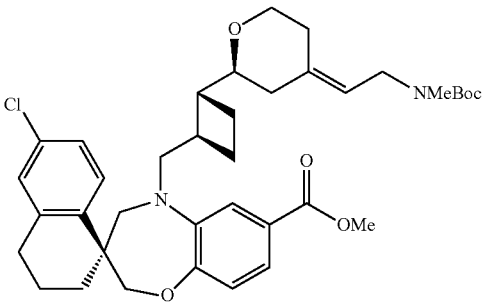

To a solution of (1'S)-methyl 6'-chloro-5-((2-((S)-4-oxo-tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (from Step 2) (1.00 g, 1.91 mmol) and tert-butyl methyl(2-((1-phenyl-H-tetrazol-5-yl)sulfonyl)ethyl)carbamate (from Step 4) (1.12 g, 3.05 mmol) in THF (15.9 mL) cooled in an ice-water bath was added lithium bis(trimethylsilyl)amide, 1.0 M solution in THF (7.63 mL, 7.63 mmol) (slowly as a steady stream down the side of the flask). The reaction was maintained at room temperature. After 12 h, the reaction mixture was diluted with saturated aqueous NH₄Cl and extracted with EtOAc (2×). The organic extract was washed with saturated aqueous NaCl and dried over Na₂SO₄. The solution was filtered and concentrated in vacuo to give the crude material. The crude material was absorbed onto a plug of silica gel and purified by chromatography through a Redi-Sep pre-packed silica gel column (80 g), eluting with a gradient of 0% to 70% EtOAc in hexane, to provide the above compounds (1.12 g, 88% yield, as a mixture of olefin isomers) as an off-white solid: ¹H NMR (300 MHz, CDCl₃) δ 7.70 (d, J=8.6 Hz, 1H), 7.45 (d, J=1.9 Hz, 1H), 7.38 (dd, J=1.7, 8.3 Hz, 1H), 7.17 (dd, J=2.2, 8.5 Hz, 1H), 7.09 (d, J=2.3 Hz, 1H), 6.91 (d, J=8.2 Hz, 1H), 5.22 (q, J=6.6 Hz, 1H), 4.13-4.01 (m, 3H), 3.90-3.78 (m, 5H), 3.77-3.61 (m, 2H), 3.54-3.38 (m, 1H), 3.35-3.12 (m, 3H), 2.84-2.72 (m, 5H), 2.60-2.28 (m, 3H), 2.16-1.97 (m, 5H), 1.96-1.78 (m, 4H), 1.78-1.58 (m, 3H), 1.47 (d, J=1.6 Hz, 9H). LRMS: m/z (ESI, +ve ion) 665.2 (M+H)⁺.

Step 6. (1'S)-METHYL 5-((2-((2S,4R)-4-(2-((TERT-BUTOXYCARBONYL)(METHYL)AMINO)ETHYL)TETRAHYDRO-2H-PYRAN-2-YL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALENE]-7-CARBOXYLATE (Relative Configuration Assigned by x-Ray of a Derivative of the Epimer, Refer to Example 6)

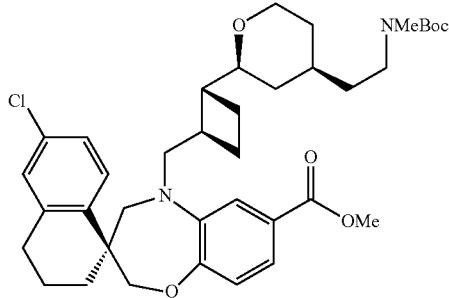

To a solution of (S)-methyl 5-(((1R,2R)-2-((S,Z)-4-(2-((tert-butoxycarbonyl)(methyl)amino)ethylidene)tetrahydro-2H-pyran-2-yl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 5-(((1R,2R)-2-((S,E)-4-(2-((tert-butoxycarbonyl)(methyl)amino)ethylidene)tetrahydro-2H-pyran-2-yl)cyclobutyl)methyl)-6'-chloro-3',4,4',5-tetrahydro-2H,2'H-spiro[benzo[b][1,4]oxazepine-3,1'-naphthalene]-7-carboxylate (mixture of olefin isomers from Step 5) (1.12 g, 1.68 mmol) in ethanol (69.6 mL) and chloroform (6.96 mL) (for solubility) in a thick-walled, high-pressure glass vessel fitted with a rubber-lined teflon screw top under an under a N₂ atmosphere was added platinum (IV) oxide (96.0 mg, 0.421 mmol). The reaction mixture was exposed to an atmosphere of H₂ (~20 psi, by connection of the pressure vessel to a hydrogen gas tank both fitted with pressure regulators), with stirring for 3 h (analysis by LCMS indicated consumption of the starting material and formation of diastereomeric products in a <2:1 ratio favoring the isomer with longer retention time). The hydrogen atmosphere was replaced with a N₂ atmosphere (via multiple cycles of vacuum evacuation/back-filling), then the reaction mixture was filtered through a pad of celite eluting with EtOH, and the mixture was concentrated under reduced pressure. The crude material was absorbed onto a plug of silica gel and purified by chromatography through a Redi-Sep pre-packed silica gel column (80 g), eluting with a gradient of 0% to 60% EtOAc in hexane, to provide (after 2 chromatography purifications) the above compound (500 mg, 45% yield, major/faster-eluting isomer) and the undesired epimer (1'S)-methyl 5-((2-((2S,4S)-4-(2-((tert-butoxycarbonyl)(methyl)amino)ethyl) tetrahydro-2H-pyran-2-yl)cyclobutyl)methyl)-6'-chloro-3',4,4',5-tetrahydro-2H,2'H-spiro[benzo[b][1,4]oxazepine-3,1'-naphthalene]-7-carboxylate (353 mg, 31% yield, minor/later-eluting isomer) as off-white films. Characterization data for above the compound: ¹H NMR (300 MHz, CDCl₃) δ 7.70 (d, J=8.6 Hz, 1H), 7.46 (d, J=1.9 Hz, 1H), 7.38 (dd, J=1.9, 8.2 Hz, 1H), 7.16 (dd, J=2.3, 8.6 Hz, 1H), 7.08 (d, J=2.2 Hz, 1H), 6.90 (d, J=8.3 Hz, 1H), 4.11-4.00 (m, 3H), 3.87 (s, 3H), 3.76-3.60 (m, 2H), 3.50 (t, J=11.0 Hz, 1H), 3.36-3.11 (m, 5H), 2.83 (s, 3H), 2.81-2.74 (m, 2H), 2.59-2.43 (m, 1H), 2.04-1.92 (m, 3H), 1.92-1.82 (m, 3H), 1.73-1.41 (m, 18H), 0.79 (q, J=12.4 Hz, 1H). LRMS: m/z (ESI, +ve ion) 667.1 (M+H)⁺.

Step 7. (S)-5-(((1R,2R)-2-((2S,4R)-4-(2-((TERT-BUTOXYCARBONYL)(METHYL)AMINO)ETHYL)TETRAHYDRO-2H-PYRAN-2-YL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALENE]-7-CARBOXYLIC ACID

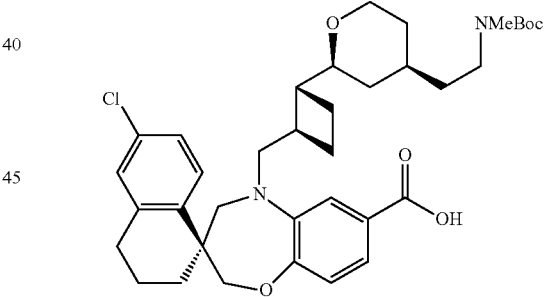

To a solution of (1'S)-methyl 5-((2-((2S,4R)-4-(2-((tert-butoxycarbonyl)(methyl)amino) ethyl)tetrahydro-2H-pyran-2-yl)cyclobutyl)methyl)-6'-chloro-3',4,4',5-tetrahydro-2H,2'H-spiro[benzo[b][1,4]oxazepine-3,1'-naphthalene]-7-carboxylate (from Step 6) (500 mg, 0.749 mmol) in THF (3.75 mL) and methanol (3.75 mL) was added lithium hydroxide (1N) (7.00 mL, 7.00 mmol). The reaction mixture was stirred at 50° C. for 2 d, then acidified by the addition of 1N HCl (pH<4). The reaction mixture was diluted with water and extracted with EtOAc (3×). The organic extract was washed with saturated aqueous NaCl and dried over Na₂SO₄. The solution was filtered and concentrated in vacuo to give the above compound (490 mg, 100% yield) (LRMS: m/z (ESI, +ve ion) 653.2 (M+H)⁺) in sufficient purity to carry forward immediately.

Step 8. 2-((S)-5-((((1R,2R)-2-((2S,4R)-4-(2-((TERT-BUTOXYCARBONYL)(METHYL)AMINO)ETHYL)TETRAHYDRO-2H-PYRAN-2-YL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALEN]-7-YL)-2-OXOACETIC ACID Step 9. METHYL 2-((S)-5-((((1R,2R)-2-((2S,4R)-4-(2-((TERT-BUTOXYCARBONYL)(METHYL)AMINO)ETHYL)TETRAHYDRO-2H-PYRAN-2-YL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALEN]-7-YL)-2-OXOACETATE

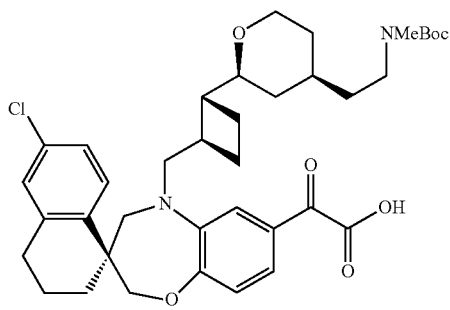

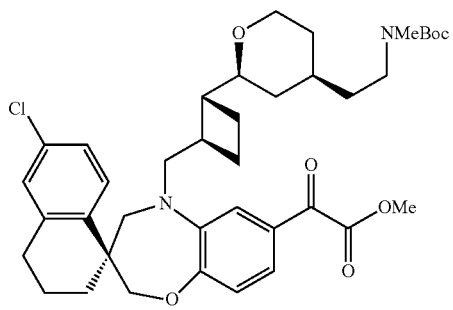

To a solution of the crude (S)-5-((((1R,2R)-2-((2S,4R)-4-(2-((tert-butoxycarbonyl)(methyl)amino)ethyl)tetrahydro-2H-pyran-2-yl)cyclobutyl)methyl)-6'-chloro-3',4,4',5-tetrahydro-2H,2'H-spiro[benzo[b][1,4]oxazepine-3,1'-naphthalene]-7-carboxylic acid (from Step 7) in N,N-dimethylformamide (8.42 mL) was added sequentially 1-(cyanomethyl)tetrahydro-1H-thiophen-1-ium bromide (438 mg, 2.105 mmol), HATU (0-(-7-azabenzotriazol-1-yl)-N,'N,'N,'N'-tetramethyluronium PF$_6$, 480 mg, 1.26 mmol) then N,N-diisopropylethylamine (0.586 mL, 3.37 mmol). The reaction mixture was maintained at room temperature for 3 h (analysis by LCMS indicated formation of the intermediate sulfur ylide; LRMS: m/z (ESI, +ve ion) 762.0 (M+H)$^+$). Then, the reaction mixture was diluted with MgSO$_4$ NH$_4$Cl and extracted with EtOAc (3×). The organic extract was washed with saturated aqueous LiCl, and saturated aqueous NaCl, then dried over Na$_2$SO$_4$. The solution was filtered and concentrated in vacuo to give the thiophene ylide intermediate, which was processed in the next transformation immediately. To a solution of the intermediate sulfur ylide in THF (10 mL) and water (3 mL) was added oxone (1553 mg, 2.53 mmol). The resulting suspension was stirred for 1 hour (analysis by LCMS indicated formation of the intermediate oxalic acid; LRMS: m/z (ESI, +ve ion) 681.0 (M+H)$^+$). The reaction mixture was diluted with saturated aqueous NH$_4$Cl and extracted with EtOAc (3×). The organic extract was washed with saturated aqueous NaCl, then dried over Na$_2$SO$_4$. The solution was filtered and concentrated in vacuo to give the above compound, which was carried forward immediately.

To a solution of 2-((S)-5-((((1R,2R)-2-((2S,4R)-4-(2-((tert-butoxycarbonyl)(methyl) amino)ethyl)tetrahydro-2H-pyran-2-yl)cyclobutyl)methyl)-6'-chloro-3',4,4',5-tetrahydro-2H,2'H-spiro[benzo[b][1,4]oxazepine-3,1'-naphthalen]-7-yl)-2-oxoacetic acid (from Step 8) and triethylamine (117 µL, 0.843 mmol) in CH$_2$Cl$_2$ (8.43 mL) was added methyl chloroformate (65.1 µL, 0.843 mmol). The reaction mixture was maintained at room temperature for 30 min (analysis by LCMS indicated incomplete conversion to the desired product (as well as some decomposition). Additional triethylamine (117 µL, 0.843 mmol) and methyl chloroformate (65.1 µL, 0.843 mmol) were added to the reaction mixture. After 30 min, the reaction mixture was quenched by the addition of saturated aqueous NH$_4$Cl, then extracted with EtOAc (2×). The organic extract was washed with saturated aqueous NaCl and dried over Na$_2$SO$_4$. The solution was filtered and concentrated in vacuo to give the crude material. The crude material was absorbed onto a plug of silica gel and purified by chromatography through a Redi-Sep pre-packed silica gel column (40 g), eluting with a gradient of 0% to 40% EtOAc in hexane, to provide methyl oxoacetate intermediate (530 mg, LRMS: m/z (ESI, +ve ion) 695.2 (M+H)$^+$) as an off-white foam. Note, the decomposition product co-eluted with the desired product, thus the desired product was carried forward not in pure form.

187

Step 10. (R)-4-TERT-BUTYL 1-METHYL 2-((S)-5-(((1R,2R)-2-((2S,4R)-4-(2-((TERT-BUTOXYCARBONYL)(METHYL)AMINO)ETHYL)TETRAHYDRO-2H-PYRAN-2-YL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALEN]-7-YL)-2-HYDROXYSUCCINATE AND (S)-4-TERT-BUTYL 1-METHYL 2-((S)-5-(((1R,2R)-2-((2S,4R)-4-(2-((TERT-BUTOXYCARBONYL)(METHYL)AMINO) ETHYL)TETRAHYDRO-2H-PYRAN-2-YL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALEN]-7-YL)-2-HYDROXYSUCCINATE

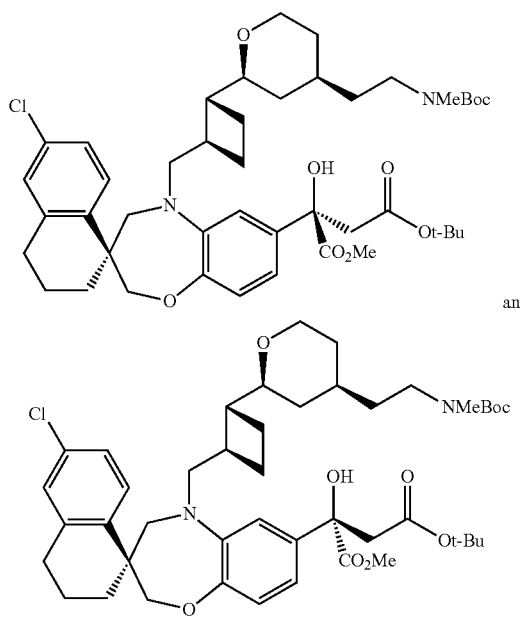

and

To a solution of methyl 2-((S)-5-(((1R,2R)-2-((2S,4R)-4-(2-((tert-butoxycarbonyl)(methyl)amino)ethyl)tetrahydro-2H-pyran-2-yl)cyclobutyl)methyl)-6'-chloro-3',4,4',5-tetrahydro-2H,2'H-spiro[benzo[b][1,4]oxazepine-3,1'-naphthalen]-7-yl)-2-oxoacetate (from Step 9) (0.530 g, 0.762 mmol) in THF (7.62 mL) was added 2-tert-butoxy-2-oxoethylzinc chloride, 0.5 min diethyl ether solution (3.81 mL, 1.91 mmol). The reaction was maintained at room temperature for 20 minutes. The reaction mixture was diluted with saturated aqueous NH$_4$Cl and extracted with EtOAc (3×). The organic extract was washed with saturated aqueous NaCl and dried over Na$_2$SO$_4$. The solution was filtered and concentrated in vacuo to give the crude material. The crude material was purified by chromatography through a Redi-Sep pre-packed silica gel column (24 g), eluting with a gradient of 0% to 90% EtOAc in hexane, to provide the above compounds (325 mg, 0.401 mmol, 53% overall yield, a mixture of epimers) as an off-white film: $^1$H NMR (300 MHz, CDCl$_3$) δ 7.70 (d, J=4.1 Hz, 1H), 7.68 (d, J=4.1 Hz, 1H), 7.16 (d, J=2.0 Hz, 1H), 7.13 (d, J=2.2 Hz, 1H), 7.07 (m, 1H), 6.96 (m, 1H), 6.87-6.78 (m, 2H), 4.35 (m, 1H), 4.01 (m, 3H), 3.79 (m, 3H), 3.78-3.60 (m, 3H), 3.55-3.34 (m, 2H), 3.33-3.04 (m, 6H), 2.88-2.73 (m, 7H), 2.63-2.44 (m, 1H), 2.03-1.78 (m, 5H), 1.69-1.52 (m, 5H), 1.49-1.38 (m, 22H), 0.85-0.67 (m, 1H). LRMS: m/z (ESI, +ve ion) 811.1 (M+H)$^+$.

Step 11. METHYL (3R,6R,7S,11R,17R,24S)-6'-CHLORO-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXYLATE OR METHYL (3R,6R,7S,11R,17S,24S)-6'-CHLORO-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXYLATE

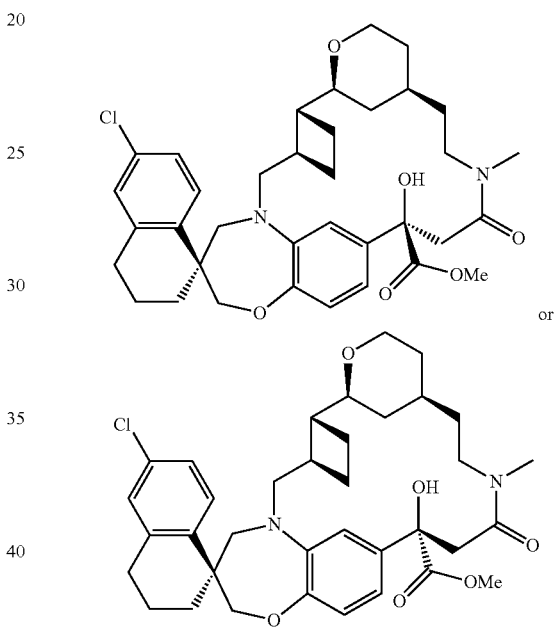

or

A solution of (R)-4-tert-butyl 1-methyl 2-((S)-5-(((1R,2R)-2-((2S,4R)-4-(2-((tert-butoxycarbonyl)(methyl)amino)ethyl)tetrahydro-2H-pyran-2-yl)cyclobutyl)methyl)-6'-chloro-3',4,4',5-tetrahydro-2H,2'H-spiro[benzo[b][1,4]oxazepine-3,1'-naphthalen]-7-yl)-2-hydroxysuccinate and (S)-4-tert-butyl 1-methyl 2-((S)-5-(((1R,2R)-2-((2S,4R)-4-(2-((tert-butoxycarbonyl)(methyl)amino)ethyl)tetrahydro-2H-pyran-2-yl)cyclobutyl)methyl)-6'-chloro-3',4,4',5-tetrahydro-2H,2'H-spiro[benzo[b][1,4]oxazepine-3,1'-naphthalen]-7-yl)-2-hydroxysuccinate (from Step 10, mixture of epimers) (325 mg, 0.401 mmol) and trifluoroacetic acid (1.87 mL, 25.2 mmol) in DCM (1.60 mL) was maintained at rt. Analysis by LCMS indicated complete consumption of the starting material after 2 h. The reaction was diluted with toluene and concentrated in vacuo. This sequence was repeated two times to afford the desired amino acid intermediate (310 mg, 0.403 mmol, 100% yield; TFA salt) in sufficient purity to carry forward (LRMS: m/z (ESI, +ve ion) 655.1 (M+H)$^+$). To a solution of the amino acid intermediate (310 mg, 0.403 mmol) and HATU (0-(-7-azabenzotriazol-1-yl)-n,'n,'n,'n'-tetramethyluronium PF$_6$) (306 mg, 0.806 mmol) in N, N-dimethylformamide (40.3 mL) was added N,N-diisopropylethylamine (0.421 mL, 2.42 mmol). The reaction mixture was maintained at room temperature. Analysis by LCMS indicated complete consumption of the starting material after 1.5 h. The reaction mixture was diluted with saturated aqueous NH$_4$Cl and extracted with EtOAc (3×). The organic extract was washed with saturated aqueous LiCl (3×), brine (1×) and dried over Na$_2$SO$_4$. The solution was filtered and concentrated in vacuo to give the crude material. The crude material was absorbed onto a plug of silica gel and purified by chromatography through a Redi-Sep pre-packed silica gel column (12 g), eluting with a gradient of 0% to 70% acetone/hexanes, to provide above compounds, the faster-eluting isomer (91 mg, 0.143 mmol, 35% yield) and later-eluting isomer (110 mg, 0.173 mmol, 43% yield) as off-white solids. Characterization data for the faster-eluting isomer: $^1$H NMR (300 MHz, CDCl$_3$) δ 7.76 (d, J=8.5 Hz, 1H), 7.17 (td, J=2.6, 8.3 Hz, 2H), 7.07 (d, J=2.0 Hz, 1H), 6.92 (d, J=8.0 Hz, 1H), 6.45 (d, J=2.0 Hz, 1H), 5.87 (s, 1H), 4.09-3.97 (m, 3H), 3.82-3.70 (m, 5H), 3.70-3.57 (m, 3H), 3.48 (d, J=16.2 Hz, 1H), 3.22 (d, J=14.2 Hz, 1H), 3.07-2.95 (m, 2H), 2.93 (s, 3H), 2.79-2.71 (m, 2H), 2.64 (d, J=17.1 Hz, 1H), 2.50-2.36 (m, 2H), 2.12-1.77 (m, 9H), 1.68-1.60 (m, 1H), 1.52-1.23 (m, 4H), 1.12 (q, J=12.9 Hz, 1H). LRMS: m/z (ESI, +ve ion) 637.1 (M+H)$^+$. Characterization data for the later-eluting isomer: $^1$H NMR (300 MHz, CDCl$_3$) δ 7.76 (d, J=8.5 Hz, 1H), 7.17 (dd, J=2.3, 8.6 Hz, 1H), 7.08 (d, J=2.2 Hz, 1H), 6.83 (d, J=8.2 Hz, 1H), 6.78 (d, J=2.0 Hz, 1H), 6.64 (dd, J=2.0, 8.3 Hz, 1H), 4.48-4.41 (m, 1H), 4.09-3.96 (m, 3H), 3.96-3.89 (m, 3H), 3.89-3.65 (m, 4H), 3.58-3.43 (m, 2H), 3.33 (d, J=15.8 Hz, 1H), 3.25-3.16 (m, 1H), 3.13-3.01 (m, 2H), 2.92 (s, 3H), 2.83-2.71 (m, 2H), 2.52-2.34 (m, 2H), 2.03-1.62 (m, 8H), 1.46-1.30 (m, 4H), 1.10 (q, J=11.6 Hz, 1H). LRMS: m/z (ESI, +ve ion) 637.1 (M+H)$^+$.

Step 12. (3R,6R,7S,11R,17R,24S)-6'-CHLORO-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$] OCTACOSA-18,20,26-TRIENE-24,1'-NAPHTHALENE]-17-CARBOXYLIC ACID OR (3R,6R,7S,11R,17S,24S)-6'-CHLORO-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXYLIC ACID (the Relative Configuration of the Tertiary Alcohol Stereocenter of the Title Compound has not Been Definitively Established)

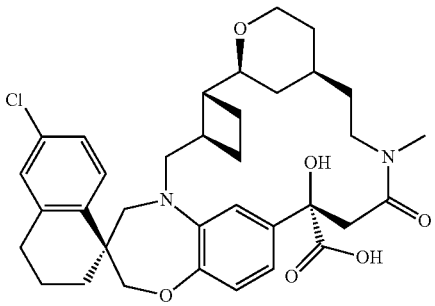

The title compound (20 mg, 97% yield) was prepared from the faster-eluting isomer from Step 11 in a similar fashion as described for the synthesis of Example 4: $^1$H NMR (400 MHz, (CD$_3$)$_2$SO) δ 7.67 (d, J=8.4 Hz, 1H), 7.25 (dd, J=2.2, 8.5 Hz, 1H), 7.16 (d, J=2.2 Hz, 1H), 6.98 (dd, J=1.9, 8.3 Hz, 1H), 6.83 (d, J=8.4 Hz, 1H), 6.53 (d, J=1.8 Hz, 1H), 3.95 (q, J=7.6 Hz, 2H), 3.89-3.75 (m, 2H), 3.57 (d, J=12.5 Hz, 1H), 3.50-3.25 (m, 5H), 3.17 (d, J=14.1 Hz, 1H), 3.05 (dd, J=9.9, 15.4 Hz, 1H), 2.94 (d, J=15.1 Hz, 1H), 2.81 (s, 3H), 2.79-2.62 (m, 3H), 2.46-2.45 (m, 1H), 2.46-2.36 (m, 1H), 2.35-2.23 (m, 1H), 2.05 (d, J=12.5 Hz, 1H), 1.99-1.91 (m, 1H), 1.91-1.58 (m, 8H), 1.46-1.31 (m, 2H), 1.25-1.13 (m, 2H), 0.97 (q, J=11.5 Hz, 1H). LRMS: m/z (ESI, +ve ion) 623.2 (M+H)$^+$.

Example 70

(3R,6R,7S,11R,17R,24S)-6'-CHLORO-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$] OCTACOSA-18,20,26-TRIENE-24,1'-NAPHTHALENE]-17-CARBOXYLIC ACID OR (3R,6R,7S,11R,17S,24S)-6'-CHLORO-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$] OCTACOSA-18,20,26-TRIENE-24,1'-NAPHTHALENE]-17-CARBOXYLIC ACID (the Relative Configuration of the Tertiary Alcohol Stereocenter of the Title Compound has not been Definitively Established, and is Epimeric to Example 1)

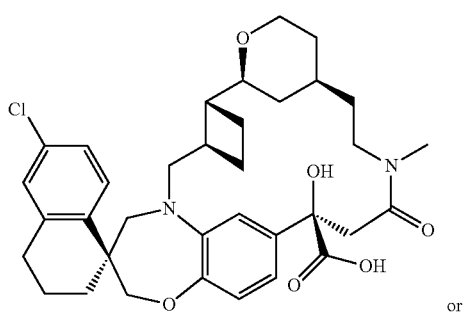

or

191

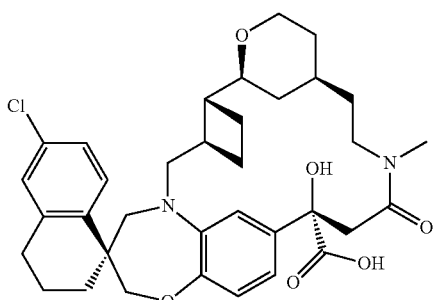

The title compound (20 mg, 90% yield) was prepared from the later-eluting isomer from Example 69, Step 11 in a similar fashion as described for the synthesis of Example 4. $^1$H NMR (400 MHz, (CD$_3$)$_2$SO) δ 7.67 (d, J=8.4 Hz, 1H), 7.25 (dd, J=2.3, 8.4 Hz, 1H), 7.16 (d, J=2.2 Hz, 1H), 6.77 (d, J=8.4 Hz, 1H), 6.73 (d, J=2.0 Hz, 1H), 6.67 (dd, J=2.0, 8.2 Hz, 1H), 4.06-3.94 (m, 2H), 3.90-3.82 (m, 2H), 3.76-3.65 (m, 2H), 3.58 (d, J=14.1 Hz, 1H), 3.40-3.27 (m, 2H), 3.22-3.12 (m, 2H), 3.12-3.00 (m, 2H), 2.83-2.74 (m, 4H), 2.74-2.61 (m, 1H), 2.46-2.37 (m, 1H), 2.36-2.23 (m, 1H), 2.01-1.57 (m, 9H), 1.56-1.44 (m, 1H), 1.43-1.32 (m, 2H), 1.31-1.13 (m, 2H), 0.99 (q, J=11.5 Hz, 1H). LRMS: m/z (ESI, +ve ion) 623.2 (M+H)$^+$.

Example 71

(3R,6R,7S,11R,17R,24S)-6'-CHLORO-N-(DIMETHYLSULFAMOYL)-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXAMIDE OR (3R,6R,7S,11R,17S,24S)-6'-CHLORO-N-(DIMETHYLSULFAMOYL)-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXAMIDE (the Relative Configuration of the Tertiary Alcohol Stereocenter of the Title Compound has not been Definitively Established)

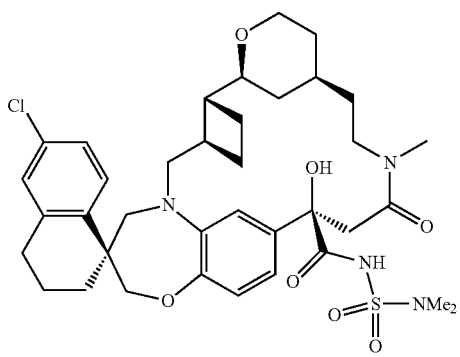

or

192

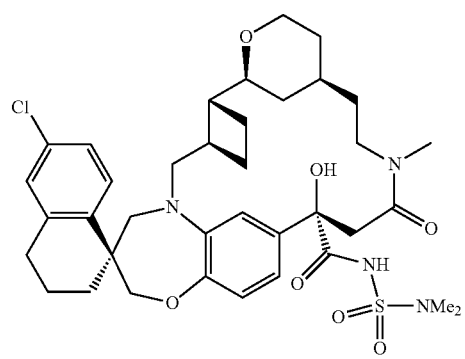

The title compound (9.0 mg, 31% yield) was prepared from Example 69 in a similar fashion as described for the synthesis of Example 5. $^1$H NMR (300 MHz, CD$_2$Cl$_2$) δ 8.93 (s, 1H), 7.75 (d, J=8.6 Hz, 1H), 7.16 (dd, J=2.3, 8.5 Hz, 1H), 7.12-7.00 (m, 2H), 6.99 (s, 1H), 6.88 (d, J=8.2 Hz, 1H), 6.47 (d, J=2.0 Hz, 1H), 4.02 (s, 2H), 3.95 (dd, J=3.8, 11.7 Hz, 1H), 3.76-3.48 (m, 6H), 3.23 (d, J=14.3 Hz, 1H), 3.10-2.95 (m, 2H), 2.90 (s, 3H), 2.85 (s, 6H), 2.82-2.69 (m, 2H), 2.51 (d, J=16.4 Hz, 1H), 2.47-2.31 (m, 2H), 2.07-1.95 (m, 3H), 1.95-1.61 (m, 7H), 1.50-1.28 (m, 4H), 1.06 (q, J=11.8 Hz, 1H). LRMS: m/z (ESI, +ve ion) 729.4 (M+H)$^+$.

Example 72

(3R,6R,7S,11R,17R,24S)-6'-CHLORO-17-HYDROXY-14-METHYL-N-(METHYLSULFONYL)-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXAMIDE OR (3R,6R,7S,11R,17S,24S)-6'-CHLORO-17-HYDROXY-14-METHYL-N-(METHYLSULFONYL)-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXAMIDE (the Relative Configuration of the Tertiary Alcohol Stereocenter of the Title Compound has not been Definitively Established)

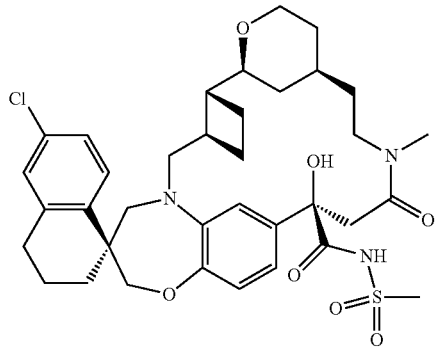

or

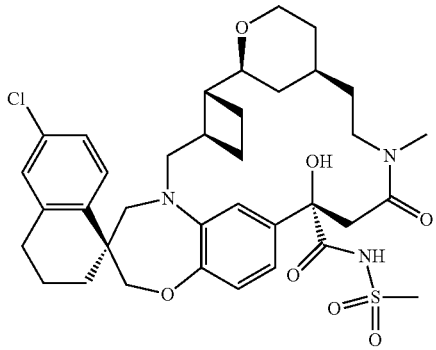

The title compound (8 mg, 57% yield) was prepared from Example 69 in a similar fashion as described for the synthesis of Example 5. $^1$H NMR (500 MHz, CD$_2$Cl$_2$) δ 9.01 (s, J=5.7 Hz, 1H), 7.75 (d, J=8.6 Hz, 1H), 7.16 (dd, J=2.3, 8.5 Hz, 1H), 7.07 (d, J=2.0 Hz, 1H), 7.03 (dd, J=2.1, 8.3 Hz, 1H), 6.88 (d, J=8.3 Hz, 1H), 6.77 (s, 1H), 6.41 (d, J=2.0 Hz, 1H), 4.06-3.99 (m, 2H), 3.96 (dd, J=3.6, 11.3 Hz, 1H), 3.79-3.54 (m, 5H), 3.51 (d, J=16.6 Hz, 1H), 3.23 (d, J=14.3 Hz, 1H), 3.18 (s, 3H), 3.07-2.95 (m, 2H), 2.90 (s, 3H), 2.81-2.69 (m, 2H), 2.59 (d, J=16.6 Hz, 1H), 2.45-2.34 (m, 2H), 2.06-1.95 (m, 3H), 1.94-1.72 (m, 6H), 1.71-1.61 (m, 1H), 1.47 (d, J=12.8 Hz, 1H), 1.40-1.23 (m, 3H), 1.09 (d, J=12.6 Hz, 1H). LRMS. m/z (ESI, +ve ion) 700.0 (M+H)$^+$.

Example 73

(3R,6R,7S,11R,17R,24S)-6'-CHLORO-N-(CYCLOPROPYLSULFONYL)-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXAMIDE OR (3R,6R,7S,11R,17S,24S)-6'-CHLORO-N-(CYCLOPROPYLSULFONYL)-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXAMIDE (the Relative Configuration of the Tertiary Alcohol Stereocenter of the Title Compound has not been Definitively Established)

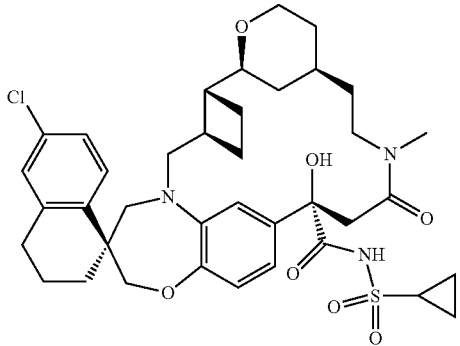

The title compound (20 mg, 64% yield) was prepared from Example 69 in a similar fashion as described for the synthesis of Example 5. $^1$H NMR (500 MHz, CD$_2$Cl$_2$) δ=8.93 (br. s., 1H), 7.75 (d, J=8.6 Hz, 1H), 7.16 (dd, J=2.3, 8.5 Hz, 1H), 7.08-7.07 (m, 1H), 7.04 (d, J=8.2 Hz, 1H), 6.94 (s, 1H), 6.89 (d, J=8.2 Hz, 1H), 6.43 (d, J=2.1 Hz, 1H), 4.01 (dd, J=1.6, 12.2 Hz, 2H), 3.96 (dd, J=3.5, 11.3 Hz, 1H), 3.73-3.64 (m, 3H), 3.60 (td, J=3.8, 13.2 Hz, 1H), 3.55 (d, J=15.2 Hz, 1H), 3.52 (d, J=18.0 Hz, 1H), 3.22 (d, J=14.3 Hz, 1H), 3.06-2.94 (m, 2H), 2.89 (s, 3H), 2.82-2.71 (m, 3H), 2.55 (d, J=16.9 Hz, 1H), 2.47-2.32 (m, 2H), 2.06-1.95 (m, 3H), 1.94-1.71 (m, 6H), 1.70-1.60 (m, 1H), 1.50-1.43 (m, 1H), 1.39-1.23 (m, 4H), 1.21-1.00 (m, 4H), 0.94-0.85 (m, 1H). LRMS: m/z (ESI, +ve ion) 726.1 (M+H)$^+$.

Example 74

(3R,6R,7S,11S,17R,24S)-6'-CHLORO-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXYLIC ACID (the Relative and Absolute Configuration of the Methyl Ester Intermediate from Step 2 was Confirmed by x-Ray)

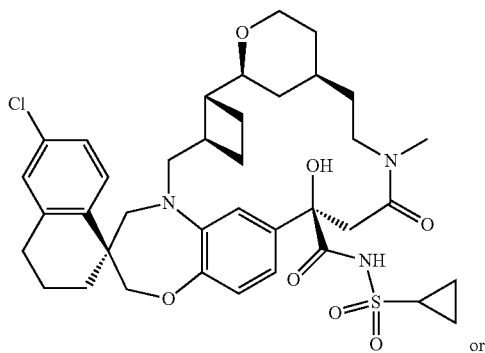
or

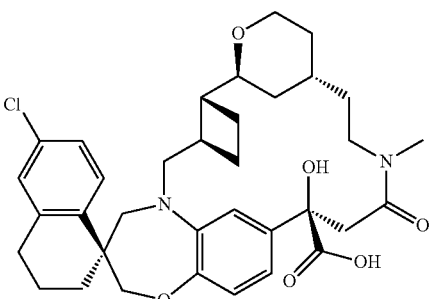

Step 1. (1'S)-METHYL 5-((2-((2S,4S)-4-(2-((TERT-BUTOXYCARBONYL)(METHYL) AMINO) ETHYL)TETRAHYDRO-2H-PYRAN-2-YL)CYCLOBUTYL)METHYL)-6'-CHLORO-3',4,4',5-TETRAHYDRO-2H,2'H-SPIRO[BENZO[B][1,4] OXAZEPINE-3,1'-NAPHTHALENE]-7-CARBOXYLATE

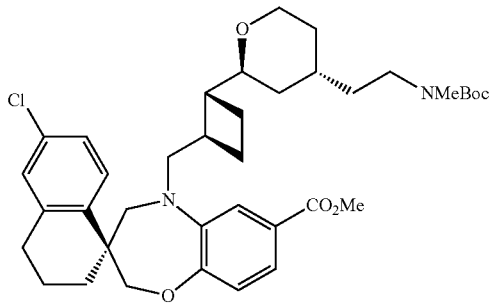

To a solution of (S)-methyl 5-(((1R,2R)-2-((S,Z)-4-(2-((tert-butoxycarbonyl)(methyl)amino) ethylidene)tetrahydro-2H-pyran-2-yl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 5-(((1R,2R)-2-((S,E)-4-(2-((tert-butoxycarbonyl)(methyl)amino) ethylidene)tetrahydro-2H-pyran-2-yl)cyclobutyl)methyl)-6'-chloro-3',4,4',5-tetrahydro-2H,2'H-spiro[benzo[b][1,4] oxazepine-3,1'-naphthalene]-7-carboxylate (from Example 69, Step 5; a mixture of olefin isomers) (0.720 g, 1.08 mmol) in DCM (21.6 mL) in a thick-walled, high-pressure glass vessel fitted with a rubber-lined teflon screw top under an under a $N_2$ atmosphere was added ((4R,5R)-(+)-O-[1-Benzyl-1-(5-methyl-2-phenyl-4,5-dihydrooxazol-4-yl)-2-phenylethyl](dicyclohexylphosphinite)(1,5-COD)iridium(I) tetrakis(3,5-bis(trifluoromethyl)phenylborate ((R,R)-[COD]Ir [cy2PThrePHOX], 260 mg, 0.150 mmol) and ((4S,5S)-(+)-O-[1-Benzyl-1-(5-methyl-2-phenyl-4,5-dihydrooxazol-4-yl)-2-phenylethyl] (dicyclohexylphosphinite)(1,5-COD) iridium(I) tetrakis(3,5-bis(trifluoromethyl)phenylborate ((S,S)-[COD]Ir[cy2PThrePHOX], 260 mg, 0.150 mmol). The reaction mixture was exposed to an atmosphere of $H_2$ (~20 psi, by connection of the pressure vessel to a hydrogen gas tank both fitted with pressure regulators), with stirring for 4 h (analysis by LCMS indicated consumption of the starting material and formation of diastereomeric products in ~6:1 ratio favoring the isomer with shorter retention time). The hydrogen atmosphere was replaced with a $N_2$ atmosphere (via multiple cycles of vacuum evacuation/back-filling). In a separate reaction, 230 mg of the identical starting material was processed in an analogous fashion. The crude mixtures from both reactions were combined and absorbed onto a plug of silica gel and purified by chromatography through a Redi-Sep pre-packed silica gel column (80 g), eluting with a gradient of 0% to 60% EtOAc in hexane, to provide the undesired epimer (142 mg, 15% yield, minor/faster-eluting isomer/major product from Example 1, Step 6) and the above compound (728 mg, 76% yield, major/later-eluting isomer) as off-white films. Characterization data for the above: $^1$H NMR (300 MHz, CDCl$_3$) δ 7.69 (d, J=8.5 Hz, 1H), 7.48 (d, J=1.9 Hz, 1H), 7.38 (d, J=8.1 Hz, 1H), 7.17 (d, J=8.6 Hz, 1H), 7.09 (d, J=2.2 Hz, 1H), 6.90 (d, J=8.2 Hz, 1H), 4.11-4.03 (m, 2H), 3.88 (s, 3H), 3.83-3.59 (m, 4H), 3.49 (d, J=6.6 Hz, 1H), 3.35-3.16 (m, 4H), 2.85 (s, 3H), 2.82-2.71 (m, 2H), 2.61-2.44 (m, 1H), 2.10-1.98 (m, 2H), 1.93-1.57 (m, 9H), 1.56-1.44 (m, 11H), 1.43-1.34 (m, 3H). LRMS: m/z (ESI, +ve ion) 667.1 (M+H)$^+$.

Step 2. METHYL (3R,6R,7S,11S,17R,24S)-6'-CHLORO-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$] OCTACOSA-18,20,26-TRIENE-24,1'-NAPHTHALENE]-17-CARBOXYLATE (Relative and Absolute Configuration Confirmed by x-Ray)

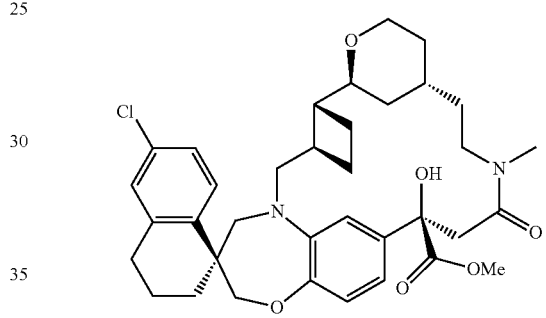

The above compound (250 mg, 33% overall yield) was prepared as the faster-eluting epimeric product from (1'S)-methyl 5-((2-((2S,4S)-4-(2-((tert-butoxycarbonyl)(methyl) amino)ethyl)tetrahydro-2H-pyran-2-yl)cyclobutyl)methyl)-6'-chloro-3',4,4',5-tetrahydro-2H,2'H-spiro[benzo[b][1,4] oxazepine-3,1'-naphthalene]-7-carboxylate (from Step 1) in a similar fashion as described for the synthesis of the intermediates from Example 69, Step 11. $^1$H NMR (300 MHz, CDCl$_3$) δ=7.76 (d, J=8.5 Hz, 1H), 7.23-7.14 (m, 2H), 7.07 (d, J=2.2 Hz, 1H), 6.93 (d, J=8.3 Hz, 1H), 6.64 (s, 1H), 6.44 (d, J=2.0 Hz, 1H), 4.08-3.96 (m, 2H), 3.87-3.63 (m, 9H), 3.50 (d, J=15.9 Hz, 1H), 3.30 (d, J=14.2 Hz, 1H), 3.14-2.98 (m, 4H), 2.97-2.83 (m, J=14.8 Hz, 1H), 2.80-2.72 (m, 2H), 2.59 (d, J=15.8 Hz, 1H), 2.43-2.22 (m, 3H), 2.08-1.82 (m, 8H), 1.81-1.67 (m, 3H), 1.57-1.50 (m, 1H), 1.46-1.31 (m, 2H). LRMS: m/z (ESI, +ve ion) 637.4 (M+H)$^+$. The resulting solid was slowly recrystallized from hot EtOAc, which gave a crystalline solid (>10:1 dr; NMR). The absolute and relative configuration of the above compound was confirmed by single-crystal x-ray diffraction (as described below).

Step 3. (3R,6R,7S,11S,17R,24S)-6'-CHLORO-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXYLIC ACID (the Relative and Absolute Configuration of the Methyl Ester Precursor from Step 2 was Confirmed by x-Ray)

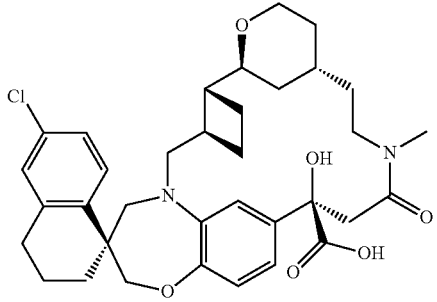 [SMILES: CN1CC[C@H]2CCO[C@@H](C2)[C@@H]2CC[C@H]2CN2C[C@@]3(CCCc4cc(Cl)ccc43)COc3ccc(cc32)[C@@](O)(C(=O)O)CC1=O]

The title compound (8.7 mg, 68% yield) was prepared from the methyl ester intermediate from Step 2 in a similar fashion as described for the synthesis of the title compound of Example 4: $^1$H NMR (400 MHz, (CD$_3$)$_2$SO) δ 7.67 (d, J=8.6 Hz, 1H), 7.27 (d, J=14.1 Hz, 1H), 7.16 (d, J=2.3 Hz, 1H), 6.98 (dd, J=2.0, 8.4 Hz, 1H), 6.83 (d, J=8.4 Hz, 1H), 6.52 (d, J=1.8 Hz, 1H), 3.99 (d, J=14.1 Hz, 1H), 3.90 (d, J=12.3 Hz, 1H), 3.83 (dd, J=10.9, 13.8 Hz, 1H), 3.70-3.30 (m, 5H), 3.39-3.24 (m, 2H), 3.10 (dd, J=10.6, 15.5 Hz, 1H), 2.94-2.64 (m, 7H), 2.38 (d, J=9.0 Hz, 1H), 2.30-2.19 (m, 1H), 2.10-1.61 (m, 12H), 1.58-1.48 (m, 1H), 1.41-1.29 (m, 2H). LRMS: m/z (ESI, +ve ion) 623.2 (M+H)$^+$.

Example 75

(3R,6R,7S,11S,17S,24S)-6'-CHLORO-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXYLIC ACID (the Relative Configuration of the Tertiary Alcohol Stereocenter of the Title Compound is Epimeric to the Title Compound of Example 74)

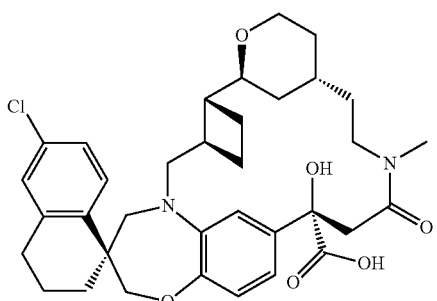

Step 1. METHYL (3R,6R,7S,11S,17S,24S)-6'-CHLORO-17-HYDROXY-14-METHYL-5-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXYLATE

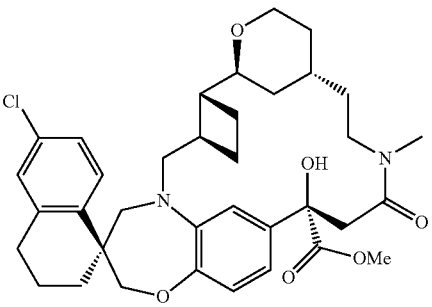 [SMILES: COC(=O)[C@]1(O)CC(=O)N(C)CC[C@H]2CCO[C@@H](C2)[C@@H]2CC[C@H]2CN2C[C@@]3(CCCc4cc(Cl)ccc43)COc3ccc1cc32]

The above compound (205 mg, 27% overall yield) was prepared as the later-eluting epimeric product from (1'S)-methyl 5-((2-((2S,4S)-4-(2-((tert-butoxycarbonyl)(methyl)amino)ethyl)tetrahydro-2H-pyran-2-yl)cyclobutyl)methyl)-6'-chloro-3',4,4',5-tetrahydro-2H,2'H-spiro[benzo[b][1,4]oxazepine-3,1'-naphthalene]-7-carboxylate (from Example 74, Step 1) in a similar fashion as described for the synthesis of the intermediates from Example 69, Step 11. LRMS: m/z (ESI, +ve ion) 637.4 (M+H)$^+$.

Step 2. (3R,6R,7S,11S,17S,24S)-6'-CHLORO-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXYLIC ACID

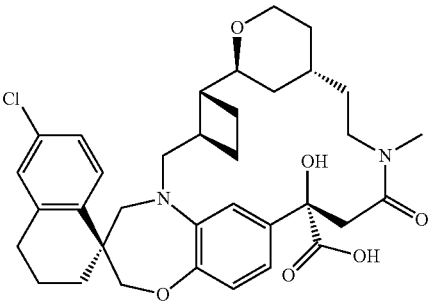 [SMILES: CN1CC[C@H]2CCO[C@@H](C2)[C@@H]2CC[C@H]2CN2C[C@@]3(CCCc4cc(Cl)ccc43)COc3ccc(cc32)[C@](O)(C(=O)O)CC1=O]

The title compound (8.0 mg, 55% overall yield) was prepared from the methyl ester intermediate from Step 1 in a similar fashion as described for the synthesis of Example 4: $^1$H NMR (400 MHz, (CD$_3$)$_2$SO) δ 7.72-7.61 (m, 1H), 7.29-7.23 (m, 1H), 7.16 (d, J=2.2 Hz, 1H), 6.82-6.75 (m, 1H), 6.72-6.64 (m, 2H), 4.00 (d, J=12.3 Hz, 1H), 3.88-3.78 (m, 2H), 3.71-3.57 (m, 2H), 3.57-3.46 (m, 1H), 3.40-3.24 (m, 4H), 3.13-3.02 (m, 1H), 2.99-2.63 (m, 7H), 2.46-2.35 (m, 1H), 2.44-2.35 (m, 1H), 2.29-2.15 (m, 1H), 2.09-1.46 (m, 13H), 1.41-1.29 (m, 2H). LRMS: m/z (ESI, +ve ion) 623.2 (M+H)$^+$.

Example 76

(3R,6R,7S,11S,17R,24S)-6'-CHLORO-N-(DIMETHYLSULFAMOYL)-17-HYDROXY-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXAMIDE

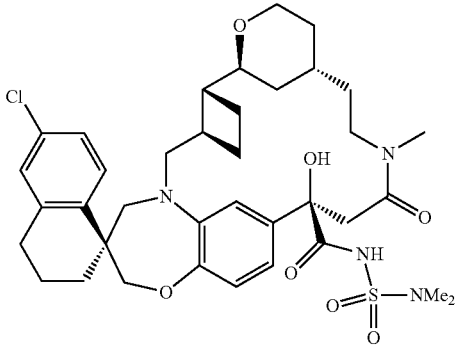 [SMILES: CN1CC[C@H]2CCO[C@@H](C2)[C@@H]2CC[C@H]2CN2C[C@@]3(CCCc4cc(Cl)ccc43)COc3ccc(cc32)[C@@](O)(C(=O)NS(=O)(=O)N(C)C)CC1=O]

The title compound (26 mg, 44% yield) was prepared from (3R,6R,7S,11S,17R,24S)-6'-chloro-17-hydroxy-14-methyl-15-oxo-3',4'-dihydro-2'H-spiro[8,22-dioxa-1,14-diazapentacyclo[16.7.2.17,11.03,6.021,26]octacosa-18,20,26-triene-24,1'-naphthalene]-17-carboxylic acid (Example 74) in a similar fashion as described for the synthesis of Example 5: $^1$H NMR (300 MHz, CD$_2$Cl$_2$) δ 9.00 (s, 1H), 7.75 (d, J=8.6 Hz, 1H), 7.69 (s, 1H), 7.16 (dd, J=2.3, 8.5 Hz, 1H), 7.11-7.04 (m, 2H), 6.88 (d, J=8.2 Hz, 1H), 6.52 (d, J=1.9 Hz, 1H), 4.08-3.92 (m, 2H), 3.80-3.49 (m, 7H), 3.31 (d, J=14.3 Hz, 1H), 3.14-3.03 (m, 1H), 2.98 (s, 3H), 2.95-2.82 (m, 1H), 2.82-2.72 (m, 8H), 2.47 (d, J=15.9 Hz, 1H), 2.41-2.25 (m, 3H), 2.10-1.80 (m, 8H), 1.77-1.66 (m, 3H), 1.47-1.30 (m, 3H). LRMS: m/z (ESI, +ve ion) 729.0 (M+H)$^+$.

Example 77

(3R,6R,7S,11S,17R,24S)-6'-CHLORO-17-HYDROXY-14-METHYL-N-(METHYLSULFAMOYL)-15-OXO-3',4'-DIHYDRO-2'H-SPIRO[8,22-DIOXA-1,14-DIAZAPENTACYCLO [16.7.2.1$^{7,11}$.0$^{3,6}$.0$^{21,26}$]OCTACOSA-18,20,26-TRIENE-24,1'-NAPHTHALENE]-17-CARBOXAMIDE

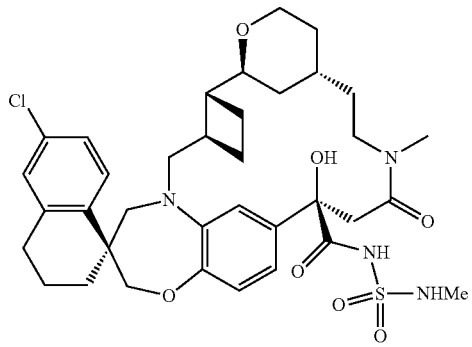 [SMILES: CNS(=O)(=O)NC(=O)[C@@]1(O)CC(=O)N(C)CC[C@H]2CCO[C@@H](C2)[C@@H]2CC[C@H]2CN2C[C@@]3(CCCc4cc(Cl)ccc43)COc3ccc1cc32]

The title compound (29 mg, 65% yield) was prepared from 3R,6R,7S,11S,17R,24S)-6'-chloro-17-hydroxy-14-methyl-15-oxo-3',4'-dihydro-2'H-spiro[8,22-dioxa-1,14-diazapentacyclo[16.7.2.17,11.03,6.021,26]octacosa-18,20,26-triene-24,1'-naphthalene]-17-carboxylic acid (Example 74) in a similar fashion as described for the synthesis of Example 5: $^1$H NMR (300 MHz, CD$_2$Cl$_2$) δ 9.07 (s, 1H), 7.74 (d, J=8.5 Hz, 1H), 7.58 (s, 1H), 7.16 (dd, J=2.3, 8.5 Hz, 1H), 7.07 (dt, J=2.2, 4.1 Hz, 2H), 6.89 (d, J=8.3 Hz, 1H), 6.47 (d, J=2.0 Hz, 1H), 5.08-5.00 (m, 1H), 4.01 (q, J=12.9 Hz, 2H), 3.80-3.59 (m, 6H), 3.54 (d, J=16.1 Hz, 1H), 3.31 (d, J=14.3 Hz, 1H), 3.08 (dd, J=9.8, 15.3 Hz, 1H), 2.97 (s, 3H), 2.95-2.81 (m, 1H), 2.81-2.71 (m, 2H), 2.58-2.46 (m, 4H), 2.33 (d, J=4.7 Hz, 2H), 2.24 (dd, J=3.4, 12.4 Hz, 1H), 2.08-1.98 (m, 2H), 1.98-1.80 (m, 6H), 1.80-1.67 (m, 3H), 1.59-1.54 (m, 1H), 1.43-1.31 (m, 2H); LRMS: m/z (ESI, +ve ion) 715.0 (M+H)$^+$.

Example 78

(3R,6R,7S,11S,17R,24S)-6'-CHLORO-17-HYDROXY-14-METHYL-N-(METHYLSULFONYL)-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXAMIDE

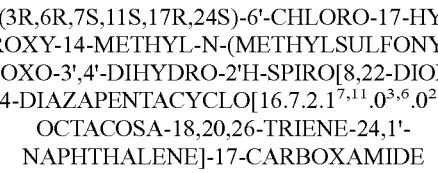
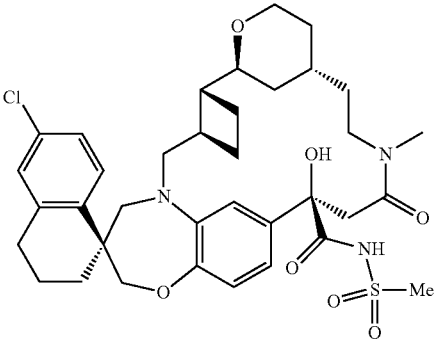 [SMILES: CN1CC[C@H]2CCO[C@@H](C2)[C@@H]2CC[C@H]2CN2C[C@@]3(CCCc4cc(Cl)ccc43)COc3ccc(cc32)[C@@](O)(C(=O)NS(C)(=O)=O)CC1=O]

The title compound (54 mg, 80% yield) was prepared from 3R,6R,7S,11S,17R,24S)-6'-chloro-17-hydroxy-14-methyl-15-oxo-3',4'-dihydro-2'H-spiro[8,22-dioxa-1,14-diazapentacyclo[16.7.2.17,11.03,6.021,26]octacosa-18,20,26-triene-24,1'-naphthalene]-17-carboxylic acid (Example 74) in a similar fashion as described for the synthesis of Example 5: ¹H NMR (400 MHz, CD$_2$Cl$_2$) δ 9.05 (s, 1H), 7.75 (d, J=8.4 Hz, 1H), 7.57 (s, 1H), 7.16 (dd, J=2.2, 8.5 Hz, 1H), 7.10-7.03 (m, 2H), 6.89 (d, J=8.2 Hz, 1H), 6.47 (d, J=2.0 Hz, 1H), 4.02 (dd, J=12.1, 17.8 Hz, 2H), 3.80-3.62 (m, 6H), 3.54 (d, J=16.2 Hz, 1H), 3.32 (d, J=14.3 Hz, 1H), 3.14 (s, 3H), 3.12-3.03 (m, 1H), 2.97 (s, 3H), 2.89 (dt, J=5.3, 13.6 Hz, 1H), 2.83-2.68 (m, 2H), 2.54 (d, J=16.0 Hz, 1H), 2.39-2.30 (m, 2H), 2.24 (td, J=3.5, 12.5 Hz, 1H), 2.11-2.01 (m, 2H), 1.99-1.69 (m, 9H), 1.57-1.52 (m, 1H), 1.46-1.31 (m, 2H). LRMS: m/z (ESI, +ve ion) 700.1 (M+H)⁺.

Example 79

(3R,6R,7S,11S,17R,24S)-6'-CHLORO-N-(CYCLO-PROPYLSULFONYL)-17-HYDROXY-14-METHYL-15-OXO-3',4'-DIHYDRO-2'H-SPIRO[8,22-DIOXA-1,14-DIAZAPENTACYCLO [16.7.2.1$^{7,11}$.0$^{3,6}$.0$^{21,26}$]OCTACOSA-18,20,26-TRIENE-24,1'-NAPHTHALENE]-17-CARBOXAMIDE

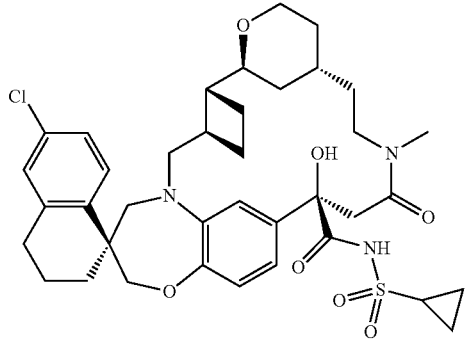 [SMILES: CN1CC[C@H]2CCO[C@@H](C2)[C@@H]2CC[C@H]2CN2C[C@@]3(CCCc4cc(Cl)ccc43)COc3ccc(cc32)[C@@](O)(C(=O)NS(=O)(=O)C2CC2)CC1=O]

The title compound (53 mg, 76% yield) was prepared from 3R,6R,7S,11S,17R,24S)-6'-chloro-17-hydroxy-14-methyl-15-oxo-3',4'-dihydro-2'H-spiro[8,22-dioxa-1,14-diazapentacyclo[16.7.2.17,11.03,6.021,26]octacosa-18,20,26-triene-24,1'-naphthalene]-17-carboxylic acid (Example 74) in a similar fashion as described for the synthesis of Example 5: ¹H NMR (400 MHz, CD$_2$Cl$_2$) δ 8.99 (br. s., 1H), 7.82-7.69 (m, 2H), 7.16 (d, J=7.4 Hz, 1H), 7.11-7.03 (m, 2H), 6.89 (d, J=8.2 Hz, 1H), 6.50 (br. s., 1H), 4.10-3.92 (m, 2H), 3.82-3.60 (m, 6H), 3.54 (d, J=15.8 Hz, 1H), 3.31 (d, J=14.3 Hz, 1H), 3.08 (dd, J=8.3, 14.0 Hz, 1H), 2.97 (s, 3H), 2.94-2.82 (m, 1H), 2.82-2.70 (m, 3H), 2.50 (d, J=15.7 Hz, 1H), 2.40-2.24 (m, 3H), 2.08-2.00 (m, 2H), 1.97-1.88 (m, 3H), 1.88-1.78 (m, 3H), 1.77-1.65 (m, 3H), 1.59-1.52 (m, 1H), 1.45-1.29 (m, 2H), 1.27-1.17 (m, 2H), 1.10-0.95 (m, 1H), 0.95-0.83 (m, 1H). LRMS: m/z (ESI, +ve ion) 726.0 (M+H)⁺.

Example 80

(3R,6R,7S,11S,17S,24S)-6'-CHLORO-N-(DIMETH-YLSULFAMOYL)-17-FLUORO-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXAMIDE OR (3R,6R,7S,11S,17R,24S)-6'-CHLORO-N-(DIMETHYLSULFAMOYL)-17-FLUORO-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXAMIDE (Major Isomeric Product after Chiral Separation; the Relative Configuration of the Alkyl Fluoride Stereocenter was not Established)

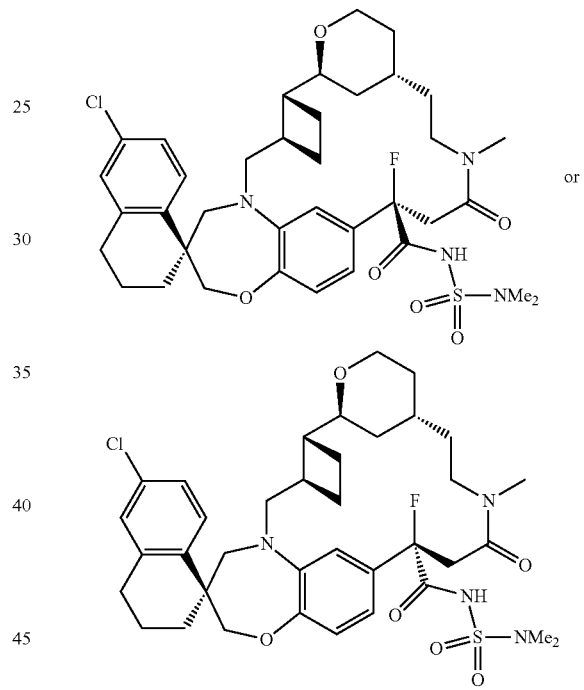

To a solution of (3R,6R,7S,11S,17R,24S)-6'-chloro-N-(dimethylsulfamoyl)-17-hydroxy-14-methyl-15-oxo-3',4'-dihydro-2'H-spiro[8,22-dioxa-1,14-diazapentacyclo[16.7.2.1$^{7,11}$.0$^{3,6}$.0$^{21,26}$]octacosa-18,20,26-triene-24,1'-naphthalene]-17-carboxamide or (3R,6R,7S,11S,17S,24S)-6'-chloro-N-(dimethylsulfamoyl)-17-hydroxy-14-methyl-15-oxo-3',4'-dihydro-2'H-spiro[8,22-dioxa-1,14-diazapentacyclo[16.7.2.1$^{7,11}$.0$^{3,6}$.0$^{21,26}$]octacosa-18,20,26-triene-24,1'-naphthalene]-17-carboxamide (Example 76, (20 mg, 0.027 mmol) in DCM (270 µL) cooled in an ice-water bath was added bis(2-methoxyethyl)aminosulfur trifluoride (50% solution in toluene) (18 mg, 0.041 mmol). The reaction mixture was maintained in the chilled bath for 30 minutes. Analysis by LCMS (after 30 minutes) indicated partial conversion to the desired product. Additional bis(2-methoxyethyl)aminosulfur trifluoride (50% solution in toluene) (18 mg, 0.041 mmol) was added to the reaction mixture. After 15 minutes, complete consumption of the starting material was observed by LCMS. The reaction mixture was diluted with saturated aqueous NH₄Cl and extracted with EtOAc (2×). The organic extract was washed with saturated aqueous NaCl and dried over Na₂SO₄. The solution was filtered and concentrated in vacuo to give the crude material. The crude material was absorbed onto a plug of silica gel and purified by chromatography through a Redi-Sep pre-packed silica gel column (12 g), eluting with a gradient of 0% to 80% acetone in hexanes, to provide the desired product (16 mg) as a mixture of isomers (>5:1 dr). The sample (14 mg) was submitted to chiral separation (conditions: Thar 200 SFC with 30×250 mm AS-H column with 60.75 mL/min methanol (neat)⁺74 g/min CO₂, 45% co-solvent at 135 g/min. Temp.=30° C., Outlet pressure=100 bar, Wavelength=224 nm. Injected 2.0 mL of 14 mg sample dissolved in 5 mL MeOH; c=2.8 mg/mL, i.e. 5.6 mg per injection. Fractions collected manually). Concentration under reduced pressure of the major isomer, gave the above compound (8 mg, 40% yield) as a colorless solid. $^1$H NMR (500 MHz, CD₂Cl₂) δ 8.69 (br. s., 1H), 7.73 (d, J=8.4 Hz, 1H), 7.17 (dd, J=2.3, 8.5 Hz, 1H), 7.08 (d, J=2.3 Hz, 1H), 6.91 (d, J=8.3 Hz, 1H), 6.83 (d, J=8.2 Hz, 1H), 6.42 (s, 1H), 4.08-3.97 (m, 2H), 3.81 (dd, J=8.9, 14.7 Hz, 2H), 3.73 (dd, J=4.3, 11.6 Hz, 1H), 3.69-3.49 (m, 4H), 3.33 (d, J=14.5 Hz, 1H), 3.24 (dd, J=9.0, 16.5 Hz, 1H), 3.07 (dd, J=10.4, 15.4 Hz, 1H), 2.97 (s, 3H), 2.95-2.93 (m, 6H), 2.94 (s, 6H), 2.84-2.70 (m, 2H), 2.43-2.30 (m, 2H), 2.07 (d, J=13.7 Hz, 1H), 2.02-1.68 (m, 10H), 1.53-1.48 (m, 1H), 1.42-1.32 (m, 2H). LRMS: m/z (ESI, +ve ion) 731.2 (M+H)⁺.

Example 81

(3R,6R,7S,11S,17S,24S)-6'-CHLORO-N-(DIMETH-YLSULFAMOYL)-17-FLUORO-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXAMIDE OR (3R,6R,7S,11S,17R,24S)-6'-CHLORO-N-(DIMETHYLSULFAMOYL)-17-FLUORO-14-METHYL-15-OXO-3',4'-DIHYDRO-2'H-SPIRO[8,22-DIOXA-1,14-DIAZAPENTACYCLO[16.7.2.1$^{7,11}$.0$^{3,6}$.0$^{21,26}$]OCTACOSA-18,20,26-TRIENE-24,1'-NAPHTHALENE]-17-CARBOXAMIDE (Major Isomeric Product after Chiral Separation; the Relative Configuration of the Alkyl Fluoride Stereocenter is Epimeric to the Title Compound of Example 80)

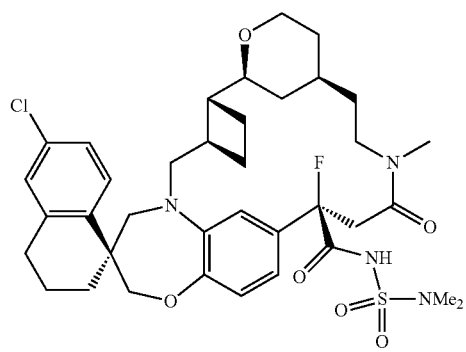

or

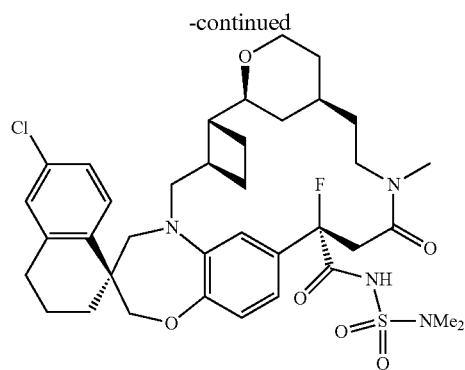

The title compound (23 mg, 46% overall yield) was prepared from (3R,6R,7S,11S,17S,24S)-6'-chloro-17-hydroxy-14-methyl-15-oxo-3',4'-dihydro-2'H-spiro[8,22-dioxa-1,14-diazapentacyclo[16.7.2.1$^{7,11}$.0$^{3,6}$.0$^{21,26}$]octacosa-18,20,26-triene-24,1'-naphthalene]-17-carboxylic acid (Example 75) in a similar fashion as described for the synthesis of Example 80: $^1$H NMR (500 MHz, CD₂Cl₂) δ=8.70-8.63 (m, 1H), 7.73 (d, J=8.6 Hz, 1H), 7.17 (dd, J=2.3, 8.4 Hz, 1H), 7.08 (d, J=2.2 Hz, 1H), 6.86 (dd, J=1.1, 8.3 Hz, 1H), 6.67 (td, J=2.2, 8.2 Hz, 1H), 6.56 (d, J=1.7 Hz, 1H), 4.07 (d, J=12.1 Hz, 1H), 3.96 (d, J=12.1 Hz, 1H), 3.81 (dd, J=10.4, 14.7 Hz, 2H), 3.73 (dd, J=4.1, 11.6 Hz, 1H), 3.66-3.43 (m, 4H), 3.32 (d, J=14.5 Hz, 1H), 3.21 (dd, J=8.7, 16.4 Hz, 1H), 3.13-3.06 (m, 1H), 3.06 (s, 6H), 2.95 (s, 3H), 2.95-2.87 (m, 1H), 2.83-2.69 (m, 2H), 2.41-2.30 (m, 2H), 2.09-1.68 (m, 12H), 1.53-1.47 (m, 1H), 1.43-1.33 (m, 2H). LRMS: m/z (ESI, +ve ion) 731.0 (M+H)⁺.

Example 82

(1S,3'R,6'R,7'S,8'Z,16'R)-6-CHLORO-7',16'-DIHYDROXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLIC ACID OR (1S,3'R,6'R,7'S,8'Z,16'S)-6-CHLORO-7',16'-DIHYDROXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLIC ACID (the Relative Configuration of the Tertiary Alcohol Stereocenter of the Title Compound has not been Definitively Established; the Geometry of the Olefin was Assigned by J-Values)

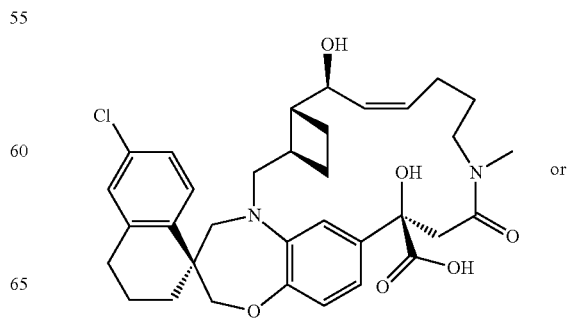

or

-continued

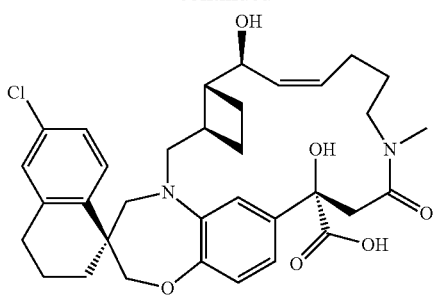

Step 1. (R)-METHYL 2-((S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXY-4-(METHYL(PENT-4-EN-1-YL)AMINO)-4-OXOBUTANOATE AND (S)-METHYL 2-((S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXY-4-(METHYL(PENT-4-EN-1-YL)AMINO)-4-OXOBUTANOATE

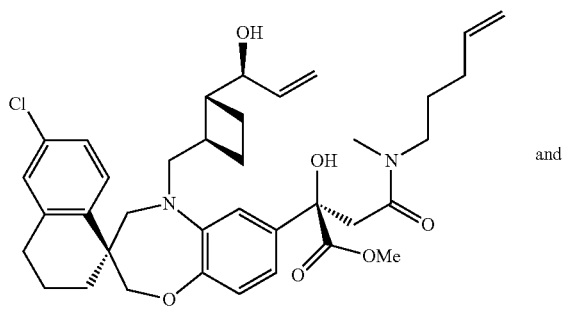 and

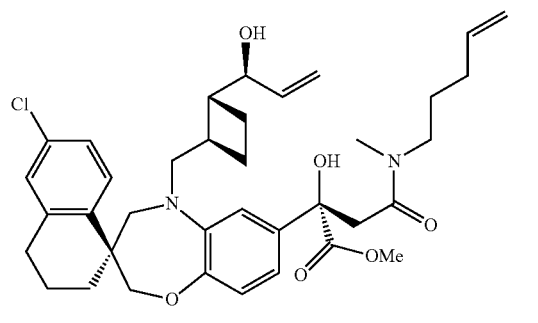

The above compounds (200 mg, 64% yield, 1.5:1 dr) were prepared from 3-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-3-hydroxy-4-methoxy-4-oxobutanoic acid (Example 1, Step 5) in a similar fashion as described for the synthesis of (R)- and (S)-methyl 4-(but-3-en-1-yl(methyl)amino)-2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-4-oxobutanoate (Example 1, Step 6): $^1$H NMR (300 MHz, CDCl$_3$) δ 7.75-7.67 (m, 1H), 7.22 (dd, J=2.2, 3.7 Hz, 0.6H), 7.20-7.11 (m, 1H), 7.08 (d, J=2.2 Hz, 1.4H), 6.94-6.83 (m, 1.4H), 6.79-6.71 (m, 0.6H), 5.95-5.90 (m, 1H), 5.90-5.73 (m, 2H), 5.30-5.18 (m, 1H), 5.12-4.96 (m, 3H), 4.11-3.98 (m, 3H), 3.92-3.80 (m, 1H), 3.78-3.64 (m, 4H), 3.62-3.44 (m, 2H), 3.44-3.17 (m, 3H), 3.16-3.03 (m, 1H), 3.02-2.90 (m, 3H), 2.83-2.63 (m, 3H), 2.49 (m, 1H), 2.13-1.97 (m, 5H), 1.93-1.78 (m, 3H), 1.75-1.58 (m, 4H), 1.55-1.38 (m, 1H). LRMS: m/z (ESI, +ve ion) 651.0 (M+H)$^+$.

Step 2. METHYL (1S,3'R,6'R,7'S,8'Z,16'R)-6-CHLORO-7',16'-DIHYDROXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLATE OR METHYL (1S,3'R,6'R,7'S,8'Z,16'S)-6-CHLORO-7',16'-DIHYDROXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLATE

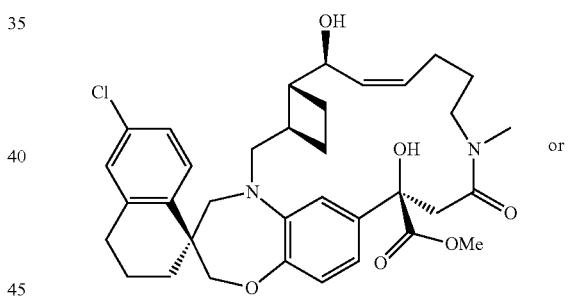 or

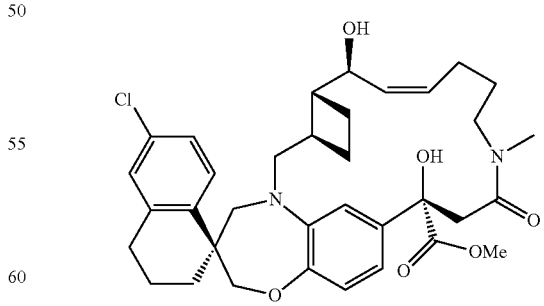

The above compound (150 mg, 10% yield) was prepared as the first-eluting, isomeric product from the intermediates from Step 1 in a similar fashion as described for the synthesis of methyl (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 1, Step 7): $^1$H NMR (300 MHz, CDCl$_3$) δ 7.78 (d, J=8.5 Hz, 1H), 7.27 (dd, J=2.0, 8.3 Hz, 2H), 7.17 (dd, J=2.2, 8.3 Hz, 1H), 7.10 (s, 1H), 7.08 (d, J=2.0 Hz, 1H), 6.97 (d, J=8.3 Hz, 1H), 6.64 (d, J=1.9 Hz, 1H), 5.86-5.76 (m, 1H), 5.43 (t, J=10.3 Hz, 1H), 4.49 (dt, J=3.9, 8.8 Hz, 1H), 4.05 (s, 2H), 4.01-4.00 (m, 1H), 3.95 (d, J=15.2 Hz, 1H), 3.83-3.70 (m, 4H), 3.67-3.41 (m, 2H), 3.28 (d, J=4.2 Hz, 1H), 3.17 (d, J=14.3 Hz, 1H), 3.06-2.88 (m, 5H), 2.83-2.69 (m, 2H), 2.59 (d, J=16.1 Hz, 1H), 2.50-2.30 (m, 1H), 2.18-2.10 (m, 2H), 2.09-1.56 (m, 9H), 1.51-1.32 (m, 2H). LRMS: m/z (ESI, +ve ion) 623.0 (M+H)$^+$.

Step 3. (1S,3'R,6'R,7'S,8'Z,16'R)-6-CHLORO-7',16'-DIHYDROXY-13'-METHYL-14'-OXO-3,4-DIHYDRO-2H-SPIRO[NAPHTHALENE-1,23'-[21]OXA[1,13]DIAZATETRACYCLO [15.7.2.0$^{3,6}$.0$^{20,25}$]HEXACOSA[8,17,19,25]TETRAENE]-16'-CARBOXYLIC ACID OR (1S,3'R,6'R,7'S,8'Z,16'S)-6-CHLORO-7',16'-DIHYDROXY-13'-METHYL-14'-OXO-3,4-DIHYDRO-2H-SPIRO [NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLIC ACID The title compound (7.0 mg, 48% yield) was prepared from the methyl ester derivative from Step 1 in a similar fashion as described for the synthesis of Example 4: $^1$H NMR (400 MHz, DMSO-d$_6$) δ=7.68 (d, J=8.4 Hz, 1H), 7.26 (d, J=8.4 Hz, 1H), 7.16 (s, J=6.1 Hz, 1H), 6.98 (d, J=8.4 Hz, 1H), 6.87 (s, 1H), 6.81 (d, J=8.2 Hz, 1H), 5.74-5.60 (m, 1H), 5.40-5.30 (m, 1H), 4.24 (t, J=8.2 Hz, 1H), 4.04-3.91 (m, 4H), 3.85-3.75 (m, 1H), 3.65-3.50 (m, 3H), 3.21 (d, J=14.3 Hz, 1H), 3.05 (dd, J=9.6, 14.3 Hz, 2H), 2.95-2.62 (m, 2H), 2.29-2.11 (m, 1H), 2.09-1.72 (m, 7H), 1.71-1.55 (m, 3H), 1.55-1.33 (m, 2H). LRMS: m/z (ESI, +ve ion) 609.0 (M+H)$^+$.

Example 83

(1S,3'R,6'R,7'S,8'E,16'R)-6-CHLORO-7',16'-DIHYDROXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLIC ACID OR (1S,3'R,6'R,7'S,8'E,16'S)-6-CHLORO-7',16'-DIHYDROXY-13'-METHYL-14'-OXO-3,4-DIHYDRO-2H-SPIRO [NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLIC ACID (the Relative Configuration of the Tertiary Alcohol Stereocenter of the Title Compound has not been Definitively Established; the Geometry of the Olefin was Assigned by J-Values)

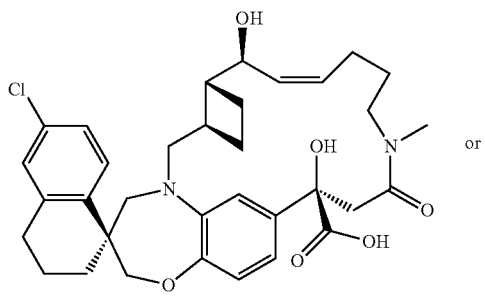 or 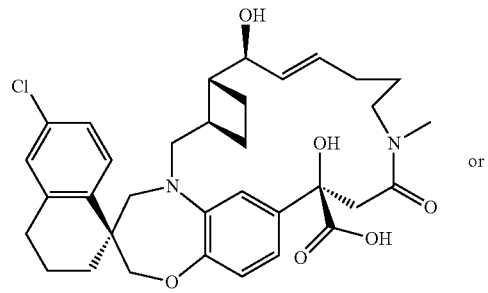 or

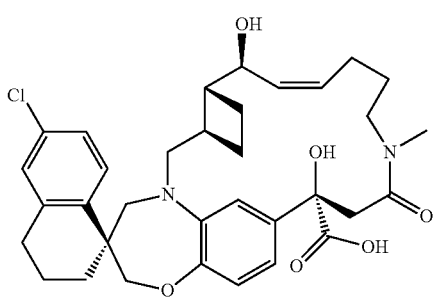

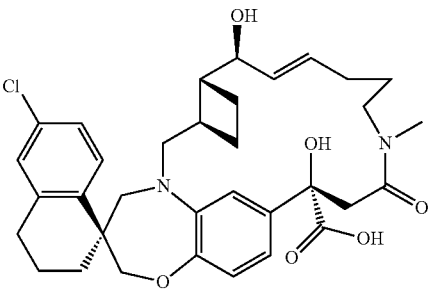

Step 1. METHYL (1S,3'R,6'R,7'S,8'E,16'R)-6-CHLORO-7',16'-DIHYDROXY-13'-METHYL-14'-OXO-3,4-DIHYDRO-2H-SPIRO[NAPHTHA-LENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLATE OR METHYL (1S,3'R,6'R,7'S,8'E,16'S)-6-CHLORO-7',16'-DIHYDROXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLATE

Step 2. (1S,3'R,6'R,7'S,8'E,16'R)-6-CHLORO-7',16'-DIHYDROXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLIC ACID OR (1S,3'R,6'R,7'S,8'E,16'S)-6-CHLORO-7',16'-DIHYDROXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLIC ACID

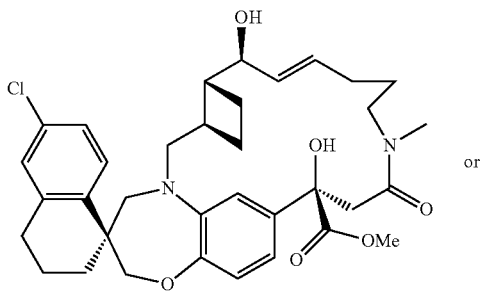

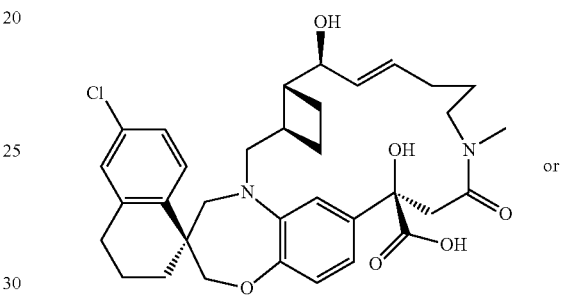

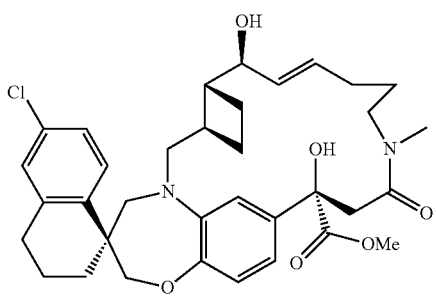

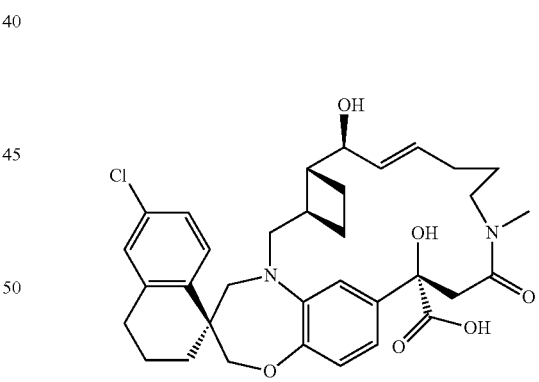

The above compound (700 mg, 45% yield) was prepared as the second-eluting, isomeric product from Example 82, Step 2. $^1$H NMR (300 MHz, CDCl$_3$) δ 7.73 (d, J=8.5 Hz, 1H), 7.21-7.06 (m, 3H), 6.97-6.83 (m, 2H), 5.94 (s, 1H), 5.66-5.55 (m, 2H), 4.12-4.00 (m, 2H), 3.90 (d, J=7.9 Hz, 1H), 3.84-3.69 (m, 4H), 3.62-3.22 (m, 5H), 3.10 (br. s., 1H), 2.95 (s, 3H), 2.85-2.69 (m, 2H), 2.64 (s, 1H), 2.54 (d, J=16.2 Hz, 1H), 2.37 (t, J=8.1 Hz, 1H), 2.25-2.07 (m, 2H), 2.04-1.61 (m, 8H), 1.61-1.40 (m, 3H). LRMS: m/z (ESI, +ve ion) 623.2 (M+H)$^+$.

The title compound (8.0 mg, 74% yield) was prepared from the methyl ester derivative from Step 1 in a similar fashion as described for the synthesis of Example 4. $^1$H NMR (400 MHz, (CD$_3$)$_2$SO) δ 7.67 (d, J=8.4 Hz, 1H), 7.24 (dd, J=2.2, 8.5 Hz, 1H), 7.17 (d, J=2.2 Hz, 1H), 6.97-6.84 (m, 2H), 6.80 (d, J=8.2 Hz, 1H), 5.88 (s, 1H), 5.63-5.45 (m, 2H), 4.44 (d, J=4.5 Hz, 1H), 4.03-3.92 (m, 2H), 3.81 (q, J=4.9 Hz, 1H), 3.53-3.39 (m, 2H), 3.37-3.33 (m, 1H), 3.28-3.16 (m, 4H), 2.82 (s, 3H), 2.79-2.67 (m, 2H), 2.62-2.53 (m, 2H), 2.26-2.17 (m, 1H), 2.03-1.76 (m, 7H), 1.75-1.58 (m, 3H), 1.58-1.39 (m, 2H). LRMS: m/z (ESI, +ve ion) 609.0 (M+H)+.

Example 84

(1S,3'R,6'R,7'S,8'E,16'R)-6-CHLORO-7',16'-DIHYDROXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLIC ACID OR (1S,3'R,6'R,7'S,8'E,16'S)-6-CHLORO-7',16'-DIHYDROXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLIC ACID (the Relative Configuration of the Tertiary Alcohol Stereocenter of the Title Compound has not been Definitively Established, and is Epimeric to the Title Compound of Example 15; the Geometry of the Olefin was Assigned by J-Values)

Step 1. METHYL (1S,3'R,6'R,7'S,8'E,16'R)-6-CHLORO-7',16'-DIHYDROXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLATE OR METHYL (1S,3'R,6'R,7'S,8'E,16'S)-6-CHLORO-7',16'-DIHYDROXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLATE

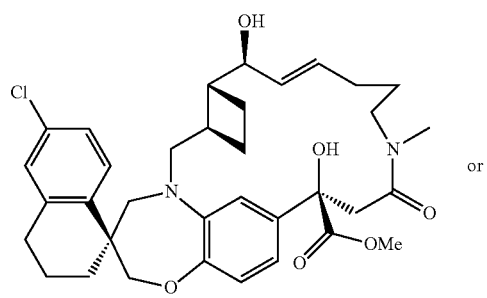

or

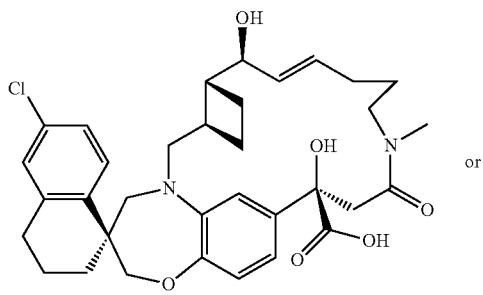

or

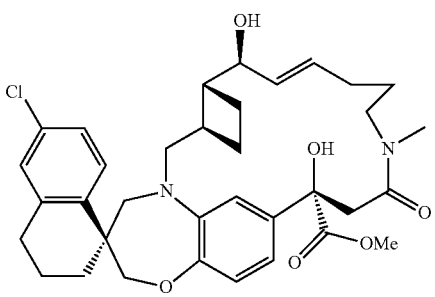

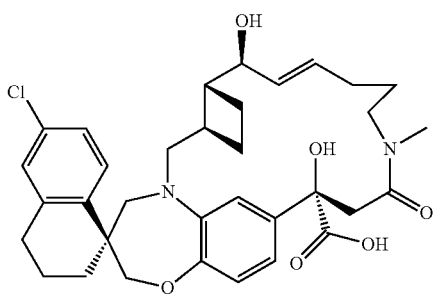

The above compound (350 mg, 23% yield) was prepared as the third-eluting, isomeric product from Example 82, Step 2. $^1$H NMR (300 MHz, CDCl$_3$) δ 7.72 (d, J=8.5 Hz, 1H), 7.16 (dd, J=2.2, 8.5 Hz, 1H), 7.12-7.05 (m, 2H), 6.89 (d, J=8.3 Hz, 1H), 6.74 (d, J=1.9 Hz, 1H), 5.95 (s, 1H), 5.88-5.75 (m, 1H), 5.69 (dd, J=3.9, 15.6 Hz, 1H), 4.07-3.97 (m, 3H), 3.81 (s, 3H), 3.72 (d, J=13.7 Hz, 2H), 3.59 (dd, J=5.7, 14.8 Hz, 1H), 3.40-3.07 (m, 6H), 3.02-2.88 (m, 3H), 2.81-2.66 (m, 3H), 2.41-2.25 (m, 2H), 2.23-1.70 (m, 10H), 1.70-1.59 (m, 1H), 1.55-1.44 (m, 1H). LRMS: m/z (ESI, +ve ion) 623.2 (M+H)+.

213

Step 2. (1S,3'R,6'R,7'S,8'E,16'R)-6-CHLORO-7',16'-DIHYDROXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLIC ACID OR (1S,3'R,6'R,7'S,8'E,16'S)-6-CHLORO-7',16'-DIHYDROXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLIC ACID

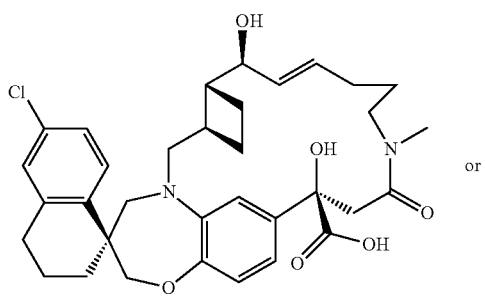

or

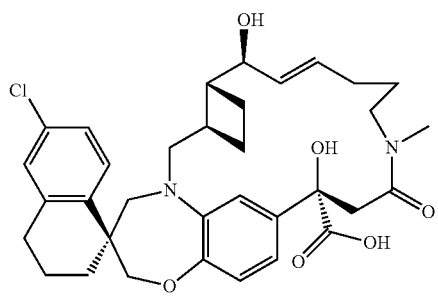

The title compound (8.9 mg, 69% yield) was prepared from the methyl ester derivative from Step 1 in a similar fashion as described for the synthesis of Example 4. $^1$H NMR (400 MHz, (CD$_3$)$_2$SO) δ 7.66 (d, J=8.6 Hz, 1H), 7.23 (dd, J=2.3, 8.4 Hz, 1H), 7.17 (d, J=2.2 Hz, 1H), 6.93 (dd, J=1.8, 8.2 Hz, 1H), 6.81 (d, J=8.2 Hz, 1H), 6.71 (d, J=5.3 Hz, 1H), 5.62 (dd, J=10.2, 18.4 Hz, 1H), 5.56-5.43 (m, 1H), 4.04-3.94 (m, 2H), 3.76 (dd, J=4.0, 6.0 Hz, 1H), 3.40-3.15 (m, 7H), 2.82 (s, 3H), 2.79-2.68 (m, 3H), 2.36-2.27 (m, 1H), 2.07-1.92 (m, 3H), 1.92-1.72 (m, 5H), 1.69-1.43 (m, 4H). LRMS: m/z (ESI, +ve ion) 609.1 (M+H)$^+$.

214

Example 85

(1S,3'R,6'R,7'S,8'E,16'R)-6-CHLORO-16'-HYDROXY-7'-METHOXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLIC ACID OR (1S,3'R,6'R,7'S,8'E,16'S)-6-CHLORO-16'-HYDROXY-7'-METHOXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXYLIC ACID

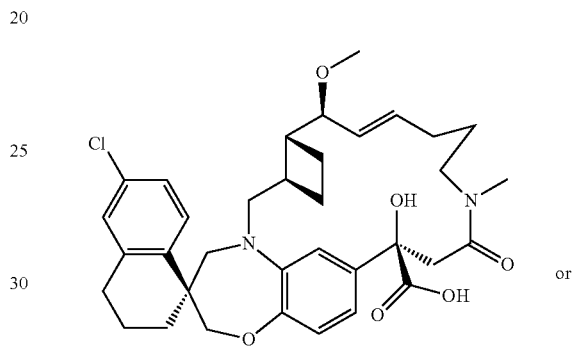

or

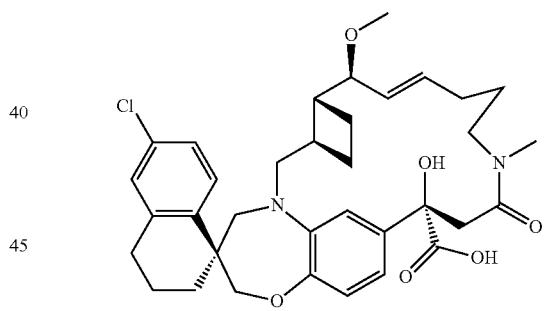

The title compound (83 mg, 41% overall yield) was prepared from the methyl ester derivative of Example 83, Step 1 via methylation through a procedure similar to that used for the synthesis of Example 3, followed by saponification through a procedure similar to that used for the synthesis of Example 4. $^1$H NMR (400 MHz, (CD$_3$)$_2$SO) δ 7.65 (d, J=8.4 Hz, 1H), 7.23 (dd, J=2.2, 8.4 Hz, 1H), 7.18 (s, 1H), 6.90-6.84 (m, 2H), 6.84-6.79 (m, 1H), 5.87 (br. s., 1H), 5.60-5.51 (m, 1H), 5.46 (dd, J=8.8, 17.0 Hz, 1H), 4.02-3.92 (m, 2H), 3.49 (d, J=13.9 Hz, 1H), 3.46-3.37 (m, 2H), 3.30-3.14 (m, 5H), 3.07 (s, 3H), 2.82 (s, 3H), 2.80-2.65 (m, 2H), 2.61 (d, J=15.8 Hz, 1H), 2.56-2.52 (m, 1H), 2.38-2.29 (m, 1H), 2.07 (m, 2H), 2.01-1.94 (m, 1H), 1.89-1.78 (m, 4H), 1.76-1.59 (m, 3H), 1.53 (d, J=9.4 Hz, 2H). LRMS: m/z (ESI, +ve ion) 623.0 (M+H)$^+$.

Example 86

(1S,3'R,6'R,7'S,8'E,16'R)-6-CHLORO-16'-HYDROXY-7'-METHOXY-13'-METHYL-N-(METHYLSULFONYL)-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXAMIDE OR (1S,3'R,6'R,7'S,8'E,16'S)-6-CHLORO-16'-HYDROXY-7'-METHOXY-13'-METHYL-N-(METHYLSULFONYL)-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXAMIDE

Example 87

(1S,3'R,6'R,7'S,8'E,16'R)-6-CHLORO-N-(DIMETHYLSULFAMOYL)-16'-HYDROXY-7'-METHOXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXAMIDE OR (1S,3'R,6'R,7'S,8'E,16'S)-6-CHLORO-N-(DIMETHYLSULFAMOYL)-16'-HYDROXY-7'-METHOXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXAMIDE

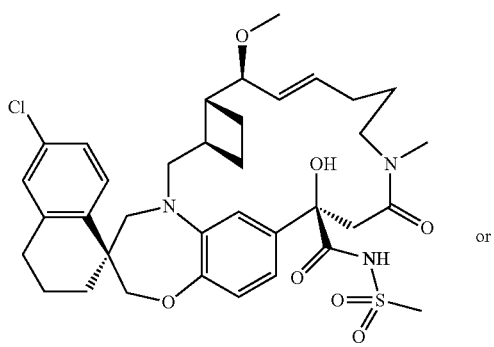 or 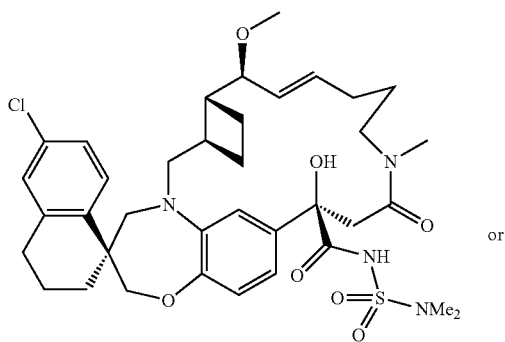 or

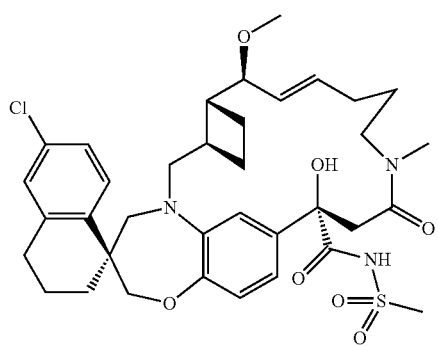 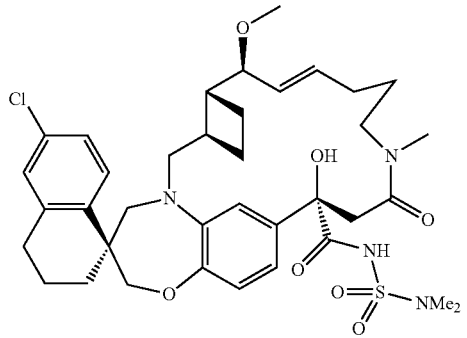

The title compound (35 mg, 80% yield) was prepared from Example 85 in a similar fashion as described for the synthesis of Example 5: $^1$H NMR (300 MHz, CD$_2$Cl$_2$) δ 9.17 (br. s., 1H), 7.73 (d, J=8.5 Hz, 1H), 7.19-7.08 (m, 2H), 7.02-6.92 (m, 1H), 6.90-6.83 (m, 1H), 6.78 (d, J=1.8 Hz, 1H), 5.77-5.66 (m, 1H), 5.49 (dd, J=6.8, 15.7 Hz, 1H), 4.13-3.93 (m, 2H), 3.73-3.51 (m, 3H), 3.46 (d, J=16.4 Hz, 1H), 3.38-3.30 (m, 1H), 3.26 (t, J=7.9 Hz, 2H), 3.23-3.10 (m, 7H), 2.97-2.86 (m, 3H), 2.82-2.72 (m, 2H), 2.63-2.51 (m, 2H), 2.38-2.27 (m, 1H), 2.20-2.08 (m, 2H), 2.06-1.93 (m, 3H), 1.89-1.60 (m, 6H), 1.53-1.41 (m, 1H). LRMS: m/z (ESI, +ve ion) 700.1 (M+H)$^+$.

The title compound (33 mg, 72% yield) was prepared from Example 85 in a similar fashion as described for the synthesis of Example 5. $^1$H NMR (300 MHz, CD$_2$Cl$_2$) δ 9.08 (s, 1H), 7.73 (d, J=8.5 Hz, 1H), 7.26 (s, 1H), 7.16 (dd, J=2.3, 8.5 Hz, 1H), 7.13-7.07 (m, 1H), 6.99 (t, J=3.9 Hz, 1H), 6.90-6.82 (m, 1H), 6.79 (d, J=2.0 Hz, 1H), 5.74 (d, J=15.6 Hz, 1H), 5.49 (dd, J=6.9, 15.7 Hz, 1H), 4.07-3.96 (m, 2H), 3.77-3.45 (m, 4H), 3.41-3.23 (m, 3H), 3.23-3.09 (m, 4H), 2.95-2.89 (m, 3H), 2.89-2.82 (m, 6H), 2.82-2.71 (m, 2H), 2.65-2.47 (m, 2H), 2.33 (dd, J=5.6, 7.7 Hz, 1H), 2.22-2.08 (m, 2H), 2.03-1.61 (m, 9H), 1.53-1.41 (m, 1H). LRMS: m/z (ESI, +ve ion) 729.0 (M+H)$^+$.

Example 88

(1S,3'R,6'R,7'S,8'E,16'R)-6-CHLORO-7',16'-DIHYDROXY-13'-METHYL-N-(METHYLSULFONYL)-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXAMIDE OR (1S,3'R,6'R,7'S,8'E,16'S)-6-CHLORO-7',16'-DIHYDROXY-13'-METHYL-N-(METHYLSULFONYL)-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXAMIDE

Example 89

(1S,3'R,6'R,7'S,8'E,16'R)-6-CHLORO-N-(DIMETHYLSULFAMOYL)-7',16'-DIHYDROXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXAMIDE OR (1S,3'R,6'R,7'S,8'E,16'S)-6-CHLORO-N-(DIMETHYLSULFAMOYL)-7',16'-DIHYDROXY-13'-METHYL-14'-OXO-3,4-DIHYDRO-2H-SPIRO[NAPHTHALENE-1,23'-[21]OXA[1,13]DIAZATETRACYCLO[15.7.2.0$^{3,6}$.0$^{20,25}$]HEXACOSA[8,17,19,25]TETRAENE]-16'-CARBOXAMIDE

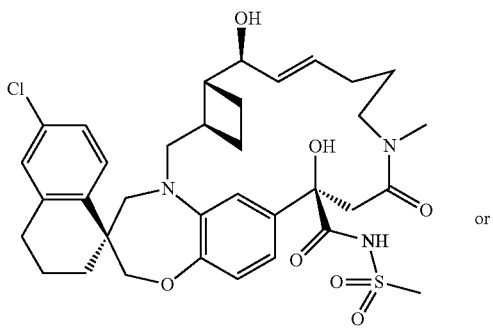

or

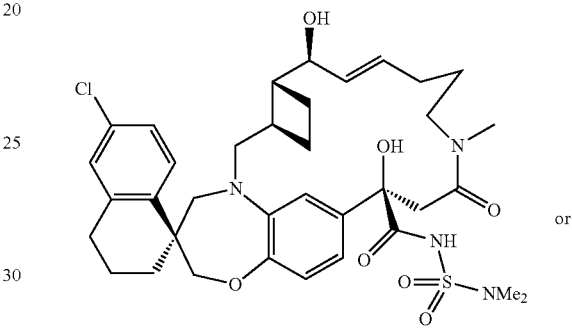

or

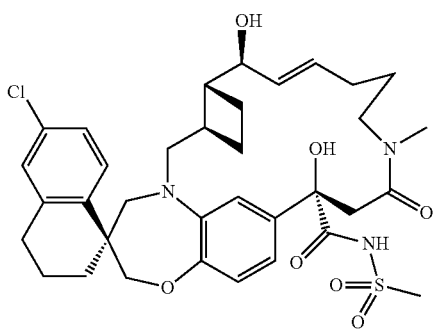

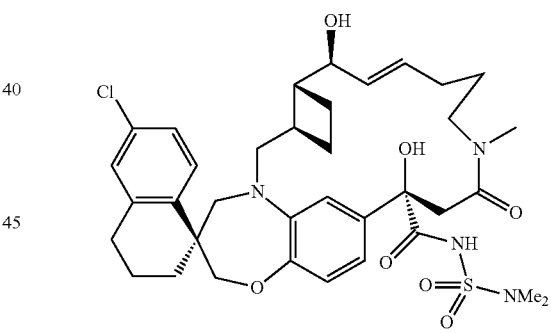

The title compound (33 mg, 69% yield) was prepared from the methyl ester derivative of Example 84, Step 1 in a similar fashion as described for the synthesis of Example 43. $^1$H NMR (300 MHz, CD$_2$Cl$_2$) δ 7.74 (d, J=8.5 Hz, 1H), 7.17 (dd, J=2.3, 8.3 Hz, 2H), 7.08 (d, J=2.2 Hz, 1H), 7.04-6.99 (m, 1H), 6.93-6.85 (m, 2H), 5.64-5.58 (m, 2H), 4.10-4.03 (m, 2H), 3.92 (dd, J=5.6, 8.3 Hz, 1H), 3.73 (d, J=14.8 Hz, 1H), 3.54 (d, J=12.9 Hz, 2H), 3.47-3.26 (m, 3H), 3.28 (d, J=5.1 Hz, 1H), 3.21 (s, 4H), 3.16-3.01 (m, 1H), 2.95-2.89 (m, 4H), 2.84-2.73 (m, 2H), 2.67-2.55 (m, 1H), 2.42 (d, J=16.4 Hz, 1H), 2.34 (t, J=8.3 Hz, 1H), 2.19-2.09 (m, 1H), 2.07-1.92 (m, 3H), 1.92-1.74 (m, 4H), 1.74-1.60 (m, 2H), 1.43 (m, 2H). LRMS. m/z (ESI, +ve ion) 686.0 (M+H)$^+$.

The title compound (49 mg, 68% yield) was prepared from the methyl ester derivative of Example 84, Step 1 in a similar fashion as described for the synthesis of Example 43. $^1$H NMR (300 MHz, CD$_2$Cl$_2$) δ 9.05 (s, 1H), 7.74 (d, J=8.6 Hz, 1H), 7.20-7.14 (m, 1H), 7.09 (d, J=2.3 Hz, 1H), 7.03 (dd, J=2.0, 8.6 Hz, 1H), 6.92-6.86 (m, 2H), 5.65-5.57 (m, 2H), 5.34-5.30 (m, 12H), 4.12-4.01 (m, 2H), 3.95-3.87 (m, 1H), 3.73 (d, J=14.8 Hz, 1H), 3.62-3.33 (m, 4H), 3.27 (dd, J=5.2, 15.1 Hz, 1H), 3.14-2.99 (m, 1H), 2.95-2.90 (m, 3H), 2.87 (s, 6H), 2.82-2.72 (m, 2H), 2.60 (m, 1H), 2.42-2.30 (m, J=16.4 Hz, 2H), 2.20-2.10 (m, 1H), 2.07-1.92 (m, 3H), 1.92-1.77 (m, 4H), 1.75-1.58 (m, 2H), 1.53-1.38 (m, 2H). LRMS: m/z (ESI, +ve ion) 715.1 (M+H)$^+$.

Example 90

(1S,3'R,6'R,7'S,8'E,15'R)-6-CHLORO-15'-HYDROXY-15'-(HYDROXYMETHYL)-7'-METHOXY-12'-METHYL-3,4-DIHYDRO-2H,13'H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAEN]-13'-ONE (the Relative Configuration of the Title Compound has been Confirmed by x-Ray Co-Crystal Structure of Mcl1+ the Title Compound of Example 4)

Example 91

((((1S,3'R,6'R,7'S,8'E,15'R)-6-CHLORO-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAEN]-15'-YL)METHOXY)ACETIC ACID (the Relative Configuration of the Title Compound has been Confirmed by Xray Co-Crystal Structure of Mcl1+ the Title Compound of Example 4)

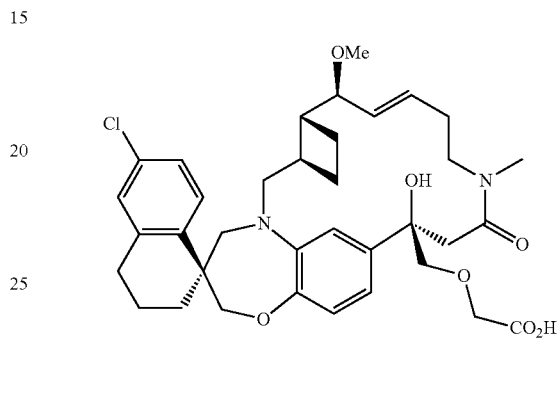

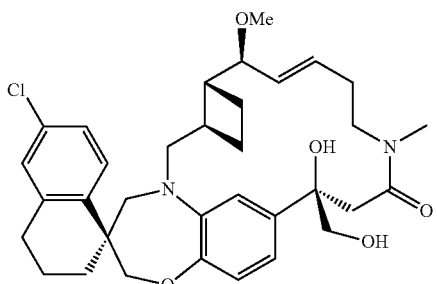

Step 1. TERT-BUTYL ((((1S,3'R,6'R,7'S,8'E,15'R)-6-CHLORO-15'-HYDROXY-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAEN]-15'-YL)METHOXY)ACETATE

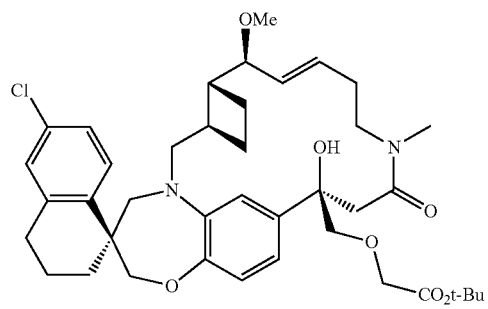 [SMILES: CO[C@H]1/C=C/CCN(C)C(=O)C[C@](O)(COCC(=O)OC(C)(C)C)c2ccc3c(c2)N(C[C@@H]2CC[C@H]21)C[C@@]1(CCCc2cc(Cl)ccc21)CO3]

To a solution of methyl (1S,3'R,6'R,7'S,8'E,15'R)-6-chloro-15'-hydroxy-7'-methoxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 1, Step 7) (55 mg, 0.088 mmol) in THF (1.0 mL) at room temperature was added sodium borohydride (9.0 mg, 0.27 mmol). The reaction mixture was stirred at room temperature. Analysis by LCMS indicated sluggish conversion to the diol product. The reaction mixture was subsequently heated at 35° C. over the weekend to complete conversion to the desired product. The reaction mixture was diluted with saturated aqueous NH$_4$Cl and extracted with EtOAc (2×). The organic extract was washed with saturated aqueous NaCl and dried over Na$_2$SO$_4$. The solution was filtered and concentrated in vacuo to give the crude material. The crude material was absorbed onto a plug of silica gel and purified by chromatography through a Redi-Sep pre-packed silica gel column (12 g), eluting with a gradient of 0% to 100% acetone/hexanes, to provide the title compound (33 mg, 0.055 mmol, 63% yield) as a white solid. $^1$H NMR (400 MHz, CD$_2$Cl$_2$) δ 7.36-7.13 (m, 2H), 7.13-7.03 (m, 2H), 6.93 (d, J=8.2 Hz, 1H), 6.77 (dd, J=2.0, 8.2 Hz, 0.4H), 6.60 (dd, J=2.0, 8.2 Hz, 0.6H), 5.40-5.33 (m, 0.4H), 5.22 (dd, J=8.9, 15.7 Hz, 0.6H), 4.44-4.26 (m, 1H), 3.93-3.69 (m, 2H), 3.68-3.36 (m, 3H), 3.35-3.19 (m, 2H), 3.17-3.04 (m, 4H), 3.03-2.94 (m, 1H), 2.90 (s, 2H), 2.86-2.76 (m, 4H), 2.75-2.53 (m, 2H), 2.49-2.13 (m, 5H), 2.08-2.01 (m, 1H), 1.93-1.81 (m, 3H), 1.77-1.67 (m, 2H), 1.62-1.36 (m, 1H). LRMS. m/z (ESI, +ve ion) 595.2 (M+H)$^+$.

To a solution of (1S,3'R,6'R,7'S,8'E,15'R)-6-chloro-15'-hydroxy-15'-(hydroxymethyl)-7'-methoxy-12'-methyl-3,4-dihydro-2H,13'H-spiro[naphthalene-1,22'-[20]oxa[1,12]diazatetracyclo[14.7.2.0$^{3,6}$.0$^{19,24}$]pentacosa[8,16,18,24]tetraen]-13'-one (Example 90)(25 mg, 0.042 mmol) in THF (420 μl) was added sodium bis(trimethylsilyl)amide, 1.0 M in THF (84 μl, 0.084 mmol) then tert-butyl bromoacetate (13.56 μl, 0.084 mmol). The resulting suspension was stirred vigorously. Analysis by LCMS indicated rapid consumption (<10 minutes) of the starting material. The reaction mixture was diluted with saturated aqueous NH₄Cl and extracted with EtOAc (3×). The organic extract was washed with saturated aqueous NaCl and dried over Na₂SO₄. The solution was filtered and concentrated in vacuo to give the crude material as a white solid. LRMS: m/z (ESI, +ve ion) 709.2 (M+H)⁺.

Step 2. ((((1S,3'R,6'R,7'S,8'E,15'R)-6-CHLORO-15'-HYDROXY-7'-METHOXY-12'-METHYL-13'-OXO-3,4-DIHYDRO-2H-SPIRO[NAPHTHA-LENE-1,22'-[20]OXA[1,12]DIAZATETRACYCLO[14.7.2.0³,⁶.0¹⁹,²⁴]PENTACOSA[8,16,18,24]TETRAEN]-15'-YL)METHOXY)ACETIC ACID

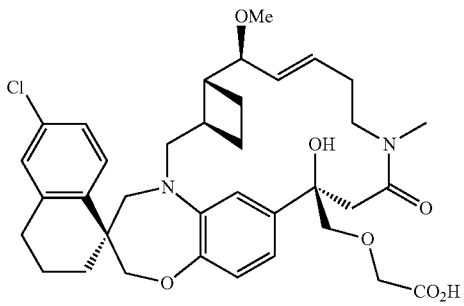 [SMILES: CO[C@H]1/C=C/CCN(C)C(=O)C[C@](O)(COCC(=O)O)c2ccc3c(c2)N(C[C@@H]2CC[C@H]21)C[C@@]1(CCCc2cc(Cl)ccc21)CO3]

To a solution of the tert-butyl ester derivative (from Step 1) (14 mg, 0.020 mmol) in 1,2-dichloroethane (0.40 mL) was added trifluoroacetic acid (0.10 mL, 1.4 mmol). The reaction was maintained at room temperature for 3 h. The reaction mixture was diluted with toluene and concentrated under reduced pressure. This procedure was repeated twice. The crude mixture was purified by chromatography through a Redi-Sep pre-packed silica gel column (4 g), eluting with a gradient of 0% to 12.5% MeOH in CH₂Cl₂, to provide the title compound (6.4 mg, 50% yield) as a white solid. ¹H NMR (400 MHz, (CD₃)₂SO) δ 7.57-7.45 (m, 0.4H), 7.35 (d, J=8.2 Hz, 0.6H), 7.25-7.04 (m, 3H), 6.97-6.72 (m, 3H), 5.42 (dd, J=9.3, 15.4 Hz, 0.4H), 5.14 (dd, J=8.3, 15.4 Hz, 0.6H), 4.32-3.60 (m, 7H), 3.52-3.38 (m, 2H), 3.23-3.15 (m, 2H), 3.10-2.99 (m, 3H), 2.97-2.63 (m, 7H), 2.42-2.15 (m, 4H), 2.11-1.89 (m, 2H), 1.89-1.51 (m, 6H), 1.50-1.37 (m, 1H). LRMS: m/z (ESI, +ve ion) 653.2 (M+H)⁺.

Example 92

((((1S,13'R)-6-CHLORO-13'-HYDROXY-10'-METHYL-11'-OXO-3,4-DIHYDRO-2H-SPIRO[NAPHTHALENE-1,20'-[18]OXA[1,10]DIAZA-TRICYCLO[12.7.2.0¹⁷,²²]TRICOSA[14,16,22]TRIEN]-13'-YL)METHOXY)ACETIC ACID AND ((((1S,13'S)-6-CHLORO-13'-HYDROXY-10'-METHYL-11'-OXO-3,4-DIHYDRO-2H-SPIRO[NAPHTHALENE-1,20'-[18]OXA[1,10]DIAZA-TRICYCLO[12.7.2.0¹⁷,²²]TRICOSA[14,16,22]TRIEN]-13'-YL)METHOXY)ACETIC ACID

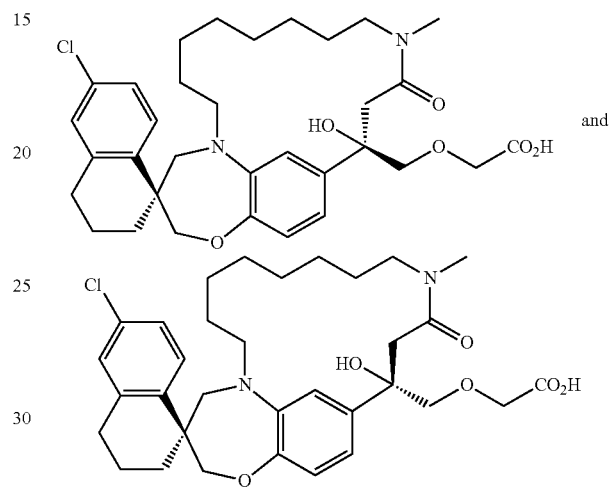

Step 1. METHYL (1S,6'E,13'R)-6-CHLORO-13'-HYDROXY-10'-METHYL-11'-OXO-3,4-DI-HYDRO-2H-SPIRO[NAPHTHALENE-1,20'-[18]OXA[1,10]DIAZATRICYCLO[12.7.2.0¹⁷,²²]TRICOSA[6,14,16,22]TETRAENE]-13'-CARBOXYLATE, METHYL (1S,6'E,13'S)-6-CHLORO-13'-HYDROXY-10'-METHYL-11'-OXO-3,4-DIHYDRO-2H-SPIRO[NAPHTHALENE-1,20'-[18]OXA[1,10]DIAZATRICYCLO[12.7.2.0¹⁷,²²]TRICOSA[6,14,16,22]TETRAENE]-13'-CARBOXYLATE, METHYL (1S,6'Z,13'R)-6-CHLORO-13'-HYDROXY-10'-METHYL-11'-OXO-3,4-DIHYDRO-2H-SPIRO[NAPHTHALENE-1,20'-[18]OXA[1,10]DIAZATRICYCLO[12.7.2.0¹⁷,²²]TRICOSA[6,14,16,22]TETRAENE]-13'-CARBOXYLATE AND METHYL (1S,6'Z,13'S)-6-CHLORO-13'-HYDROXY-10'-METHYL-11'-OXO-3,4-DIHYDRO-2H-SPIRO[NAPHTHALENE-1,20'-[18]OXA[1,10]DIAZATRICYCLO[12.7.2.0¹⁷,²²]TRICOSA[6,14,16,22]TETRAENE]-13'-CARBOXYLATE

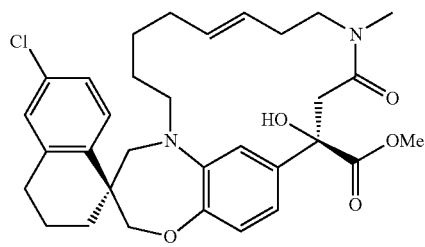
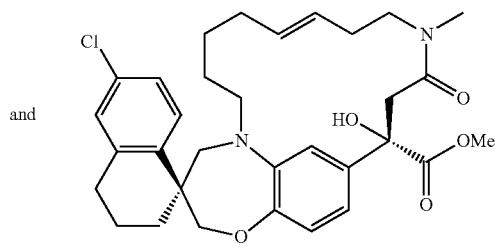

-continued

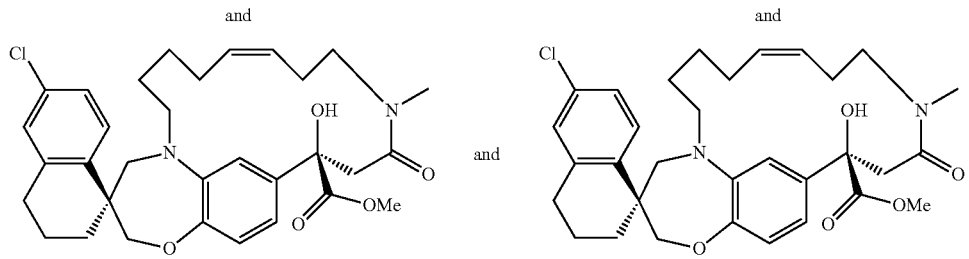

The above compounds (120 mg, 38% overall yield, 9 steps) were prepared from (S)-methyl 6'-chloro-3',4,4',5-tetrahydro-2H,2'H-spiro[benzo[b][1,4]oxazepine-3,1'-naphthalene]-7-carboxylate (from Intermediate 11A1 Step 11A) as a mixture of products in a similar fashion as described for the synthesis of Example 62 (Steps 1-3). LRMS: m/z (ESI, +ve ion) 567.2 (M+H)$^+$.

Step 2. ALCOHOL INTERMEDIATES

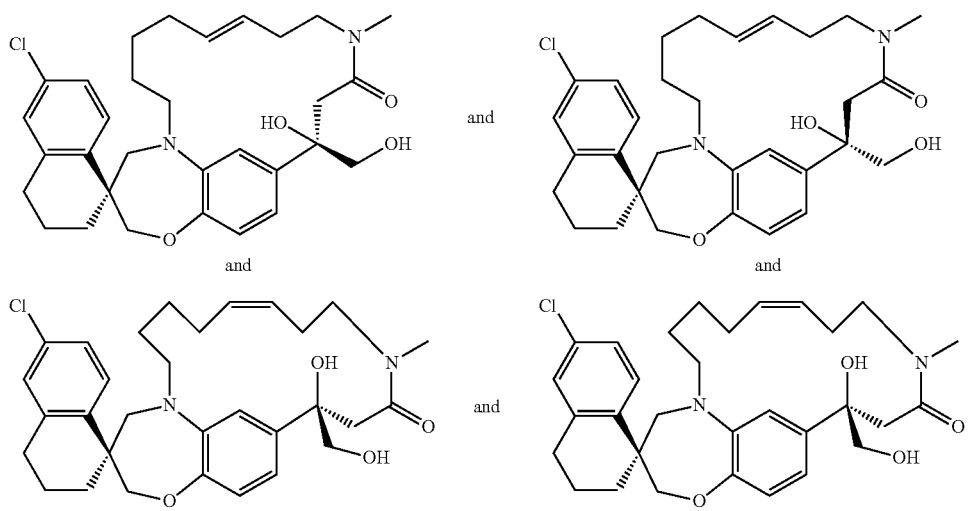 [SMILES: CN1CC/C=C/CCCCN2C[C@@]3(CCCc4cc(Cl)ccc43)COc3ccc(cc32)[C@@](O)(CO)CC1=O ; CN1CC/C=C/CCCCN2C[C@@]3(CCCc4cc(Cl)ccc43)COc3ccc(cc32)[C@](O)(CO)CC1=O ; CN1CC/C=C\CCCCN2C[C@@]3(CCCc4cc(Cl)ccc43)COc3ccc(cc32)[C@@](O)(CO)CC1=O ; CN1CC/C=C\CCCCN2C[C@@]3(CCCc4cc(Cl)ccc43)COc3ccc(cc32)[C@@](O)(CO)CC1=O]

To a solution of the methyl ester derivatives (from Step 1) (50 mg, 0.088 mmol) in THF (0.89 mL) was added sodium borohydride (6.7 mg, 0.18 mmol). The reaction mixture was stirred vigorously for 2 h. Methanol (0.55 mL) and another portion of sodium borohydride (6.7 mg, 0.18 mmol) was added to the reaction mixture. After 2 h at room temperature, the reaction was quenched by the addition of saturated aqueous NH$_4$Cl. The reaction mixture was extracted with EtOAc (3×). The combined organic phase was washed with brine, dried over Na$_2$SO$_4$, filtered and concentrated under reduced pressure. The crude material was absorbed onto a plug of silica gel and purified by chromatography through a Redi-Sep pre-packed silica gel column (12 g), eluting with a gradient of 0% to 100% EtOAc in hexane, to provide above products (19 mg, 40% yield) as an off-white solid. LRMS: m/z (ESI, +ve ion) 539.2 (M+H)$^+$.

Step 3. TERT-BUTYL ACETATE INTERMEDIATES

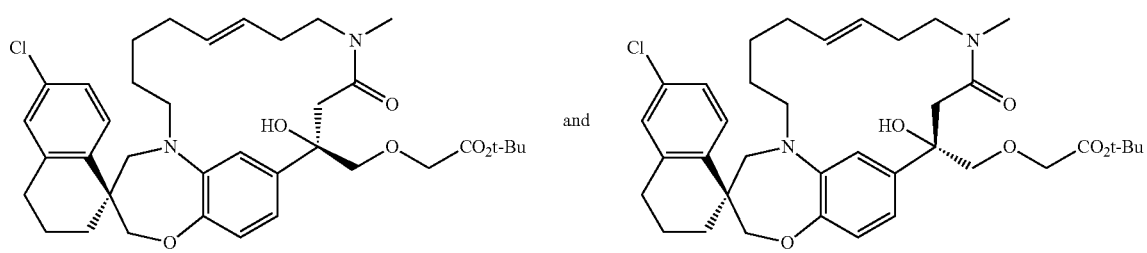

and 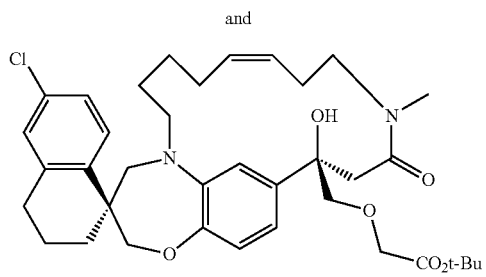 and 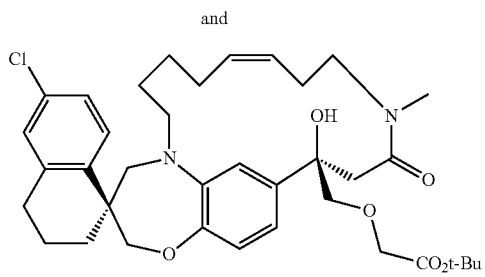 and

To a solution of the diol derivatives (from Step 2) (15 mg, 0.028 mmol) in DMF (0.14 mL) was added silver(i) oxide (19 mg, 0.083 mmol) and tert-butyl bromoacetate (27 μL, 0.17 mmol). The reaction was stirred vigorously at room temperature. Analysis by LCMS indicated consumption of the desired product after 24 h. The reaction mixture was quenched by the addition of saturated aqueous NH$_4$Cl and the mixture was extracted with EtOAc (3×). The combined organic layer was washed with brine, dried over Na$_2$SO$_4$, filtered and concentrated under reduced pressure. The crude material was absorbed onto a plug of silica gel and purified by chromatography through a Redi-Sep pre-packed silica gel column (12 g), eluting with a gradient of 0% to 60% EtOAc in hexane, to provide the above compound (10 mg, 55% yield) as an off-white solid. LRMS: m/z (ESI, +ve ion) 653.2 (M+H)$^+$.

Step 4. (((1S,13'R)-6-CHLORO-13'-HYDROXY-10'-METHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[14,16,22]TRIEN]-13'-YL)METHOXY)ACETIC ACID AND (((1S,13'S)-6-CHLORO-13'-HYDROXY-10'-METHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[14,16,22]TRIEN]-13'-YL)METHOXY)ACETIC ACID A mixture of the ester derivatives (from Step 3) (10 mg, 0.015 mmol) and platinum (IV) oxide (0.87 mg, 3.8 μmol) in EtOAc (0.77 mL) were stirred under an atmosphere of H$_2$ (balloon) at room temperature for 1 h. The reaction mixture was then filtered through a syringe filter to remove solid catalyst and concentrated under reduced pressure. The crude material was dissolved in a 1:1 mixture of DCE (0.40 mL) and trifluoroacetic acid (0.40 mL, 5.4 mmol). The reaction mixture was maintained at room temperature for 1 h. The mixture was diluted with toluene then concentrated under reduced pressure. This sequence was repeated twice, then the crude residue was purified by reverse-phase preparative HPLC (conditions: Phenomenex Gemini column, 10 micron, C18, 100 Å, 150×30 mm, eluting with a gradient of 50% to 90% acetonitrile in water (both solvents containing 0.1% TFA) over a period of 27 minutes to provide the title compounds (6.0 mg, 65% yield) as a white powder. $^1$H NMR (400 MHz, (CD$_3$)$_2$SO) δ 7.72-7.59 (m, 1H), 7.29-7.11 (m, 2H), 6.97-6.64 (m, 3H), 4.13-4.10 (m, 1H), 4.07-3.87 (m, 4H), 3.66-3.54 (m, 1H), 3.52-3.20 (m, 5H), 3.18-2.97 (m, 2H), 2.93-2.86 (m, 1H), 2.85-2.80 (m, 2H), 2.79-2.53 (m, 3H), 1.94-1.71 (m, 3H), 1.69-0.81 (m, 13H). LRMS: m/z (ESI, +ve ion) 599.2 (M+H)$^+$.

Example 93

(((1S,3'R,6'R,7'S,8'E,15'R)-6-CHLORO-15'-HYDROXY-15'-(METHOXYCARBONYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAEN]-7'-YL)OXY)ACETIC ACID (the Relative Configuration of the Title Compound has been Confirmed by Xray Co-Crystal Structure of Mcl1+Example 4)

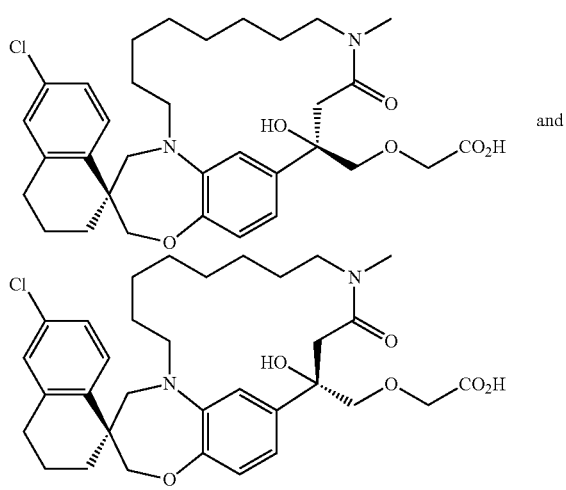 and

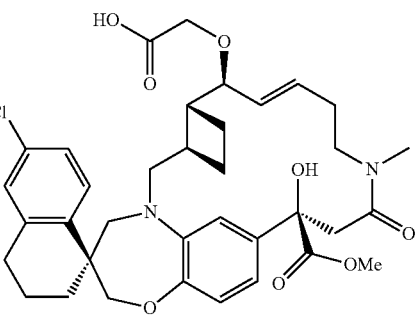

227

Step 1. TERT-BUTYL ((((1S,3'R,6'R,7'S,8'E,15'R)-6-CHLORO-15'-HYDROXY-15'-(METHOXYCARBONYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAEN]-7'-YL)OXY)ACETATE

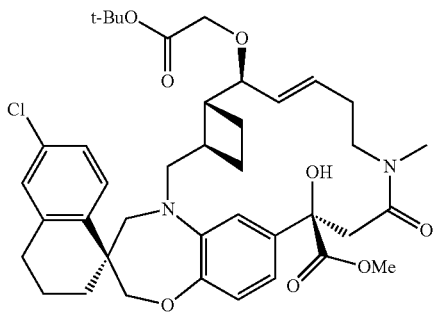 [SMILES: COC(=O)[C@@]1(O)CC(=O)N(C)CC/C=C/[C@H](OCC(=O)OC(C)(C)C)[C@@H]2CC[C@H]2CN2C[C@@]3(CCCc4cc(Cl)ccc43)COc3ccc1cc32]

To a solution of methyl (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 1, Step 7) (20 mg, 0.033 mmol) in DMF (0.30 mL) was added sodium bis(trimethylsilyl)amide, 1.0 M in THF (98 μL, 0.098 mmol) then tert-butyl bromoacetate (16 μL, 0.098 mmol). The reaction was stirred for 10 minutes then quenched by addition of saturated aqueous NH$_4$Cl. The reaction was extracted with EtOAc (2×). The organic extract was washed with saturated aqueous NaCl and dried over Na$_2$SO$_4$. The solution was filtered and concentrated in vacuo to give the crude material. The crude material was absorbed onto a plug of silica gel and purified by chromatography through a Redi-Sep pre-packed silica gel column (12 g), eluting with a gradient of 0% to 100% acetone/hexanes, to provide above product (12 mg, 51% yield) as an off-white solid. LRMS: m/z (ESI, +ve ion) 723.2 (M+H)$^+$.

228

Step 2. ((((1S,3'R,6'R,7'S,8'E,15'R)-6-CHLORO-15'-HYDROXY-15'-(METHOXYCARBONYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAEN]-7'-YL)OXY)ACETIC ACID

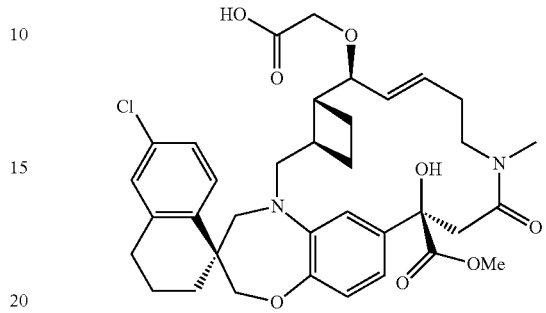

To a solution of tert-butyl ester derivative (from Step 1) (10 mg, 0.014 mmol) in 1,2-dichloroethane (1.0 mL) was added trifluoroacetic acid (0.50 mL, 6.7 mmol). The reaction mixture was maintained at room temperature for 2 h, then was diluted with toluene and concentrated under reduced pressure. This sequence was repeated twice. The crude mixture was purified by chromatography through a Redi-Sep pre-packed silica gel column (4 g), eluting with a gradient of 0% to 12.5% MeOH in CH$_2$Cl$_2$, to provide the title compound (8.5 mg, 92% yield) as a white solid. $^1$H NMR (400 MHz, CD$_2$Cl$_2$) δ 7.72 (d, J=8.4 Hz, 1H), 7.16 (dd, J=2.3, 8.4 Hz, 1H), 7.08 (d, J=2.3 Hz, 1H), 7.00 (dd, J=2.2, 8.2 Hz, 1H), 6.84 (d, J=8.2 Hz, 1H), 6.46 (s, 1H), 6.31 (t, J=12.8 Hz, 1H), 6.38-6.25 (m, 1H), 5.72 (dd, J=9.5, 16.5 Hz, 1H), 4.05-3.96 (m, 4H), 3.76-3.69 (m, 4H), 3.66-3.52 (m, 2H), 3.43 (d, J=16.6 Hz, 1H), 3.32 (d, J=14.5 Hz, 1H), 3.21-3.04 (m, 2H), 2.96 (s, 3H), 2.84-2.59 (m, 3H), 2.58-2.38 (m, 3H), 2.36-2.24 (m, 1H), 1.80-1.75 (m, 1H), 2.12-1.73 (m, 7H), 1.39 (t, J=12.3 Hz, 1H). LRMS: m/z (ESI, +ve ion) 667.2 (M+H)$^+$.

Example 94

(1S,3'R,6'R,7'S,8'E,11'S,15'R)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID (the Relative Configuration of the Title Compound has been Confirmed by x-Ray Co-Crystal Structure of Mcl1+ the Title Compound of Example 96)

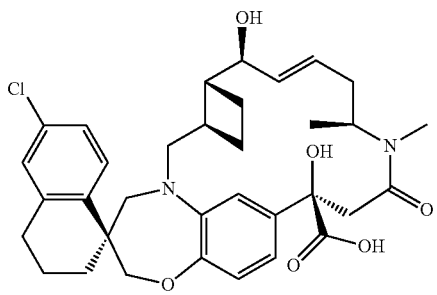 [SMILES: C[C@H]1C/C=C/[C@H](O)[C@@H]2CC[C@H]2CN2C[C@@]3(CCCc4cc(Cl)ccc43)COc3ccc(cc32)[C@@](O)(C(=O)O)CC(=O)N1C]

Step 1. (R)-METHYL 2-((S)-6'-CHLORO-5-(((1R, 2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXY-4-(METHYL((S)-PENT-4-EN-2-YL)AMINO)-4-OXOBUTANOATE AND (S)-METHYL 2-((S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXY-4-(METHYL((S)-PENT-4-EN-2-YL)AMINO)-4-OXOBUTANOATE

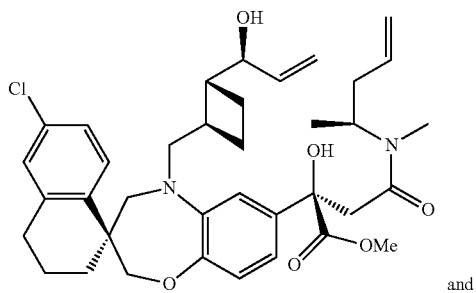

and

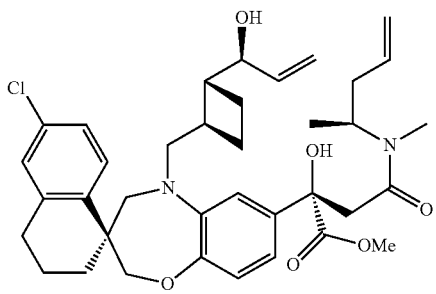

The above compounds (310 mg, 87% yield, 1.5:1 dr) were prepared from 3-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-3-hydroxy-4-methoxy-4-oxobutanoic acid (Example 1, Step 5) in a similar fashion as described for the synthesis of (R)- and (S)-methyl 4-(but-3-en-1-yl(methyl)amino)-2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-4-oxobutanoate (Example 1, Step 6). $^1$H NMR (400 MHz, CD$_2$Cl$_2$) δ 7.74-7.67 (m, 1H), 7.20-7.01 (m, 3H), 6.86-6.66 (m, 2H), 6.01-5.78 (m, 2H), 5.78-5.60 (m, 1H), 5.26-4.98 (m, 4H), 4.81-4.71 (m, 1H), 4.05-3.93 (m, 3H), 3.87-3.78 (m, 1H), 3.73-3.63 (m, 4H), 3.58-3.35 (m, 2H), 3.29-3.18 (m, 1H), 3.12 (dd, J=9.0, 15.1 Hz, 1H), 2.84-2.64 (m, 6H), 2.47 (m, 1H), 2.40-2.15 (m, 2H), 2.08-1.96 (m, 3H), 1.96-1.77 (m, 3H), 1.70-1.52 (m, 1H), 1.52-1.38 (m, 1H), 1.26-1.07 (m, 3H). LRMS: m/z (ESI, +ve ion) 637.2 (M+H)$^+$.

Step 2. METHYL (1S,3'R,6'R,7'S,8'E,11'S,15'R)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE

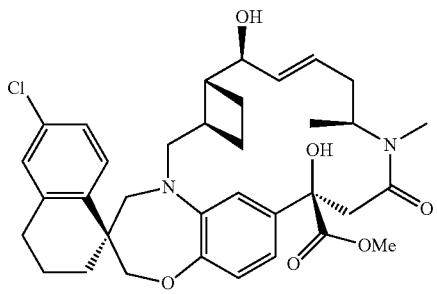 [SMILES: COC(=O)[C@@]1(O)CC(=O)N(C)[C@@H](C)C/C=C/[C@H](O)[C@@H]2CC[C@H]2CN2C[C@@]3(CCCc4cc(Cl)ccc43)COc3ccc1cc32]

The above compound (96 mg, 46% yield) was prepared as the first-eluting, isomeric product from the intermediates from Step 1 in a similar fashion as described for the synthesis of methyl (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 1, Step 7). $^1$H NMR (400 MHz, CD$_2$Cl$_2$) δ 7.73 (d, J=8.6 Hz, 1H), 7.15 (dd, J=2.3, 8.4 Hz, 1H), 7.06 (d, J=6.8 Hz, 1H), 6.99 (dd, J=2.2, 8.2 Hz, 1H), 6.82 (d, J=8.2 Hz, 1H), 6.48 (d, J=2.2 Hz, 1H), 6.17-6.08 (m, 1H), 5.96-5.87 (m, 1H), 5.34 (s, 1H), 4.26 (d, J=8.8 Hz, 1H), 4.05-3.94 (m, 2H), 3.86 (ddd, J=2.0, 6.7, 11.7 Hz, 1H), 3.76-3.68 (m, 4H), 3.62 (d, J=15.3 Hz, 1H), 3.48 (d, J=16.6 Hz, 1H), 3.32 (d, J=14.5 Hz, 1H), 3.07 (dd, J=10.0, 15.3 Hz, 1H), 2.81-2.70 (m, 5H), 2.53 (d, J=16.6 Hz, 1H), 2.50-2.31 (m, 3H), 2.18-1.70 (m, 8H), 1.42-1.30 (m, 1H), 1.19 (d, J=6.7 Hz, 3H). LRMS: m/z (ESI, +ve ion) 623.2 (M+H)$^+$.

Step 3. (1S,3'R,6'R,7'S,8'E,11'S,15'R)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

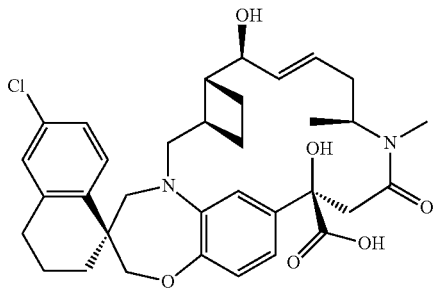 [SMILES: C[C@H]1C/C=C/[C@H](O)[C@@H]2CC[C@H]2CN2C[C@@]3(CCCc4cc(Cl)ccc43)COc3ccc(cc32)[C@@](O)(C(=O)O)CC(=O)N1C]

The title compound (8.0 mg, 55% yield) was prepared from the methyl ester derivative from Step 2 in a similar fashion as described for the synthesis of Example 4. $^1$H NMR (400 MHz, (CD$_3$)$_2$SO) δ 7.66 (d, J=8.6 Hz, 1H), 7.25

(dd, J=2.2, 8.5 Hz, 1H), 7.16 (t, J=5.6 Hz, 1H), 6.90 (dd, J=1.8, 8.2 Hz, 1H), 6.79 (d, J=8.2 Hz, 1H), 6.61 (d, J=1.8 Hz, 1H), 5.92-5.76 (m, 2H), 4.02-3.85 (m, 3H), 3.56 (d, J=15.1 Hz, 1H), 3.47 (m, 1H), 3.34 (d, J=16.8 Hz, 1H), 3.27 (d, J=14.1 Hz, 1H), 3.07 (dd, J=9.7, 15.2 Hz, 1H), 2.84-2.60 (m, 6H), 2.43-2.31 (m, 1H), 2.30-2.20 (m, 2H), 2.10 (dd, J=10.9, 13.6 Hz, 1H), 2.02-1.68 (m, 8H), 1.42-1.30 (m, 1H), 1.12 (d, J=6.7 Hz, 3H). LRMS: m/z (ESI, +ve ion) 609.2 (M+H)+.

Example 95

(1S,3'R,6'R,7'S,8'E,11'S,15'S)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID (the Relative Configuration of the Title Compound has been Confirmed by Xray Co-Crystal Structure of Mcl1+ the Title Compound of Example 27)

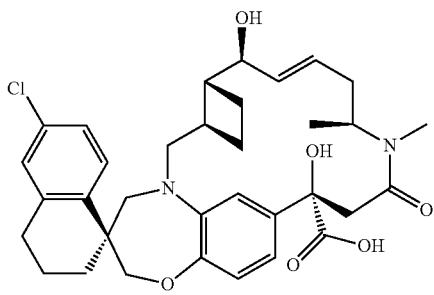 [SMILES: C[C@H]1C/C=C/[C@H](O)[C@@H]2CC[C@H]2CN2C[C@@]3(CCCc4cc(Cl)ccc43)COc3ccc(cc32)[C@](O)(C(=O)O)CC(=O)N1C]

Step 1. METHYL (1S,3'R,6'R,7'S,8'E,11'S,15'S)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE

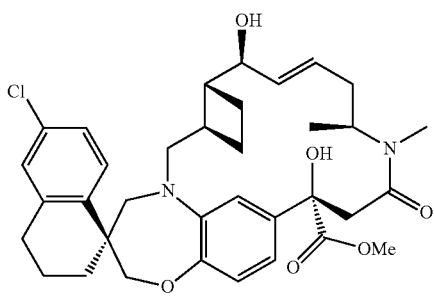 [SMILES: COC(=O)[C@]1(O)CC(=O)N(C)[C@@H](C)C/C=C/[C@H](O)[C@@H]2CC[C@H]2CN2C[C@@]3(CCCc4cc(Cl)ccc43)COc3ccc1cc32]

The above compound (40 mg, 19% yield) was prepared as the second-eluting, isomeric product from Example 94, Step 2. $^1$H NMR (400 MHz, CD$_2$Cl$_2$) δ 7.74 (d, J=8.4 Hz, 1H), 7.16 (dd, J=2.3, 8.4 Hz, 1H), 7.08 (d, J=2.3 Hz, 1H), 6.77 (s, 1H), 6.74 (d, J=8.2 Hz, 1H), 6.48-6.44 (m, 1H), 5.89 (dd, J=7.2, 15.7 Hz, 1H), 5.78-5.68 (m, 1H), 4.70 (s, 1H), 4.15 (d, J=6.7 Hz, 1H), 4.07-3.87 (m, 3H), 3.85-3.72 (m, 5H), 3.29 (d, J=14.1 Hz, 1H), 3.21 (d, J=16.4 Hz, 1H), 3.08 (dd, J=9.1, 15.2 Hz, 1H), 3.00 (d, J=16.4 Hz, 1H), 2.83-2.72 (m, 5H), 2.47-2.32 (m, 3H), 2.18-2.09 (m, 4H), 2.05 (td, J=3.6, 10.5 Hz, 2H), 1.95-1.70 (m, 6H), 1.41-1.34 (m, 1H), 1.20 (d, J=6.5 Hz, 3H). LRMS: m/z (ESI, +ve ion) 623.2 (M+H)+.

Step 2. (1S,3'R,6'R,7'S,8'E,11'S,15'S)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

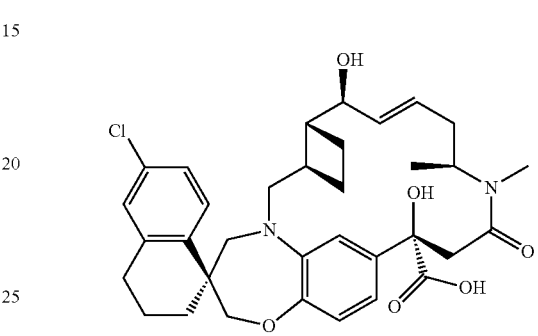

The title compound (10 mg, 51% yield) was prepared from the methyl ester derivative from Step 2 in a similar fashion as described for the synthesis of Example 4. $^1$H NMR (400 MHz, (CD$_3$)$_2$SO) δ 7.66 (d, J=8.4 Hz, 1H), 7.25 (dd, J=2.3, 8.4 Hz, 1H), 7.19-7.14 (m, 1H), 6.78 (d, J=1.6 Hz, 1H), 6.73 (d, J=8.2 Hz, 1H), 6.61-6.56 (m, 1H), 5.79 (dd, J=8.1, 15.6 Hz, 1H), 5.64 (dd, J=3.0, 9.9 Hz, 1H), 4.01-3.89 (m, 3H), 3.86 (d, J=12.1 Hz, 1H), 3.66 (d, J=14.9 Hz, 1H), 3.58 (d, J=14.3 Hz, 1H), 3.23 (d, J=14.3 Hz, 1H), 3.12-2.97 (m, 2H), 2.91-2.62 (m, 6H), 2.42-2.05 (m, 4H), 1.98-1.60 (m, 7H), 1.44-1.31 (m, 1H), 1.15-1.06 (m, 3H). LRMS: m/z (ESI, +ve ion) 609.2 (M+H)+.

Example 96

(1S,3'R,6'R,7'S,8'E,11'S,15'R)-6-CHLORO-15'-HYDROXY-7'-METHOXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID (the Relative Configuration of the Title Compound has been Confirmed by x-Ray Co-Crystal Structure of Mcl1+ the Title Compound)

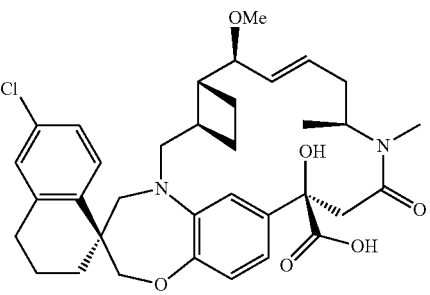 [SMILES: CO[C@H]1/C=C/C[C@H](C)N(C)C(=O)C[C@](O)(C(=O)O)c2ccc3c(c2)N(C[C@@H]2CC[C@H]21)C[C@@]1(CCCc2cc(Cl)ccc21)CO3]

233

The title compound (18 mg, 43% overall yield) was prepared from methyl (1S,3'R,6'R,7'S,8'E,11'S,15'R)-6-chloro-7',15'-dihydroxy-11',12'-dimethyl-13'-oxo-3,4-dihydro-2H-spiro[naphthalene-1,22'-[20]oxa[1,12]diazatetracyclo[14.7.2.0$^{3,6}$.0$^{19,24}$] pentacosa[8,16,18,24]tetraene]-15'-carboxylate (from Example 94, Step 2) in a similar fashion as described for the synthesis of Example 4. $^1$H NMR (400 MHz, (CD$_3$)$_2$SO) δ 7.66 (d, J=8.4 Hz, 1H), 7.25 (dd, J=2.3, 8.4 Hz, 1H), 7.16 (d, J=7.3 Hz, 1H), 6.90 (d, J=10.0 Hz, 1H), 6.80 (d, J=8.2 Hz, 1H), 6.63-6.58 (m, 1H), 6.02-5.94 (m, J=2.9 Hz, 1H), 5.70-5.62 (m, 1H), 5.46 (br. s., 1H), 3.99-3.86 (m, 3H), 3.61-3.52 (m, 2H), 3.48 (d, J=14.9 Hz, 1H), 3.29-3.22 (m, 1H), 3.11 (dd, J=10.4, 14.3 Hz, 1H), 3.05 (s, 3H), 2.83-2.60 (m, 7H), 2.45-2.28 (m, 2H), 2.21-2.12 (m, 1H), 2.03-1.69 (m, J=10.2 Hz, 1H), 1.41-1.31 (m, 1H), 1.13 (d, J=6.5 Hz, 3H). LRMS: m/z (ESI, +ve ion) 623.2 (M+H)$^+$.

Example 97

(1S,3'R,6'R,7'S,8'E,11'R,15'S)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID OR (1S,3'R,6'R,7'S,8'E,11'R,15'R)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID (the Relative Configuration of the Tertiary Alcohol Stereocenter of the Title Compound has not been Definitively Established)

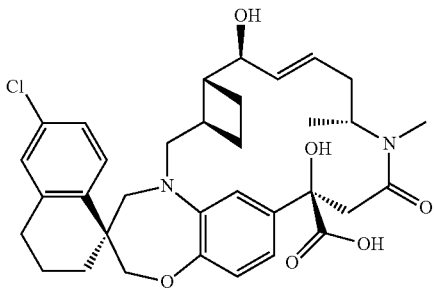

or

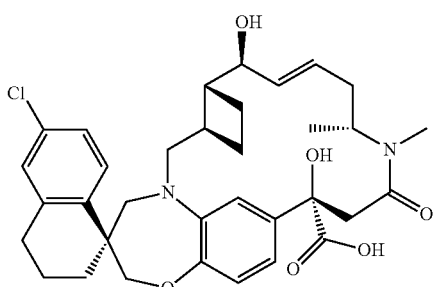

234

Step 1. (R)-METHYL 2-((S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXY-4-(METHYL((R)-PENT-4-EN-2-YL)AMINO)-4-OXOBUTANOATE AND (S)-METHYL 2-((S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXY-4-(METHYL((R)-PENT-4-EN-2-YL)AMINO)-4-OXOBUTANOATE

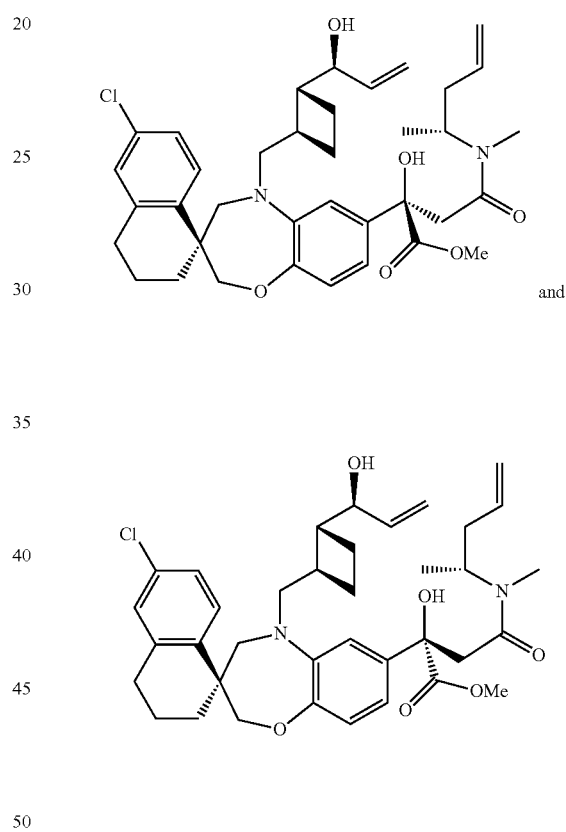

The above compounds (60 mg, 88% yield, 1.5:1 dr) were prepared from 3-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-3-hydroxy-4-methoxy-4-oxobutanoic acid (Example 1, Step 5) in a similar fashion as described for the synthesis of (R)- and (S)-methyl 4-(but-3-en-1-yl(methyl)amino)-2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-4-oxobutanoate (Example 1, Step 6). $^1$H NMR (400 MHz, CD$_2$Cl$_2$) δ 7.74-7.69 (m, 1H), 7.10-7.03 (m, 3H), 6.87-6.68 (m, 2H), 5.99 (s, 0.3H), 5.91 (s, 0.6H), 5.89-5.78 (m, 1H), 5.76-5.61 (m, 1H), 5.23 (m, 1H), 5.19-4.97 (m, 3H), 4.83-

4.71 (m, 1H), 4.06-3.93 (m, 3H), 3.82 (d, J=14.7 Hz, 1H), 3.73-3.62 (m, 4H), 3.56-3.40 (m, 2H), 3.24 (dd, J=7.6, 14.3 Hz, 1H), 3.12 (m, 1H), 2.83-2.67 (m, 6H), 2.48 (t, J=8.3 Hz, 1H), 2.39-2.16 (m, 2H), 2.08-2.01 (m, 2H), 1.95-1.54 (m, 6H), 1.52-1.39 (m, 1H), 1.18-1.06 (m, 3H). LRMS: m/z (ESI, +ve ion) 651.2 (M+H)$^+$.

Step 2. METHYL (1S,3'R,6'R,7'S,8'E,11'R,15'S)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE OR METHYL (1S,3'R,6'R,7'S,8'E,11'R,15'R)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE

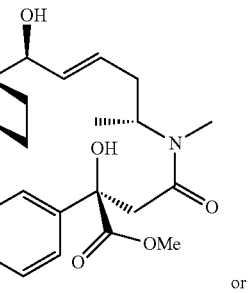

or

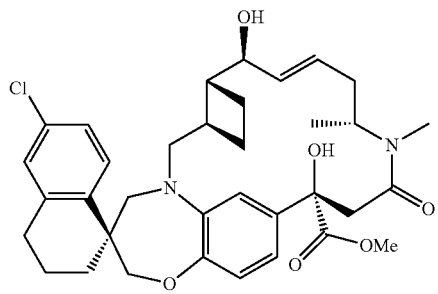

The above compound (20 mg, 35% yield) was prepared as the first-eluting, isomeric product from the intermediates from Step 1 in a similar fashion as described for the synthesis of methyl (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 1, Step 7): $^1$H NMR (400 MHz, CD$_2$Cl$_2$) δ 7.74 (d, J=8.4 Hz, 1H), 7.16 (d, J=8.4 Hz, 1H), 7.12-7.04 (m, 1H), 6.98 (d, J=8.2 Hz, 1H), 6.87-6.80 (m, 1H), 6.52 (s, 1H), 5.99-5.84 (m, 1H), 5.79-5.69 (m, 1H), 5.18 (s, 1H), 4.05-3.99 (m, 1H), 3.99-3.89 (m, 3H), 3.84-3.66 (m, 6H), 3.61 (d, J=15.1 Hz, 1H), 3.47 (d, J=11.7 Hz, 1H), 3.33 (d, J=14.3 Hz, 1H), 3.07 (dd, J=11.2, 14.8 Hz, 1H), 2.87-2.65 (m, 7H), 2.52 (d, J=16.4 Hz, 1H), 2.40 (app t, J=13.3 Hz, 1H), 2.27-2.14 (m, 2H), 2.09-1.82 (m, 7H), 1.82-1.71 (m, 1H), 1.71-1.59 (m, 2H), 1.39 (app t, J=12.0 Hz, 1H), 1.21-1.12 (m, 3H). LRMS: m/z (ESI, +ve ion) 623.2 (M+H)$^+$.

Step 3. (1S,3'R,6'R,7'S,8'E,11'R,15'S)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID OR (1S,3'R,6'R,7'S,8'E,11'R,15'R)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

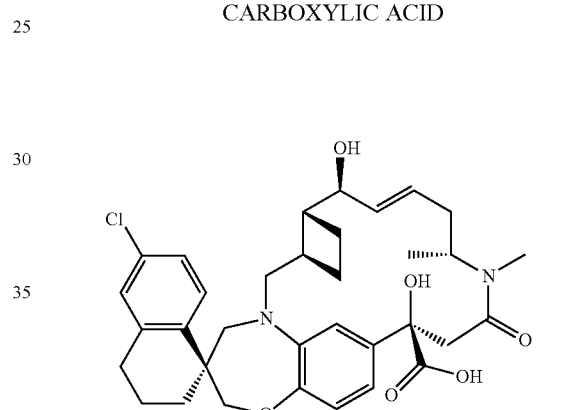

or

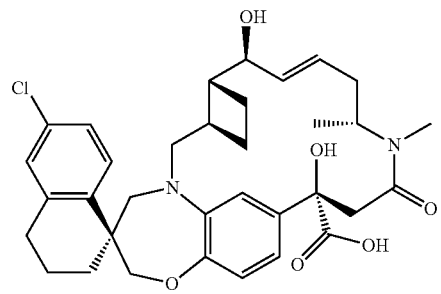

The title compound (6.0 mg, 61% overall yield) was prepared from the methyl ester derivative (from Step 2) in a similar fashion as described for the synthesis of Example 4. $^1$H NMR (400 MHz, (CD$_3$)$_2$SO) δ 7.71-7.58 (m, 1H), 7.29-7.13 (m, 2H), 7.09-7.02 (m, 0.2H), 6.90-6.81 (m, 1H), 6.80-6.75 (m, 0.8H), 6.64-6.46 (m, 1H), 5.68 (m, 1H), 5.58-5.45 (m, 0.2H), 5.44-5.18 (m, 0.8H), 4.85-4.70 (m, 0.2H), 4.19-4.06 (m, 0.8H), 4.00-3.78 (m, 3H), 3.70-3.39 (m, 3H), 3.29-3.19 (m, 1H), 3.15-2.96 (m, 1H), 2.85-2.59 (m, 6H), 2.41-2.28 (m, 1H), 2.27-2.13 (m, 2H), 1.98-1.92 (m, 1H), 1.88-1.75 (m, 4H), 1.73-1.60 (m, 2H), 1.54-1.31 (m, 1H), 1.11-0.94 (m, 3H). LRMS. m/z (ESI, +ve ion) 609.2 (M+H)$^+$.

Example 98

(1S,3'R,6'R,7'S,8'E,11'R,15'S)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID OR (1S,3'R,6'R,7'S,8'E,11'R,15'R)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID (the Relative Configuration of the Tertiary Alcohol Stereocenter of the Title Compound has not been Definitively Established, and is Epimeric to the Title Compound of Example 97)

Step 1. METHYL (1S,3'R,6'R,7'S,8'E,11'R,15'S)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE OR METHYL (1S,3'R,6'R,7'S,8'E,11'R,15'R)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE

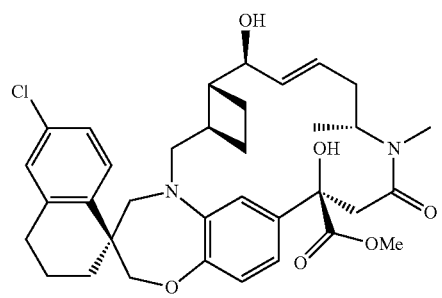

or

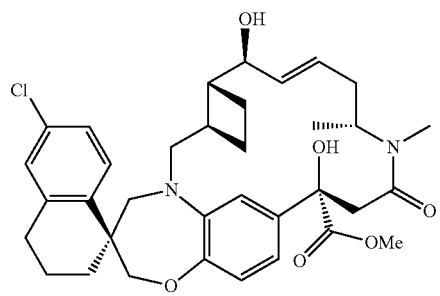

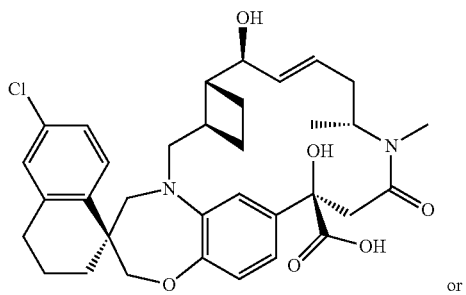

or

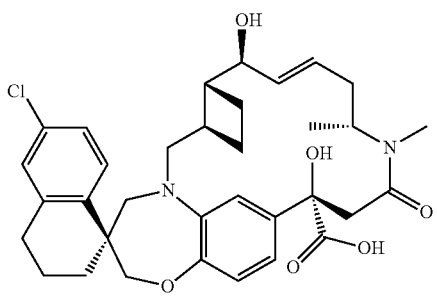

The above compound (37 mg, 64% yield) was prepared as the second-eluting, isomeric product from Example 97, Step 2. $^1$H NMR (400 MHz, CD$_2$Cl$_2$) δ 7.47 (br. s., 1H), 7.10 (m, 3H), 6.85 (d, J=8.0 Hz, 1H), 6.64 (d, J=7.4 Hz, 1H), 5.55 (d, J=14.9 Hz, 1H), 5.28-4.89 (m, 1H), 4.21-3.99 (m, 2H), 3.96-3.55 (m, 8H), 3.49-3.22 (m, 3H), 3.15-2.90 (m, 2H), 2.88-2.73 (m, 5H), 2.63-2.20 (m, 4H), 2.17-1.99 (m, 3H), 1.98-1.54 (m, 9H), 1.21-1.11 (m, 3H). LRMS: m/z (ESI, +ve ion) 623.2 (M+H)$^+$.

Step 2. (1S,3'R,6'R,7'S,8'E,11'R,15'S)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID OR (1S,3'R,6'R,7'S,8'E,11'R,15'R)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

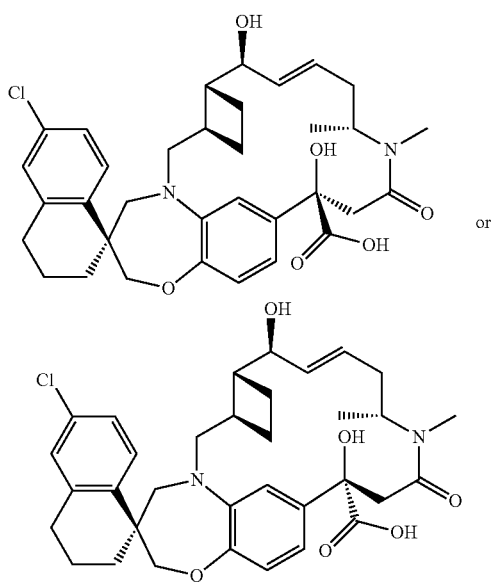

The title compound (10 mg, 51% overall yield) was prepared from the methyl ester derivative (from Step 1) in a similar fashion as described for the synthesis of Example 4. $^1$H NMR (400 MHz, (CD$_3$)$_2$SO) δ 7.56 (d, J=8.0 Hz, 0.1H), 7.41 (d, J=8.6 Hz, 0.9H), 7.19 (d, J=2.2 Hz, 1H), 7.13 (d, J=8.4 Hz, 1H), 6.93 (app s, 1H), 6.88 (d, J=8.0 Hz, 1H), 6.74 (d, J=8.0 Hz, 1H), 5.46-5.30 (m, 1H), 4.40 (d, J=4.5 Hz, 1H), 3.97 (d, J=11.7 Hz, 1H), 3.88-3.72 (m, 3H), 3.54 (d, J=10.2 Hz, 1H), 3.43-3.35 (m, 1H), 3.28-3.21 (m, 1H), 3.20-3.08 (m, 1H), 3.05-2.92 (m, 1H), 2.86-2.73 (m, 3H), 2.66 (s, 3H), 2.34-2.11 (m, 4H), 2.10-2.00 (m, 1H), 1.89-1.77 (m, 3H), 1.73-1.46 (m, 4H), 1.09-0.95 (m, 3H). LRMS: m/z (ESI, +ve ion) 609.2 (M+H)$^+$.

Example 99

(1S,3'R,6'R,7'S,8'E,14'S,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID OR (1S,3'R,6'R,7'S,8'E,14'R,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID OR (1S,3'R,6'R,7'S,8'E,14'R,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID, OR (1S,3'R,6'R,7'S,8'E,14'S,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID (the Relative Configuration of this Single Isomer has not been Definitively Established, and is Isomeric to the Title Compound of Example 100, Example 101, and Example 102)

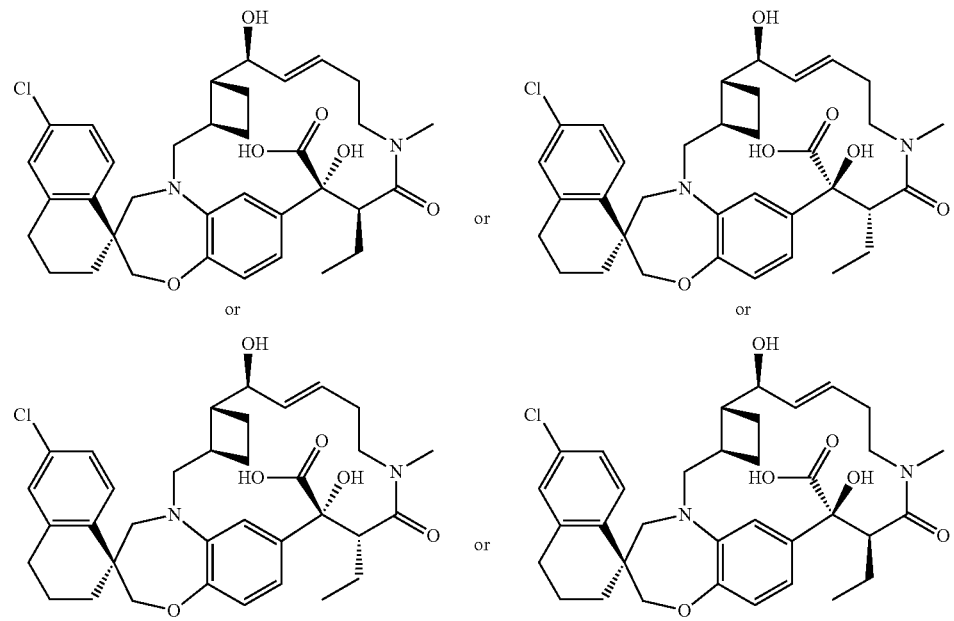 [SMILES: CC[C@@H]1C(=O)N(C)CC/C=C/[C@H](O)[C@@H]2CC[C@H]2CN2C[C@@]3(CCCc4cc(Cl)ccc43)COc3ccc(cc32)[C@@]1(O)C(=O)O ; CC[C@H]1C(=O)N(C)CC/C=C/[C@H](O)[C@@H]2CC[C@H]2CN2C[C@@]3(CCCc4cc(Cl)ccc43)COc3ccc(cc32)[C@]1(O)C(=O)O ; CC[C@H]1C(=O)N(C)CC/C=C/[C@H](O)[C@@H]2CC[C@H]2CN2C[C@@]3(CCCc4cc(Cl)ccc43)COc3ccc(cc32)[C@@]1(O)C(=O)O ; CC[C@@H]1C(=O)N(C)CC/C=C/[C@H](O)[C@@H]2CC[C@H]2CN2C[C@@]3(CCCc4cc(Cl)ccc43)COc3ccc(cc32)[C@]1(O)C(=O)O]

Step 1. (2R,3S)-3-(TERT-BUTOXYCARBONYL)-2-((S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXYPENTANOIC ACID AND/OR (2S,3R)-3-(TERT-BUTOXYCARBONYL)-2-((S)-6'-CHLORO-5-(((1R,2R)-2-((S,E)-1-HYDROXYBUT-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXYPENTANOIC ACID AND/OR (2R,3R)-3-(TERT-BUTOXYCARBONYL)-2-((S)-6'-CHLORO-5-(((1R,2R)-2-((S,E)-1-HYDROXYBUT-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXYPENTANOIC ACID AND/OR (2S,3S)-3-(TERT-BUTOXYCARBONYL)-2-((S)-6'-CHLORO-5-(((1R,2R)-2-((S,E)-1-HYDROXYBUT-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXYPENTANOIC ACID Under an argon atmosphere, to a solution of lithium diisopropylamide, 2.0 M heptane/THF/ethylbenzene (1.23 mL, 2.45 mmol) in toluene (1.31 mL) at −78° C. was added tert-butyl butyrate (3.53 mL, 2.45 mmol) (as a solution in 0.100 mL of toluene). The reaction was maintained at −78° C. for 4 h, then methyl 2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-oxoacetate (Example 1, Step 3) (250 mg, 0.490 mmol) was added (as a 0.500 mL solution in THF) slowly. After 1 h, the reaction mixture was quenched by the addition of water, then saturated aqueous ammonium chloride was added. The reaction mixture was extracted with EtOAc (3×). The combined organic layer was dried over sodium sulfate, filtered and concentrated under reduced pressure. The crude material was absorbed onto a plug of silica gel and purified by chromatography through a Redi-Sep pre-packed silica gel column (40 g), eluting with a gradient of 0% to 100% EtOAc in hexane, to provide the above compounds as the first-eluting isomers (1:1 mixture of two diastereomers, 90 mg, 28% yield) and the second-eluting isomers (1:1 mixture of two diastereomers, 140 mg, 44% yield). Characterization data for the first-eluting isomers: $^1$H NMR (400 MHz, CD$_2$Cl$_2$) δ 7.76 (dd, J=1.7, 8.5 Hz, 1H), 7.19 (dd, J=2.3, 8.4 Hz, 1H), 7.14-7.09 (m, 1.5H), 7.02 (m, 0.5H), 6.93-6.84 (m,

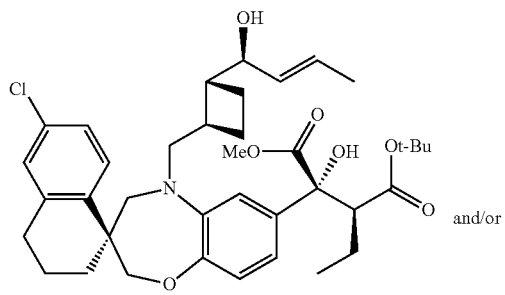

and/or

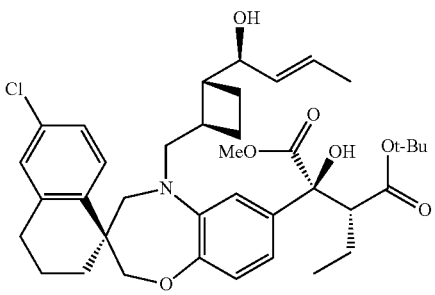

and/or

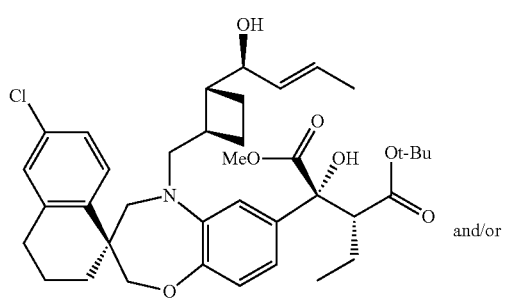

and/or

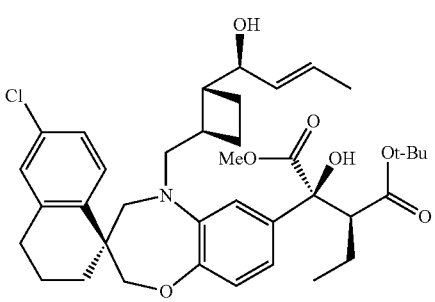

2H), 5.94-5.84 (m, 1H), 5.29 (m, 1H), 5.13 (td, J=1.5, 5.0 Hz, 0.5H), 5.10 (td, J=1.5, 5.0 Hz, 0.5H), 4.62 (s, 0.5H), 4.58 (s, 0.5H), 4.11-3.98 (m, 3H), 3.88-3.79 (m, 1H), 3.75 (s, 1.5H), 3.73 (s, 1.5H), 3.70 (d, J=14.3 Hz, 1H), 3.31-3.06 (m, 4H), 2.86-2.73 (m, 2H), 2.49 (d, J=8.4 Hz, 1H), 2.12-2.02 (m, 3H), 2.00-1.82 (m, 3H), 1.76-1.55 (m, 4H), 1.52 (d, J=1.4 Hz, 9H), 1.49-1.33 (m, 2H), 0.99-0.90 (m, 3H). LRMS: m/z (ESI, +ve ion) 654.2 (M+H)+.

Step 2. METHYL (1S,3'R,6'R,7'S,8'E,14'S,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE OR METHYL (1S,3'R,6'R,7'S, 8'E,14'R,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE OR METHYL (1S,3'R,6'R,7'S, 8'E,14'R,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE OR METHYL (1S,3'R,6'R,7'S, 8'E,14'S,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE

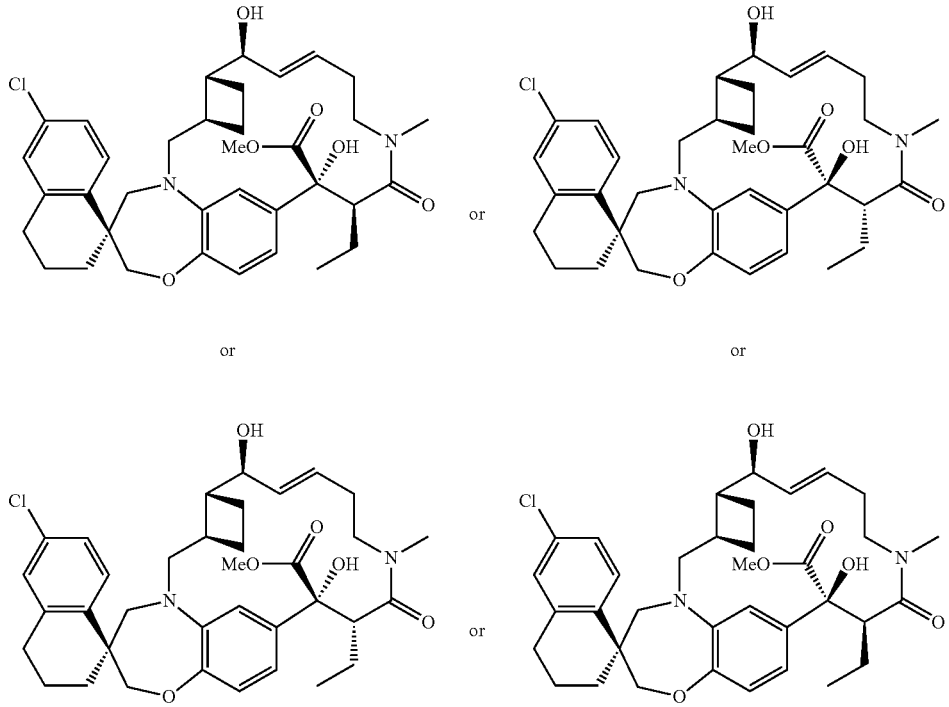

The title compound (30 mg, 35% overall yield) was prepared as the first-eluting, isomeric product from the intermediates from Step 1 in a similar fashion as described for the synthesis of methyl (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 1, Step 7). $^1$H NMR (400 MHz, CD$_2$Cl$_2$) δ 7.74 (d, J=8.4 Hz, 1H), 7.15 (dd, J=2.1, 8.5 Hz, 1H), 7.10-7.03 (m, 1H), 6.94 (dd, J=1.7, 8.1 Hz, 1H), 6.80 (d, J=8.0 Hz, 1H), 6.58-6.52 (m, 1H), 6.16-6.06 (m, 1H), 5.68 (d, J=15.7 Hz, 1H), 5.07 (s, 1H), 4.05-3.87 (m, 3H), 3.80-3.67 (m, 6H), 3.59 (d, J=14.3 Hz, 1H), 3.47 (t, J=6.3 Hz, 1H), 3.33 (d, J=14.5 Hz, 1H), 3.17 (dd, J=2.7, 14.3 Hz, 1H), 3.09-2.98 (m, 1H), 2.93 (s, 3H), 2.82-2.57 (m, 4H), 2.29-2.14 (m, 2H), 2.07-1.81 (m, 5H), 1.77-1.49 (m, 4H), 1.48-1.31 (m, 2H), 0.65 (t, J=7.6 Hz, 3H). LRMS. m/z (ESI, +ve ion) 637.2 (M+H)+.

Step 3. (1S,3'R,6'R,7'S,8'E,14'S,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID OR (1S,3'R,6'R,7'S,8'E,14'R,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID OR (1S,3'R,6'R,7'S,8'E,14'R,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID OR (1S,3'R,6'R,7'S,8'E,14'S,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID

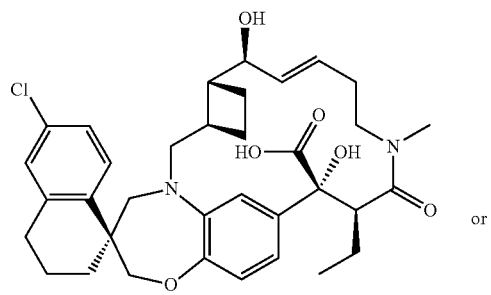

or

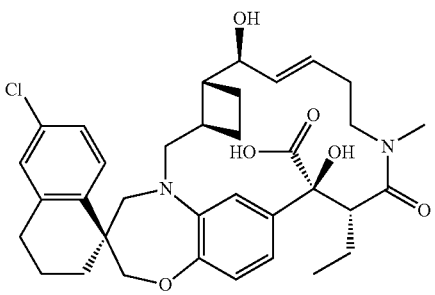

or

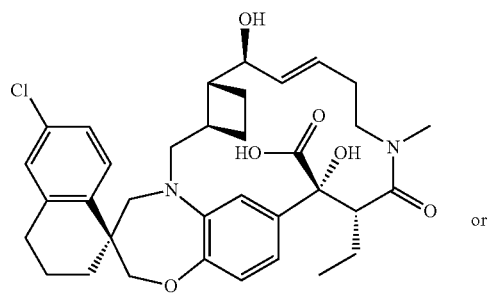

or

The title compound (11 mg, 94% yield) was prepared from the methyl ester derivative from Step 2 in a similar fashion as described for the synthesis of Example 4. $^1$H NMR (400 MHz, (CD$_3$)$_2$SO) δ 7.74-7.56 (m, 1H), 7.34-7.08 (m, 3H), 7.04-6.86 (m, 1H), 6.81 (d, J=7.6 Hz, 1H), 6.75-6.58 (m, 1H), 5.67 (m, 1.4H), 5.29 (m, 0.6H), 4.25-3.91 (m, 2H), 3.90-3.77 (m, 3H), 3.75-3.64 (m, 2H), 3.58-3.42 (m, 2H), 3.27-3.07 (m, 1H), 3.04 (s, 1H), 2.87 (s, 2H), 2.83-2.68 (m, 2H), 2.24 (m, 2H), 2.05-1.90 (m, 1H), 1.89-1.76 (m, 4H), 1.73-1.27 (m, 6H), 0.97-0.60 (m, 3H). LRMS: m/z (ESI, +ve ion) 623.2 (M+H)$^+$.

Example 100

(1S,3'R,6'R,7'S,8'E,14'S,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID OR (1S,3'R,6'R,7'S,8'E,14'R,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID OR (1S,3'R,6'R,7'S,8'E,14'R,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID OR (1S,3'R,6'R,7'S,8'E,14'S,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID (the Relative Configuration of this Single Isomer has not been Definitively Established, and is Isomeric to the Title Compound of Example 100, Example 101, and Example 102)

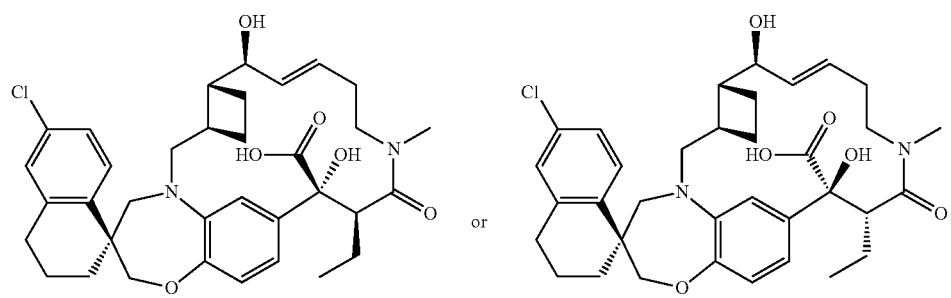

or

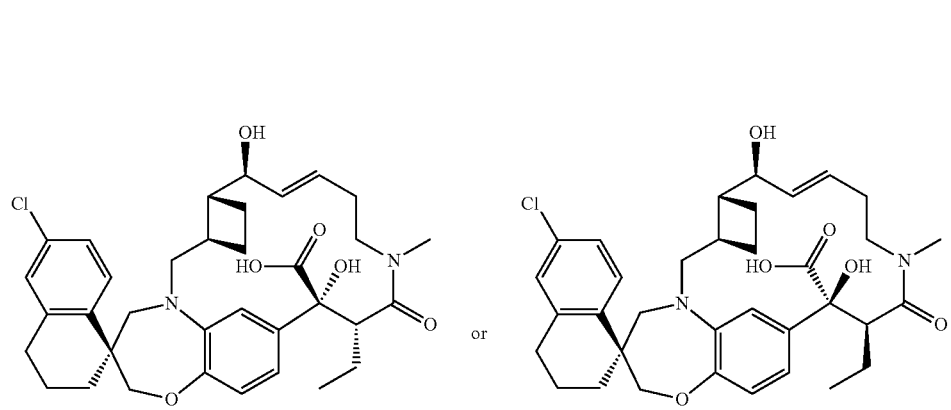

Step 1. METHYL (1S,3'R,6'R,7'S,8'E,14'S,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLATE OR METHYL (1S,3'R,6'R,7'S,8'E,14'R,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLATE OR METHYL (1S,3'R,6'R,7'S,8'E,14'R,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLATE OR METHYL (1S,3'R,6'R,7'S,8'E,14'S,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLATE

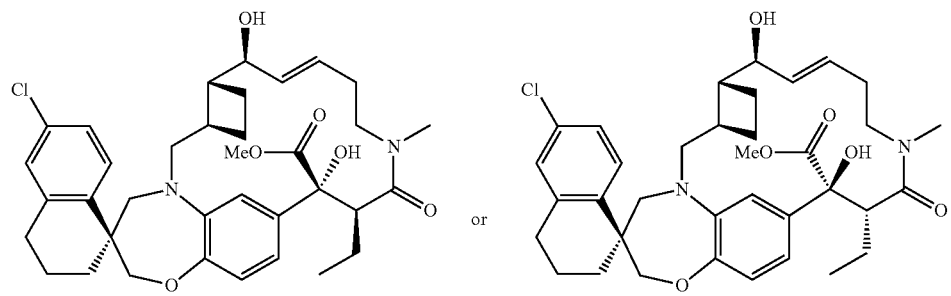

or

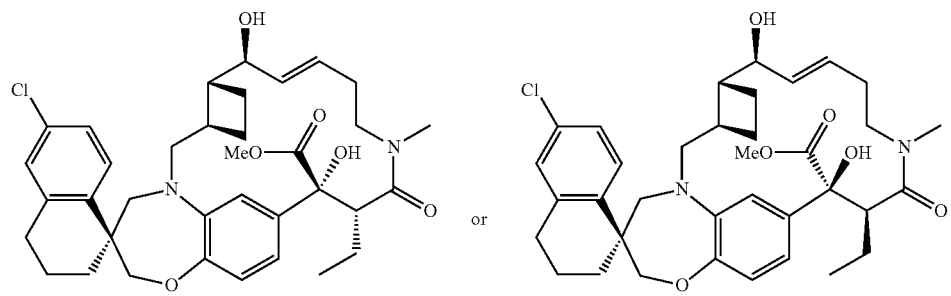

The above compound (24 mg, 28% overall yield) was prepared as the second-eluting, isomeric product from Example 99, Step 2. ¹H NMR (400 MHz, CD$_2$Cl$_2$) δ 7.75 (d, J=8.6 Hz, 1H), 7.16 (dd, J=2.2, 8.5 Hz, 1H), 7.08 (d, J=2.2 Hz, 1H), 7.01 (d, J=7.7 Hz, 1H), 6.83 (d, J=8.2 Hz, 1H), 6.58 (ddd, J=2.9, 11.3, 14.9 Hz, 1H), 6.49 (d, J=2.0 Hz, 1H), 5.85-5.77 (m, 2H), 4.25 (d, J=9.0 Hz, 1H), 4.05-3.95 (m, 2H), 3.78-3.56 (m, 6H), 3.34 (d, J=14.5 Hz, 1H), 3.28-3.15 (m, 2H), 3.07 (dd, J=10.2, 15.3 Hz, 1H), 2.93 (s, 3H), 2.84-2.70 (m, 2H), 2.67-2.54 (m, 1H), 2.40-2.17 (m, 3H), 2.07-1.80 (m, 6H), 1.79-1.59 (m, 2H), 1.46-1.31 (m, 3H), 0.60 (t, J=7.6 Hz, 2H). LRMS: m/z (ESI, +ve ion) 637.2 (M+H)⁺.

Step 2. (1S,3'R,6'R,7'S,8'E,14'S,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID OR (1S,3'R,6'R,7'S,8'E,14'R,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID OR (1S,3'R,6'R,7'S,8'E,14'R,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID OR (1S,3'R,6'R,7'S,8'E,14'S,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID

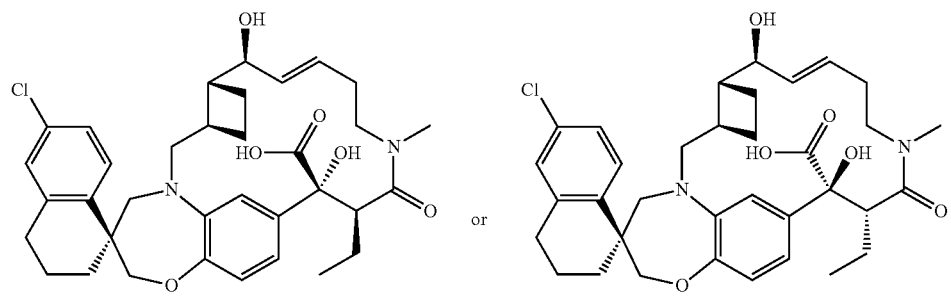

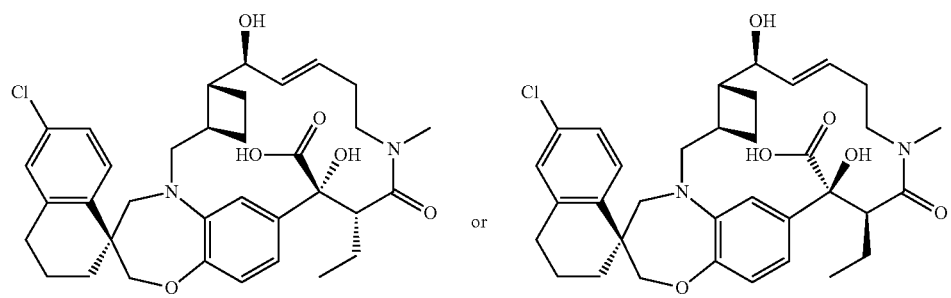

The title compound (11 mg, 75% yield) was prepared from the methyl ester derivative from Step 1 in a similar fashion as described for the synthesis of Example 4. $^1$H NMR (400 MHz, (CD$_3$)$_2$SO) δ 7.66 (d, J=8.6 Hz, 1H), 7.24 (dd, J=7.9, 13.9 Hz, 1H), 7.15 (d, J=2.2 Hz, 1H), 6.93-6.86 (m, 1H), 6.81 (d, J=8.2 Hz, 1H), 6.71-6.55 (m, 1H), 6.33 (app t, J=11.8 Hz, 1H), 5.86-5.73 (br s, 1H), 5.68 (dd, J=8.8, 15.7 Hz, 1H), 4.06-3.87 (m, 3H), 3.57 (d, J=14.3 Hz, 1H), 3.48 (d, J=14.9 Hz, 1H), 3.30-3.22 (m, 1H), 3.22-3.16 (m, 1H), 3.07 (dd, J=10.5, 15.0 Hz, 1H), 2.86 (s, 3H), 2.84-2.62 (m, 2H), 2.30-2.15 (m, 3H), 2.02-1.92 (m, 1H), 1.90-1.64 (m, 7H), 1.59 (td, J=7.4, 14.7 Hz, 1H), 1.42-1.31 (m, 1H), 1.31-1.21 (m, 1H), 0.50 (t, J=7.5 Hz, 3H). LRMS: m/z (ESI, +ve ion) 623.2 (M+H)$^+$.

Example 101

(1S,3'R,6'R,7'S,8'E,14'S,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID, (1S,3'R,6'R,7'S,8'E,14'R,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID, (1S,3'R,6'R,7'S,8'E,14'R,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID, OR (1S,3'R,6'R,7'S,8'E,14'S,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID (the Relative Configuration of this Single Isomer has not been Definitively Established, and is Isomeric to the Title Compound of Example 100, Example 101, and Example 102)

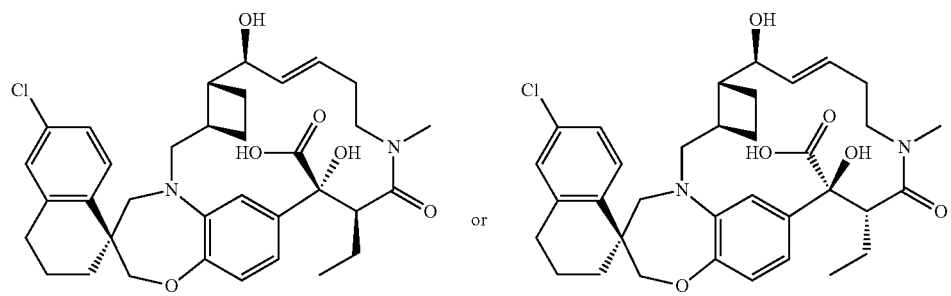

or

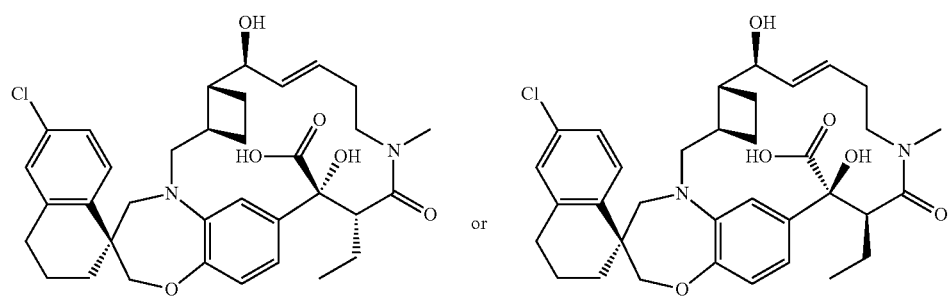

Step 1. (2R,3S)-3-(TERT-BUTOXYCARBONYL)-2-((S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXYPENTANOIC ACID AND/OR (2S,3R)-3-(TERT-BUTOXYCARBONYL)-2-((S)-6'-CHLORO-5-(((1R,2R)-2-((S,E)-1-HYDROXYBUT-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXYPENTANOIC ACID AND/OR (2R,3R)-3-(TERT-BUTOXYCARBONYL)-2-((S)-6'-CHLORO-5-(((1R,2R)-2-((S,E)-1-HYDROXYBUT-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXYPENTANOIC ACID, AND/OR (2S,3S)-3-(TERT-BUTOXYCARBONYL)-2-((S)-6'-CHLORO-5-(((1R,2R)-2-((S,E)-1-HYDROXYBUT-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXYPENTANOIC ACID

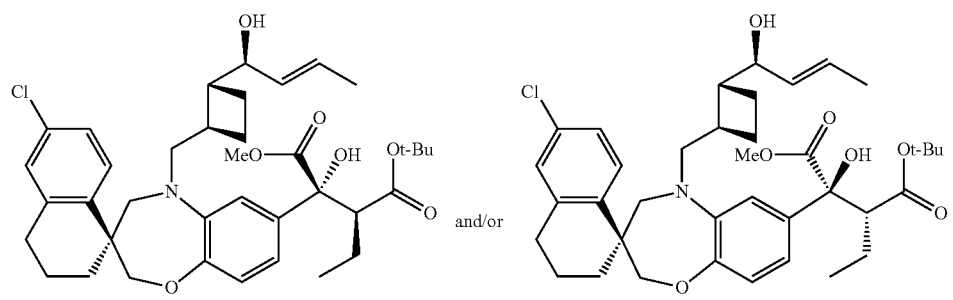

and/or

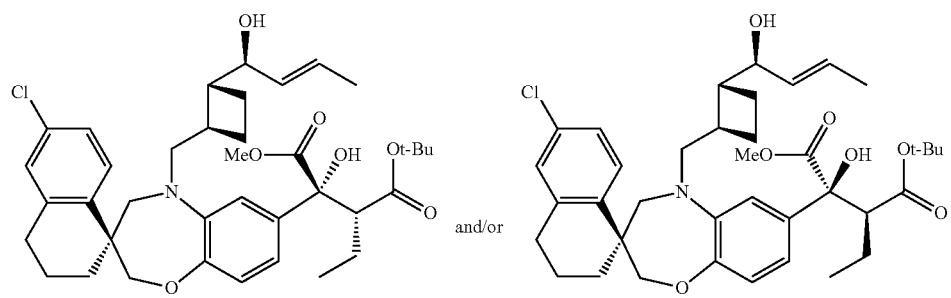

The above compounds (1:1 mixture of two diastereomers, 140 mg, 44% overall yield) was prepared as the second-eluting, isomeric products from Example 99, Step 1. $^1$H NMR (400 MHz, CD$_2$Cl$_2$) δ 7.72-7.68 (m, 1H), 7.19-7.07 (m, 3H), 6.86-6.78 (m, 2H), 5.91-5.81 (m, 1H), 5.27 (td, J=1.6, 7.1 Hz, 0.5H), 5.23 (td, J=1.6, 7.1 Hz, 0.5H), 5.08 (td, J=1.6, 4.5 Hz, 0.5H), 5.06 (td, J=1.5, 4.4 Hz, 0.5H), 4.35 (s, 0.5H), 4.26 (s, 0.5H), 4.05-3.94 (m, 2H), 3.80 (dd, J=1.9, 5.8 Hz, 1H), 3.75 (s, 1.5H), 3.72 (s, 1.5H), 3.63 (dd, J=10.2, 14.1 Hz, 1H), 3.41-3.17 (m, 3H), 3.13-3.04 (m, 1H), 2.81-2.69 (m, 2H), 2.55-2.43 (m, 1H), 2.09-1.76 (m, 7H), 1.72-1.37 (m, 5H), 1.24 (d, J=9.0 Hz, 9H), 0.98 (q, J=7.3 Hz, 3H). LRMS: m/z (ESI, +ve ion) 654.2 (M+H)$^+$.

Step 2. (2R,3S)-METHYL 3-(BUT-3-EN-1-YL (METHYL)CARBAMOYL)-2-((S)-6'-CHLORO-5-(((1R,2R)-2-((S)-1-HYDROXYALLYL)CY-CLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXYPENTANOATE AND/OR (2S,3R)-METHYL 3-(BUT-3-EN-1-YL(METHYL) CARBAMOYL)-2-((S)-6'-CHLORO-5-(((1R,2R)-2-((S)-1-HYDROXYALLYL)CYCLOBUTYL) METHYL)-3',4,4',5-TETRAHYDRO-2H,2'H-SPIRO[BENZO[B][1,4]OXAZEPINE-3,1'-NAPHTHALEN]-7-YL)-2-HYDROXYPENTANOATE AND/OR (2R,3R)-METHYL 3-(BUT-3-EN-1-YL(METHYL) CARBAMOYL)-2-((S)-6'-CHLORO-5-(((1R,2R)-2-((S)-1-HYDROXYALLYL)CYCLOBUTYL) METHYL)-3',4,4',5-TETRAHYDRO-2H,2'H-SPIRO[BENZO[B][1,4]OXAZEPINE-3,1'-NAPHTHALEN]-7-YL)-2-HYDROXYPENTANOATE AND/OR (2S,3S)-METHYL 3-(BUT-3-EN-1-YL(METHYL) CARBAMOYL)-2-((S)-6'-CHLORO-5-(((1R,2R)-2-((S)-1-HYDROXYALLYL)CYCLOBUTYL) METHYL)-3',4,4',5-TETRAHYDRO-2H,2'H-SPIRO[BENZO[B][1,4]OXAZEPINE-3,1'-NAPHTHALEN]-7-YL)-2-HYDROXYPENTANOATE

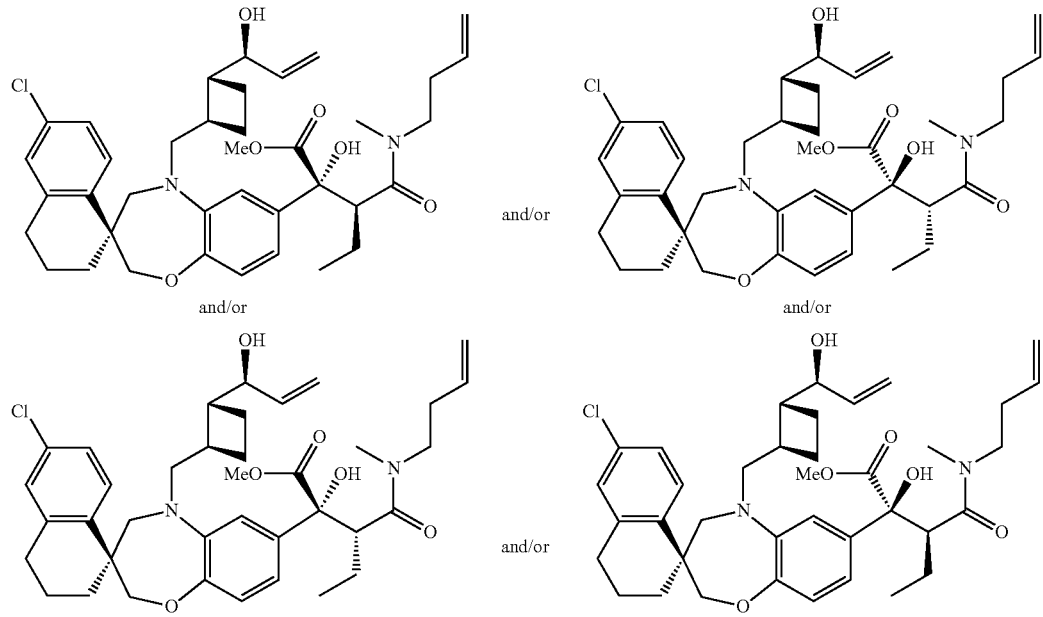 [SMILES: C=CCCN(C)C(=O)[C@@H](CC)[C@](O)(C(=O)OC)c1ccc2c(c1)N(C[C@@H]1CC[C@H]1[C@@H](O)C=C)C[C@@]1(CCCc3cc(Cl)ccc31)CO2 ; C=CCCN(C)C(=O)[C@H](CC)[C@@](O)(C(=O)OC)c1ccc2c(c1)N(C[C@@H]1CC[C@H]1[C@@H](O)C=C)C[C@@]1(CCCc3cc(Cl)ccc31)CO2 ; C=CCCN(C)C(=O)[C@H](CC)[C@](O)(C(=O)OC)c1ccc2c(c1)N(C[C@@H]1CC[C@H]1[C@@H](O)C=C)C[C@@]1(CCCc3cc(Cl)ccc31)CO2 ; C=CCCN(C)C(=O)[C@@H](CC)[C@@](O)(C(=O)OC)c1ccc2c(c1)N(C[C@@H]1CC[C@H]1[C@@H](O)C=C)C[C@@]1(CCCc3cc(Cl)ccc31)CO2]

To a flask containing the intermediates from Step 1 (140 mg, 0.21 mmol) was added trifluoroacetic acid (1.0 mL, 13 mmol) (neat). The reaction mixture was stirred at room temperature for 1 h, then diluted with toluene (10 mL) and concentrated in vacuo. This sequence was repeated twice to afford the acid intermediates (125 mg, 98% yield) as an off-white solid in sufficient purity to carry forward (LRMS: m/z (ESI, +ve ion) 598.2 (M+H)$^+$). To a solution of the acid intermediates (83 mg, 0.140 mmol) in THF (0.90 mL) was added N-hydroxysuccinimide (24 mg, 0.21 mmol) and dicyclohexylcarbodiimide (34 mg, 0.17 mmol). The reaction was maintained for 1 h (LCMS indicated formation of the hydroxysuccinimde ester intermediate (LRMS: m/z (ESI, +ve ion) 695.2 (M+H)$^+$). Then, N-methylbut-3-en-1-amine hydrochloride (220 mg, 1.8 mmol) in THF (0.50 mL) was added. The vessel was sealed and the reaction mixture was maintained at room temperature for 7 d. The reaction mixture was quenched by pouring into saturated NH$_4$Cl. The product was extracted with EtOAc (2×). The combined organic layer was washed with saturated aqueous LiCl, brine then dried over Na$_2$SO$_4$, filtered and concentrated. under reduced pressure.

The crude material was absorbed onto a plug of silica gel and purified by chromatography through a Redi-Sep prepacked silica gel column (12 g), eluting with a gradient of 0% to 100% EtOAc in hexane, to provide the above compounds (69 mg, 0.104 mmol, 75% yield) as a white solid. LRMS: m/z (ESI, +ve ion) 665.2 (M+H)+.

Step 3. METHYL (1S,3'R,6'R,7'S,8'E,14'S,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE OR METHYL (1S,3'R,6'R,7'S,8'E,14'R,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE OR METHYL (1S,3'R,6'R,7'S,8'E,14'R,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE OR METHYL (1S,3'R,6'R,7'S,8'E,14'S,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE

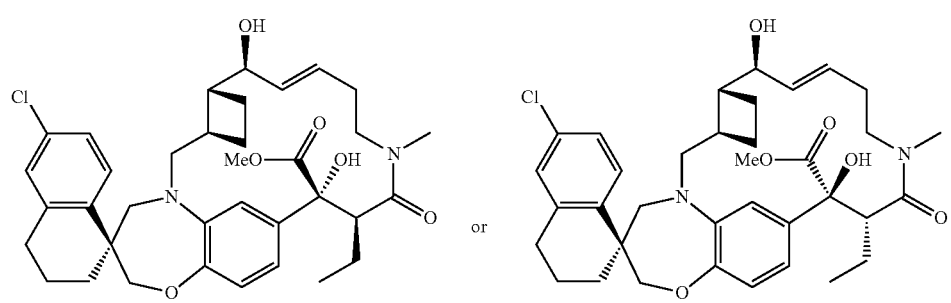

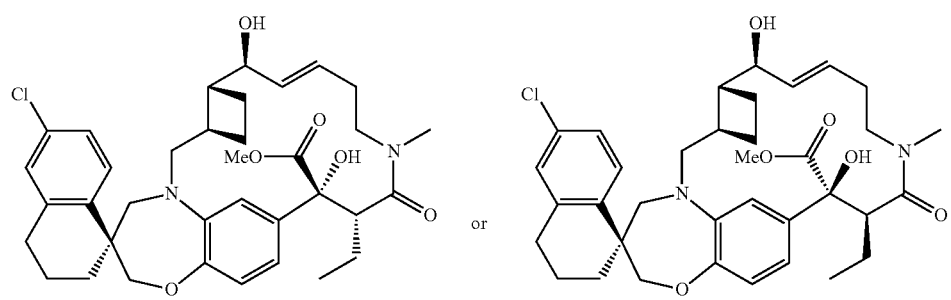

The title compound (15 mg, 31% overall yield) was prepared as the first-eluting, isomeric product from the intermediates from Step 2 in a similar fashion as described for the synthesis of methyl (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 1, Step 7). LRMS: m/z (ESI, +ve ion) 637.2 (M+H)+.

Step 4. (1S,3'R,6'R,7'S,8'E,14'S,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID OR (1S,3'R,6'R,7'S,8'E,14'R,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID OR (1S,3'R,6'R,7'S,8'E,14'R,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID OR (1S,3'R,6'R,7'S,8'E,14'S,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

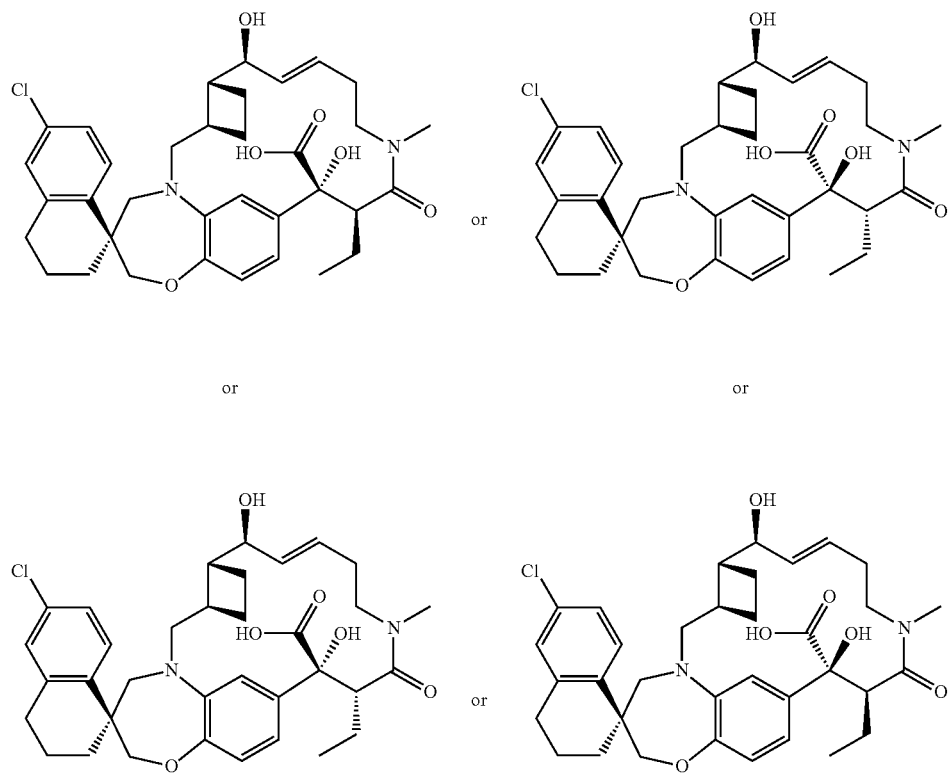

The title compound (6.0 mg, 77% yield) was prepared from the methyl ester derivative from Step 3 in a similar fashion as described for the synthesis of Example 4. $^1$H NMR (400 MHz, (CD$_3$)$_2$SO) δ 7.41-7.27 (m, 1H), 7.22-6.98 (m, 4H), 6.97-6.90 (m, 1H), 6.68-6.53 (m, 1H), 5.34-5.15 (m, 1H), 4.29 (d, J=2.5 Hz, 1H), 4.23 (t, J=12.9 Hz, 1H), 4.02-3.89 (m, 1H), 3.89-3.63 (m, 4H), 3.59-3.43 (m, 1H), 3.19-2.97 (m, 2H), 2.94 (s, 2H), 2.84-2.57 (m, 5H), 2.34-2.02 (m, 4H), 1.87-1.78 (m, 3H), 1.77-1.49 (m, 4H), 1.48-1.38 (m, 1H), 0.91 (t, J=7.5 Hz, 2H), 0.78 (t, J=7.3 Hz, 1H). LRMS: m/z (ESI, +ve ion) 623.2 (M+H)$^+$.

Example 102

(1S,3'R,6'R,7'S,8'E,14'S,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID OR (1S,3'R,6'R,7'S,8'E,14'R,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID, (1S,3'R,6'R,7'S,8'E,14'R,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID, OR (1S,3'R,6'R,7'S,8'E,14'S,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID (the Relative Configuration of this Single Isomer has not been Definitively Established, and is Isomeric to the Title Compound of Example 100, Example 101, and Example 102)

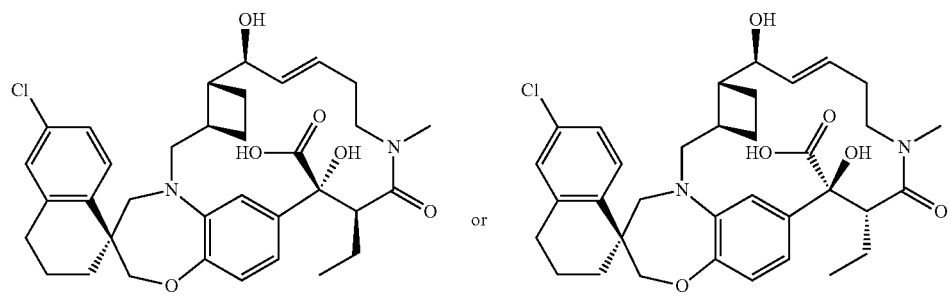

or

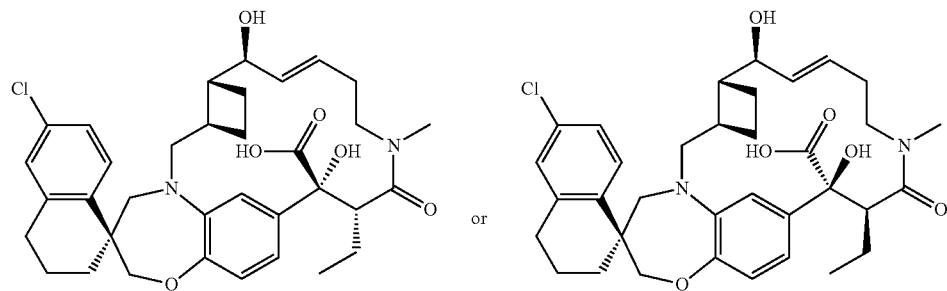

Step 1. METHYL (1S,3'R,6'R,7'S,8'E,14'S,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE OR METHYL (1S,3'R,6'R,7'S,8'E,14'R,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE, METHYL (1S,3'R,6'R,7'S,8'E,14'R,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE, OR METHYL (1S,3'R,6'R,7'S,8'E,14'S,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE

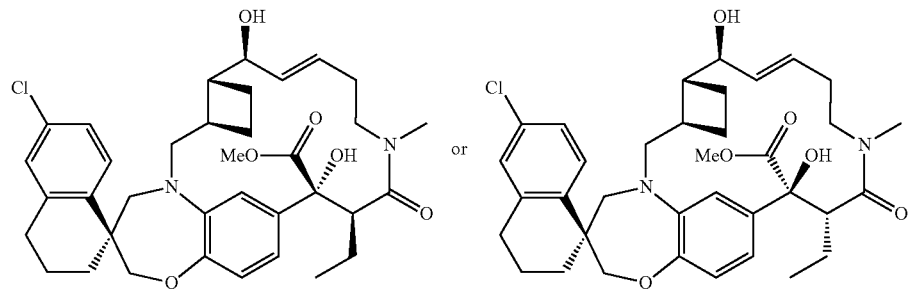

or

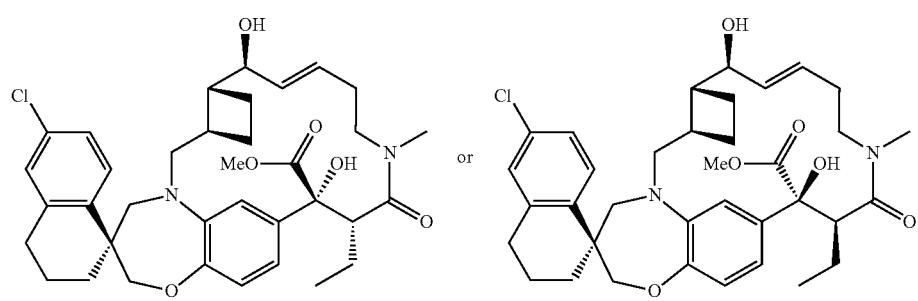

The above compound (23 mg, 48% yield) was prepared as the second-eluting, isomeric product from Example 101, Step 3. LRMS: m/z (ESI, +ve ion) 637.2 (M+H)+.

Step 2. (1S,3'R,6'R,7'S,8'E,14'S,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID, OR (1S,3'R,6'R,7'S,8'E,14'R,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID, (1S,3'R,6'R,7'S,8'E,14'R,15'R)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID, OR (1S,3'R,6'R,7'S,8'E,14'S,15'S)-6-CHLORO-14'-ETHYL-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

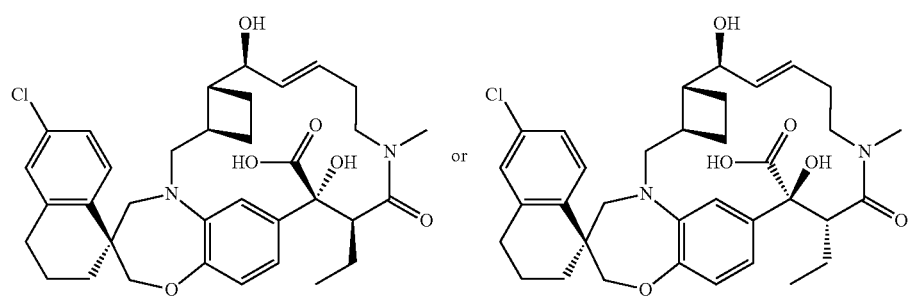

or

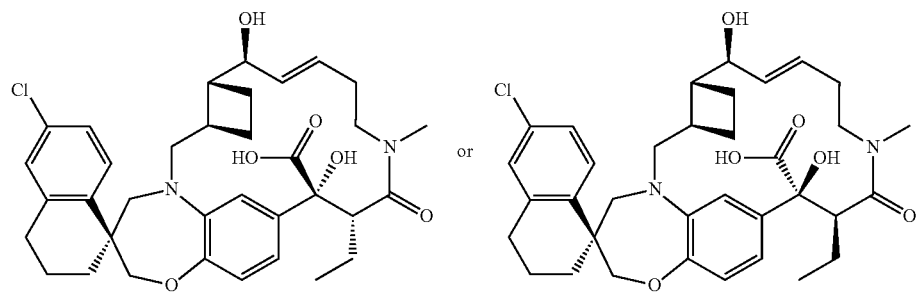

The title compound (5.5 mg, 56% yield) was prepared from the methyl ester derivative from Step 1 in a similar fashion as described for the synthesis of Example 4. $^1$H NMR (400 MHz, (CD$_3$)$_2$SO) δ 7.72-7.61 (m, 0.2H), 7.45 (d, J=7.4 Hz, 0.8H), 7.28-7.09 (m, 3H), 7.02-6.71 (m, 2H), 5.73-5.43 (m, 1H), 5.74-5.42 (m, 0.4H), 4.84 (m, 1.6H), 4.15-3.92 (m, 3H), 3.91-3.80 (m, 1H), 3.79-3.64 (m, 2H), 3.28-3.16 (m, 1H), 3.15-3.01 (m, 4H), 2.88-2.60 (m, 4H), 2.46-2.25 (m, 2H), 2.15 (m, 1H), 2.02-1.35 (m, 11H), 0.96 (t, J=7.6 Hz, 2.4H), 0.71 (t, J=7.4 Hz, 0.6H). LRMS: m/z (ESI, +ve ion) 623.2 (M+H)$^+$.

Example 103

(1S,5'E,11'R)-6-CHLORO-11'-HYDROXY-8'-METHYL-9'-OXO-3,4-DIHYDRO-2H-SPIRO[NAPHTHALENE-1,18'-[16]OXA[1,8]DIAZATRICYCLO[10.7.2.0$^{15,20}$]HENICOSA[5,12,14,20]TETRAENE]-11'-CARBOXYLIC ACID OR (1S,5'E,11'S)-6-CHLORO-11'-HYDROXY-8'-METHYL-9'-OXO-3,4-DIHYDRO-2H-SPIRO[NAPHTHALENE-1,18'-[16]OXA[1,8]DIAZATRICYCLO[10.7.2.0$^{15,20}$]HENICOSA[5,12,14,20]TETRAENE]-11'-CARBOXYLIC ACID (the Relative Configuration of the Title Compound has not been Definitively Established, and is Isomeric to the Title Compound of Example 104)

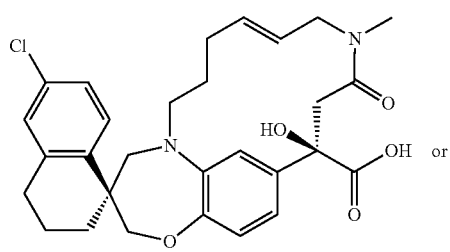

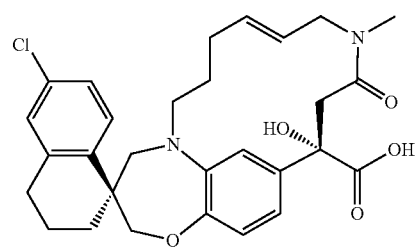

Step 1. METHYL (1S,5'E,11'R)-6-CHLORO-11'-HYDROXY-8'-METHYL-9'-OXO-3,4-DIHYDRO-2H-SPIRO[NAPHTHALENE-1,18'-[16]OXA[1,8]DIAZATRICYCLO[10.7.2.0$^{15,20}$]HENICOSA[5,12,14,20]TETRAENE]-11'-CARBOXYLATE OR METHYL (1S,5'E,11'S)-6-CHLORO-11'-HYDROXY-8'-METHYL-9'-OXO-3,4-DIHYDRO-2H-SPIRO[NAPHTHALENE-1,18'-[16]OXA[1,8]DIAZATRICYCLO[10.7.2.0$^{15,20}$]HENICOSA[5,12,14,20]TETRAENE]-11'-CARBOXYLATE

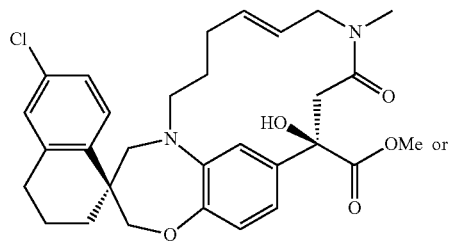

The above compound (28 mg, 8.0% overall yield, 9 steps) was prepared as the faster-eluting isomeric product (upon chiral separation: SFC; AS-H (2×15 cm) 25% MeOH/CO$_2$, 100 bar, 60 mL/min) from (S)-methyl 6'-chloro-3',4,4',5-tetrahydro-2H,2'H-spiro[benzo[b][1,4]oxazepine-3,1'-naphthalene]-7-carboxylate (from Intermediate 11A1 Step 11A) in a similar fashion as described for the synthesis of Example 62. $^1$H NMR (400 MHz, CD$_2$Cl$_2$) δ 7.76 (d, J=8.6 Hz, 1H), 7.16 (dd, J=2.3, 8.4 Hz, 1H), 7.09 (d, J=2.3 Hz, 1H), 7.03 (dd, J=2.1, 8.3 Hz, 1H), 6.83 (d, J=8.2 Hz, 1H), 6.38 (d, J=1.8 Hz, 1H), 6.09 (s, 1H), 6.03-5.94 (m, 1H), 5.80-5.71 (m, 1H), 4.30 (d, J=11.9 Hz, 1H), 4.21 (dd, J=9.6, 15.8 Hz, 1H), 4.00 (d, J=11.9 Hz, 1H), 3.77-3.62 (m, 5H), 3.51-3.36 (m, 3H), 3.06-2.90 (m, 5H), 2.77-2.71 (m, 2H), 2.33-2.21 (m, 1H), 1.90-1.70 (m, 7H), 1.65-1.51 (m, 1H). LRMS: m/z (ESI, +ve ion) 539.2 (M+H)$^+$.

271

(1S,5'E,11'R)-6-CHLORO-11'-HYDROXY-8'-METHYL-9'-OXO-3,4-DIHYDRO-2H-SPIRO[NAPHTHALENE-1,18'-[16]OXA[1,8]DIAZATRICYCLO[10.7.2.0$^{15,20}$]HENICOSA[5,12,14,20]TETRAENE]-11'-CARBOXYLIC ACID OR (1S,5'E,11'S)-6-CHLORO-11'-HYDROXY-8'-METHYL-9'-OXO-3,4-DIHYDRO-2H-SPIRO[NAPHTHALENE-1,18'-[16]OXA[1,8]DIAZATRICYCLO[10.7.2.0$^{15,20}$]HENICOSA[5,12,14,20]TETRAENE]-11'-CARBOXYLIC ACID

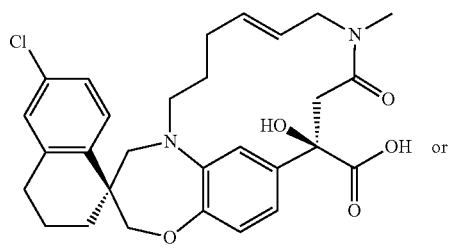

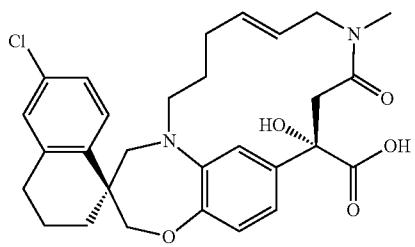

The title compound (14 mg, 68% yield) was prepared from the methyl ester from Step 1 in a similar fashion as described for the synthesis of Example 4. $^1$H NMR (400 MHz, (CD$_3$)$_2$SO) δ 7.70 (t, J=7.5 Hz, 1H), 7.25 (dd, J=2.2, 8.4 Hz, 1H), 7.20-7.14 (m, 1H), 6.88-6.82 (m, 1H), 6.82-6.76 (m, 1H), 6.45-6.39 (m, 1H), 6.00-5.88 (m, 1H), 5.83-5.72 (m, 1H), 4.24-4.08 (m, 2H), 3.93 (d, J=12.1 Hz, 1H), 3.87-3.77 (m, 1H), 3.49 (m, 1H), 3.33-3.25 (m, 1H), 3.24-2.99 (m, 4H), 2.93 (s, 3H), 2.78-2.66 (m, 2H), 2.20-2.09 (m, 1H), 1.91-1.45 (m, 7H). LRMS: m/z (ESI, +ve ion) 525.2 (M+H)$^+$.

272

Example 104

(1S,5'E,11'R)-6-CHLORO-11'-HYDROXY-8'-METHYL-9'-OXO-3,4-DIHYDRO-2H-SPIRO[NAPHTHALENE-1,18'-[16]OXA[1,8]DIAZATRICYCLO[10.7.2.0$^{15,20}$]HENICOSA[5,12,14,20]TETRAENE]-11'-CARBOXYLIC ACID OR (1S,5'E,11'S)-6-CHLORO-11'-HYDROXY-8'-METHYL-9'-OXO-3,4-DIHYDRO-2H-SPIRO[NAPHTHALENE-1,18'-[16]OXA[1,8]DIAZATRICYCLO[10.7.2.0$^{15,20}$]HENICOSA[5,12,14,20]TETRAENE]-11'-CARBOXYLIC ACID (the Relative Configuration of the Title Compound has not been Definitively Established, and is Isomeric to the Title Compound of Example 103)

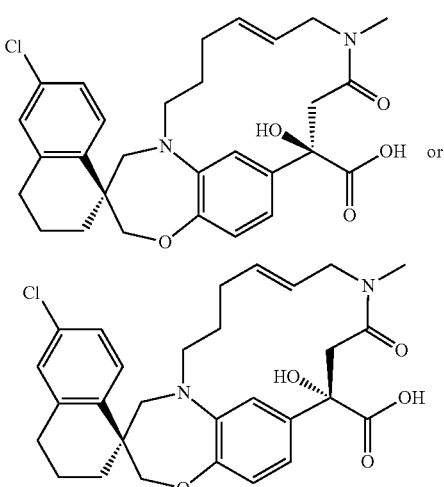

Step 1. METHYL (1S,5'E,11'R)-6-CHLORO-11'-HYDROXY-8'-METHYL-9'-OXO-3,4-DIHYDRO-2H-SPIRO[NAPHTHALENE-1,18'-[16]OXA[1,8]DIAZATRICYCLO[10.7.2.0$^{15,20}$]HENICOSA[5,12,14,20]TETRAENE]-11'-CARBOXYLATE OR METHYL (1S,5'E,11'S)-6-CHLORO-11'-HYDROXY-8'-METHYL-9'-OXO-3,4-DIHYDRO-2H-SPIRO[NAPHTHALENE-1,18'-[16]OXA[1,8]DIAZATRICYCLO[10.7.2.0$^{15,20}$]HENICOSA[5,12,14,20]TETRAENE]-11'-CARBOXYLATE

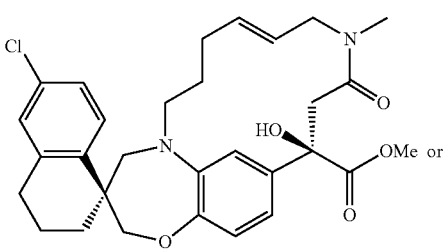

-continued

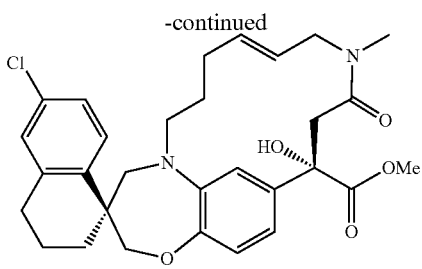

The above compound (25 mg, 7% overall yield, 9 steps) was prepared as the slower-eluting isomeric product from Example 103, Step 1. $^1$H NMR (400 MHz, CD$_2$Cl$_2$) δ 7.73 (d, J=8.6 Hz, 1H), 7.16 (dd, J=2.2, 8.4 Hz, 1H), 7.09-7.08 (m, 1H), 7.05 (d, J=7.8 Hz, 1H), 6.85 (d, J=8.4 Hz, 1H), 6.41 (d, J=2.0 Hz, 1H), 6.09 (s, 1H), 5.98 (td, J=7.7,15.4 Hz, 1H), 5.77-5.69 (m, 1H), 4.21 (dd, J=9.6, 16.0 Hz, 1H), 4.15-4.07 (m, 1H), 4.07-3.99 (m, 1H), 3.75 (d, J=16.8 Hz, 1H), 3.71-3.62 (m, 5H), 3.46 (t, J=13.2 Hz, 1H), 3.27 (d, J=14.3 Hz, 1H), 3.16-3.01 (m, 1H), 2.99 (s, 3H), 2.90 (d, J=17.0 Hz, 1H), 2.82-2.70 (m, 2H), 2.40-2.23 (m, 1H), 2.00 (td, J=3.8, 13.3 Hz, 1H), 1.92-1.73 (m, 4H), 1.60-1.42 (m, 2H). LRMS: m/z (ESI, +ve ion) 539.2 (M+H)$^+$.

Step 2. (1S,5'E,11'R)-6-CHLORO-11'-HYDROXY-8'-METHYL-9'-OXO-3,4-DIHYDRO-2H-SPIRO[NAPHTHALENE-1,18'-[16]OXA[1,8]DIAZATRI-CYCLO[10.7.2.0$^{15,20}$]HENICOSA[5,12,14,20]TETRAENE]-11'-CARBOXYLIC ACID OR (1S,5'E,11'S)-6-CHLORO-11'-HYDROXY-8'-METHYL-9'-OXO-3,4-DIHYDRO-2H-SPIRO[NAPHTHALENE-1,18'-[16]OXA[1,8]DIAZATRICYCLO[10.7.2.0$^{15,20}$]HENICOSA[5,12,14,20]TETRAENE]-11'-CARBOXYLIC ACID

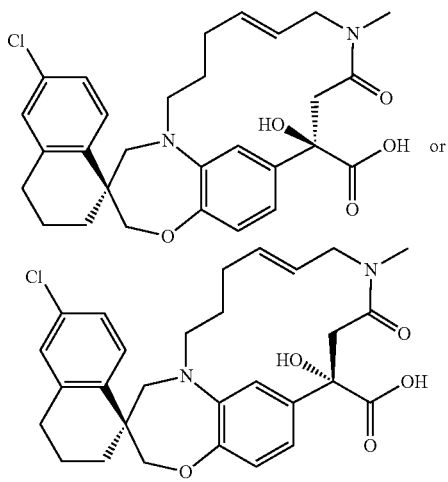

The title compound (1.1 mg, 17% yield) was prepared from the methyl ester from Step 1 in a similar fashion as described for the synthesis of Example 4. $^1$H NMR (400 MHz, (CD$_3$)$_2$SO) δ 7.66 (d, J=8.6 Hz, 1H), 7.29-7.20 (m, 1H), 7.16 (d, J=2.3 Hz, 1H), 6.89 (dd, J=2.0, 8.2 Hz, 1H), 6.82-6.71 (m, 1H), 6.44 (s, 1H), 5.90 (td, J=7.6,14.6 Hz, 1H), 5.83-5.71 (m, 1H), 4.26-4.09 (m, 1H), 3.97 (s, 2H), 3.82-3.70 (m, 1H), 3.58-3.43 (m, 1H), 3.19-2.96 (m, 4H), 2.95-2.86 (m, 3H), 2.84-2.68 (m, 3H), 2.29-2.16 (m, 1H), 2.03-1.69 (m, 6H), 1.47-1.35 (m, 1H). LRMS: m/z (ESI, +ve ion) 525.2 (M+H)$^+$.

Example 105

(1S,5'Z,12'S)-6-CHLORO-12'-HYDROXY-9'-METHYL-10'-OXO-3,4-DIHYDRO-2H-SPIRO[NAPHTHALENE-1,19'-[17]OXA[1,9]DIAZATRI-CYCLO[11.7.2.0$^{16,21}$]DOCOSA[5,13,15,21]TETRAENE]-12'-CARBOXYLIC ACID OR (1S,5'Z,12'R)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLIC ACID (the Relative Configuration of the Title Compound has not been Definitively Established, and is Isomeric to the Title Compound of Example 106)

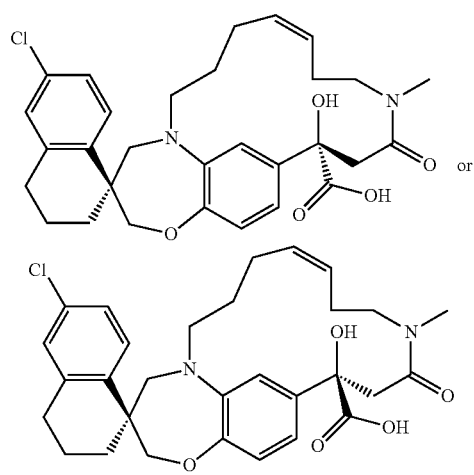

Step 1. METHYL (1S,5'Z,12'S)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLATE OR METHYL (1S,5'Z,12'R)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLATE

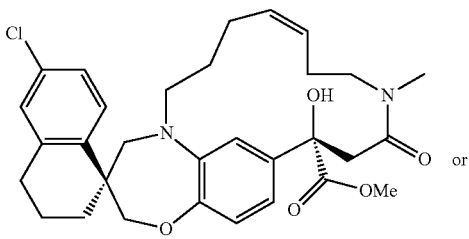

275
-continued

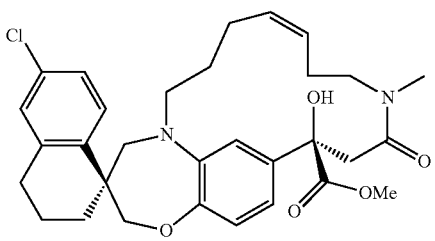

The above compound (12 mg, 7.3% overall yield, 9 steps) was prepared as the first-eluting isomeric product (upon chiral separation: SFC; AS-H (2×15 cm) 15% MeOH/CO$_2$, 100 bar, 60 mL/min) from (S)-methyl 6'-chloro-3',4,4',5-tetrahydro-2H,2'H-spiro[benzo[b][1,4]oxazepine-3,1'-naphthalene]-7-carboxylate (from Intermediate 11A1 Step 11A) in a similar fashion as described for the synthesis of Example 62. LRMS: m/z (ESI, +ve ion) 553.2 (M+H)$^+$.

Step 2. (1S,5'Z,12'S)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLIC ACID OR (1S,5'Z,12'R)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLIC ACID

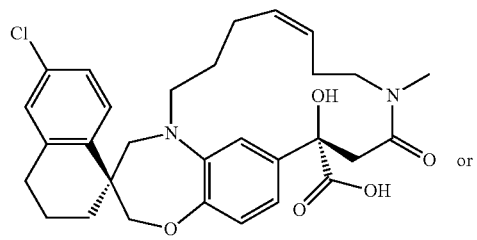

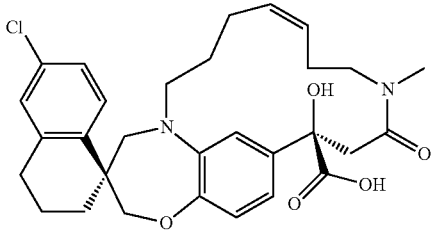

The title compound (6.8 mg, 63% yield) was prepared from the methyl ester from Step 1 in a similar fashion as described for the synthesis of Example 4: $^1$H NMR (400 MHz, (CD$_3$)$_2$SO) δ 7.72 (d, J=8.6 Hz, 1H), 7.24 (dd, J=2.2, 8.5 Hz, 1H), 7.17 (d, J=2.0 Hz, 1H), 6.89 (d, J=8.4 Hz, 1H), 6.80 (d, J=8.2 Hz, 1H), 6.73-6.67 (m, 1H), 5.57 (dt, J=6.2, 10.1 Hz, 1H), 5.28 (td, J=5.3,10.7 Hz, 1H), 4.11 (d, J=12.1 Hz, 1H), 3.97 (d, J=12.1 Hz, 1H), 3.46-3.39 (m, 1H), 3.31 (d, J=14.1 Hz, 1H), 3.27-3.06 (m, 4H), 2.87 (s, 3H), 2.78-2.58 (m, 4H), 2.43-2.18 (m, 2H), 1.91-1.56 (m, 7H), 1.49-1.35 (m, 1H). LRMS: m/z (ESI, +ve ion) 539.2 (M+H)$^+$.

276
Example 106

(1S,5'Z,12'S)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLIC ACID OR (1S,5'Z,12'R)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLIC ACID (the Relative Configuration of the Title Compound has not been Definitively Established, and is Isomeric to the Title Compound of Example 105)

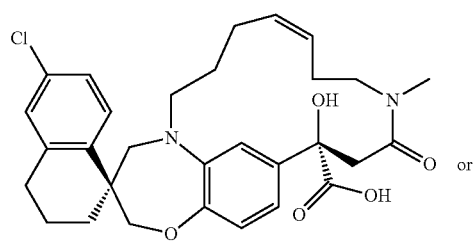

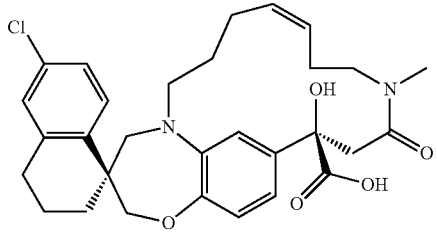

Step 1. METHYL (1S,5'Z,12'S)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLATE OR METHYL (1S,5'Z,12'R)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLATE

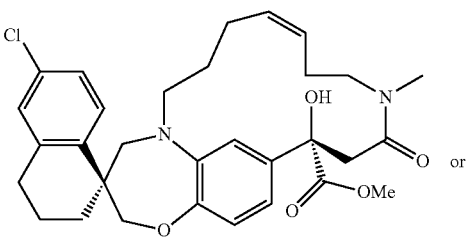

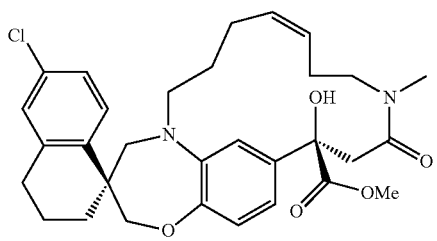

The above compound (11 mg, 6.5% overall yield, 9 steps) was prepared as the third-eluting isomeric product from Example 105, Step 1. LRMS: m/z (ESI, +ve ion) 553.2 (M+H)$^+$.

Step 2. (1S,5'Z,12'S)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLIC ACID OR (1S,5'Z,12'R)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLIC ACID

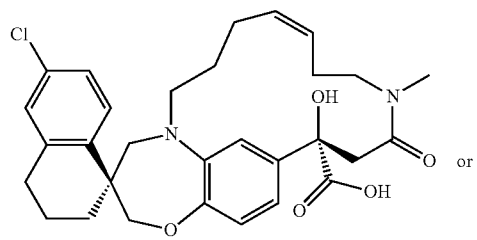

or

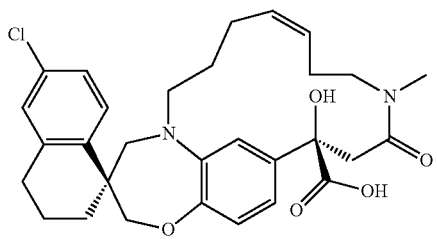

The title compound (9.0 mg, 84% yield) was prepared from the methyl ester from Step 1 in a similar fashion as described for the synthesis of Example 4. $^1$H NMR (400 MHz, (CD$_3$)$_2$SO) δ 7.69 (d, J=8.6 Hz, 1H), 7.26 (t, J=7.5 Hz, 1H), 7.19-7.15 (m, 1H), 6.93-6.87 (m, 1H), 6.84-6.79 (m, 1H), 6.70 (s, 1H), 5.56 (dt, J=5.7, 10.2 Hz, 1H), 5.28 (dt, J=4.3, 10.7 Hz, 1H), 4.05-3.94 (m, 2H), 3.50-3.43 (m, 1H), 3.32-3.09 (m, 5H), 2.90-2.84 (m, 3H), 2.80-2.60 (m, 4H), 2.41-2.20 (m, 2H), 1.98-1.62 (m, 6H), 1.50-1.31 (m, J=5.5 Hz, 2H). LRMS. m/z (ESI, +ve ion) 539.2 (M+H)$^+$.

Example 107

(1S,5'E,12'S)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLIC ACID OR (1S,5'E,12'R)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLIC ACID (the Relative Configuration of the Title Compound has not been Definitively Established, and is Isomeric to the Title Compound of Example 108)

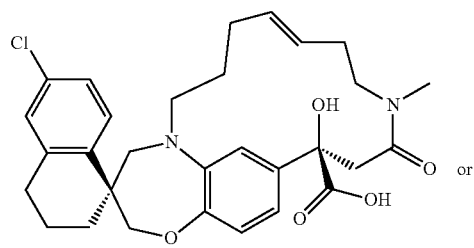

or

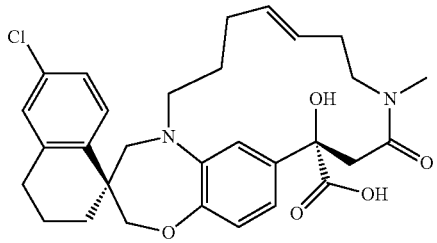

Step 1. METHYL (1S,5'E,12'S)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLATE OR METHYL (1S,5'E,12'R)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLATE

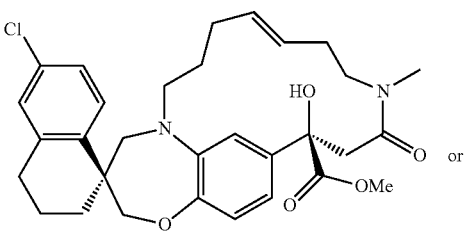

or

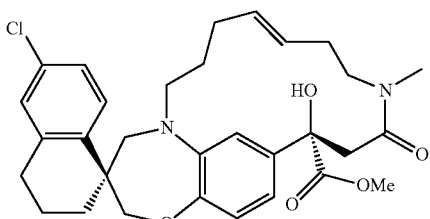

The above compound (12 mg, 7.3% overall yield, 9 steps) was prepared as the second-eluting isomeric product from Example 105, Step 1. LRMS: m/z (ESI, +ve ion) 553.2 (M+H)+.

Step 2. (1S,5'E,12'S)-6-CHLORO-12'-HYDROXY-9'-METHYL-10'-OXO-3,4-DIHYDRO-2H-SPIRO[NAPHTHALENE-1,19'-[17]OXA[1,9]DIAZATRI-CYCLO[11.7.2.0$^{16,21}$]DOCOSA[5,13,15,21]TETRAENE]-12'-CARBOXYLIC ACID OR (1S,5'E,12'R)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLIC ACID

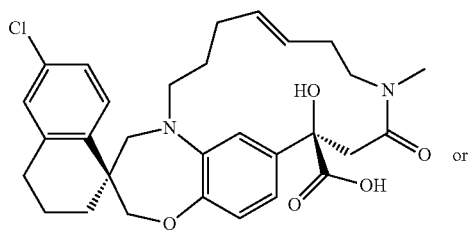

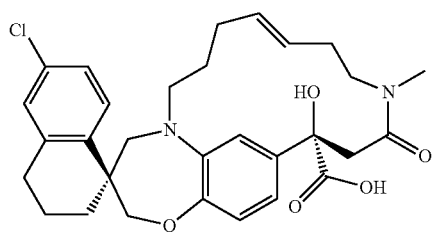

The title compound (7.0 mg, 65% yield) was prepared from the methyl ester from Step 1 in a similar fashion as described for the synthesis of Example 4: $^1$H NMR (400 MHz, (CD$_3$)$_2$SO) δ 7.71 (d, J=8.6 Hz, 1H), 7.24 (dd, J=2.2, 8.5 Hz, 1H), 7.16 (d, J=2.2 Hz, 1H), 6.90 (dd, J=1.6, 8.2 Hz, 1H), 6.80 (d, J=8.2 Hz, 1H), 6.70-6.63 (m, 1H), 5.80-5.63 (m, 2H), 4.06 (d, J=11.9 Hz, 1H), 3.96 (d, J=12.1 Hz, 1H), 3.45-3.36 (m, 4H), 3.34-3.16 (m, 4H), 2.84 (s, 3H), 2.78-2.66 (m, 3H), 2.36-2.24 (m, 2H), 2.15-2.02 (m, 1H), 1.99-1.87 (m, 1H), 1.85-1.69 (m, 4H), 1.63-1.52 (m, 1H), 1.52-1.37 (m, 1H). LRMS: m/z (ESI, +ve ion) 539.2 (M+H)+.

Example 108

(1S,5'E,12'S)-6-CHLORO-12'-HYDROXY-9'-METHYL-10'-OXO-3,4-DIHYDRO-2H-SPIRO[NAPHTHALENE-1,19'-[17]OXA[1,9]DIAZATRI-CYCLO[11.7.2.0$^{16,21}$]DOCOSA[5,13,15,21]TETRAENE]-12'-CARBOXYLIC ACID OR (1S,5'E,12'R)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLIC ACID (the Relative Configuration of the Title Compound has not been Definitively Established, and is Isomeric to the Title Compound of Example 107)

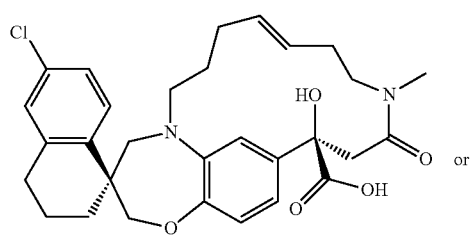

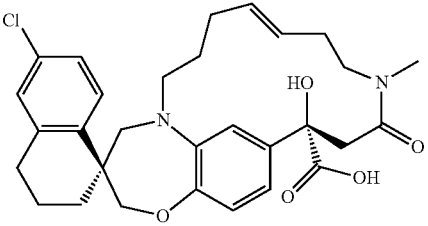

Step 1. METHYL (1S,5'E,12'S)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLATE OR METHYL (1S,5'E,12'R)-6-CHLORO-12'-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[5,13,15,21]TETRAENE]-12'-CARBOXYLATE

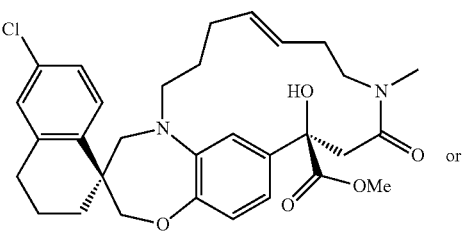

281
-continued

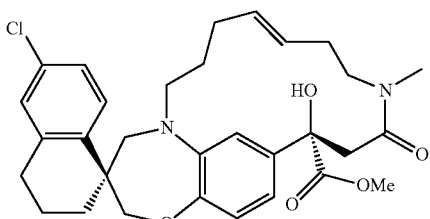

The above compound (11 mg, 6.5% overall yield, 9 steps) was prepared as the fourth-eluting isomeric product from Example 105, Step 1. LRMS. m/z (ESI, +ve ion) 553.2 (M+H)+.

Step 2. (1S,5'E,12'S)-6-CHLORO-12'-HYDROXY-9'-METHYL-10'-OXO-3,4-DIHYDRO-2H-SPIRO [NAPHTHALENE-1,19'-[17]OXA[1,9]DIAZATRI-CYCLO[11.7.2.0$^{16,21}$]DOCOSA[5,13,15,21] TETRAENE]-12'-CARBOXYLIC ACID OR (1S, 5'E,12'R)-6-CHLORO-12'-HYDROXY-9'-METHYL-10'-OXO-3,4-DIHYDRO-2H-SPIRO [NAPHTHALENE-1,19'-[17]OXA[1,9] DIAZATRICYCLO[11.7.2.0$^{16,21}$]DOCOSA[5,13,15, 21]TETRAENE]-12'-CARBOXYLIC ACID

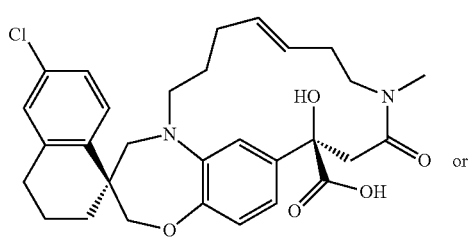

or

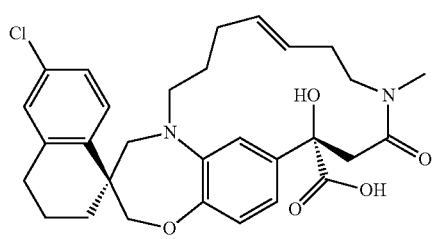

The title compound (6.0 mg, 56% yield) was prepared from the methyl ester from Step 1 in a similar fashion as described for the synthesis of Example 4. $^1$H NMR (400 MHz, (CD$_3$)$_2$SO) δ 7.69 (d, J=8.6 Hz, 1H), 7.26 (dd, J=1.9, 8.5 Hz, 1H), 7.19-7.15 (m, 1H), 6.89 (d, J=7.6 Hz, 1H), 6.80 (d, J=8.2 Hz, 1H), 6.68-6.64 (m, 1H), 5.82-5.66 (m, 2H), 4.06-3.91 (m, 2H), 3.54-3.40 (m, 4H), 3.31-3.17 (m, 3H), 2.84 (s, 3H), 2.80-2.64 (m, 3H), 2.30 (m, 2H), 2.18-2.05 (m, 1H), 1.95-1.72 (m, 5H), 1.50-1.31 (m, 2H). LRMS: m/z (ESI, +ve ion) 539.2 (M+H).

282

Example 109

(1S,6'E,12'S)-6-CHLORO-12'-HYDROXY-9'-METHYL-3,4-DIHYDRO-2H-SPIRO[NAPHTHA-LENE-1,19'-[17]OXA[10]THIA[1,9]DIAZATRICY-CLO[11.7.2.0$^{16,21}$]DOCOSA[6,13,15,21] TETRAENE]-12'-CARBOXYLIC ACID 10',10'-DIOXIDE AND (1S,6'E,12'R)-6-CHLORO-12'-HYDROXY-9'-METHYL-3,4-DIHYDRO-2H-SPIRO[NAPHTHALENE-1,19'-[17]OXA[10]THIA [1,9]DIAZATRICYCLO[11.7.2.0$^{16,21}$]DOCOSA[6, 13,15,21]TETRAENE]-12'-CARBOXYLIC ACID 10',10'-DIOXIDE (the Constitution of the Title Compounds Confirmed by x-Ray Co-Crystal Structure with Mel1)

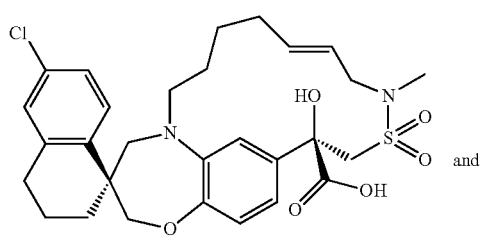

and

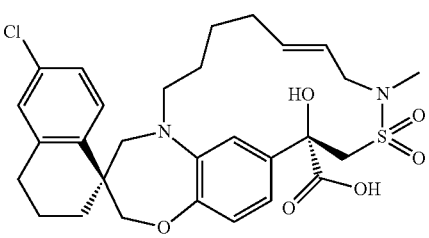

Step 1. (R)-METHYL 3-(N-ALLYL-N-METHYL-SULFAMOYL)-2-((S)-6'-CHLORO-5-(HEX-5-EN-1-YL)-3',4,4',5-TETRAHYDRO-2H,2'H-SPIRO [BENZO[B][1,4]OXAZEPINE-3,1'-NAPHTHALEN]-7-YL)-2-HYDROXYPROPANOATE AND (S)-METHYL 3-(N-ALLYL-N-METHYLSULFAMOYL)-2-((S)-6'-CHLORO-5-(HEX-5-EN-1-YL)-3',4,4',5-TET-RAHYDRO-2H,2'H-SPIRO[BENZO[B][1,4] OXAZEPINE-3,1'-NAPHTHALEN]-7-YL)-2-HYDROXYPROPANOATE

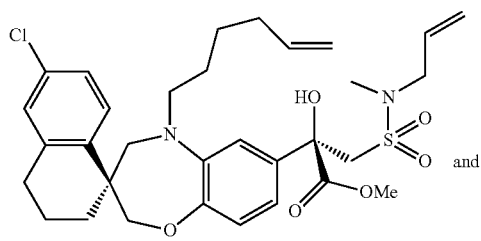

and

-continued

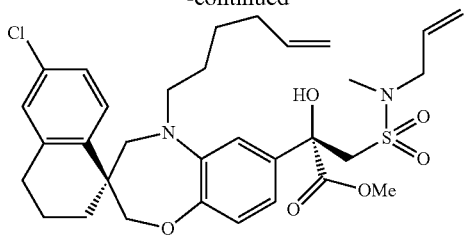

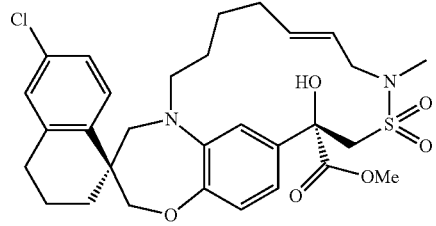

To a solution of N-allyl-N-methylmethanesulfonamide (71.7 mg, 0.481 mmol) in THF (1.92 mL) cooled to −78° C. was added N-butyllithium solution, 2.5 M in hexanes (0.192 mL, 0.481 mmol) slowly down the side of the flask. The reaction mixture was maintained at −78° C. for 30 minutes, then a solution of (S)-methyl 2-(6'-chloro-5-(hex-5-en-1-yl)-3',4,4',5-tetrahydro-2H,2'H-spiro[benzo[b][1,4]oxazepine-3,1'-naphthalen]-7-yl)-2-oxoacetate (180 mg, 0.385 mmol) (Example 62) in THF (1.00 mL) was slowly added to the mixture. The reaction mixture changed color from orange to pale yellow. After 3 h, at −78° C., the reaction was quenched by the addition of acetic acid (27.8 µL, 0.481 mmol). The reaction mixture was diluted with saturated aqueous NH$_4$Cl and extracted with EtOAc (2×). The organic extract was washed with saturated aqueous NaCl and dried over Na$_2$SO$_4$. The solution was filtered and concentrated in vacuo to give the crude material. The crude material was absorbed onto a plug of silica gel and purified by chromatography through a Redi-Sep pre-packed silica gel column (40 g), eluting with a gradient of 0% to 40% EtOAc in hexane, to provide the above compounds (110 mg, 46% yield) as an off-white solid. $^1$H NMR (400 MHz, CD$_2$Cl$_2$) δ 7.72 (dd, J=2.3, 8.6 Hz, 1H), 7.15 (d, J=8.6 Hz, 1H), 7.09 (d, J=2.2 Hz, 1H), 6.91 (d, J=1.4 Hz, 1H), 6.90-6.82 (m, 2H), 5.84 (ddd, J=4.5, 10.4, 17.0 Hz, 2H), 5.33-5.23 (m, 2H), 5.04 (qd, J=1.7, 17.1 Hz, 1H), 5.00-4.96 (m, 1H), 4.26-4.17 (m, 1H), 4.12-3.97 (m, 3H), 3.89-3.77 (m, 4H), 3.72 (d, J=6.3 Hz, 1H), 3.61-3.46 (m, 2H), 3.29 (dd, J=6.7, 14.1 Hz, 3H), 2.82-2.72 (m, 5H), 2.13 (q, J=7.0 Hz, 2H), 1.99-1.93 (m, 1H), 1.85 (br. s., 3H), 1.69-1.53 (m, 3H), 1.53-1.40 (m, 2H). LRMS. m/z (ESI, +ve ion) 617.2 (M+H)$^+$.

Step 2. METHYL (1S,6'E,12'S)-6-CHLORO-12'-HYDROXY-9'-METHYL-3,4-DIHYDRO-2H-SPIRO[NAPHTHALENE-1,19'-[17]OXA[10]THIA[1,9]DIAZATRICYCLO[11.7.2.0$^{16,21}$]DOCOSA[6,13,15,21]TETRAENE]-12'-CARBOXYLATE 10',10'-DIOXIDE AND (1S,6'E,12'R)-6-CHLORO-12'-HYDROXY-9'-METHYL-3,4-DIHYDRO-2H-SPIRO[NAPHTHALENE-1,19'-[17]OXA[10]THIA[1,9]DIAZATRICYCLO[11.7.2.0$^{16,21}$]DOCOSA[6,13,15,21]TETRAENE]-12'-CARBOXYLATE 10',10'-DIOXIDE A solution of the intermediates from Step 1 (110 mg, 0.178 mmol) in 1,2-dichloroethane (81.0 mL) was purged with argon for 15 minutes, then Hoveyda-Grubbs catalyst 2nd generation (16.8 mg, 27.0 µmol) in 1.00 mL dichloroethane was added. The reaction was stirred at 50° C. overnight. To the warm solution was added di(ethylene glycol) vinyl ether (19.0 µL, 0.143 mmol), then the solution was allowed to cool to room temperature. The crude mixture was concentrated under reduced pressure, then absorbed onto a plug of silica gel and purified by chromatography through a Redi-Sep pre-packed silica gel column (12 g), eluting with a gradient of 0% to 50% EtOAc in hexane, to provide the above compounds (100 mg, 95% yield) as an off-white solid. $^1$H NMR (400 MHz, CD$_2$Cl$_2$) δ 7.75 (dd, J=2.2, 8.6 Hz, 1H), 7.19-7.13 (m, 1H), 7.09 (d, J=2.2 Hz, 1H), 6.85-6.72 (m, 3H), 5.82-5.72 (m, 2H), 4.16-4.01 (m, 3H), 3.93-3.86 (m, 4H), 3.78-3.63 (m, 1H), 3.52 (d, J=14.1 Hz, 1H), 3.43 (dd, J=7.0, 14.3 Hz, 1H), 3.38-3.26 (m, 2H), 3.26-3.14 (m, 1H), 2.92 (d, J=1.4 Hz, 3H), 2.84-2.71 (m, 2H), 2.31-2.20 (m, 1H), 2.14 (dd, J=9.0, 13.9 Hz, 1H), 1.92-1.77 (m, 3H), 1.70-1.35 (m, 6H). LRMS: m/z (ESI, +ve ion) 589.2 (M+H)$^+$.

Step 3. (1S,6'E,12'S)-6-CHLORO-12'-HYDROXY-9'-METHYL-3,4-DIHYDRO-2H-SPIRO[NAPHTHALENE-1,19'-[17]OXA[10]THIA[1,9]DIAZATRICYCLO[11.7.2.0$^{16,21}$]DOCOSA[6,13,15,21]TETRAENE]-12'-CARBOXYLIC ACID 10',10'-DIOXIDE AND (1S,6'E,12'R)-6-CHLORO-12'-HYDROXY-9'-METHYL-3,4-DIHYDRO-2H-SPIRO[NAPHTHALENE-1,19'-[17]OXA[10]THIA[1,9]DIAZATRICYCLO[11.7.2.0$^{16,21}$]DOCOSA[6,13,15,21]TETRAENE]-12'-CARBOXYLIC ACID 10',10'-DIOXIDE

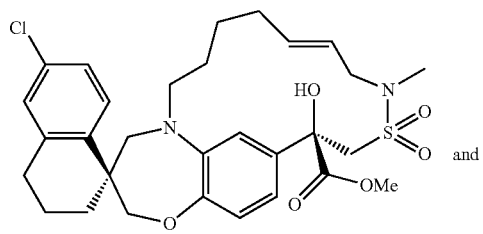

and

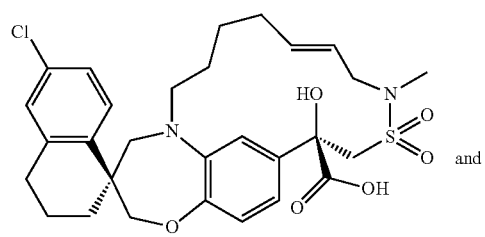

and

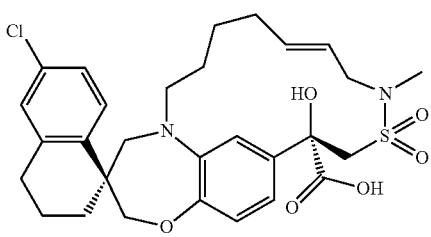

The title compounds (17 mg, 68% yield) were prepared from the intermediates from Step 2 in a similar fashion as described for the synthesis of Example 4. $^1$H NMR (400 MHz, (CD$_3$)$_2$SO) δ 7.70 (d, J=3.1 Hz, 0.5H), 7.68 (d, J=3.1 Hz, 0.5H), 7.28-7.22 (m, 1H), 7.18-7.15 (m, 1H), 6.81-6.71 (m, 3H), 5.88-5.79 (m, 1H), 5.78-5.68 (m, 1H), 4.10-3.89 (m, 2H), 3.86-3.77 (m, 1H), 3.75-3.67 (m, 1H), 3.43 (m, 1H), 3.37-3.22 (m, 3H), 3.17 (m, 1H), 2.86-2.80 (m, 3H), 2.80-2.65 (m, 2H), 2.22-2.00 (m, 2H), 1.88-1.72 (m, 3H), 1.64-1.46 (m, 4H), 1.45-1.30 (m, 1H). LRMS: m/z (ESI, +ve ion) 575.2 (M+H)$^+$.

Example 110

(1S,12'S)-6-CHLORO-12'-HYDROXY-9'-METHYL-3,4-DIHYDRO-2H-SPIRO[NAPHTHALENE-1,19'-[17]OXA[10]THIA[1,9]DIAZATRICYCLO[11.7.2.0$^{16,21}$]DOCOSA[13,15,21]TRIENE]-12'-CARBOXYLIC ACID 10',10'-DIOXIDE AND (S,12'R)-6-CHLORO-12'-HYDROXY-9'-METHYL-3,4-DIHYDRO-2H-SPIRO[NAPHTHALENE-1,19'-[17]OXA[10]THIA[1,9]DIAZATRICYCLO[11.7.2.0$^{16,21}$]DOCOSA[13,15,21]TRIENE]-12'-CARBOXYLIC ACID 10',10'-DIOXIDE

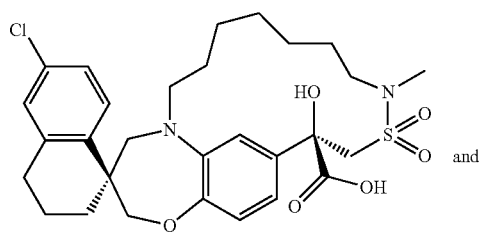 and

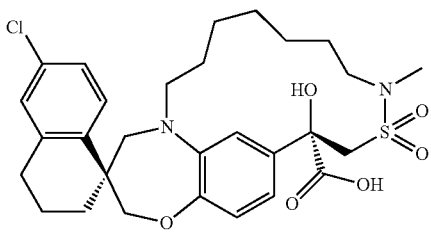

Step 1. METHYL (1S,12'S)-6-CHLORO-12'-HYDROXY-9'-METHYL-3,4-DIHYDRO-2H-SPIRO[NAPHTHALENE-1,19'-[17]OXA[10]THIA[1,9]DIAZATRICYCLO[11.7.2.0$^{16,21}$]DOCOSA[13,15,21]TRIENE]-12'-CARBOXYLATE 10',10'-DIOXIDE AND METHYL (1S,12'R)-6-CHLORO-12'-HYDROXY-9'-METHYL-3,4-DIHYDRO-2H-SPIRO[NAPHTHALENE-1,19'-[17]OXA[10]THIA[1,9]DIAZATRICYCLO[11.7.2.0$^{16,21}$]DOCOSA[13,15,21]TRIENE]-12'-CARBOXYLATE 10',10'-DIOXIDE

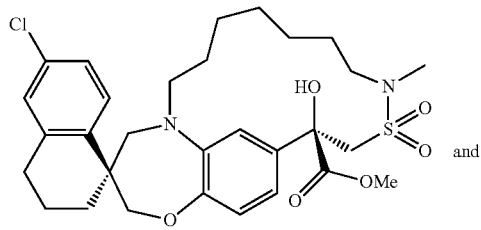 and

A mixture of (1S,6'E,12'S)-6-chloro-12'-hydroxy-9'-methyl-3,4-dihydro-2H-spiro[naphthalene-1,19'-[17]oxa[10]thia[1,9]diazatricyclo[11.7.2.0$^{16,21}$]docosa[6,13,15,21]tetraene]-12'-carboxylic acid 10',10'-dioxide and (1S,6'E,12'R)-6-chloro-12'-hydroxy-9'-methyl-3,4-dihydro-2H-spiro[naphthalene-1,19'-[17]oxa[10]thia[1,9]diazatricyclo[11.7.2.0$^{16,21}$]docosa[6,13,15,21]tetraene]-12'-carboxylic acid 10',10'-dioxide (Example 109, Step 2) (24 mg, 0.041 mmol) and platinum (IV) oxide (2.3 mg, 10 μmol) in EtOAc (2.0 mL) were stirred under H$_2$ (balloon) at room temperature for 1 h. The reaction mixture was then filtered through a syringe filter to remove solid catalyst and concentrated under reduced pressure. The above compounds were taken into the next step without further purification. LRMS. m/z (ESI, +ve ion) 591.2 (M+H)$^+$.

Step 2. (1S,12'S)-6-CHLORO-12'-HYDROXY-9'-METHYL-3,4-DIHYDRO-2H-SPIRO[NAPHTHA-LENE-1,19'-[17]OXA[10]THIA[1,9]DIAZATRICY-CLO[11.7.2.0$^{16,21}$]DOCOSA[13,15,21]TRIENE]-12'-CARBOXYLIC ACID 10',10'-DIOXIDE AND (1S,12'R)-6-CHLORO-12'-HYDROXY-9'-METHYL-3,4-DIHYDRO-2H-SPIRO[NAPHTHA-LENE-1,19'-[17]OXA[10]THIA[1,9]DIAZATRICY-CLO[11.7.2.0$^{16,21}$]DOCOSA[13,15,21]TRIENE]-12'-CARBOXYLIC ACID 10',10'-DIOXIDE

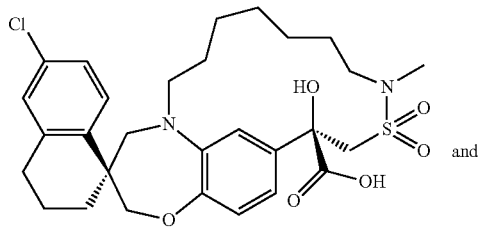

and

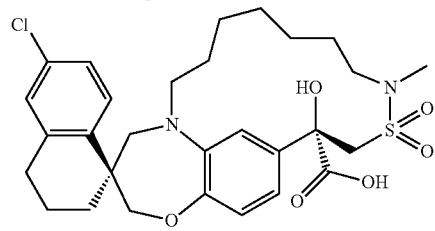

The title compounds (16 mg, 80% yield) were prepared from the intermediates from Step 1 in a similar fashion as described for the synthesis of Example 4: $^1$H NMR (400 MHz, (CD$_3$)$_2$SO) δ 7.69 (d, J=8.4 Hz, 1H), 7.25 (m, 1H), 7.17 (m, 1H), 6.90 (m, 1H), 6.80-6.77 (m, 1H), 6.77-6.70 (m, 1H), 4.09-3.90 (m, 2H), 3.82-3.74 (m, 1H), 3.52-3.23 (m, 5H), 3.22-3.11 (m, J=10.8 Hz, 1H), 3.10-2.97 (m, 1H), 2.80 (s, 3H), 2.76-2.65 (m, 2H), 1.35 (s, 14H). LRMS: m/z (ESI, +ve ion) 577.2 (M+H)$^+$.

Example 111

(1S,6'E,13'S)-6-CHLORO-13'-HYDROXY-10'-METHYL-11'-OXO-3,4-DIHYDRO-2H-SPIRO [NAPHTHALENE-1,20'-[18]OXA[1,10]DIAZA-TRICYCLO[12.7.2.0$^{17,22}$]TRICOSA[6,14,16,22] TETRAENE]-13'-CARBOXYLIC ACID (the Relative Configuration of the Title Compound has been Confirmed by Xray Co-Crystal Structure of Mcl1+ the Title Compound of Example 112)

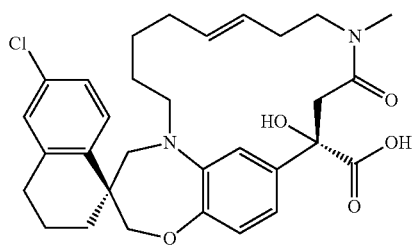 [SMILES: CN1CC/C=C/CCCCN2C[C@@]3(CCCc4cc(Cl)ccc43)COc3ccc(cc32)[C@](O)(C(=O)O)CC1=O]

The title compound (7.6 mg, 26% yield) was prepared as the first-eluting isomeric product (upon reverse-phase preparative HPLC using a Phenomenex Gemini column, 10 micron, C18, 100 Å, 150×30 mm, 0.1% TFA in CH$_3$CN/ H$_2$O, gradient 50% to 95% over 27 minutes) from the intermediates from Example 92, Step 1 in a similar fashion as described for the synthesis of Example 4. $^1$H NMR (400 MHz, (CD$_3$)$_2$SO) δ 7.70 (d, J=8.6 Hz, 1H), 7.24 (dd, J=2.2, 8.5 Hz, 1H), 7.16 (d, J=2.2 Hz, 1H), 6.89 (dd, J=2.3, 7.6 Hz, 1H), 6.82-6.79 (m, 1H), 6.89 (dd, J=1.8, 8.2 Hz, 1H), 5.79-5.70 (m, 1H), 5.51-5.42 (m, 1H), 4.09 (d, J=12.1 Hz, 1H), 3.97 (d, J=11.9 Hz, 1H), 3.49-3.30 (m, 5H), 3.19 (td, J=4.3, 14.8 Hz, 1H), 3.03-2.90 (m, 1H), 2.83 (s, 3H), 2.77-2.65 (m, 3H), 2.39-2.28 (m, 1H), 2.26-2.02 (m, 3H), 1.86-1.43 (m, 7H), 1.34-1.23 (m, 1H). LRMS: m/z (ESI, +ve ion) 553.2 (M+H)$^+$.

Example 112

(1S,6'E,13'R)-6-CHLORO-13'-HYDROXY-10'-METHYL-11'-OXO-3,4-DIHYDRO-2H-SPIRO [NAPHTHALENE-1,20'-[18]OXA[1,10]DIAZA-TRICYCLO[12.7.2.0$^{17,22}$]TRICOSA[6,14,16,22] TETRAENE]-13'-CARBOXYLIC ACID (the Relative Configuration of the Title Compound has been Confirmed by x-Ray Co-Crystal Structure of Mcl1+ the Title Compound)

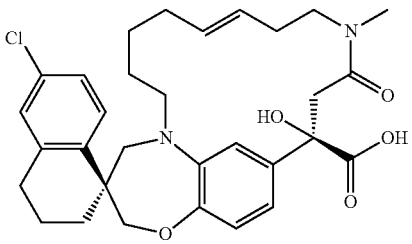 [SMILES: CN1CC/C=C/CCCCN2C[C@@]3(CCCc4cc(Cl)ccc43)COc3ccc(cc32)[C@@](O)(C(=O)O)CC1=O]

The title compound (8.8 mg, 30% yield) was prepared as the second-eluting isomeric product (upon reverse-phase preparative HPLC using a Phenomenex Gemini column, 10 micron, C18, 100 Å, 150×30 mm, 0.1% TFA in CH$_3$CN/ H$_2$O, gradient 50% to 95% over 27 minutes) from the intermediates from Example 92, Step 1 in a similar fashion as described for the synthesis of Example 4: $^1$H NMR (400 MHz, (CD$_3$)$_2$SO) δ 7.68 (d, J=8.4 Hz, 1H), 7.26 (t, J=6.5 Hz, 1H), 7.16 (d, J=2.3 Hz, 1H), 6.89 (d, J=8.5 Hz, 1H), 6.80 (d, J=8.2 Hz, 1H), 6.74 (d, J=2.0 Hz, 1H), 5.84-5.78 (m, 1H), 5.52-5.40 (m, 1H), 4.05-3.92 (m, 2H), 3.54-3.30 (m, 4H), 3.27 (d, J=14.3 Hz, 1H), 3.20-3.12 (m, 1H), 3.05-2.93 (m, 1H), 2.84 (s, 3H), 2.79-2.61 (m, 3H), 2.42-2.29 (m, 1H), 2.24-2.02 (m, 3H), 1.99-1.72 (m, 3H), 1.65-1.22 (m, 5H). LRMS: m/z (ESI, +ve ion) 553.2 (M+H)$^+$.

Example 113

(1S,6′Z,13′S)-6-CHLORO-13′-HYDROXY-10′-METHYL-11′-OXO-3,4-DIHYDRO-2H-SPIRO[NAPHTHALENE-1,20′-[18]OXA[1,10]DIAZA-TRICYCLO [12.7.2.0$^{17,22}$]TRICOSA [6,14,16,22]TETRAENE]-13′-CARBOXYLIC ACID AND (1S,6′Z,13′R)-6-CHLORO-13′-HYDROXY-10′-METHYL-11′-OXO-3,4-DIHYDRO-2H-SPIRO[NAPHTHALENE-1,20′-[18]OXA[1,10]DIAZATRICYCLO [12.7.2.0$^{17,22}$]TRICOSA [6,14,16,22]TETRAENE]-13′-CARBOXYLIC ACID

Example 114

(1S,13′S)-6-CHLORO-13′-HYDROXY-10′-METHYL-11′-OXO-3,4-DIHYDRO-2H-SPIRO[NAPHTHALENE-1,20′-[18]OXA[1,10]DIAZA-TRICYCLO[12.7.2.0$^{17,22}$]TRICOSA [14,16,22]TRIENE]-13′-CARBOXYLIC ACID OR (1S,13′R)-6-CHLORO-13′-HYDROXY-10′-METHYL-11′-OXO-3,4-DIHYDRO-2H-SPIRO[NAPHTHALENE-1,20′-[18]OXA[1,10]DIAZATRICYCLO[12.7.2.0$^{17,22}$]TRICOSA[14,16,22]TRIENE]-13′-CARBOXYLIC ACID (the Relative Configuration of the Title Compound has not been Definitively Established, and is Isomeric to the Title Compound of Example 115)

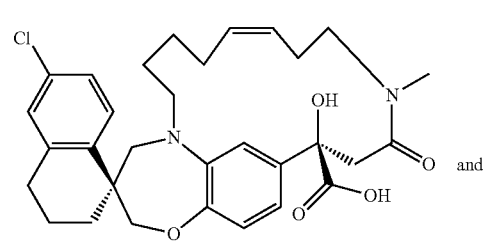

and

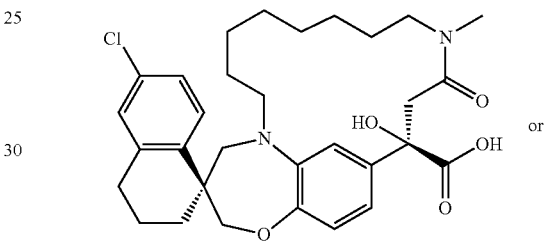

or

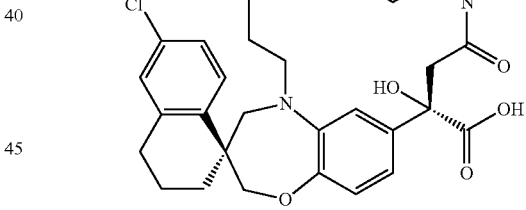

The title compounds (4.0 mg, 14% yield) were prepared as the third-eluting isomeric products (upon reverse-phase preparative HPLC using a Phenomenex Gemini column, 10 micron, C18, 100 Å, 150×30 mm, 0.1% TFA in CH$_3$CN/H$_2$O, gradient 50% to 95% over 27 minutes) from the intermediates from Example 92, Step 1 in a similar fashion as described for the synthesis of Example 4: $^1$H NMR (400 MHz, (CD$_3$)$_2$SO) δ 7.71 (d, J=8.6 Hz, 1H), 7.30-7.20 (m, 1H), 7.19-7.13 (m, 1H), 6.99-6.91 (m, 1H), 6.85-6.80 (m, 1H), 6.72-6.63 (m, 1H), 5.65-5.53 (m, 1H), 5.50-5.39 (m, 2H), 4.09-3.93 (m, 1H), 3.74-3.66 (m, 6H), 3.46-3.18 (m, 6H), 2.93-2.68 (m, 6H), 2.40-2.15 (m, 4H), 1.92-1.72 (m, 3H), 1.69-1.29 (m, 5H). LRMS: m/z (ESI, +ve ion) 553.2 (M+H)$^+$.

The title compound (5.3 mg, 27% overall yield, 2 steps) was prepared as the faster-eluting isomeric product (upon reverse-phase preparative HPLC using a Phenomenex Gemini column, 10 micron, C18, 100 Å, 150×30 mm, 0.1% TFA in CH$_3$CN/H$_2$O, gradient 50% to 95% over 27 minutes) from the intermediates from Example 91, Step 1 in a similar fashion as described for the synthesis of Example 110. $^1$H NMR (400 MHz, (CD$_3$)$_2$SO) δ 7.70 (t, J=6.9 Hz, 1H), 7.23 (d, J=8.4 Hz, 1H), 7.19-7.07 (m, 1H), 6.95 (d, J=8.4 Hz, 1H), 6.82 (d, J=8.2 Hz, 1H), 6.79-6.68 (m, 1H), 4.07 (d, J=11.7 Hz, 1H), 3.98 (d, J=11.9 Hz, 1H), 3.61-3.24 (m, 5H), 3.07-2.90 (m, 2H), 2.87-2.64 (m, 5H), 1.92-1.09 (m, 16H). LRMS: m/z (ESI, +ve ion) 555.2 (M+H)$^+$.

Example 115

(1S,13'S)-6-CHLORO-13'-HYDROXY-10'-METHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[14,16,22]TRIENE]-13'-CARBOXYLIC ACID OR (1S,13'R)-6-CHLORO-13'-HYDROXY-10'-METHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[14,16,22]TRIENE]-13'-CARBOXYLIC ACID (the Relative Configuration of the Title Compound has not been Definitively Established, and is Isomeric to the Title Compound of Example 114)

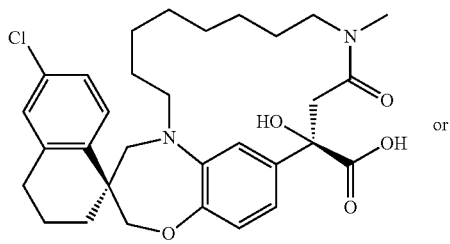

or

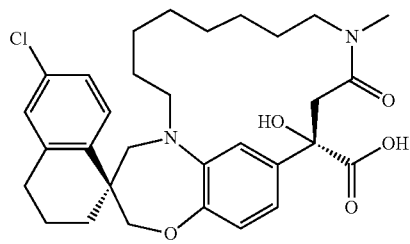

The title compound (6.2 mg, 32% overall yield, 2 steps) was prepared as the later-eluting isomeric product (upon reverse-phase preparative HPLC using a Phenomenex Gemini column, 10 micron, C18, 100 Å, 150×30 mm, 0.1% TFA in CH$_3$CN/H$_2$O, gradient 50% to 95% over 27 minutes) from the intermediates from Example 91, Step 1 in a similar fashion as described for the synthesis of Example 110: $^1$H NMR (400 MHz, (CD$_3$)$_2$SO) δ 7.69 (d, J=8.6 Hz, 1H), 7.26 (dd, J=2.2, 8.6 Hz, 1H), 7.16 (d, J=2.2 Hz, 1H), 6.94 (t, J=6.7 Hz, 1H), 6.82 (d, J=8.2 Hz, 1H), 6.77-6.70 (m, 1H), 4.02 (d, J=11.9 Hz, 1H), 3.94 (d, J=12.1 Hz, 1H), 3.61 (t, J=10.3 Hz, 1H), 3.53 (d, J=14.1 Hz, 1H), 3.40-3.25 (m, 3H), 3.09-2.96 (m, 2H), 2.80 (s, 3H), 2.77-2.62 (m, 3H), 1.96-1.87 (m, 1H), 1.86-1.71 (m, 3H), 1.68-1.54 (m, 3H), 1.50-1.26 (m, 8H), 1.21-1.08 (m, 1H). LRMS: m/z (ESI, +ve ion) 555.2 (M+H)$^+$.

Example 116

(1S,7'E,12'S,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA [7,14,16,22]TETRAENE]-13'-CARBOXYLIC ACID OR (1S,7'E,12'R,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA [7,14,16,22]TETRAENE]-13'-CARBOXYLIC ACID OR (1S,7'E,12'S,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLIC ACID OR (1S,7'E,12'R,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA [7,14,16,22]TETRAENE]-13'-CARBOXYLIC ACID OR (1S,7'Z,12'S,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLIC ACID OR (1S,7'Z,12'R,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLIC ACID OR (1S,7'Z,12'S,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA [7,14,16,22]TETRAENE]-13'-CARBOXYLIC ACID or (1S,7'Z,12'R,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLIC ACID (the Relative Configuration of the Title Compound has not been Confirmed, and is Isomeric to the Title Compounds of Example 117, 118 and 119)

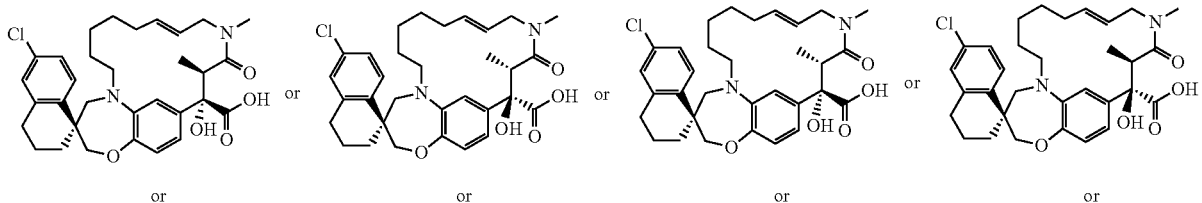

or

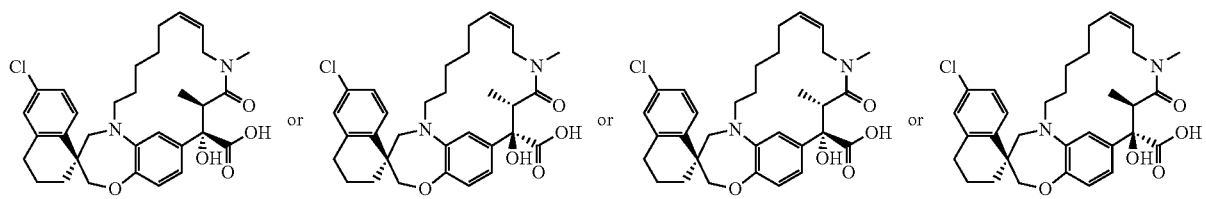

Step 1. (2R,3S)-4-TERT-BUTYL 1-METHYL 2-((S)-6'-CHLORO-5-(HEPT-6-EN-1-YL)-3,4,4,5-TETRAHYDRO-2H,2'H-SPIRO[BENZO[B][1,4]OXAZEPINE-3,1'-NAPHTHALEN]-7-YL)-2-HYDROXY-3-METHYLSUCCINATE AND/OR (2S,3R)-4-TERT-BUTYL 1-METHYL 2-((S)-6'-CHLORO-5-(HEPT-6-EN-1-YL)-3',4,4',5-TETRAHYDRO-2H,2'H-SPIRO [BENZO [B] [1,4] OXAZEPINE-3,1'-NAPHTHALEN]-7-YL)-2-HYDROXY-3-METHYLSUCCINATE AND/OR (2R,3R)-4-TERT-BUTYL 1-METHYL 2-((S)-6'-CHLORO-5-(HEPT-6-EN-1-YL)-3',4,4',5-TETRAHYDRO-2H,2'H-SPIRO[BENZO[B][1,4]OXAZEPINE-3,1'-NAPHTHALEN]-7-YL)-2-HYDROXY-3-METHYLSUCCINATE AND/OR (2S,3S)-4-TERT-BUTYL 1-METHYL 2-((S)-6'-CHLORO-5-(HEPT-6-EN-1-YL)-3',4,4',5-TETRAHYDRO-2H,2'H-SPIRO[BENZO[B][1,4]OXAZEPINE-3,1'-NAPHTHALEN]-7-YL)-2-HYDROXY-3-METHYLSUCCINATE

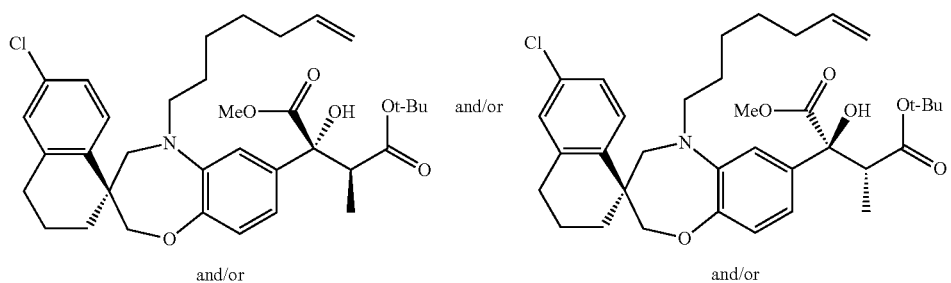

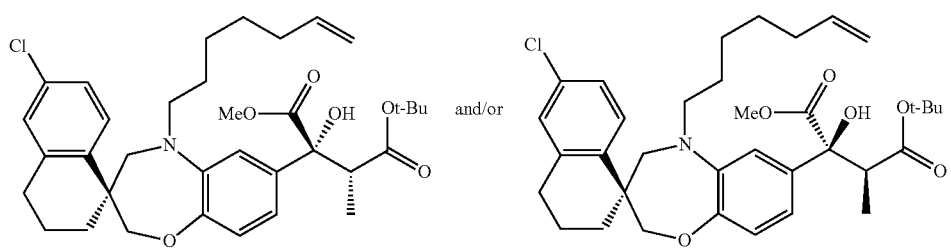

The above compounds (150 mg, 18% overall yield, 6 steps) were prepared from (S)-methyl 6'-chloro-3',4,4',5-tetrahydro-2H,2'H-spiro[benzo[b][1,4]oxazepine-3,1'-naphthalene]-7-carboxylate (from Intermediate 11A1 Step 11A) as the first-eluting diastereoisomers (2 isomers) in a similar fashion as described for the synthesis of Example 62. $^1$H NMR (400 MHz, CD$_2$Cl$_2$) δ=7.76 (d, J=3.7 Hz, 0.5H), 7.74 (d, J=3.7 Hz, 0.5H), 7.21-7.12 (m, 1H), 7.12-7.06 (m, 1H), 6.98-6.89 (m, 1H), 6.87-6.81 (m, 2H), 5.90-5.78 (m, 1H), 5.07-4.92 (m, 2H), 4.25-4.15 (m, 1H), 4.13-4.02 (m, 3H), 3.79-3.70 (m, 3H), 3.64-3.47 (m, 1H), 3.40-3.16 (m, 4H), 2.83-2.70 (m, 2H), 2.09 (q, J=6.6 Hz, 2H), 2.00-1.89 (m, 1H), 1.89-1.77 (m, 2H), 1.67-1.55 (m, 3H), 1.52-1.32 (m, 13H), 1.05-0.94 (m, 3H). LRMS. m/z (ESI, +ve ion) 612.2 (M+H)$^+$.

Step 2. METHYL (1S,7'E,12'S,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA [7,14,16,22]TETRAENE]-13'-CARBOXYLATE AND/OR METHYL (1S,7'E,12'R,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA [7,14,16,22]TETRAENE]-13'-CARBOXYLATE AND/OR METHYL (1S,7'E,12'S,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA [7,14,16,22]TETRAENE]-13'-CARBOXYLATE AND/OR METHYL (1S,7'E,12'R,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA [7,14,16,22]TETRAENE]-13'-CARBOXYLATE AND/OR METHYL (1S,7'Z,12'S,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLATE AND/OR METHYL (1S,7'Z,12'R,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLATE AND/OR METHYL (1S,7'Z,12'S,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLATE AND/OR OR METHYL (1S,7'Z,12'R,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLATE

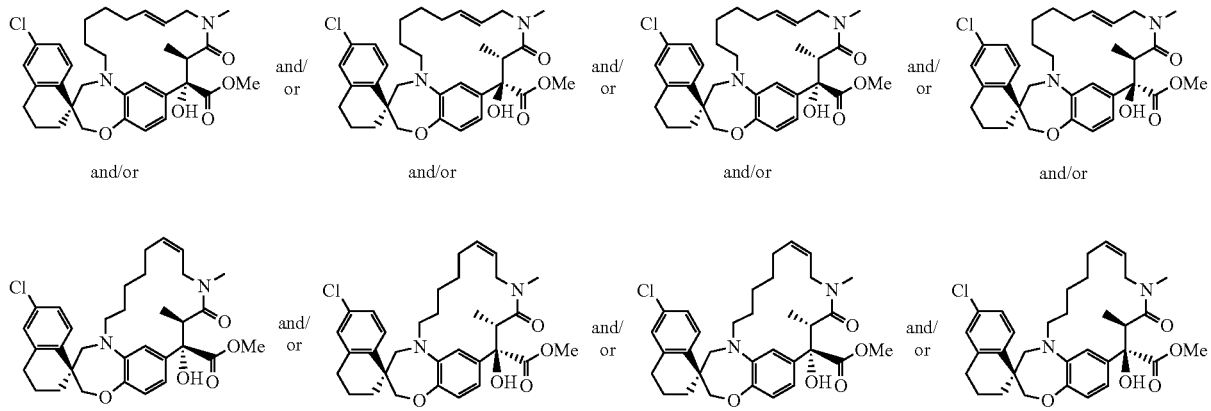

The above compounds (52 mg, 36% overall yield, 3 steps) were prepared as an unseparated mixture of 4 isomeric products from the intermediates from Step 1 in a similar fashion as described for the synthesis methyl (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 1, Step 7). LRMS: m/z (ESI, +ve ion) 581.2 (M+H)$^+$.

Step 3. (1S,7'E,12'S,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLIC ACID, (1S,7'E,12'R,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA[7,14,16,22]TETRAENE]-13'-CARBOXYLIC ACID, (1S,7'E,12'S,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLIC ACID, (1S,7'E,12'SR,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA [7,14,16,22]TETRAENE]-13'-CARBOXYLICACID, (1S,7'Z,12'S,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA [7,14,16,22]TETRAENE]-13'-CARBOXYLIC ACID, (1S,7'Z,12'R,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA [7,14,16,22]TETRAENE]-13'-CARBOXYLICACID, (1S,7'Z,12'S,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLIC ACID, OR (1S,7'Z,12'SR,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17^{22}}$]TRICOSA [7,14,16,22]TETRAENE]-13'-CARBOXYLIC ACID

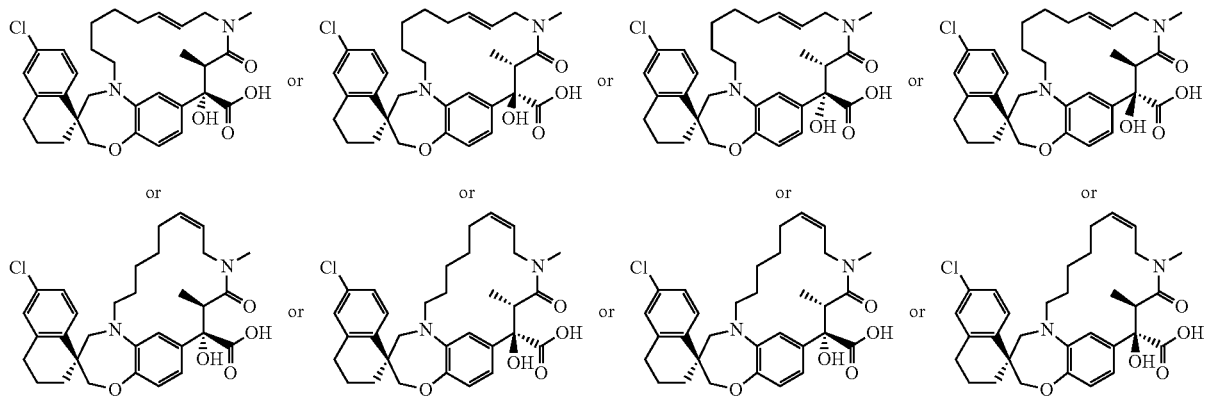

The title compound (2.2 mg, 9% yield) was prepared as the first-eluting isomeric product (upon reverse-phase preparative HPLC using a Phenomenex Gemini column, 10 micron, C18, 100 Å, 150×30 mm, 0.1% TFA in CH$_3$CN/H$_2$O, gradient 50% to 95% over 27 minutes) from the intermediates from Step 2 in a similar fashion as described for the synthesis Example 62. $^1$H NMR (400 MHz, (CD$_3$)$_2$SO) δ 7.66 (d, J=8.4 Hz, 1H), 7.22 (dd, J=2.2, 8.5 Hz, 1H), 7.16 (d, J=2.2 Hz, 1H), 6.95 (d, J=8.5 Hz, 1H), 6.80 (d, J=8.2 Hz, 1H), 6.62 (s, 1H), 5.71-5.53 (m, 2H), 4.27 (d, J=15.1 Hz, 1H), 3.99 (s, 2H), 3.76 (d, J=18.0 Hz, 1H), 3.46 (q, J=7.2 Hz, 1H), 3.32-3.20 (m, 4H), 3.09 (d, J=10.4 Hz, 1H), 2.86 (s, 3H), 2.77-2.65 (m, 2H), 2.18-2.10 (m, 1H), 2.07-1.97 (m, 1H), 1.89-1.73 (m, 3H), 1.71-1.60 (m, 1H), 1.57-1.29 (m, 6H), 0.95 (d, J=7.0 Hz, 3H). LRMS. m/z (ESI, +ve ion) 567.2 (M+H)$^+$.

Example 117

(1S,7'E,12'S,13'S)-6-CHLORO-13'-HYDROXY-10',
12'-DIMETHYL-11'-OXO-3,4-DIHYDRO-2H-
SPIRO[NAPHTHALENE-1,20'-[18]OXA[1,10]
DIAZATRICYCLO [12.7.2.0$^{17,22}$]TRICOSA [7,14,
16,22]TETRAENE]-13'-CARBOXYLICACID, (1S,
7'E,12'R,13'R)-6-CHLORO-13'-HYDROXY-10',12'-
DIMETHYL-11'-OXO-3,4-DIHYDRO-2H-SPIRO
[NAPHTHALENE-1,20'-[18]OXA[1,10]
DIAZATRICYCLO [12.7.2.0$^{17,22}$]TRICOSA [7,14,
16,22]TETRAENE]-13'-CARBOXYLIC ACID,
(1S,7'E,12'S,13'R)-6-CHLORO-13'-HYDROXY-10',
12'-DIMETHYL-11'-OXO-3,4-DIHYDRO-2H-
SPIRO[NAPHTHALENE-1,20'-[18]OXA[1,10]
DIAZATRICYCLO [12.7.2.0$^{17,22}$]TRICOSA [7,14,
16,22]TETRAENE]-13'-CARBOXYLIC ACID,
(1S,7'E,12'SR,13'S)-6-CHLORO-13'-HYDROXY-
10',12'-DIMETHYL-11'-OXO-3,4-DIHYDRO-2H-
SPIRO[NAPHTHALENE-1,20'-[18]OXA[1,10]
DIAZATRICYCLO[12.7.2.0$^{17,22}$]TRICOSA[7,14,
16,22]TETRAENE]-13'-CARBOXYLICACID, (1S,
7'Z,12'S,13'S)-6-CHLORO-13'-HYDROXY-10',12'-
DIMETHYL-11'-OXO-3,4-DIHYDRO-2H-SPIRO
[NAPHTHALENE-1,20'-[18]OXA[1,10]
DIAZATRICYCLO [12.7.2.0$^{17,22}$]TRICOSA [7,14,
16,22]TETRAENE]-13'-CARBOXYLICACID, (1S,
7'Z,12'R,13'R)-6-CHLORO-13'-HYDROXY-10',12'-
DIMETHYL-11'-OXO-3,4-DIHYDRO-2H-SPIRO
[NAPHTHALENE-1,20'-[18]OXA[1,10]
DIAZATRICYCLO [12.7.2.0$^{17,22}$]TRICOSA [7,14,
16,22]TETRAENE]-13'-CARBOXYLICACID, (1S,
7'Z,12'S,13'R)-6-CHLORO-13'-HYDROXY-10',12'-
DIMETHYL-11'-OXO-3,4-DIHYDRO-2H-SPIRO
[NAPHTHALENE-1,20'-[18]OXA[1,10]
DIAZATRICYCLO [12.7.2.0$^{17,22}$]TRICOSA [7,14,
16,22]TETRAENE]-13'-CARBOXYLIC ACID,
AND/OR (1S,7'Z,12'SR,13'S)-6-CHLORO-13'-HY-
DROXY-10',12'-DIMETHYL-11'-OXO-3,4-DI-
HYDRO-2H-SPIRO[NAPHTHALENE-1,20'-[18]
OXA[1,10]DIAZATRICYCLO [12.7.2.0$^{17,22}$]
TRICOSA [7,14,16,22]TETRAENE]-13'-
CARBOXYLIC ACID (the Relative Configuration
of the Title Compounds have not been Confirmed,
and is Isomeric to the Title Compounds of
Examples 116, 118, and 119)

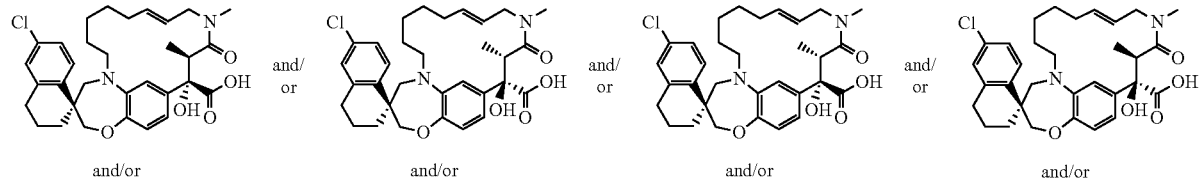

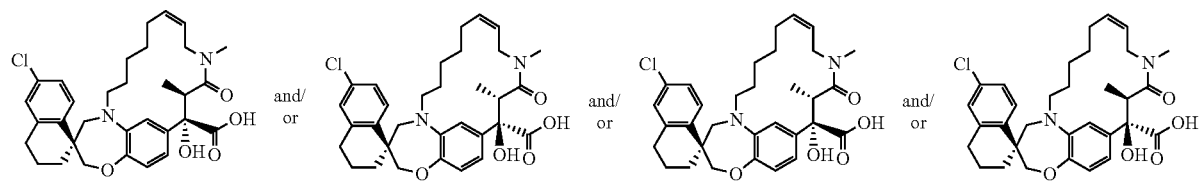

The title compounds (4.4 mg, 18% yield) were prepared as the second-eluting isomeric products (mixture of 2 isomers) (upon reverse-phase preparative HPLC using a Phenomenex Gemini column, 10 micron, C18, 100 Å, 150×30 mm, 0.1% TFA in CH$_3$CN/H$_2$O, gradient 50% to 95% over 27 minutes) from the intermediates from Example 116, Step 2 in a similar fashion as described for the synthesis of Example 4. $^1$H NMR (400 MHz, (CD$_3$)$_2$SO) δ 7.69 (m, 1H), 7.27-7.19 (m, 1H), 7.19-7.12 (m, 1H), 6.98-6.91 (m, 1H), 6.84-6.79 (m, 1H), 6.69-6.64 (m, 0.6H), 6.63-6.58 (m, 0.4H), 5.74-5.61 (m, 0.5H), 5.61-5.52 (m, 1H), 5.50-5.41 (m, 0.5H), 4.32-4.15 (m, 1H), 4.13-3.86 (m, 2H), 3.85-3.71 (m, 1H), 3.39-3.16 (m, 4H), 3.16-2.97 (m, 1H), 2.92 (s, 1.6H), 2.89-2.85 (s, 1.4H), 2.77-2.68 (m, 2H), 2.31-1.99 (m, 2H), 1.84-1.59 (m, 5H), 1.58-1.20 (m, 6H), 0.93 (d, J=7.2 Hz, 1.4H), 0.86 (d, J=7.2 Hz, 1.6H). LRMS: m/z (ESI, +ve ion) 567.2 (M+H)$^+$.

Example 118

(1S,7'Z,12'S,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA [7,14,16,22]TETRAENE]-13'-CARBOXYLIC ACID, (1S,7'Z,12'R,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLIC ACID, (1S,7'Z,12'S,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLIC ACID, AND/OR (1S,7'Z,12'SR,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA [7,14,16,22]TETRAENE]-13'-CARBOXYLIC ACID (the Relative Configuration of the Title Compounds have not been Confirmed, and is Isomeric to the Title Compounds of Examples 116, 117, and 120)

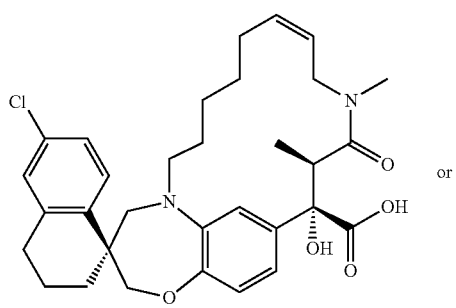

or

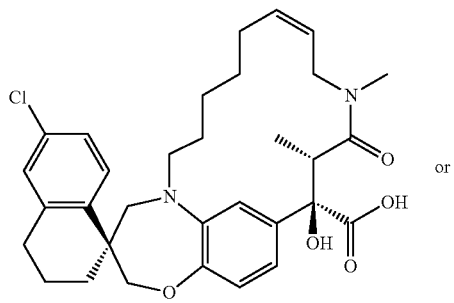

or

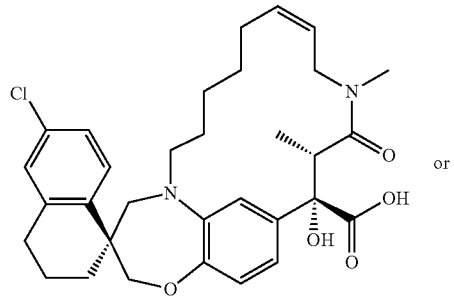

or

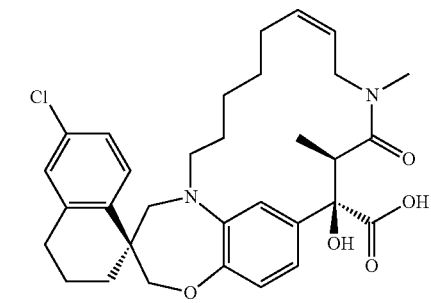

The title compound (2.5 mg, 10% yield) was prepared as the final-eluting isomeric product (upon reverse-phase preparative HPLC using a Phenomenex Gemini column, 10 micron, C18, 100 Å, 150×30 mm, 0.1% TFA in CH$_3$CN/H$_2$O, gradient 50% to 95% over 27 minutes) from the intermediates from Example 116, Step 1 in a similar fashion as described for the synthesis of Example 4. $^1$H NMR (400 MHz, (CD$_3$)$_2$SO) δ 7.70 (d, J=8.6 Hz, 1H), 7.25 (d, J=8.8 Hz, 1H), 7.19-7.14 (m, 1H), 6.91 (d, J=8.2 Hz, 1H), 6.82 (t, J=7.8 Hz, 1H), 6.63 (s, 1H), 6.27 (br. s., 1H), 5.55 (t, J=8.8 Hz, 1H), 5.50-5.41 (m, 1H), 4.32 (dd, J=8.7, 17.3 Hz, 1H), 4.02 (d, J=12.3 Hz, 1H), 3.93 (d, J=12.1 Hz, 1H), 3.69 (d, J=15.8 Hz, 1H), 3.55 (d, J=14.3 Hz, 1H), 3.32-3.19 (m, 3H), 3.10-2.97 (m, 1H), 2.90 (s, 3H), 2.90-2.62 (m, 3H), 2.35-2.18 (m, 1H), 2.06-1.89 (m, 2H), 1.87-1.24 (m, 9H), 0.84 (d, J=6.8 Hz, 3H). LRMS: m/z (ESI, +ve ion) 567.2 (M+H)$^+$.

Example 119

(1S,7'E,12'S,13'S)-6-CHLORO-13'-HYDROXY-10',
12'-DIMETHYL-11'-OXO-3,4-DIHYDRO-2H-
SPIRO[NAPHTHALENE-1,20'-[18]OXA[1,10]
DIAZATRICYCLO [12.7.2.0$^{17,22}$]TRICOSA[7,14,
16,22]TETRAENE]-13'-CARBOXYLIC ACID,
(1S,7'E,12'R,13'R)-6-CHLORO-13'-HYDROXY-10',
12'-DIMETHYL-11'-OXO-3,4-DIHYDRO-2H-
SPIRO[NAPHTHALENE-1,20'-[18]OXA[1,10]
DIAZATRICYCLO[12.7.2.0$^{17,22}$]TRICOSA[7,14,
16,22]TETRAENE]-13'-CARBOXYLIC ACID,
(1S,7'E,12'S,13'R)-6-CHLORO-13'-HYDROXY-10',
12'-DIMETHYL-11'-OXO-3,4-DIHYDRO-2H-
SPIRO[NAPHTHALENE-1,20'-[18]OXA[1,10]
DIAZATRICYCLO [12.7.2.0$^{17,22}$]TRICOSA [7,14,
16,22]TETRAENE]-13'-CARBOXYLIC ACID,
(1S,7'E,12'SR,13'S)-6-CHLORO-13'-HYDROXY-
10',12'-DIMETHYL-11'-OXO-3,4-DIHYDRO-2H-
SPIRO[NAPHTHALENE-1,20'-[18]OXA[1,10]
DIAZATRICYCLO [12.7.2.0$^{17,22}$]TRICOSA [7,14,
16,22]TETRAENE]-13'-CARBOXYLIC ACID,
(1S,7'Z,12'S,13'S)-6-CHLORO-13'-HYDROXY-10',
12'-DIMETHYL-11'-OXO-3,4-DIHYDRO-2H-
SPIRO[NAPHTHALENE-1,20'-[18]OXA[1,10]
DIAZATRICYCLO [12.7.2.0$^{17,22}$]TRICOSA [7,14,
16,22]TETRAENE]-13'-CARBOXYLIC ACID,
(1S,7'Z,12'R,13'R)-6-CHLORO-13'-HYDROXY-10',
12'-DIMETHYL-11'-OXO-3,4-DIHYDRO-2H-
SPIRO[NAPHTHALENE-1,20'-[18]OXA[1,10]
DIAZATRICYCLO [12.7.2.0$^{17,22}$]TRICOSA [7,14,
16,22]TETRAENE]-13'-CARBOXYLIC ACID,
(1S,7'Z,12'S,13'R)-6-CHLORO-13'-HYDROXY-10',
12'-DIMETHYL-11'-OXO-3,4-DIHYDRO-2H-
SPIRO[NAPHTHALENE-1,20'-[18]OXA[1,10]
DIAZATRICYCLO[12.7.2.0$^{17,22}$]TRICOSA[7,14,
16,22]TETRAENE]-13'-CARBOXYLIC ACID,
AND/OR (1S,7'Z,12'SR,13'S)-6-CHLORO-13'-HY-
DROXY-10',12'-DIMETHYL-11'-OXO-3,4-DI-
HYDRO-2H-SPIRO[NAPHTHALENE-1,20'-[18]
OXA[1,10]DIAZATRICYCLO[12.7.2.0$^{17,22}$]
TRICOSA[7,14,16,22]TETRAENE]-13'-
CARBOXYLIC ACID

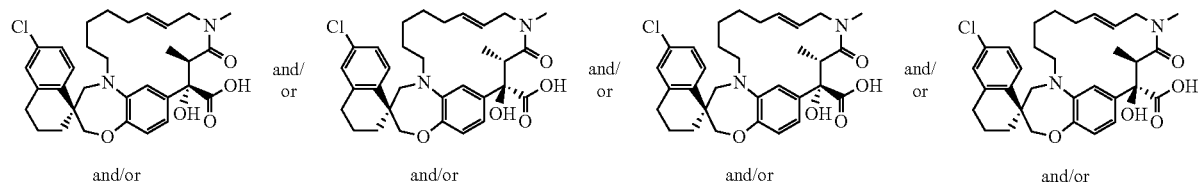

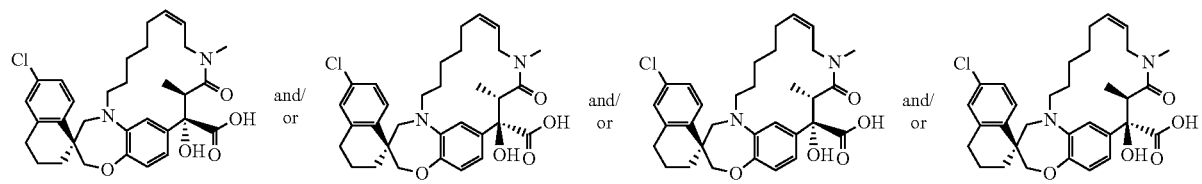

Step 1 (2R,3S)-4-TERT-BUTYL 1-METHYL 2-((S)-6'-CHLORO-5-(HEPT-6-EN-1-YL)-3',4,4',5-TETRAHYDRO-2H,2'H-SPIRO[BENZO[B][1,4] OXAZEPINE-3,1'-NAPHTHALEN]-7-YL)-2-HYDROXY-3-METHYLSUCCINATE, (2S,3R)-4-TERT-BUTYL 1-METHYL 2-((S)-6'-CHLORO-5-(HEPT-6-EN-1-YL)-3',4,4',5-TETRAHYDRO-2H,2'H-SPIRO[BENZO[B][1,4]OXAZEPINE-3,1'-NAPHTHALEN]-7-YL)-2-HYDROXY-3-METHYLSUCCINATE, (2R,3R)-4-TERT-BUTYL 1-METHYL 2-((S)-6'-CHLORO-5-(HEPT-6-EN-1-YL)-3',4,4',5-TETRAHYDRO-2H,2'H-SPIRO[BENZO[B][1,4]OXAZEPINE-3,1'-NAPHTHALEN]-7-YL)-2-HYDROXY-3-METHYLSUCCINATE AND/OR (2S,3S)-4-TERT-BUTYL 1-METHYL 2-((S)-6'-CHLORO-5-(HEPT-6-EN-1-YL)-3',4,4',5-TETRAHYDRO-2H,2'H-SPIRO[BENZO[B][1,4]OXAZEPINE-3,1'-NAPHTHALEN]-7-YL)-2-HYDROXY-3-METHYLSUCCINATE

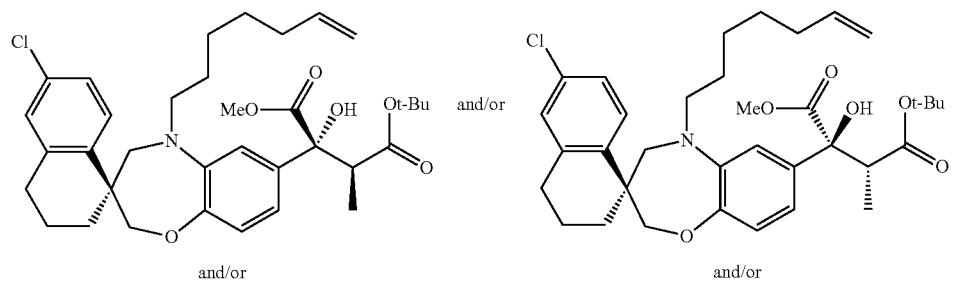

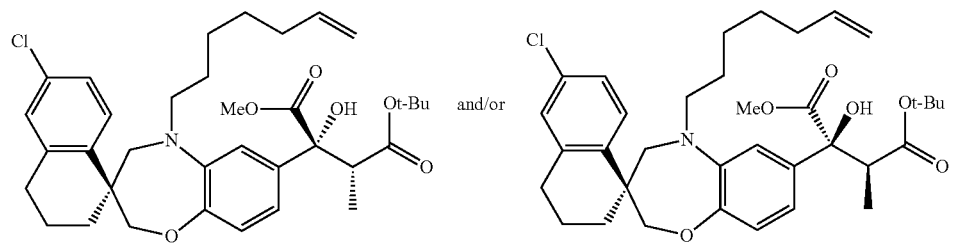

The above compounds (230 mg, 28% overall yield, 6 steps) were prepared as the second-eluting diastereoisomers (2 isomers) from Example 116, Step 1. $^1$H NMR (400 MHz, CD$_2$Cl$_2$) δ 7.73 (m, 1H), 7.17-7.13 (m, 1H), 7.09 (d, J=2.3 Hz, 1H), 7.11-7.07 (m, 1H), 7.11-7.07 (m, 1H), 7.11-7.07 (m, 1H), 6.95-6.92 (m, 1H), 6.92-6.85 (m, 1H), 6.85-6.81 (m, 1H), 5.85 (m, 1H), 5.06-5.02 (m, 0.5H), 5.02-4.99 (m, 0.5H), 4.99-4.96 (m, 0.5H), 4.96-4.94 (m, 0.5H), 4.20-4.17 (m, 1H), 4.09-4.00 (m, 2H), 3.76-3.73 (m, 3H), 3.55 (d, J=10.2, 1H), 3.51 (d, J=10.2, 1H), 3.46-3.38 (m, 1H), 3.35-3.20 (m, 3H), 2.81-2.71 (m, 2H), 2.10 (m, 2H), 1.97-1.78 (m, 3H), 1.68-1.54 (m, 3H), 1.51-1.33 (m, 4H), 1.28-1.19 (m, 12H). LRMS. m/z (ESI, +ve ion) 612.2 (M+H)$^+$.

Step 2. METHYL (1S,7'E,12'S,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLATE, METHYL (1S,7'E,12'R,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLATE, METHYL (1S,7'E,12'S,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLATE, METHYL (1S,7'E,12'SR,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLATE, METHYL (1S,7'Z,12'S,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLATE, METHYL (1S,7'Z,12'R,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA [7,14,16,22]TETRAENE]-13'-CARBOXYLATE, METHYL (1S,7'Z,12'S,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA [7,14,16,22]TETRAENE]-13'-CARBOXYLATE, OR METHYL (1S,7'Z,12'SR,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA [7,14,16,22]TETRAENE]-13'-CARBOXYLATE

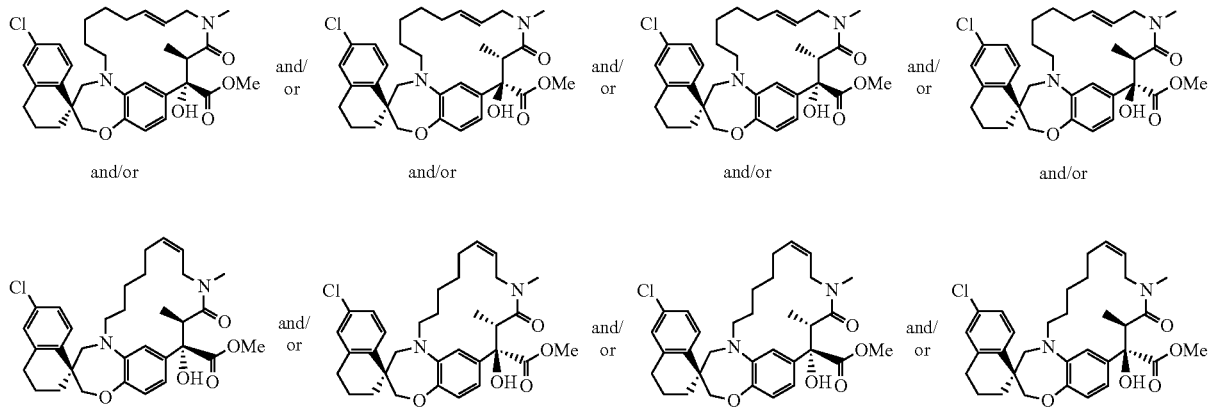

The above compounds (33 mg, 33% overall yield, 3 steps) were prepared as an unseparated mixture of 4 isomeric products from the intermediates from Step 1 in a similar fashion as described for the synthesis methyl (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 1, Step 7). LRMS: m/z (ESI, +ve ion) 581.2 (M+H)$^+$.

Step 3. (1S,7'E,12'S,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLIC ACID AND/OR (1S,7'E,12'R,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLIC ACID AND/OR (1S,7'E,12'S,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLIC ACID AND/OR (1S,7'E,12'SR,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA[7,14,16,22]TETRAENE]-13'-CARBOXYLIC ACID AND/OR (1S,7'Z,12'S,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA[7,14,16,22]TETRAENE]-13'-CARBOXYLIC ACID AND/OR (1S,7'Z,12'R,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLIC ACID AND/OR (1S,7'Z,12'S,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO [12.7.2.0$^{17,22}$]TRICOSA[7,14,16,22]TETRAENE]-13'-CARBOXYLIC ACID AND/OR (1S,7'Z,12'SR,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[7,14,16,22]TETRAENE]-13'-CARBOXYLIC ACID

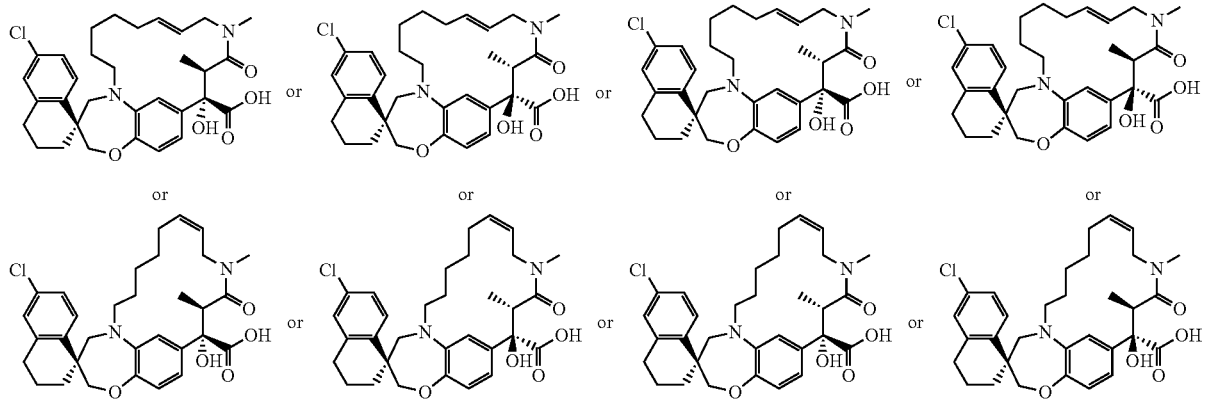

The title compounds (12 mg, 72% yield) were prepared as an unseparated mixture of 4 isomeric products (upon reverse-phase preparative HPLC using a Phenomenex Gemini column, 10 micron, C18, 100 Å, 150×30 mm, 0.1% TFA in CH$_3$CN/H$_2$O, gradient 50% to 95% over 27 minutes) from the intermediates from Step 2 in a similar fashion as described for the synthesis of Example 4. $^1$H NMR (400 MHz, (CD$_3$)$_2$SO) δ 7.72-7.54 (m, 1H), 7.27-7.14 (m, 2H), 7.08-6.66 (m, 2H), 5.64-5.55 (m, 0.4H), 5.53-5.33 (m, 1H), 5.19-4.99 (m, 0.6H), 4.43-4.31 (m, 1H), 4.20 (d, J=11.5 Hz, 1H), 4.05-3.68 (m, 3H), 3.53 (dd, J=4.6, 13.4 Hz, 1H), 3.41-3.11 (m, 3H), 3.11-2.90 (m, 2H), 2.80-2.64 (m, 3H), 2.16-1.71 (m, 5H), 1.58-1.31 (m, 5H), 1.29-1.13 (m, 5H). LRMS. m/z (ESI, +ve ion) 567.2 (M+H)$^+$.

Example 120

(1S,12'S,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZA-TRICYCLO[12.7.2.0$^{17,22}$]TRICOSA[14,16,22]TRIENE]-13'-CARBOXYLIC ACID OR (1S,12'R,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[14,16,22]TRIENE]-13'-CARBOXYLIC ACID OR (1S,12'R,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[14,16,22]TRIENE]-13'-CARBOXYLIC ACID OR (1S,12'S,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[14,16,22]TRIENE]-13'-CARBOXYLIC ACID

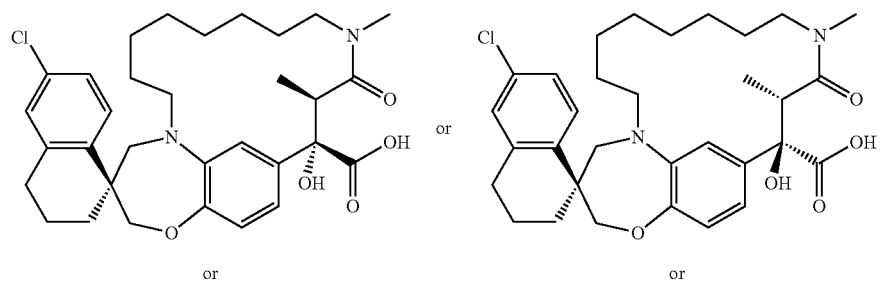

or

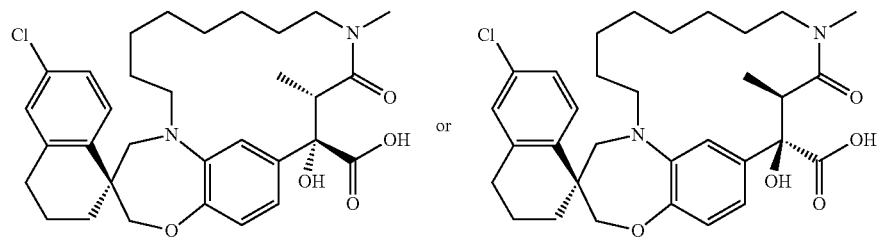

The title compound (10 mg, 41% overall yield, 2 steps) was prepared as the faster-eluting isomeric product (upon reverse-phase preparative HPLC using a Phenomenex Gemini column, 10 micron, C18, 100 Å, 150×30 mm, 0.1% TFA in CH$_3$CN/H$_2$O, gradient 50% to 95% over 27 minutes) from the intermediates from Example 116, Step 2 in a similar fashion as described for the synthesis of Example 111: $^1$H NMR (400 MHz, (CD$_3$)$_2$SO) δ 7.69 (d, J=8.6 Hz, 1H), 7.23 (dd, J=2.0, 8.8 Hz, 1H), 7.18-7.14 (m, 1H), 6.96 (dd, J=2.0, 8.2 Hz, 1H), 6.82 (d, J=8.2 Hz, 1H), 6.73 (m, 1H), 4.03 (q, J=11.9 Hz, 2H), 3.63-3.53 (m, 1H), 3.48 (q, J=7.0 Hz, 1H), 3.43-3.29 (m, 3H), 3.12-2.94 (m, 2H), 2.81 (s, 3H), 2.76-2.68 (m, 2H), 1.90-1.71 (m, 4H), 1.66-1.39 (m, 8H), 1.39-1.18 (m, 4H), 0.88 (d, J=7.0 Hz, 3H). LRMS: m/z (ESI, +ve ion) 569.2 (M+H)$^+$.

Example 121a (1S,12'S,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA [14,16,22]TRIENE]-13'-CARBOXYLIC ACID OR (1S,12'R,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA [14,16,22]TRIENE]-13'-CARBOXYLIC ACID OR (1S,12'R,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA[14,16,22]TRIENE]-13'-CARBOXYLIC ACID OR (1S,12'S,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA [14,16,22]TRIENE]-13'-CARBOXYLIC ACID

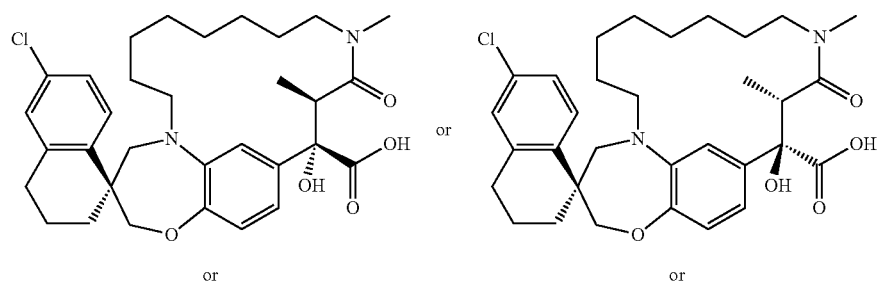

or

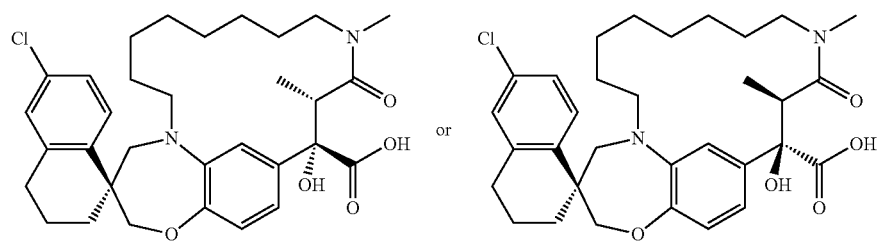

The title compound 121a (10 mg, 41% overall yield, 2 steps) was prepared as the later-eluting isomeric product (upon reverse-phase preparative HPLC using a Phenomenex Gemini column, 10 micron, C18, 100 Å, 150×30 mm, 0.1% TFA in CH$_3$CN/H$_2$O, gradient 50% to 95% over 27 minutes) from the intermediates from Example 116, Step 2 in a similar fashion as described for the synthesis of Example 110. $^1$H NMR (400 MHz, (CD$_3$)$_2$SO) δ 7.70 (d, J=8.6 Hz, 1H), 7.25 (dd, J=2.3, 8.4 Hz, 1H), 7.16 (d, J=2.3 Hz, 1H), 6.94 (dd, J=2.5, 8.0 Hz, 1H), 6.83 (d, J=8.4 Hz, 1H), 6.69 (d, J=1.8 Hz, 1H), 6.22 (br. s., 1H), 4.03 (d, J=12.1 Hz, 1H), 3.93 (d, J=12.1 Hz, 1H), 3.64-3.51 (m, 2H), 3.45 (q, J=7.2 Hz, 1H), 3.33-3.30 (m, 1H), 3.26 (d, J=14.3 Hz, 1H), 3.12-2.93 (m, 2H), 2.81 (s, 3H), 2.80-2.62 (m, 2H), 1.95-1.72 (m, 4H), 1.67-1.47 (m, 6H), 1.44-1.28 (m, 5H), 1.28-1.13 (m, 1H), 0.88 (d, J=7.2 Hz, 3H). LRMS: m/z (ESI, +ve ion) 569.2 (M+H)$^+$.

Example 121b (1S,12'S,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZA-TRICYCLO[12.7.2.0$^{17,22}$]TRICOSA[14,16,22]TRIENE]-13'-CARBOXYLIC ACID AND/OR (1S,12'R,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA [14,16,22]TRIENE]-13'-CARBOXYLIC ACID AND/OR (1S,12'R,13'S)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZA-TRICYCLO[12.7.2.0$^{17,22}$]TRICOSA [14,16,22]TRIENE]-13'-CARBOXYLIC ACID AND/OR (1S,12'S,13'R)-6-CHLORO-13'-HYDROXY-10',12'-DIMETHYL-11'-OXO-3,4-DIHYDRO-2H-SPIRO[NAPHTHALENE-1,20'-[18]OXA[1,10]DIAZATRICYCLO[12.7.2.0$^{17,22}$]TRICOSA [14,16,22]TRIENE]-13'-CARBOXYLIC ACID

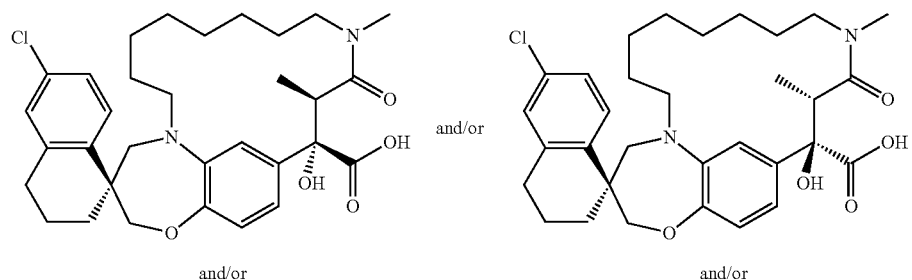

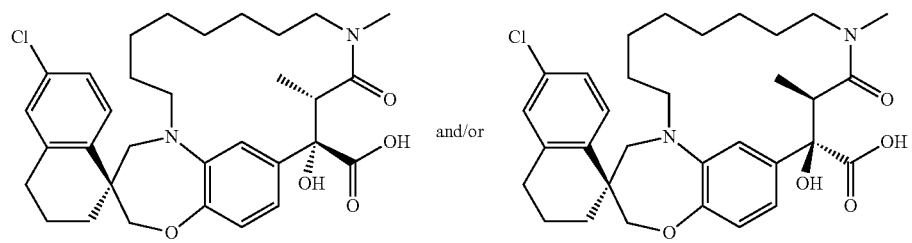

The title compound 121b (13 mg, 78% overall yield, 2 steps) was prepared as a mixture of 2 isomeric products (upon reverse-phase preparative HPLC using a Phenomenex Gemini column, 10 micron, C18, 100 Å, 150×30 mm, 0.1% TFA in CH$_3$CN/H$_2$O, gradient 50% to 95% over 27 minutes) from the intermediates from Example 119, Step 2 in a similar fashion as described for the synthesis of Example 110. $^1$H NMR (400 MHz, (CD$_3$)$_2$SO) δ 7.69 (m, 1.0H), 7.50-7.09 (m, 3.0H), 7.05-6.95 (m, 1H), 6.89-6.74 (m, 2H), 4.14-3.86 (m, 2H), 3.86-3.69 (m, 1H), 3.66-3.31 (m, 2H), 3.29-3.01 (m, 3H), 2.93-2.82 (m, 2H), 2.82-2.63 (m, 4H), 2.13-1.72 (m, 4H), 1.69-1.09 (m, 15H). LRMS. m/z (ESI, +ve ion) 569.2 (M+H)$^+$.

Example 122

(4S)-4-((3S)-6'-CHLORO-5-(((1R,2R)-2-((1S)-1-HYDROXY-2-PROPEN-1-YL)CYCLOBUTYL)METHYL)-3',4,4',5-TETRAHYDRO-2'H-SPIRO[1,5-BENZOXAZEPINE-3,1'-NAPHTHALEN]-7-YL)-4-HYDROXY-6-(4-PENTEN-1-YL)-1,2,6-THIADIAZINAN-3-ONE 1,1-DIOXIDE OR (4R)-4-((3S)-6'-CHLORO-5-(((1R,2R)-2-((1S)-1-HYDROXY-2-PROPEN-1-YL)CYCLOBUTYL)METHYL)-3',4,4',5-TETRAHYDRO-2'H-SPIRO[1,5-BENZOXAZEPINE-3,1'-NAPHTHALEN]-7-YL)-4-HYDROXY-6-(4-PENTEN-1-YL)-1,2,6-THIADIAZINAN-3-ONE 1,1-DIOXIDE

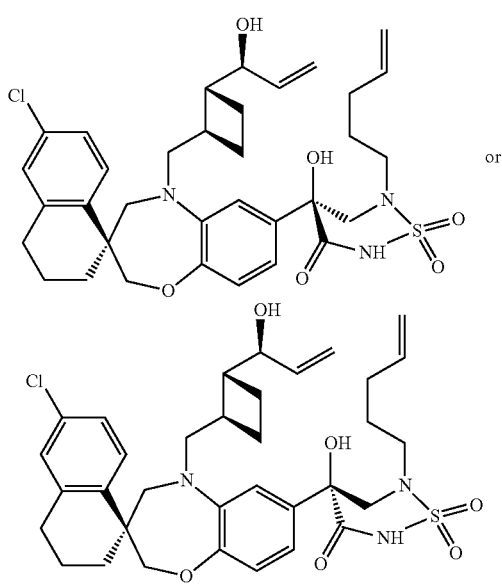

STEP 1: METHYL 2-((S)-5-(((1R,2R)-2-((S)-1-((TERT-BUTYLDIPHENYLSILYL)OXY)ALLYL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALEN]-7-YL)-2-OXOACETATE

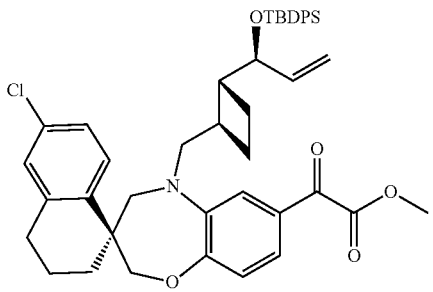

A 200 mL of round bottom flask was charged with a mixture of methyl 2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-oxoacetate (3.5 g, 6.86 mmol, Example 1, Step 3), imidazole (1.22 g, 17.8 mmol), DMAP (0.076 g, 0.62 mmol) in DCM (68.6 mL). The reaction mixture was stirred at room temperature overnight, and then diluted with DCM, quenched with 1N HCl solution. The aqueous layer was extracted with DCM (3×). The combined extracts were washed with brine, and then dried with $Na_2SO_4$. The solution was concentrated and purified by chromatography through a 330 g ISCO gold column, eluting with a gradient of 0% to 15% EtOAc in hexanes, to provide methyl 2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-oxoacetate (4.9 g, 6.55 mmol) as a viscous orange color oil. $^1$H NMR (500 MHz, $CDCl_3$) δ=7.71-7.62 (m, 5H), 7.44-7.31 (m, 8H), 7.18 (dd, J=2.4, 8.5 Hz, 1H), 7.12 (d, J=2.2 Hz, 1H), 6.96 (d, J=8.0 Hz, 1H), 5.84-5.77 (m, 1H), 4.99-4.94 (m, 2H), 4.20-4.16 (m, 1H), 4.15 (d, J=7.2 Hz, 1H), 3.96 (s, 3H), 3.48 (d, J=14.3 Hz, 1H), 3.25-3.17 (m, 3H), 2.79-2.71 (m, 2H), 2.57-2.49 (m, 1H), 2.18-2.10 (m, 1H), 1.94-1.81 (m, 3H), 1.79-1.70 (m, 3H), 1.62-1.52 (m, 2H), 1.44 (t, J=11.2 Hz, 1H), 1.06 (s, 9H).

STEP 2: (S)-METHYL 2-((S)-5-(((1R,2R)-2-((S)-1-((TERT-BUTYLDIPHENYLSILYL)OXY)ALLYL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALEN]-7-YL)-2-HYDROXY-3-NITROPROPANOATE AND (R)-METHYL 2-((S)-5-(((1R,2R)-2-((S)-1-((TERT-BUTYLDIPHENYLSILYL)OXY)ALLYL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALEN]-7-YL)-2-HYDROXY-3-NITROPROPANOATE

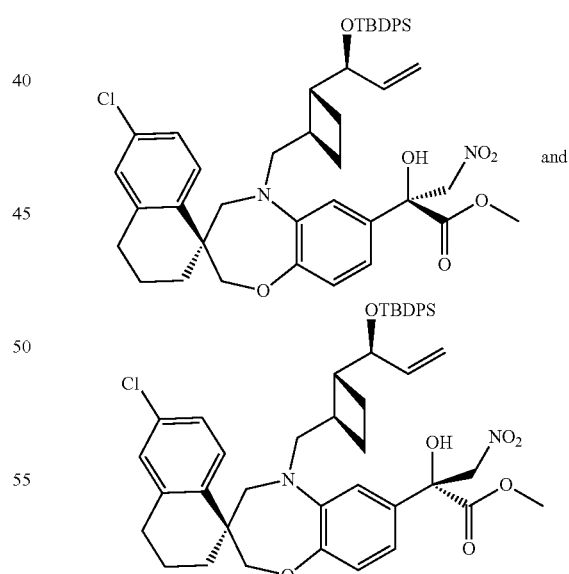

Methyl 2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-oxoacetate from Step 1 above (0.55 g, 0.735 mmol), is added to nitromethane (2.93 mL, 54.0 mmol) followed by the addition of DCM (0.459 mL) and triethylamine (0.020 mL, 0.15 mmol). The reaction mixture was stirred at room temperature overnight. The reaction mixture was concentrated and purified by chromatography through a Redi-Sep® pre-packed silica gel column (120 g), eluting with a gradient of 0% to 10% EtOAc in hexane to provide (S)-methyl 2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-hydroxy-3-nitropropanoate and (R)-methyl 2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-hydroxy-3-nitropropanoate (450 mg, 0.556 mmol). LRMS: m/z (ESI, +ve ion) 809.2 (M+H)+.

STEP 3: (S)-METHYL 3-AMINO-2-((S)-5-(((1R,2R)-2-((S)-1-((TERT-BUTYLDIPHENYLSILYL)OXY)ALLYL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALEN]-7-YL)-2-HYDROXYPROPANOATE AND (R)-METHYL 3-AMINO-2-((S)-5-(((1R,2R)-2-((S)-1-((TERT-BUTYLDIPHENYLSILYL)OXY)ALLYL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALEN]-7-YL)-2-HYDROXYPROPANOATE layer was washed with brine, dried over MgSO4, filtered, concentrated and then purified by chromatography, eluting with a gradient of 0% to 10% MeOH in DCM to give (S)-methyl 3-amino-2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-hydroxypropanoate and (R)-methyl 3-amino-2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-hydroxypropanoate (0.39 g, 0.50 mmol). LRMS: m/z (ESI, +ve ion) 779.2 (M+H)+.

STEP 4: (S)-METHYL 2-((S)-5-(((1R,2R)-2-((S)-1-((TERT-BUTYLDIPHENYLSILYL)OXY)ALLYL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALEN]-7-YL)-2-HYDROXY-3-(PENT-4-EN-1-YLAMINO)PROPANOATE AND (R)-METHYL 2-((S)-5-(((1R,2R)-2-((S)-1-((TERT-BUTYLDIPHENYLSILYL)OXY)ALLYL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALEN]-7-YL)-2-HYDROXY-3-(PENT-4-EN-1-YLAMINO)PROPANOATE

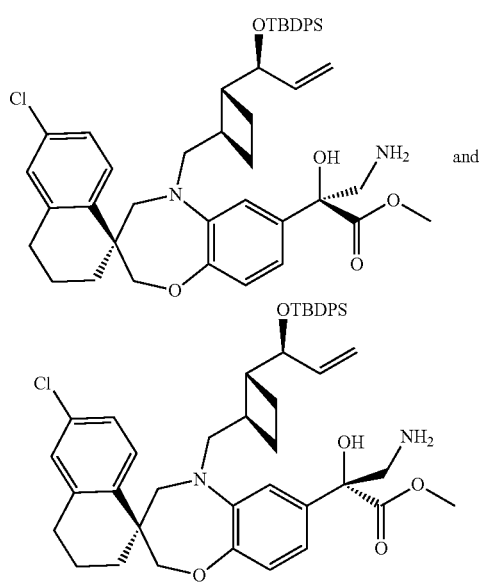

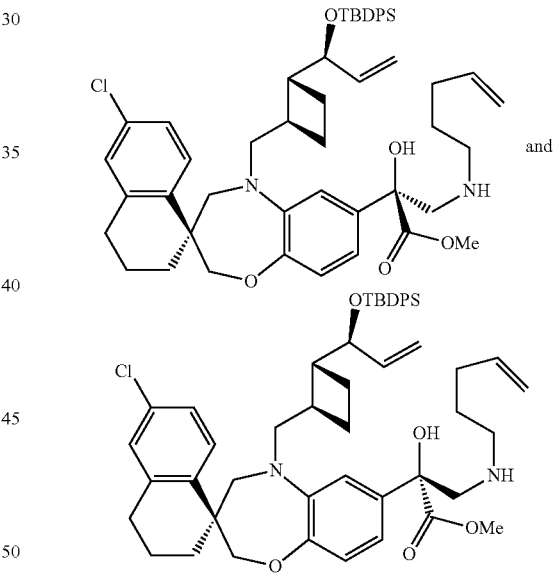

To a solution of (S)-methyl 2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-hydroxy-3-nitropropanoate and (R)-methyl 2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-hydroxy-3-nitropropanoate from Step 2 (0.45 g, 0.56 mmol) in acetic acid (7.22 mL) was added zinc dust (1.45 g, 22.24 mmol). The reaction mixture was stirred at room temperature for 90 minutes. The reaction mixture was filtered over Celite, and then neutralized by addition of an aqueous saturated solution of NaHCO3, then extracted with EtOAc (×3). The organic To a 100-mL round bottom flask was added (S)-methyl 3-amino-2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-hydroxypropanoate and (R)-methyl 3-amino-2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-hydroxypropanoate from Step 3 (300 mg, 0.39 mmol) and 4-pentenal (57.0 μl, 0.58 mmol) in DCM (7.7 mL) with a drop HOAc. After 5 minutes, sodium triacetoxyborohydride (163 mg, 0.77 mmol) was added. After 10 minutes, LC-MS showed the desired product was the major peak with a small amount of bis-addition product. The reaction was quenched with saturated aqueous NaHCO3 solution, and extracted with DCM 3 times. The organic layers were concentrated and purified by combi-flash, eluting with a gradient of 0% to 50% MeOH/DCM (⅕) in DCM to give (S)-methyl 2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-hydroxy-3-(pent-4-en-1-ylamino)propanoate and (R)-methyl 2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-hydroxy-3-(pent-4-en-1-ylamino)propanoate (273.6 mg, 0.32 mmol). LRMS: m/z (ESI, +ve ion) 847.2 (M+H)⁺.

STEP 5: (S)-METHYL 2-((S)-5-(((1R,2R)-2-((S)-1-((TERT-BUTYLDIPHENYLSILYL)OXY)ALLYL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALEN]-7-YL)-2-HYDROXY-3-(PENT-4-EN-1-YL(SULFAMOYL)AMINO)PROPANOATE AND (R)-METHYL 2-((S)-5-(((1R,2R)-2-((S)-1-((TERT-BUTYLDIPHENYLSILYL)OXY)ALLYL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALEN]-7-YL)-2-HYDROXY-3-(PENT-4-EN-1-YL(SULFAMOYL)AMINO)PROPANOATE

The reaction was concentrated and purified by combi-flash, eluting with a gradient of 0% to 30% EtOAC in hexane to give (S)-methyl 2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-hydroxy-3-(pent-4-en-1-yl(sulfamoyl)amino)propanoate and (R)-methyl 2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-hydroxy-3-(pent-4-en-1-yl(sulfamoyl)amino)propanoate (115 mg, 0.12 mmol). LRMS: m/z (ESI, +ve ion) 926.2 (M+H)⁺.

STEP 6: (S)-METHYL 2-((S)-5-(((1R,2R)-2-((S)-1-((TERT-BUTYLDIPHENYLSILYL)OXY)ALLYL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALEN]-7-YL)-2-HYDROXY-3-(PENT-4-EN-1-YL(SULFAMOYL)AMINO)PROPANOATE AND (R)-METHYL 2-((S)-5-(((1R,2R)-2-((S)-1-((TERT-BUTYLDIPHENYLSILYL)OXY)ALLYL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALEN]-7-YL)-2-HYDROXY-3-(PENT-4-EN-1-YL(SULFAMOYL)AMINO)PROPANOATE

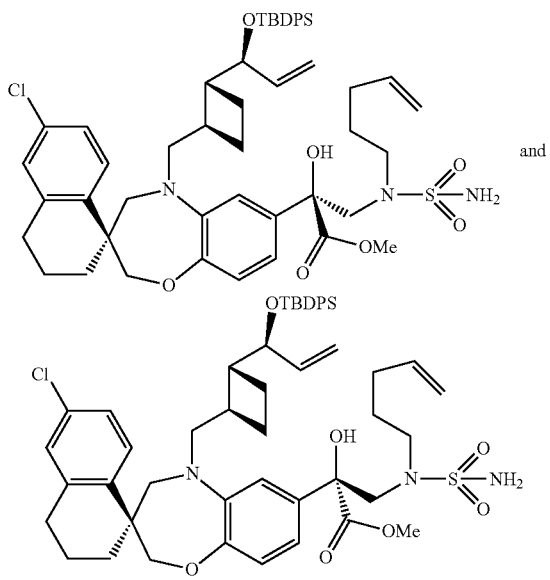

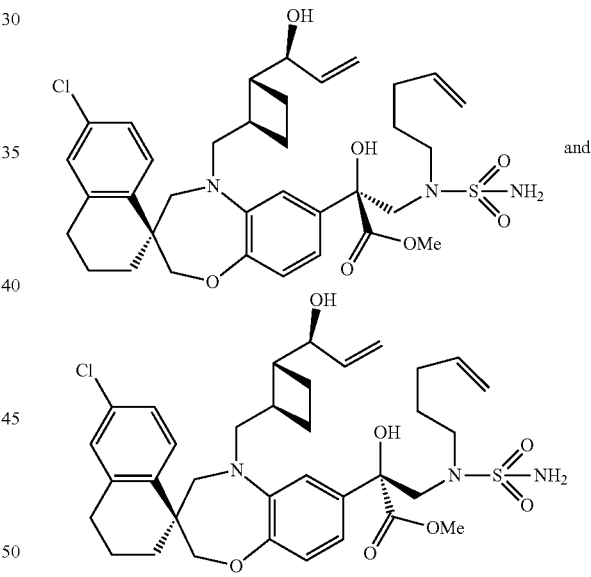

A glass microwave reaction vessel was charged (S)-methyl 2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-hydroxy-3-(pent-4-en-1-ylamino)propanoate and (R)-methyl 2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-hydroxy-3-(pent-4-en-1-ylamino)propanoate from Step 4 (210 mg, 0.25 mmol) and sulfuric diamide (42.9 mg, 0.446 mmol) in 1,4-dioxane (5.0 mL). The reaction mixture was stirred and heated in a Discover model microwave reactor (CEM, Matthews, N.C.) at 100° C. for 60 minutes. LC-MS showed SM was gone.

To a solution of (S)-methyl 2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-hydroxy-3-(pent-4-en-1-yl(sulfamoyl)amino)propanoate and (R)-methyl 2-((S)-5-(((1R,2R)-2-((S)-1-((tert-butyldiphenylsilyl)oxy)allyl)cyclobutyl)methyl)-6'-chloro-3',4,4',5-tetrahydro-2H,2'H-spiro[benzo[b][1,4]oxazepine-3,1'-naphthalen]-7-yl)-2-hydroxy-3-(pent-4-en-1-yl(sulfamoyl)amino)propanoate from Step 5 (75 mg, 0.08 mmol) in THF (1 mL) was added 1M tetra-N-butylammonium fluoride in THF (405 μl, 0.405 mmol) dropwise at 0° C., and then the reaction mixture was allowed to warm to room temperature and stirred overnight. The reaction mixture was quenched with saturated aqueous NH₄Cl solution and extracted with EtOAc, dried over MgSO₄ and concentrated. The crude material was purified by chromatography through a Redi-Sep® pre-packed silica gel column (40 g), eluting with a gradient of 0% to 90% EtOAc in hexane to provide (S)-methyl 2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-3-(pent-4-en-1-yl(sulfamoyl)amino)propanoate and (R)-methyl 2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-3-(pent-4-en-1-yl(sulfamoyl)amino)propanoate (38.2 mg, 0.058 mmol). LRMS: m/z (ESI, +ve ion) 688.3 (M+H)⁺.

STEP 7: (4S)-4-((3S)-6'-CHLORO-5-(((1R,2R)-2-((1S)-1-HYDROXY-2-PROPEN-1-YL)CYCLOBUTYL)METHYL)-3',4,4',5-TETRAHYDRO-2'H-SPIRO[1,5-BENZOXAZEPINE-3,1'-NAPHTHALEN]-7-YL)-4-HYDROXY-6-(4-PENTEN-1-YL)-1,2,6-THIADIAZINAN-3-ONE 1,1-DIOXIDE OR (4R)-4-((3S)-6'-CHLORO-5-(((1R,2R)-2-((1S)-1-HYDROXY-2-PROPEN-1-YL)CYCLOBUTYL)METHYL)-3',4,4',5-TETRAHYDRO-2'H-SPIRO[1,5-BENZOXAZEPINE-3,1'-NAPHTHALEN]-7-YL)-4-HYDROXY-6-(4-PENTEN-1-YL)-1,2,6-THIADIAZINAN-3-ONE 1,1-DIOXIDE

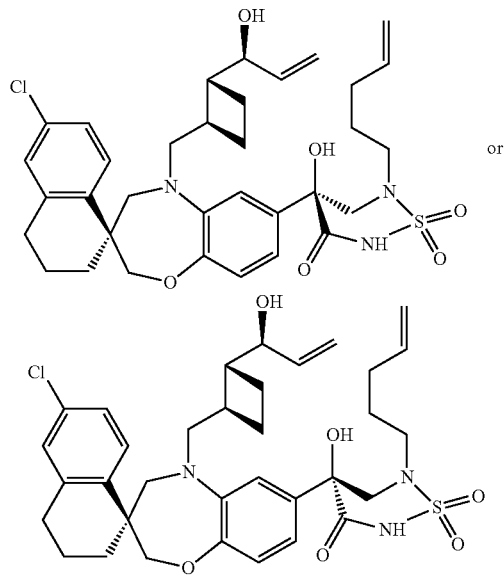

To a 25-mL round bottom flask was added (S)-methyl 2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-3-(pent-4-en-1-yl(sulfamoyl)amino)propanoate and (R)-methyl 2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-3-(pent-4-en-1-yl(sulfamoyl)amino)propanoate from Step 6 above (37.5 mg, 0.054 mmol) and 1 mL of MeOH, and then 0.1 mL of 25% NaOMe/MeOH was added. The reaction mixture was stirred at room temperature overnight. LC-MS showed a clean reaction. The reaction mixture was concentrated and purified by reversed phase preparatory HPLC (Gemini™ Prep C₁₈ 5 μm column; Phenomenex, Torrance, Calif.; gradient: 40% to 95% MeCN in water, where both solvents contain 0.1% TFA, 30 minutes method) to give (4S)-4-((3S)-6'-chloro-5-(((1R,2R)-2-((1S)-1-hydroxy-2-propen-1-yl)cyclobutyl)methyl)-3',4,4',5-tetrahydro-2'H-spiro[1,5-benzoxazepine-3,1'-naphthalen]-7-yl)-4-hydroxy-6-(4-penten-1-yl)-1,2,6-thiadiazinan-3-one 1,1-dioxide or (4R)-4-((3S)-6'-chloro-5-(((1R,2R)-2-((1S)-1-hydroxy-2-propen-1-yl)cyclobutyl)methyl)-3',4,4',5-tetrahydro-2'H-spiro[1,5-benzoxazepine-3,1'-naphthalen]-7-yl)-4-hydroxy-6-(4-penten-1-yl)-1,2,6-thiadiazinan-3-one 1,1-dioxide (15 mg, 0.023 mmol) as the first eluting major isomer out of preparative reverse phase HPLC. ¹H NMR (500 MHz, CDCl₃) δ 7.91 (s, 1H), 7.51 (d, J=8.3 Hz, 1H), 6.97 (dd, J=2.3, 8.5 Hz, 1H), 6.88 (s, 1H), 6.72 (d, J=7.9 Hz, 1H), 6.62 (d, J=8.0 Hz, 2H), 5.65-5.54 (m, 2H), 5.03 (td, J=1.2, 17.2 Hz, 1H), 4.93 (td, J=1.1, 10.5 Hz, 1H), 4.88-4.79 (m, 2H), 3.89-3.78 (m, 4H), 3.63-3.47 (m, 3H), 3.26-3.15 (m, 2H), 3.05 (d, J=14.3 Hz, 1H), 2.92 (dd, J=9.3, 14.9 Hz, 2H), 2.61-2.54 (m, 2H), 2.42-2.24 (m, 3H), 1.99-1.88 (m, 3H), 1.88-1.79 (m, 3H), 1.72 (dd, J=4.3, 9.0 Hz, 1H), 1.68-1.11 (m, 6H). LRMS: m/z (ESI, +ve ion) 656.2 (M+H)⁺.

Example 123

(4R)-4-((3S)-6'-CHLORO-5-(((1R,2R)-2-((1S)-1-HYDROXY-2-PROPEN-1-YL)CYCLOBUTYL)METHYL)-3',4,4',5-TETRAHYDRO-2'H-SPIRO[1,5-BENZOXAZEPINE-3,1'-NAPHTHALEN]-7-YL)-4-HYDROXY-6-(4-PENTEN-1-YL)-1,2,6-THIADIAZINAN-3-ONE 1,1-DIOXIDE OR (4S)-4-((3S)-6'-CHLORO-5-(((1R,2R)-2-((1S)-1-HYDROXY-2-PROPEN-1-YL)CYCLOBUTYL)METHYL)-3',4,4',5-TETRAHYDRO-2'H-SPIRO[1,5-BENZOXAZEPINE-3,1'-NAPHTHALEN]-7-YL)-4-HYDROXY-6-(4-PENTEN-1-YL)-1,2,6-THIADIAZINAN-3-ONE 1,1-DIOXIDE

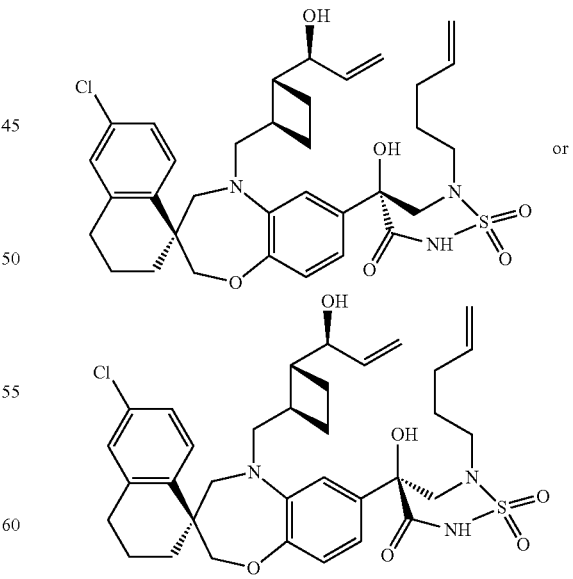

(4R)-4-((3S)-6'-chloro-5-(((1R,2R)-2-((1S)-1-hydroxy-2-propen-1-yl)cyclobutyl)methyl)-3',4,4',5-tetrahydro-2'H-spiro[1,5-benzoxazepine-3,1'-naphthalen]-7-yl)-4-hydroxy-6-(4-penten-1-yl)-1,2,6-thiadiazinan-3-one 1,1-dioxide or (4S)-4-((3S)-6'-chloro-5-(((1R,2R)-2-((1S)-1-hydroxy-2-propen-1-yl)cyclobutyl)methyl)-3',4,4',5-tetrahydro-2'H-spiro[1,5-benzoxazepine-3,1'-naphthalen]-7-yl)-4-hydroxy-6-(4-penten-1-yl)-1,2,6-thiadiazinan-3-one 1,1-dioxide (20 mg, 0.031 mmol) was isolated as the second eluting major isomer from the purification of example 122, step 7 via preparative reverse phase HPLC. $^1$H NMR (500 MHz, CDCl$_3$) δ 7.91 (s, 1H), 7.51 (d, J=8.3 Hz, 1H), 6.98 (dd, J=2.3, 8.5 Hz, 1H), 6.88 (s, 1H), 6.72 (d, J=8.0 Hz, 1H), 6.66 (d, J=1.8 Hz, 1H), 6.55 (dd, J=2.2, 8.2 Hz, 1H), 5.65-5.54 (m, 2H), 5.06-5.00 (m, 1H), 4.95-4.90 (m, 1H), 4.88-4.79 (m, 2H), 3.92-3.79 (m, 4H), 3.65-3.48 (m, 3H), 3.27-3.12 (m, 3H), 3.05 (d, J=14.3 Hz, 2H), 2.94-2.85 (m, 2H), 2.66-2.46 (m, 3H), 2.34 (td, J=7.9, 15.4 Hz, 2H), 1.87 (s, 10H). LRMS. m/z (ESI, +ve ion) 656.2 (M+H)$^+$.

Example 124

(1S,2'S,10'E,12'S,13'R,16'R)-6-CHLORO-2',12'-DIHYDROXY-3,4-DIHYDRO-2H,3'H-SPIRO[NAPHTHALENE-1,20'-[22]OXA[5]THIA[4,6,18]TRIAZAPENTACYCLO[16.7.2.1$^{2,6}$.0$^{13,16}$.0$^{23,27}$]OCTACOSA[1(25),10,23,26]TETRAEN]-3'-ONE 5',5'-DIOXIDE OR (1S,2'R,10'E,12'S,13'R,16'R)-6-CHLORO-2',12'-DIHYDROXY-3,4-DIHYDRO-2H,3'H-SPIRO[NAPHTHALENE-1,20'-[22]OXA[5]THIA[4,6,18]TRIAZAPENTACYCLO[16.7.2.1$^{2,6}$.0$^{12,16}$.0$^{23,27}$]OCTACOSA[1(25),10,23,26]TETRAEN]-3'-ONE 5',5'-DIOXIDE

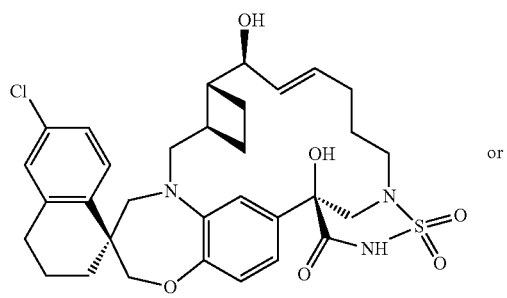

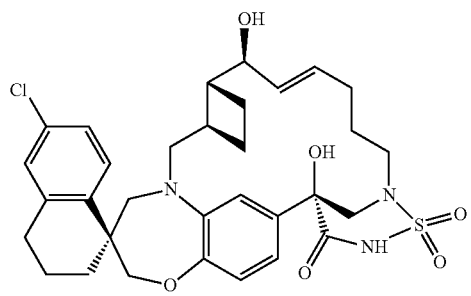

The title compound was prepared from (4S)-4-((3S)-6'-chloro-5-(((1R,2R)-2-((1S)-1-hydroxy-2-propen-1-yl)cyclobutyl)methyl)-3',4,4',5-tetrahydro-2'H-spiro[1,5-benzoxazepine-3,1'-naphthalen]-7-yl)-4-hydroxy-6-(4-penten-1-yl)-1,2,6-thiadiazinan-3-one 1,1-dioxide or (4R)-4-((3S)-6'-chloro-5-(((1R,2R)-2-((1S)-1-hydroxy-2-propen-1-yl)cyclobutyl)methyl)-3',4,4',5-tetrahydro-2'H-spiro[1,5-benzoxazepine-3,1'-naphthalen]-7-yl)-4-hydroxy-6-(4-penten-1-yl)-1,2,6-thiadiazinan-3-one 1,1-dioxide (10.9 mg, 0.017 mmol, Example 122, step 7) via a procedure similar to that used in Example 1, step 7. The crude was purified by reversed phase preparatory HPLC (Gemini™ Prep C$_{18}$ 5 µm column; Phenomenex, Torrance, Calif.; gradient: 40% to 95% MeCN in water, where both solvents contain 0.1% TFA, 30 minutes method) to give (1S,2'S,10'E,12'S,13'R,16'R)-6-chloro-2',12'-dihydroxy-3,4-dihydro-2H,3'H-spiro[naphthalene-1,20'-[22]oxa[5]thia[4,6,18]triazapentacyclo[16.7.2.1$^{2,6}$.0$^{13,16}$.0$^{23,27}$]octacosa[1(25),10,23,26]tetraen]-3'-one 5',5'-dioxide or (1S,2'R,10'E,12'S,13'R,16'R)-6-chloro-2',12'-dihydroxy-3,4-dihydro-2H,3'H-spiro[naphthalene-1,20'-[22]oxa[5]thia[4,6,18]triazapentacyclo[16.7.2.1$^{2,6}$.0$^{13,16}$.0$^{23,27}$]octacosa[1(25),10,23,26]tetraen]-3'-one 5',5'-dioxide (5.1 mg, 8.12 µmol). $^1$H NMR (500 MHz, CD$_3$OD) δ 7.89 (br. s., 1H), 7.33 (br. s., 1H), 7.09-6.96 (m, 4H), 6.42 (s, 1H), 5.46-5.33 (m, 1H), 4.76 (br. s., 1H), 4.17-4.07 (m, 3H), 3.87-3.78 (m, 2H), 3.51 (d, J=14.8 Hz, 1H), 3.34-3.17 (m, 2H), 3.11 (d, J=13.8 Hz, 1H), 2.92-2.78 (m, 2H), 2.75-2.66 (m, 2H), 2.42 (dq, J=4.3, 8.8 Hz, 1H), 2.19-2.05 (m, 2H), 2.02-1.38 (m, 11H), 1.25-1.11 (m, 2H). LRMS: m/z (ESI, +ve ion) 628.3 (M+H)$^+$.

Example 125

(1S,2'R,10'E,12'S,13'R,16'R)-6-CHLORO-2',12'-DIHYDROXY-3,4-DIHYDRO-2H,3'H-SPIRO[NAPHTHALENE-1,20'-[22]OXA[5]THIA[4,6,18]TRIAZAPENTACYCLO[16.7.2.1$^{2,6}$.0$^{13,16}$.0$^{23,27}$]OCTACOSA[1(25),10,23,26]TETRAEN]-3'-ONE 5',5'-DIOXIDE OR (1S,2'S,10'E,12'S,13'R,16'R)-6-CHLORO-2',12'-DIHYDROXY-3,4-DIHYDRO-2H,3'H-SPIRO[NAPHTHALENE-1,20'-[22]OXA[5]THIA[4,6,18]TRIAZAPENTACYCLO[16.7.2.1$^{2,6}$.0$^{12,16}$.0$^{23,27}$]OCTACOSA[1(25),10,23,26]TETRAEN]-3'-ONE 5',5'-DIOXIDE

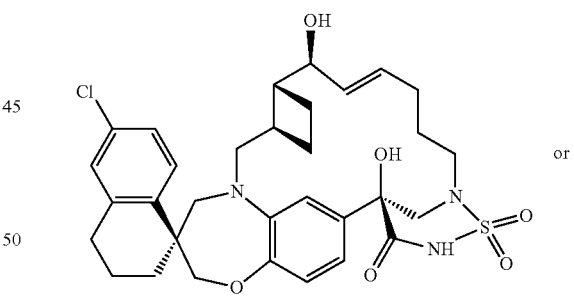

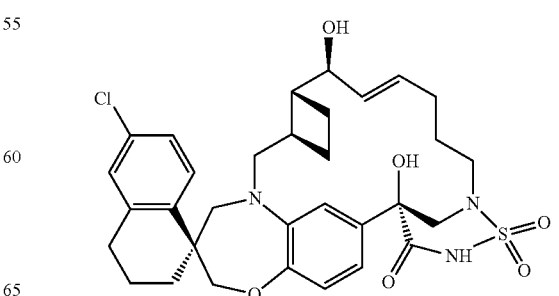

The title compound was prepared from (4R)-4-((3S)-6'-chloro-5-(((1R,2R)-2-((1S)-1-hydroxy-2-propen-1-yl)cyclobutyl)methyl)-3',4,4',5-tetrahydro-2'H-spiro[1,5-benzoxazepine-3,1'-naphthalen]-7-yl)-4-hydroxy-6-(4-penten-1-yl)-1,2,6-thiadiazinan-3-one 1,1-dioxide or (4S)-4-((3S)-6'-chloro-5-(((1R,2R)-2-((1S)-1-hydroxy-2-propen-1-yl)cyclobutyl)methyl)-3',4,4',5-tetrahydro-2'H-spiro[1,5-benzoxazepine-3,1'-naphthalen]-7-yl)-4-hydroxy-6-(4-penten-1-yl)-1,2,6-thiadiazinan-3-one 1,1-dioxide (16.9 mg, 0.026 mmol, Example 123) via a procedure similar to that used in Example 1, step 7. The crude was purified by reversed phase preparatory HPLC (Gemini™ Prep C$_{18}$ 5 μm column; Phenomenex, Torrance, Calif.; gradient 40% to 95% MeCN in water, where both solvents contain 0.1% TFA, 30 minutes method) to give (1S,2'R,10'E,12'S,13'R,16'R)-6-chloro-2',12'-dihydroxy-3,4-dihydro-2H,3'H-spiro[naphthalene-1,20'-[22]oxa[5]thia[4,6,18]triazapentacyclo[16.7.2.1$^{2,6}$.0$^{13,16}$.0$^{23,27}$]octacosa[1(25),10,23,26]tetraen]-3'-one 5',5'-dioxide or (1S,2'S,10'E,12'S,13'R,16'R)-6-chloro-2',12'-dihydroxy-3,4-dihydro-2H,3'H-spiro[naphthalene-1,20'-[22]oxa[5]thia[4,6,18]triazapentacyclo[16.7.2.1$^{2,6}$.0$^{13,16}$.0$^{23,27}$]octacosa[1(25),10,23,26]tetraen]-3'-one 5',5'-dioxide (6.5 mg, 10.35 μmol). $^1$H NMR (500 MHz, CD$_3$OD) δ 7.45 (d, J=7.7 Hz, 1H), 7.10-6.98 (m, 3H), 6.86-6.75 (m, 2H), 6.52 (dd, J=2.1, 8.2 Hz, 1H), 5.51 (dd, J=8.5, 15.3 Hz, 1H), 5.11 (ddd, J=5.2, 9.4, 15.1 Hz, 1H), 4.15-4.06 (m, 3H), 3.99-3.89 (m, 1H), 3.69 (dd, J=2.1, 14.4 Hz, 1H), 3.55-3.48 (m, 1H), 3.36-3.15 (m, 4H), 2.83 (dd, J=11.1, 14.4 Hz, 1H), 2.76-2.65 (m, 3H), 2.58-2.37 (m, 2H), 2.37-2.25 (m, 2H), 2.24-1.10 (m, 11H). LRMS: m/z (ESI, +ve ion) 628.3 (M+H)$^+$.

Example 126

(1S,6'E)-6-CHLORO-9'-CYCLOPROPYL-12'R-HYDROXY-10'-OXO-3,4-DIHYDRO-2H-SPIRO[NAPHTHALENE-1,19'-[17]OXA[1,9]DIAZATRICYCLO[11.7.2.0$^{16,21}$]DOCOSA [6,13,15,21]TETRAENE]-12'-CARBOXYLIC ACID OR (1S,6'E)-6-CHLORO-9'-CYCLOPROPYL-12'S-HYDROXY-10'-OXO-3,4-DIHYDRO-2H-SPIRO[NAPHTHALENE-1,19'-[17]OXA[1,9]DIAZATRICYCLO[11.7.2.0$^{16,21}$]DOCOSA [6,13,15,21]TETRAENE]-12'-CARBOXYLIC ACID

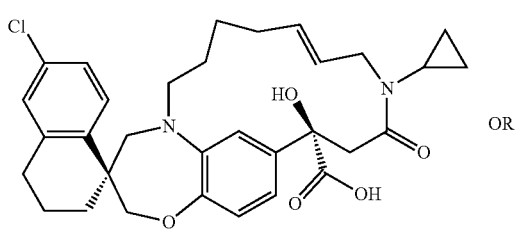 OR

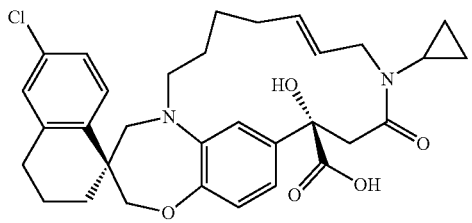

STEP 1: 3-((S)-6'-CHLORO-5-(HEX-5-EN-1-YL)-3',4,4',5-TETRAHYDRO-2H,2'H-SPIRO[BENZO[B][1,4]OXAZEPINE-3,1'-NAPHTHALEN]-7-YL)-3-HYDROXY-4-METHOXY-4-OXOBUTANOIC ACID

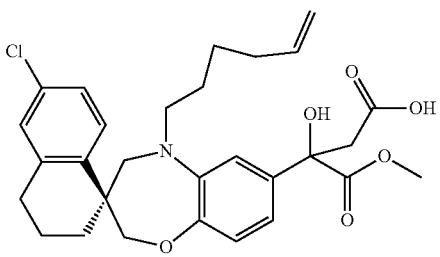 [SMILES: C=CCCCCN1C[C@@]2(CCCc3cc(Cl)ccc32)COc2ccc(C(O)(CC(=O)O)C(=O)OC)cc21]

The title compound (0.71 g, 44% over 5 steps) was synthesized from (S)-6'-chloro-5-(hex-5-en-1-yl)-3',4,4',5-tetrahydro-2H,2'H-spiro[benzo[b][1,4]oxazepine-3,1'-naphthalene]-7-carboxylic acid (Example 62, Step 2) through a procedure similar to that used for the synthesis of Example 1, Steps 1 through 5. LRMS: m/z (ESI, +ve ion) 528.2 (M+H)$^+$.

STEP 2. (R)-METHYL-4-(ALLYL(CYCLOPROPYL)AMINO)-2-((S)-6'-CHLORO-5-EN-1YL)-3',4',4',5'-TETRAHYDRO-2H-SPIRO[BENZO[B][1,4]OXAZEPINE-3,1'-NAPHTHALAEN]-7-YL)-2-HYDROXY-4-OXOBUTANOATE AND (S)-METHYL-4-(ALLYL(CYCLOPROPYL)AMINO)-2-((S)-6'-CHLORO-5-EN-1YL)-3',4',4',5'-TETRAHYDRO-2H-SPIRO[BENZO[B][1,4]OXAZEPINE-3,1'-NAPHTHALAEN]-7-YL)-2-HYDROXY-4-OXOBUTANOATE

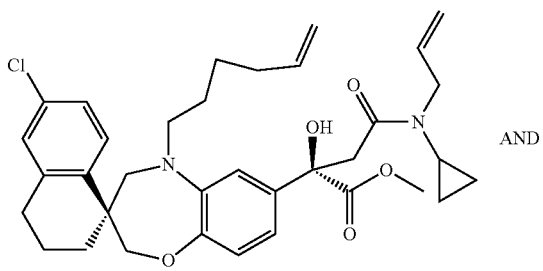 AND

-continued

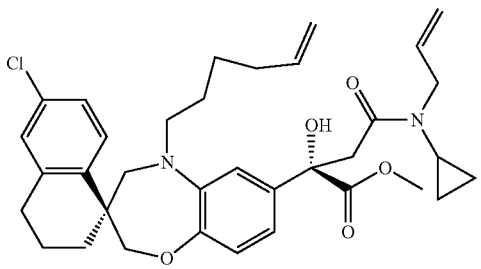

The title compounds (40 mg, 66% yield) were synthesized from N-allylcyclopropanamine (29.3 mg, 0.30 mmol) and 3-((S)-6'-chloro-5-(hex-5-en-1-yl)-3',4,4'5-tetrahydro-2H, 2H'-spiro[benzo[b][1,4]oxazepine-3,1'-naphthalen]-7-yl)-3-hydroxy-4-methoxy-4-oxobutanoic acid (from step 1, 1.5:1 mixture of isomers at benzylic position, 53 mg, 0.10 mmol) via a procedure similar to that used for the synthesis of Example 1, step 6. LRMS: m/z (ESI, +ve ion) 607.2 (M+H)$^+$.

STEP 2. (1S,6'E)-6-CHLORO-9'-CYCLOPROPYL-12'S-HYDROXY-10'-OXO-3,4-DIHYDRO-2H-SPIRO[NAPHTHALENE-1,19'-[17]OXA[1,9]DI-AZATRICYCLO[11.7.2.0$^{16,21}$]DOCOSA [6,13,15,21]TETRAENE]-12'-CARBOXYLIC ACID METHY ESTER OR (1S,6'E)-6-CHLORO-9'-CYCLOPROPYL-12'R-HYDROXY-10'-OXO-3,4-DIHYDRO-2H-SPIRO[NAPHTHALENE-1,19'-[17]OXA[1,9]DIAZATRICYCLO[11.7.2.0$^{16,21}$]DOCOSA [6,13,15,21]TETRAENE]-12'-CARBOXYLIC ACID METHYL ESTER

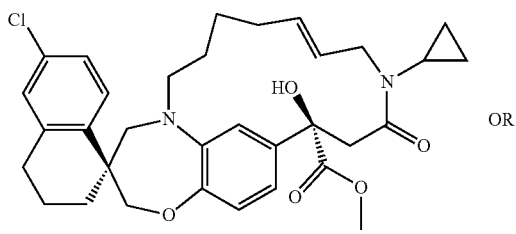

OR

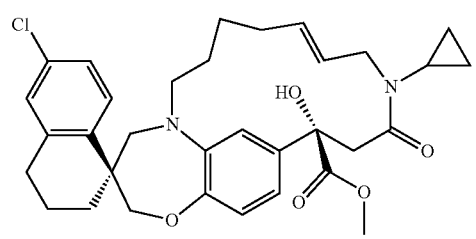

The title compound was prepared from (R)-methyl-4-(allyl(cyclopropyl)amino)-2-((S)-6'-chloro-5-en-1yl)-3',4', 4',5'-tetrahydro-2H-spiro[benzo[b][1,4]oxazepine-3,1'-naphthalaen]-7-yl)-2-hydroxy-4-oxobutanoate and (S)-methyl-4-(allyl(cyclopropyl)amino)-2-((S)-6'-chloro-5-en-1yl)-3',4',4',5'-tetrahydro-2H-spiro[benzo[b][1,4]oxazepine-3,1'-naphthalaen]-7-yl)-2-hydroxy-4-oxobutanoate (Example 126, Step 2, 39 mg, 0.064 mmol) via a procedure similar to that used for the synthesis of Example 1, step 7. The crude was chromatographed (silica gel, hexane/EtOAc, 1:0 to 1:4) to afford a white solid (30 mg, 81% yield). The resulting solid was further purified by chiral separation (AS-NT MeOH, 35% isopropanol_QCpk2) to afford Peak 1 (fast eluting isomer) and Peak 2 (slow eluting isomer), respectively as one of the title compounds. LRMS: m/z (ESI, +ve ion) 579.3 (M+H)$^+$ (for each peak).

STEP 3. (1S,6'E)-6-CHLORO-9'-CYCLOPROPYL-12'R-HYDROXY-10'-OXO-3,4-DIHYDRO-2H-SPIRO[NAPHTHALENE-1,19'-[17]OXA[1,9]DIAZATRICYCLO [11.7.2.0$^{16,21}$]DOCOSA [6,13,15,21]TETRAENE]-12'-CARBOXYLIC ACID OR (1S,6'E)-6-CHLORO-9'-CYCLOPROPYL-12'S-HYDROXY-10'-OXO-3,4-DIHYDRO-2H-SPIRO [NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID

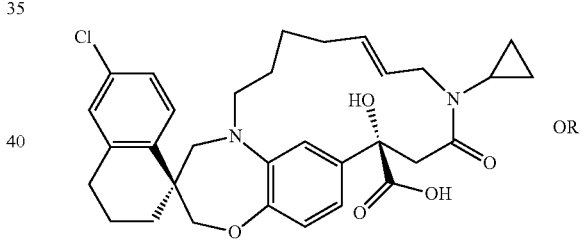

OR

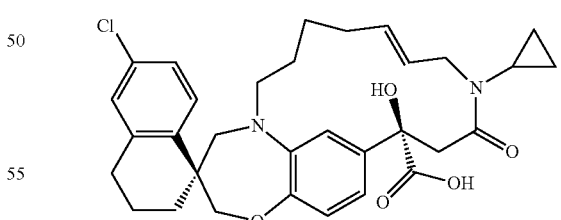

The title compound (11.1 mg, 94% yield) was prepared from Peak 1 (Example 126, step 3 (fast eluting isomer); (1S,6'E)-6-chloro-9'-cyclopropyl-12'(S)-hydroxy-10'-oxo-3,4-dihydro-2H-spiro[naphthalene-1,19'-[17]oxa[1,9]diazatricyclo[11.7.2.0^{16,21}]docosa[6,13,15,21]tetraene]-12'-carboxylic acid methy ester or (1S,6'E)-6-chloro-9'-cyclopropyl-12'(R)-hydroxy-10'-oxo-3,4-dihydro-2H-spiro[naphthalene-1,19'-[17]oxa[1,9]diazatricyclo[11.7.2.0^{16,21}]docosa[6,13,15,21]tetraene]-12'-carboxylic acid methyl ester (12 mg, 0.021 mmol) via a procedure similar to that used for the synthesis of Example 4. $^1$H NMR (500 MHz, CD$_2$Cl$_2$) δ 7.73 (d, J=8.6 Hz, 1H), 7.15 (dd, J=2.2, 8.6 Hz, 1H), 7.10-7.03 (m, 2H), 6.96-6.86 (m, 2H), 6.82 (d, J=8.1 Hz, 1H), 6.58 (s, 1H), 5.72-5.60 (m, 1H), 5.53-5.37 (m, 1H), 4.14 (d, J=12.0 Hz, 1H), 4.04 (d, J=11.7 Hz, 1H), 3.88-3.77 (m, 2H), 3.51-3.36 (m, 2H), 3.36-3.22 (m, 2H), 3.21-3.03 (m, 2H), 2.90 (d, J=17.1 Hz, 1H), 2.80-2.69 (m, 4H), 2.25-2.20 (m, 1H), 2.06-1.96 (m, 2H), 1.90-1.76 (m, 4H), 1.67-1.40 (m, 2H), 0.77-0.71 (m, 1H), 0.68-0.59 (m, 2H). LRMS: m/z (ESI, +ve ion) 565.2 (M+H)$^+$.

Example 127

(1S,6'E)-6-CHLORO-9'-CYCLOPROPYL-12'R-HYDROXY-10'-OXO-3,4-DIHYDRO-2H-SPIRO[NAPHTHALENE-1,19'-[17]OXA[1,9]DIAZATRICYCLO[11.7.2.0^{16,21}]DOCOSA [6,13,15,21]TETRAENE]-12'-CARBOXYLIC ACID OR (1S,6'E)-6-CHLORO-9'-CYCLOPROPYL-12'S-HYDROXY-10'-OXO-3,4-DIHYDRO-2H-SPIRO[NAPHTHALENE-1,19'-[17]OXA[1,9]DIAZATRICYCLO[11.7.2.0^{16,21}]DOCOSA [6,13,15,21]TETRAENE]-12'-CARBOXYLIC ACID

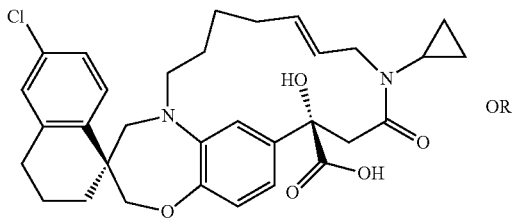

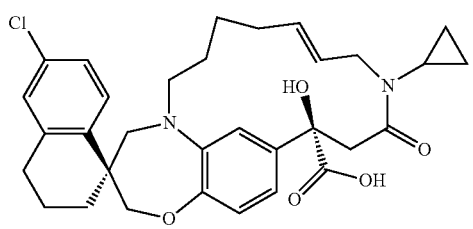

The title compound (11.6 mg, 98% yield) was prepared from Peak 2 (Example 126, step 3 (slow eluting isomer); (1S,6'E)-6-chloro-9'-cyclopropyl-12'(S)-hydroxy-10'-oxo-3,4-dihydro-2H-spiro[naphthalene-1,19'-[17]oxa[1,9]diazatricyclo[11.7.2.0^{16,21}]docosa[6,13,15,21]tetraene]-12'-carboxylic acid methy ester or (1S,6'E)-6-chloro-9'-cyclopropyl-12'(R)-hydroxy-10'-oxo-3,4-dihydro-2H-spiro[naphthalene-1,19'-[17]oxa[1,9]diazatricyclo[11.7.2.0^{16,21}]docosa[6,13,15,21]tetraene]-12'-carboxylic acid methyl ester (11.5 mg, 0.021 mmol) via a procedure similar to that used for the synthesis of Example 4. $^1$H NMR (500 MHz, CD$_2$Cl$_2$) δ 7.76 (d, J=8.6 Hz, 1H), 7.16 (dd, J=2.2, 8.6 Hz, 1H), 7.10-7.03 (m, 2H), 7.00-6.87 (m, 2H), 6.84 (d, J=8.3 Hz, 1H), 6.58 (s, 1H), 5.73-5.65 (m, 1H), 5.52-5.38 (m, 1H), 4.09-4.02 (m, 2H), 3.93-3.72 (m, 2H), 3.60 (d, J=14.2 Hz, 1H), 3.47-3.38 (m, 1H), 3.32-3.12 (m, 3H), 2.89 (d, J=17.1 Hz, 1H), 2.80-2.68 (m, 4H), 2.25-2.20 (m, 1H), 2.06-1.89 (m, 2H), 1.89-1.41 (m, 6H), 0.77-0.71 (m, 1H), 0.70-0.59 (m, 2H). LRMS: m/z (ESI, +ve ion) 565.2 (M+H)$^+$.

Example 128

4-((((1S,6'E)-6-CHLORO-12'(R)-HYDROXY-9'-METHYL-10'-OXO-3,4-DIHYDRO-2H-SPIRO[NAPHTHALENE-1,19'-[17]OXA[1,9]DIAZATRICYCLO[11.7.2.016,21]DOCOSA[6,13,15,21]TETRAEN]-12'-YL)CARBONYL)AMINO)BENZOIC ACID AND 4-((((1S,6'E)-6-CHLORO-12'(S)-HYDROXY-9'-METHYL-10'-OXO-3,4-DIHYDRO-2H-SPIRO[NAPHTHALENE-1,19'-[17]OXA[1,9]DIAZATRICYCLO[11.7.2.016,21]DOCOSA[6,13,15,21]TETRAEN]-12'-YL)CARBONYL)AMINO)BENZOIC ACID

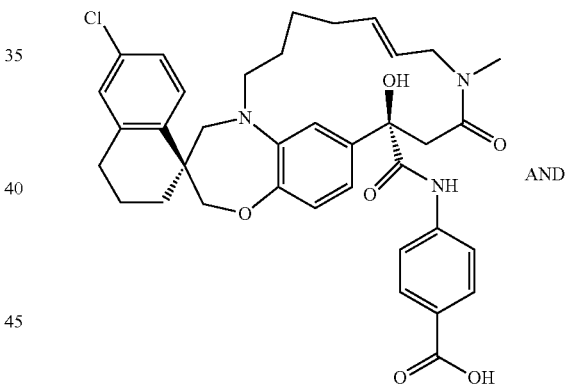

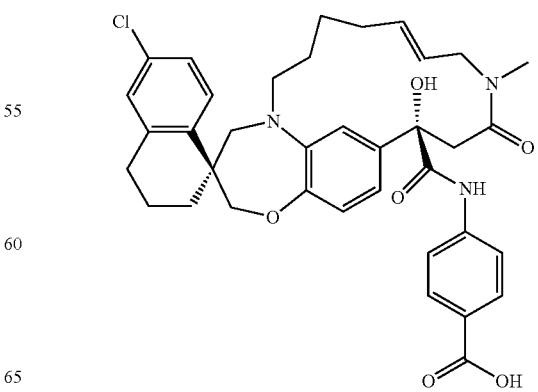

333

STEP 1. 4-((((1S,6'E)-6-CHLORO-12'(R)-HY-DROXY-9'-METHYL-10'-OXO-3,4-DIHYDRO-2H-SPIRO[NAPHTHALENE-1,19'-[17]OXA[1,9]DIAZATRICYCLO [11.7.2.0$^{16,21}$] DOCOSA [6,13,15,21]TETRAEN]-12'-YL)CARBONYL)AMINO)BENZOIC ACID METHYL ESTER AND 4-((((1S,6'E)-6-CHLORO-12'(S)-HYDROXY-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA [6,13,15,21]TETRAEN]-12'-YL)CARBONYL)AMINO)BENZOIC ACID METHYL ESTER

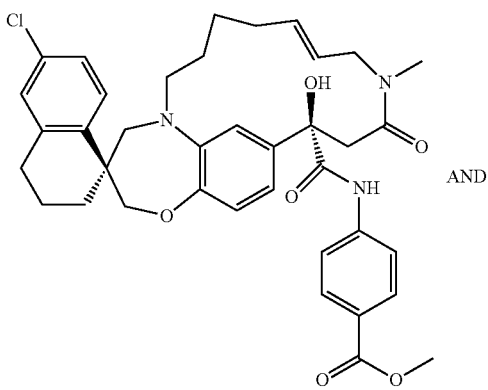

AND

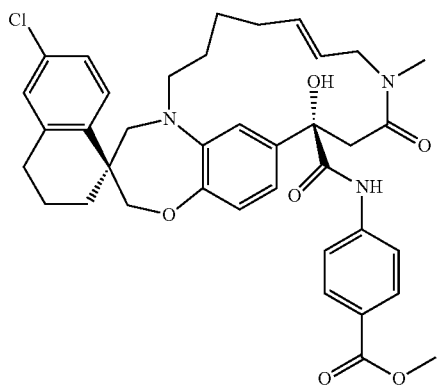

To a mixture of (1S,6'E,12'R)-6-chloro-12'-hydroxy-9'-methyl-10'-oxo-3,4-dihydro-2H-spiro[naphthalene-1,19'-[17]oxa[1,9]diazatricyclo[11.7.2.0$^{16,21}$]docosa[6,13,15,21]tetraene]-12'-carboxylic acid and (1S,6'E,12'S)-6-chloro-12'-hydroxy-9'-methyl-10'-oxo-3,4-dihydro-2H-spiro[naphthalene-1,19'-[17]oxa[1,9]diazatricyclo[11.7.2.0$^{16,21}$]docosa[6,13,15,21] tetraene]-12'-carboxylic acid (Example 62, step 3 and Example 63, mixture of epimers) (50 mg, 0.093 mmol) in DCM (1 mL) was added HATU (52.9 mg, 0.14 mmol), 4-aminobenzoic acid methyl amine (21.5 mg, 0.14 mmol) and diisopropylethylamine (0.03 mL, 0.17 mmol). The reaction mixture was stirred at room temperature overnight. The mixture was diluted with water and extracted with CH$_2$Cl$_2$. The combined organic phase was dried over magnesium sulfate, filtered and concentrated in vacuo. The crude was chromatographed (silica gel, hexanes/ethyl acetate, 1:0 to 1:4) to afford a mixture of above title compounds (11 mg, 18%) as an oil. LRMS: m/z (ESI, +ve ion) 672.2 (M+H)$^+$.

334

STEP 2. 4-((((1S,6'E)-6-CHLORO-12'(R)-HY-DROXY-9'-METHYL-10'-OXO-3,4-DIHYDRO-2H-SPIRO[NAPHTHALENE-1,19'-[17]OXA[1,9]DIAZATRICYCLO [11.7.2.016,21]DOCOSA[6,13,15,21]TETRAEN]-12'-YL)CARBONYL)AMINO)BENZOIC ACID AND 4-((((1S,6'E)-6-CHLORO-12'(S)-HYDROXY-9'-METHYL-10'-OXO-3,4-DIHYDRO-2H-SPIRO[NAPHTHALENE-1,19'-[17]OXA[1,9]DIAZATRICYCLO [11.7.2.0$^{16,21}$]DOCOSA[6,13,15,21]TETRAEN]-12'-YL)CARBONYL)AMINO)BENZOIC ACID

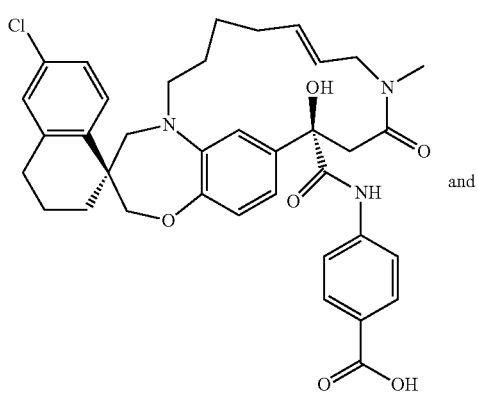

and

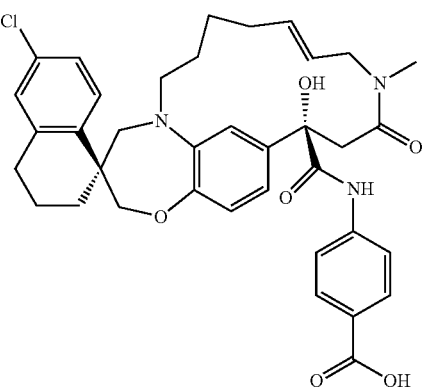

The title compound was prepared from the mixture of methyl esters obtained in step 1 via a procedure similar to that used for the synthesis of Example 4. The crude was purified by reverse phase HPLC (gradient: 25% to 75% CH$_3$CN/water, both solvents containing 0.1% TFA) to afford the title compound (2.6 mg, 27%). $^1$H NMR (400 MHz, CDCl$_3$) δ 8.92 (s, 1H), 8.02-7.97 (m, 2H), 7.78-7.65 (m, 3H), 7.19-7.01 (m, 3H), 6.83 (d, J=8.3 Hz, 1H), 6.72 (d, J=11.9 Hz, 1H), 5.81-5.63 (m, 1H), 5.60-5.52 (m, 1H), 4.17-4.11 (m, 1H), 4.08-4.00 (m, 1H), 3.93 (dd, J=6.2, 16.7 Hz, 1H), 3.77-3.69 (m, 1H), 3.44-3.25 (m, 3H), 3.16-3.05 (m, 2H), 2.96 (s, 3H), 2.74 (br. s., 2H), 2.36-2.25 (m, 1H), 2.18-1.35 (m, 10H). LRMS: m/z (ESI, +ve ion) 658.2 (M+H)$^+$.

Example 129

(1S,3'R,6'R,7'S,8'E,15'R)-6-CHLORO-N-(ETHYL-SULFAMOYL)-7',15'-DIHYDROXY-12'-METHYL-13'-OXO-3,4-DIHYDRO-2H-SPIRO[NAPHTHALENE-1,22'-[20]OXA[1,12]DIAZATETRACYCLO [14.7.2.0$^{3,6}$.0$^{19,24}$]PENTACOSA[8,16,18,24]TETRAENE]-15'-CARBOXAMIDE

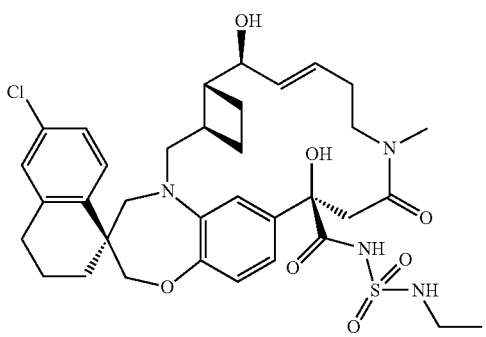 [SMILES: CCNS(=O)(=O)NC(=O)[C@@]1(O)CC(=O)N(C)CC/C=C/[C@H](O)[C@@H]2CC[C@H]2CN2C[C@@]3(CCCc4cc(Cl)ccc43)COc3ccc1cc32]

The title compound (14 mg, 54%) was synthesized from Example 43, step 2 through a procedure similar to that used for the synthesis of Example 43, step 3. $^1$H NMR (500 MHz, CD$_2$Cl$_2$) δ 7.72 (d, J=8.6 Hz, 1H), 7.15 (dd, J=2.1, 8.5 Hz, 1H), 7.08 (s, 1H), 6.97 (dd, J=1.8, 8.2 Hz, 1H), 6.85 (d, J=8.2 Hz, 1H), 6.53 (br. s., 1H), 6.46 (br. s., 1H), 6.36 (t, J=12.2 Hz, 1H), 5.89 (dd, J=9.7, 14.5 Hz, 1H), 4.36 (d, J=8.8 Hz, 1H), 4.04-3.99 (m, 1H), 3.98-3.93 (m, 1H), 3.71 (d, J=14.4 Hz, 1H), 3.64-3.51 (m, 2H), 3.32 (d, J=14.4 Hz, 1H), 3.18-3.04 (m, 2H), 3.01-2.90 (m, 4H), 2.83-2.68 (m, 4H), 2.64-2.48 (m, 2H), 2.40-2.33 (m, 2H), 2.27 (t, J=13.2 Hz, 1H), 2.06-1.97 (m, 2H), 1.97-1.81 (m, 4H), 1.73 (td, J=9.2, 18.1 Hz, 1H), 1.55-1.42 (m, 1H), 1.41-1.19 (m, 3H), 1.11-1.02 (m, 3H). LRMS: m/z (ESI, +ve ion) 701.1 (M+H)$^+$.

Example 130

(1S,3'R,6'R,7'S,8'E,15'R)-6-CHLORO-7',15'-DIHYDROXY-12'-METHYL-13'-OXO-N-(1-PYRROLIDINYLSULFONYL)-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

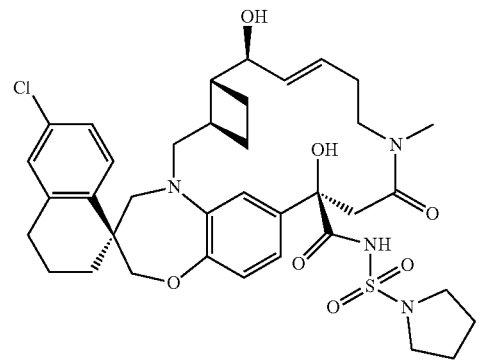 [SMILES: CN1CC/C=C/[C@H](O)[C@@H]2CC[C@H]2CN2C[C@@]3(CCCc4cc(Cl)ccc43)COc3ccc(cc32)[C@@](O)(C(=O)NS(=O)(=O)N2CCCC2)CC1=O]

The title compound (18 mg, 83%) was synthesized from Example 43, step 2 through a procedure similar to that used for the synthesis of Example 43, step 3. $^1$H NMR (500 MHz, CD$_2$Cl$_2$) δ 7.73 (d, J=8.4 Hz, 1H), 7.15 (d, J=8.3 Hz, 1H), 7.08 (s, 1H), 6.97 (d, J=8.1 Hz, 1H), 6.85 (d, J=8.2 Hz, 1H), 6.53 (br. s., 1H), 6.34 (br. s., 1H), 5.88 (dd, J=9.4, 14.5 Hz, 1H), 4.31 (d, J=8.6 Hz, 1H), 4.05-3.95 (m, 2H), 3.71 (d, J=14.4 Hz, 1H), 3.64-3.48 (m, 3H), 3.44-3.37 (m, 5H), 3.33 (d, J=14.5 Hz, 2H), 2.93 (s, 3H), 2.82-2.70 (m, 2H), 2.61-2.52 (m, 4H), 2.41-2.33 (m, 2H), 2.27 (t, J=12.9 Hz, 1H), 2.04-1.98 (m, 2H), 1.96-1.73 (m, 4H), 1.49-1.43 (m, 2H), 1.40-1.30 (m, 2H). LRMS: m/z (ESI, +ve ion) 727.2 (M+H)$^+$.

Example 131

(1S,3'R,6'R,7'S,8'E,15'R)-6-CHLORO-7',15'-DIHYDROXY-N-((2-METHOXYETHYL) (METHYL)SULFAMOYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24] TETRAENE]-15'-CARBOXAMIDE

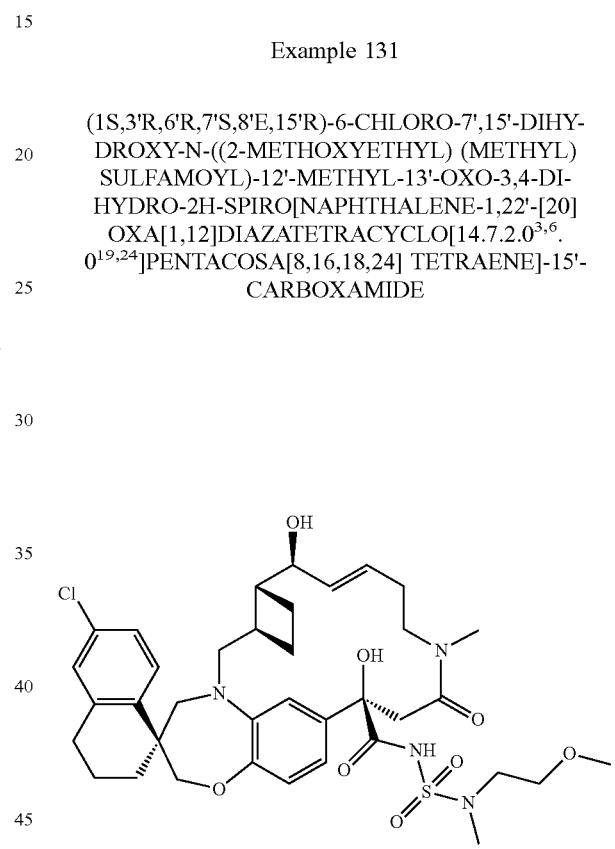

The title compound (18 mg, 72%) was synthesized from Example 43, step 2 through a procedure similar to that used for the synthesis of Example 43, step 3. $^1$H NMR (500 MHz, CD$_2$Cl$_2$) δ=7.73 (d, J=8.4 Hz, 1H), 7.15 (d, J=8.2 Hz, 1H), 7.08 (d, J=2.2 Hz, 1H), 6.97 (d, J=7.6 Hz, 1H), 6.84 (d, J=8.2 Hz, 1H), 6.50 (s, 1H), 6.53 (s, 1H), 6.36 (br. s., 1H), 5.88 (dd, J=9.3, 14.4 Hz, 1H), 4.33 (d, J=8.6 Hz, 1H), 4.03-3.97 (m, 2H), 3.70 (d, J=14.4 Hz, 1H), 3.64-3.44 (m, 6H), 3.40-3.31 (m, 5H), 3.22-3.06 (m, 2H), 2.95 (s, 3H), 2.87 (s, 3H), 2.70-2.65 (m, 2H), 2.64-2.53 (m, 1H), 2.49 (d, J=16.5 Hz, 1H), 2.37 (br. s., 2H), 2.26 (t, J=13.0 Hz, 1H), 2.06-1.97 (m, 2H), 1.97-1.81 (m, 4H), 1.77-1.61 (m, 2H), 1.40-1.35 (m, 2H). LRMS: m/z (ESI, +ve ion) 745.1 (M+H)$^+$.

Example 132

(1S,3'R,6'R,7'S,8'E,11'S, 15'R)-6-CHLORO-N-(DI-METHYLSULFAMOYL)-7',15'-DIHYDROXY-11',12'-DIMETHYL-13'-OXO-3,4-DIHYDRO-2H-SPIRO [NAPHTHALENE-1,22'-[20]OXA[1,12]DIAZATETRACYCLO[14.7.2.0$^{3,6}$.0$^{19,24}$] PENTACOSA[8,16,18,24]TETRAENE]-15'-CARBOXAMIDE OR (1S,3'R,6'R,7'S,8'E,11'S, 15'S)-6-CHLORO-N-(DIMETHYLSULFAMOYL)-7',15'-DIHYDROXY-11',12'-DIMETHYL-13'-OXO-3,4-DIHYDRO-2H-SPIRO [NAPHTHALENE-1,22'-[20]OXA[1,12]DIAZATETRACYCLO[14.7.2.0$^{3,6}$.0$^{19,24}$] PENTACOSA[8,16,18,24]TETRAENE]-15'-CARBOXAMIDE

STEP 1. (2R)-2-((3S)-6'-CHLORO-5-(((1R,2R)-2-((1S)-1-HYDROXY-2-PROPEN-1-YL)CYCLOBUTYL)METHYL)-3',4,4',5-TETRA-HYDRO-2'H-SPIRO[1,5-BENZOXAZEPINE-3,1'-NAPHTHALEN]-7-YL)-2-HYDROXY-4-(METHYL((2S)-4-PENTEN-2-YL)AMINO)-4-OXOBUTANOIC ACID METHYL ESTER AND (2S)-2-((3S)-6'-CHLORO-5-(((1R,2R)-2-((1S)-1-HYDROXY-2-PROPEN-1-YL)CYCLOBUTYL)METHYL)-3',4,4',5-TETRAHYDRO-2'H-SPIRO[1,5-BENZOXAZEPINE-3,1'-NAPHTHALEN]-7-YL)-2-HYDROXY-4-(METHYL((2S)-4-PENTEN-2-YL)AMINO)-4-OXOBUTANOIC ACID METHYL ESTER

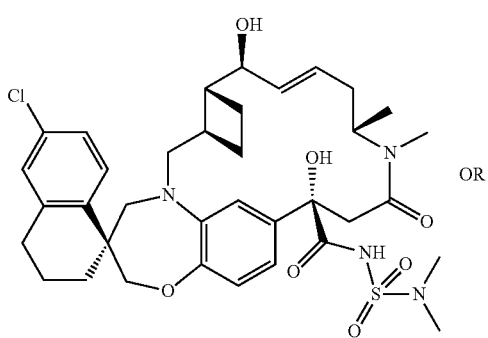

OR

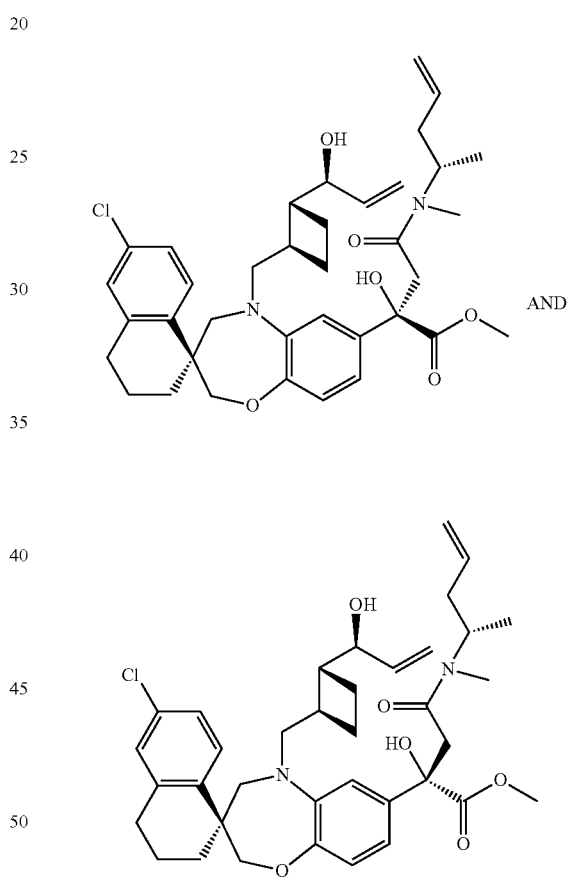

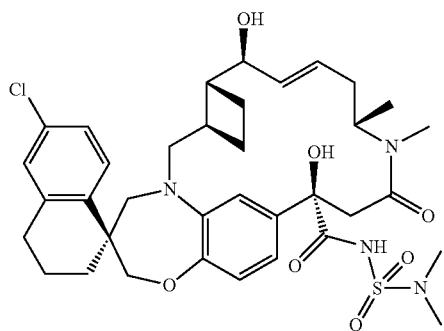

The title compounds were synthesized from 3-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-3-hydroxy-4-methoxy-4-oxobutanoic acid (Example 1, Step 5, a 2:1 mixture of isomers) and (S)-N-methyl-2-methyl-but-3-en-1-amine through a procedure similar to that used for the synthesis of Example 1, Step 6. The above compounds were isolated as a mixture of isomers (390 mg, 85% yield). LRMS: m/z (ESI, +ve ion) 651.9 (M+H)$^+$.

STEP 2. (1S,3'R,6'R,7'S,8'E,11'S, 15'R)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO [14.7.2.0$^{3,6}$.0$^{19,24}$]PENTACOSA[8,16,18,24]TETRAENE]-15'-CARBOXYLIC ACID METHYL ESTER OR (1S,3'R,6'R,7'S, 8'E,11'S, 15'S)-6-CHLORO-7',15'-DIHYDROXY-11',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24] TETRAENE]-15'-CARBOXYLIC ACID METHYL ESTER

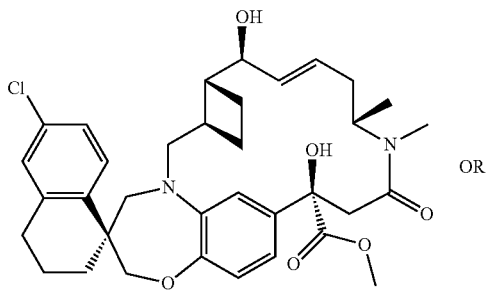

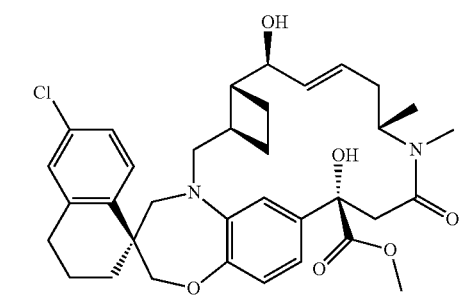

The above compound was synthesized from Example 132, Step 1 through a procedure similar to that used for the synthesis of Example 1, Step 7. The crude was chromatographed (silica gel, hexane/ethyl acetate, 3:1 to 0:1) to afford Peak 1 (fastest eluting isomer) (100 mg, 28%) and Peak 2 (slowest eluting isomer) (80 mg, 23%). LRMS: m/z (ESI, +ve ion) 623.0 (M+H)$^+$ for each compound.

STEP 3. (1S,3'R,6'R,7'S,8'E,11'S, 15'R)-6-CHLORO-N-(DIMETHYLSULFAMOYL)-7',15'-DIHYDROXY-11',12'-DIMETHYL-13'-OXO-3,4-DIHYDRO-2H-SPIRO [NAPHTHALENE-1,22'-[20]OXA[1,12]DIAZATETRACYCLO[14.7.2.0$^{3,6}$.0$^{19,24}$] PENTACOSA[8,16,18,24] TETRAENE]-15'-CARBOXAMIDE OR (1S,3'R,6'R,7'S, 8'E,11'S, 15'S)-6-CHLORO-N-(DIMETHYLSULFAMOYL)-7',15'-DIHYDROXY-11',12'-DIMETHYL-13'-OXO-3,4-DIHYDRO-2H-SPIRO [NAPHTHALENE-1,22'-[20]OXA[1,12]DIAZATETRACYCLO[14.7.2.0$^{3,6}$.0$^{19,24}$] PENTACOSA[8,16,18,24]TETRAENE]-15'-CARBOXAMIDE

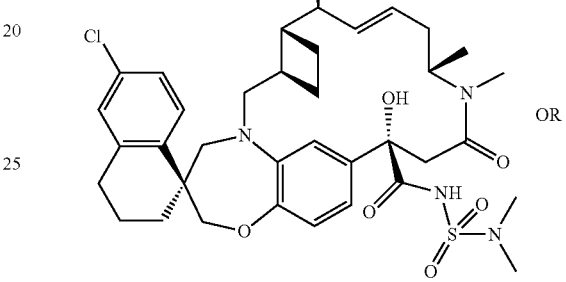

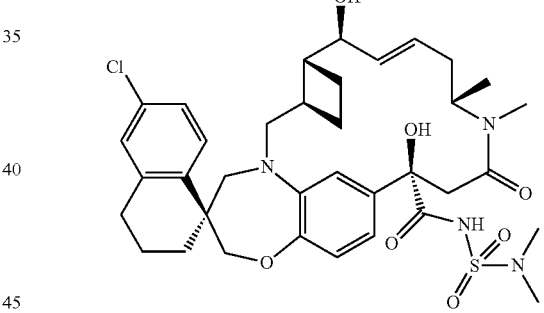

The title compound (12 mg, 46%) was synthesized from Example 132, Step 2, Peak 1 through a procedure similar to that used for the synthesis of Example 43, Steps 1 through 3. The crude residue was chromatographed (silica gel, hexane/EtOAc, 1:0 to 0:1). $^1$H NMR (500 MHz, CD$_2$Cl$_2$) δ 7.74 (d, J=8.4 Hz, 1H), 7.16 (d, J=8.5 Hz, 1H), 7.08 (s, 1H), 6.97 (dd, J=2.1, 8.2 Hz, 1H), 6.85 (d, J=8.2 Hz, 1H), 6.52 (d, J=2.0 Hz, 1H), 6.33 (br. s., 1H), 6.27 (ddd, J=2.9, 11.4, 14.8 Hz, 1H), 5.90 (ddd, J=1.7, 9.3, 15.0 Hz, 1H), 4.35 (dd, J=2.2, 9.3 Hz, 1H), 4.04-3.97 (m, 2H), 3.86 (ddd, J=1.7, 6.7, 11.6 Hz, 1H), 3.71 (d, J=14.4 Hz, 1H), 3.64-3.54 (m, 2H), 3.33 (d, J=14.5 Hz, 1H), 3.09 (dd, J=10.0, 15.2 Hz, 1H), 2.87-2.85 (m, 6H), 2.81 (s, 3H), 2.79-2.74 (m, 2H), 2.69-2.60 (m, 2H), 2.53-2.43 (m, 2H), 2.41-2.29 (m, 2H), 2.19-2.10 (m, 1H), 2.06-1.85 (m, 4H), 1.79-1.69 (m, 1H), 1.51 (quin, J=7.8 Hz, 2H), 1.40-1.25 (m, 2H). LRMS: m/z (ESI, +ve ion) 714.8 (M+H)$^+$.

Example 133

(1S,3'R,6'R,7'S,8'E,15'R)-6-CHLORO-7',15'-DIHYDROXY-N-((4-HYDROXY-1-PIPERIDINYL)SULFONYL)-12'-METHYL-13'-OXO-3,4-DIHYDRO-2H-SPIRO[NAPHTHALENE-1,22'-[20]OXA[1,12]DIAZATETRACYCLO [14.7.2.0³,⁶.0¹⁹,²⁴]PENTACOSA[8,16,18,24]TETRAENE]-15'-CARBOXAMIDE

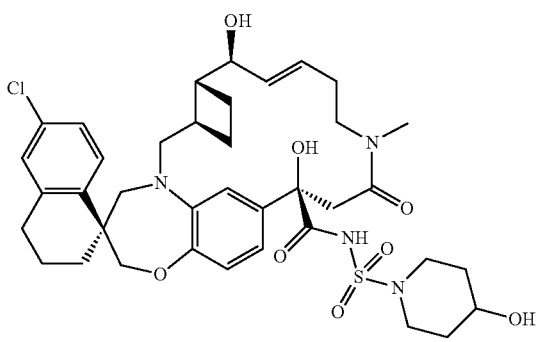 [SMILES: CN1CC/C=C/[C@H](O)[C@@H]2CC[C@H]2CN2C[C@@]3(CCCc4cc(Cl)ccc43)COc3ccc(cc32)[C@@](O)(C(=O)NS(=O)(=O)N2CCC(O)CC2)CC1=O]

The title compound (5 mg, 38%) was synthesized from Example 43, step 2 through a procedure similar to that used for the synthesis of Example 43, step 3. The crude residue was chromatographed (silica gel, MeOH in CH$_2$Cl$_2$, 0% to 10%). $^1$H NMR (500 MHz, CDCl$_3$) δ 8.95 (s, 1H), 7.74 (d, J=8.4 Hz, 1H), 7.28 (s, 3H), 7.18 (d, J=8.4 Hz, 1H), 7.08 (s, 1H), 7.01 (d, J=8.4 Hz, 1H), 6.90 (d, J=8.2 Hz, 1H), 6.53-6.31 (m, 2H), 5.95-5.83 (m, 1H), 4.45-4.35 (m, 1H), 4.09-3.98 (m, 2H), 3.82-3.65 (m, 6H), 3.63-3.55 (m, 2H), 3.34-3.14 (m, 4H), 2.98 (s, 3H), 2.84-2.73 (m, 2H), 2.67-2.50 (m, 2H), 2.46-2.25 (m, 3H), 1.99-1.50 (m, 11H). LRMS: m/z (ESI, +ve ion) 757.1 (M+Na)$^+$.

Example 134

(1S,3'R,6'R,7'S,8'E,15'R)-6-CHLORO-N-(CYCLOPROPYLSULFAMOYL)-7',15'-DIHYDROXY-12'-METHYL-13'-OXO-3,4-DIHYDRO-2H-SPIRO[NAPHTHALENE-1,22'-[20]OXA [1,12]DIAZATETRACYCLO[14.7.2.0³,⁶.0¹⁹,²⁴]PENTACOSA[8,16,18,24] TETRAENE]-15'-CARBOXAMIDE

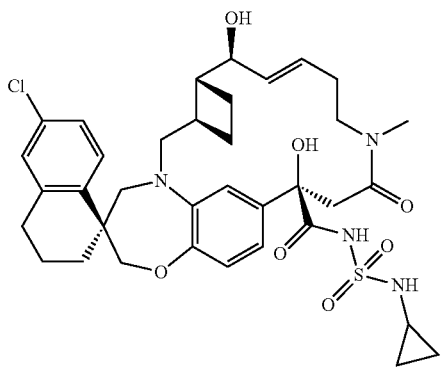 [SMILES: CN1CC/C=C/[C@H](O)[C@@H]2CC[C@H]2CN2C[C@@]3(CCCc4cc(Cl)ccc43)COc3ccc(cc32)[C@@](O)(C(=O)NS(=O)(=O)NC2CC2)CC1=O]

The title compound (18 mg, 70%) was synthesized from Example 43, Step 2 through a procedure similar to that used for the synthesis of Example 43, Step 3. The resulting residue was and chromatographed (silica gel, hexane/ethyl acetate, 5:1 to 0:1). $^1$H NMR (500 MHz, CDCl$_3$) δ 9.06 (s, 1H), 7.73 (d, J=8.4 Hz, 1H), 7.28 (s, 3H), 7.18 (d, J=7.9 Hz, 1H), 7.12-7.01 (m, 2H), 6.91 (d, J=8.2 Hz, 1H), 6.52 (br. s., 1H), 6.47 (s, 1H), 5.91 (dd, J=9.2, 14.1 Hz, 1H), 5.65 (s, 1H), 4.43 (d, J=8.3 Hz, 1H), 4.14 (q, J=7.1 Hz, 2H), 4.03 (q, J=12.2 Hz, 2H), 3.76 (d, J=14.3 Hz, 1H), 3.69-3.54 (m, 3H), 3.32 (d, J=14.5 Hz, 1H), 3.19 (d, J=14.8 Hz, 1H), 3.11-3.00 (m, 1H), 2.96 (s, 3H), 2.84-2.73 (m, 2H), 2.67-2.53 (m, 2H), 2.48-2.27 (m, 4H), 2.51-2.23 (m, 1H), 2.04-1.39 (m, 5H), 0.83-0.75 (m, 1H), 0.73-0.60 (m, 3H). LRMS: m/z (ESI, +ve ion) 713.2 (M+H)$^+$.

Example 135

(1S,3'R,6'R,7'S,8'E,15'R)-6-CHLORO-7',15'-DIHYDROXY-12'-METHYL-13'-OXO-N-(2-PROPANYLSULFAMOYL)-3,4-DIHYDRO-2H-SPIRO[NAPHTHALENE-1,22'-[20]OXA [1,12]DIAZATETRACYCLO[14.7.2.0³,⁶.0¹⁹,²⁴]PENTACOSA[8,16,18,24]TETRAENE]-15'-CARBOXAMIDE

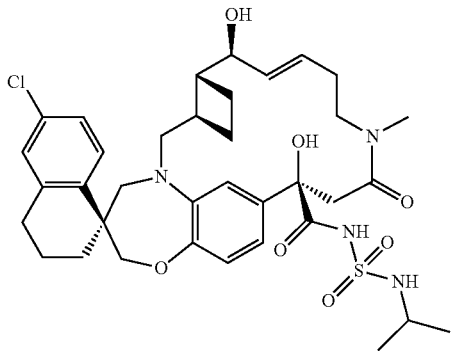 [SMILES: CC(C)NS(=O)(=O)NC(=O)[C@@]1(O)CC(=O)N(C)CC/C=C/[C@H](O)[C@@H]2CC[C@H]2CN2C[C@@]3(CCCc4cc(Cl)ccc43)COc3ccc1cc32]

The title compound (2.0 mg, 12%) was synthesized from Example 43, Step 2 through a procedure similar to that used for the synthesis of Example 43, Step 3. The organic residue was chromatographed (silica gel, hexane/ethyl acetate, 5:1 to 0:1). $^1$H NMR (500 MHz, CD$_2$Cl$_2$) δ 7.72 (d, J=8.6 Hz, 1H), 7.16 (dd, J=2.3, 8.5 Hz, 1H), 7.08 (d, J=2.2 Hz, 1H), 6.97 (dd, J=2.1, 8.2 Hz, 1H), 6.85 (d, J=8.2 Hz, 1H), 6.56 (s, 1H), 6.52 (s, 1H), 6.34 (t, J=12.2 Hz, 1H), 5.89 (dd, J=9.5, 14.9 Hz, 1H), 5.05 (d, J=5.3 Hz, 1H), 4.35 (d, J=8.9 Hz, 1H), 4.05-3.99 (m, 1H), 3.97-3.92 (m, 1H), 3.71 (d, J=14.4 Hz, 1H), 3.63-3.52 (m, 3H), 3.41-3.29 (m, 2H), 3.18-3.03 (m, 2H), 2.96-2.92 (m, 3H), 2.84-2.70 (m, 2H), 2.62-2.48 (m, 2H), 2.37 (br. s., 2H), 2.33-2.18 (m, 1H), 2.06-1.18 (m, 3H), 1.10-0.90 (m, 3H), 0.90-0.85 (m, 2H). LRMS: m/z (ESI, +ve ion) 715.1 (M+H)$^+$.

Example 136

METHYL (2R)-2-((3S)-6'-CHLORO-5-(CYCLOBUTYLMETHYL)-3',4,4',5-TETRAHYDRO-2'H-SPIRO[1,5-BENZOXAZEPINE-3,1'-NAPHTHALEN]-7-YL)-4-(DIMETHYLAMINO)-4-OXOBUTANOATE AND METHYL (2S)-2-((3S)-6'-CHLORO-5-(CYCLOBUTYLMETHYL)-3',4,4',5-TETRAHYDRO-2'H-SPIRO[1,5-BENZOXAZEPINE-3,1'-NAPHTHALEN]-7-YL)-4-(DIMETHYLAMINO)-4-OXOBUTANOATE

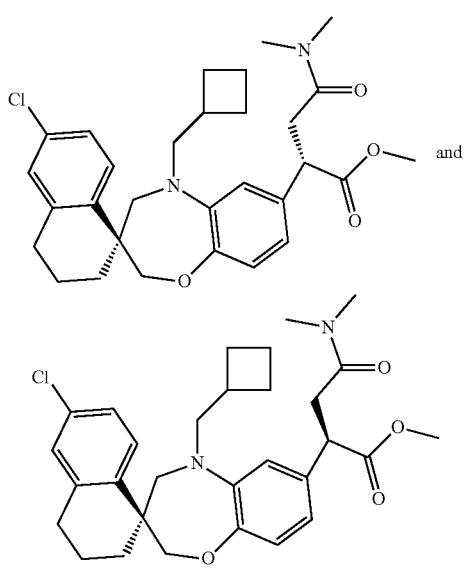

and

STEP 1: (S)-(6'-CHLORO-3',4,4',5-TETRAHYDRO-2H,2'H-SPIRO[BENZO[B][1,4]OXAZEPINE-3,1'-NAPHTHALEN]-7-YL)METHANOL

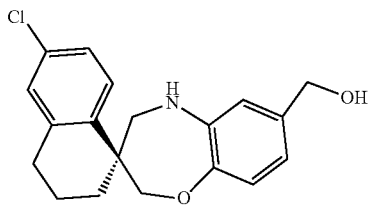 [SMILES: N#CCc1ccc2c(c1)NC[C@@]1(CCCc3cc(Cl)ccc31)CO2]

Lithium aluminum hydride, 2.0 M in THF (5.24 mL, 10.48 mmol) was added to a solution of (S)-methyl 6'-chloro-3',4,4',5-tetrahydro-2H,2'H-spiro[benzo[b][1,4]oxazepine-3,1'-naphthalene]-7-carboxylate (from Intermediate 11A1 Step 11A, 2.5 g, 6.99 mmol) in THF (58.2 mL) at 0° C. After stirring at room temperature for 60 minutes, the reaction mixture was poured slowly into ice, extracted (DCM) and washed (brine). The combined organic layers were dried over $Na_2SO_4$ and concentrated under reduced pressure. The residue was injected into a 80 g ISCO Gold column and purified by combi-flash, eluting with a gradient of 20% to 40% ethyl acetate/hexanes to give the above compound (2.30 g, 6.97 mmol). LRMS: m/z (ESI, +ve ion) 330 (M+H)$^+$.

STEP 2: (S)-2-(6'-CHLORO-3',4,4',5-TETRAHYDRO-2H,2'H-SPIRO[BENZO[B][1,4]OXAZEPINE-3,1'-NAPHTHALEN]-7-YL)ACETONITRILE

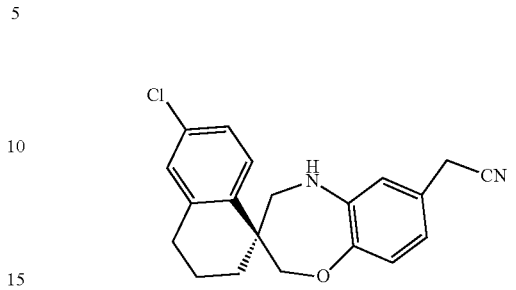

Diethyl azodicarboxylate, 40 wt. % solution in toluene (4.11 mL, 26.1 mmol) in THF (10 mL) was added dropwise slowly (during a period of 30 min) to a solution of (S)-(6'-chloro-3',4,4',5-tetrahydro-2H,2'H-spiro[benzo[b][1,4]oxazepine-3,1'-naphthalen]-7-yl)methanol (2.30 g, 6.97 mmol) (Example 136, Step 1), acetone cyanohydrin (6.37 mL, 69.7 mmol) and triphenylphosphine (2.74 g, 10.46 mmol) in THF (34.9 mL), at 0° C. After being stirred at room temperature for 60 minutes, the reaction mixture was concentrated under reduced pressure. The residue was injected into a 80 g ISCO Gold column and purified by combi-flash, eluting with a gradient of 10% to 20% EtOAc/hexanes to give the above compound (1.60 g, 4.72 mmol). LRMS: m/z (ESI, +ve ion) 339 (M+H)$^+$.

STEP 3: (S)-2-(6'-CHLORO-5-(CYCLOBUTYLMETHYL)-3',4,4',5-TETRAHYDRO-2H,2'H-SPIRO[BENZO[B][1,4]OXAZEPINE-3,1'-NAPHTHALEN]-7-YL)ACETONITRILE

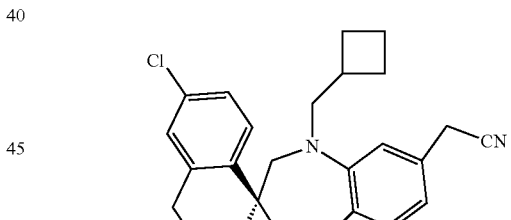

To a 250-mL round-bottomed flask was added (S)-2-(6'-chloro-3',4,4',5-tetrahydro-2H,2'H-spiro[benzo[b][1,4]oxazepine-3,1'-naphthalen]-7-yl)acetonitrile (1.60 g, 4.72 mmol) (Example 136, Step 2), acetic acid (0.818 mL, 14.17 mmol) and cyclobutanecarbaldehyde (10.62 mL, 21.25 mmol) in DCM (23.6 mL). The mixture was cooled to 0° C. Sodium triacetoxyborohydride (3.00 g, 14.17 mmol) was added in portions at 0° C. After being stirred at room temperature for 4 h, the reaction mixture was quenched with saturated aqueous $NH_4Cl$, extracted (DCM) and washed (brine). The combined organic layers were dried over $MgSO_4$ and concentrated under reduced pressure. The residue was injected into a 40 g ISCO Gold column and purified by combi-flash, eluting with a gradient of 0% to 20% EtOAc/hexanes to give the above compound (0.700 g, 1.720 mmol). LRMS: m/z (ESI, +ve ion) 407 (M+H)$^+$.

STEP 4: (S)-2-(6'-CHLORO-5-(CYCLOBUTYLMETHYL)-3',4,4',5-TETRAHYDRO-2H,2'H-SPIRO[BENZO[B][1,4]OXAZEPINE-3,1'-NAPHTHALEN]-7-YL)ACETIC ACID

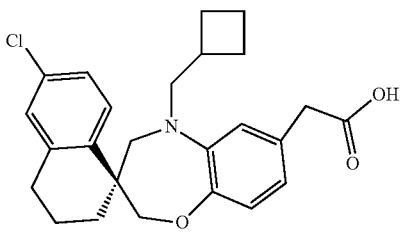 [SMILES: O=C(O)Cc1ccc2c(c1)N(CC1CCC1)C[C@@]1(CCCc3cc(Cl)ccc31)CO2]

LiOH (0.659 g, 27.5 mmol) was added to a solution of (S)-2-(6'-chloro-5-(cyclobutylmethyl)-3',4,4',5-tetrahydro-2H,2'H-spiro[benzo[b][1,4]oxazepine-3,1'-naphthalen]-7-yl)acetonitrile (0.700 g, 1.720 mmol) (Example 136, Step 3) in isopropanol (46.5 mL) and water (10 mL) in a flask equipped with a reflux condenser. After being stirred at 95° C. for 24 h, the reaction mixture was concentrated under reduced pressure to 20 mL, acidified with 1N HCl to about pH 3 and extracted (DCM). The combined organic layer was further washed with brine, dried over MgSO$_4$ filtered and concentrated under reduced pressure. The crude material was used in next step without purification. LRMS: m/z (ESI, +ve ion) 426 (M+H)$^+$.

STEP 5: (S)-METHYL 2-(6'-CHLORO-5-(CYCLOBUTYLMETHYL)-3',4,4',5-TETRAHYDRO-2H,2'H-SPIRO[BENZO[B][1,4]OXAZEPINE-3,1'-NAPHTHALEN]-7-YL)ACETATE

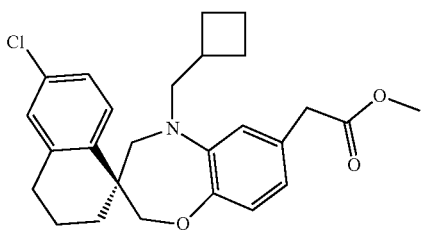 [SMILES: COC(=O)Cc1ccc2c(c1)N(CC1CCC1)C[C@@]1(CCCc3cc(Cl)ccc31)CO2]

To a solution of (S)-2-(6'-chloro-5-(cyclobutylmethyl)-3',4,4',5-tetrahydro-2H,2'H-spiro[benzo[b][1,4]oxazepine-3,1'-naphthalen]-7-yl)acetic acid (0.620 g, 1.456 mmol) (Example 136, Step 4) in MeOH (1.5 mL) and DCM (6.0 mL) was added (trimethylsilyl)diazomethane, 2.0 M in diethyl ether (0.95 mL, 1.89 mmol) at 0° C. dropwise. The reaction was allowed to warm to room temperature. After being stirred at room temperature for 15 minutes, the reaction mixture was concentrated under reduced pressure. The residue was injected into a 12 g ISCO Gold column and purified by combi-flash, eluting with a gradient of 0% to 10% ethyl acetate/hexanes to give the above compound (0.540 g, 1.227 mmol). LRMS: m/z (ESI, +ve ion) 440 (M+H)$^+$.

STEP 6: 4-TERT-BUTYL 1-METHYL (2R)-2-((3S)-6'-CHLORO-5-(CYCLOBUTYLMETHYL)-3',4,4',5-TETRAHYDRO-2H,2'H-SPIRO[BENZO[B][1,4]OXAZEPINE-3,1'-NAPHTHALEN]-7-YL)SUCCINATE AND 4-TERT-BUTYL 1-METHYL (2S)-2-((3S)-6'-CHLORO-5-(CYCLOBUTYLMETHYL)-3',4,4',5-TETRAHYDRO-2H,2'H-SPIRO[BENZO[B][1,4]OXAZEPINE-3,1'-NAPHTHALEN]-7-YL)SUCCINATE

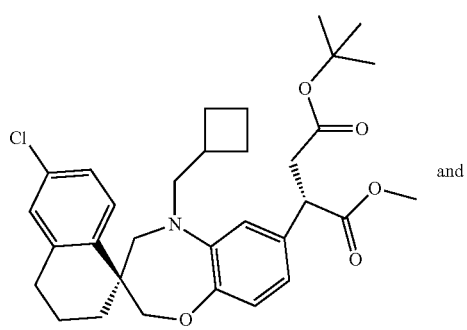

and

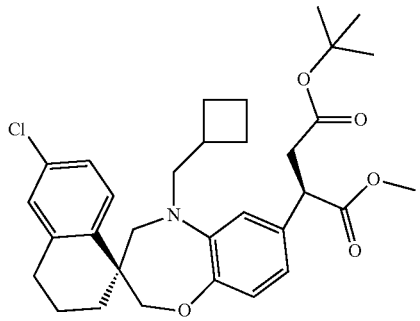

Lithium diisopropylamide, 2.0 M heptane/tetrahydrofuran/ethylbenzene (1.29 mL, 2.58 mmol) was added dropwise to a solution of (S)-methyl 2-(6'-chloro-5-(cyclobutylmethyl)-3',4,4',5-tetrahydro-2H,2'H-spiro[benzo[b][1,4]oxazepine-3,1'-naphthalen]-7-yl)acetate (0.42 g, 0.95 mmol) (Example 136, Step 5) in THF (4.8 mL) at −78° C. After being stirred at −78° C. for 10 minutes, bromoacetic acid tert-butyl ester (0.18 mL, 1.15 mmol) was added and stirred at −78° C. for 40 minutes. The reaction mixture was quenched with saturated aqueous NH$_4$Cl, extracted (DCM) and washed (brine). The combined organic layers were dried over MgSO$_4$, filtered and concentrated under reduced pressure. The residue was injected into a 12 g ISCO Gold column and purified by combi-flash, eluting with a gradient of 0% to 20% ethyl acetate/hexanes to give the above compound (0.300 g, 0.541 mmol). LRMS: m/z (ESI, +ve ion) 554 (M+H)$^+$.

STEP 7: (2R)-2-((3S)-6'-CHLORO-5-(CYCLOBUTYLMETHYL)-3',4,4',5-TETRAHYDRO-2H,2'H-SPIRO[BENZO[B][1,4]OXAZEPINE-3,1'-NAPHTHALEN]-7-YL)-4-METHOXY-4-OXOBUTANOIC ACID AND (2S)-2-((3S)-6'-CHLORO-5-(CYCLOBUTYLMETHYL)-3',4,4',5-TETRAHYDRO-2H,2'H-SPIRO[BENZO[B][1,4]OXAZEPINE-3,1'-NAPHTHALEN]-7-YL)-4-METHOXY-4-OXOBUTANOIC ACID

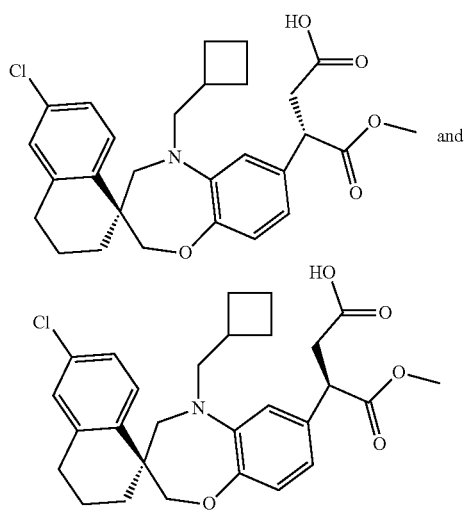
and

The product from the previous step (Example 136, Step 6, 0.300 g, 0.541 mmol) was dissolved in TFA (5.2 mL), Water (0.52 mL) and DCM (5.2 mL). After being stirred at room temperature for 24 h, the reaction was quenched (brine), extracted (EtOAc), and washed (brine). The combined organic layers were dried over MgSO4 and concentrated under reduced pressure. The residue was injected into a 12 g ISCO Gold column and purified by combi-flash, eluting with a gradient of 15% to 35% ethyl acetate/hexane containing 0.3% HOAc to give the above compound (0.20 g, 0.40 mmol). LRMS: m/z (ESI, +ve ion) 498 (M+H)+.

STEP 8: METHYL (2R)-2-((3S)-6'-CHLORO-5-(CYCLOBUTYLMETHYL)-3',4,4',5-TETRAHYDRO-2'H-SPIRO[1,5-BENZOXAZEPINE-3,1'-NAPHTHALEN]-7-YL)-4-(DIMETHYLAMINO)-4-OXOBUTANOATE AND METHYL (2S)-2-((3S)-6'-CHLORO-5-(CYCLOBUTYLMETHYL)-3',4,4',5-TETRAHYDRO-2'H-SPIRO[1,5-BENZOXAZEPINE-3,1'-NAPHTHALEN]-7-YL)-4-(DIMETHYLAMINO)-4-OXOBUTANOATE

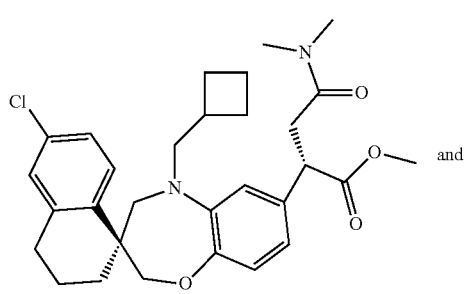
and

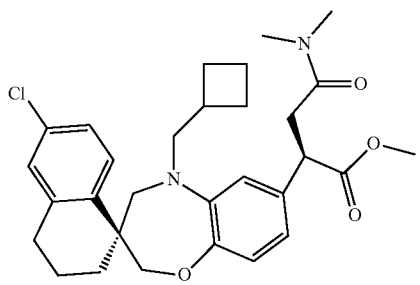

To a solution of the product from the previous step (Example 136, Step 7, 0.100 g, 0.201 mmol), methylamine (33% wt. solution in absolute ethanol, 0.089 mL, 2.008 mmol) and N,N-diisopropylamine (0.078 g, 0.602 mmol) in DMF (1.0 mL) was added HATU (0.19 g, 0.50 mmol) at room temperature. After being stirred at room temperature for 1 h, the reaction mixture was concentrated under reduced pressure. The crude product was purified by reversed phase HPLC (Gemini™ Prep $C_{18}$ 5 μm column; Phenomenex, Torrance, Calif.; gradient elution of 45% to 80% MeCN in water, where both solvents contain 0.1% TFA, 30 minutes method) to provide the title compound (0.040 g, 0.078 mmol, 85% yield). $^1$H NMR (500 MHz, CDCl$_3$) δ 7.69-7.62 (m, 1H) 7.18-7.13 (m, 1H) 7.11-7.07 (m, 1H) 6.86 (dd, J=8.31, 2.20 Hz, 1H) 6.63-6.54 (m, 2H) 4.12-4.03 (m, 3H) 3.74-3.68 (m, 3H) 3.61-3.54 (m, 1H) 3.34-3.25 (m, 3H) 3.03-2.94 (m, 1H) 2.83 (d, J=4.65 Hz, 3H) 2.80-2.74 (m, 2H) 2.66-2.60 (m, 1H) 2.59 (d, J=5.14 Hz, 1H) 2.07 (td, J=4.95, 3.30 Hz, 2H) 1.96-1.92 (m, 1H) 1.91-1.68 (m, 6H) 1.6-1.55 (m, 1H). LRMS: m/z (ESI, +ve ion) 525 (M+H)+.

Example 137

(2R)-2-((3S)-6'-CHLORO-5-(CYCLOBUTYLMETHYL)-3',4,4',5-TETRAHYDRO-2'H-SPIRO[1,5-BENZOXAZEPINE-3,1'-NAPHTHALEN]-7-YL)-4-(DIMETHYLAMINO)-4-OXOBUTANOIC ACID AND (2S)-2-((3S)-6'-CHLORO-5-(CYCLOBUTYLMETHYL)-3',4,4',5-TETRAHYDRO-2'H-SPIRO [1,5-BENZOXAZEPINE-3,1'-NAPHTHALEN]-7-YL)-4-(DIMETHYLAMINO)-4-OXOBUTANOIC ACID

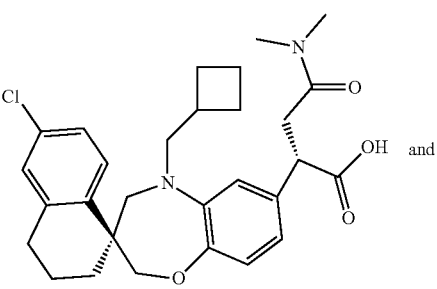
and

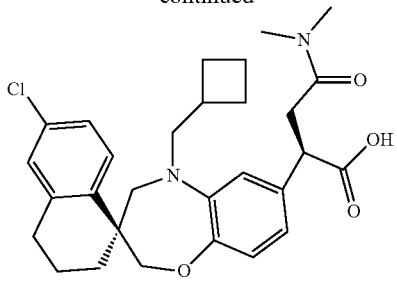

A mixture of methyl (2R)-2-((3S)-6'-chloro-5-(cyclobutylmethyl)-3',4,4',5-tetrahydro-2'H-spiro[1,5-benzoxazepine-3,1'-naphthalen]-7-yl)-4-(dimethylamino)-4-oxobutanoate and methyl (2S)-2-((3S)-6'-chloro-5-(cyclobutylmethyl)-3',4,4',5-tetrahydro-2'H-spiro[1,5-benzoxazepine-3,1'-naphthalen]-7-yl)-4-(dimethylamino)-4-oxobutanoate (0.030 g, 0.057 mmol) (Example 136, step 8) and lithium hydroxide hydrate (0.022 g, 0.514 mmol) in MeOH (2 mL) and THF (2 mL) (with a few drops of water) was stirred at room temperature for 1 h. The reaction mixture was concentrated under reduced pressure, acidified with 1N HCl to about pH 3 and extracted (DCM). The combined organic layer was further washed with brine, dried over $MgSO_4$, filtered and concentrated under reduced pressure. The residue was injected into a 4 g ISCO Gold column and purified by combi-flash, eluting with 20- to 30% ethyl acetate/hexanes containing 0.3% HOAc to give the title compound as a 1:1 mixture of isomers (0.022 g, 0.043 mmol, 75% yield). $^1$H NMR (500 MHz, $CDCl_3$) δ 7.67 (t, J=7.1 Hz, 1H), 7.15 (dd, J=2.1, 8.4 Hz, 1H), 7.09 (s, 1H), 6.88 (d, J=8.1 Hz, 1H), 6.71-6.59 (m, 2H), 4.15-4.09 (m, 1H), 4.06 (s, 2H), 3.58 (dd, J=6.5, 14.3 Hz, 1H), 3.35-3.27 (m, 2H), 3.22 (ddd, J=3.1, 10.9, 16.4 Hz, 1H), 3.05 (s, 3H), 3.00 (s, 3H), 2.83-2.73 (m, 2H), 2.73-2.63 (m, 2H), 2.11-2.03 (m, 2H), 1.98-1.91 (m, 1H), 1.90-1.70 (m, 6H). LRMS: m/z (ESI, +ve ion) 511 (M+H)$^+$.

Example 138

METHYL (2R)-2-((3S)-6'-CHLORO-5-(CYCLOBUTYLMETHYL)-3',4,4',5-TETRAHYDRO-2'H-SPIRO[1,5-BENZOXAZEPINE-3,1'-NAPHTHALEN]-7-YL)-4-(METHYLAMINO)-4-OXOBUTANOATE OR METHYL (2S)-2-((3S)-6'-CHLORO-5-(CYCLOBUTYLMETHYL)-3',4,4',5-TETRAHYDRO-2'H-SPIRO[1,5-BENZOXAZEPINE-3,1'-NAPHTHALEN]-7-YL)-4-(METHYLAMINO)-4-OXOBUTANOATE

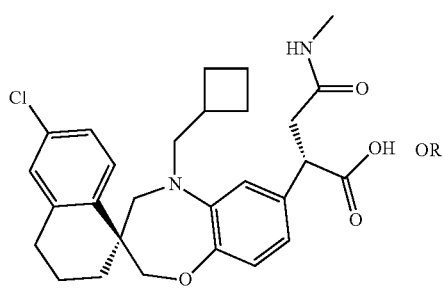

OR

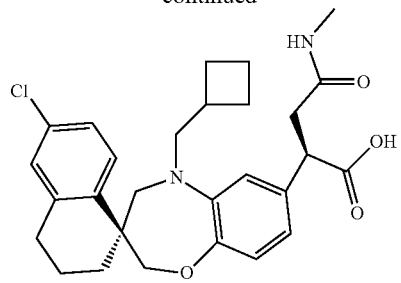

The title compound was synthesized from Example 136, step 7 via a procedure similar to that used for the synthesis of Example 136, step 8 followed by a procedure similar to that used for the synthesis of Example 137. The crude product was purified by reversed phase preparatory HPLC (Gemini™ Prep $C_{18}$ 5 µm column; Phenomenex, Torrance, Calif.; gradient elution of 45% to 70% MeCN in water, where both solvents contain 0.1% TFA, 30 minutes method) to provide the title compound as the fast eluting isomer. $^1$H NMR (500 MHz, $CDCl_3$) δ 7.66 (dd, J=8.44, 2.32 Hz, 1H) 7.15 (dd, J=8.56, 2.20 Hz, 1H) 7.09 (s, 1H) 6.88 (d, J=8.07 Hz, 1H) 6.61 (t, J=8.44 Hz, 2H) 5.82 (br. s., 1H) 4.12 (dd, J=9.41, 3.79 Hz, 1H) 4.05 (s, 2H) 3.58 (d, J=13.94 Hz, 1H) 3.38-3.21 (m, 3H) 2.99 (dd, J=15.04, 9.90 Hz, 1H) 2.84 (d, J=4.89 Hz, 3H) 2.80-2.71 (m, 2H) 2.71-2.55 (m, 2H) 2.09-2.00 (m, 2H) 1.94 (d, J=10.51 Hz, 1H) 1.91-1.68 (m, 6H) 1.61 (d, J=10.03 Hz, 1H). LRMS: m/z (ESI, +ve ion) 497 (M+H)$^+$.

Example 139

METHYL (2R)-2-((3S)-6'-CHLORO-5-(CYCLOBUTYLMETHYL)-3',4,4',5-TETRAHYDRO-2'H-SPIRO [1,5-BENZOXAZEPINE-3,1'-NAPHTHALEN]-7-YL)-4-(METHYLAMINO)-4-OXOBUTANOATE OR METHYL (2S)-2-((3S)-6'-CHLORO-5-(CYCLOBUTYLMETHYL)-3',4,4',5-TETRAHYDRO-2'H-SPIRO[1,5-BENZOXAZEPINE-3,1'-NAPHTHALEN]-7-YL)-4-(METHYLAMINO)-4-OXOBUTANOATE

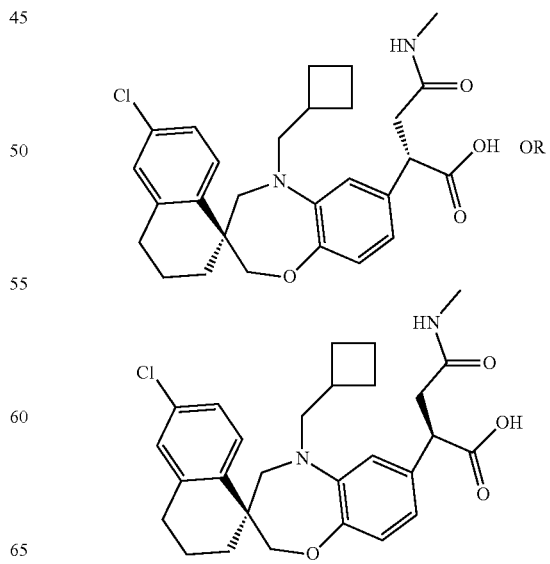

One of the title compounds was obtained as the slow eluting isomer from the reversed phase preparatory HPLC separation in Example 138. $^1$H NMR (500 MHz, CDCl$_3$) δ 7.65 (d, J=8.31 Hz, 1H) 7.16 (dd, J=8.31, 2.20 Hz, 1H) 7.13-7.07 (m, 1H) 6.91 (d, J=8.07 Hz, 1H) 6.59 (m, 1H) 6.47-6.56 (m, 1H) 5.78 (br. s., 1H) 4.07 (s, 2H) 3.87 (dd, J=9.29, 4.16 Hz, 1H) 3.61 (dd, J=14.31, 5.26 Hz, 1H) 3.39-3.20 (m, 4H) 2.88-2.80 (m, 3H) 2.80-2.69 (m, 3H) 2.63 (dt, J=14.67, 7.09 Hz, 1H) 2.11-2.00 (m, 2H) 2.00-1.91 (m, 1H) 1.91-1.68 (m, 6H) 1.63 (d, J=10.76 Hz, 1H). LRMS: m/z (ESI, +ve ion) 497 (M+H)$^+$.

Example 140

(1S,6'E,12'R)-6-CHLORO-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID OR (1S,6'E,12'S)-6-CHLORO-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID

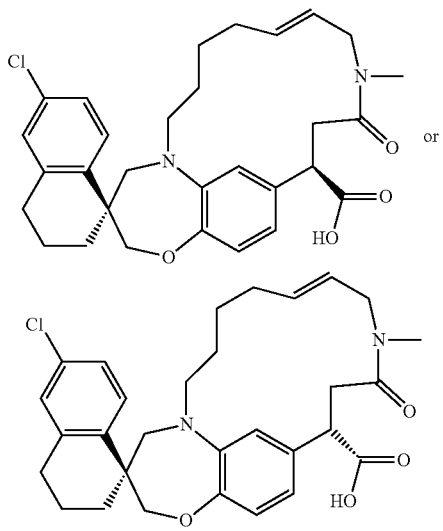

STEP 1. (S)-2-(6'-CHLORO-5-(HEX-5-EN-1-YL)-3',4,4',5-TETRAHYDRO-2H,2'H-SPIRO[BENZO[B][1,4]OXAZEPINE-3,1'-NAPHTHALEN]-7-YL)ACETONITRILE

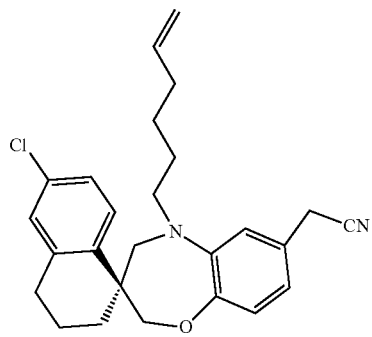 [SMILES: C=CCCCCN1C[C@@]2(CCCc3cc(Cl)ccc32)COc2ccc(CC#N)cc21]

The title compound was prepared from (S)-(6'-chloro-3',4,4',5-tetrahydro-2H,2'H-spiro[benzo[b][1,4]oxazepine-3,1'-naphthalen]-7-yl)methanol (Example 136, Step 1) by a procedure analogous to that described in Example 136, Steps 1 through 3, replacing cyclobutanecarbaldehyde with hex-5-enal. The crude product was purified by combi-flash, eluting with a gradient of 0% to 20% ethyl acetate/hexanes to give the above compound (3.10 g, 50% yield). LRMS: m/z (ESI, +ve ion) 421 (M+H)$^+$.

STEP 2. (S)-2-(6'-CHLORO-5-(HEX-5-EN-1-YL)-3',4,4',5-TETRAHYDRO-2H,2'H-SPIRO[BENZO[B][1,4]OXAZEPINE-3,1'-NAPHTHALEN]-7-YL)ACETIC ACID

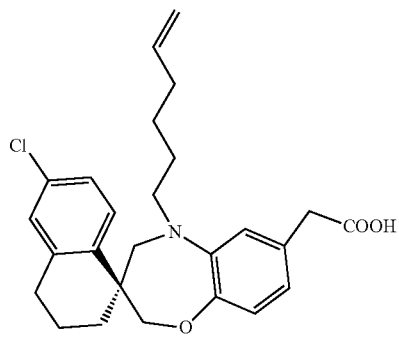 [SMILES: C=CCCCCN1C[C@@]2(CCCc3cc(Cl)ccc32)COc2ccc(CC(=O)O)cc21]

LiOH (2.73 g, 114 mmol) was added to a solution of (S)-2-(6'-chloro-5-(hex-5-en-1-yl)-3',4,4',5-tetrahydro-2H,2'H-spiro[benzo[b][1,4]oxazepine-3,1'-naphthalen]-7-yl)acetonitrile (3.0 g, 7.13 mmol) (Example 140, Step 1) in isopropanol (71.3 mL) and water (10 mL) in a flask equipped with a reflux condenser. After being stirred at 95° C. over the weekend, the reaction mixture was concentrated under reduced pressure to 20 mL, acidified with 1N HCl to about pH 3, and extracted (DCM). The combined organic layer was further washed with brine, dried over MgSO$_4$, filtered and concentrated under reduced pressure. The residue was injected into a 40 g ISCO Gold column and purified by combi-flash, eluting with a gradient of 15% to 30% ethyl acetate/hexanes containing 0.3% HOAc to give the title compound (2.00 g, 4.55 mmol, 64% yield). LRMS: m/z (ESI, +ve ion) 440 (M+H)$^+$.

STEP 3. (S)-TERT-BUTYL 2-(6'-CHLORO-5-(HEX-5-EN-1-YL)-3',4,4',5-TETRAHYDRO-2H,2'H-SPIRO[BENZO[B][1,4]OXAZEPINE-3,1'-NAPHTHALEN]-7-YL)ACETATE

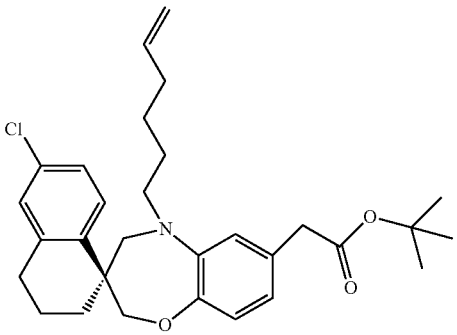 [SMILES: C=CCCCCN1C[C@@]2(CCCc3cc(Cl)ccc32)COc2ccc(CC(=O)OC(C)(C)C)cc21]

To a solution of (S)-2-(6'-chloro-5-(hex-5-en-1-yl)-3',4,4',5-tetrahydro-2H,2'H-spiro[benzo[b][1,4]oxazepine-3,1'-naphthalen]-7-yl)acetic acid (2.00 g, 4.55 mmol) (Example 140, Step 2) in DCE (30.3 mL) and t-butanol (15.1 mL) was added di-tert-butyl dicarbonate (2.48 g, 11.3 mmol) and 4-(dimethylamino)pyridine (0.44 g, 3.6 mmol) at room temperature. After being stirred at 50° C. overnight, the reaction mixture was concentrated under reduced pressure, diluted (ethyl acetate and 10% aqueous citric acid), extracted (EtOAc), and washed (brine). The combined organic layers were dried over MgSO$_4$, filtered and concentrated under the reduced pressure. The residue was injected into a 40 g ISCO Gold column and purified by combi-flash, eluting with a gradient of 0% to 15% EtOAc/hexanes to give the above compound (1.3 g, 2.62 mmol, 57% yield). LRMS: m/z (ESI, +ve ion) 496 (M+H)$^+$.

STEP 4. 1-TERT-BUTYL 4-METHYL (2R)-2-((3S)-6'-CHLORO-5-(HEX-5-EN-1-YL)-3',4,4',5-TETRAHYDRO-2H,2'H-SPIRO[BENZO[B][1,4]OXAZEPINE-3,1'-NAPHTHALEN]-7-YL)SUCCINATE AND 1-TERT-BUTYL 4-METHYL (2S)-2-((3S)-6'-CHLORO-5-(HEX-5-EN-1-YL)-3',4,4',5-TETRAHYDRO-2H,2'H-SPIRO[BENZO[B][1,4]OXAZEPINE-3,1'-NAPHTHALEN]-7-YL)SUCCINATE

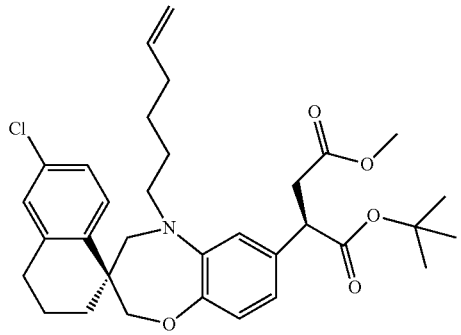

and

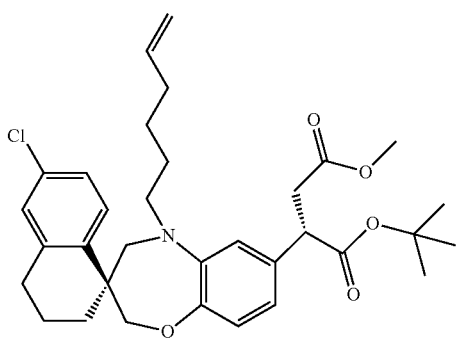

Lithium diisopropylamide (2.0M heptane/tetrahydrofuran/ethylbenzene) (1.63 ml, 3.27 mmol) was added dropwise to a solution of (S)-tert-butyl 2-(6'-chloro-5-(hex-5-en-1-yl)-3',4,4',5-tetrahydro-2H,2'H-spiro[benzo[b][1,4]oxazepine-3,1'-naphthalen]-7-yl)acetate (0.600 g, 1.209 mmol)) (Example 140, Step 3) in THF (6.0 mL) at −78° C. After being stirred at −78° C. for 10 minutes, methyl 2-bromoacetate (0.22 g, 1.45 mmol) was added. After being stirred at −78° C. for 40 minutes, the reaction was quenched (water) and extracted (EtOAc). The combined organic layers were dried over MgSO$_4$, filtered and concentrated under the reduced pressure to afford the above compounds. The crude mixture of the title compounds was used in next step without further purification. LRMS: m/z (ESI, +ve ion) 568 (M+H)$^+$.

STEP 5. 4-(TERT-BUTOXY)-(2R)-2-((3S)-6'-CHLORO-5-(HEX-5-EN-1-YL)-3',4,4',5-TETRAHYDRO-2H,2'H-SPIRO[BENZO[B][1,4]OXAZEPINE-3,1'-NAPHTHALEN]-7-YL)-4-OXOBUTANOIC ACID AND 4-(TERT-BUTOXY)-(2S)-2-((3S)-6'-CHLORO-5-(HEX-5-EN-1-YL)-3',4,4',5-TETRAHYDRO-2H,2'H-SPIRO[BENZO[B][1,4]OXAZEPINE-3,1'-NAPHTHALEN]-7-YL)-4-OXOBUTANOIC ACID

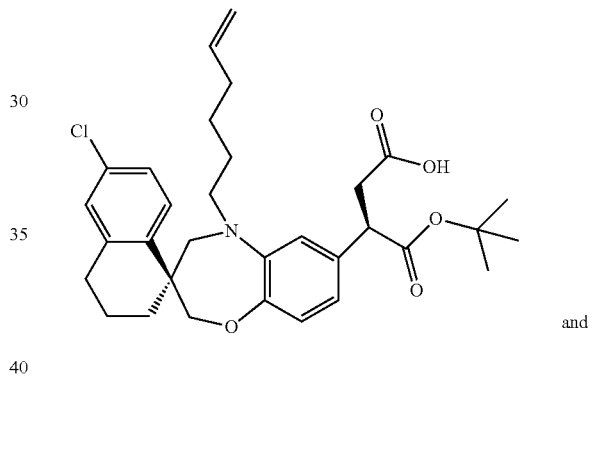

and

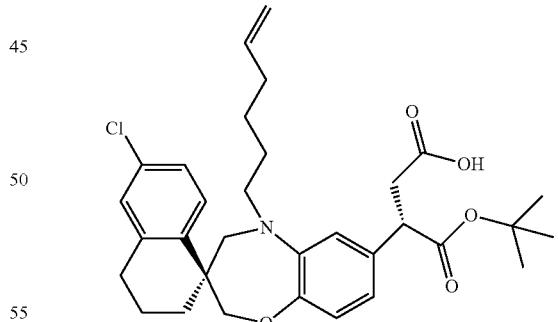

A mixture of the title compounds (0.140 g, 0.253 mmol, 21% yield) was prepared from the mixture of products obtained in the previous step (Example 140, Step 4) (0.68 g, 1.21 mmol) using a procedure similar to that used for the synthesis of Example 137. LRMS: m/z (ESI, +ve ion) 554 (M+H)$^+$.

STEP 6. TERT-BUTYL 4-(ALLYL(METHYL)AMINO)-(2R)-2-((3S)-6'-CHLORO-5-(HEX-5-EN-1-YL)-3',4,4',5-TETRAHYDRO-2H,2'H-SPIRO[BENZO[B][1,4]OXAZEPINE-3,1'-NAPHTHALEN]-7-YL)-4-OXOBUTANOATE AND TERT-BUTYL 4-(ALLYL(METHYL)AMINO)-(2S)-2-((3S)-6'-CHLORO-5-(HEX-5-EN-1-YL)-3',4,4',5-TETRAHYDRO-2H,2'H-SPIRO[BENZO[B][1,4]OXAZEPINE-3,1'-NAPHTHALEN]-7-YL)-4-OXOBUTANOATE

STEP 7. TERT-BUTOXY-(1S,6'E,12'R)-6-CHLORO-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACETATE AND TERT-BUTOXY-(1S,6'E,12'S)-6-CHLORO-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACETATE

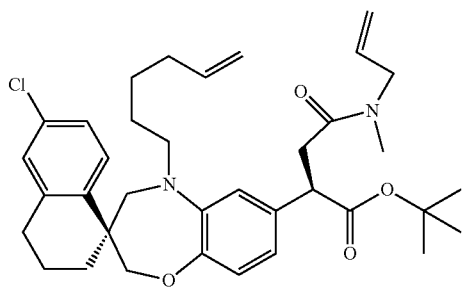

and

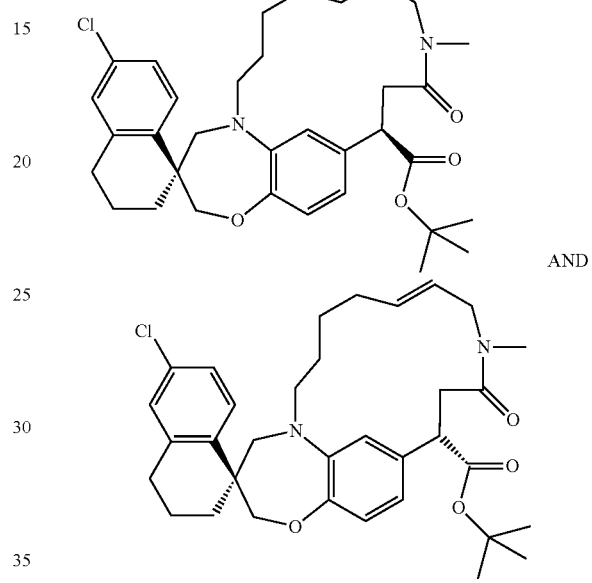

AND

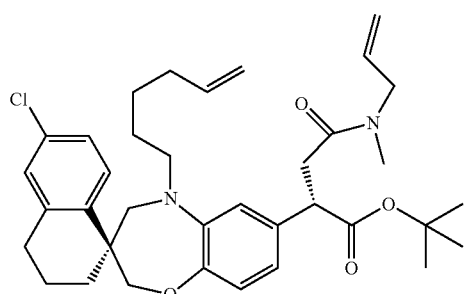

The title compounds were prepared from the mixture of products obtained in the previous step (Example 140, Step 6) (0.080 g, 0.132 mmol) using a procedure similar to that used for the synthesis of Example 1, step 7. The crude, which corresponds to a mixture of the title compounds, was used into the next step without further purification. LRMS. m/z (ESI, +ve ion) 579 (M+H)$^+$.

STEP 8. (1S,6'E,12'R)-6-CHLORO-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID OR (1S,6'E,12'S)-6-CHLORO-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID

The title compounds were prepared from the mixture of products obtained in the previous step (Example 140, Step 5) (0.13 g, 0.23 mmol) and N-methylallylamine (0.067 mL, 0.94 mmol) using a procedure similar to that used for the synthesis of Example 1, step 7. The crude product was purified by reversed phase preparatory HPLC (Gemini™ Prep C$_{18}$ 5 μm column; Phenomenex, Torrance, Calif.; gradient elution of 65% to 90% MeCN in water, where both solvents contain 0.1% TFA, 30 minutes method) to provide the above compounds as a mixture (0.080 g, 0.132 mmol, 56% yield). LRMS: m/z (ESI, +ve ion) 607 (M+H)$^+$.

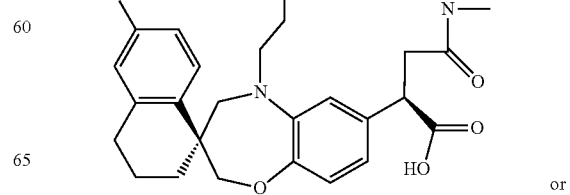

or

357
-continued

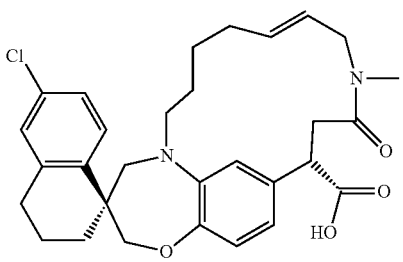

The mixture of products obtained in the previous step (Example 140, Step 7) was dissolved in solvents of TFA (1.25 mL), Water (0.13 mL) and DCM (1.25 mL). After being stirred at room temperature overnight, the reaction mixture was quenched (brine), extracted (EtOAc) and washed (brine). The combined organic layers were dried over MgSO$_4$, filtered and concentrated under reduced pressure. The crude product was purified by reversed phase preparatory HPLC (Gemini™ Prep C$_{18}$ 5 μm column; Phenomenex, Torrance, Calif.; gradient elution of 50% to 75% MeCN in water, where both solvents contain 0.1% TFA, 30 minutes method) to provide a mixture of two isomers, which was further purified by Thar 80 SFC (250×21 mm IC column; with 27.5 g/min MeOH (neat)$^+$27.5 g/min CO$_2$, 50% co-solvent at 55 g/min) to give one of the title compounds as the fast eluting isomer (13 mg, 18% yield). $^1$H NMR (400 MHz, CDCl$_3$) δ 7.75 (d, J=8.4 Hz, 1H), 7.19-7.02 (m, 2H), 6.83 (t, J=6.7 Hz, 1H), 6.72 (d, J=7.8 Hz, 1H), 6.38 (s, 1H), 5.71-5.51 (m, 1H), 5.51-5.35 (m, 1H), 4.24-4.00 (m, 3H), 3.95 (dd, J=3.6, 17.3 Hz, 1H), 3.75-3.58 (m, 1H), 3.47 (d, J=13.9 Hz, 1H), 3.37-3.22 (m, 2H), 3.21-3.06 (m, 2H), 3.03-2.94 (m, 3H), 2.93-2.77 (m, 1H), 2.74 (m., 2H), 2.32-2.11 (m, 1H), 2.10-1.92 (m, 1H), 1.81 (d, J=5.5 Hz, 3H), 1.65 (d, J=9.4 Hz, 2H), 1.56-1.33 (m, 3H). LRMS: m/z (ESI, +ve ion) 523 (M+H)$^+$.

Example 141

(1S,6'E,12'R)-6-CHLORO-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID OR (1S,6'E,12'S)-6-CHLORO-9'-METHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID

358
-continued

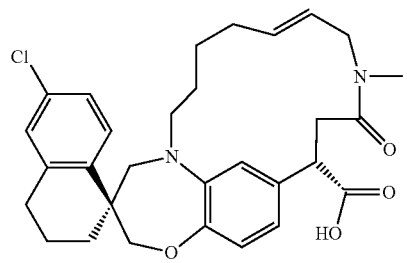

The title compound (12 mg, 18% yield) was obtained as the second (slow) eluting isomer from the reversed separation in Example 140, Step 8. $^1$H NMR (500 MHz, CDCl$_3$) δ 7.75 (d, J=8.3 Hz, 1H), 7.16 (d, J=8.8 Hz, 1H), 7.11-7.03 (m, 1H), 6.85 (d, J=8.1 Hz, 1H), 6.74 (d, J=7.8 Hz, 1H), 6.33 (m, 1H), 5.58 (m, 1H), 5.50-5.38 (m, 1H), 4.17-4.00 (m, 3H), 3.93 (m, 1H), 3.75 (m, 1H), 3.54 (m, 1H), 3.26-3.08 (m, 4H), 3.07-2.91 (m, 3H), 2.85 (m, 1H), 2.80-2.67 (m, 2H), 2.16 (m, 1H), 2.08 (m, 1H), 1.96-1.74 (m, 4H), 1.67-1.15 (m, 4H). LRMS: m/z (ESI, +ve ion) 523 (M+H)$^+$.

Example 142

(1S,6'E,11'S,12'S)-6-CHLORO-9',11'-DIMETHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID AND (1S,6'E,11'R,12'R)-6-CHLORO-9',11'-DIMETHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID OR (1S,6'E,11'S,12'R)-6-CHLORO-9',11'-DIMETHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID OR (1S,6'E,11'R,12'S)-6-CHLORO-9',11'-DIMETHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID

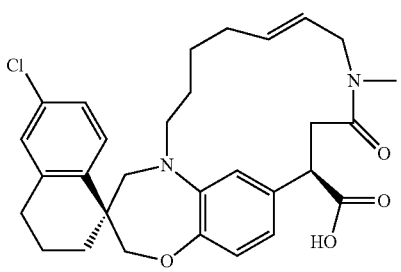

or

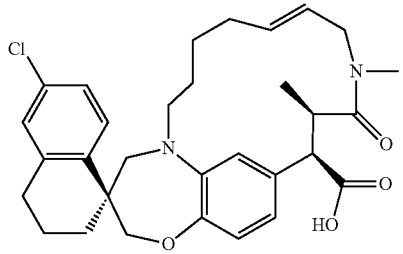

and

359
-continued

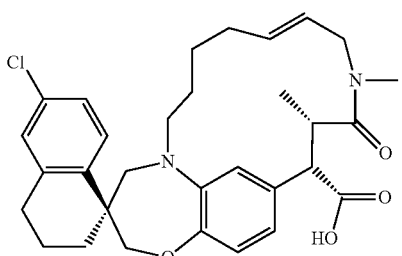

or

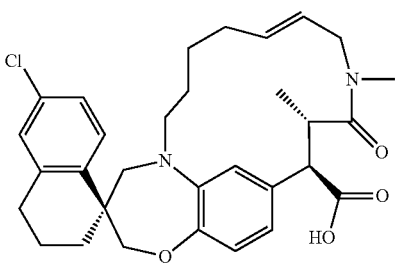

and

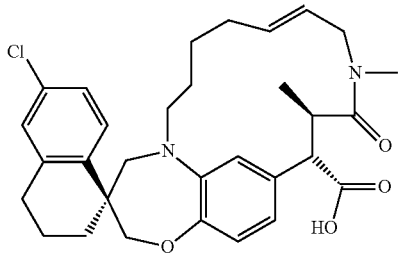

One set of the title compounds was prepared from (S)-2-(6'-chloro-5-(hex-5-en-1-yl)-3',4,4',5-tetrahydro-2H,2'H-spiro[benzo[b][1,4]oxazepine-3,1'-naphthalen]-7-yl)acetonitrile (Example 140, Step 1) by a procedure analogous to that described in Example 140, Steps 1 through 8, replacing methyl 2-bromoacetate in Step 4 with methyl 2-bromopropionate. The crude product was purified by reversed phase preparatory HPLC (Gemini™ Prep $C_{18}$ 5 μm column; Phenomenex, Torrance, Calif.; gradient elution of 50% to 70% MeCN in water, where both solvents contain 0.1% TFA, 30 minutes method) to provide one set of the title compounds as the fast eluting isomers as a 1:1 mixture of isomers (14 mg, 15% yield). $^1$H NMR (500 MHz, CDCl$_3$) δ 7.74 (dd, J=8.4, 16.8 Hz, 1H), 7.16 (dd, J=2.0, 8.6 Hz, 1H), 7.11-7.00 (m, 2H), 6.92 (m, 1H), 6.16 (br. s., 1H), 5.38 (m, 2H), 4.19-4.00 (m, 3H), 3.96 (d, J=2.7 Hz, 1H), 3.63 (d, J=17.1 Hz, 1H), 3.42-3.08 (m, 4H), 3.08-2.99 (m, 3H), 2.94-2.85 (m, 1H), 2.82-2.69 (m, 2H), 2.31 (br. s., 1H), 1.97 (m, 2H), 1.91-1.75 (m, 3H), 1.71-1.53 (m, 3H), 1.38 (dd, J=3.4, 7.3 Hz, 4H), 1.29-1.21 (m, 1H); m/z (ESI, +ve ion) 537 (M+H)$^+$.

360
Example 143

(1S,6'E,12'S)-6-CHLORO-9',12'-DIMETHYL-10'-OXO-3,4-DIHYDRO-2H-SPIRO[NAPHTHA-LENE-1,19'-[17]OXA[1,9]DIAZATRICYCLO [11.7.2.0$^{16,21}$]DOCOSA[6,13,15,21]TETRAENE]-12'-CARBOXYLIC ACID AND (1S,6'E,12'R)-6-CHLORO-9',12'-DIMETHYL-10'-OXO-3,4-DIHYDRO-2H-SPIRO[NAPHTHALENE-1,19'-[17] OXA[1,9]DIAZATRICYCLO[11.7.2. 0$^{16,21}$] DOCOSA[6,13,15,21]TETRAENE]-12'-CARBOXYLIC ACID

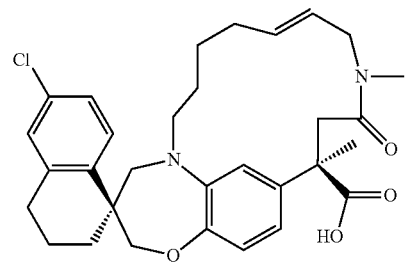

and

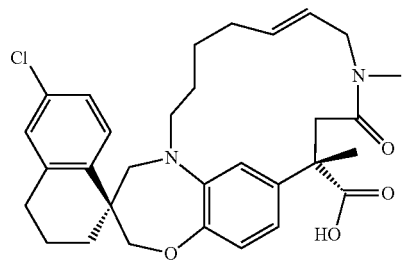

STEP 1. (R)-TERT-BUTYL 2-((S)-6'-CHLORO-5-(HEX-5-EN-1-YL)-3',4,4',5-TETRAHYDRO-2H, 2'H-SPIRO[BENZO[B][1,4]OXAZEPINE-3,1'-NAPHTHALEN]-7-YL)PROPANOATE AND (S)-TERT-BUTYL 2-((S)-6'-CHLORO-5-(HEX-5-EN-1-YL)-3',4,4',5-TETRAHYDRO-2H,2'H-SPIRO [BENZO[B][1,4]OXAZEPINE-3,1'-NAPHTHALEN]-7-YL)PROPANOATE

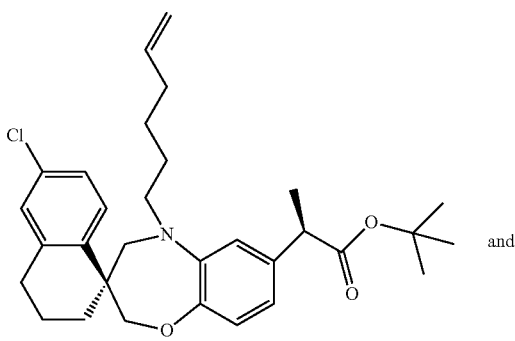

and

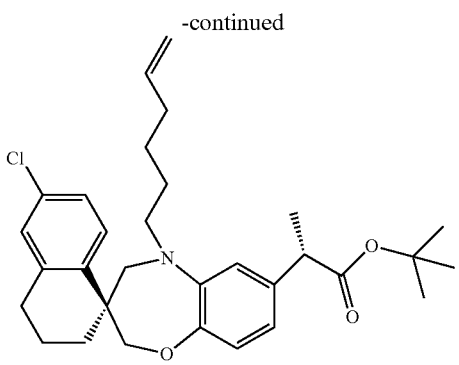

At −78° C., Lithium diisopropylamide, 2.0 M heptane/tetrahydrofuran/ethylbenzene (0.60 mL, 1.20 mmol) was added dropwise to a solution of (S)-tert-butyl 2-(6'-chloro-5-(hex-5-en-1-yl)-3',4,4',5-tetrahydro-2H,2'H-spiro[benzo[b][1,4]oxazepine-3,1'-naphthalen]-7-yl)acetate (0.220 g, 0.443 mmol) (Example 140, Step 3) in THF (4.4 mL). After being stirred at −78° C. for 10 minutes, iodomethane (0.069 g, 0.49 mmol) was added. After being stirring at −78° C. for 60 minutes, the reaction was quenched (water) and extracted (EtOAc). The combined organic layers were dried over MgSO$_4$, filtered and concentrated under the reduced pressure. The residue was injected into a 40 g ISCO Gold column and purified by combi-flash, eluting with a gradient of 0% to 20% ethyl acetate in hexanes to give the title compounds as a mixture (0.210 g, 0.412 mmol, 93% yield). LRMS. m/z (ESI, +ve ion) 510 (M+H)$^+$.

STEP 2. (1S,6'E,12'S)-6-CHLORO-9',12'-DIMETHYL-10'-OXO-3,4-DIHYDRO-2H-SPIRO[NAPHTHALENE-1,19'-[17]OXA[1,9]DIAZATRICYCLO[11.7.2. 0$^{16,21}$]DOCOSA[6,13,15,21]TETRAENE]-12'-CARBOXYLIC ACID AND (1S,6'E,12'R)-6-CHLORO-9',12'-DIMETHYL-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXYLIC ACID

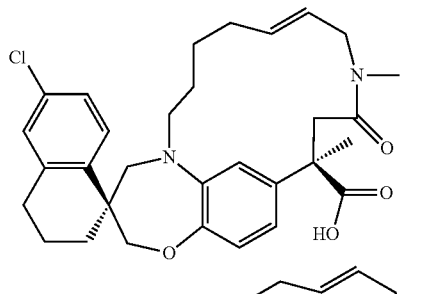

and

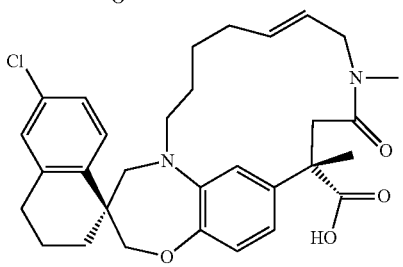

The title compounds were prepared from the mixture of products obtained in the previous step (Example 143, Step 1) by a procedure analogous to that described in Example 140, Steps 4 through 8. The crude product was purified by reversed phase preparatory HPLC (Gemini™ Prep C$_{18}$ 5 μm column; Phenomenex, Torrance, Calif.; gradient elution of 45% to 90% MeCN in water, where both solvents contain 0.1% TFA, 30 minutes method) to provide the title compounds (14 mg, 57% yield) as a 1:1 mixture of isomers. $^1$H NMR (500 MHz, CDCl$_3$) δ 7.75 (dd, J=2.6, 8.4 Hz, 1H), 7.16 (d, J=8.1 Hz, 1H), 7.11-7.00 (m, 1H), 6.85 (dd, J=3.5, 8.2 Hz, 1H), 6.73 (m, 1H), 6.50 (m 1H), 5.75-5.65 (m, 1H), 5.49-5.46 (m, 1H), 4.19-3.98 (m, 3H), 3.74-3.61 (m, 1H), 3.61-3.42 (m, 1H), 3.31-3.09 (m, 4H), 3.31 (s, 3H), 2.86-2.71 (m, 3H), 2.17 (m, 2H), 1.94-1.75 (m, 4H), 1.71-1.48 (m, 7H). LRMS: m/z (ESI, +ve ion) 537 (M+H)$^+$.

Example 144

(1S,6'E,12'R)-6-CHLORO-9'-METHYL-N-(METHYLSULFONYL)-10'-OXO-3,4-DIHYDRO-2H-SPIRO[NAPHTHALENE-1,19'-[17]OXA[1,9]DIAZATRICYCLO[11.7.2. 0$^{16,21}$]DOCOSA[6,13,15,21]TETRAENE]-12'-CARBOXAMIDE AND (1S,6'E,12'S)-6-CHLORO-9'-METHYL-N-(METHYLSULFONYL)-10'-OXO-3,4-DIHYDRO-2H-SPIRO[NAPHTHALENE-1,19'-[17]OXA[1,9]DIAZATRICYCLO[11.7.2.0$^{16,21}$]DOCOSA[6,13,15,21]TETRAENE]-12'-CARBOXAMIDE

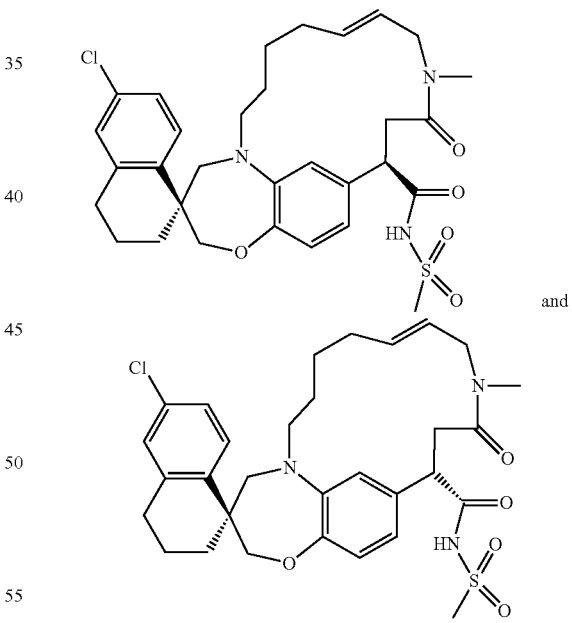

EDC (0.020 g, 0.103 mmol) was added to a solution of (1S,6'E,12'R)-6-chloro-9'-methyl-10'-oxo-3,4 dihydro-2H-spiro[naphthalene-1,19'-[17]oxa[1,9]diazatricyclo[11.7.2.0$^{16,21}$]docosa[6,13,15,21]tetraene]-12'-carboxylic acid and (1S,6'E,12'S)-6-chloro-9'-methyl-10'-oxo-3,4-dihydro-2H-spiro[naphthalene-1,19'-[17]oxa[1,9]diazatricyclo[11.7.2.0$^{16,21}$]docosa[6,13,15,21]tetraene]-12'-carboxylic acid (0.018 g, 0.034 mmol) (Example 140, Step 8), diisopropylethylamine (0.018 mL, 0.103 mmol) and methanesulfonamide (7.20 μL, 0.103 mmol) in DCM (1 mL).

Then, N,N-dimethylpyridin-4-amine (DMAP) (7.57 mg, 0.062 mmol) was added. After being stirred at room temperature overnight, the reaction mixture was concentrated under reduced pressure. The crude product was purified by reversed phase preparatory HPLC (Gemini™ Prep $C_{18}$S 5 μm column; Phenomenex, Torrance, Calif.; gradient elution of 40% to 80% MeCN in water, where both solvents contain 0.1% TFA, 30 minutes method) to provide the title compounds as a 1:1 mixture of isomers (0.012 g, 0.020 mmol, 58% yield). $^1$H NMR (500 MHz, CDCl$_3$) δ 8.51 (br. s., 1H), 7.76 (t, J=9.0 Hz, 1H), 7.16 (d, J=8.2 Hz, 1H), 7.08 (s, 1H), 6.85 (dd, J=2.0, 7.8 Hz, 1H), 6.68-6.62 (m, 1H), 6.33 (m, 1H), 5.67-5.52 (m, 1H), 5.49-5.42 (m, 1H), 4.24-4.03 (m, 3H), 4.00-3.85 (m, 1H), 3.81-3.66 (m, 1H), 3.63-3.45 (m, 1H), 3.39-3.21 (m, 6H), 3.14-3.05 (m, 1H), 2.98 (s, 3H), 2.88-2.79 (m, 1H), 2.75 (m, 2H), 2.32-2.15 (m, 1H), 1.87-1.60 (m, 6H), 1.57-1.34 (m, 3H). LRMS: m/z (ESI, +ve ion) 600 (M+H)$^+$.

Example 145

(1S,13'R)-6-CHLORO-9'-METHYL-10'-OXO-3,4-DIHYDRO-2H-SPIRO[NAPHTHALENE-1,20'-[18]OXA[1,9]DIAZATRICYCLO[12.7.2.0$^{17,22}$]TRICOSA[6,14,16,22]TETRAENE]-13'-CARBOXYLIC ACID AND (1S,13'S)-6-CHLORO-9'-METHYL-10'-OXO-3,4-DIHYDRO-2H-SPIRO[NAPHTHALENE-1,20'-[18]OXA[1,9]DIAZATRICYCLO[12.7.2. 0'$^{22}$]TRICOSA[6,14,16,22]TETRAENE]-13'-CARBOXYLIC ACID

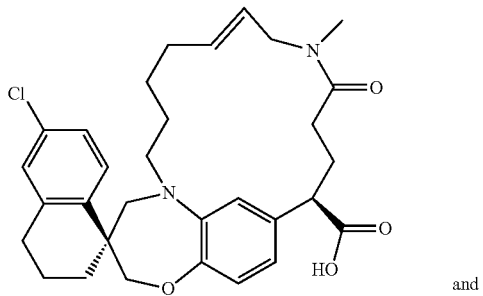

and

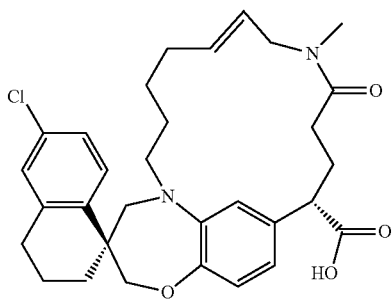

STEP 1. (R)-1-TERT-BUTYL 5-METHYL 2-((S)-6'-CHLORO-5-(HEX-5-EN-1-YL)-3',4,4',5-TETRAHYDRO-2H,2'H-SPIRO[BENZO[B][1,4]OXAZEPINE-3,1'-NAPHTHALEN]-7-YL)PENTANEDIOATE AND (S)-1-TERT-BUTYL 5-METHYL 2-((S)-6'-CHLORO-5-(HEX-5-EN-1-YL)-3',4,4',5-TETRAHYDRO-2H,2'H-SPIRO[BENZO[B][1,4]OXAZEPINE-3,1'-NAPHTHALEN]-7-YL)PENTANEDIOATE

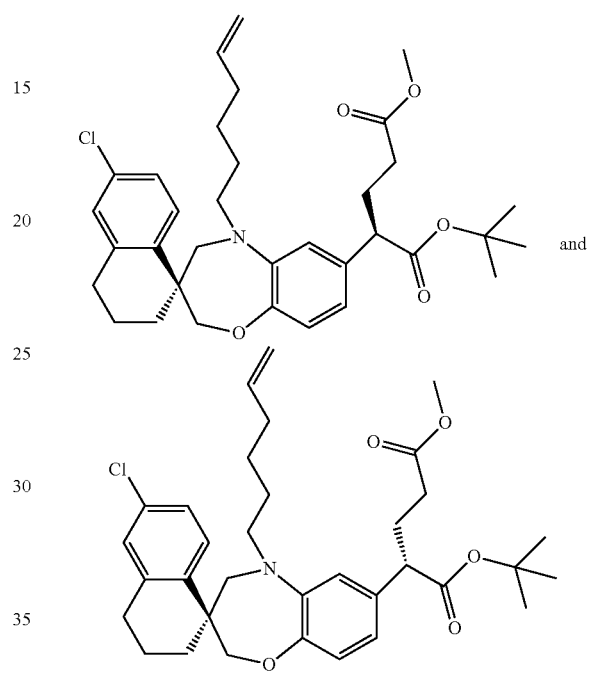

To a solution of (S)-tert-butyl 2-(6'-chloro-5-(hex-5-en-1-yl)-3',4,4',5-tetrahydro-2H,2'H-spiro[benzo[b][1,4]oxazepine-3,1'-naphthalen]-7-yl)acetate (0.100 g, 0.20 mmol) (Example 140, Step 3) and methyl methacrylate (26 mg, 0.30 mmol) in THF (2.0 mL) was added 1 M KO$^t$Bu in THF (0.030 mL, 0.030 mmol) slowly at 0° C. After being stirred for 30 minutes at 0° C., the reaction was allowed to warm to room temperature. After being stirred at room temperature overnight, the reaction was quenched (water) and extracted (EtOAc). The combined organic layers were dried over MgSO$_4$, filtered and concentrated under reduced pressure. The residue was injected into a 12 g ISCO Gold column and purified by combi-flash, eluting with a gradient of 0% to 20% ethyl acetate/hexanes to give the title compounds as a mixture (0.050 g, 0.086 mmol, 43% yield). LRMS. m/z (ESI, +ve ion) 582 (M+H)$^+$.

STEP 2. (1S,13'R)-6-CHLORO-9'-METHYL-10'-OXO-3,4-DIHYDRO-2H-SPIRO[NAPHTHALENE-1,20'-[18]OXA[1,9]DIAZATRICYCLO[12.7.2. 0$^{17,22}$]TRICOSA[6,14,16,22]TETRAENE]-13'-CARBOXYLIC ACID AND (1S,13'S)-6-CHLORO-9'-METHYL-10'-OXO-3,4-DIHYDRO-2H-SPIRO[NAPHTHALENE-1,20'-[18]OXA[1,9]DIAZATRICYCLO[12.7.2. 0'$^{22}$]TRICOSA[6,14,16,22]TETRAENE]-13'-CARBOXYLIC ACID

The title compounds were prepared from the mixture of products obtained in the previous step (Example 145, Step 1) by a procedure analogous to that described in Example 140, Steps 4 through 8. The crude product was purified by reversed phase preparatory HPLC (Gemini™ Prep $C_{18}$ 5 μm column; Phenomenex, Torrance, Calif.; gradient elution of 45% to 90% MeCN in water, where both solvents contain 0.1% TFA, 30 minutes method) to provide the title compounds as a 1:1 mixture of isomers (4 mg, 31% yield). $^1$H NMR (500 MHz, $CD_2Cl_2$) δ 7.78-7.71 (m, 1H), 7.19-7.11 (m, 1H), 7.09 (s, 1H), 6.91-6.84 (m, 1H), 6.70-6.61 (m, 1H), 6.41-6.33 (m, 1H), 5.68-5.47 (m, 1H), 5.40 (br. s., 1H), 4.22-3.95 (m, 3H), 3.81-3.68 (m, 1H), 3.65-3.40 (m, 2H), 3.37-3.03 (m, 4H), 3.01-2.81 (m, 3H), 2.80-2.67 (m, 2H), 2.60-2.33 (m, 2H), 2.32-2.18 (m, 1H), 2.10-1.56 (m, 6H), 1.49-1.26 (m, 3H). LRMS: m/z (ESI, +ve ion) 537 (M+H)$^+$.

Example 146

(1S,3'R,6'R,7'S, 8'E,15'S)-6-CHLORO-7'-HYDROXY-12'-METHYL-13'-OXO-3,4-DIHYDRO-2H-SPIRO[NAPHTHALENE-1,22'-[20]OXA[1,12] DIAZATETRACYCLO[14.7.2.0$^{3,6}$.0$^{19,24}$] PENTACOSA[8,16,18,24]TETRAENE]-15'-CARBOXYLIC ACID OR (1S,3'R,6'R,7'S,8'E, 15'R)-6-CHLORO-7'-HYDROXY-12'-METHYL-13'-OXO-3,4-DIHYDRO-2H-SPIRO [NAPHTHALENE-1,22'-[20]OXA[1,12] DIAZATETRACYCLO[14.7.2. 0$^{3,6}$.0$^{19,24}$] PENTACOSA[8,16,18,24]TETRAENE]-15'-CARBOXYLIC ACID

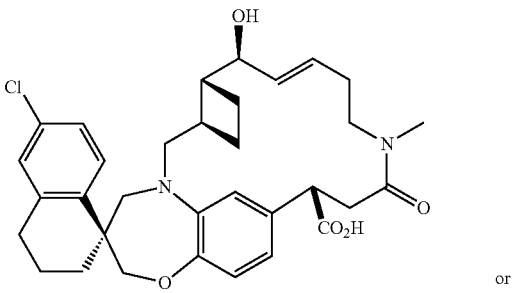

or

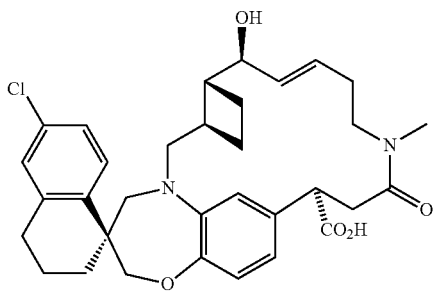

STEP 1. (S)-METHYL 2-(6'-CHLORO-3',4,4',5-TETRAHYDRO-2H,2'H-SPIRO[BENZO[B][1,4] OXAZEPINE-3,1'-NAPHTHALEN]-7-YL)ACETATE

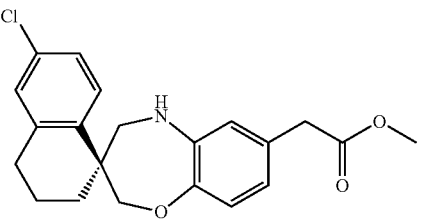 [SMILES: COC(=O)Cc1ccc2c(c1)NC[C@@]1(CCCc3cc(Cl)ccc31)CO2]

The title compound was prepared from (S)-methyl 6'-chloro-3',4,4',5-tetrahydro-2H,2'H-spiro[benzo[b][1,4] oxazepine-3,1'-naphthalene]-7-carboxylate (from Intermediate 11A1 Step 11A) by a procedure analogous to that described in Example 136, Steps 1, 2, 4 and 5. The residue was purified by combi-flash, eluting with a gradient of 10% to 20% EtOAc/hexanes to give the title compound (1.50 g, 41% yield). LRMS: m/z (ESI, +ve ion) 372 (M+H)$^+$.

STEP 2. METHYL 2-((S)-5-(((1R,2R)-2-(((TERT-BUTYLDIPHENYLSILYL)OXY)METHYL) CYCLOBUTYL)METHYL)-6'-CHLORO-3',4,4',5-TETRAHYDRO-2H,2'H-SPIRO[BENZO[B][1,4] OXAZEPINE-3,1'-NAPHTHALEN]-7-YL)ACETATE

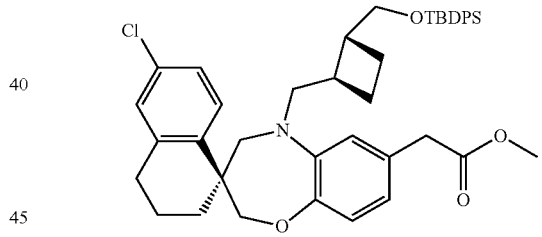

To a solution of (S)-methyl 2-(6'-chloro-3',4,4',5-tetrahydro-2H,2'H-spiro[benzo[b][1,4]oxazepine-3,1'-naphthalen]-7-yl)acetate (740 mg, 2.0 mmol) (Example 146, Step 1) in DCM (13.3 mL) and AcOH (6.6 mL) was added (1R, 2R)-2-(((tert-butyldiphenylsilyl)oxy)methyl)cyclobutanecarbaldehyde (1.05 g, 2.98 mmol). The resulting mixture was stirred at 0° C. for 10 minutes. Sodium cyanoborohydride, 1.0 M in THF (2.0 mL, 2.0 mmol) was added using syringe pump (rate: 2 mL/h) while maintained at 0° C. over 1 h. After the addition was completed, the reaction mixture was stirred at 0° C. for 0.5 h. The mixture was poured slowly into saturated aqueous $Na_2CO_3$, layers were separated, then the aqueous layer was extracted (EtOAc). The combined organic layers were dried over $MgSO_4$, filtered and concentrated under reduced pressure. The residue was injected into a 40 g ISCO Gold column and purified by combi-flash, eluting with a gradient of 0% to 20% ethyl acetate in hexanes to give the title compound (1.05 g, 1.482 mmol, 74% yield).

STEP 3. (R)-4-TERT-BUTYL 1-METHYL 2-((S)-5-(((1R,2R)-2-(((TERT-BUTYLDIPHENYLSILYL)OXY)METHYL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALEN]-7-YL)SUCCINATE AND (S)-4-TERT-BUTYL 1-METHYL 2-((S)-5-(((1R,2R)-2-(((TERT-BUTYLDIPHENYLSILYL)OXY)METHYL)CYCLOBUTYL)METHYL)-6'-CHLORO-3',4,4',5-TETRAHYDRO-2H,2'H-SPIRO[BENZO[B][1,4]OXAZEPINE-3,1'-NAPHTHALEN]-7-YL)SUCCINATE

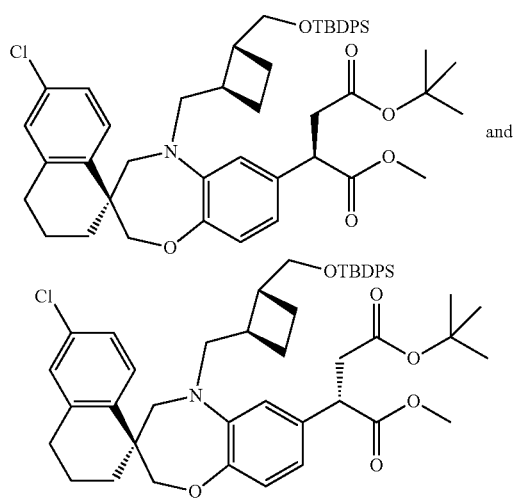

The title compounds were prepared from methyl 2-((S)-5-(((1R,2R)-2-(((tert-butyldiphenylsilyl)oxy)methyl)cyclobutyl)methyl)-6'-chloro-3',4,4',5-tetrahydro-2H,2'H-spiro[benzo[b][1,4]oxazepine-3,1'-naphthalen]-7-yl)acetate (Example 146, Step 2) by a procedure analogous to that described in Example 136, Step 6. The residue was purified by combi-flash, silica gel chromatography, eluting with a gradient of 0% to 20% EtOAc in hexanes to give the title compounds as a mixture (86 mg, 74% yield).

STEP 4. (R)-4-TERT-BUTYL 1-METHYL 2-((S)-6'-CHLORO-5-(((1R,2R)-2-(HYDROXYMETHYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)SUCCINATE AND (S)-4-TERT-BUTYL 1-METHYL 2-((S)-6'-CHLORO-5-(((1R,2R)-2-(HYDROXYMETHYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)SUCCINATE

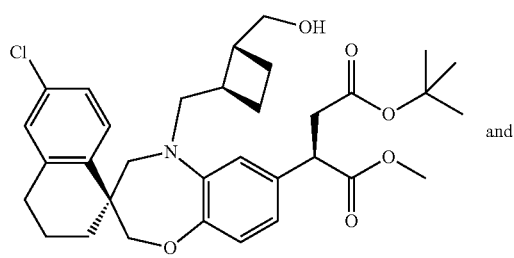

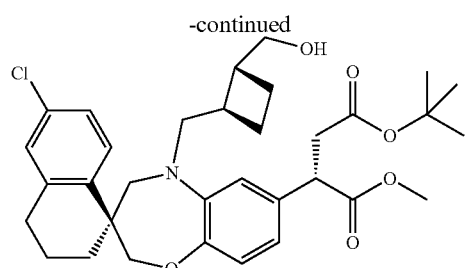

To a solution of the mixture of products obtained in the previous step (0.130 g, 0.158 mmol) (Example 146, Step 3) in THF (5 mL) was added tetrabutylammonium fluoride, 1.0 M solution in tetrahydrofuran (0.95 mL, 0.95 mmol). After being stirred at room temperature for 5 h, the reaction was quenched (saturated aqueous NH$_4$Cl) and extracted (EtOAc). The combined organic layers were dried over MgSO$_4$, filtered and concentrated under reduced pressure. The crude material, which corresponds to a mixture of the title compounds, was used in the next step without further purification. LRMS: m/z (ESI, +ve ion) 584 (M+H)$^+$.

STEP 5. (R)-4-TERT-BUTYL 1-METHYL 2-((S)-6'-CHLORO-5-(((1R,2R)-2-FORMYLCYCLOBUTYL)METHYL)-3',4,4',5-TETRAHYDRO-2H,2'H-SPIRO[BENZO[B][1,4]OXAZEPINE-3,1'-NAPHTHALEN]-7-YL)SUCCINATE AND (S)-4-TERT-BUTYL 1-METHYL 2-((S)-6'-CHLORO-5-(((1R,2R)-2-FORMYLCYCLOBUTYL)METHYL)-3',4,4',5-TETRAHYDRO-2H,2'H-SPIRO[BENZO[B][1,4]OXAZEPINE-3,1'-NAPHTHALEN]-7-YL)SUCCINATE

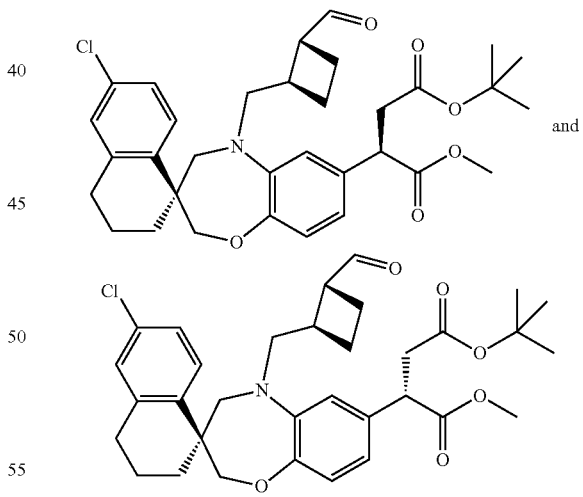

A solution of dimethyl sulfoxide anhydrous (0.032 mL, 0.45 mmol) in DCM (1.7 mL) was cooled to −78° C. Then, oxalyl chloride, 2.0 M solution in DCM (0.11 mL, 0.22 mmol) was added dropwise. After being stirred for 10 minutes at this temperature, the mixture of products obtained in the previous step (Example 146, Step 4) (0.100 g, 0.171 mmol) in DCM (0.5 mL) was added dropwise. After being stirred for 10 minutes at −78° C., triethylamine (0.10 mL, 0.72 mmol) was added, then the bath was removed and the reaction mixture was allowed to warm to room temperature. The reaction was quenched (water) and extracted (EtOAc). The combined organic layers were dried over MgSO$_4$, filtered and concentrated under reduced pressure. The crude material, which corresponds to a mixture of the title compounds, was used in next step without purification. LRMS: m/z (ESI, +ve ion) 582 (M+H)$^+$.

STEP 6. (R)-4-TERT-BUTYL 1-METHYL 2-((S)-6'-CHLORO-5-(((1R,2R)-2-((S)-1-HYDROXYAL-LYL)CYCLOBUTYL)METHYL)-3',4,4',5-TETRA-HYDRO-2H,2'H-SPIRO[BENZO[B][1,4]OXAZEPINE-3,1'-NAPHTHALEN]-7-YL) SUCCINATE AND (S)-4-TERT-BUTYL 1-METHYL 2-((S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL) SUCCINATE sponds to a mixture of the title compounds, was used in next step without purification. LRMS: m/z (ESI, +ve ion) 610 (M+H)$^+$.

STEP 7. (R)-METHYL 4-(BUT-3-EN-1-YL (METHYL)AMINO)-2-((S)-6'-CHLORO-5-(((1R,2R)-2-((S)-1-HYDROXYALLYL)CYCLOBUTYL) METHYL)-3',4,4',5-TETRAHYDRO-2H,2'H-SPIRO[BENZO[B][1,4]OXAZEPINE-3,1'-NAPHTHALEN]-7-YL)-4-OXOBUTANOATE OR (S)-METHYL 4-(BUT-3-EN-1-YL(METHYL) AMINO)-2-((S)-6'-CHLORO-5-(((1R,2R)-2-((S)-1-HYDROXYALLYL)CYCLOBUTYL)METHYL)-3', 4,4',5-TETRAHYDRO-2H,2'H-SPIRO[BENZO[B][1,4]OXAZEPINE-3,1'-NAPHTHALEN]-7-YL)-4-OXOBUTANOATE

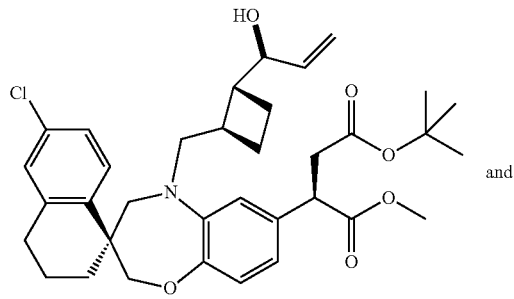 and

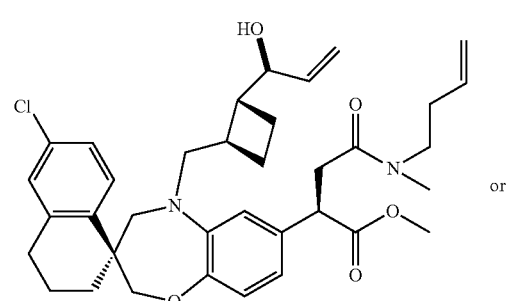 or

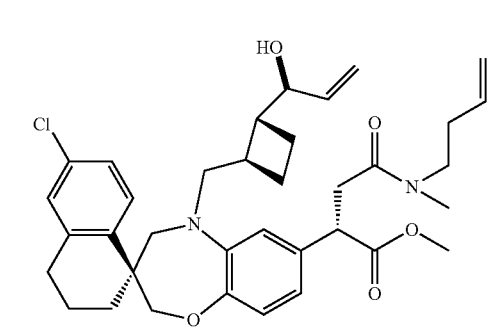

To a solution of (1R,2S)-2-morpholino-1-phenylpropan-1-ol (95 mg, 0.429 mmol) in toluene (0.83 mL) at 0° C. was added butyllithium solution, 2.5 M in hexanes (0.17 mL, 0.43 mmol). After being stirred at 0° C. for 30 minutes, divinylzinc (0.24 M in toluene) (1.79 mL, 0.43 mmol) was added. After being stirred at 0° C. for 90 minutes, the mixture of products obtained in the previous step (100 mg, 0.172 mmol) (Example 146, Step 5) was added as a solution in toluene (1.0 mL) and the solution was stirred at 0° C. for 30 minutes. The reaction was quenched (10 wt. % aqueous citric acid) and extracted (EtOAc). The combined organic layers were dried over MgSO$_4$, filtered and concentrated under reduced pressure. The crude material, which corre- The title compounds was prepared from the mixture of products obtained in the previous step (Example 146, Step 6) by a procedure analogous to that described in Example 136, Steps 7 and 8. The crude material was purified by reversed phase preparatory HPLC (Gemini™ Prep C$_{18}$ 5 µm column; Phenomenex, Torrance, Calif.; gradient elution of 55% to 85% MeCN in water, where both solvents contain 0.1% TFA, 30 minutes method) to provide one of the title compound as the fast eluting isomer (25 mg, 22% yield). LRMS: m/z (ESI, +ve ion) 621 (M+H)$^+$.

STEP 8. (1S,3'R,6'R,7'S,8'E,15'S)-6-chloro-7'-hydroxy-12'-methyl-13'-oxo-3,4-dihydro-2H-spiro[naphthalene-1,22'-[20]oxa[1,12]diazatetracyclo[14.7.2.0³,⁶.0¹⁹,²⁴]pentacosa[8,16,18,24]tetraene]-15'-carboxylic Acid or (1S,3'R,6'R,7'S,8'E,15'R)-6-chloro-7'-hydroxy-12'-methyl-13'-oxo-3,4-dihydro-2H-spiro[naphthalene-1,22'-[20]oxa[1,12]diazatetracyclo[14.7.2.0³,⁶.0¹⁹,²⁴]pentacosa[8,16,18,24]tetraene]-15'-carboxylic Acid

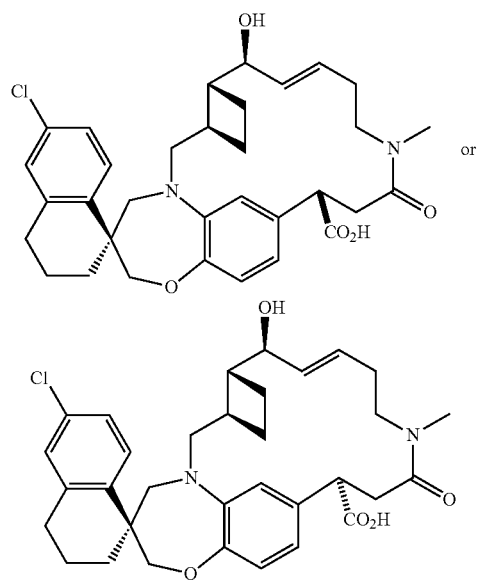

A solution of the product obtained in the previous step (Example 146, Step 7, fast eluting isomer) (0.028 g, 0.045 mmol) in 1,1-dichloroethane (22 mL) was purged with argon for 15 minutes. Then Hoveyda-Grubbs-II catalyst (5.6 mg, 0.009 mmol) in 1 mL DCE was added to the reaction mixture. After being stirred at 50° C. overnight, the crude mixture was cooled to room temperature and concentrated under reduced pressure. The crude was added to a solution of lithium hydroxide hydrate (0.022 g, 0.514 mmol) in MeOH (2 mL) and THF (2 mL) (with a few drops of water). After being stirred at room temperature for 1 h, the reaction mixture was concentrated under reduced pressure, acidified with 1N HCl to about pH 3 and extracted (DCM). The combined organic layer was further washed with brine, dried over MgSO₄, filtered and concentrated under reduced pressure. The crude product was purified by reversed phase preparatory HPLC (Gemini™ Prep $C_{18}$ 5 μm column; Phenomenex, Torrance, Calif.; gradient elution of 40% to 70% MeCN in water, where both solvents contain 0.1% TFA, 30 minutes method) to provide one of the title compounds (14 mg, 60% yield). ¹H NMR (500 MHz, CD₂Cl₂) δ 7.71 (d, J=8.3 Hz, 1H), 7.15 (dd, J=2.4, 8.6 Hz, 1H), 7.08 (d, J=2.2 Hz, 1H), 6.78 (d, J=7.8 Hz, 1H), 6.58-6.51 (m, 2H), 6.21 (m, 1H), 5.85 (dd, J=8.6, 14.4 Hz, 1H), 4.19 (dd, J=2.8, 8.7 Hz, 1H), 4.04-3.94 (m, 3H), 3.70 (d, J=14.4 Hz, 1H), 3.66-3.53 (m, 2H), 3.31 (d, J=14.2 Hz, 1H), 3.23-3.10 (m, 3H), 2.99-2.90 (m, 3H), 2.81-2.72 (m, 1H), 2.66-2.47 (m, 2H), 2.46-2.22 (m, 4H), 2.11-1.99 (m, 2H), 1.97-1.81 (m, 4H), 1.80-1.68 (m, 1H), 1.41 (t, J=12.8 Hz, 1H). LRMS: m/z (ESI, +ve ion) 579 (M+H)⁺.

Example 147

(1S,3'R,6'R,7'S, 8'E,15'S)-6-CHLORO-7'-HYDROXY-12'-METHYL-13'-OXO-3,4-DIHYDRO-2H-SPIRO[NAPHTHALENE-1,22'-[20]OXA[1,12]DIAZATETRACYCLO[14.7.2. 0³,⁶.0¹⁹,²⁴]PENTACOSA[8,16,18,24]TETRAENE]-15'-CARBOXYLIC ACID OR (1S,3'R,6'R,7'S,8'E, 15'R)-6-CHLORO-7'-HYDROXY-12'-METHYL-13'-OXO-3,4-DIHYDRO-2H-SPIRO[NAPHTHALENE-1,22'-[20]OXA[1,12]DIAZATETRACYCLO[14.7.2. 0³,6.09,24]PENTACOSA[8,16,18,24]TETRAENE]-15'-CARBOXYLIC ACID

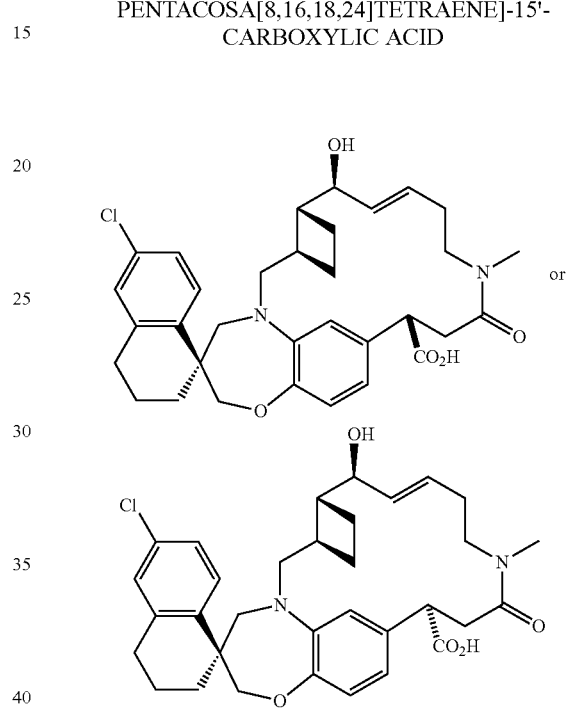

The title compound was prepared from (R)-methyl 4-(but-3-en-1-yl(methyl)amino)-2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-4-oxobutanoate or (S)-methyl 4-(but-3-en-1-yl(methyl)amino)-2-((S)-6'-chloro-5-(((1R,2R)-2-((S)-1-hydroxyallyl)cyclobutyl)methyl)-3',4,4',5-tetrahydro-2H, 2'H-spiro[benzo[b][1,4]oxazepine-3,1'-naphthalen]-7-yl)-4-oxobutanoate (Example 146, Step 7, slow eluting isomer) by a procedure analogous to that described in Example 146, Step 8. The crude product was purified by reversed phase preparatory HPLC (Gemini™ Prep $C_{18}$ 5 μm column; Phenomenex, Torrance, Calif.; gradient elution of 40% to 70% MeCN in water, where both solvents contain 0.1% TFA, 30 minutes method) to provide the title compound (8 mg, 33% yield). ¹H NMR (500 MHz, CD₂Cl₂) δ 7.70 (d, J=8.3 Hz, 1H), 7.16-7.09 (m, 1H), 7.07 (d, J=2.2 Hz, 1H), 6.79-6.74 (m, 1H), 6.60 (dd, J=1.7, 7.8 Hz, 1H), 6.51 (s, 1H), 5.99 (br. s., 1H), 5.72 (d, J=15.6 Hz, 1H), 4.03-3.91 (m, 4H), 3.76-3.63 (m, 2H), 3.58 (d, J=14.7 Hz, 1H), 3.43-3.23 (m, 2H), 3.22-3.13 (m, 1H), 3.13-3.01 (m, 1H), 2.96 (s, 3H), 2.86-2.50 (m, 6H), 2.31-2.14 (m, 2H), 2.05-1.96 (m, 1H), 1.94-1.72 (m, 4H), 1.62 (t, J=8.8 Hz, 1H), 1.48-1.34 (m, 1H). LRMS: m/z (ESI, +ve ion) 579 (M+H)⁺.

Example 148

METHYL (1S,3'R,6'R,7'S, 8'E,15'S)-6-CHLORO-7'-HYDROXY-12'-METHYL-13'-OXO-3,4-DIHYDRO-2H-SPIRO[NAPHTHALENE-1,22'-[20]OXA[1,12]DIAZATETRACYCLO [14.7.2. 0$^{3,6}$. 0$^{19,24}$]PENTACOSA[8,16,18,24]TETRAENE]-15'-CARBOXYLATE OR METHYL (1S,3'R,6'R,7'S, 8'E,15'R)-6-CHLORO-7'-HYDROXY-12'-METHYL-13'-OXO-3,4-DIHYDRO-2H-SPIRO [NAPHTHALENE-1,22'-[20]OXA[1,12] DIAZATETRACYCLO[14.7.2. 0$^{3,6}$.0$^{19,24}$] PENTACOSA[8,16,18,24]TETRAENE]-15'-CARBOXYLATE AND METHYL (1S,3'R,6'R,7'S, 8'E,15'S)-6-CHLORO-7'-METHOXY-12'-METHYL-13'-OXO-3,4-DIHYDRO-2H-SPIRO [NAPHTHALENE-1,22'-[20]OXA[1,12]DIAZATETRACYCLO[14.7.2. 0$^{3,6}$.0$^{19,24}$]PENTACOSA[8,16,18,24]TETRAENE]-15'-CARBOXYLATE OR METHYL (1S,3'R,6'R,7'S,8'E,15'R)-6-CHLORO-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2. 0$^{3,6}$. 0$^{19,24}$]PENTACOSA[8,16,18,24]TETRAENE]-15'-CARBOXYLATE

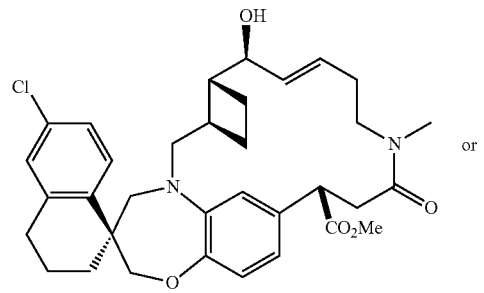 or

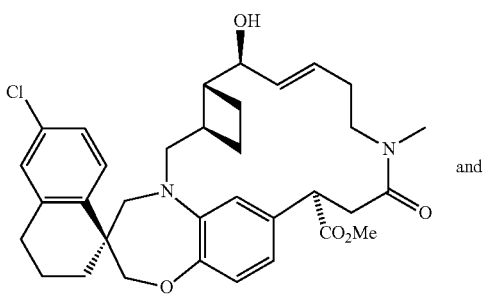 and

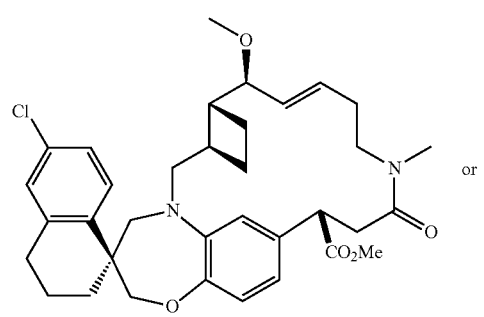 or

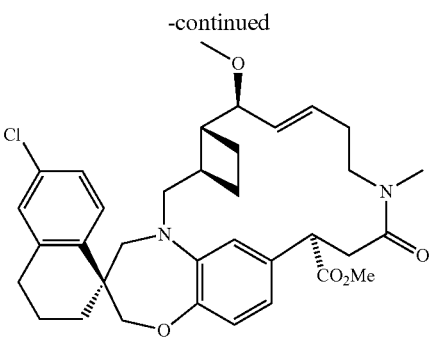

To a solution of methyl (1S,3'R,6'R,7'S, 8'E,15'S)-6-chloro-7'-hydroxy-12'-methyl-13'-oxo-3,4-dihydro-2H-spiro[naphthalene-1,22'-[20]oxa[1,12]diazatetracyclo [14.7.2. 0$^{3,6}$.0$^{19,24}$]pentacosa[8,16,18,24]tetraene]-15-carboxylate or methyl (1S,3'R,6'R,7'S,8'E,15'R)-6-chloro-7'-hydroxy-12'-methyl-13'-oxo-3,4-dihydro-2H-spiro [naphthalene-1,22'-[20]oxa[1,12]diazatetracyclo[14.7.2. 0$^{3,6}$.0$^{19,24}$]pentacosa[8,16,18,24]tetraene]-15'-carboxylate (methyl ester intermediate from Example 146, step 8), fast eluting isomer (mixture of isomers had been separated prior use in this case) using a procedure similar to that used for the synthesis of Example 146, step 8 but stopped at methyl ester stage) (0.020 g, 0.034 mmol) in DCM (0.67 mL) was added trimethylsilyl)diazomethane, 2.0 M in diethyl ether (0.020 mL, 0.040 mmol) at 0° C. After being stirred for 1 h, the reaction was quenched (MeOH), diluted (cold water) and extracted (EtOAc). The combined organic layers were washed (brine), dried over MgSO$_4$, filtered and concentrated under reduced pressure. The crude product was purified by reversed phase preparatory HPLC (Gemini™ Prep C$_{18}$ 5 μm column; Phenomenex, Torrance, Calif.; gradient elution of 55% to 80% MeCN in water, where both solvents contain 0.1% TFA, 30 minutes method) to provide the starting material as one of the title compounds 148 (0.007 g, 0.012 mmol, 35% yield) and methyl (1S,3'R,6'R,7'S, 8'E,15'S)-6-chloro-7'-methoxy-12'-methyl-13'-oxo-3,4-dihydro-2H-spiro[naphthalene-1,22'-[20]oxa[1,12]diazatetracyclo [14.7.2. 0$^{3,6}$.0$^{19,24}$]pentacosa[8,16,18,24]tetraene]-15'-carboxylate or methyl (1S,3'R,6'R,7'S,8'E,15'R)-6-chloro-7'-methoxy-12'-methyl-13'-oxo-3,4-dihydro-2H-spiro [naphthalene-1,22'-[20]oxa[1,12]diazatetracyclo[14.7.2. 0$^{3,6}$.0$^{19,24}$]pentacosa[8,16,18,24]tetraene]-15'-carboxylate as the other title compounds (5 mg, 24% yield). Starting material (methyl (1S,3'R,6'R,7'S, 8'E,15'S)-6-chloro-7'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate or methyl (1S,3'R,6'R,7'S,8'E,15'R)-6-chloro-7'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate): $^1$H NMR (500 MHz, CD$_2$Cl$_2$) δ 7.71 (d, J=8.6 Hz, 1H), 7.15 (dd, J=2.3, 8.4 Hz, 1H), 7.12-7.07 (m, 1H), 6.76 (d, J=7.8 Hz, 1H), 6.52 (dd, J=2.0, 8.1 Hz, 1H), 6.46 (s, 1H), 6.27 (br. s., 1H), 5.86 (dd, J=9.2, 15.5 Hz, 1H), 4.25 (dd, J=2.1, 8.7 Hz, 1H), 4.04-3.98 (m, 2H), 3.98-3.91 (m, 1H), 3.73-3.65 (m, 4H), 3.64-3.51 (m, 2H), 3.31 (d, J=14.2 Hz, 1H), 3.23-3.05 (m, 3H), 2.91 (s, 3H), 2.83-2.70 (m, 2H), 2.59-2.48 (m, 2H), 2.43-2.34 (m, 2H), 2.29-2.20 (m, 1H), 2.06-1.98 (m, 2H), 1.96-1.79 (m, 4H), 1.78-1.57 (m, 1H), 1.41 (t, J=12.8 Hz, 1H). LRMS: m/z (ESI, +ve ion) 593 (M+H)$^+$. Methyl (1S,3'R,6'R,7'S, 8'E, 15'S)-6-chloro-7'-methoxy-12'-methyl-13'-oxo-3,4-dihydro-2H-spiro[naphthalene-1,22'-[20]oxa[1,12]diazatetracyclo

[14.7.2.0³,⁶.0¹⁹,²⁴]pentacosa[8,16,18,24]tetraene]-15'-carboxylate or methyl (1S,3'R,6'R,7'S,8'E,15'R)-6-chloro-7'-methoxy-12'-methyl-13'-oxo-3,4-dihydro-2H-spiro[naphthalene-1,22'-[20]oxa[1,12]diazatetracyclo[14.7.2. 0³,⁶.0¹⁹,²⁴]pentacosa[8,16,18,24]tetraene]-15'-carboxylate, LRMS: m/z (ESI, +ve ion) 607.2 (M+H)⁺, 629.2 (M+Na)⁺.

Example 149

METHYL (1S,3'R,6'R,7'S, 8'E,15'S)-6-CHLORO-7'-HYDROXY-12'-METHYL-13'-OXO-3,4-DIHYDRO-2H-SPIRO[NAPHTHALENE-1,22'-[20]OXA[1,12]DIAZATETRACYCLO[14.7.2. 0³,⁶.0¹⁹,²⁴]PENTACOSA[8,16,18,24]TETRAENE]-15'-CARBOXYLATE OR METHYL (1S,3'R,6'R,7'S, 8'E,15'R)-6-CHLORO-7'-HYDROXY-12'-METHYL-13'-OXO-3,4-DIHYDRO-2H-SPIRO[NAPHTHALENE-1,22'-[20]OXA[1,12]DIAZATETRACYCLO[14.7.2. 0³,⁶.0¹⁹,²⁴]PENTACOSA[8,16,18,24]TETRAENE]-15'-CARBOXYLATE AND METHYL (1S,3'R,6'R,7'S, 8'E,15'S)-6-CHLORO-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2. 0³,⁶.0¹⁹,²⁴]PENTACOSA[8,16,18,24]TETRAENE]-15'-CARBOXYLATE OR METHYL (1S,3'R,6'R,7'S,8'E,15'R)-6-CHLORO-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2. 0³,⁶.0¹⁹,²⁴]PENTACOSA[8,16,18,24]TETRAENE]-15'-CARBOXYLATE

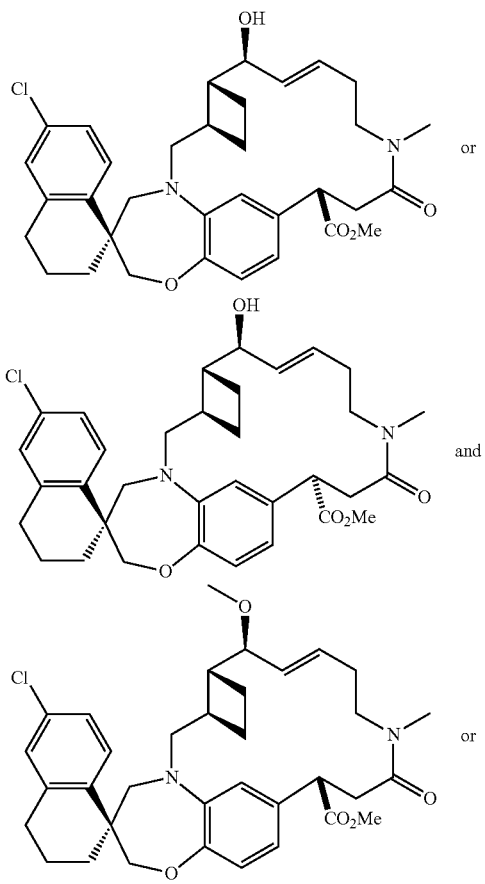

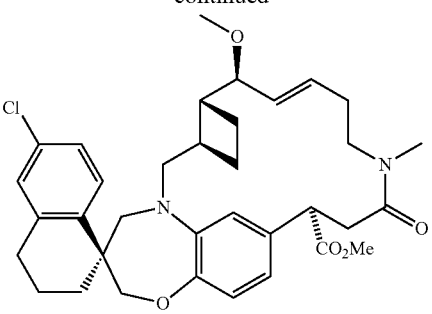

The title compounds were prepared from methyl (1S,3'R, 6'R,7'S, 8'E,15'S)-6-chloro-7'-hydroxy-12'-methyl-13'-oxo-3,4-dihydro-2H-spiro[naphthalene-1,22'-[20]oxa[1,12]diazatetracyclo[14.7.2. 0³,⁶.0¹⁹,²⁴]pentacosa[8,16,18,24]tetraene]-15-carboxylate or methyl (1S,3'R,6'R,7'S,8'E, 15'R)-6-chloro-7'-hydroxy-12'-methyl-13'-oxo-3,4-dihydro-2H-spiro[naphthalene-1,22'-[20]oxa[1,12]diazatetracyclo[14.7.2.0³,⁶.0¹⁹,²⁴]pentacosa[8,16,18,24]tetraene]-15'-carboxylate (methyl ester intermediate from Example 146, step 8), slow eluting isomer (mixture of isomers had been separated prior use in this case) using a procedure similar to that used for the synthesis of Example 146, step 8 but stopped at methyl ester stage) via a procedure analogous to that described in Example 148. The crude product was purified by reversed phase preparatory HPLC (Gemini™ Prep C₁₈ 5 μm column; Phenomenex, Torrance, Calif.; gradient elution of 55% to 80% MeCN in water, where both solvents contain 0.1% TFA, 30 min method) to provide the starting material as one of the title compounds 149 (8 mg, 32% yield) and methyl (1S,3'R,6'R,7'S, 8'E,15'S)-6-chloro-7'-methoxy-12'-methyl-13'-oxo-3,4-dihydro-2H-spiro[naphthalene-1,22'-[20]oxa[1,12]diazatetracyclo[14.7.2. 0³,⁶.0¹⁹,²⁴]pentacosa[8,16,18,24]tetraene]-15'-carboxylate or methyl (1S,3'R,6'R,7'S,8'E,15'R)-6-chloro-7'-methoxy-12'-methyl-13'-oxo-3,4-dihydro-2H-spiro[naphthalene-1, 22'-[20]oxa[1,12]diazatetracyclo[14.7.2. 0³,⁶.0¹⁹,²⁴]pentacosa[8,16,18,24]tetraene]-15'-carboxylate as the other title compounds (6 mg, 23%). Starting material (methyl (1S,3'R, 6'R,7'S, 8'E,15'S)-6-chloro-7'-hydroxy-12'-methyl-13'-oxo-3,4-dihydro-2H-spiro[naphthalene-1,22'-[20]oxa[1,12]diazatetracyclo[14.7.2. 0³,⁶.0¹⁹,²⁴]pentacosa[8,16,18,24]tetraene]-15-carboxylate or methyl (1S,3'R,6'R,7'S,8'E, 15'R)-6-chloro-7'-hydroxy-12'-methyl-13'-oxo-3,4-dihydro-2H-spiro[naphthalene-1,22'-[20]oxa[1,12]diazatetracyclo[14.7.2.0³,⁶.0¹⁹,²⁴]pentacosa[8,16,18,24]tetraene]-15'-carboxylate): ¹H NMR (500 MHz, CD₂Cl₂) δ 7.72 (d, J=8.6 Hz, 1H), 7.16 (dd, J=2.3, 8.4 Hz, 1H), 7.08 (d, J=2.2 Hz, 1H), 6.75 (d, J=7.8 Hz, 1H), 6.55 (dd, J=2.0, 7.8 Hz, 1H), 6.49 (s, 1H), 6.02 (m, 1H), 5.79-5.74 (m, 1H), 4.04-3.88 (m, 4H), 3.73-3.55 (m, 6H), 3.43-3.25 (m, 2H), 3.24-3.13 (m, 1H), 3.10 (m, 1H), 2.94 (s, 3H), 2.85-2.46 (m, 6H), 2.35-2.18 (m, 2H), 2.02-1.83 (m, 4H), 1.81-1.75 (m, 1H), 1.71-1.59 (m, 1H), 1.40 (m, 1H). LRMS: m/z (ESI, +ve ion) 593 (M+H). Methyl (1S,3'R,6'R,7'S, 8'E,15'S)-6-chloro-7'-methoxy-12'-methyl-13'-oxo-3,4-dihydro-2H-spiro[naphthalene-1,22'-[20]oxa[1,12]diazatetracyclo[14.7.2. 0³,⁶.0⁹,²⁴]pentacosa[8,16,18,24]tetraene]-15'-carboxylate or methyl (1S,3'R,6'R,7'S,8'E,15'R)-6-chloro-7'-methoxy-12'-methyl-13'-oxo-3,4-dihydro-2H-spiro[naphthalene-1,22'-[20]oxa[1,12]diazatetracyclo[14.7.2.0³,⁶.0¹⁹,²⁴]pentacosa[8,16,18,24]tetraene]-15'-carboxylate: LRMS: m/z (ESI, +ve ion) 607.2 (M+H)f.

Example 150

METHYL (1S,3'R,6'R,7'S, 8'E,15'S)-6-CHLORO-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2. 0$^{3,6}$.0$^{19,24}$]PENTACOSA[8,16,18,24]TETRAENE]-15'-CARBOXYLIC ACID OR METHYL (1S,3'R,6'R,7'S,8'E,15'R)-6-CHLORO-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2. 0$^{3,6}$.0$^{19,24}$]PENTACOSA[8,16,18,24]TETRAENE]-15'-CARBOXYLIC ACID

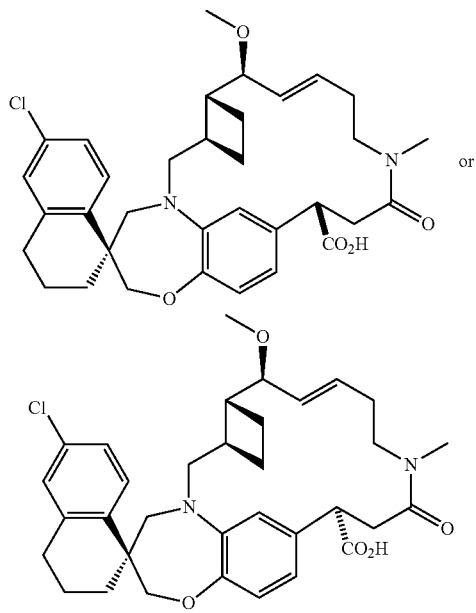

Example 151

METHYL (1S,3'R,6'R,7'S, 8'E,15'S)-6-CHLORO-7'-METHOXY-12'-METHYL-13'-OXO-3,4-DIHYDRO-2H-SPIRO[NAPHTHALENE-1,22'-[20]OXA[1,12]DIAZATETRACYCLO [14.7.2. 0$^{3,6}$.0$^{19,24}$]PENTACOSA[8,16,18,24]TETRAENE]-15'-CARBOXYLIC ACID OR METHYL (1S,3'R,6'R,7'S,8'E,15'R)-6-CHLORO-7'-METHOXY-12'-METHYL-13'-OXO-3,4-DIHYDRO-2H-SPIRO [NAPHTHALENE-1,22'-[20]OXA[1,12]DIAZATETRACYCLO[14.7.2. 0$^{3,6}$.0$^{19,24}$]PENTACOSA[8,16,18,24]TETRAENE]-15'-CARBOXYLIC ACID

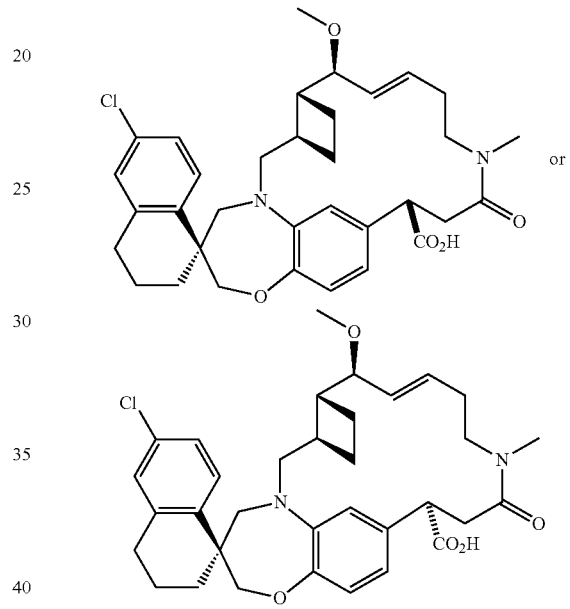

The title compound was prepared from methyl (1S,3'R,6'R,7'S, 8'E,15'S)-6-chloro-7'-methoxy-12'-methyl-13'-oxo-3,4-dihydro-2H-spiro[naphthalene-1,22'-[20]oxa[1,12]diazatetracyclo[14.7.2. 0$^{3,6}$.0$^{19,24}$]pentacosa[8,16,18,24]tetraene]-15'-carboxylate or methyl (1S,3'R,6'R,7'S,8'E,15'R)-6-chloro-7'-methoxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 148) using a procedure similar to that used for the synthesis of Example 4. The crude product was purified by reversed phase preparatory HPLC (Gemini™ Prep $C_{18}$S 5 μm column; Phenomenex, Torrance, Calif.; gradient elution of 40% to 70% MeCN in water, where both solvents contain 0.1% TFA, 30 minutes method) to provide one of the title compounds (0.003 g, 0.005 mmol, 60% yield). $^1$H NMR (400 MHz, $CD_2Cl_2$) δ 7.69 (d, J=8.6 Hz, 1H), 7.16-7.06 (m, 2H), 6.77 (d, J=7.8 Hz, 1H), 6.54 (dd, J=1.8, 7.8 Hz, 1H), 6.49 (s, 1H), 6.13 (br. s., 1H), 5.61 (dd, J=9.3, 15.2 Hz, 1H), 4.02-3.95 (m, 3H), 3.72-3.54 (m, 4H), 3.30 (d, J=14.3 Hz, 1H), 3.23-3.08 (m, 6H), 2.94 (s, 3H), 2.82-2.65 (m, 3H), 2.60 (m, 2H), 2.41 (m, 2H), 2.35-2.18 (m, 1H), 2.04-1.63 (m, 7H), 1.47-1.33 (m, 1H). LRMS: m/z (ESI, +ve ion) 593 (M+H)$^+$.

The title compound was prepared from methyl (1S,3'R,6'R,7'S, 8'E,15'S)-6-chloro-7'-methoxy-12'-methyl-13'-oxo-3,4-dihydro-2H-spiro[naphthalene-1,22'-[20]oxa[1,12]diazatetracyclo[14.7.2. 0$^{3,6}$.0$^{19,24}$]pentacosa[8,16,18,24]tetraene]-15-carboxylate or methyl (1S,3'R,6'R,7'S,8'E,15'R)-6-chloro-7'-methoxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 149) using a procedure similar to that used for the synthesis of Example 4. The crude product was purified by reversed phase preparatory HPLC (Gemini™ Prep $C_8$ 5 μm column; Phenomenex, Torrance, Calif.; gradient elution of 40% to 70% MeCN in water, where both solvents contain 0.1% TFA, 30 minutes method) to provide one of the title compounds (5.86 mg, 100% yield). $^1$H NMR (500 MHz, $CD_2Cl_2$) δ 7.72 (d, J=8.6 Hz, 1H), 7.16 (dd, J=2.3, 8.4 Hz, 1H), 7.08 (d, J=2.2 Hz, 1H), 6.75 (d, J=7.8 Hz, 1H), 6.55 (dd, J=2.0, 7.8 Hz, 1H), 6.49 (s, 1H), 6.02 (m, 1H), 5.79-5.74 (m, 1H), 4.04-3.88 (m, 4H), 3.73-3.55 (m, 6H), 3.43-3.25 (m, 2H), 3.24-3.13 (m, 1H), 3.10 (m, 1H), 3.05 (s, 3H), 2.85-2.46 (m, 6H), 2.35-2.18 (m, 2H), 2.02-1.83 (m, 4H), 1.81-1.75 (m, 1H), 1.71-1.59 (m, 1H), 1.40 (m, 1H). LRMS: m/z (ESI, +ve ion) 593 (M+H)$^+$.

Example 152

(1S,3'R,6'R,7'S,8'E,15'R)-6-CHLORO-7'-(2-(3,3-DIFLUORO-1-AZETIDINYL)ETHOXY)-N-(ETHYLSULFAMOYL)-15'-HYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

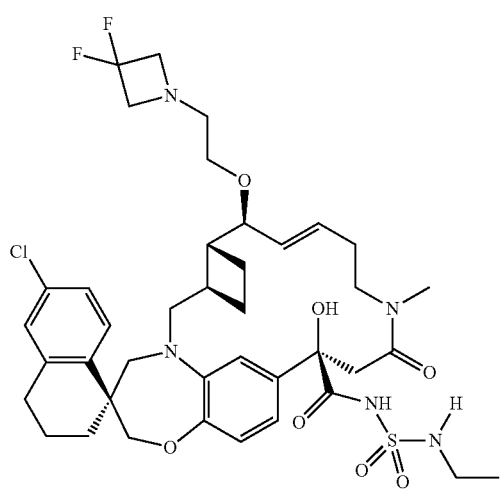 [SMILES: CCNS(=O)(=O)NC(=O)[C@@]1(O)CC(=O)N(C)CC/C=C/[C@H](OCCN2CC(F)(F)C2)[C@@H]2CC[C@H]2CN2C[C@@]3(CCCc4cc(Cl)ccc43)COc3ccc1cc32]

The title compound was prepared from (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid (Example 175) and (ethylsulfamoyl)amine using a procedure similar to that used for the synthesis of Example 5. The crude product was purified by reversed phase preparatory HPLC (Gemini™ Prep C$_{18}$ 5 μm column; Phenomenex, Torrance, Calif.; gradient elution of 55% to 70% MeCN in water, where both solvents contain 0.1% TFA, 30 minutes method) to provide the title compound (0.040 g, 0.043 mmol, 51% yield) as TFA salt. $^1$H NMR (500 MHz, CDCl$_3$) δ 8.99 (s, 1H), 7.73 (d, J=8.4 Hz, 1H), 7.17 (dd, J=2.3, 8.4 Hz, 1H), 7.07 (s, 1H), 7.00 (dd, J=2.0, 8.3 Hz, 1H), 6.89 (d, J=8.2 Hz, 1H), 6.53 (br. s., 1H), 6.45 (d, J=1.8 Hz, 1H), 6.16 (br. s., 1H), 5.65 (dd, J=9.8, 14.7 Hz, 1H), 4.18-4.12 (m, 1H), 4.05 (d, J=12.1 Hz, 1H), 3.94 (d, J=12.1 Hz, 1H), 3.76-3.57 (m, 6H), 3.51 (d, J=16.8 Hz, 1H), 3.36 (m, 1H), 3.26 (d, J=14.5 Hz, 1H), 3.17 (d, J=14.8 Hz, 1H), 3.09-2.89 (m, 6H), 2.85-2.61 (m, 5H), 2.50 (d, J=16.6 Hz, 1H), 2.45-2.25 (m, 4H), 2.09-1.91 (m, 4H), 1.37 (t, J=13.0 Hz, 1H), 1.04 (t, J=7.3 Hz, 3H).

Example 153

(1S,3'R,6'R,7'S,8'E,15'R)-6-CHLORO-N-(CYCLOPROPYLSULFAMOYL)-7'-(2-(3,3-DIFLUORO-1-AZETIDINYL)ETHOXY)-15'-HYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

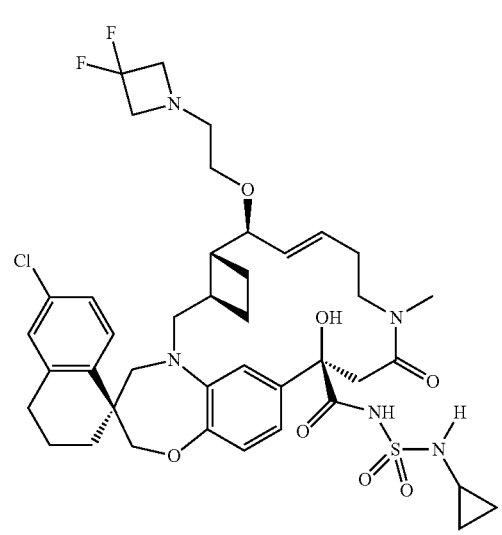 [SMILES: CN1CC/C=C/[C@H](OCCN2CC(F)(F)C2)[C@@H]2CC[C@H]2CN2C[C@@]3(CCCc4cc(Cl)ccc43)COc3ccc(cc32)[C@@](O)(C(=O)NS(=O)(=O)NC2CC2)CC1=O]

The title compound was prepared from (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid (Example 175) and (cyclopropylsulfamoyl)amine using a procedure similar to that used for the synthesis of Example 5. The crude product was purified by reversed phase preparatory HPLC (Gemini™ Prep C$_{18}$ 5 μm column; Phenomenex, Torrance, Calif.; gradient elution of 55% to 70% MeCN in water, where both solvents contain 0.1% TFA, 30 minutes method) to provide the title compound (18 mg, 34% yield) as TFA salt. $^1$H NMR (500 MHz, CD$_2$Cl$_2$) δ 9.13 (s, 1H), 7.75 (d, J=8.6 Hz, 1H), 7.19 (dd, J=2.3, 8.4 Hz, 1H), 7.12 (d, J=2.3 Hz, 1H), 7.01 (dd, J=2.1, 8.2 Hz, 1H), 6.88 (d, J=8.2 Hz, 1H), 6.66 (br. s., 1H), 6.49 (m, 2H), 5.70 (ddd, J=1.7, 9.7, 15.2 Hz, 1H), 4.14 (dd, J=2.1, 9.7 Hz, 1H), 4.06 (d, J=12.1 Hz, 1H), 3.93 (d, J=12.2 Hz, 1H), 3.78-3.55 (m, 7H), 3.36-3.30 (m, 2H), 3.19 (td, J=3.1, 14.7 Hz, 1H), 3.10 (dd, J=10.1, 15.5 Hz, 1H), 3.01 (s, 3H), 2.89-2.74 (m, 2H), 2.73-2.62 (m, 1H), 2.55 (d, J=16.9 Hz, 1H), 2.47-2.24 (m, 5H), 2.13-1.70 (m, 10H), 1.40 (m, 1H), 0.62 (m, 1H), 0.55-0.49 (m, 1H), 0.44-0.33 (m, 2H).

Example 154

(1S,3'R,6'R,7'S,8'E,15'R)-6-CHLORO-N-(ISOPROPYLSULFAMOYL)-7'-(2-(3,3-DIFLUORO-1-AZETIDINYL)ETHOXY)-15'-HYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

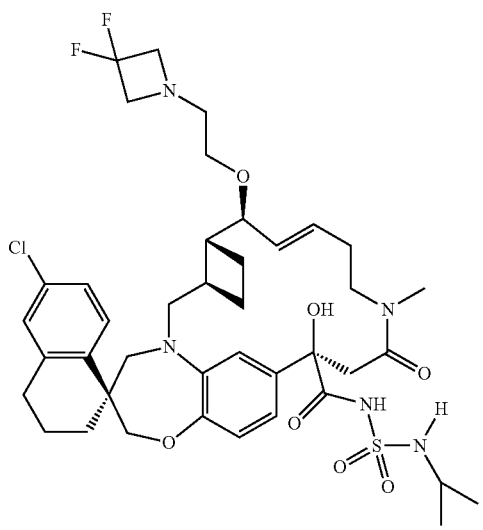 [SMILES: CC(C)NS(=O)(=O)NC(=O)[C@@]1(O)CC(=O)N(C)CC/C=C/[C@H](OCCN2CC(F)(F)C2)[C@@H]2CC[C@H]2CN2C[C@@]3(CCCc4cc(Cl)ccc43)COc3ccc1cc32]

The title compound was prepared from (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid (Example 175) and (isopropylsulfamoyl)amine using a procedure similar to that used for the synthesis of Example 5. The crude product was purified by reversed phase preparatory HPLC (Gemini™ Prep C$_{18}$ 5 µm column; Phenomenex, Torrance, Calif.; gradient elution of 55% to 70% MeCN in water, where both solvents contain 0.1% TFA, 30 minutes method) to provide the title compound (18 mg, 34% yield) as TFA salt. $^1$H NMR (500 MHz, CD$_2$Cl$_2$) δ 7.71 (d, J=8.6 Hz, 1H), 7.15 (dd, J=2.3, 8.5 Hz, 1H), 7.07 (d, J=2.1 Hz, 1H), 6.95 (dd, J=2.0, 8.3 Hz, 1H), 6.84 (d, J=8.0 Hz, 1H), 6.49 (d, J=1.7 Hz, 1H), 6.36 (t, J=12.7 Hz, 1H), 6.02 (d, J=6.4 Hz, 1H), 5.70-5.62 (m, 1H), 4.59 (br. s., 3H), 4.07-3.95 (m, 3H), 3.95-3.82 (m, 1H), 3.75-3.52 (m, 7H), 3.34-3.23 (m, 3H), 3.21-3.11 (m, 1H), 3.05 (dd, J=9.7, 15.3 Hz, 1H), 2.96 (s, 3H), 2.84-2.71 (m, 2H), 2.65 (t, J=13.0 Hz, 1H), 2.52 (d, J=16.9 Hz, 1H), 2.45-2.26 (m, 5H), 2.11-1.67 (m, 10H), 1.35 (t, J=12.0 Hz, 1H), 1.11 (d, J=6.6 Hz, 3H), 0.81 (d, J=6.6 Hz, 3H).

Example 155

(((1S,3'R,6'R,7'S,8'E,15'S)-6-CHLORO-15'-(METHOXYCARBONYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAEN]-7'-YL)OXY)ACETIC ACID or (((1S,3'R,6'R,7'S,8'E,15'R)-6-CHLORO-15'-(METHOXYCARBONYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAEN]-7'-YL)OXY)ACETIC ACID

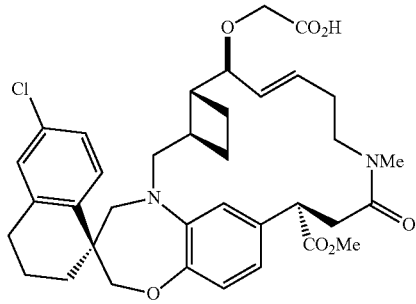

OR

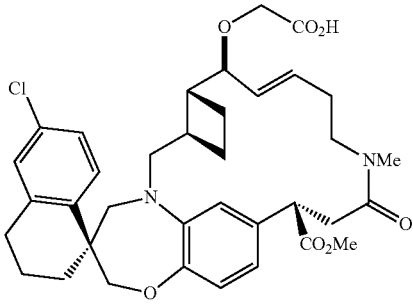

STEP 1: (((1S,3'R,6'R,7'S,8'E,15'S)-6-CHLORO-15'-(METHOXYCARBONYL)-12'-METHYL-13'-OXO-3,4-DIHYDRO-2H-SPIRO[NAPHTHA-LENE-1,22'-[20]OXA[1,12]DIAZATETRACYCLO[14.7.2.0$^{3,6}$.0$^{19,24}$]PENTACOSA[8,16,18,24]TETRAEN]-7'-YL)OXY)ACETIC ACID TERT-BUTYL ESTER AND (((1S,3'R,6'R,7'S,8'E,15'R)-6-CHLORO-15'-(METHOXYCARBONYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAEN]-7'-YL)OXY)ACETIC ACID TERT-BUTYL ESTER

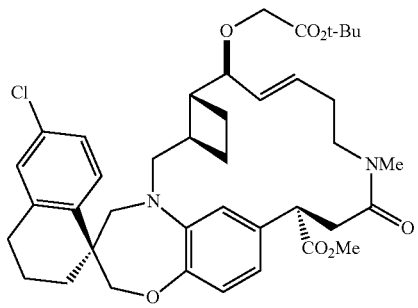

AND

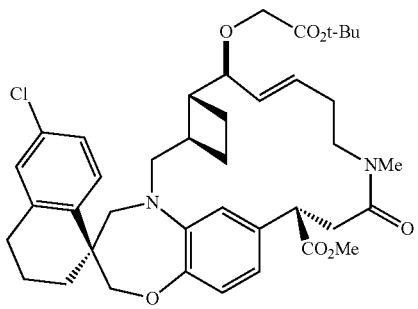

To a 2-dram vial was added methyl (1S,3'R,6'R,7'S,8'E,15'S)-6-chloro-7'-hydroxy-12'-methyl-13'-oxo-3,4-dihydro-2H-spiro[naphthalene-1,22'-[20]oxa[1,12]diazatetracyclo[14.7.2. 0$^{3,6}$.0$^{19,24}$]pentacosa[8,16,18,24]tetraene]-15'-carboxylate and methyl (1S,3'R,6'R,7'S,8'E,15'R)-6-chloro-7'-hydroxy-12'-methyl-13'-oxo-3,4-dihydro-2H-spiro[naphthalene-1,22'-[20]oxa[1,12]diazatetracyclo[14.7.2. 0$^{3,6}$.0$^{19,24}$]pentacosa[8,16,18,24]tetraene]-15'-carboxylate (Example 146, step 8 but stopped at methyl ester stage, isomers not separated) (15 mg, 0.025 mmol) and rhodium (II) acetate dimer (3.35 mg, 7.59 µmol) in methylene chloride (253 µL) at room temperature. To the vessel was added tert-butyl diazoacetate (17.49 µL, 0.126 mmol), and the mixture was stirred for 1 h before being diluted with water and methylene chloride. The aqueous layer was extracted with methylene chloride (×3). The combined organic layers were dried with sodium sulfate, filtered, and concentrated. The crude material, which corresponds to the title compounds, was used in the next step without further purification (17.9 mg, 0.025 mmol, 99% yield). LRMS: m/z (ESI, +ve ion) 707.3 (M+H)$^+$.

STEP 2: (((1S,3'R,6'R,7'S,8'E,15'S)-6-CHLORO-15'-(METHOXYCARBONYL)-12'-METHYL-13'-OXO-3,4-DIHYDRO-2H-SPIRO[NAPHTHA-LENE-1,22'-[20]OXA[1,12]DIAZATETRACYCLO[14.7.2.0$^{3,6}$.0$^{19,24}$]PENTACOSA[8,16,18,24]TETRAEN]-7'-YL)OXY)ACETIC ACID OR (((1S,3'R,6'R,7'S,8'E,15'R)-6-CHLORO-15'-(METHOXYCARBONYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAEN]-7'-YL)OXY)ACETIC ACID

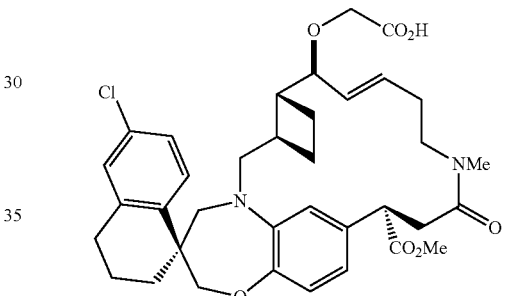

OR

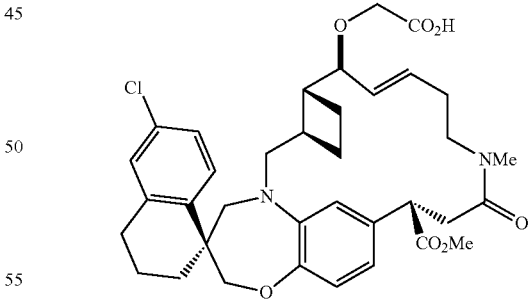

To a 2-dram vial was added (1S,3'R,6'R,7'S,8'E,15'S)-6-chloro-15'-(methoxycarbonyl)-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraen]-7'-yl)oxy)acetic acid tert-butyl ester and (1S,3'R,6'R,7'S,8'E,15'R)-6-chloro-15'-(methoxycarbonyl)-12'-methyl-13'-oxo- 3,4-dihydro-2H-spiro[naphthalene-1,22'-[20]oxa[1,12]diazatetracyclo[14.7.2.0³,⁶.0¹⁹,²⁴]pentacosa[8,16,18,24]tetraen]-7'-yl)oxy)acetic acid tert-butyl ester (Example 155, Step 1, 10 mg, 0.014 mmol) and methylene chloride (141 μL) at room temperature. To the vessel was added trifluoroacetic acid (141 L), and the mixture was stirred for 1 hour before being concentrated and purified by reverse phase HPLC (Gemini™ Prep C$_{18}$ 5 μm column; Phenomenex, Torrance, Calif.; gradient elution of 5% to 100% MeCN in water, where both solvents contain 0.1% trifluoroacetic acid, 45 minutes method) to give one of the title product as the slowest eluting isomer (2 mg, 3.07 mol, 22% yield). ¹H NMR (400 MHz, CDCl$_3$) δ 7.68 (d, J=8.4 Hz, 1H), 7.18-7.07 (m, 3H), 6.82 (d, J=8.0 Hz, 1H), 6.57 (d, J=8.2 Hz, 1H), 6.50 (s, 1H), 5.93-5.84 (m, 1H), 5.58 (dd, J=15.5 Hz, 6.1 Hz, 1H), 4.09-3.96 (m, 4H), 3.78-3.60 (m, 6H), 3.53-3.17 (m, 7H), 2.97 (s, 3H), 2.80-2.63 (m, 5H), 2.44 (br s, 3H), 2.10-1.70 (m, 6H). LRMS: m/z (ESI, +ve ion) 651.3 (M+H)⁺.

Example 156

(((1S,3'R,6'R,7'S,8'E,15'S)-6-CHLORO-15'-(METHOXYCARBONYL)-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAEN]-7'-YL)OXY)ACETIC ACID or (((1S,3'R,6'R,7'S,8'E,15'R)-6-CHLORO-15'-(METHOXYCARBONYL)-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAEN]-7'-YL)OXY)ACETIC ACID

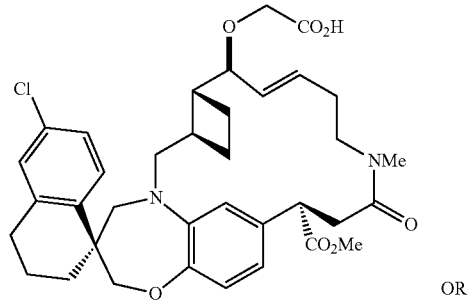

OR

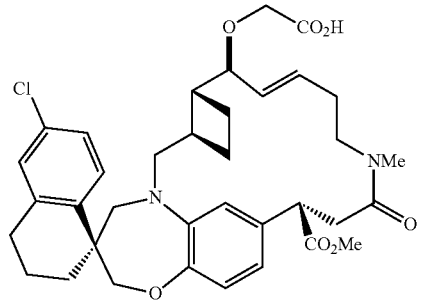

One of the title compounds (2.5 mg, 3.8 mol, 27% yield) corresponds to the fastest eluting isomer of Example 155. ¹H NMR (400 MHz, CDCl$_3$) δ ppm 7.75-7.66 (m, 1H), 7.16 (d, J=8.4 Hz, 1H), 7.09 (s, 1H), 6.83 (d, J=8.0 Hz, 1H), 6.57 (d, J=8.2 Hz, 1H), 6.49-6.35 (m, 2H), 5.72-5.64 (m, 1H), 4.10-3.99 (m, 4H), 3.79-3.60 (m, 5H), 3.30-3.10 (m, 4H), 2.98 (s, 3H), 2.80-2.50 (m, 11H), 2.08-1.71 (m, 8H), 1.49-1.43 (m, 1H). LRMS: m/z (ESI, +ve ion) 651.3 (M+H)⁺.

Example 157

(1S,3'R,6'R,7'S,8'E,15'S)-6-CHLORO-7'-HYDROXY-15'-(HYDROXYMETHYL)-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID or (1S,3'R,6'R,7'S,8'E,15'R)-6-CHLORO-7'-HYDROXY-15'-(HYDROXYMETHYL)-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID

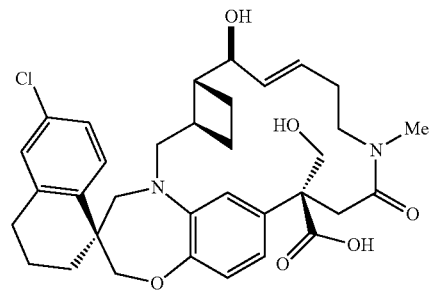

OR

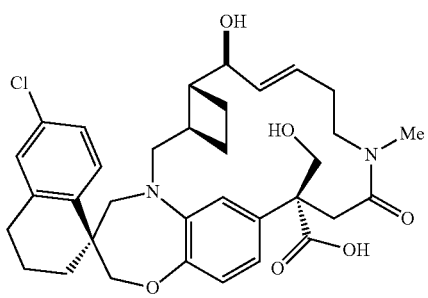

387

STEP 1. METHYL (1S,3'R,6'R,7'S,8'E,15'S)-6-CHLORO-7'-TERT-BUTYLDIMETHYLSILYLOXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE or METHYL (1S,3'R,6'R,7'S,8'E,15'R)-6-CHLORO-7'-TERT-BUTYLDIMETHYLSILYLOXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE

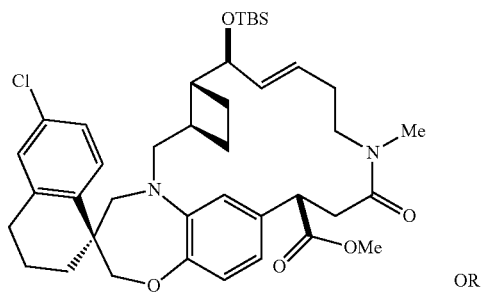

OR

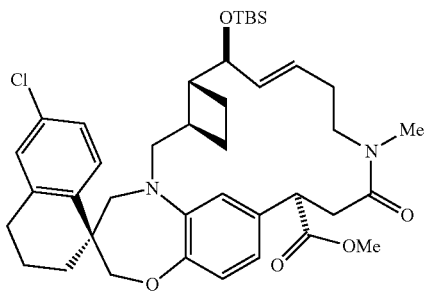

To a 2-dram vial was added methyl (1S,3'R,6'R,7'S,8'E,15'S)-6-chloro-7'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate or methyl (1S,3'R,6'R,7'S,8'E,15'R)-6-chloro-7'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 149) (20 mg, 0.034 mmol) and imidazole (6.89 mg, 0.101 mmol) in N,N-dimethylformamide (169 μL) at room temperature. To the vessel was then added tert-butylchlorodimethylsilane (5.59 mg, 0.037 mmol), and the mixture was stirred overnight. The process was quenched with saturated aqueous ammonium chloride and diluted with water. The aqueous layer was extracted with ethyl acetate (×3), and the combined organic layers were dried over sodium sulfate, filtered, and concentrated. The crude, which corresponds to one of the title compounds, was used without further purification (22.2 mg, 0.03 mmol, 30% yield). LRMS: m/z (ESI, +ve ion) 708.4 (M+H)$^+$.

388

STEP 2. (1S,3'R,6'R,7'S,8'E,15'S)-6-CHLORO-7'-TERT-BUTYLDIMETHYLSILYLOXY-15'-(HYDROXYMETHYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID or (1S,3'R,6'R,7'S,8'E,15'R)-6-CHLORO-7'-TERT-BUTYLDIMETHYLSILYLOXY-15'-(HYDROXYMETHYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

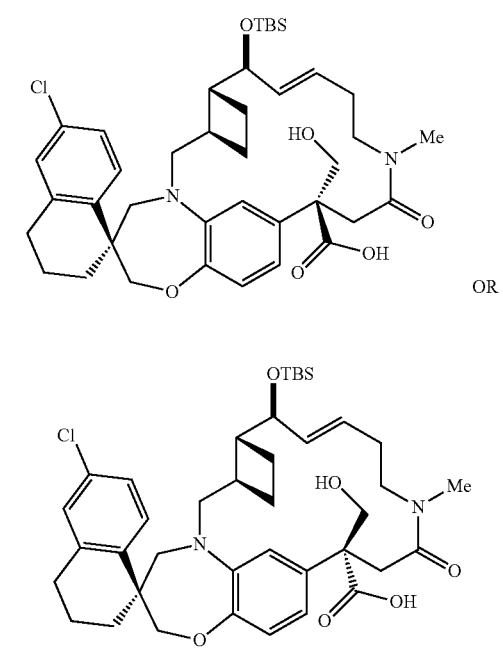

To a 2-dram vial was added methyl (1S,3'R,6'R,7'S,8'E,15'S)-6-chloro-7'-tert-butyldimethylsilyloxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate or methyl (1S,3'R,6'R,7'S,8'E,15'R)-6-chloro-7'-tert-butyldimethylsilyloxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 157, step 1) (22.2 mg, 0.031 mmol) in tetrahydrofuran (314 μl) at −78° C. To the vessel was added sodium bis(trimethylsilyl)amide (57.5 μL, 0.6 M in toluene, 0.035 mmol), and the mixture was stirred for 15 minutes at −78° C. Then paraformaldehyde (2.83 mg, 0.094 mmol) was added, and the mixture was stirred at −78° C. for 45 minutes before being warmed to 0° C. and stirred for an additional 1 hour. The process was quenched with saturated aqueous ammonium chloride and diluted with ethyl acetate. The aqueous layer was acidified to pH 2 with 1 N HCl and extracted with ethyl acetate (×2). The organic layers were dried over sodium sulfate, filtered, and concentrated. The residue was dissolved in tetrahydrofuran (0.35 mL), 2 M LiOH (0.75 mL), and MeOH (0.15 mL). The mixture was stirred for 1 hour at room temperature before being quenched with 1 M HCl, extracted with ethyl acetate (×2), dried over sodium sulfate, filtered and concentrated. The crude, which corresponds to one of the title compounds, was used as such without further purification (11.3 mg, 0.015 mmol, 50% yield). LRMS: m/z (ESI, +ve ion) 723.4 (M+H)+.

STEP 3: (1S,3'R,6'R,7'S,8'E,15'S)-6-CHLORO-7'-HYDROXY-15'-(HYDROXYMETHYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID or (1S,3'R,6'R,7'S,8'E,15'R)-6-CHLORO-7'-HYDROXY-15'-(HYDROXYMETHYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

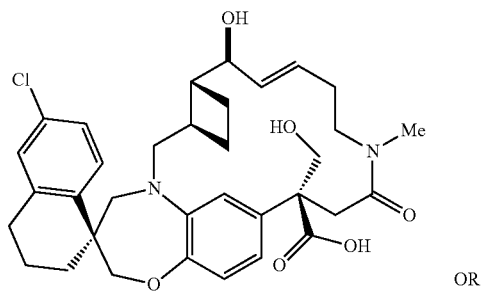

OR

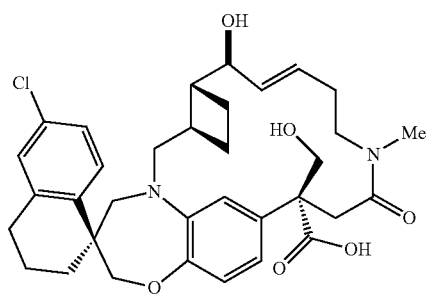

To a 2-dram vial was added (1S,3'R,6'R,7'S,8'E,15'S)-6-chloro-7'-tert-butyldimethylsilyloxy-15'-(hydroxymethyl)-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid or (1S,3'R,6'R,7'S,8'E,15'R)-6-chloro-7'-tert-butyldimethylsilyloxy-15'-(hydroxymethyl)-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid (Example 157, step 2) (15 mg, 0.021 mmol) and tetrahydrofuran (0.415 mL) at room temperature, followed by the addition of TBAF (104 µL, 1M in tetrahydrofuran, 0.104 mmol). The mixture was stirred for 2 hours then diluted with ammonium chloride and water. The aqueous layer was extracted with ethyl acetate (×1). The aqueous layer was acidified with 1 N HCl until pH 2 and extracted with ethyl acetate (×2). The combined organic layers were dried over sodium sulfate, filtered, and concentrated. The crude product was purified by reverse phase HPLC (Gemini™ Prep C$_{18}$ 5 µm column; Phenomenex, Torrance, Calif.; gradient elution of 5% to 100% MeCN in water, where both solvents contain 0.1% trifluoroacetic acid, 45 minutes method) to yield one of the title products (2.1 mg, 0.003 mmol, 17% yield). $^1$H NMR (400 MHz, CDCl$_3$) δ 7.73 (d, J=8.0 Hz, 1H), 7.17 (d, J=8.2 Hz, 1H), 7.09-7.03 (m, 2H), 6.89 (d, J=8.0 Hz, 1H), 6.68-6.52 (m, 1H), 6.35-6.20 (m, 1H), 5.93-5.84 (m, 1H), 4.32 (br s, 1H), 4.04 (s, 2H), 3.80 (s, 3H), 3.74-3.42 (m, 5H), 2.99 (s, 3H), 2.80-2.53 (m, 4H), 2.45-2.26 (m, 3H), 2.09-1.61 (m, 9H), 1.50-1.38 (m, 2H). LRMS: m/z (ESI, +ve ion) 609.3 (M+H)+.

Example 158

(3S)-3-((3S)-6'-CHLORO-5-(((1R,2R)-2-((1S)-1-HYDROXY-2-PROPEN-1-YL)CYCLOBUTYL)METHYL)-3',4,4',5-TETRAHYDRO-2'H-SPIRO[1,5-BENZOXAZEPINE-3,1'-NAPHTHALEN]-7-YL)-4-METHOXY-4-OXOBUTANOIC ACID or (3R)-3-((3S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-4-METHOXY-4-OXOBUTANOIC ACID

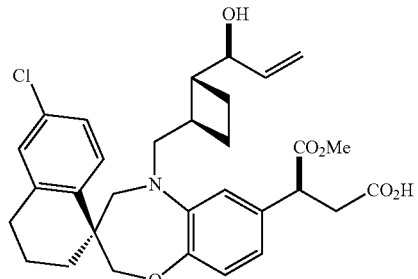

OR

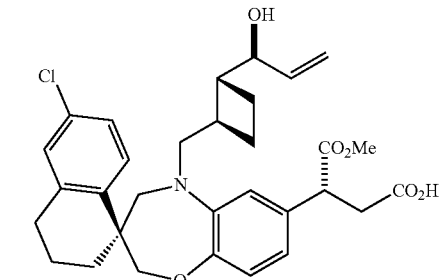

To a 50 mL flask was added (1R,2S)-2-morpholino-1-phenylpropan-1-ol (0.874 g, 3.95 mmol). The ligand was dissolved in toluene (15.6 mL), and the solution was cooled in an ice-water bath before the addition of n-butyllithium (1.580 mL, 3.95 mmol) in a dropwise fashion. To the vessel was added divinylzinc (16.46 mL, 3.95 mmol), and the solution was stirred in the ice bath for 90 minutes. To the mixture was then added 4-tert-butyl 1-methyl 2-((S)-6'-chloro-5-(((1R,2R)-2-formylcyclobutyl)methyl)-3',4,4',5-tetrahydro-2H,2'H-spiro[benzo[b][1,4]oxazepine-3,1'-naphthalen]-7-yl)succinate (Example 146, step 5) (1.0 g, 1.718 mmol) as a solution in toluene (1.0 mL) and the solution was stirred in an ice bath for an additional 30 mins. The process was quenched with 10% w/w aqueous citric acid, then warmed to room temperature. The aqueous layer was extracted with ethyl acetate (×3), and the organic layers were washed with water (×1), brine (×1), dried with magnesium sulfate, filtered, and concentrated. The residue was then dissolved in 1:1 methylene chloride:trifluoroacetic acid until 0.1 M, and the mixture was stirred at room temperature for 1 hour before being concentrated and purified by column chromatography with 0-50% ethyl acetate in hexanes over 30 min to give one of the title compounds as the first eluting isomer (901 mg, 1.5 mmol, 87% yield). $^1$H NMR (400 MHz, CDCl$_3$) δ 7.72 (d, J=8.6 Hz, 1H), 7.16 (dd, J=8.5 Hz, 2.2 Hz, 1H), 7.07 (d, J=2.2 Hz, 1H), 6.84 (d, J=8.0 Hz, 1H), 6.79 (d, J=2.0 Hz, 1H), 6.56 (dd, J=8.1 Hz, 1.9 Hz, 1H), 5.85 (ddd, J=17.2 Hz, 10.5 Hz, 5.8 Hz, 1H), 5.28 (dt, J=17.4 Hz, 1.4 Hz, 1H), 5.12 (dd, J=11.8 Hz, 1.3 Hz, 1H), 3.99-3.95 (m, 1H), 3.81 (d, J=13.1 Hz, 1H), 3.74-3.68 (m, 4H), 3.24-3.15 (m, 2H), 3.06 (dd, J=15.1 Hz, 9.6 Hz, 1H), 2.77-2.67 (m, 3H), 2.46-2.40 (m, 1H), 2.15-1.75 (m, 7H), 1.69-1.57 (m, 2H), 1.46-1.35 (m, 2H), 1.32-1.24 (m, 1H), 0.80-0.60 (m, 2H), m/z (ESI, +ve ion) 555.1 (M+H)$^+$.

Example 159

(3R)-3-((3S)-6'-CHLORO-5-(((1R,2R)-2-((1S)-1-HYDROXY-2-PROPEN-1-YL)CYCLOBUTYL)METHYL)-3',4,4',5-TETRAHYDRO-2'H-SPIRO[1,5-BENZOXAZEPINE-3,1'-NAPHTHALEN]-7-YL)-4-METHOXY-4-OXOBUTANOIC ACID or (3S)-3-((3S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-4-METHOXY-4-OXOBUTANOIC ACID

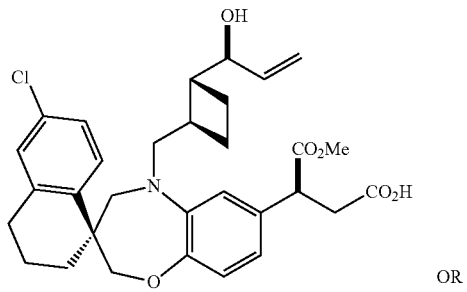

OR

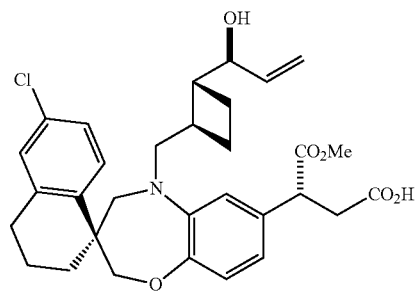

One of the title compounds corresponds to the second eluting isomer from Example 158. $^1$H NMR (400 MHz, CDCl$_3$) δ 7.70 (d, J=8.4 Hz, 1H), 7.16 (dd, J=8.6 Hz, 2.3 Hz, 1H), 7.08 (d, J=2.2 Hz, 1H), 6.85 (d, J=8.0 Hz, 1H), 6.79 (d, J=2.0 Hz, 1H), 6.57 (dd, J=8.1 Hz, 1.9 Hz, 1H), 5.82 (ddd, J=17.0 Hz, 10.7 Hz, 6.2 Hz, 1H), 5.28-5.22 (m, 1H), 5.11 (d, J=10.6 Hz, 1H), 4.07-3.99 (m, 4H), 3.77-3.67 (m, 4H), 3.26-3.18 (m, 2H), 3.11 (dd, J=14.8 Hz, 9.3 Hz, 1H), 2.80-2.71 (m, 3H), 2.58-2.51 (m, 1H), 2.11-2.00 (m, 3H), 1.97-1.78 (m, 3H), 1.69-1.58 (m, 2H), 1.52-1.41 (m, 1H), 1.33-1.24 (m, 1H), 0.91-0.83 (m, 1H), m/z (ESI, +ve ion) 555.1 (M+H)$^+$.

Example 160

(2S)-2-((3S)-6'-CHLORO-5-(((1R,2R)-2-((1S)-1-HYDROXY-2-PROPEN-1-YL)CYCLOBUTYL)METHYL)-3',4,4',5-TETRAHYDRO-2'H-SPIRO[1,5-BENZOXAZEPINE-3,1'-NAPHTHALEN]-7-YL)-4-(DIMETHYLAMINO)-4-OXOBUTANOIC ACID or (R)-2-((S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-4-(DIMETHYLAMINO)-4-OXOBUTANOIC ACID

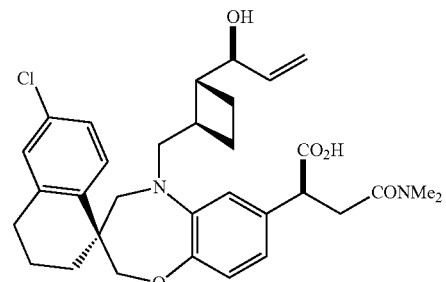

OR

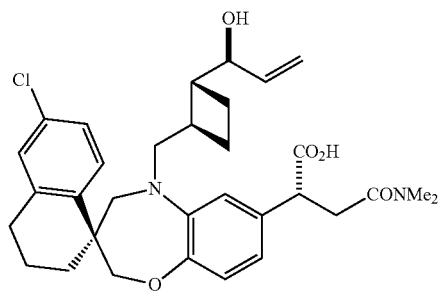

To a 5-mL round-bottomed flask was added 3-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-4-methoxy-4-oxobutanoic acid (mixture of isomers, Example 158+159) (20 mg, 0.036 mmol) and dimethylamine, 2.0 M solution in tetrahydrofuran (54.1 μL, 0.108 mmol) in N,N-dimethylformamide (361 μl) at room temperature. To the vessel was added diisopropylethylamine (31.4 μL, 0.180 mmol) and HATU (27.4 mg, 0.072 mmol), and the mixture was stirred for 30 minutes before being diluted with water and ethyl acetate. The aqueous layer was extracted with ethyl acetate (×3), dried with sodium sulfate, filtered, and concentrated. The residue was dissolved in 1 mL 3:1 tetrahydrofuran:MeOH, and 100 mg LiOH monohydrate was added. The mixture was stirred at 50° C. for 1 hour then cooled to room temperature. The contents of the flask were purified by reverse phase HPLC (Gemini™ Prep C$_{18}$ 5 µm column; Phenomenex, Torrance, Calif.; gradient elution of 5% to 100% MeCN in water, where both solvents contain 0.1% trifluoroacetic acid, 45 minutes method) to give one of the title compounds as the first eluting isomer (3.0 mg, 15% yield). $^1$H NMR (400 MHz, CDCl$_3$) δ 7.74-7.70 (m, 1H), 7.16 (d, J=8.6 Hz, 1H), 7.08 (s, 1H), 6.92-6.83 (m, 2H), 6.63-6.56 (m, 1H), 5.87-5.76 (m, 1H), 5.29-5.20 (m, 1H), 5.08 (d, J=10.4 Hz, 1H), 4.17-4.11 (m, 1H), 4.06-4.00 (m, 3H), 3.89-3.68 (m, 2H), 3.28-2.97 (m, 5H), 2.94 (s, 3H), 2.81-2.47 (m, 4H), 2.09-1.98 (m, 3H), 1.97-1.77 (m, 3H), 1.70-1.34 (m, 4H), 1.29-1.20 (m, 1H). LRMS: m/z (ESI, +ve ion) 567.2 (M+H)$^+$.

Example 161

(2S)-2-((3S)-6'-CHLORO-5-(((1R,2R)-2-((1S)-1-HYDROXY-2-PROPEN-1-YL)CYCLOBUTYL) METHYL)-3',4,4',5-TETRAHYDRO-2'H-SPIRO[1, 5-BENZOXAZEPINE-3,1'-NAPHTHALEN]-7-YL)-4-(DIMETHYLAMINO)-4-OXOBUTANOIC ACID or (R)-2-((S)-6'-CHLORO-5-(((1R,2R)-2-((S)-1-HYDROXYALLYL)CYCLOBUTYL) METHYL)-3',4,4',5-TETRAHYDRO-2H,2'H-SPIRO[BENZO[B][1,4]OXAZEPINE-3,1'-NAPHTHALEN]-7-YL)-4-(DIMETHYLAMINO)-4-OXOBUTANOIC ACID

NMR (400 MHz, CDCl$_3$) δ 7.72 (t, J=8.4 Hz, 1H), 7.16 (d, J=8.4 Hz, 1H), 7.08 (s, 1H), 6.90 (s, 1H), 6.85 (dd, J=7.9 Hz, 6.7 Hz, 1H), 6.62-6.56 (m, 1H), 5.88-5.76 (m, 1H), 5.24 (dd, J=17.1 Hz, 12.2 Hz, 1H), 5.08 (d, J=10.6 Hz, 1H), 4.17-4.10 (m, 1H), 4.06-3.99 (m, 3H), 3.88-3.71 (m, 2H), 3.29-2.98 (m, 6H), 2.94 (d, J=6.1 Hz, 3H), 2.80-2.73 (m, 2H), 2.65 (dd, J=16.5 Hz, 4.4 Hz, 1H), 2.59-2.47 (m, 1H), 2.08-1.76 (m, 7H), 1.70-1.36 (m, 4H). LRMS: m/z (ESI, +ve ion) 567.2 (M+H)$^+$.

Examples 162a and 162b (1S,3'R,6'R,7'S,8'E,15'R)-15'-(2-TERT-BUTOXY-2-OXOETHYL)-6-CHLORO-7'-HYDROXY-12'-METHYL-13'-OXO-3,4-DIHYDRO-2H-SPIRO [NAPHTHALENE-1,22'-[20]OXA[1,12] DIAZATETRACYCLO[14.7.2.0$^{3,6}$.0$^{19,24}$] PENTACOSA[8,16,18,24]TETRAENE]-15'-CARBOXYLIC ACID or (1S,3'R,6'R,7'S,8'E,15'S)-15'-(2-TERT-BUTOXY-2-OXOETHYL)-6-CHLORO-7'-HYDROXY-12'-METHYL-13'-OXO-3,4-DIHYDRO-2H-SPIRO[NAPHTHALENE-1,22'-[20]OXA[1,12]DIAZATETRACYCLO[14.7.2. 0$^{3,6}$.0$^{19,24}$]PENTACOSA[8,16,18,24]TETRAENE]-15'-CARBOXYLIC ACID

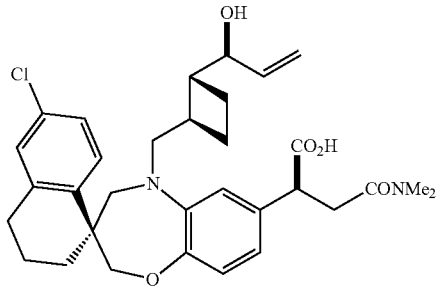

OR

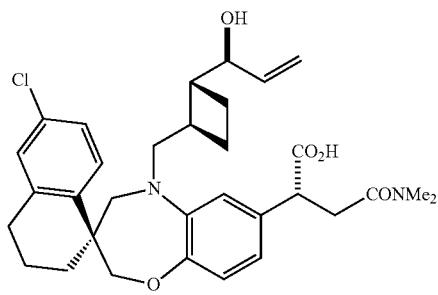

One of the title compound (4.0 mg, 20% yield) corresponds to the second eluting isomer from Example 160. $^1$H

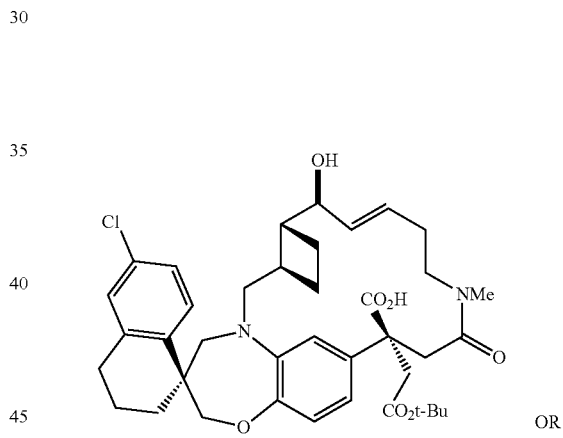

OR

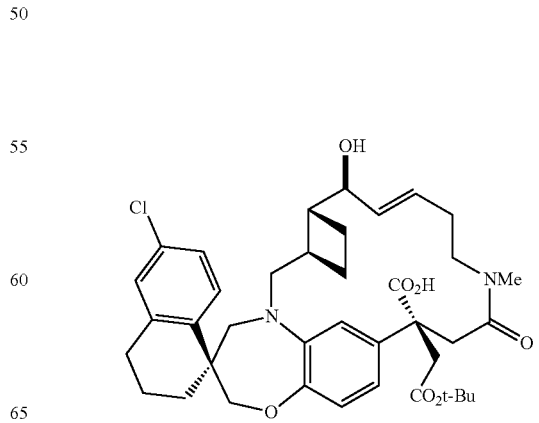

STEP 1. (1S,3'R,6'R,7'S,8'E,15'S)-6-CHLORO-7'-TERT-BUTYLDIMETHYLSILYLOXY-15'-(HYDROXYMETHYL)-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID METHYL ESTER and (1S,3'R,6'R,7'S,8'E,15'R)-6-CHLORO-7'-TERT-BUTYLDIMETHYLSILYLOXY-15'-(HYDROXYMETHYL)-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID METHYL ESTER

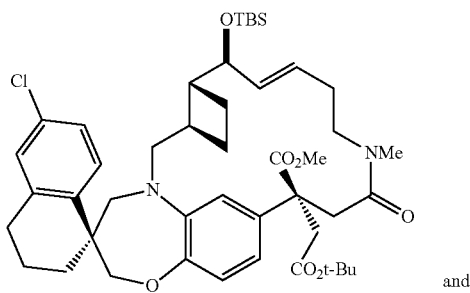

and

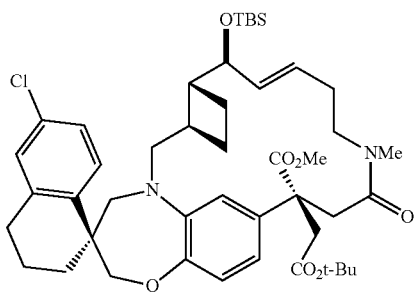

To a 2-dram vial was added (1S,3'R,6'R,7'S,8'E,15'S)-6-chloro-7'-tert-butyldimethylsilyloxy-12'-methyl-13'-oxo-3,4-dihydro-2H-spiro[naphthalene-1,22'-[20]oxa[1,12]diazatetracyclo[14.7.2.0³,⁶.0¹⁹,²⁴]pentacosa[8,16,18,24]tetraene]-15'-carboxylate and (1S,3'R,6'R,7'S,8'E,15'R)-6-chloro-7'-tert-butyldimethylsilyloxy-12'-methyl-13'-oxo-3,4-dihydro-2H-spiro[naphthalene-1,22'-[20]oxa[1,12]diazatetracyclo[14.7.2.0³,⁶.0¹⁹,²⁴]pentacosa[8,16,18,24]tetraene]-15'-carboxylate (mixture of isomers, obtained via a procedure similar to that used for Example 157, step 1) (65 mg, 0.092 mmol) and tetrahydrofuran (459 µL) at −78° C., to which potassium tert-butoxide, 1.0 M solution in tetrahydrofuran (184 µL, 0.184 mmol) was added in a dropwise fashion. To the vessel was immediately added bromoacetic acid tert-butyl ester (44.5 µL, 0.276 mmol) and the mixture was stirred at −78° C. for 90 minutes. The vessel was warmed to 0° C. for 15 minutes, and the mixture was quenched with saturated aqueous ammonium chloride. The aqueous layer was extracted with ethyl acetate (×2), and the combined organic layers were dried with sodium sulfate, filtered, and concentrated. The crude material, which corresponds to the title compounds, was used as such in the next step (40 mg, 0.045 mmol, 50% yield). LRMS: m/z (ESI, +ve ion) 821.4 (M+H)⁺.

STEP 2. (1S,3'R,6'R,7'S,8'E,15'R)-15'-(2-TERT-BUTOXY-2-OXOETHYL)-6-CHLORO-7'-HYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID or (1S,3'R,6'R,7'S,8'E,15'S)-15'-(2-TERT-BUTOXY-2-OXOETHYL)-6-CHLORO-7'-HYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXYLIC ACID

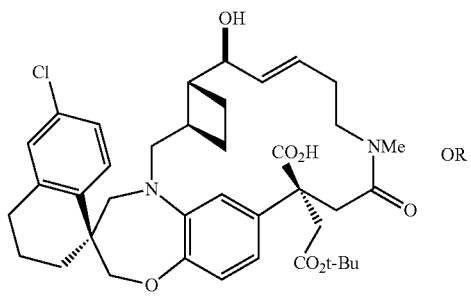

OR

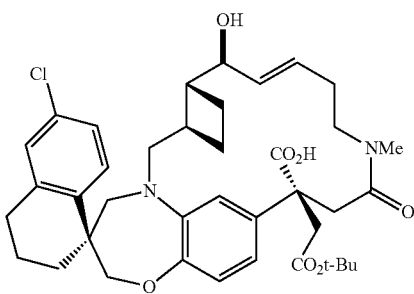

To a 2-dram vial was added (1S,3'R,6'R,7'S,8'E,15'S)-6-chloro-7'-tert-butyldimethylsilyloxy-15'-(hydroxymethyl)-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid methyl ester and (1S,3'R,6'R,7'S,8'E,15'R)-6-chloro-7'-tert-butyldimethylsilyloxy-15'-(hydroxymethyl)-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid methyl ester (Example 162, Step 1, 20 mg, 0.024 mmol), lithium hydroxide (58.3 mg, 2.434 mmol), MeOH (60.9 µL) and in tetrahydrofuran (183 µL). The mixture was stirred at 80° C. overnight before being cooled to room temperature and diluted with ethyl acetate and water. The aqueous layer was acidified to pH 2 with 1 N HCl and extracted with ethyl acetate (×3). The combined organics were dried over sodium sulfate, filtered, and concentrated. The residue was dissolved in 0.2 mL tetrahydrofuran, and 0.2 mL of 1 M TBAF in tetrahydrofuran was added in a dropwise fashion. The mixture was stirred at room temperature for 1 hour then quenched with saturated aqueous ammonium chloride and diluted with ethyl acetate. The aqueous layer was acidified to pH 2 with 1 N HCl and extracted with ethyl acetate (×3). The combined organic layers were dried with sodium sulfate, filtered, and concentrated. The product was purified by reverse phase HPLC (Gemini™ Prep C$_{18}$ 5 µm column; Phenomenex, Torrance, Calif.; gradient elution of 5% to 100% MeCN in water, where both solvents contain 0.1% trifluoroacetic acid, 45 minutes method) to give one of the title compounds as the first eluting isomer 162b (1.9 mg, 11% yield). $^1$H NMR (400 MHz, CDCl$_3$) δ 7.69 (d, J=9.2 Hz, 1H), 7.16 (d, J=9.0 Hz, 1H), 7.08 (s, 1H), 6.81 (d, J=8.4 Hz, 1H), 6.71-6.60 (m, 2H), 5.73 (d, J=14.3 Hz, 1H), 5.46-5.36 (m, 1H), 4.10-3.94 (m, 3H), 3.75-3.40 (m, 3H), 3.32-3.15 (m, 3H), 2.96 (s, 3H), 2.78 (s, 3H), 2.56 (s, 3H), 2.36-1.60 (m, 10H), 1.51-1.37 (m, 9H). LRMS: m/z (ESI, +ve ion) 693.3 (M+H)$^+$.

The other title compound 162a (2.0 mg, 0.003 mmol, 12% yield) corresponds to the second eluting isomer. $^1$H NMR (400 MHz, CDCl$_3$) δ 7.76 (d, J=8.2 Hz, 1H), 7.17 (d, J=8.6 Hz, 1H), 7.08 (s, 1H), 6.81 (d, J=8.1 Hz, 1H), 6.52 (d, J=8.1 Hz 2H), 6.39 (s, 1H), 6.17-6.02 (m, 1H), 5.73 (d, J=15.8 Hz, 1H), 4.15-3.94 (m, 3H), 3.76-3.41 (m, 5H), 3.32-3.05 (m, 4H), 2.95 (s, 3H), 2.82-2.74 (m, 3H), 2.45 (s, 3H), 2.08-1.67 (m, 9H), 1.48-1.30 (m, 10H). LRMS: m/z (ESI, +ve ion) 693.3 (M+H)$^+$.

Example 163

(1S,3'R,6'R,7'S,8'E,10'S,15'S)-6-CHLORO-7',15'-DIHYDROXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID or (1S,3'R,6'R,7'S,8'E,10'R,15'S)-6-CHLORO-7',15'-DIHYDROXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID or (1S,3'R,6'R,7'S,8'E,10'S,15'R)-6-CHLORO-7',15'-DIHYDROXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID or (1S,3'R,6'R,7'S,8'E,10'R,15'R)-6-CHLORO-7',15'-DIHYDROXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

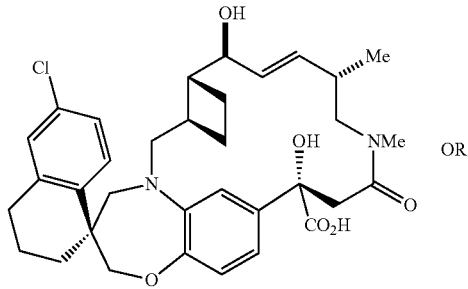

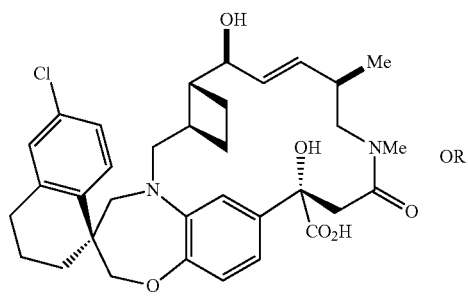

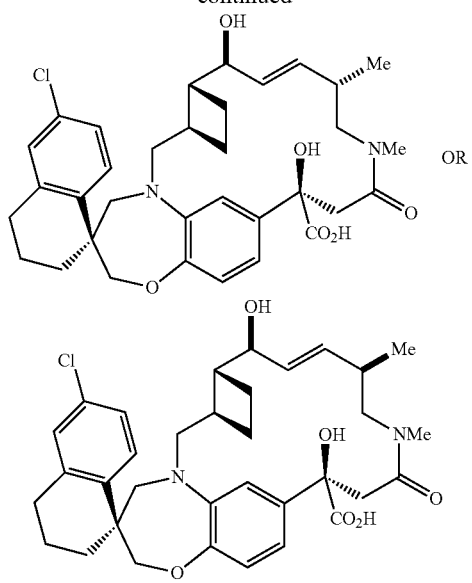

STEP 1. (S)-METHYL 2-((S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXY-4-(METHYL((S)-2-METHYLBUT-3-EN-1-YL)AMINO)-4-OXOBUTANOATE and/or (R)-METHYL 2-((S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXY-4-(METHYL((S)-2-METHYLBUT-3-EN-1-YL)AMINO)-4-OXOBUTANOATE and/or (R)-METHYL 2-((S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXY-4-(METHYL((S)-2-METHYLBUT-3-EN-1-YL)AMINO)-4-OXOBUTANOATE and/or (R)-METHYL 2-((S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALEN]-7-YL)-2-HYDROXY-4-(METHYL((R)-2-METHYLBUT-3-EN-1-YL)AMINO)-4-OXOBUTANOATE

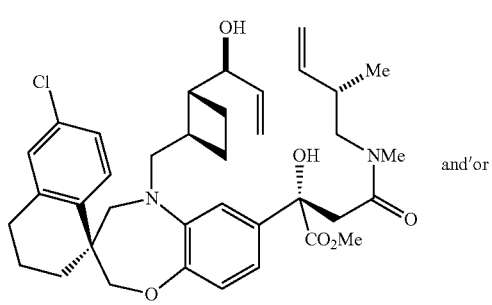

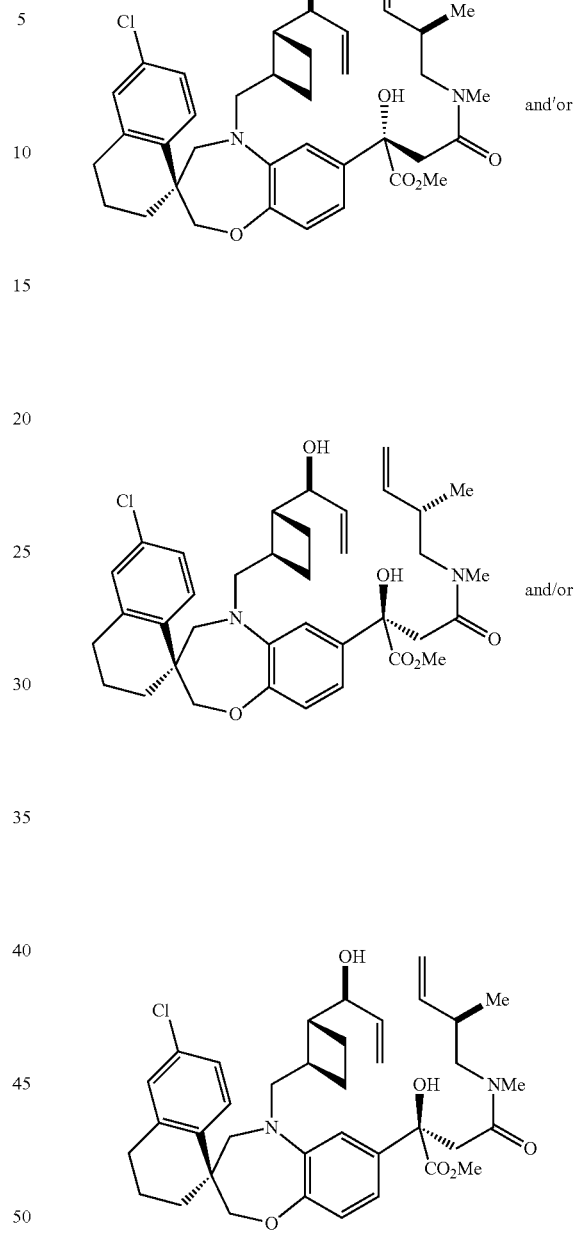

The title compounds were synthesized from 3-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-3-hydroxy-4-methoxy-4-oxobutanoic acid (Example 1 step 5, 250 mg, 0.439 mmol) and N,2-dimethylbut-3-en-1-amine hydrochloride (178 mg, 1.316 mmol) using a procedure similar to that used for the synthesis of Example 1, step 6. The residue was purified by column chromatography eluting with a gradient of 0% to 100% ethyl acetate over 25 min (286 mg, 0.35 mmol, 80% yield) to give some of the title products. LRMS: m/z (ESI, +ve ion) 651.2 (M+H)$^+$.

STEP 2. (1S,3'R,6'R,7'S,8'E,10'S,15'S)-6-CHLORO-7',15'-DIHYDROXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID METHYL ESTER and/or (1S,3'R,6'R,7'S,8'E,10'R,15'S)-6-CHLORO-7',15'-DIHYDROXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID METHYL ESTER and/or (1S,3'R,6'R,7'S,8'E,10'S,15'R)-6-CHLORO-7',15'-DIHYDROXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID METHYL ESTER and/or (1S,3'R,6'R,7'S,8'E,10'R,15'R)-6-CHLORO-7',15'-DIHYDROXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID METHYL ESTER

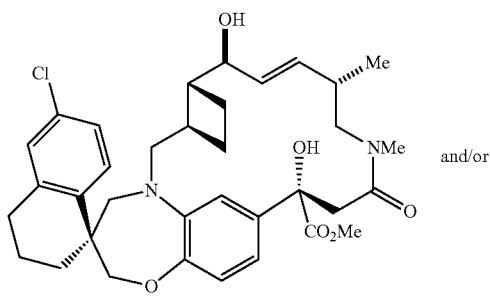

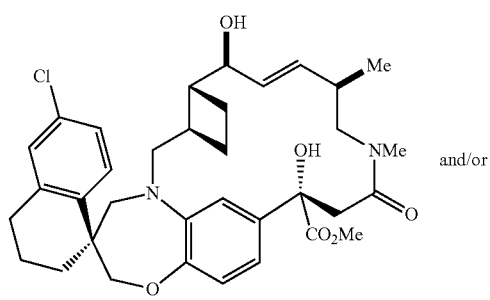

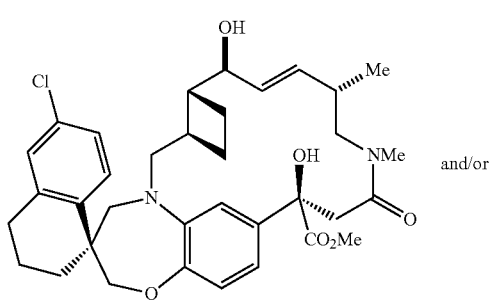

-continued

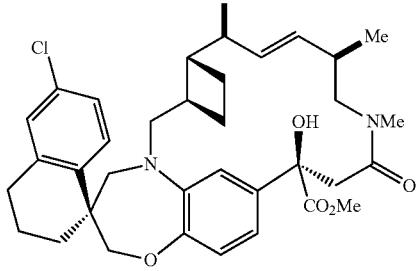

The title compounds were synthesized from the mixture of products resulting from Example 163, step 1 (0.165 g, 0.253 mmol) through a procedure similar to that used for the synthesis of Example 1, step 7. The contents of the flask were concentrated and purified by column chromatography 0-40% ethyl acetate in hexanes. All diastereomers elute in one fraction. The residue was purified a second time by column chromatography with 0-25% acetone in hexanes over 20 min to give some of the title products (55.0 mg, 0.09 mmol, 35% yield). LRMS: m/z (ESI, +ve ion) 623.3 (M+H)$^+$.

STEP 3. (1S,3'R,6'R,7'S,8'E,10'S,15'S)-6-CHLORO-7',15'-DIHYDROXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID or (1S,3'R,6'R,7'S,8'E,10'R,15'S)-6-CHLORO-7',15'-DIHYDROXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID or (1S,3'R,6'R,7'S,8'E,10'S,15'R)-6-CHLORO-7',15'-DIHYDROXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID or (1S,3'R,6'R,7'S,8'E,10'R,15'R)-6-CHLORO-7',15'-DIHYDROXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

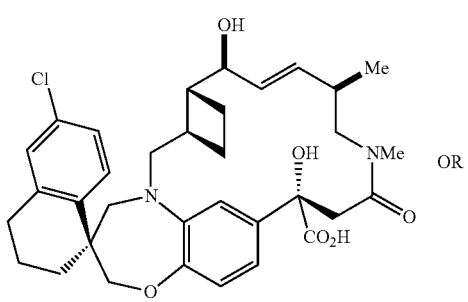

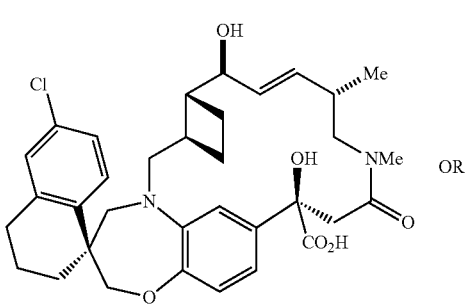

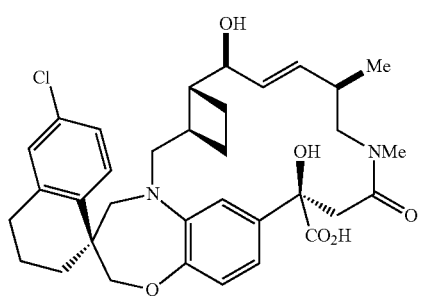

One of the title compounds was synthesized from the mixture of products obtained in Example 163, Step 2 through a procedure similar to that used for the synthesis of Example 4. The residue was purified by column chromatography with a gradient of 0% to 10% MeOH in methylene chloride over 15 min to give one of the title products as the second eluting isomer (5.8 mg, 59% yield). $^1$H NMR (400 MHz, CDCl$_3$) δ ppm 7.74 (d, J=8.6 Hz, 1H), 7.16 (dd, J=8.5 Hz, 2.2 Hz, 1H), 7.10-7.01 (m, 2H), 6.88 (d, J=8.4 Hz, 1H), 6.66 (br s, 1H), 6.54 (d, J=15.8 Hz, 1H), 5.85 (dd, J=14.4 Hz, 10.1 Hz, 1H), 4.52-4.48 (m, 1H), 4.06-3.97 (m, 2H), 3.77-3.67 (m, 2H), 3.56-3.47 (m, 1H), 3.36-3.27 (m, 2H), 3.11-2.93 (m, 5H), 2.81-2.56 (m, 5H), 2.49-2.27 (m, 2H), 2.18 (s, 1H), 2.10-1.70 (m, 6H), 1.13 (d, J=6.7 Hz, 3H). LRMS: m/z (ESI, +ve ion 609.3 (M+H)$^+$.

Example 164

(1S,3'R,6'R,7'S,8'E,10'S,15'S)-6-CHLORO-15'-HYDROXY-7'-METHOXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID or (1S,3'R,6'R,7'S,8'E,10'R,15'S)-6-CHLORO-15'-HYDROXY-7'-METHOXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID or (1S,3'R,6'R,7'S,8'E,10'S,15'R)-6-CHLORO-15'-HYDROXY-7'-METHOXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID or (1S,3'R,6'R,7'S,8'E,10'R,15'R)-6-CHLORO-15'-HYDROXY-7'-METHOXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

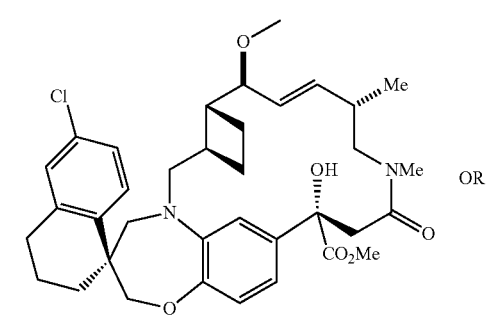

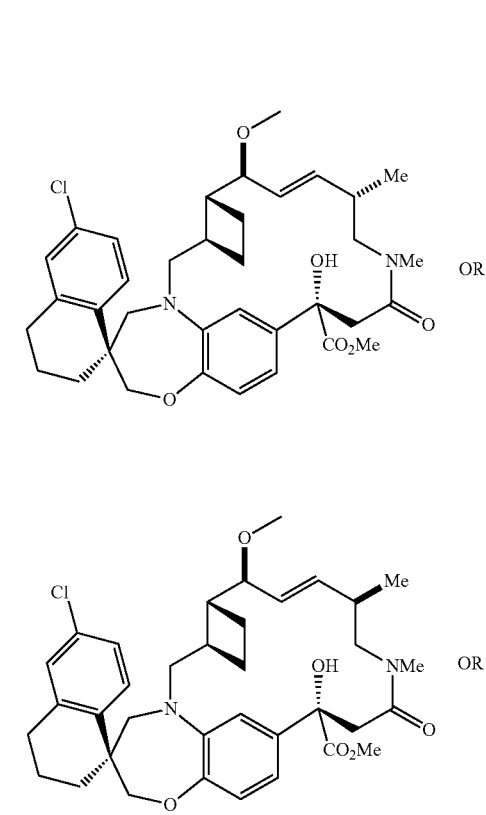

405
-continued

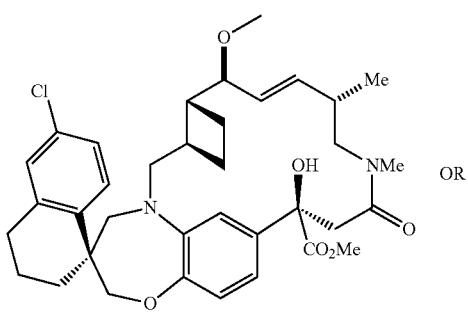

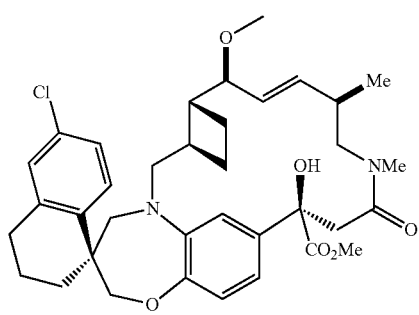

To a 2-dram vial was added the mixture of products isolated in Example 163, step 2 (20 mg, 0.032 mmol) in tetrahydrofuran (292 μl) at room temperature. To the vessel was added sodium bis(trimethylsilyl)amide, 1.0 m in tetrahydrofuran (128 μl, 0.128 mmol) then immediately iodomethane (19.94 μl, 0.321 mmol) was added. The mixture was stirred for 30 min then quenched with ammonium chloride. The contents of the vessel were diluted with methylene chloride and water, and the aqueous layer was extracted with ethyl acetate (×3). The combined organic layers were dried with sodium sulfate, filtered, and concentrated. The residue was dissolved in 0.2 mL tetrahydrofuran, 0.1 mL MeOH, and 0.2 mL 2N LiOH(aq). The mixture was stirred at room temperature for 30 min. then acidified with 1N HCl until pH=2. The mixture was extracted with ethyl acetate (×2), and the combined organic layers were dried with sodium sulfate, filtered, and concentrated. The residue was purified by column chromatography 0-10% MeOH in methylene chloride over 20 min to give one of the title product as the first eluting isomer (7.5 mg, 0.012 mmol, 38% yield). $^1$H NMR (400 MHz, CDCl$_3$) δ 7.66 (d, J=8.5 Hz, 1H), 7.09 (dd, J=8.5 Hz, 2.3 Hz, 1H), 7.00 (d, J=2.1 Hz, 1H), 6.96 (dd, J=8.3 Hz, 1.9 Hz, 1H), 6.81 (d, J=8.3 Hz, 1H), 6.55 (s, 1H), 6.46 (d, J=14.9 Hz, 1H), 5.53 (dd, J=15.9 Hz, 9.0 Hz, 1H), 3.89-3.97 (m, 2H), 3.81 (dd, J=9.3 Hz, 2.3 Hz, 1H), 3.80-3.64 (m, 2H), 3.46 (d, J=16.8 Hz, 1H), 3.29-3.20 (m, 2H), 3.14 (s, 3H), 3.02-2.87 (m, 5H), 2.72-2.66 (m, 3H), 2.51 (d, J=16.8 Hz, 1H), 2.43-2.27 (m, 2H), 2.10 (s, 1H), 1.98-1.86 (m, 4H), 1.67-1.63 (m, 1H), 1.33-1.26 (m, 2H), 1.07 (d, J=6.6 Hz, 3H). LRMS. m/z (ESI, +ve ion 623.2 (M+H)$^+$.

Example 165

(1S,3'R,6'R,7'S,8'E,10'S,15'S)-6-CHLORO-7',15'-DIHYDROXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID or (1S,3'R,6'R,7'S,8'E,10'R,15'S)-6-CHLORO-7',15'-DIHYDROXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID or (1S,3'R,6'R,7'S,8'E,10'S,15'R)-6-CHLORO-7',15'-DIHYDROXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID or (1S,3'R,6'R,7'S,8'E,10'R,15'R)-6-CHLORO-7',15'-DIHYDROXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

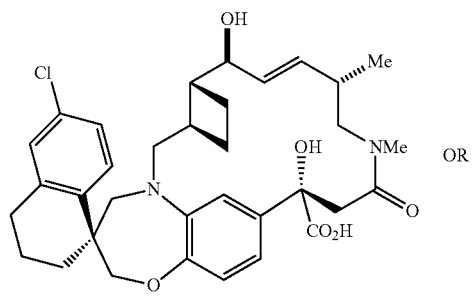

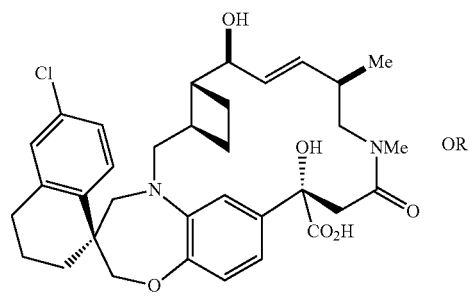

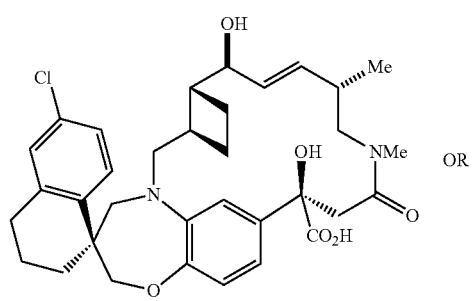

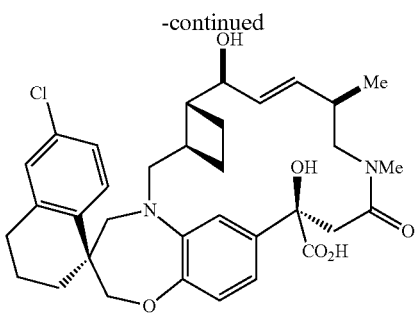

One of the title compounds (7.5 mg, 77% yield) correspond to the first eluting isomer isolated in Example 163, Step 3. $^1$H NMR (400 MHz, CDCl$_3$) δ 7.66 (d, J=8.6 Hz, 1H), 7.08 (dd, J=8.5 Hz, 2.2 Hz, 1H), 7.02-6.94 (m, 2H), 6.80 (d, J=8.4 Hz, 1H), 6.58 (br s, 1H), 6.46 (d, J=15.8 Hz, 1H), 5.77 (dd, J=14.4 Hz, 10.1 Hz, 1H), 4.44-4.40 (m, 1H), 3.98-3.90 (m, 2H), 3.69-3.59 (m, 2H), 3.48-3.39 (m, 1H), 3.28-3.19 (m, 2H), 3.03-2.88 (m, 5H), 2.73-2.45 (m, 5H), 2.36-2.20 (m, 3H), 2.10 (s, 1H), 2.01-1.75 (m, 4H), 1.68-1.63 (m, 1H), 1.35-1.26 (m, 2H), 1.05 (d, J=6.7 Hz, 3H). LRMS: m/z (ESI, +ve ion) 609.3 (M+H)$^+$.

Example 166

(1S,3'R,6'R,7'S,8'E,10'S,15'S)-6-CHLORO-15'-HYDROXY-7'-METHOXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID or (1S,3'R,6'R,7'S,8'E,10'R,15'S)-6-CHLORO-15'-HYDROXY-7'-METHOXY-10',12'-DIMETHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

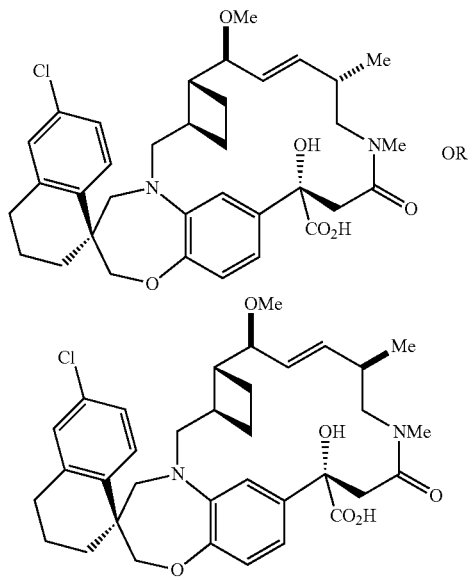

To a 2-dram vial was added (1S,3'R,6'R,7'S,8'E,10'S,15'S)-6-chloro-7',15'-dihydroxy-10',12'-dimethyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid (Example 163, step 2) (20 mg, 0.032 mmol) in tetrahydrofuran (292 µl) at room temperature. To the vessel was added sodium bis(trimethylsilyl)amide, 1.0 m in tetrahydrofuran (128 µl, 0.128 mmol) then immediately iodomethane (19.94 µl, 0.321 mmol) was added. The mixture was stirred for 30 min then quenched with ammonium chloride. The contents of the vessel were diluted with methylene chloride and water, and the aqueous layer was extracted with ethyl acetate (×3). The combined organic layers were dried with sodium sulfate, filtered, and concentrated. The residue was dissolved in 0.2 mL tetrahydrofuran, 0.1 mL MeOH, and 0.2 mL 2N LiOH(aq). The mixture was stirred at room temperature for 30 min. then acidified with 1N HCl until pH=2. The mixture was extracted with ethyl acetate (×2), and the combined organic layers were dried with sodium sulfate, filtered, and concentrated. The residue was purified by column chromatography 0-10% MeOH in methylene chloride over 20 min to give one of the title products, eluting first from the column (3 mg, 15% yield). $^1$H NMR (400 MHz, CDCl$_3$) δ ppm 7.66 (d, J=8.4 Hz, 1H), 7.09 (dd, J=8.4 Hz, 2.3 Hz, 1H), 7.00-6.75 (m, 5H), 5.51 (dd, J=15.8 Hz, 9.0 Hz, 1H), 3.98-3.89 (m, 2H), 3.80 (dd, J=9.3 Hz, 2.1 Hz, 1H), 3.81-3.64 (m, 2H), 3.42 (d, J=16.6 Hz, 1H), 3.30-3.20 (m, 2H), 3.10 (s, 3H), 3.02-2.87 (m, 5H), 2.73-2.67 (m, 3H), 2.50 (d, J=16.7 Hz, 1H), 2.47-2.25 (m, 2H), 2.10 (s, 1H), 2.00-1.85 (m, 4H), 1.65-1.32 (m, 3H), 1.00 (d, J=6.6 Hz, 3H). LRMS: m/z (ESI, +ve ion) 623.3 (M+H)$^+$.

Example 167

METHYL (1S,3'R,6'R,7'R,8'E,15'S)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE

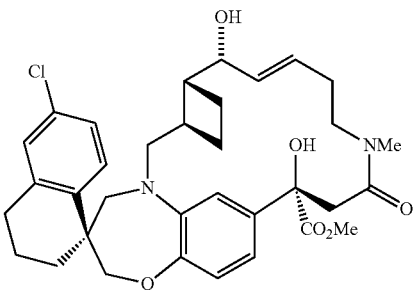 [SMILES: COC(=O)[C@]1(O)CC(=O)N(C)CC/C=C/[C@@H](O)[C@@H]2CC[C@H]2CN2C[C@@]3(CCCc4cc(Cl)ccc43)COc3ccc1cc32]

STEP 1. METHYL (1S,3'R,6'R,7'R,8'E,15'S)-6-CHLORO-7'-KETO-,15'-HYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE

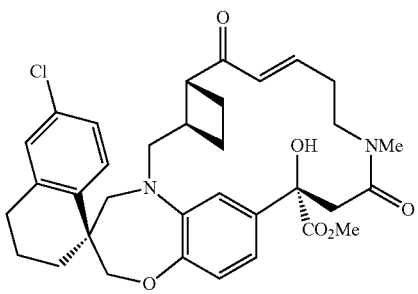 [SMILES: COC(=O)[C@]1(O)CC(=O)N(C)CC/C=C/C(=O)[C@@H]2CC[C@H]2CN2C[C@@]3(CCCc4cc(Cl)ccc43)COc3ccc1cc32]

To a 25-mL round-bottomed flask was added methyl (1S,3'R,6'R,7'S,8'E,15'S)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (0.2 g, 0.328 mmol) in dichloromethane (2.53 mL) at 0 deg C. To the vessel was added Dess-Martin periodinane (0.167 g, 0.394 mmol) in three portions over 5 minutes. The mixture was stirred at 0 deg C. for 30 min then warmed to rt and stirred for an additional 2 hours. The contents of the flask were loaded directly onto a silica gel column eluting with 0-100% ethyl acetate over 35 minutes to yield the title product (0.19 g, 0.32 mmol, 98% yield). LRMS: m/z (ESI, +ve ion) 607.1 (M+H)$^+$.

STEP 2. METHYL (1S,3'R,6'R,7'R,8'E,15'S)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE

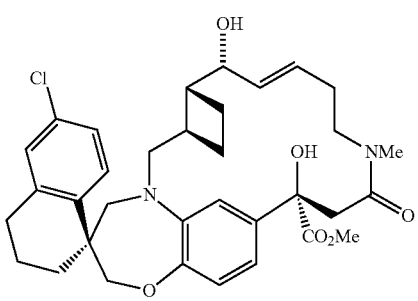 [SMILES: COC(=O)[C@]1(O)CC(=O)N(C)CC/C=C/[C@@H](O)[C@@H]2CC[C@H]2CN2C[C@@]3(CCCc4cc(Cl)ccc43)COc3ccc1cc32]

To a 2-dram vial was added methyl (1S,3'R,6'R,7'R,8'E,15'S)-6-chloro-7'-keto-,15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 167, step 1) (20 mg, 0.033 mmol) and sodium borohydride (2.493 mg, 0.066 mmol) in tetrahydrofuran (165 µL) at room temperature. The mixture was stirred for 15 minutes then quenched with ammonium chloride (aq) and diluted with water. The aqueous layer was extracted with ethyl acetate (×3), and the combined organic layers were dried with sodium sulfate, filtered, and concentrated. The crude material was purified by reverse phase HPLC (Gemini™ Prep C$_{18}$ 5 µm column; Phenomenex, Torrance, Calif.; gradient elution of 5% to 100% MeCN in water, where both solvents contain 0.1% trifluoroacetic acid, 45 minutes method) to give the title compound (1.8 mg, 0.003 mmol, 9% yield) after lyophilization. $^1$H NMR (400 MHz, CDCl$_3$) δ ppm 7.76 (d, J=8.2 Hz, 1H), 7.19-7.15 (m, 1H), 7.11-7.06 (m, 2H), 6.89 (d, J=8.2 Hz, 1H), 6.56 (d, J=2.0 Hz, 1H), 6.22-6.13 (m, 1H), 6.08-6.00 (m, 1H), 5.70 (s, 1H), 4.28 (br s, 1H), 4.04 (s, 2H), 3.81-3.73 (m, 5H), 3.66-3.54 (m, 2H), 3.32 (d, J=14.3 Hz, 1H), 3.17-3.07 (m, 3H), 2.99 (s, 3H), 2.81-2.73 (m, 2H), 2.66-2.49 (m, 4H), 2.35-2.29 (m, 1H), 2.03-1.79 (m, 6H), 1.43-1.33 (m, 1H). LRMS: m/z (ESI, +ve ion) 609.2 (M+H)$^+$.

Example 168

(1S,3'R,6'R,7'R,8'E,15'S)-6-CHLORO-7',15'-DIHYDROXY-12'-METHYL-13'-OXO-3,4-DIHYDRO-2H-SPIRO[NAPHTHALENE-1,22'-[20]OXA[1,12]DIAZATETRACYCLO [14.7.2.0$^{3,6}$.0$^{19,24}$]PENTACOSA[8,16,18,24]TETRAENE]-15'-CARBOXYLIC ACID

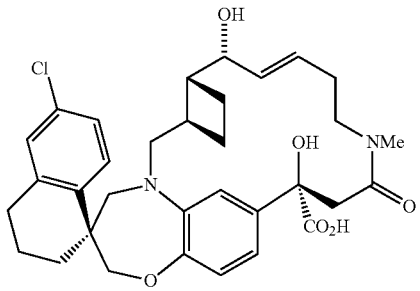 [SMILES: CN1CC/C=C/[C@@H](O)[C@@H]2CC[C@H]2CN2C[C@@]3(CCCc4cc(Cl)ccc43)COc3ccc(cc32)[C@](O)(C(=O)O)CC1=O]

The title compound was synthesized from methyl (1S,3'R,6'R,7'R,8'E,15'S)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 167, step 2) through a procedure similar to that used for Example 4. The crude material was purified by reverse phase HPLC (Gemini™ Prep C$_{18}$ 5 µm column; Phenomenex, Torrance, Calif.; gradient elution of 5% to 100% MeCN in water, where both solvents contain 0.1% trifluoroacetic acid, 45 minutes method) to give the title compound (18 mg, 0.029 mmol, 95% yield) after lyophilization. $^1$H NMR (400 MHz, CDCl$_3$) δ ppm 7.74 (d, J=8.5 Hz, 1H), 7.17 (dd, J=8.5 Hz, 2.3 Hz, 1H), 7.10-7.06 (m, 2H), 6.89 (d, J=8.3 Hz, 1H), 6.64 (d, J=1.9 Hz, 1H), 6.22-6.14 (m, 1H), 6.01 (d, J=15.5 Hz, 1H), 4.30 (br s, 1H), 4.05-3.95 (m, 2H), 3.81-3.53 (m, 4H), 3.31 (d, J=14.5 Hz, 1H), 3.20-3.17 (m, 1H), 3.07-2.94 (m, 4H), 2.82-2.74 (m, 2H), 2.67-2.50 (m, 3H), 2.37-2.28 (m, 1H), 2.07-1.69 (m, 7H), 1.40-1.25 (m, 2H). LRMS: m/z (ESI, +ve ion) 595.1 (M+H)$^+$.

Example 169

((1S,3'R,6'R,7'S,8'E,15'S)-6-CHLORO-7'-HYDROXY-15'-(METHOXYCARBONYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAEN]-15'-YL)ACETIC ACID or ((1S,3'R,6'R,7'S,8'E,15'R)-6-CHLORO-7'-HYDROXY-15'-(METHOXYCARBONYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAEN]-15'-YL)ACETIC ACID

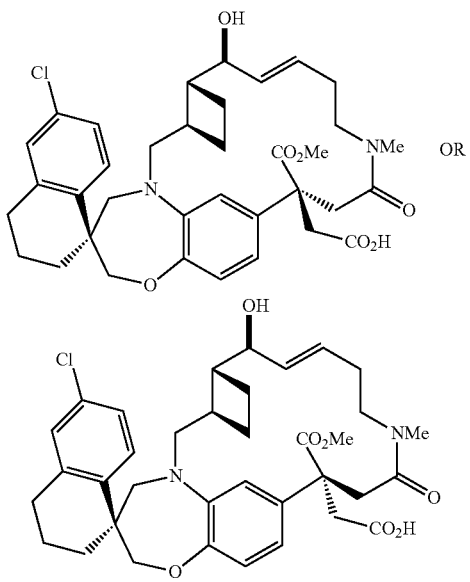

To a 2-dram vial was added methyl (1S,3'R,6'R,7'S,8'E,15'S)-6-chloro-7'-tert-butyldimethylsilyloxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate or methyl (1S,3'R,6'R,7'S,8'E,15'R)-6-chloro-7'-tert-butyldimethylsilyloxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 157, step 1) (30 mg, 0.037 mmol) in methylene chloride (365 µl) at room temperature. To the vessel was added trifluoroacetic acid (365 µl), and the mixture was stirred for 3 hours and concentrated. The residue was dissolved in 0.2 mL tetrahydrofuran, and 0.2 mL 1M TBAF in tetrahydrofuran was added, and the mixture was stirred for 2 hours. The process was quenched with ammonium chloride solution, diluted with ethyl acetate, and acidified to pH=2 with 1 N HCl. The aqueous layer was extracted with ethyl acetate (×3), and the combined organic layers were dried with sodium sulfate, filtered, and concentrated. The residue was purified by reverse phase HPLC (Gemini™ Prep C$_{18}$ 5 µm column; Phenomenex, Torrance, Calif.; gradient elution of 5% to 100% MeCN in water, where both solvents contain 0.1% trifluoroacetic acid, 45 minutes method) to give one of the title products (5.2 mg, 0.007 mmol, 19% yield) after lyophilization. $^1$H NMR (400 MHz, CDCl$_3$) δ 7.73-7.69 (m, 1H), 7.19-7.17 (m, 1H), 7.08 (s, 1H), 6.86-6.77 (m, 1H), 6.61-6.54 (m, 1H), 6.45 (br s, 1H), 6.06-5.94 (m, 1H), 5.61-5.56 (m, 1H), 4.12-4.01 (m, 2H), 3.83-3.52 (m, 6H), 3.42 (d, J=14.1 Hz, 1H), 3.33-3.14 (m, 4H), 3.08-3.02 (m, 1H), 2.96 (s, 3H), 2.78 (br s, 2H), 2.69-2.50 (m, 3H), 2.37-2.27 (m, 2H), 2.07-1.75 (m, 7H), 1.65 (d, J=9.2 Hz, 1H), 1.42 (d, J=12.1 Hz, 1H). LRMS: m/z (ESI, +ve ion) 651.3 (M+H)$^+$.

Example 170

(1S,3'R,6'R,7'R,8'E,15'S)-6-CHLORO-7',15'-DIMETHOXY-12'-METHYL-13'-OXO-3,4-DIHYDRO-2H-SPIRO[NAPHTHALENE-1,22'-[20]OXA[1,12]DIAZATETRACYCLO [14.7.2.0$^{3,6}$.0$^{19,24}$]PENTACOSA[8,16,18,24]TETRAENE]-15'-CARBOXYLIC ACID

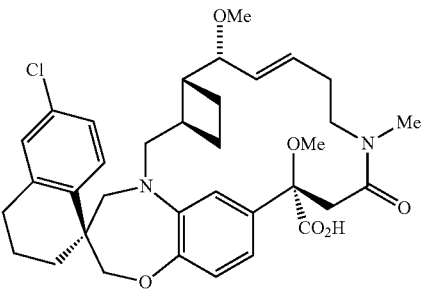 [SMILES: CO[C@@H]1/C=C/CCN(C)C(=O)C[C@@](OC)(C(=O)O)c2ccc3c(c2)N(C[C@@H]2CC[C@H]21)C[C@@]1(CCCc2cc(Cl)ccc21)CO3]

To a 2-dram vial was added methyl (1S,3'R,6'R,7'R,8'E,15'S)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 167, step 2) (18.0 mg, 0.030 mmol) and tetrahydrofuran (0.295 mL) at room temperature. To the vessel was added sodium bis(trimethylsilyl)amide (148 µl, 0.6 M in tetrahydrofuran, 0.089 mmol) followed by methyl iodide (14.78 µl, 0.236 mmol), and the mixture was stirred for 1 hour. The mixture was quenched with 1 N HCl, extracted with ethyl acetate (×2), dried with sodium sulfate, filtered, and concentrated. To the vessel was then added tetrahydrofuran (0.35 mL), 2M LiOH (0.75 mL), and MeOH (0.15 mL). The mixture was stirred for 5 hours at room temperature before being quenched with 1M HCl, extracted with ethyl acetate (×2), dried, filtered, and concentrated. The crude product was purified by reverse phase HPLC (Gemini™ Prep C$_{18}$ 5 µm column; Phenomenex, Torrance, Calif.; gradient elution of 5% to 100% MeCN in water, where both solvents contain 0.1% trifluoroacetic acid, 45 minutes method) to yield the title product (1.9 mg, 0.003 mmol, 8.8% yield) after lyophilization. $^1$H NMR (400 MHz, CDCl$_3$) δ ppm 7.76 (d, J=8.6, 1H), 7.20-7.15 (m, 1H), 7.09 (d, J=2.2, 1H), 6.83 (d, J=8.2, 1H), 6.55-6.49 (m, 2H), 6.15-6.09 (m, 1H), 5.70-5.64 (m, 1H), 4.10-3.91 (m, 6H), 3.83-3.65 (m, 5H), 3.56 (s, 3H), 3.35 (s, 3H), 3.25-3.13 (m, 5H), 2.99 (s, 3H), 2.80-2.75 (m, 3H), 2.08-2.00 (m, 4H), 0.90-0.82 (m, 3H). LRMS: m/z (ESI, +ve ion) 623.2 (M+H)$^+$.

Example 171

METHYL (1S,3'R,6'R,7'S,8'E,15'R)-7'-(ACETY-LOXY)-6-CHLORO-15'-HYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLATE

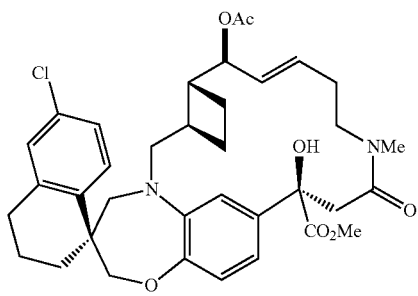 [SMILES: COC(=O)[C@@]1(O)CC(=O)N(C)CC/C=C/[C@H](OC(C)=O)[C@@H]2CC[C@H]2CN2C[C@@]3(CCCc4cc(Cl)ccc43)COc3ccc1cc32]

Example 172

(1S,3'R,6'R,7'S,8'E,15'R)-6-CHLORO-15'-HY-DROXY-7'-(2-METHOXYETHOXY)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

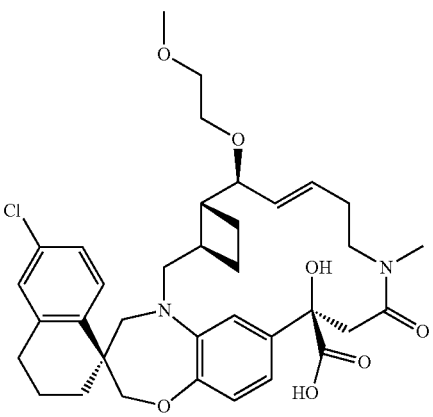 [SMILES: COCCO[C@H]1/C=C/CCN(C)C(=O)C[C@](O)(C(=O)O)c2ccc3c(c2)N(C[C@@H]2CC[C@H]21)C[C@@]1(CCCc2cc(Cl)ccc21)CO3]

To a 5-mL round-bottomed flask was added methyl (1S,3'R,6'R,7'R,8'E,15'S)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (from Example 1 step 7, 38 mg, 0.062 mmol) and 4-dimethylaminopyridine (0.762 mg, 6.24 µmol) in dichloromethane (624 µl) at room temperature. To the vessel was added triethylamine (30.4 µl, 0.218 mmol) and acetic anhydride (8.83 µl, 0.094 mmol). The mixture was stirred at room temperature and stirred for 2 hours before being quenched with ammonium chloride, and diluted with water and methylene chloride. The aqueous layer was extracted with methylene chloride (×2), and the combined organic layers were dried with sodium sulfate, filtered, and concentrated. The residue was purified by column chromatography 0-50% ethyl acetate over 15 min to give the title product (35 mg, 0.054 mmol, 80% yield). $^1$H NMR (400 MHz, CDCl$_3$) δ ppm 7.74 (d, J=8.4 Hz, 1H), 7.16-7.14 (m, 1H), 7.08-7.06 (m, 2H), 6.85-6.75 (m, 2H), 6.04-5.94 (m, 1H), 5.73-5.65 (m, 1H), 4.04-3.94 (m, 2H), 3.83 (s, 3H), 3.78-3.76 (m, 1H), 3.45-3.28 (m, 3H), 3.09-2.97 (m, 4H), 2.78-2.74 (m, 2H), 2.42-2.40 (m, 2H), 2.14 (s, 2H), 2.06-1.99 (m, 4H), 1.91-1.66 (m, 6H), 1.41-1.35 (m, 1H), 1.28-1.20 (m, 3H). LRMS: m/z (ESI, +ve ion) 651.2 (M+H)$^+$.

To a solution of methyl (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 1-step 7, 23 mg, 0.038 mmol) in THF (0.5 mL) was added sodium bis(trimethylsilyl)amide (LOM solution in THF) (0.132 mL, 0.132 mmol) followed by 2-bromoethyl methyl ether (0.018 mL, 0.189 mmol). The reaction mixture was stirred at room temperature for 72 hrs. The reaction mixture was quenched with water and extracted with ethyl acetate. The layers were separated and the aqueous phase was further extracted with ethyl acetate (2×). The combined organic phases were dried over MgSO4, filtered and concentrated. The crude was purified by flash column chromatography eluting with a gradient of 0% to 10% MeOH in DCM to give the title compound (4 mg, 6.12 µmol, 16.22% yield) as a white solid. $^1$H NMR (400 MHz, CD$_2$Cl$_2$) δ ppm 7.72 (d, J=8.6 Hz, 1H), 7.15 (dd, J=2.2, 8.3 Hz, 1H), 7.08 (d, J=2.0 Hz, 1H), 6.99 (dd, J=1.8, 8.2 Hz, 1H), 6.85 (d, J=8.2 Hz, 1H), 6.61 (s, 1H), 6.35-6.23 (m, 1H), 5.72-5.63 (m, 1H), 4.05-3.95 (m, 2H), 3.91-3.84 (m, 1H), 3.76-3.28 (m, 12H), 3.20-3.05 (m, 2H), 2.96 (s, 3H), 2.84-2.54 (m, 5H), 2.48-2.36 (m, 2H), 2.34-2.24 (m, 1H), 2.06-1.66 (m, 7H), 1.44-1.34 (m, 1H) LRMS: (ESI, +ve ion) m/z 653.3 (M+H)$^+$.

Example 173

(1S,3'R,6'R,7'S,8'E,15'R)-6-CHLORO-15'-HYDROXY-12'-METHYL-7'-(2-(4-MORPHOLINYL)ETHOXY)-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

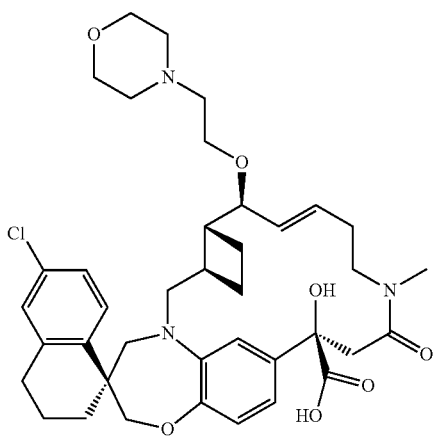 [SMILES: CN1CC/C=C/[C@H](OCCN2CCOCC2)[C@@H]2CC[C@H]2CN2C[C@@]3(CCCc4cc(Cl)ccc43)COc3ccc(cc32)[C@@](O)(C(=O)O)CC1=O]

Step 1: Methyl (1S,3'R,6'R,7'S,8'E,15'R)-6-chloro-15'-hydroxy-7'-(2-bromoethoxy)-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate

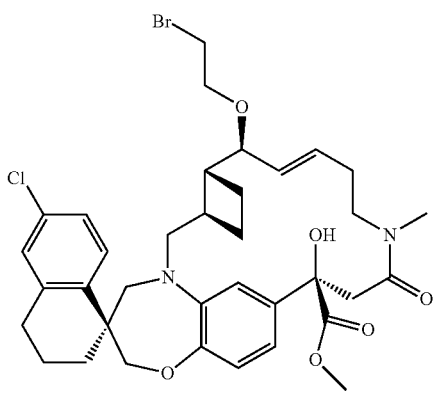 [SMILES: COC(=O)[C@@]1(O)CC(=O)N(C)CC/C=C/[C@H](OCCBr)[C@@H]2CC[C@H]2CN2C[C@@]3(CCCc4cc(Cl)ccc43)COc3ccc1cc32]

To a solution of methyl (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 1-step 7, 0.55 g, 0.90 mmol) in CHCl$_3$ (3.0 mL) were added 2,6-di-tert-butylpyridine (2.0 ml, 9.03 mmol) and 2-bromoethyl trifluoromethanesulfonate (1.16 g, 4.51 mmol). The reaction mixture heated at 60° C. and stirred overnight at that temperature. After cooling, the reaction mixture was diluted with EtOA$_c$ and washed successively with 0.1N HCl (2×), and brine. The organic layer was dried over MgSO$_4$, filtered and evaporated under reduced pressure. The crude material was absorbed onto a plug of silica gel and purified by chromatography through a Redi-Sep pre-packed silica gel column, eluting with a gradient of 0% to 10% MeOH in DCM, to provide the title compound (0.49 g, 0.68 mmol, 76% yield) as white solid. LRMS: (ESI, +ve ion) m/z 716.1 (M+H)$^+$. Note: 2-bromoethyl trifluoromethanesulfonate was synthesized from 2-bromoethanol: ref Sajadi, M.; Berndt, F.: Richter, C.; Gcrecke, M; Mahrwald, R. Ernsting, N. P. Observing the Hydration Layer of Trehalose with a. Linked Molecular Terahenz Probe *J. Phys. Chem. Lett.* 2014, 5, 1845-1849. Adapted from reference: To a stirred solution of pyridine (7.12 mL, 88 mmol) in DCM (267 mL) at −20° C. was added trifluoromethanesulfonic anhydride (13.46 mL, 80 mmol) dropwise. The resulting suspension was stirred for 10 min at −20° C. and then 2-bromoethanol (5.65 mL, 80 mmol) was slowly added. The reaction mixture was stirred 20 min at −20° C. and then 10 min at RT. The resulting suspension was filtered and concentrated in vacuo while maintaining the water bath temperature below 18° C. The mixture was filtered again and evaporated under reduced pressure. The crude was quickly purified by chromatography through a short silica gel column eluting with 0% to 8% diethyl ether in pentane to give 2-bromoethyl trifluoromethanesulfonate (14.96 g, 58.2 mmol, 72.8% yield) as a colorless oil. H-NMR (00 MHz, CDCl$_3$): δ [pp]:=4.75 (t, 1=6.4 Hz, 21-), 3.62 (t, =: 6.4 Hz, 1H). When not in use, the reagent was stored at 0° C.

Step 2: Methyl (1S,3'R,6'R,7'S,8'E,15'R)-6-chloro-15'-hydroxy-12'-methyl-7'-(2-(4-morpholinyl)ethoxy)-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate

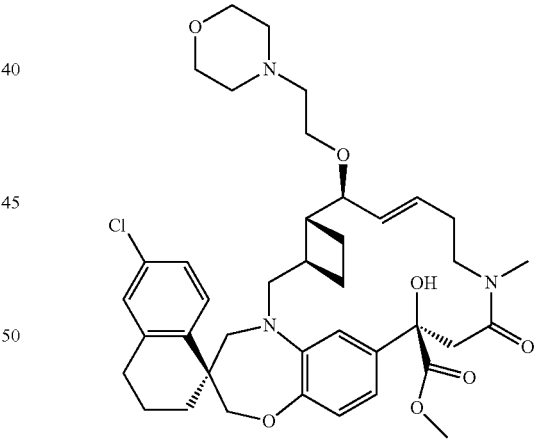

To a solution of methyl (1S,3'R,6'R,7'S,8'E,15'R)-6-chloro-15'-hydroxy-7'-(2-bromoethoxy)-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (0.012 g, 0.017 mmol) in DMSO (0.372 ml) was added morpholine (0.015 ml, 0.168 mmol). The reaction mixture was stirred overnight at 55° C. The reaction was allowed to cool to RT and was then partitioned between water and ethyl acetate. The aqueous phase was separated and further extracted with ethyl acetate (2×). The combined organic layers were washed with brine, dried over magnesium sulfate, filtered and concentrated. The crude material was purified by flash column chromatography eluting with a gradient of 0% to 8% MeOH in DCM to give the title compound (0.008 g, 0.011 mmol, 66.1% yield) as a white powder. $^1$H NMR (400 MHz, CD$_2$Cl$_2$) δ ppm 7.73 (d, J=8.4 Hz, 1H), 7.16 (dd, J=2.3, 8.4 Hz, 1H), 7.08 (d, J=2.3 Hz, 1H), 7.00 (dd, J=2.2, 8.2 Hz, 1H), 6.84 (d, J=8.2 Hz, 1H), 6.48 (d, J=2.0 Hz, 1H), 6.25-6.14 (m, 1H), 5.68 (ddd, J=1.7, 9.5, 15.2 Hz, 1H), 5.60 (s, 1H), 4.06-3.94 (m, 2H), 3.80-3.70 (s+m, 5H), 3.67-3.63 (m, 4H), 3.63-3.47 (m, 4H), 3.40-3.30 (m, 2H), 3.17-3.03 (m, 2H), 2.95 (s, 3H), 2.84-2.70 (m, 2H), 2.69-2.59 (m, 1H), 2.57-2.38 (m, 9H), 2.34-2.24 (m, 1H), 2.07-1.70 (m, 7H), 1.44-1.34 (m, 1H). LRMS: (ESI, +ve ion) m/z 722.5 (M+H)$^+$.

Step 3: (1S,3'R,6'R,7'S,8'E,15'R)-6-chloro-15'-hydroxy-12'-methyl-7'-(2-(4-morpholinyl)ethoxy)-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic Acid

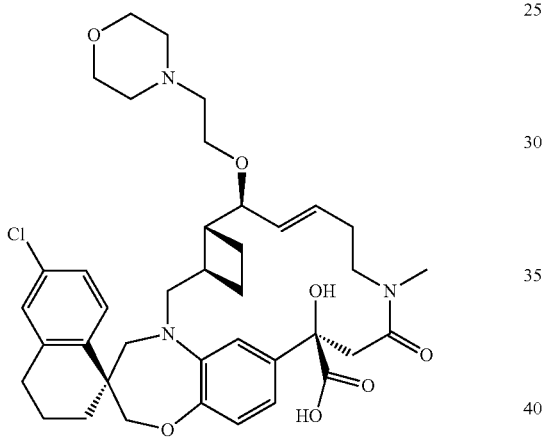

To a solution of methyl (1S,3'R,6'R,7'S,8'E,15'R)-6-chloro-15'-hydroxy-12'-methyl-7'-(2-(4-morpholinyl)ethoxy)-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (7.9 mg, 10.94 µmol) in a mixture of THF (150 µl) and MeOH (150 µl) was added lithium hydroxide (2N in H$_2$O) (150 µl, 0.300 mmol). The reaction mixture was stirred at RT for 2 hrs. The reaction was quenched by slowly adding 1N HCl till formation of a white precipitate. DCM was added and the layers were separated. The aqueous phase was further extracted with DCM (2×). The combined organic phases were dried over magnesium sulfate and concentrated under vacuo to give the title compound (5.7 mg, 8.05 µmol, 73.6% yield) as a white solid. $^1$H NMR (300 MHz, CDCl$_3$) δ ppm 7.72 (d, J=8.5 Hz, 1H), 7.16 (dd, J=2.2, 8.5 Hz, 1H), 7.10-7.03 (m, 2H), 6.86 (d, J=8.3 Hz, 1H), 6.74-6.67 (m, 1H), 6.54-6.39 (m, 1H), 5.71-5.59 (m, 1H), 4.09-3.47 (m, 14H), 3.33-3.04 (m, 8H), 3.01 (s, 3H), 2.86-2.65 (m, 3H), 2.56 (d, J=16.5 Hz, 1H), 2.46-2.35 (m, 2H), 2.35-2.20 (m, 1H), 2.08-1.66 (m, 7H), 1.42-1.30 (m, 1H). LRMS: (ESI, +ve ion) m/z 708.3 (M+H)$^+$.

Example 174

(1S,3'R,6'R,7'S,8'E,15'R)-6-CHLORO-15'-HYDROXY-12'-METHYL-13'-OXO-7'-(2-(1-PIPERIDINYL)ETHOXY)-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

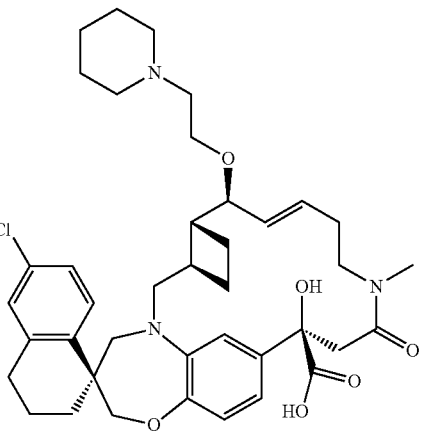

Step 1: Methyl(1S,3'R,6'R,7'S,8'E,15'R)-6-chloro-15'-hydroxy-12'-methyl-13'-oxo-7'-(2-(1-piperidinyl)ethoxy)-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate

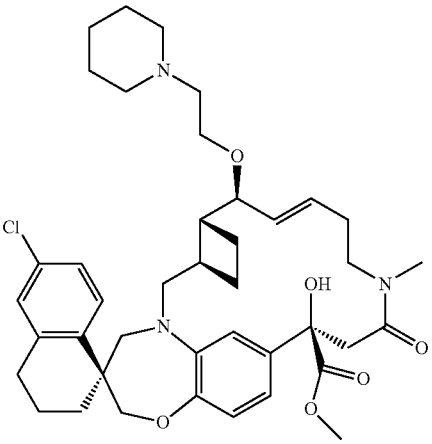 [SMILES: COC(=O)[C@@]1(O)CC(=O)N(C)CC/C=C/[C@H](OCCN2CCCCC2)[C@@H]2CC[C@H]2CN2C[C@@]3(CCCc4cc(Cl)ccc43)COc3ccc1cc32]

The title compound (28 mg, 57%) was synthesized from methyl (1S,3'R,6'R,7'S,8'E,15'R)-6-chloro-15'-hydroxy-7'-(2-bromoethoxy)-12'-methyl-13'-oxo-3,4-dihydro-2H-spiro[naphthalene-1,22'-[20]oxa[1,12]diazatetracyclo[14.7.2.0$^{3,6}$.0$^{19,24}$] pentacosa[8,16,18,24]tetraene]-15'-carboxylate (Example 173, Step 1) and piperidine through a procedure similar to that used for the synthesis of Example 173, Step 2. $^1$H NMR (400 MHz, CD$_2$Cl$_2$) δ ppm 7.73 (d, J=8.4 Hz, 1H), 7.16 (dd, J=2.3, 8.4 Hz, 1H), 7.08 (d, J=2.2 Hz, 1H), 7.00 (dd, J=2.2, 8.2 Hz, 1H), 6.84 (d, J=8.2 Hz, 1H), 6.47 (d, J=2.0 Hz, 1H), 6.30-6.18 (m, 1H), 5.68 (ddd, J=1.8, 9.4, 15.2 Hz, 1H), 5.60 (s, 1H), 4.06-3.95 (m, 2H), 3.83 (br d, J=9.4 Hz, 1H), 3.76-3.69 (m+s, 4H), 3.68-3.53 (m, 3H), 3.47 (d, J=16.6 Hz, 1H), 3.32 (d, J=14.5 Hz, 1H), 3.18-3.04 (m, 3H), 2.95 (s, 3H), 2.85-2.63 (m, 6H), 2.58-2.51 (m, 4H), 2.47-2.39 (m, 2H), 2.34-2.23 (m, 1H), 2.09-1.70 (m, 13H), 1.44-1.34 (m, 1H). LRMS: (ESI, +ve ion) m/z 720.5 (M+H)+.

Step 2: (1S,3'R,6'R,7'S,8'E,15'R)-6-chloro-15'-hydroxy-12'-methyl-13'-oxo-7'-(2-(1-piperidinyl)ethoxy)-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic Acid

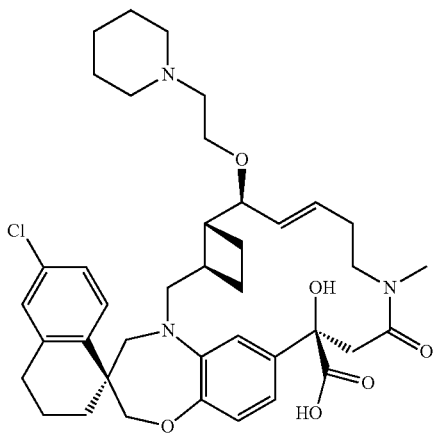 [SMILES: CN1CC/C=C/[C@H](OCCN2CCCCC2)[C@@H]2CC[C@H]2CN2C[C@@]3(CCCc4cc(Cl)ccc43)COc3ccc(cc32)[C@@](O)(C(=O)O)CC1=O]

The title compound (9.2 mg, 78%) was synthesized from methyl (1S,3'R,6'R,7'S,8'E,15'R)-6-chloro-15'-hydroxy-12'-methyl-13'-oxo-7'-(2-(1-piperidinyl)ethoxy)-3,4-dihydro-2H-spiro[naphthalene-1,22'-[20]oxa[1,12]diazatetracyclo[14.7.2.0$^{3,6}$.0$^{19,24}$]pentacosa[8,16,18,24] tetraene]-15'-carboxylate via saponification through a procedure similar to that used for the synthesis of Example 173, Step 3. $^1$H NMR (400 MHz, CD$_2$Cl$_2$) δ ppm 7.74 (d, J=8.6 Hz, 1H), 7.16 (dd, J=2.2, 8.4 Hz, 1H), 7.08 (d, J=2.2 Hz, 1H), 6.99 (d, J=7.8 Hz, 1H), 6.85 (br s, 1H), 6.79 (d, J=8.2 Hz, 1H), 6.51-6.40 (m, 1H), 5.70-5.59 (m, 1H), 4.05-3.92 (m, 3H), 3.77-3.56 (m, 5H), 3.51-3.40 (m, 1H), 3.30 (d, J=14.7 Hz, 1H), 3.17-2.98 (m, 6H), 2.96-2.88 (m+s, 4H), 2.84-2.68 (m, 3H), 2.66-2.55 (m, 1H), 2.53-2.37 (m, 2H), 2.36-2.18 (m, 2H), 2.09-1.64 (m, 13H), 1.46-1.35 (m, 1H). LRMS: (ESI, +ve ion) m/z 706.4 (M+H)+.

Example 175

(1S,3'R,6'R,7'S,8'E,15'R)-6-CHLORO-7'-(2-(3,3-DIFLUORO-1-AZETIDINYL)ETHOXY)-15'-HYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXYLIC ACID

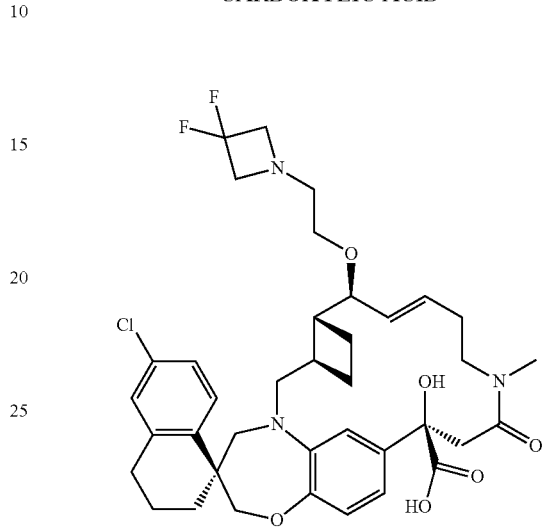

Step 1: Methyl (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate

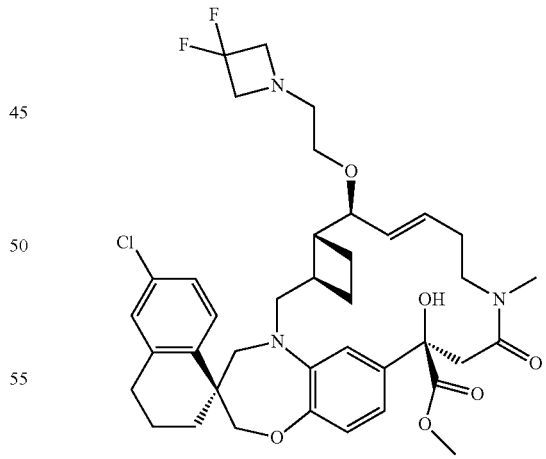

To a solution of 3,3-difluoroazetidine hydrochloride (362 mg, 2.79 mmol) in DMSO (7.8 mL) was added Et$_3$N (487 µL, 3.49 mmol) and KI (869 mg, 5.24 mmol). The reaction mixture was stirred at RT till obtention of a clear solution. Methyl (1S,3'R,6'R,7'S,8'E,15'R)-6-chloro-15'-hydroxy-7'-(2-bromoethoxy)-12'-methyl-13'-oxo-3,4-dihydro-2H-spiro[naphthalene-1,22'[20]oxa[1,12]diazatetracyclo[14.7.2.0$^{3,6}$.0$^{19,24}$]pentacosa[8,16,18,24]tetraene]-15'-carboxylate (Example 173, Step 1, 250 mg, 0.35 mmol) was then added and the reaction mixture was immediately placed on a stirrer plate at 55° C. and stirred at that temperature for 3 h. After cooling, the mixture was partitioned between water and EtOAc. The aqueous phase was separated and further extracted with ethyl acetate (2×). The combined organic layers were washed with brine, dried over MgSO$_4$, filtered and concentrated in vacuo. The crude material was absorbed onto a plug of silica gel and purified by chromatography through a Redi-Sep pre-packed silica gel column, eluting with a gradient of 20% to 50% acetone in heptanes, to provide the title compound (197 mg, 0.27 mmol, 77% yield). $^1$H NMR (300 MHz, CDCl$_3$) δ ppm 7.74 (d, J=8.5 Hz, 1H), 7.17 (dd, J=2.2, 8.5 Hz, 1H), 7.11 (dd, J=2.0, 8.2 Hz, 1H), 7.08 (d, J=2.2 Hz, 1H), 6.90 (d, J=8.3 Hz, 1H), 6.49 (d, J=1.9 Hz, 1H), 6.35-6.21 (m, 1H), 5.74-5.61 (m+br s, 2H), 4.02 (s, 2H), 3.84 (br d, J=9.6 Hz, 1H), 3.80-3.48 (m+s, 12H), 3.40-3.27 (m, 2H), 3.21-3.12 (m, 1H), 3.11-3.01 (m, 1H), 3.00 (s, 3H), 2.81-2.64 (m, 5H), 2.59 (br d, J=16.4 Hz, 1H), 2.48-2.35 (m, 2H), 2.35-2.22 (m, 1H), 2.11-1.67 (m, 7H), 1.46-1.32 (m, 1H). LRMS: (ESI, +ve ion) m/z 728.2 (M+H)$^+$.

Step 2: (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic Acid

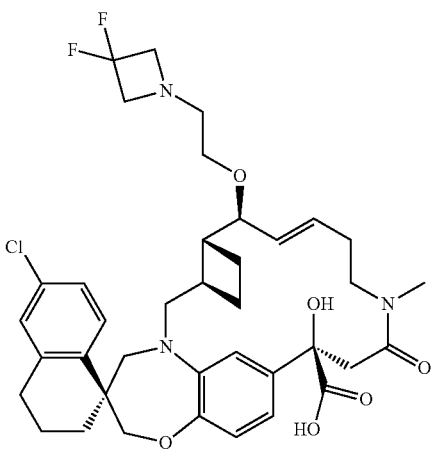 [SMILES: CN1CC/C=C/[C@H](OCCN2CC(F)(F)C2)[C@@H]2CC[C@H]2CN2C[C@@]3(CCCc4cc(Cl)ccc43)COc3ccc(cc32)[C@@](O)(C(=O)O)CC1=O]

To a solution of methyl (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (250 mg, 0.34 mmol) in a mixture of THF (4.6 mL) and MeOH (4.6 mL) was added aqueous LiOH (2M, 1.36 mL, 2.72 mmol). The reaction mixture was stirred at 40° C. for 90 min. After cooling, the reaction mixture was quenched by slowly adding 1N HCl till formation of a white precipitate. DCM was added and the layers were separated. The aqueous phase was further extracted with DCM (2×). The combined organic phases were dried over magnesium sulfate and concentrated under vacuo to give the title compound (245 mg, 0.34 mmol, 100% yield). $^1$H NMR (300 MHz, CDCl$_3$) δ ppm 7.73 (d, J=8.5 Hz, 1H), 7.19-7.10 (m, 1H), 7.10-7.02 (m, 2H), 6.89 (d, J=8.2 Hz, 1H), 6.69-6.61 (m, 1H), 6.44-6.29 (m, 1H), 5.72-5.59 (m, 1H), 4.07-3.95 (m, 2H), 3.90 (br d, J=9.6 Hz, 1H), 3.84-3.50 (m, 9H), 3.47-3.36 (m, 1H), 3.30 (br d, J=14.3 Hz, 1H), 3.22-3.12 (m, 1H), 3.11-3.01 (m, 1H), 2.99 (s, 3H), 2.89-2.64 (m, 5H), 2.60 (br d, J=16.7 Hz, 1H), 2.44-2.35 (m, 2H), 2.35-2.22 (m, 1H), 2.11-1.62 (m, 7H), 1.44-1.32 (m, 1H). LRMS: (ESI, +ve ion) m/z 714.2 (M+H)$^+$.

Example 176

(1S,3'R,6'R,7'S,8'E,15'R)-6-CHLORO-7'-(2-(3,3-DIFLUORO-1-AZETIDINYL)ETHOXY)-15'-HYDROXY-12'-METHYL-N-(METHYLSULFONYL)-13'-OXO-3,4-DIHYDRO-2H-SPIRO[NAPHTHALENE-1,22'-[20]OXA[1,12]DIAZATETRACYCLO [14.7.2.0$^{3,6}$.0$^{19,24}$]PENTACOSA[8,16,18,24]TETRAENE]-15'-CARBOXAMIDE

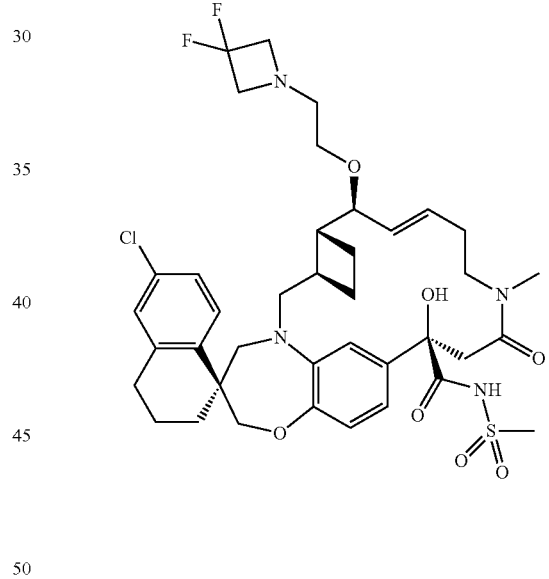

The title compound (2.2 mg, 17%) was synthesized from (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid (Example 175, step 2) and methanesulfonamide through a procedure similar to that used for the synthesis of Example 5. $^1$H NMR (400 MHz, CD$_2$Cl$_2$) δ ppm 8.99 (br s, 1H), 7.72 (d, J=8.5 Hz, 1H), 7.16 (dd, J=2.3, 8.6 Hz, 1H), 7.08 (d, J=2.0 Hz, 1H), 7.01-6.94 (m, 1H), 6.90-6.83 (m, 1H), 6.48 (d, J=1.8 Hz, 1H), 6.36-6.20 (m, 1H), 5.74-5.60 (m, 1H), 4.02 (s, 2H), 3.89-3.81 (m, 1H), 3.77-3.47 (m, 8H), 3.37-3.29 (m, 2H), 3.24-3.03 (m+s, 5H), 2.96 (s, 3H), 2.81-2.51 (m, 6H), 2.47-2.24 (m, 4H), 2.09-1.65 (m, 7H), 1.45-1.36 (m, 1H). LRMS: (ESI, +ve ion) m/z 791.2 (M+H)$^+$.

Example 177

(1S,3'R,6'R,7'S,8'E,15'R)-6-CHLORO-N-(CYCLO-PROPYLSULFONYL)-7'-(2-(3,3-DIFLUORO-1-AZETIDINYL)ETHOXY)-15'-HYDROXY-12'-METHYL-13'-OXO-3,4-DIHYDRO-2H-SPIRO[NAPHTHALENE-1,22'-[20]OXA[1,12]DIAZATETRACYCLO [14.7.2.0$^{3,6}$.0$^{19,24}$]PENTACOSA[8,16,18,24]TETRAENE]-15'-CARBOXAMIDE

Example 178

(1S,3'R,6'R,7'S, 8'E,15'R)-6-CHLORO-N-(CYCLOPROPYLSULFONYL)-15'-HYDROXY-12'-METHYL-7'-(2-(4-MORPHOLINYL)ETHOXY)-13'-OXO-3,4-DIHYDRO-2H-SPIRO[NAPHTHALENE-1,22'-[20] OXA[1,12]DIAZATETRACYCLO [14.7.2.03,6.019,24]PENTACOSA[8,16,18,24]TETRAENE]-15'-CARBOXAMIDE

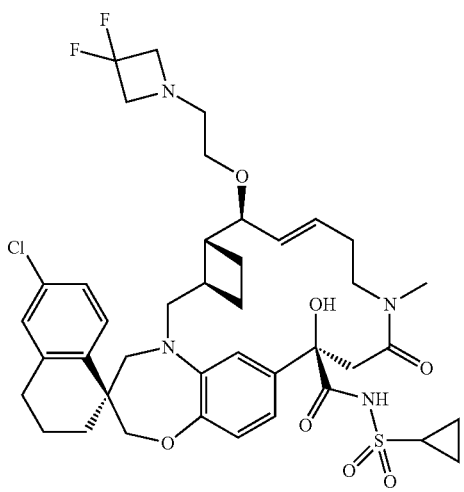 [SMILES: CN1CC/C=C/[C@H](OCCN2CC(F)(F)C2)[C@@H]2CC[C@H]2CN2C[C@@]3(CCCc4cc(Cl)ccc43)COc3ccc(cc32)[C@@](O)(C(=O)NS(=O)(=O)C2CC2)CC1=O]

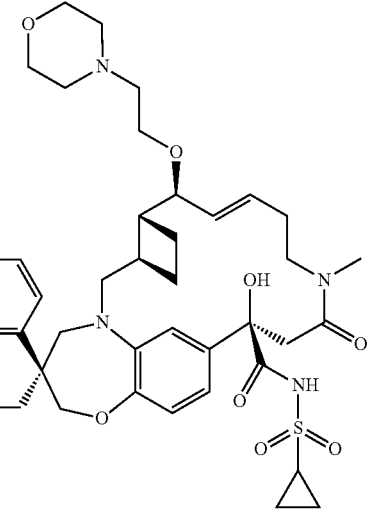

The title compound (19.2 mg, 42%) was synthesized from (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid (Example 175, step 2) and cyclopropanesulfonamide through a procedure similar to that used for the synthesis of Example 5. $^1$H NMR (300 MHz, CDCl$_3$) δ ppm 7.73 (d, J=8.5 Hz, 1H), 7.17 (dd, J=2.2, 8.5 Hz, 1H), 7.08 (d, J=2.2 Hz, 1H), 7.01 (dd, J=2.0, 8.3 Hz, 1H), 6.92-6.87 (m, 1H), 6.61 (br s, 1H), 6.48 (d, J=1.8 Hz, 1H), 6.44-6.27 (m, 1H), 5.73-5.59 (m, 1H), 4.09-3.97 (m, 2H), 3.87 (dd, J=1.6, 9.5 Hz, 1H), 3.78-3.46 (m, 9H), 3.43-3.26 (m, 2H), 3.22-2.96 (m+s, 5H), 2.91-2.51 (m, 7H), 2.45-2.23 (m, 3H), 2.09-1.64 (m, 7H), 1.47-1.31 (m, 3H), 1.12-0.96 (m, 2H). LRMS: (ESI, +ve ion) m/z 817.2 (M+H)$^+$.

The title compound (41 mg, 58%) was synthesized from (1S,3'R,6'R,7'S,8'E,15'R)-6-chloro-15'-hydroxy-12'-methyl-7'-(2-(4-morpholinyl)ethoxy)-13'-oxo-3,4-dihydro-2H-spiro[naphthalene-1,22'-[20]oxa[1,12]diazatetracyclo[14.7.2.03,6.019,24]pentacosa[8,16,18,24]tetraene]-15'-carboxylic acid (Example 173, step 3) and cyclopropanesulfonamide through a procedure similar to that used for the synthesis of Example 5. $^1$H NMR (300 MHz, CDCl$_3$) δ ppm 7.72 (d, J=8.5 Hz, 1H), 7.16 (dd, J=2.3, 8.5 Hz, 1H), 7.08 (d, J=2.2 Hz, 1H), 7.04-6.98 (m, 1H), 6.92-6.87 (m, 1H), 6.59 (br s, 1H), 6.50 (d, J=1.2 Hz, 1H), 6.45-6.27 (m, 1H), 5.67 (br dd, J=9.6, 14.6 Hz, 1H), 4.09-3.97 (m, 2H), 3.90 (dd, J=1.8, 9.5 Hz, 1H), 3.79-3.41 (m, 10H), 3.30 (d, J=14.5 Hz, 1H), 3.23-2.96 (m, 5H), 2.92-2.73 (m, 3H), 2.72-2.23 (m, 11H), 2.08-1.64 (m, 7H), 1.47-1.31 (m, 3H), 1.14-0.96 (m, 2H). LRMS: (ESI, +ve ion) m/z 811.2 (M+H)$^+$.

Example 179

(1S,3'R,6'R,7'S,8'E,15'R)-6-CHLORO-7'-(2-(3,3-DIFLUORO-1-AZETIDINYL)ETHOXY)-N-(DIMETHYLSULFAMOYL)-15'-HYDROXY-12'-METHYL-13'-OXO-3,4-DIHYDRO-2H-SPIRO[NAPHTHALENE-1,22'-[20]OXA[1,12]DIAZATETRACYCLO [14.7.2.0$^{3,6}$.0$^{19,24}$]PENTACOSA[8,16,18,24]TETRAENE]-15'-CARBOXAMIDE

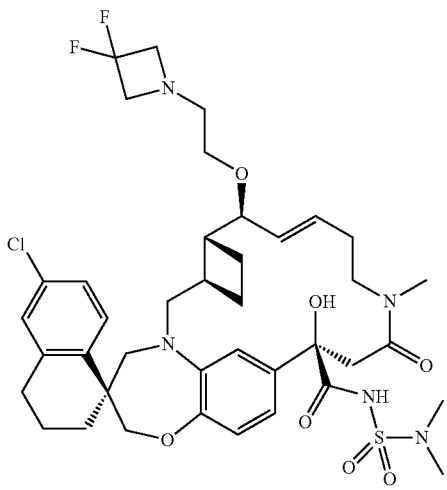 [SMILES: CN1CC/C=C/[C@H](OCCN2CC(F)(F)C2)[C@@H]2CC[C@H]2CN2C[C@@]3(CCCc4cc(Cl)ccc43)COc3ccc(cc32)[C@@](O)(C(=O)NS(=O)(=O)N(C)C)CC1=O]

The title compound (195.6 mg, 70%) was synthesized from (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid (Example 175, step 2) and N,N-dimethylsulfamide through a procedure similar to that used for the synthesis of Example 5. $^1$H NMR (500 MHz, CD$_2$Cl$_2$) δ ppm 8.95 (br s, 1H), 7.72 (d, J=8.6 Hz, 1H), 7.15 (dd, J=2.3, 8.6 Hz, 1H), 7.08 (d, J=2.2 Hz, 1H), 6.98 (dd, J=2.1, 8.3 Hz, 1H), 6.85 (d, J=8.2 Hz, 1H), 6.58 (br s, 1H), 6.51 (d, J=1.8 Hz, 1H), 6.39-6.29 (m, 1H), 5.65 (ddd, J=1.6, 9.6, 15.1 Hz, 1H), 4.04-3.95 (m, 2H), 3.81 (dd, J=1.4, 9.5 Hz, 1H), 3.70 (br d, J=14.3 Hz, 1H), 3.62-3.51 (m, 7H), 3.46 (ddd, J=4.5, 6.1, 10.1 Hz, 1H), 3.32 (d, J=14.4 Hz, 1H), 3.25 (ddd, J=4.4, 5.9, 10.0 Hz, 1H), 3.15 (td, J=3.2, 14.8 Hz, 1H), 3.09 (br dd, J=9.8, 15.3 Hz, 1H), 2.96 (s, 3H), 2.85 (s, 6H), 2.83-2.60 (m, 5H), 2.50 (br d, J=16.6 Hz, 1H), 2.43-2.36 (m, 2H), 2.33-2.25 (m, 1H), 2.06-1.79 (m, 6H), 1.77-1.67 (m, 1H), 1.42-1.34 (m, 1H). LRMS: (ESI, +ve ion) m/z 820.2 (M+H)$^+$.

Example 180

(1S,3'R,6'R,7'S,8'E,15'R)—N-(1-AZETIDINYLSULFONYL)-6-CHLORO-7'-(2-(3,3-DIFLUORO-1-AZETIDINYL)ETHOXY)-15'-HYDROXY-12'-METHYL-13'-OXO-3,4-DIHYDRO-2H-SPIRO[NAPHTHALENE-1,22'-[20]OXA[1,12]DIAZATETRACYCLO [14.7.2.0$^{3,6}$.0$^{19,24}$]PENTACOSA[8,16,18,24]TETRAENE]-15'-CARBOXAMIDE

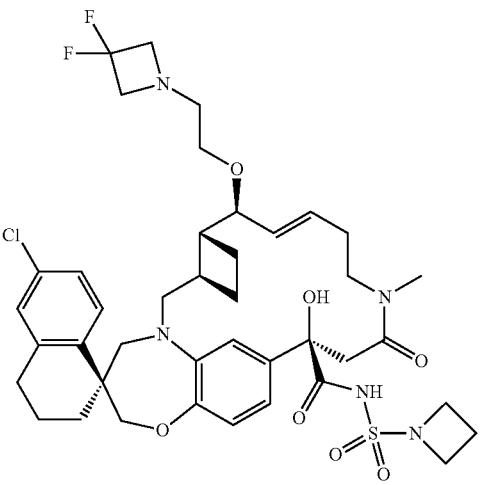 [SMILES: CN1CC/C=C/[C@H](OCCN2CC(F)(F)C2)[C@@H]2CC[C@H]2CN2C[C@@]3(CCCc4cc(Cl)ccc43)COc3ccc(cc32)[C@@](O)(C(=O)NS(=O)(=O)N2CCC2)CC1=O]

The title compound (15 mg, 31%) was synthesized from (1S,3'R,6'R,7'S,8'E,15'R)-6-choro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid (Example 175, step 2) and azetidine-1-sulfonamide through a procedure similar to that used for the synthesis of Example 5. $^1$H NMR (400 MHz, CD$_2$Cl$_2$) δ ppm 8.98 (br s, 1H), 7.73 (d, J=8.5 Hz, 1H), 7.16 (dd, J=2.3, 8.5 Hz, 1H), 7.08 (d, J=2.2 Hz, 1H), 7.01 (dd, J=2.0, 8.2 Hz, 1H), 6.87 (d, J=8.3 Hz, 1H), 6.61-6.52 (m, 2H), 6.42-6.26 (m, 1H), 5.75-5.59 (m, 1H), 4.18-3.92 (m, 6H), 3.83 (dd, J=1.8, 9.5 Hz, 1H), 3.73 (br d, J=14.3 Hz, 1H), 3.67-3.52 (m, 7H), 3.51-3.42 (m, 1H), 3.37-3.24 (m, 2H), 3.22-3.02 (m, 2H), 2.97 (s, 3H), 2.82-2.51 (m, 6H), 2.48-2.23 (m, 3H), 2.19-1.68 (m, 9H), 1.45-1.31 (m, 1H). LRMS: (ESI, +ve ion) m/z 832.2 (M+H)$^+$.

Example 181

(1S,3'R,6'R,7'S,8'E,15'R)-6-CHLORO-N-(DIMETH-YLSULFAMOYL)-7'-(2-(3-FLUORO-1-AZETIDI-NYL)ETHOXY)-15'-HYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

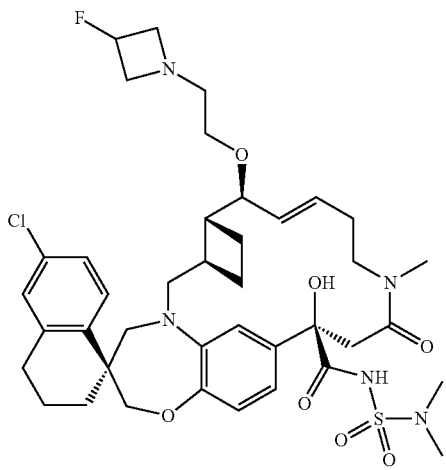 [SMILES: CN1CC/C=C/[C@H](OCCN2CC(F)C2)[C@@H]2CC[C@H]2CN2C[C@@]3(CCCc4cc(Cl)ccc43)COc3ccc(cc32)[C@@](O)(C(=O)NS(=O)(=O)N(C)C)CC1=O]

Step 1: Methyl(1S,3'R,6'R,7'S,8'E,15'R)-6-chloro-7'-(2-(3-fluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate

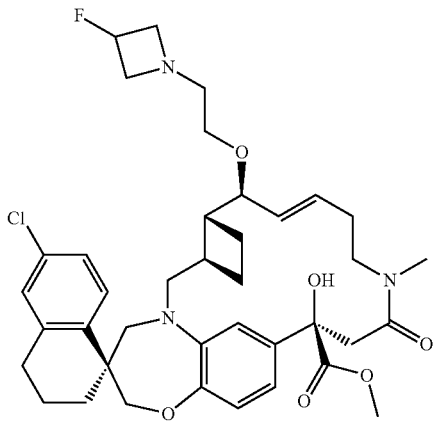 [SMILES: COC(=O)[C@@]1(O)CC(=O)N(C)CC/C=C/[C@H](OCCN2CC(F)C2)[C@@H]2CC[C@H]2CN2C[C@@]3(CCCc4cc(Cl)ccc43)COc3ccc1cc32]

The title compound (36.3 mg, 73%) was synthesized from methyl (1S,3'R,6'R,7'S,8'E,15'R)-6-chloro-15'-hydroxy-7'-(2-bromoethoxy)-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 173, Step 1) and 3-fluoroazetidine through a procedure similar to that used for the synthesis of Example 175, Step 1. LRMS: (ESI, +ve ion) m/z 710.3 (M+H)$^+$.

Step 2: (1S,3'R,6'R,7'S,8'E,15'R)-6-chloro-7'-(2-(3-fluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic Acid

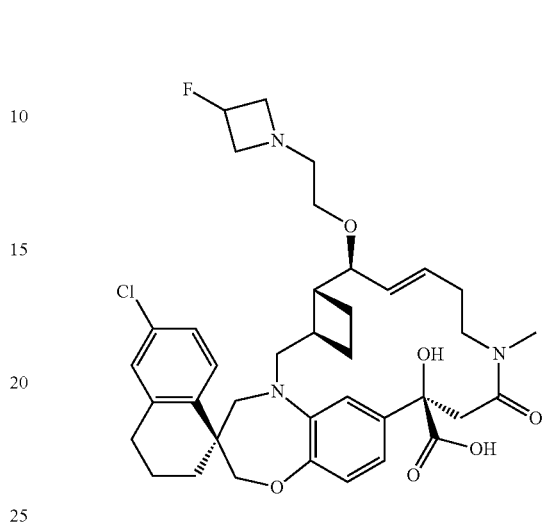

The title compound (34.9 mg, 99%) was synthesized from methyl (1S,3'R,6'R,7'S,8'E,15'R)-6-chloro-7'-(2-(3-fluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$] pentacosa[8,16,18,24] tetraene]-15'-carboxylate via saponification through a procedure similar to that used for the synthesis of Example 175, Step 2. LRMS: (ESI, +ve ion) m/z 696.2 (M+H)$^+$.

Step 3: (1S,3'R,6'R,7'S,8'E,15'R)-6-chloro-n-(dimethylsulfamoyl)-7'-(2-(3-fluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$] pentacosa[8,16,18,24]tetraene]-15'-carboxamide

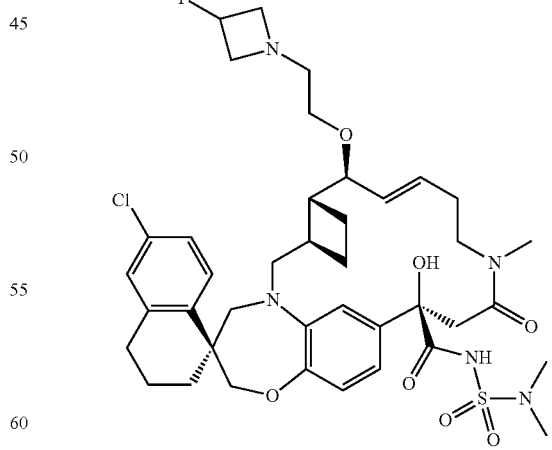

The title compound (9 mg, 22%) was synthesized from (1S,3'R,6'R,7'S,8'E,15'R)-6-chloro-7'-(2-(3-fluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'- carboxylic acid and N,N-dimethylsulfamide through a procedure similar to that used for the synthesis of Example 5. ¹H NMR (400 MHz, CDCl₃) δ ppm 7.73 (d, J=8.4 Hz, 1H), 7.16 (dd, J=1.9, 8.5 Hz, 1H), 7.08 (d, J=1.6 Hz, 1H), 7.01 (dd, J=1.6, 8.2 Hz, 1H), 6.89 (d, J=8.2 Hz, 1H), 6.57 (br s, 1H), 6.51-6.38 (m, 2H), 5.66 (br dd, J=9.8, 14.9 Hz, 1H), 4.09-3.81 (m, 6H), 3.78-3.45 (m, 6H), 3.41-3.22 (m, 3H), 3.21-3.13 (m, 1H), 3.06 (br dd, J=10.1, 15.4 Hz, 1H), 2.98 (s, 3H), 2.92 (s, 6H), 2.88-2.66 (m, 4H), 2.51 (br d, J=16.6 Hz, 1H), 2.47-2.26 (m, 4H), 2.12-1.67 (m, 7H), 1.46-1.35 (m, 1H). LRMS: (ESI, +ve ion) m/z 802.2 (M+H)⁺.

Example 182

(1S,3'R,6'R,7'S,8'E,15'R)-6-CHLORO-N-(DIMETHYLSULFAMOYL)-15'-HYDROXY-12'-METHYL-7'-(2-(4-MORPHOLINYL)ETHOXY)-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXAMIDE

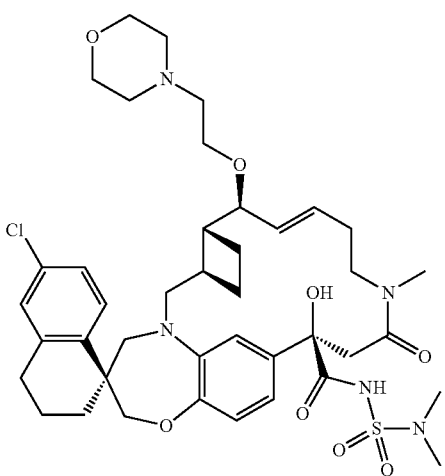 [SMILES: CN1CC/C=C/[C@H](OCCN2CCOCC2)[C@@H]2CC[C@H]2CN2C[C@@]3(CCCc4cc(Cl)ccc43)COc3ccc(cc32)[C@@](O)(C(=O)NS(=O)(=O)N(C)C)CC1=O]

The title compound (13 mg, 34%) was synthesized from (1S,3'R,6'R,7'S,8'E,15'R)-6-chloro-15'-hydroxy-12'-methyl-7'-(2-(4-morpholinyl)ethoxy)-13'-oxo-3,4-dihydro-2H-spiro[naphthalene-1,22'-[20]oxa[1,12]diazatetracyclo[14.7.2.0³,⁶.0¹⁹,²⁴]pentacosa[8,16,18,24]tetraene]-15'-carboxylic acid (Example 173, step 3) and N,N-dimethylsulfamide through a procedure similar to that used for the synthesis of Example 5. ¹H NMR (400 MHz, CD₂Cl₂) δ ppm 8.96 (s, 1H), 7.73 (d, J=8.6 Hz, 1H), 7.16 (dd, J=2.3, 8.6 Hz, 1H), 7.08 (d, J=2.2 Hz, 1H), 6.99 (dd, J=2.0, 8.2 Hz, 1H), 6.86 (d, J=8.2 Hz, 1H), 6.49 (d, J=2.0 Hz, 1H), 6.46-6.32 (m, 1H), 5.68 (ddd, J=1.5, 9.6, 15.1 Hz, 1H), 4.07-3.78 (m, 8H), 3.71 (br d, J=14.3 Hz, 1H), 3.64-3.47 (m, 6H), 3.32 (d, J=14.5 Hz, 1H), 3.24-2.95 (m+s, 8H), 2.86 (s, 6H), 2.81-2.62 (m, 3H), 2.55-2.23 (m, 5H), 2.10-1.69 (m, 7H), 1.47-1.32 (m, 1H). LRMS: (ESI, +ve ion) m/z 814.2 (M+H)⁺.

Example 183

(1S,3'R,6'R,7'S,8'E,11'S,18'S)-6-CHLORO-N-(DIMETHYLSULFAMOYL)-18'-HYDROXY-7'-METHOXY-16'-OXO-3,4-DIHYDRO-2H-SPIRO[NAPHTHALENE-1,25'-[23]OXA[1,15]DIAZAPENTACYCLO[17.7.2.0-3,6-.0¹¹,¹⁵.0-22,27]OCTACOSA[8,19,21,27]TETRAENE]-18'-CARBOXAMIDE OR (1S,3'R,6'R,7'S,8'E,11'S,18'R)-6-CHLORO-N-(DIMETHYLSULFAMOYL)-18'-HYDROXY-7'-METHOXY-16'-OXO-3,4-DIHYDRO-2H-SPIRO[NAPHTHALENE-1,25'-[23]OXA[1,15]DIAZAPENTACYCLO [17.7.2.0-3,6-.0¹¹,¹⁵.0-22,27]OCTACOSA[8,19,21,27]TETRAENE]-18'-CARBOXAMIDE

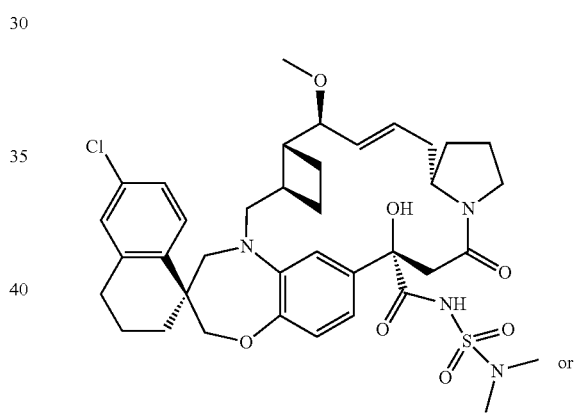

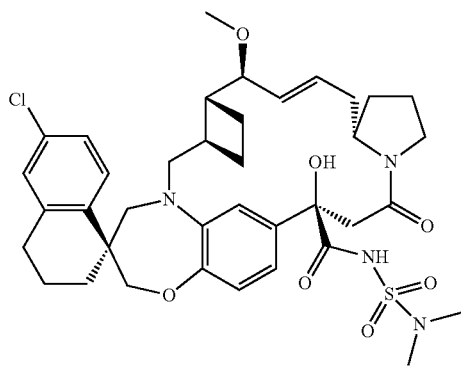

Step 1: Methyl(S)-4-((S)-2-allylpyrrolidin-1-yl)-2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-4-oxobutanoate and methyl (R)-4-((S)-2-allylpyrrolidin-1-yl)-2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-4-oxobutanoate

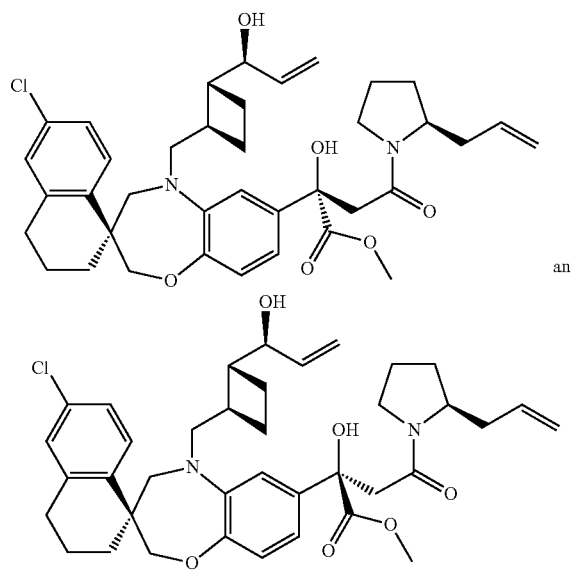

The title compounds as a mixture (104 mg, 89%) were synthesized from 3-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-3-hydroxy-4-methoxy-4-oxobutanoic acid (Example 1, step 5) and (S)-2-allylpyrrolidine through a procedure similar to that used for the synthesis of Example 1, step 6. LRMS: (ESI, +ve ion) m/z 663.2 (M+H)+.

Step 2: Methyl(1S,3'R,6'R,7'S,8'E,11S,18'S)-6-chloro-7',18'-dihydroxy-16'-oxo-3,4-dihydro-2H-spiro[naphthalene-1,25'-[23]oxa[1,15]diazapentacyclo[17.7.2.0~3,6~.0~11,15~.0~22,27~]octacosa[8,19,21,27]tetraene]-18'-carboxylate and Methyl (1S,3'R,6'R,7'S,8'E,11S,18'R)-6-chloro-7',18'-dihydroxy-16'-oxo-3,4-dihydro-2H-spiro[naphthalene-1,25'-[23]oxa[1,15]diazapentacyclo[17.7.2.0~3,6~.0~11,15~.0~22,27~]octacosa[8,19,21,27]tetraene]-18'-carboxylate

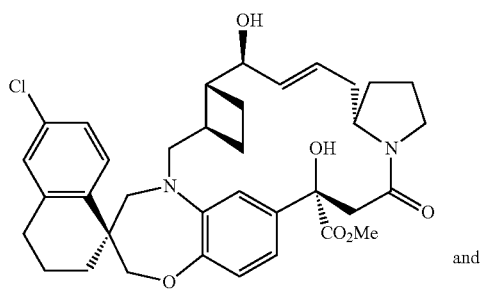

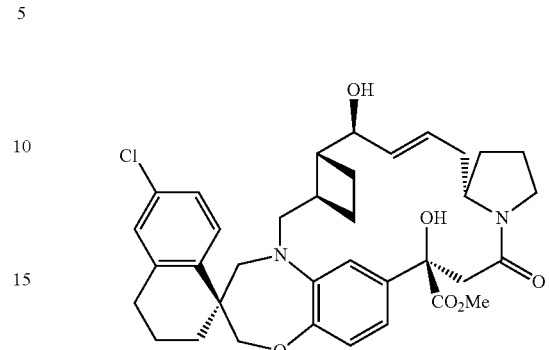

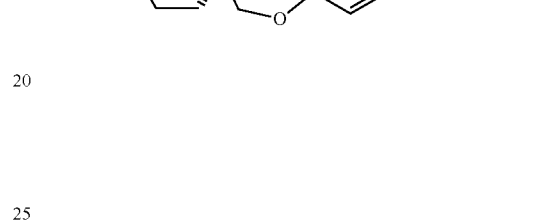

The title compounds (first eluting isomer: 48.3 mg, 48% and second eluting isomer: 30 mg, 30%) were synthesized from the mixture of isomers obtained in step 1 (methyl (S)-4-((S)-2-allylpyrrolidin-1-yl)-2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-4-oxobutanoate and methyl (R)-4-((S)-2-allylpyrrolidin-1-yl)-2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-4-oxobutanoate) via ring closing metathesis through a procedure similar to that used for the synthesis of Example 1, step 7. The crude was purified by chromatography through a Grace pre-packed silica gel column (12 g), eluting with a gradient of 0% to 60% acetone in hexanes. First eluting isomer (one of the title compound eluted with 40-42% acetone in hexanes): $^1$H NMR (300 MHz, CDCl$_3$) δ ppm 7.76 (d, J=8.5 Hz, 1H), 7.17 (dd, J=2.3, 8.5 Hz, 1H), 7.12 (dd, J=2.0, 8.2 Hz, 1H), 7.08 (d, J=2.2 Hz, 1H), 6.90 (d, J=8.3 Hz, 1H), 6.49 (d, J=2.0 Hz, 1H), 6.44-6.31 (m, 1H), 5.98-5.86 (m, 2H), 4.41 (br d, J=9.2 Hz, 1H), 4.08-3.90 (m, 3H), 3.82-3.63 (m, 7H), 3.58 (d, J=16.7 Hz, 1H), 3.47-3.37 (m, 1H), 3.30 (d, J=14.3 Hz, 1H), 3.11-3.00 (m, 1H), 2.82-2.73 (m, 2H), 2.57 (d, J=16.8 Hz, 1H), 2.49-2.33 (m, 3H), 2.25-2.14 (m, 1H), 2.13-1.68 (m, 11H), 1.44-1.31 (m, 1H). LRMS: (ESI, +ve ion) m/z 635.2 (M+H)+. Second eluting isomer (the other title compound eluted with 42-44% acetone in hexanes): $^1$H NMR (300 MHz, CDCl$_3$) δ ppm 7.75 (d, J=8.6 Hz, 1H), 7.17 (dd, J=2.2, 8.5 Hz, 1H), 7.07 (d, J=2.2 Hz, 1H), 7.00 (d, J=1.9 Hz, 1H), 6.81 (d, J=8.3 Hz, 1H), 6.63 (dd, J=2.0, 8.3 Hz, 1H), 5.96-5.84 (m, 1H), 5.80-5.68 (m, 1H), 4.89 (br s, 1H), 4.14-3.65 (m, 10H), 3.46-3.34 (m, 1H), 3.29 (d, J=3.5 Hz, 1H), 3.24 (s, 1H), 3.12-2.96 (m, 2H), 2.81-2.72 (m, 2H), 2.60-2.43 (m, 2H), 2.41-2.26 (m, 1H), 2.25-2.13 (m, 1H), 2.10-1.64 (m, 11H), 1.45-1.31 (m, 1H). LRMS: (ESI, +ve ion) m/z 635.2 (M+H)+.

Step 3: Methyl (1S,3'R,6'R,7'S,8'E,11'S,18'S)-6-chloro-18'-hydroxy-7'-methoxy-16'-oxo-3,4-dihydro-2H-spiro[naphthalene-1,25'-[23]oxa[1,15]diazapentacyclo[17.7.2.0~3,6~.0~11,15~.0~22,27~]octacosa[8,19,21,27]tetraene]-18'-carboxylate or methyl (1S,3'R,6'R,7'S,8'E,11'S,18'R)-6-chloro-18'-hydroxy-7'-methoxy-16'-oxo-3,4-dihydro-2H-spiro[naphthalene-1,25'-[23]oxa[1,15]diazapentacyclo[17.7.2.0~3,6~.0~11,15~.0~22,27~]octacosa[8,19,21,27]tetraene]-18'-carboxylate Step 4: (1S,3'R,6'R,7'S,8'E,11'S,18'S)-6-chloro-18'-hydroxy-7'-methoxy-16'-oxo-3,4-dihydro-2H-spiro[naphthalene-1,25'-[23]oxa[1,15]diazapentacyclo[17.7.2.0~3,6~.0~11,15~.0~22,27]octacosa[8,19,21,27]tetraene]-18'-carboxylic acid or (1S,3'R,6'R,7'S,8'E,11'S,18'R)-6-chloro-18'-hydroxy-7'-methoxy-16'-oxo-3,4-dihydro-2H-spiro[naphthalene-1,25'-[23]oxa[1,15]diazapentacyclo[17.7.2.0~3,6~.0~11,15~.0~22,27~]octacosa[8,19,21,27] tetraene]-18'-carboxylic acid

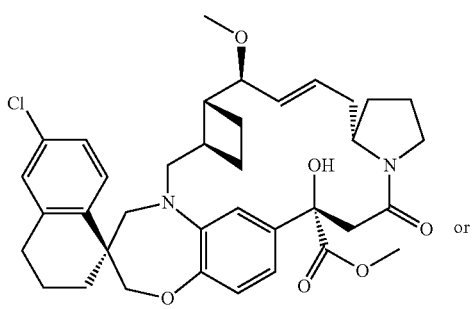

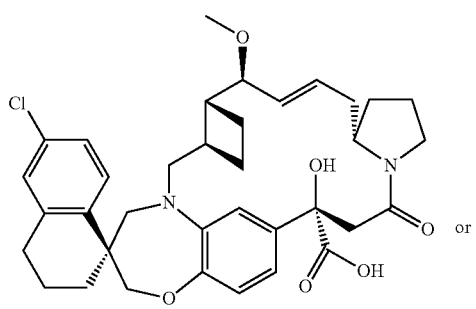

The title compound (27 mg, 55%) was synthesized from the second eluting isomer obtained in step 2 (methyl (1S,3'R,6'R,7'S,8'E,11'S,18'S)-6-chloro-7',18'-dihydroxy-16'-oxo-3,4-dihydro-2H-spiro[naphthalene-1,25'-[23]oxa[1,15]diazapentacyclo[17.7.2.0~3,6~.0~11,15~.0~22,27~]octacosa[8,19,21,27]tetraene]-18'-carboxylate or methyl (1S,3'R,6'R,7'S,8'E,11'S,18'R)-6-chloro-7',18'-dihydroxy-16'-oxo-3,4-dihydro-2H-spiro[naphthalene-1,25'-[23]oxa[1,15]diazapentacyclo[17.7.2.0~3,6~.0~11,15~.0~22,27~]octacosa[8,19,21,27]tetraene]-18'-carboxylate) and methyl iodide through a procedure similar to that used for the synthesis of Example 3. $^1$H NMR (300 MHz, CDCl$_3$) δ ppm 7.76 (d, J=8.5 Hz, 1H), 7.17 (dd, J=2.3, 8.5 Hz, 1H), 7.12 (dd, J=2.0, 8.3 Hz, 1H), 7.08 (d, J=2.2 Hz, 1H), 6.90 (d, J=8.3 Hz, 1H), 6.48 (d, J=2.0 Hz, 1H), 6.41-6.27 (m, 1H), 5.87 (br s, 1H), 5.68 (ddd, J=1.6, 9.6, 15.3 Hz, 1H), 4.06-3.93 (m, 3H), 3.83-3.64 (m+s, 7H), 3.61 (d, J=16.8 Hz, 1H), 3.52-3.41 (m, 1H), 3.31 (d, J=14.3 Hz, 1H), 3.25 (s, 3H), 3.10-2.98 (m, 1H), 2.82-2.73 (m, 2H), 2.66-2.36 (m, 4H), 2.30-2.18 (m, 1H), 2.12-1.82 (m, 9H), 1.79-1.67 (m, 2H), 1.44-1.32 (m, 1H). LRMS: (ESI, +ve ion) m/z 671.2 (M+Na)$^+$.

The title compound (17.2 mg, 65%) was synthesized from the product obtained in step 3 (methyl (1S,3'R,6'R,7'S,8'E,11'S,18'S)-6-chloro-18'-hydroxy-7'-methoxy-16'-oxo-3,4-dihydro-2H-spiro[naphthalene-1,25'-[23]oxa[1,15]diazapentacyclo[17.7.2.0~3,6~.0~11,15~.0~22,27~]octacosa[8,19,21,27]tetraene]-18'-carboxylate or methyl (1S,3'R,6'R,7'S,8'E,11'S,18'R)-6-chloro-18'-hydroxy-7'-methoxy-16'-oxo-3,4-dihydro-2H-spiro[naphthalene-1,25'-[23]oxa[1,15]diazapenta cyclo[17.7.2.0~3,6~.011,15.022,27]octacosa[8,19,21,27]tetraene]-18'-carboxylate) via saponification through a procedure similar to that used for the synthesis of Example 173, Step 3. $^1$H NMR (300 MHz, CDCl$_3$) δ ppm 7.75 (d, J=8.5 Hz, 1H), 7.17 (dd, J=2.2, 8.5 Hz, 1H), 7.10-7.02 (m, 2H), 6.89 (d, J=8.2 Hz, 1H), 6.62 (d, J=2.0 Hz, 1H), 6.50-6.38 (m, 1H), 5.67 (ddd, J=1.7, 9.6, 15.2 Hz, 1H), 4.08-3.93 (m, 3H), 3.86 (dd, J=1.9, 9.6 Hz, 1H), 3.82-3.60 (m, 4H), 3.52-3.41 (m, 1H), 3.30 (d, J=14.5 Hz, 1H), 3.24 (s, 3H), 3.10-2.98 (m, 1H), 2.82-2.73 (m, 2H), 2.63-2.36 (m, 4H), 2.30-2.17 (m, 1H), 2.11-1.66 (m, 11H), 1.44-1.31 (m, 1H). LRMS: (ESI, +ve ion) m/z 635.2 (M+H)$^+$.

Step 5: (1S,3'R,6'R,7'S,8'E,11'S,18'S)-6-chloro-N-(dimethylsulfamoyl)-18'-hydroxy-7'-methoxy-16'-oxo-3,4-dihydro-2H-spiro[naphthalene-1,25'-[23]oxa[1,15]diazapentacyclo [17.7.2.0~3,6~.0~11,15~.0~22,27~]octacosa[8,19,21,27]tetraene]-18'-carboxamide or (1S,3'R,6'R,7'S,8'E,11'S,18'R)-6-chloro-N-(dimethylsulfamoyl)-18'-hydroxy-7'-methoxy-16'-oxo-3,4-dihydro-2H-spiro[naphthalene-1,25'-[23]oxa[1,15]diazapentacyclo[17.7.2.0~3,6~.0~11,15~.0~22,27~]octacosa[8,19,21,27]tetraene]-18'-carboxamide

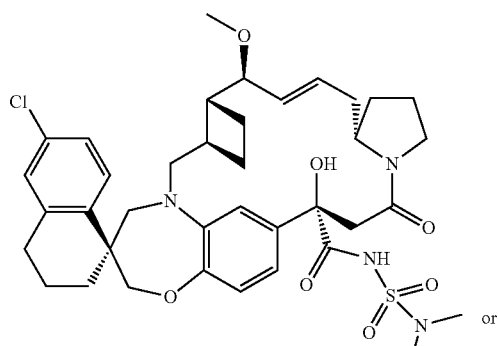

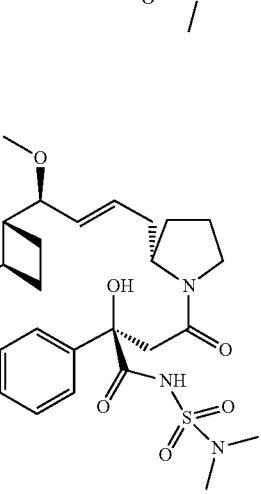

The title compound (6.3 mg, 32%) was synthesized from the product obtained in step 4 ((1S,3'R,6'R,7'S,8'E,11'S,18'S)-6-chloro-18'-hydroxy-7'-methoxy-16'-oxo-3,4-dihydro-2H-spiro[naphthalene-1,25'-[23]oxa[1,15]diazapentacyclo[17.7.2.0~3,6~.0~11,15~.0~22,27~]octacosa[8,19,21,27]tetraene]-18'-carboxylic acid or (1S,3'R,6'R,7'S,8'E,11'S,18'R)-6-chloro-18'-hydroxy-7-methoxy-16'-oxo-3,4-dihydro-2H-spiro[naphthalene-1,25'-[23]oxa[1,15]diazapentacyclo[17.7.2.0~3,6~.0~11,15~.0~22,27~] octacosa[8,19,21,27] tetraene]-18'-carboxylic acid) and N,N-dimethylsulfamide through a procedure similar to that used for the synthesis of Example 5. $^1$H NMR (300 MHz, CDCl$_3$) δ ppm 8.93 (s, 1H), 7.76 (d, J=8.5 Hz, 1H), 7.18 (dd, J=2.3, 8.5 Hz, 1H), 7.09 (d, J=2.3 Hz, 1H), 7.05-7.00 (m, 1H), 6.90 (d, J=8.3 Hz, 1H), 6.84 (s, 1H), 6.56-6.42 (m, 2H), 5.68 (ddd, J=1.5, 9.5, 15.1 Hz, 1H), 4.10-3.93 (m, 3H), 3.85 (dd, J=2.1, 9.4 Hz, 1H), 3.81-3.58 (m, 4H), 3.52-3.40 (m, 1H), 3.30 (d, J=14.3 Hz, 1H), 3.22 (s, 3H), 3.12-2.99 (m, 1H), 2.94 (s, 6H), 2.83-2.74 (m, 2H), 2.59-2.35 (m, 4H), 2.31-2.18 (m, 1H), 2.12-1.66 (m, 12H), 1.46-1.34 (m, 2H). LRMS: (ESI, +ve ion) m/z 741.2 (M+H)$^+$.

Example 184

(1S,3'R,6'R,7'S,15'R)-6-CHLORO-7'-(2-(3,3-DIFLUORO-1-AZETIDINYL)ETHOXY)-N-(DIMETHYLSULFAMOYL)-15'-HYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[16,18,24]TRIENE]-15'-CARBOXAMIDE

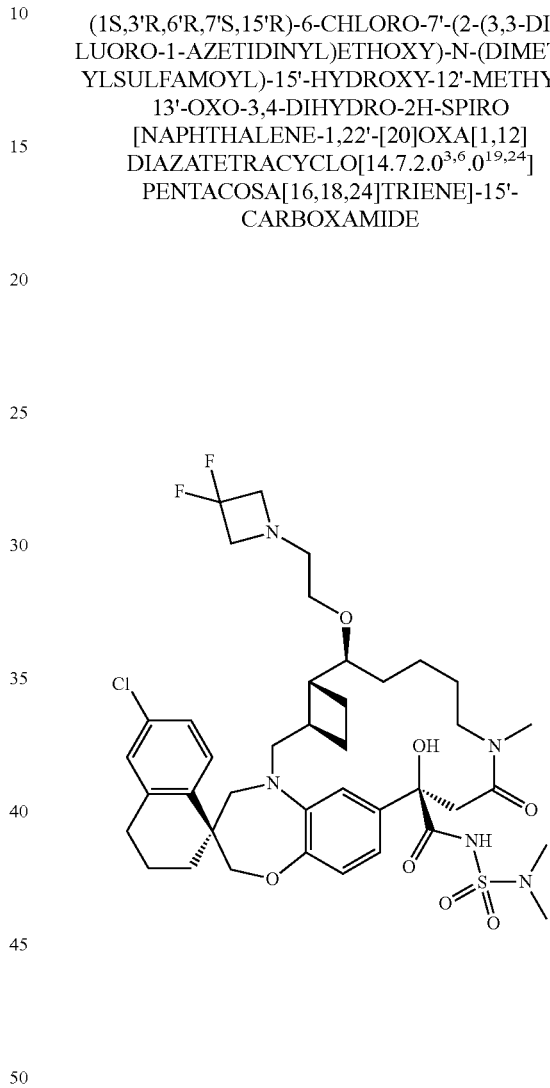

The title compound (9.1 mg, 91%) was synthesized from (1S,3'R,6'R,7'S,8'E,15'R)-6-chloro-7'-(2-(3,3-difluoro-1-azetidinyl)ethoxy)-N-(dimethylsulfamoyl)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide (Example 179) via hydrogenation with platinum oxide through a procedure similar to that used for the synthesis of Example 39. $^1$H NMR (300 MHz, CDCl$_3$) δ ppm 8.94 (br s, 1H), 7.76 (d, J=8.5 Hz, 1H), 7.17 (dd, J=2.3, 8.6 Hz, 1H), 7.09-7.04 (m, 3H), 6.91 (d, J=8.2 Hz, 1H), 6.46 (d, J=2.0 Hz, 1H), 4.10-3.97 (m, 2H), 3.79-3.38 (m, 11H), 3.23 (d, J=14.2 Hz, 1H), 3.07-2.89 (m+s, 11H), 2.81-2.73 (m, 3H), 2.56-2.34 (m, 3H), 2.10-1.33 (m, 15H). LRMS: (ESI, +ve ion) m/z 822.3 (M+H)$^+$.

Example 185

(1S,3'R,6'R,7'S,8'E,15'R)-6-CHLORO-N-(DIETH-YLSULFAMOYL)-7'-(2-(3,3-DIFLUORO-1-AZE-TIDINYL)ETHOXY)-15'-HYDROXY-12'-METHYL-13'-OXO-3,4-DIHYDRO-2H-SPIRO[NAPHTHALENE-1,22'-[20]OXA[1,12]DIAZATETRACYCLO [14.7.2.0$^{3,6}$.0$^{19,24}$]PENTACOSA[8,16,18,24]TETRAENE]-15'-CARBOXAMIDE

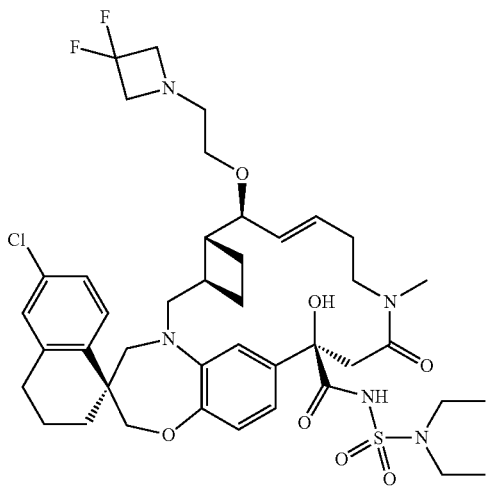 [SMILES: CCN(CC)S(=O)(=O)NC(=O)[C@@]1(O)CC(=O)N(C)CC/C=C/[C@H](OCCN2CC(F)(F)C2)[C@@H]2CC[C@H]2CN2C[C@@]3(CCCc4cc(Cl)ccc43)COc3ccc1cc32]

The title compound as TFA salt (14.3 mg, 31%) was synthesized from (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid (Example 175, step 2) and N,N-diethylsulfamide through a procedure similar to that used for the synthesis of Example 5. $^1$H NMR (300 MHz, CD$_2$Cl$_2$) δ ppm 8.98 (s, 1H), 7.72 (d, J=8.6 Hz, 1H), 7.16 (dd, J=2.3, 8.6 Hz, 1H), 7.08 (d, J=2.2 Hz, 1H), 6.97 (dd, J=2.0, 8.3 Hz, 1H), 6.88-6.81 (m, 1H), 6.51-6.34 (m, 2H), 5.72-5.59 (m, 1H), 4.06-3.68 (m, 8H), 3.64-3.46 (m, 5H), 3.42-3.03 (m, 10H), 2.95 (s, 3H), 2.86-2.58 (m, 3H), 2.53-2.23 (m, 4H), 2.10-1.68 (m, 7H), 1.46-1.29 (m, 1H), 1.06 (t, J=7.2 Hz, 6H). LRMS: (ESI, +ve ion) m/z 848.1 (M+H)$^+$.

Example 186

(1S,3'R,6'R,7'S,8'E,15'R)-6-CHLORO-7'-(2-(3,3-DIFLUORO-1-AZETIDINYL)ETHOXY)-15'-HYDROXY-N-((2-METHOXYETHYL)(METHYL)SULFAMOYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

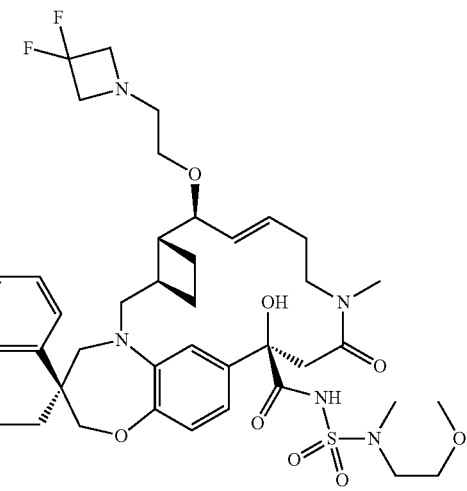

The title compound (27 mg, 64%) was synthesized from (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid (Example 175, step 2) and [(2-methoxyethyl)(methyl)sulfamoyl]amine through a procedure similar to that used for the synthesis of Example 5. $^1$H NMR (300 MHz, CD$_2$Cl$_2$) δ ppm 9.33-9.14 (m, 1H), 7.73 (d, J=8.5 Hz, 1H), 7.16 (dd, J=2.3, 8.5 Hz, 1H), 7.08 (d, J=2.2 Hz, 1H), 6.98 (dd, J=2.0, 8.3 Hz, 1H), 6.85 (d, J=8.2 Hz, 1H), 6.56 (br s, 1H), 6.52 (d, J=1.9 Hz, 1H), 6.43-6.28 (m, 1H), 5.66 (ddd, J=1.3, 9.5, 15.1 Hz, 1H), 4.06-3.95 (m, 2H), 3.83 (br d, J=9.6 Hz, 1H), 3.71 (br d, J=14.3 Hz, 1H), 3.65-3.23 (m, 17H), 3.21-3.03 (m, 2H), 2.96 (s, 3H), 2.88 (s, 3H), 2.81-2.57 (m, 5H), 2.54-2.22 (m, 4H), 2.09-1.68 (m, 7H), 1.46-1.32 (m, 1H). LRMS: (ESI, +ve ion) m/z 864.0 (M+H)$^+$.

Example 187

(1S,3'R,6'R,7'S,8'E,15'R)-6-CHLORO-7'-(3-(3,3-DIFLUORO-1-AZETIDINYL)PROPOXY)-N-(DIMETHYLSULFAMOYL)-15'-HYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

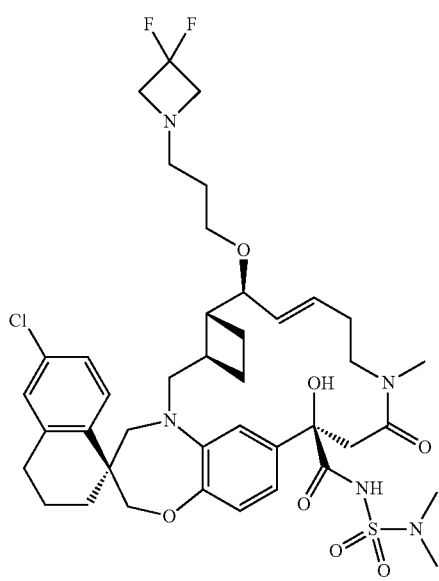 [SMILES: CN1CC/C=C/[C@H](OCCCN2CC(F)(F)C2)[C@@H]2CC[C@H]2CN2C[C@@]3(CCCc4cc(Cl)ccc43)COc3ccc(cc32)[C@@](O)(C(=O)NS(=O)(=O)N(C)C)CC1=O]

Step 1: Methyl(1S,3'R,6'R,7'S,8'E,15'R)-6-chloro-15'-hydroxy-7'-(2-bromopropoxy)-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate

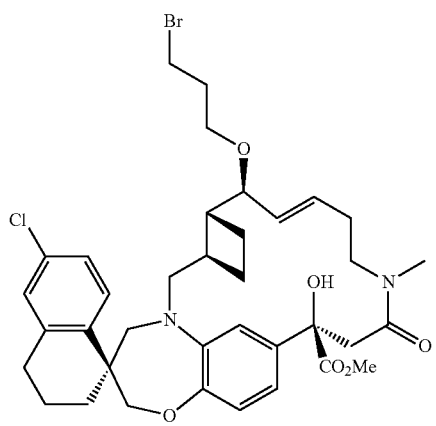 [SMILES: COC(=O)[C@@]1(O)CC(=O)N(C)CC/C=C/[C@H](OCCCBr)[C@@H]2CC[C@H]2CN2C[C@@]3(CCCc4cc(Cl)ccc43)COc3ccc1cc32]

The title compound (116 mg, 69%) was synthesized from methyl (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 1, step 7) and 3-bromopropyl trifluoromethanesulfonate through a procedure similar to that used for the synthesis of Example 173, Step 1. LRMS: (ESI, +ve ion) m/z 731.0 (M+H)$^+$. Note: 3-bromopropyl trifluoromethanesulfonate was synthesized from 3-bromopropan-1-ol through a procedure similar to that used for the synthesis of 2-bromoethyl trifluoromethanesulfonate (procedure described in Example 173, step 1).

Step 2: Methyl (1S,3'R,6'R,7'S,8'E,15'R)-6-chloro-7'-(2-(3,3-difluoro-1-azetidinyl)propoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate

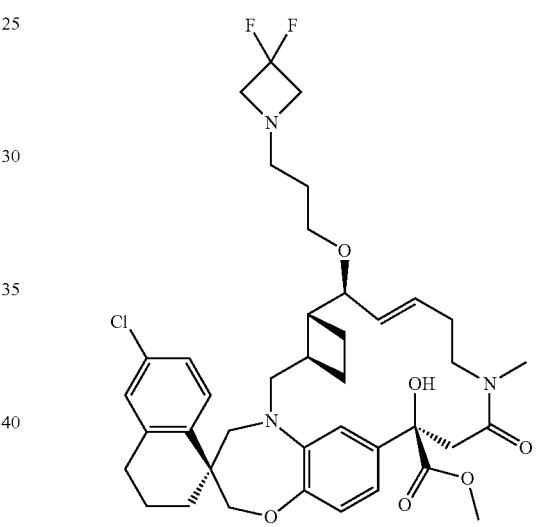

The title compound (91 mg, 81%) was synthesized from methyl (1S,3'R,6'R,7'S,8'E,15'R)-6-chloro-15'-hydroxy-7'-(2-bromopropoxy)-12'-methyl-13'-oxo-3,4-dihydro-2H-spiro[naphthalene-1,22'-[20]oxa[1,12]diazatetracyclo[14.7.2.0$^{3,6}$.0$^{19,24}$] pentacosa[8,16,18,24]tetraene]-15'-carboxylate and 3,3-difluoroazetidine hydrochloride through a procedure similar to that used for the synthesis of Example 175, Step 1. $^1$H NMR (300 MHz, CDCl$_3$) δ ppm 7.74 (d, J=8.5 Hz, 1H), 7.16 (dd, J=2.3, 8.5 Hz, 1H), 7.11 (dd, J=2.0, 8.3 Hz, 1H), 7.07 (d, J=2.2 Hz, 1H), 6.90 (d, J=8.3 Hz, 1H), 6.51 (d, J=1.9 Hz, 1H), 6.35-6.17 (m, 1H), 5.76-5.61 (m, 2H), 4.02 (s, 2H), 3.86-3.41 (m+s, 13H), 3.38-3.27 (m, 2H), 3.22-2.97 (m+s, 5H), 2.84-2.56 (m, 6H), 2.49-2.37 (m, 2H), 2.35-2.22 (m, 1H), 2.11-1.57 (m, 9H), 1.46-1.32 (m, 1H). LRMS: (ESI, +ve ion) m/z 742.3 (M+H)$^+$, 764.2 (M+Na)$^+$.

Step 3: (1S,3'R,6'R,7'S,8'E,15'R)-6-chloro-7'-(2-(3,3-difluoro-1-azetidinyl)propoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic Acid Step 4: (1S,3'R,6'R,7'S,8'E,15'R)-6-chloro-7'-(3-(3,3-difluoro-1-azetidinyl)propoxy)-n-(dimethylsulfamoyl)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide

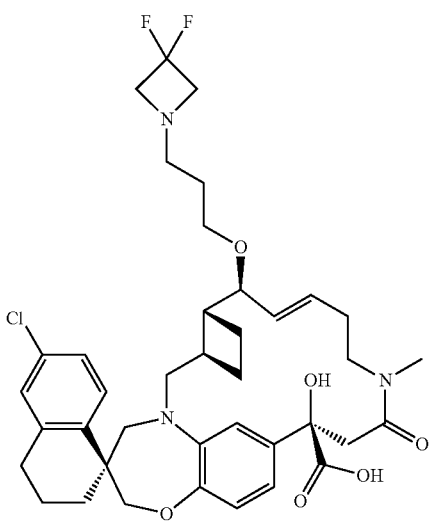 [SMILES: CN1CC/C=C/[C@H](OCCCN2CC(F)(F)C2)[C@@H]2CC[C@H]2CN2C[C@@]3(CCCc4cc(Cl)ccc43)COc3ccc(cc32)[C@@](O)(C(=O)O)CC1=O]

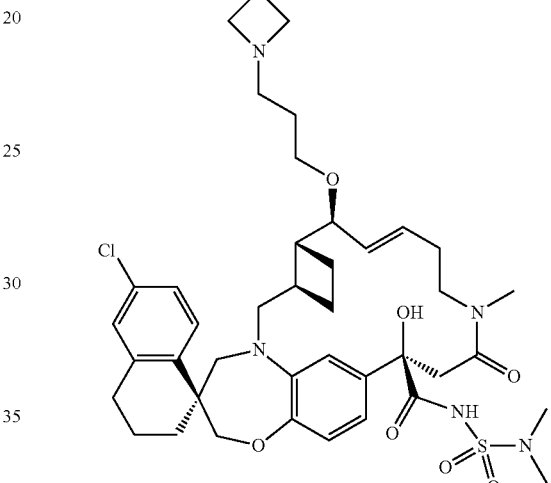

The title compound (89 mg, 100%) was synthesized from methyl (1S,3'R,6'R,7'S,8'E,15'R)-6-chloro-7'-(2-(3,3-difluoro-1-azetidinyl)propoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate via saponification through a procedure similar to that used for the synthesis of Example 175, Step 2. $^1$H NMR (300 MHz, CDCl$_3$) δ ppm 7.73 (d, J=8.5 Hz, 1H), 7.17 (dd, J=2.3, 8.5 Hz, 1H), 7.12-7.03 (m, 2H), 6.89 (d, J=8.2 Hz, 1H), 6.66 (d, J=1.6 Hz, 1H), 6.44-6.29 (m, 1H), 5.74-5.61 (m, 1H), 4.08-3.96 (m, 2H), 3.93 (br d, J=9.1 Hz, 1H), 3.83-3.26 (m, 11H), 3.23-2.97 (m+s, 5H), 2.84-2.55 (m, 6H), 2.45-2.23 (m, 3H), 2.10-1.78 (m, 6H), 1.78-1.63 (m, 3H), 1.46-1.33 (m, 1H). LRMS: (ESI, +ve ion) m/z 728.2 (M+H)$^+$.

The title compound as TFA salt (63.4 mg, 62%) was synthesized from (1S,3'R,6'R,7'S,8'E,15'R)-6-chloro-7'-(2-(3,3-difluoro-1-azetidinyl)propoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid and N,N-dimethylsulfamide through a procedure similar to that used for the synthesis of Example 5. $^1$H NMR (300 MHz, CD$_2$Cl$_2$) δ ppm 8.97 (s, 1H), 7.73 (d, J=8.6 Hz, 1H), 7.16 (dd, J=2.3, 8.4 Hz, 1H), 7.08 (d, J=2.2 Hz, 1H), 6.99 (dd, J=2.0, 8.3 Hz, 1H), 6.89-6.83 (m, 1H), 6.50 (d, J=1.9 Hz, 1H), 6.45-6.28 (m, 1H), 5.67 (ddd, J=1.2, 9.5, 15.1 Hz, 1H), 4.62-4.41 (m, 4H), 4.07-3.94 (m, 2H), 3.86 (d, J=8.3 Hz, 1H), 3.71 (br d, J=14.3 Hz, 1H), 3.65-3.43 (m, 4H), 3.38-3.23 (m, 4H), 3.21-3.03 (m, 2H), 2.96 (s, 3H), 2.86 (s, 6H), 2.82-2.72 (m, 2H), 2.72-2.59 (m, 1H), 2.50 (d, J=16.7 Hz, 1H), 2.46-2.36 (m, 2H), 2.35-2.22 (m, 1H), 2.10-1.68 (m, 9H), 1.46-1.32 (m, 1H). LRMS: (ESI, +ve ion) m/z 834.2 (M+H)$^+$.

Example 188

(1S,3'R,6'R,7'S,8'E,15'R)-6-CHLORO-7'-(2-(DIMETHYLAMINO)-2-OXOETHOXY)-N-(DIMETHYLSULFAMOYL)-15'-HYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

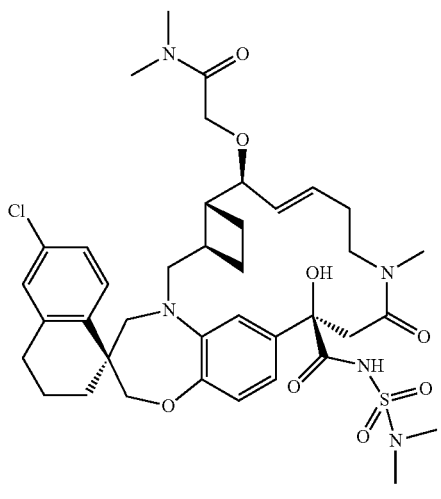 [SMILES: CN(C)C(=O)CO[C@H]1/C=C/CCN(C)C(=O)C[C@](O)(C(=O)NS(=O)(=O)N(C)C)c2ccc3c(c2)N(C[C@@H]2CC[C@H]21)C[C@@]1(CCCc2cc(Cl)ccc21)CO3]

To a stirred solution of (1S,3'R,6'R,7'S,8'E,15'R)-6-chloro-N-(dimethylsulfamoyl)-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide (Example 43 step 3, 0.037 g, 0.053 mmol) in THF (0.694 ml) was added sodium bis(trimethylsilyl)amide (1M in THF) (0.211 ml, 0.211 mmol) followed by 2-bromo-N,N-dimethylacetamide (0.035 g, 0.211 mmol). The reaction mixture was stirred at RT for 15 min. 4 additional equivalents of 2-bromo-N,N-dimethylacetamide were added and the reaction mixture was stirred at RT for 15 min. The reaction mixture was diluted with a saturated solution of NH$_4$Cl and extracted with EtOAc (3×). The organic layer was washed with brine, dried over MgSO$_4$, filtered and concentrated in vacuo. The crude material was purified by flash column chromatography, eluting with a gradient of 0% to 5% methanol in DCM, to provide the title compound (0.0098 g, 23.62% yield) as a white solid. $^1$H NMR (300 MHz, CD$_2$Cl$_2$) δ ppm 8.93 (br s, 1H), 7.73 (d, J=8.5 Hz, 1H), 7.16 (dd, J=2.3, 8.5 Hz, 1H), 7.08 (d, J=2.2 Hz, 1H), 6.99 (dd, J=2.0, 8.2 Hz, 1H), 6.86 (d, J=8.2 Hz, 1H), 6.50 (d, J=1.9 Hz, 1H), 6.47-6.34 (m, 1H), 5.77-5.64 (m, 1H), 4.12-3.89 (m, 4H), 3.72 (br d, J=14.5 Hz, 1H), 3.66-3.48 (m, 2H), 3.33 (d, J=14.3 Hz, 1H), 3.21-3.05 (m, 2H), 2.97 (s, 3H), 2.96 (s, 3H), 2.91 (s, 2H), 2.83 (s, 6H), 2.81-2.58 (m, 5H), 2.55-2.24 (m, 4H), 2.10-1.70 (m, 7H), 1.47-1.32 (m, 1H). LRMS: (ESI, +ve ion) m/z 786.2 (M+H)$^+$.

Example 189

(1S,3'R,6'R,7'S,8'E,15'R)-6-CHLORO-7'-(2-(3,3-DIFLUORO-1-AZETIDINYL)ETHOXY)-15'-HYDROXY-12'-METHYL-N-(METHYLSULFAMOYL)-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

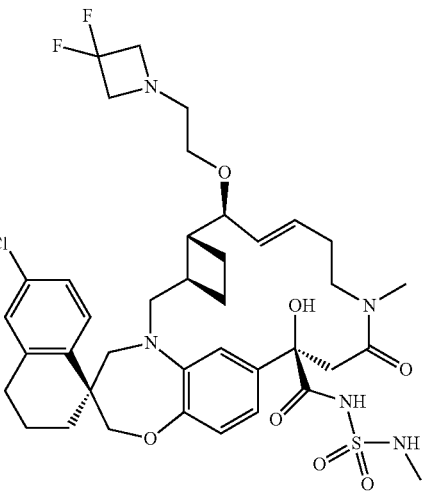

The title compound as TFA salt (54.5 mg, 79%) was synthesized from (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid (Example 175, step 2) and N-methylsulfamide through a procedure similar to that used for the synthesis of Example 5. $^1$H NMR (300 MHz, CD$_2$Cl$_2$) δ ppm 9.00 (br s, 1H), 7.72 (d, J=8.5 Hz, 1H), 7.15 (dd, J=2.3, 8.5 Hz, 1H), 7.08 (d, J=2.2 Hz, 1H), 6.98 (dd, J=2.0, 8.2 Hz, 1H), 6.85 (d, J=8.2 Hz, 1H), 6.56-6.42 (m, 2H), 6.40-6.30 (m, 1H), 5.66 (ddd, J=1.8, 9.8, 15.5 Hz, 1H), 4.72-4.48 (m, 3H), 4.12 (dd, J=1.5, 9.6 Hz, 1H), 4.07-3.99 (m, 1H), 3.96-3.89 (m, 1H), 3.75-3.47 (m, 9H), 3.36-3.24 (m, 2H), 3.21-3.01 (m, 2H), 2.97 (s, 3H), 2.81-2.58 (m, 3H), 2.49 (d, J=16.7 Hz, 1H), 2.42-2.23 (m+s, 6H), 2.11-1.67 (m, 7H), 1.45-1.31 (m, 1H). LRMS: (ESI, +ve ion) m/z 806.1 (M+H)$^+$.

Example 190

(1S,3'R,6'R,7'S,8'E,15'R)-6-CHLORO-7'-(2-(3,3-DIFLUORO-1-AZETIDINYL)ETHOXY)-15'-HYDROXY-12'-METHYL-13'-OXO-N-SULFAMOYL-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

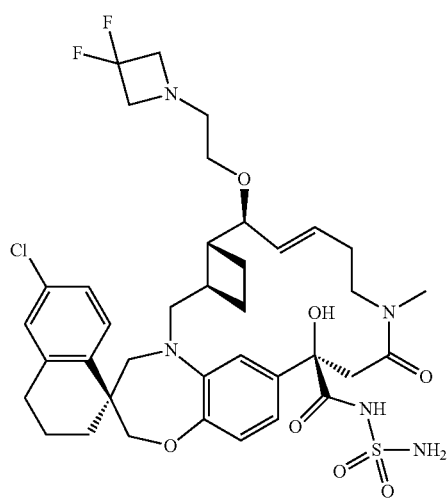 [SMILES: CN1CC/C=C/[C@H](OCCN2CC(F)(F)C2)[C@@H]2CC[C@H]2CN2C[C@@]3(CCCc4cc(Cl)ccc43)COc3ccc(cc32)[C@@](O)(C(=O)NS(N)(=O)=O)CC1=O]

The title compound as TFA salt (58 mg, 86%) was synthesized from (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$] pentacosa[8,16,18,24]tetraene]-15'-carboxylic acid (Example 175, step 2) and sulfamide through a procedure similar to that used for the synthesis of Example 5. $^1$H NMR (300 MHz, CD$_2$Cl$_2$) δ ppm 9.21 (br s, 1H), 7.72 (d, J=8.5 Hz, 1H), 7.15 (dd, J=2.3, 8.6 Hz, 1H), 7.08 (d, J=2.3 Hz, 1H), 7.00-6.91 (m, 1H), 6.89-6.82 (m, 1H), 6.55-6.41 (m, 2H), 5.86 (br s, 1H), 5.67 (ddd, J=1.5, 9.6, 15.2 Hz, 1H), 4.77-4.51 (m, 4H), 4.11 (dd, J=2.0, 9.7 Hz, 1H), 4.01 (s, 2H), 3.79-3.46 (m, 7H), 3.43-3.25 (m, 2H), 3.20-3.11 (m, 1H), 3.05 (dd, J=9.8, 15.3 Hz, 1H), 2.97 (s, 3H), 2.87-2.72 (m, 2H), 2.72-2.58 (m, 1H), 2.50 (d, J=16.8 Hz, 1H), 2.46-2.23 (m, 3H), 2.11-1.68 (m, 7H), 1.45-1.31 (m, 1H). LRMS: (ESI, +ve ion) m/z 792.2 (M+H)$^+$.

Example 191

(1S,3'R,6'R,7'S,8'E,15'R)-6-CHLORO-7'-(2-(2,2-DIFLUOROETHOXY)ETHOXY)-N-(DIMETHYLSULFAMOYL)-15'-HYDROXY-12'-METHYL-13'-OXO-3,4-DIHYDRO-2H-SPIRO[NAPHTHALENE-1,22'-[20]OXA[1,12]DIAZATETRACYCLO [14.7.2.0$^{3,6}$.0$^{19,24}$]PENTACOSA[8,16,18,24]TETRAENE]-15'-CARBOXAMIDE

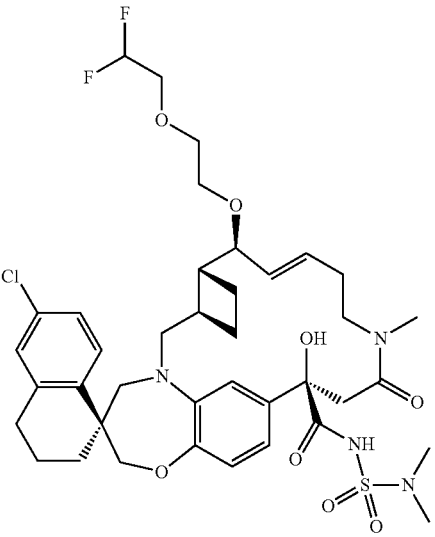 [SMILES: CN1CC/C=C/[C@H](OCCOCC(F)F)[C@@H]2CC[C@H]2CN2C[C@@]3(CCCc4cc(Cl)ccc43)COc3ccc(cc32)[C@@](O)(C(=O)NS(=O)(=O)N(C)C)CC1=O]

Step 1: Methyl(1S,3'R,6'R,7'S,8'E,15'R)-6-chloro-7'-(2-(2,2-difluoroethoxy)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$] pentacosa[8,16,18,24]tetraene]-15'-carboxylate

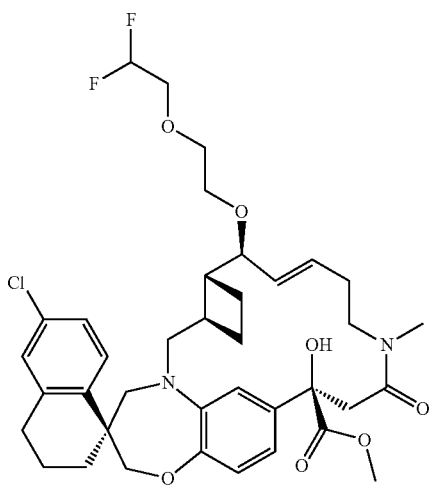 [SMILES: COC(=O)[C@@]1(O)CC(=O)N(C)CC/C=C/[C@H](OCCOCC(F)F)[C@@H]2CC[C@H]2CN2C[C@@]3(CCCc4cc(Cl)ccc43)COc3ccc1cc32]

In a vial, a stirred solution of methyl (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'- carboxylate (Example 1 step 7, 0.06 g, 0.098 mmol), 2-(2,2-difluoroethoxy)ethyl trifluoromethanesulfonate (0.127 g, 0.492 mmol) and 2,6-di-tert-butylpyridine (0.221 ml, 0.985 mmol) in dichloromethane (0.5 ml) was heated at 60° C. for 5 hrs. After cooling, the reaction mixture was then diluted with ethyl acetate and washed with 0.1N HCl (2×). The organic layer was washed with brine, dried over magnesium sulfate, filtered and concentrated. The crude material was absorbed onto a plug of silica gel and purified by chromatography through a Redi-Sep pre-packed silica gel column, eluting with a gradient of 0% to 5% MeOH in DCM, to provide the title compound (0.037 g, 52.4% yield) as white solid. $^1$H NMR (300 MHz, CD$_2$Cl$_2$) δ ppm 7.74 (d, J=8.5 Hz, 1H), 7.17 (dd, J=2.3, 8.5 Hz, 1H), 7.11 (dd, J=2.0, 8.3 Hz, 1H), 7.08 (d, J=2.2 Hz, 1H), 6.90 (d, J=8.3 Hz, 1H), 6.51 (d, J=1.9 Hz, 1H), 6.37-6.23 (m, 1H), 6.1, 5.91, 5.74-5.63 (m, 3H), 4.02 (s, 2H), 3.91 (dd, J=2.2, 9.5 Hz, 1H), 3.80-3.45 (m+s, 14H), 3.31 (d, J=14.3 Hz, 1H), 3.23-2.97 (m+s, 5H), 2.84-2.55 (m, 4H), 2.54-2.23 (m, 3H), 2.11-1.67 (m, 7H), 1.46-1.35 (m, 1H). LRMS: (ESI, +ve ion) m/z 716.2 (M+H)$^+$, 739.1 (M+Na)$^+$.

Note: 2-(2,2-difluoroethoxy)ethanol was synthesized from 2,2-difluoroethanol: ref WO2009026537. 2-(2,2-difluoroethoxy)ethyl trifluoromethanesulfonate was synthesized from 2-(2,2-difluoroethoxy)ethanol: ref WO2016046164 (A1).

Step 2: (1S,3'R,6'R,7'S,8'E,15'R)-6-chloro-7'-(2-(2,2-difluoroethoxy)ethoxy)-15'-hydroxy-12'-methyl-13'-oxo-3,4-dihydro-2H-spiro[naphthalene-1,22'-[20]oxa[1,12] diazatetracyclo[14.7.2.0$^{3,6}$.0$^{19,24}$]pentacosa[8,16,18,24]tetraene]-15'-carboxylic acid

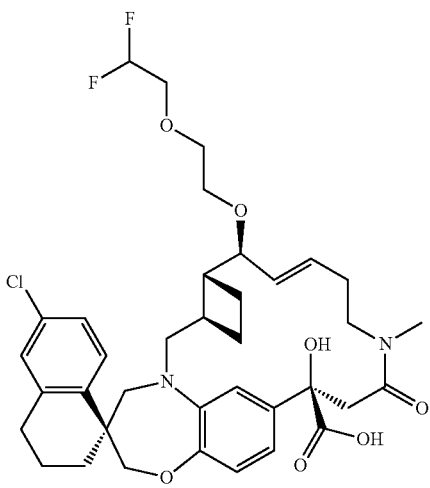 [SMILES: CN1CC/C=C/[C@H](OCCOCC(F)F)[C@@H]2CC[C@H]2CN2C[C@@]3(CCCc4cc(Cl)ccc43)COc3ccc(cc32)[C@@](O)(C(=O)O)CC1=O]

The title compound (36 mg, 99%) was synthesized from methyl (1S,3'R,6'R,7'S,8'E,15'R)-6-chloro-7'-(2-(2,2-difluoroethoxy)ethoxy)-15'-hydroxy-12'-methyl-13'-oxo-3,4-dihydro-2H-spiro[naphthalene-1,22'-[20]oxa[1,12] diazatetracyclo[14.7.2.0$^{3,6}$.0$^{19,24}$]pentacosa[8,16,18,24] tetraene]-15'-carboxylate via saponification through a procedure similar to that used for the synthesis of Example 175, Step 2. $^1$H NMR (300 MHz, CDCl$_3$) δ ppm 7.73 (d, J=8.5 Hz, 1H), 7.17 (dd, J=2.3, 8.4 Hz, 1H), 7.09-7.02 (m, 2H), 6.94-6.87 (m, 2H), 6.63 (d, J=1.8 Hz, 1H), 6.45-6.30 (m, 1H), 6.09, 5.90, 5.75-5.63 (m, 2H), 4.07-3.93 (m, 3H), 3.80-3.43 (m, 10H), 3.30 (d, J=14.3 Hz, 1H), 3.23-2.99 (m+s, 5H), 2.84-2.56 (m, 4H), 2.53-2.24 (m, 3H), 2.10-1.65 (m, 7H), 1.46-1.34 (m, 1H). LRMS: (ESI, +ve ion) m/z 703.1 (M+H)$^+$.

Step 3: (1S,3'R,6'R,7'S,8'E,15'R)-6-chloro-7'-(2-(2,2-difluoroethoxy)ethoxy)-N-(dimethylsulfamoyl)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide

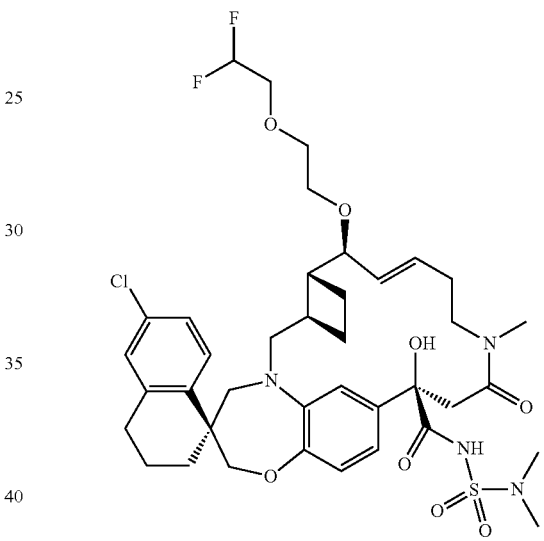

The title compound as TFA salt (27.2 mg, 59%) was synthesized from (1S,3'R,6'R,7'S,8'E,15'R)-6-chloro-7'-(2-(2,2-difluoroethoxy)ethoxy)-15'-hydroxy-12'-methyl-13'-oxo-3,4-dihydro-2H-spiro[naphthalene-1,22'-[20]oxa[1,12] diazatetracyclo[14.7.2.0$^{3,6}$.0$^{19,24}$]pentacosa[8,16,18,24]tetraene]-15'-carboxylic acid and N,N-dimethylsulfamide through a procedure similar to that used for the synthesis of Example 5. $^1$H NMR (300 MHz, CD$_2$Cl$_2$) δ ppm 8.94 (br s, 1H), 7.73 (d, J=8.5 Hz, 1H), 7.16 (dd, J=2.3, 8.5 Hz, 1H), 7.08 (d, J=2.3 Hz, 1H), 6.99 (dd, J=2.0, 8.2 Hz, 1H), 6.86 (d, J=8.2 Hz, 1H), 6.53 (d, J=2.0 Hz, 1H), 6.43-6.30 (m, 1H), 6.07, 5.88, 5.74-5.60 (m, 2H), 4.07-3.95 (m, 2H), 3.88 (dd, J=1.8, 9.6 Hz, 1H), 3.76-3.50 (m, 9H), 3.43-3.29 (m, 2H), 3.21-3.04 (m, 2H), 2.97 (s, 3H), 2.86 (s, 6H), 2.82-2.57 (m, 3H), 2.50 (d, J=16.8 Hz, 1H), 2.46-2.23 (m, 3H), 2.09-1.66 (m, 7H), 1.47-1.33 (m, 1H). LRMS: (ESI, +ve ion) m/z 809.1 (M+H)$^+$.

449

Example 192

(1S,3'R,6'R,7'S,8'E,15'R)-6-CHLORO-7'-(2-(3,3-DIFLUORO-1-AZETIDINYL)ETHOXY)-15'-HYDROXY-12'-METHYL-N-(4-MORPHOLINYLSULFONYL)-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

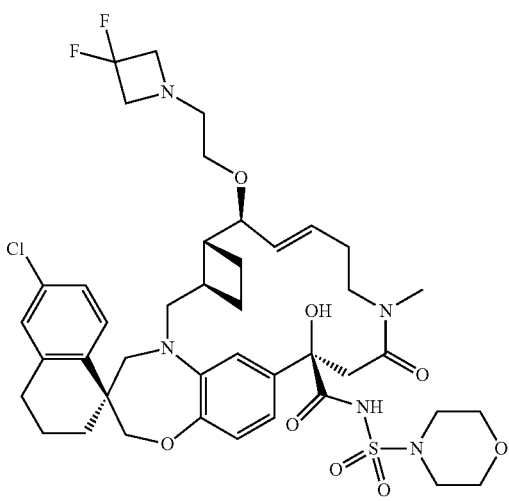 [SMILES: CN1CC/C=C/[C@H](OCCN2CC(F)(F)C2)[C@@H]2CC[C@H]2CN2C[C@@]3(CCCc4cc(Cl)ccc43)COc3ccc(cc32)[C@@](O)(C(=O)NS(=O)(=O)N2CCOCC2)CC1=O]

The title compound as TFA salt (16.2 mg, 41%) was synthesized from (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid (Example 175, step 2) and morpholine-4-sulfonamide through a procedure similar to that used for the synthesis of Example 5. $^1$H NMR (400 MHz, CD$_2$Cl$_2$) δ ppm 9.00 (br s, 1H), 7.73 (d, J=8.4 Hz, 1H), 7.16 (dd, J=2.2, 8.5 Hz, 1H), 7.08 (d, J=2.2 Hz, 1H), 6.98 (dd, J=2.0, 8.2 Hz, 1H), 6.86 (d, J=8.2 Hz, 1H), 6.48 (d, J=2.0 Hz, 1H), 6.41-6.29 (m, 1H), 5.67 (ddd, J=1.4, 9.8, 15.1 Hz, 1H), 4.72-4.49 (m, 4H), 4.07-3.95 (m, 2H), 3.88 (br d, J=9.4 Hz, 1H), 3.82-3.71 (m, 2H), 3.70-3.50 (m, 8H), 3.48-3.25 (m, 5H), 3.20-3.05 (m, 4H), 2.97 (s, 3H), 2.85-2.61 (m, 3H), 2.54 (d, J=16.8 Hz, 1H), 2.47-2.37 (m, 2H), 2.36-2.27 (m, 1H), 2.09-1.68 (m, 7H), 1.44-1.33 (m, 1H). LRMS: (ESI, +ve ion) m/z 862.0 (M+H)$^+$.

450

Example 193

(1S,3'R,6'R,7'S,8'E,15'R)-6-CHLORO-N-(DIMETHYLSULFAMOYL)-7'-(2-(1,1-DIOXIDO-4-THIOMORPHOLINYL)ETHOXY)-15'-HYDROXY-12'-METHYL-13'-OXO-3,4-DIHYDRO-2H-SPIRO[NAPHTHALENE-1,22'-[20]OXA[1,12]DIAZATETRACYCLO [14.7.2.0$^{3,6}$.0$^{19,24}$]PENTACOSA[8,16,18,24]TETRAENE]-15'-CARBOXAMIDE

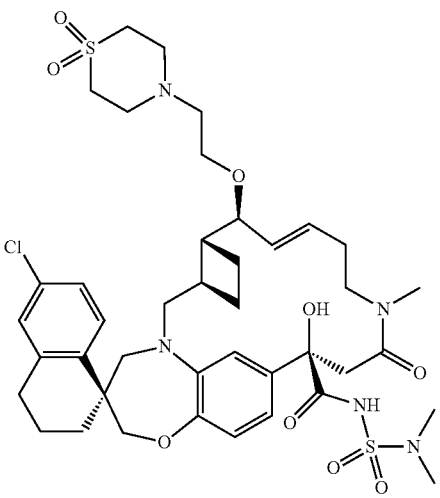 [SMILES: CN1CC/C=C/[C@H](OCCN2CCS(=O)(=O)CC2)[C@@H]2CC[C@H]2CN2C[C@@]3(CCCc4cc(Cl)ccc43)COc3ccc(cc32)[C@@](O)(C(=O)NS(=O)(=O)N(C)C)CC1=O]

Step 1: Methyl (1S,3'R,6'R,7'S,8'E,15'R)-6-chloro-7'-(2-(1,1-dioxido-4-thiomorpholinyl) ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate

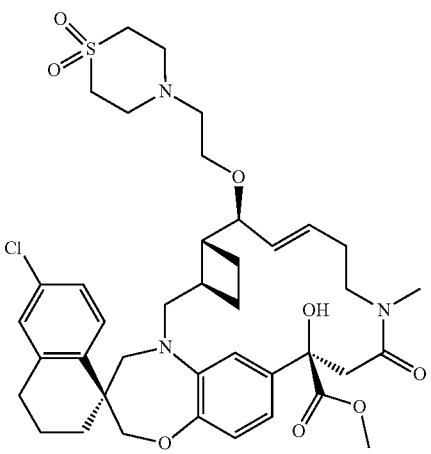 [SMILES: COC(=O)[C@@]1(O)CC(=O)N(C)CC/C=C/[C@H](OCCN2CCS(=O)(=O)CC2)[C@@H]2CC[C@H]2CN2C[C@@]3(CCCc4cc(Cl)ccc43)COc3ccc1cc32]

The title compound (41.1 mg, 76%) was synthesized from methyl (1S,3'R,6'R,7'S,8'E,15'R)-6-chloro-15'-hydroxy-7'-(2-bromoethoxy)-12'-methyl-13'-oxo-3,4-dihydro-2H-spiro[naphthalene-1,22'-[20]oxa[1,12]diazatetracyclo[14.7.2.0$^{3,6}$.0$^{19,24}$] pentacosa[8,16,18,24]tetraene]-15'-carboxylate (Example 173, step 1) and thiomorpholine 1,1-dioxide through a procedure similar to that used for the synthesis of Example 173, step 2. $^1$H NMR (300 MHz, CDCl$_3$) δ ppm 7.73 (d, J=8.5 Hz, 1H), 7.17 (dd, J=2.2, 8.5 Hz, 1H), 7.11 (dd, J=2.0, 8.3 Hz, 1H), 7.08 (d, J=2.2 Hz, 1H), 6.90 (d, J=8.2 Hz, 1H), 6.49 (d, J=1.9 Hz, 1H), 6.35-6.20 (m, 1H), 5.75-5.61 (m, 2H), 4.07-3.97 (m, 2H), 3.85 (br d, J=9.5 Hz, 1H), 3.80-3.71 (m, 4H), 3.70-3.49 (m, 4H), 3.47-3.38 (m, 1H), 3.31 (d, J=14.3 Hz, 1H), 3.22-3.02 (m, 10H), 3.00 (s, 3H), 2.85-2.64 (m, 5H), 2.60 (br d, J=16.7 Hz, 1H), 2.47-2.24 (m, 3H), 2.11-1.67 (m, 7H), 1.46-1.33 (m, 1H). LRMS: (ESI, +ve ion) m/z 770.0 (M+H)$^+$.

Step 2: (1S,3'R,6'R,7'S,8'E,15'R)-6-chloro-7'-(2-(1,1-dioxido-4-thiomorpholinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid

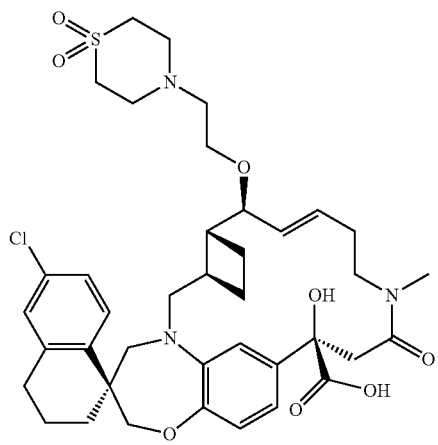 [SMILES: CN1CC/C=C/[C@H](OCCN2CCS(=O)(=O)CC2)[C@@H]2CC[C@H]2CN2C[C@@]3(CCCc4cc(Cl)ccc43)COc3ccc(cc32)[C@@](O)(C(=O)O)CC1=O]

The title compound (38 mg, 97%) was synthesized from methyl (1S,3'R,6'R,7'S,8'E,15'R)-6-chloro-7'-(2-(1,1-dioxido-4-thiomorpholinyl) ethoxy)-15'-hydroxy-12'-methyl-13'-oxo-3,4-dihydro-2H-spiro[naphthalene-1,22'-[20]oxa[1,12] diazatetracyclo[14.7.2.0$^{3,6}$.0$^{19,24}$] pentacosa[8,16,18,24]tetraene]-15'-carboxylate via saponification through a procedure similar to that used for the synthesis of Example 175, Step 2. $^1$H NMR (300 MHz, CDCl$_3$) δ ppm 7.76-7.70 (m, 1H), 7.17 (dd, J=2.2, 8.5 Hz, 1H), 7.10-7.03 (m, 2H), 6.90 (d, J=8.3 Hz, 1H), 6.61 (d, J=1.3 Hz, 1H), 6.46-6.31 (m, 1H), 5.76-5.60 (m, 1H), 4.09-3.93 (m, 3H), 3.81-3.39 (m, 6H), 3.30 (d, J=14.3 Hz, 1H), 3.25-3.04 (m, 10H), 3.01 (s, 3H), 2.85-2.65 (m, 5H), 2.59 (br d, J=16.5 Hz, 1H), 2.46-2.24 (m, 3H), 2.14-1.62 (m, 7H), 1.46-1.33 (m, 1H). LRMS: (ESI, +ve ion) m/z 755.9 (M+H)$^+$.

Step 3: (1S,3'R,6'R,7'S,8'E,15'R)-6-chloro-n-(dimethylsulfamoyl)-7'-(2-(1,1-dioxido-4-thiomorpholinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide

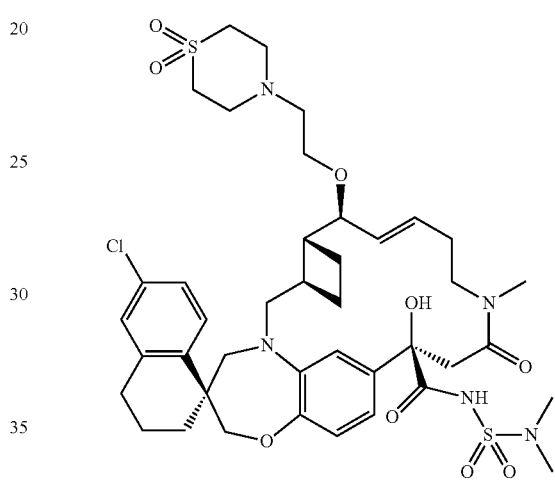

The title compound (14.3 mg, 34%) was synthesized from (1S,3'R,6'R,7'S,8'E,15'R)-6-chloro-7'-(2-(1,1-dioxido-4-thiomorpholinyl) ethoxy)-15'-hydroxy-12'-methyl-13'-oxo-3,4-dihydro-2H-spiro[naphthalene-1,22'-[20]oxa[1,12] diazatetracyclo[14.7.2.0$^{3,6}$.0$^{19,24}$]pentacosa[8,16,18,24]tetraene]-15'-carboxylic acid and N,N-dimethylsulfamide through a procedure similar to that used for the synthesis of Example 5. $^1$H NMR (300 MHz, CD$_2$Cl$_2$) δ ppm 8.95 (br s, 1H), 7.73 (d, J=8.5 Hz, 1H), 7.16 (dd, J=2.3, 8.6 Hz, 1H), 7.08 (d, J=2.2 Hz, 1H), 6.99 (dd, J=2.1, 8.3 Hz, 1H), 6.86 (d, J=8.3 Hz, 1H), 6.58 (br s, 1H), 6.51 (d, J=2.0 Hz, 1H), 6.44-6.28 (m, 1H), 5.73-5.60 (m, 1H), 4.07-3.94 (m, 2H), 3.84 (dd, J=1.3, 9.5 Hz, 1H), 3.71 (br d, J=14.5 Hz, 1H), 3.65-3.48 (m, 4H), 3.41-3.28 (m, 2H), 3.23-2.98 (m, 10H), 2.97 (s, 3H), 2.86 (s, 6H), 2.81-2.58 (m, 5H), 2.51 (d, J=16.7 Hz, 1H), 2.45-2.23 (m, 3H), 2.08-1.68 (m, 7H), 1.46-1.34 (m, 1H). LRMS: (ESI, +ve ion) m/z 862.0 (M+H)$^+$.

Example 194

(1S,3'R,6'R,7'S,8'E,15'R)-6-CHLORO-N-(DIMETHYLSULFAMOYL)-15'-HYDROXY-12'-METHYL-7'-(2-((3S)-3-METHYL-4-MORPHOLINYL)ETHOXY)-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

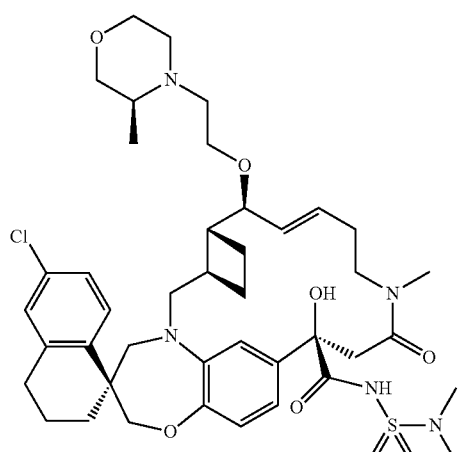

Step 1: Methyl(1S,3'R,6'R,7'S,8'E,15'R)-6-chloro-15'-hydroxy-12'-methyl-7'-(2-((3S)-3-methyl-4-morpholinyl)ethoxy)-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate

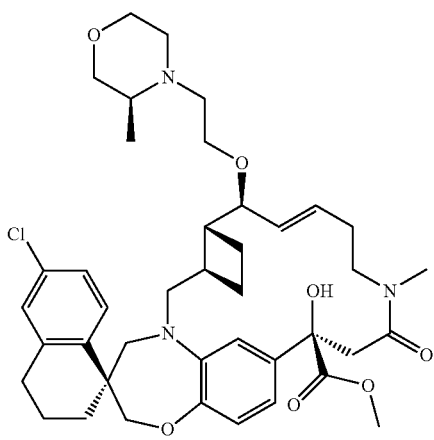 [SMILES: COC(=O)[C@@]1(O)CC(=O)N(C)CC/C=C/[C@H](OCCN2CCOC[C@@H]2C)[C@@H]2CC[C@H]2CN2C[C@@]3(CCCc4cc(Cl)ccc43)COc3ccc1cc32]

The title compound (21 mg, 64%) was synthesized from methyl (1S,3'R,6'R,7'S,8'E,15'R)-6-chloro-15'-hydroxy-7'-(2-bromoethoxy)-12'-methyl-13'-oxo-3,4-dihydro-2H-spiro[naphthalene-1,22'-[20]oxa[1,12]diazatetracyclo[14.7.2.0$^{3,6}$.0$^{19,24}$] pentacosa[8,16,18,24]tetraene]-15'-carboxylate (Example 173, step 1) and (S)-3-methylmorpholine through a procedure similar to that used for the synthesis of Example 173, step 2. $^1$H NMR (300 MHz, CDCl$_3$) δ ppm 7.74 (d, J=8.5 Hz, 1H), 7.17 (dd, J=2.3, 8.6 Hz, 1H), 7.11 (dd, J=2.0, 8.2 Hz, 1H), 7.07 (d, J=2.2 Hz, 1H), 6.90 (d, J=8.2 Hz, 1H), 6.51 (d, J=1.9 Hz, 1H), 6.35-6.20 (m, 1H), 5.75-5.63 (m, 2H), 4.02 (s, 2H), 3.90-3.84 (m, 1H), 3.83-3.50 (m+s, 11H), 3.47-3.38 (m, 1H), 3.34-3.01 (m, 4H), 3.00 (s, 3H), 2.96-2.23 (m, 12H), 2.10-1.68 (m, 7H), 1.47-1.32 (m, 1H), 1.00 (d, J=6.3 Hz, 3H). LRMS: (ESI, +ve ion) m/z 736.0 (M+H)$^+$.

Step 2: (1S,3'R,6'R,7'S,8'E,15'R)-6-chloro-15'-hydroxy-12'-methyl-7'-(2-((3S)-3-methyl-4-morpholinyl)ethoxy)-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid

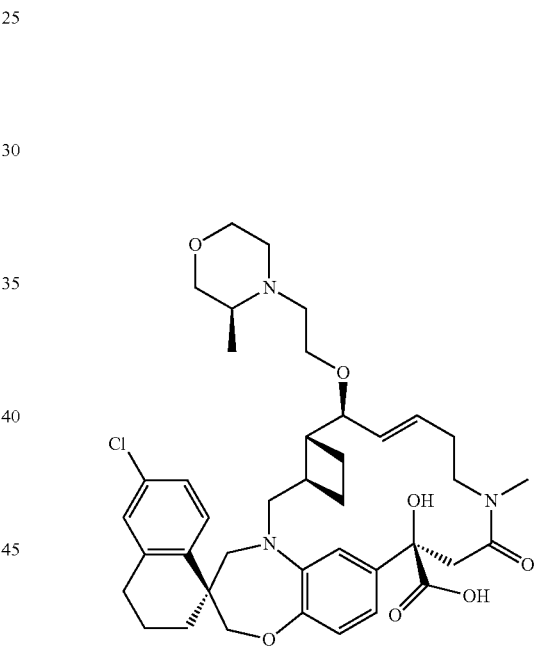

The title compound (19.5 mg, 98%) was synthesized from methyl (1S,3'R,6'R,7'S,8'E,15'R)-6-chloro-15'-hydroxy-12'-methyl-7'-(2-((3S)-3-methyl-4-morpholinyl)ethoxy)-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate via saponification through a procedure similar to that used for the synthesis of Example 175, Step 2. $^1$H NMR (300 MHz, CDCl$_3$) δ ppm 7.73 (d, J=8.5 Hz, 1H), 7.16 (dd, J=2.3, 8.6 Hz, 1H), 7.10-7.03 (m, 2H), 6.87 (d, J=8.2 Hz, 1H), 6.64 (d, J=1.3 Hz, 1H), 6.47-6.32 (m, 1H), 5.68 (br dd, J=9.5, 14.8 Hz, 1H), 4.11-3.02 (m, 21H), 3.01 (s, 3H), 2.85-2.64 (m, 3H), 2.58 (br d, J=16.7 Hz, 1H), 2.50-2.23 (m, 3H), 2.14-1.67 (m, 7H), 1.44-1.31 (m+d, 4H) LRMS: (ESI, +ve ion) m/z 722.0 (M+H)+.

Step 3: (1S,3'R,6'R,7'S,8'E,15'R)-6-chloro-n-(dimethylsulfamoyl)-15'-hydroxy-12'-methyl-7'-(2-((3S)-3-methyl-4-morpholinyl)ethoxy)-13'-oxo-3,4-dihydro-2H-spiro[naphthalene-1,22'-[20]oxa[1,12]diazatetracyclo[14.7.2.0³,⁶.0¹⁹,²⁴]pentacosa[8,16,18,24]tetraene]-15'-carboxamide

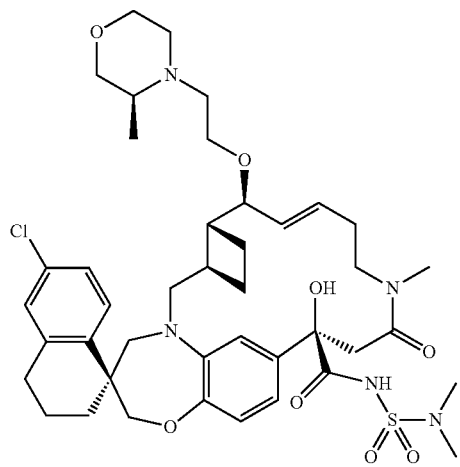 [SMILES: C[C@H]1COCCN1CCO[C@H]1/C=C/CCN(C)C(=O)C[C@](O)(C(=O)NS(=O)(=O)N(C)C)c2ccc3c(c2)N(C[C@@H]2CC[C@H]21)C[C@@]1(CCCc2cc(Cl)ccc21)CO3]

The title compound as TFA salt (7.3 mg, 30%) was synthesized from (1S,3'R,6'R,7'S,8'E,15'R)-6-chloro-15'-hydroxy-12'-methyl-7'-(2-((3S)-3-methyl-4-morpholinyl)ethoxy)-13'-oxo-3,4-dihydro-2H-spiro[naphthalene-1,22'-[20]oxa[1,12] diazatetracyclo[14.7.2.0³,⁶.0¹⁹,²⁴] pentacosa [8,16,18,24]tetraene]-15'-carboxylic acid and N,N-dimethylsulfamide through a procedure similar to that used for the synthesis of Example 5. ¹H NMR (300 MHz, CD₂Cl₂) δ ppm 8.96 (s, 1H), 7.72 (d, J=8.5 Hz, 1H), 7.16 (dd, J=2.2, 8.5 Hz, 1H), 7.08 (d, J=2.0 Hz, 1H), 7.02-6.95 (m, 1H), 6.86 (d, J=8.3 Hz, 1H), 6.49 (d, J=1.6 Hz, 1H), 6.45-6.30 (m, 1H), 5.77-5.57 (m, 1H), 4.07-3.83 (m, 6H), 3.80-3.40 (m, 9H), 3.36-3.28 (m, 2H), 3.23-3.07 (m, 4H), 2.97 (s, 3H), 2.86 (s, 6H), 2.81-2.60 (m, 3H), 2.56-2.24 (m, 4H), 2.10-1.69 (m, 7H), 1.46-1.29 (m, 4H). LRMS: (ESI, +ve ion) m/z 828.3 (M+H)+.

Example 195

(1S,3'R,6'R,7'S,8'E,15'R)-6-CHLORO-N-(DIMETHYLSULFAMOYL)-15'-HYDROXY-12'-METHYL-7'-(2-(6-OXA-1-AZASPIRO[3.3]HEPT-1-YL)ETHOXY)-13'-OXO-3,4-DIHYDRO-2H-SPIRO[NAPHTHALENE-1,22'-[20]OXA[1,12]DIAZATETRACYCLO [14.7.2.0³,⁶.0¹⁹,²⁴]PENTACOSA[8,16,18,24]TETRAENE]-15'-CARBOXAMIDE

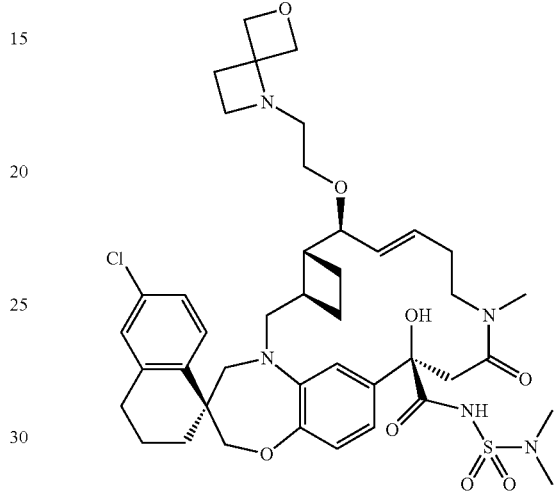

Step 1: Methyl(1S,3'R,6'R,7'S,8'E,15'R)-6-chloro-15'-hydroxy-12'-methyl-7'-(2-(6-oxa-1-azaspiro[3.3]hept-1-yl)ethoxy)-13'-oxo-3,4-dihydro-2H-spiro[naphthalene-1,22'-[20]oxa[1,12]diazatetracyclo [14.7.2.0³,⁶.0¹⁹,²⁴]pentacosa[8,16,18,24]tetraene]-15'-carboxylate

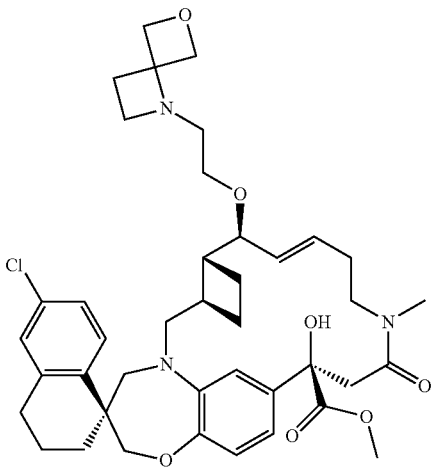 [SMILES: COC(=O)[C@@]1(O)CC(=O)N(C)CC/C=C/[C@H](OCCN2CCC23COC3)[C@@H]2CC[C@H]2CN2C[C@@]3(CCCc4cc(Cl)ccc43)COc3ccc1cc32]

To a solution of methyl (1S,3'R,6'R,7'S,8'E,15'R)-6-chloro-15'-hydroxy-7'-(2-bromoethoxy)-12'-methyl-13'-oxo-3,4-dihydro-2H-spiro[naphthalene-1,22'-[20]oxa[1,12] diazatetraciclo [14.7.2.0³,⁶.0¹⁹,²⁴]pentacosa[8,16,18,24]tetraene]-15'-carboxylate (Example 173, Step 1, 0.050 g, 0.070 mmol) in dimethyl sulfoxide (1.552 ml) was added N,N-diisopropylamine (0.122 ml, 0.698 mmol) and 6-oxa-1-azaspiro[3.3]heptane hemioxalate (0.161 g, 0.559 mmol). The reaction mixture was stirred at 55° C. for 1 h 30 then at 40° C. for 22 h. The reaction mixture was then partitioned between water and ethyl acetate. The aqueous phase was separated and further extracted with ethyl acetate (2×). The combined organic layers were washed with brine, dried over magnesium sulfate, filtered and concentrated. The crude material was absorbed onto a plug of silica gel and purified by chromatography through a Redi-Sep pre-packed silica gel column, eluting with a gradient of 0% to 60% acetone in hexanes, to provide the title compound (22 mg, 43%) as white solid. $^1$H NMR (400 MHz, CDCl$_3$) δ ppm 7.74 (d, J=8.4 Hz, 1H), 7.16 (dd, J=2.2, 8.5 Hz, 1H), 7.11 (dd, J=2.0, 8.2 Hz, 1H), 7.07 (d, J=2.0 Hz, 1H), 6.90 (d, J=8.2 Hz, 1H), 6.51 (d, J=1.8 Hz, 1H), 6.35-6.23 (m, 1H), 5.75-5.65 (m+br s, 2H), 4.96 (dd, J=7.1, 12.4 Hz, 2H), 4.59 (dd, J=4.5, 7.0 Hz, 2H), 4.02 (s, 2H), 3.89 (dd, J=2.2, 9.5 Hz, 1H), 3.79-3.72 (m+s, 4H), 3.68-3.51 (m, 4H), 3.43-3.35 (m, 1H), 3.31 (d, J=14.5 Hz, 1H), 3.20-3.11 (m, 3H), 3.05 (br dd, J=10.1, 15.2 Hz, 1H), 2.99 (s, 3H), 2.87-2.73 (m, 4H), 2.72-2.56 (m, 2H), 2.52-2.35 (m, 4H), 2.34-2.24 (m, 1H), 2.04-1.67 (m, 7H), 1.43-1.33 (m, 1H) LRMS: (ESI, +ve ion) m/z 734.1 (M+H)$^+$, 756.0 (M+H)$^+$.

Step 2: (1S,3'R,6'R,7'S,8'E,15'R)-6-chloro-15'-hydroxy-12'-methyl-7'-(2-(6-oxa-1-azaspiro[3.3]hept-1-yl)ethoxy)-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid

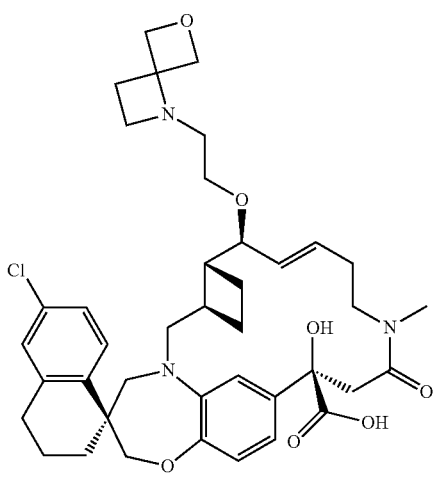 [SMILES: CN1CC/C=C/[C@H](OCCN2CCC23COC3)[C@@H]2CC[C@H]2CN2C[C@@]3(CCCc4cc(Cl)ccc43)COc3ccc(cc32)[C@@](O)(C(=O)O)CC1=O]

The title compound (21 mg, 97%) was synthesized from methyl (1S,3'R,6'R,7'S,8'E,15'R)-6-chloro-15'-hydroxy-12'-methyl-7'-(2-(6-oxa-1-azaspiro[3.3]hept-1-yl)ethoxy)-13'-oxo-3,4-dihydro-2H-spiro[naphthalene-1,22'-[20]oxa[1,12]diazatetracyclo[14.7.2.0$^{3,6}$.0$^{19,24}$] pentacosa[8,16,18,24]tetraene]-15'-carboxylate via saponification through a procedure similar to that used for the synthesis of Example 175, Step 2. $^1$H NMR (300 MHz, CDCl$_3$) δ ppm 7.73 (d, J=8.5 Hz, 1H), 7.16 (dd, J=2.2, 8.5 Hz, 1H), 7.11-7.04 (m, 2H), 6.88 (d, J=8.3 Hz, 1H), 6.66 (br s, 1H), 6.52-6.38 (m, 1H), 5.70 (br dd, J=10.0, 14.8 Hz, 1H), 5.20 (dd, J=8.2, 16.5 Hz, 2H), 4.69 (dd, J=3.2, 8.2 Hz, 2H), 4.10-3.98 (m, 3H), 3.81-3.49 (m, 9H), 3.28 (br d, J=14.3 Hz, 1H), 3.22-3.02 (m, 3H), 3.00 (s, 3H), 2.86-2.24 (m, 9H), 2.13-1.66 (m, 7H), 1.43-1.31 (m, 1H) LRMS: (ESI, +ve ion) m/z 720.0 (M+H)$^+$.

Step 3: (1S,3'R,6'R,7'S,8'E,15'R)-6-chloro-N-(dimethylsulfamoyl)-15'-hydroxy-12'-methyl-7'-(2-(6-oxa-1-azaspiro[3.3]hept-1-yl)ethoxy)-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide

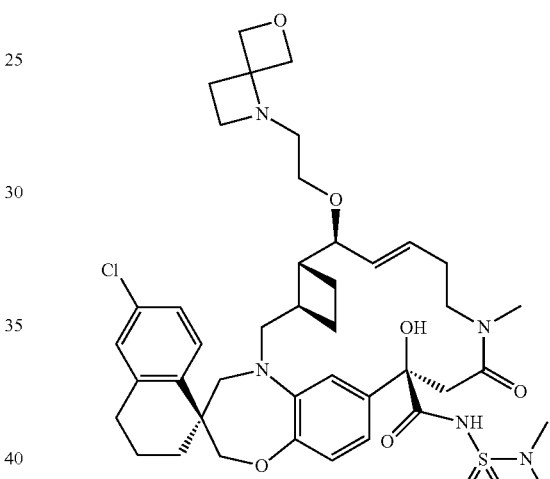

The title compound as TFA salt (7.5 mg, 28%) was synthesized from (1S,3'R,6'R,7'S,8'E,15'R)-6-chloro-15'-hydroxy-12'-methyl-7'-(2-(6-oxa-1-azaspiro[3.3]hept-1-yl)ethoxy)-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid and N,N-dimethylsulfamide through a procedure similar to that used for the synthesis of Example 5. $^1$H NMR (300 MHz, CD$_2$Cl$_2$) δ ppm $^1$H NMR (300 MHz, DICHLOROMETHANE-d$_2$) 6=8.95 (s, 1H), 7.78-7.68 (m, 1H), 7.15 (br d, J=8.6 Hz, 1H), 7.10-7.05 (m, 1H), 6.99 (br d, J=8.3 Hz, 1H), 6.89-6.81 (m, 1H), 6.53-6.33 (m, 2H), 5.76-5.59 (m, 1H), 4.71 (br d, J=8.9 Hz, 2H), 4.07-3.79 (m, 5H), 3.76-3.47 (m, 7H), 3.36-3.28 (m, 1H), 3.22-3.03 (m, 3H), 2.96 (s, 3H), 2.85 (s, 6H), 2.81-2.60 (m, 5H), 2.55-2.22 (m, 6H), 2.09-1.68 (m, 7H), 1.46-1.31 (m, 1H). LRMS: (ESI, +ve ion) m/z 826.0 (M+H)$^+$.

Example 196

(1S,3'R,6'R,7'S,8'E,15'R)-6-CHLORO-7'-(2-(4,4-DIFLUORO-1-PIPERIDINYL)ETHOXY)-N-(DIMETHYLSULFAMOYL)-15'-HYDROXY-12'-METHYL-13'-OXO-3,4-DIHYDRO-2H-SPIRO[NAPHTHALENE-1,22'-[20]OXA[1,12]DIAZATETRACYCLO[14.7.2.0³,⁶.0¹⁹,²⁴]PENTACOSA[8,16,18,24]TETRAENE]-15'-CARBOXAMIDE

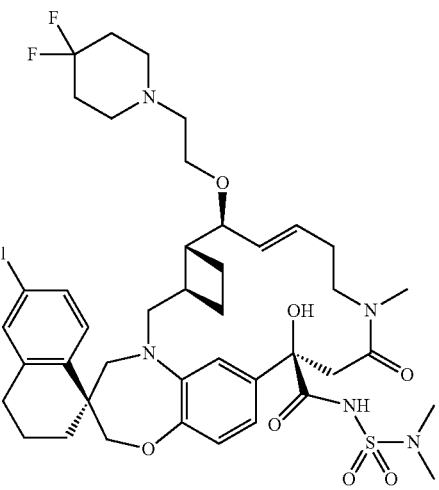

Step 1: Methyl (1S,3'R,6'R,7'S,8'E,15'R)-6-chloro-15'-hydroxy-12'-methyl-7'-(2-(4,4-difluoro-1-piperidinyl)ethoxy)-13'-oxo-3,4-dihydro-2H-spiro[naphthalene-1,22'-[20]oxa[1,12]diazatetracyclo[14.7.2.0³,⁶.0¹⁹,²⁴]pentacosa[8,16,18,24]tetraene]-15'-carboxylate

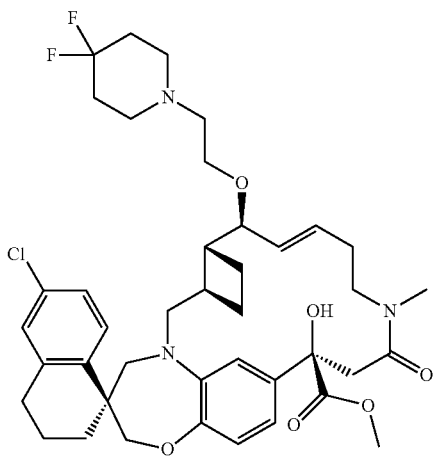 [SMILES: COC(=O)[C@@]1(O)CC(=O)N(C)CC/C=C/[C@H](OCCN2CCC(F)(F)CC2)[C@@H]2CC[C@H]2CN2C[C@@]3(CCCc4cc(Cl)ccc43)COc3ccc1cc32]

The title compound (31.8 mg, 60%) was synthesized from methyl (1S,3'R,6'R,7'S,8'E,15'R)-6-chloro-15'-hydroxy-7'-(2-bromoethoxy)-12'-methyl-13'-oxo-3,4-dihydro-2H-spiro[naphthalene-1,22'-[20]oxa[1,12]diazatetracyclo[14.7.2.0³,⁶.0¹⁹,²⁴] pentacosa[8,16,18,24]tetraene]-15'-carboxylate (Example 173, Step 1) and 4,4-difluoropiperidine hydrochloride through a procedure similar to that used for the synthesis of Example 175, Step 1. ¹H NMR (400 MHz, CDCl₃) δ ppm 7.74 (d, J=8.4 Hz, 1H), 7.17 (dd, J=2.3, 8.4 Hz, 1H), 7.11 (dd, J=2.0, 8.2 Hz, 1H), 7.07 (d, J=2.2 Hz, 1H), 6.90 (d, J=8.2 Hz, 1H), 6.51 (d, J=1.6 Hz, 1H), 6.37-6.18 (m, 1H), 5.76-5.64 (m, 2H), 4.02 (s, 2H), 3.86 (dd, J=1.8, 9.4 Hz, 1H), 3.79-3.72 (m+s, 4H), 3.69-3.51 (m, 4H), 3.43 (td, J=6.1, 10.0 Hz, 1H), 3.31 (d, J=14.3 Hz, 1H), 3.21-3.13 (m, 1H), 3.06 (br dd, J=9.7, 15.0 Hz, 1H), 3.00 (s, 3H), 2.85-2.73 (m, 2H), 2.67-2.60 (m, 8H), 2.49-2.35 (m, 2H), 2.34-2.25 (m, 1H), 2.09-1.70 (m, 11H), 1.46-1.33 (m, 1H). LRMS: (ESI, +ve ion) m/z 756.1 (M+H)⁺.

Step 2: (1S,3'R,6'R,7'S,8'E,15'R)-6-chloro-15'-hydroxy-12'-methyl-7'-(2-(4,4-difluoro-1-piperidinyl)ethoxy)-13'-oxo-3,4-dihydro-2H-spiro[naphthalene-1,22'-[20]oxa[1,12]diazatetracyclo[14.7.2.0³,⁶.0¹⁹,²⁴]pentacosa[8,16,18,24]tetraene]-15'-carboxylic acid

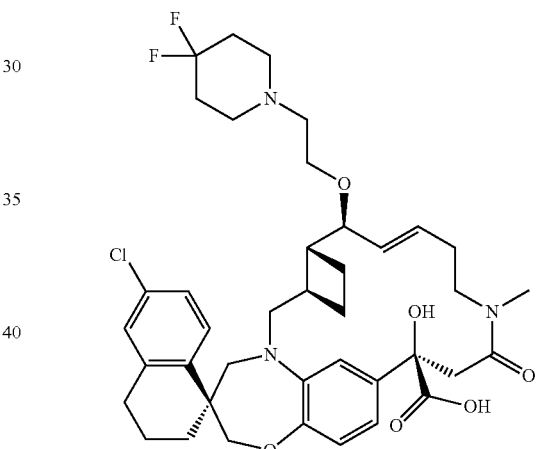

The title compound (30 mg, 96%) was synthesized from methyl (1S,3'R,6'R,7'S,8'E,15'R)-6-chloro-15'-hydroxy-12'-methyl-7'-(2-(4,4-difluoro-1-piperidinyl)ethoxy)-13'-oxo-3,4-dihydro-2H-spiro[naphthalene-1,22'-[20]oxa[1,12] diazatetracyclo[14.7.2.0³,⁶.0¹⁹,²⁴]pentacosa[8,16,18,24]tetraene]-15'-carboxylate via saponification through a procedure similar to that used for the synthesis of Example 175, Step 2. ¹H NMR (300 MHz, CDCl₃) δ ppm 7.73 (d, J=8.5 Hz, 1H), 7.16 (dd, J=2.3, 8.6 Hz, 1H), 7.11-7.04 (m, 2H), 6.87 (d, J=8.2 Hz, 1H), 6.68-6.65 (m, 1H), 6.51-6.35 (m, 1H), 5.74-5.60 (m, 1H), 4.08-3.95 (m, 3H), 3.89-3.46 (m, 9H), 3.35-3.24 (m, 3H), 3.22-3.05 (m, 3H), 3.02 (s, 3H), 2.82-2.65 (m, 3H), 2.57 (br d, J=16.7 Hz, 1H), 2.50-2.24 (m, 7H), 2.14-1.67 (m, 7H), 1.44-1.30 (m, 1H). LRMS: (ESI, +ve ion) m/z 742.1 (M+H)⁺.

Step 3: (1S,3'R,6'R,7'S,8'E,15'R)-6-chloro-7'-(2-(4,4-difluoro-1-piperidinyl)ethoxy)-n-(dimethylsulfamoyl)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide

Example 197

(1S,3'R,6'R,7'S,8'E,15'R)-6-CHLORO-N-(DIMETHYLSULFAMOYL)-15'-HYDROXY-7'-(2-(3-METHOXY-1-AZETIDINYL)ETHOXY)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

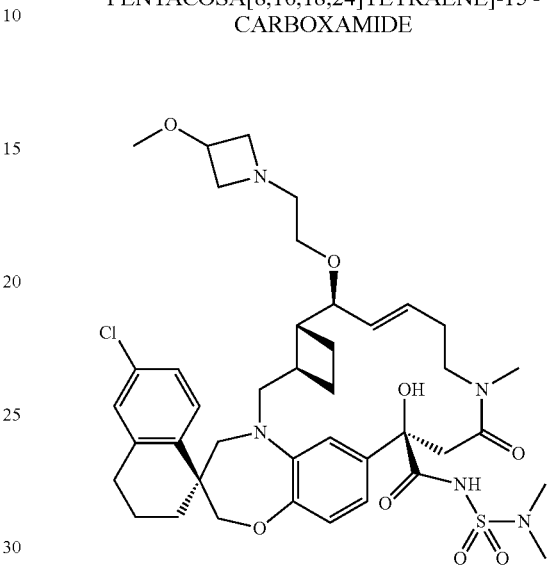

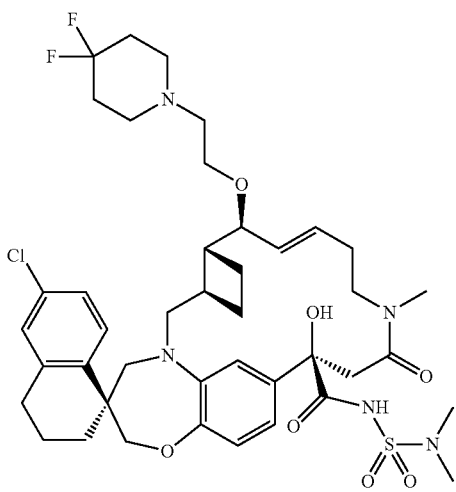 [SMILES: CN1CC/C=C/[C@H](OCCN2CCC(F)(F)CC2)[C@@H]2CC[C@H]2CN2C[C@@]3(CCCc4cc(Cl)ccc43)COc3ccc(cc32)[C@@](O)(C(=O)NS(=O)(=O)N(C)C)CC1=O]

Step 1: Methyl(1S,3'R,6'R,7'S,8'E,15'R)-6-chloro-15'-hydroxy-7'-(2-(3-methoxy-1-azetidinyl)ethoxy)-12'-methyl-13'-oxo-3,4-dihydro-2H-spiro[naphthalene-1,22'-[20]oxa[1,12]diazatetracyclo[14.7.2.0~3,6~.019,24]pentacosa[8,16,18,24]tetraene]-15'-carboxylate

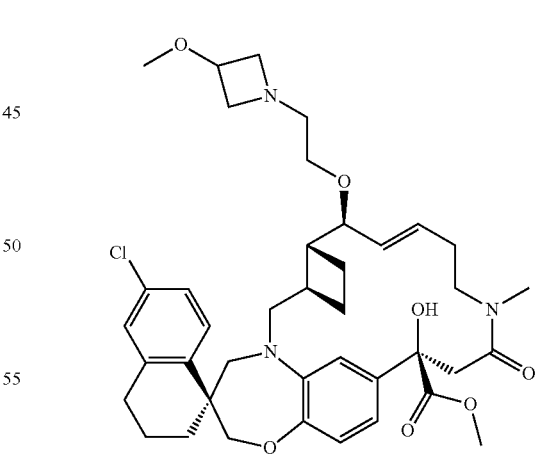

The title compound as TFA salt (5.5 mg, 14%) was synthesized from (1S,3'R,6'R,7'S,8'E,15'R)-6-chloro-15'-hydroxy-12'-methyl-7'-(2-(4,4-difluoro-1-piperidinyl)ethoxy)-13'-oxo-3,4-dihydro-2H-spiro[naphthalene-1,22'-[20]oxa[1,12] diazatetracyclo[14.7.2.0$^{3,6}$.0$^{19,24}$] pentacosa[8,16,18,24]tetraene]-15'-carboxylic acid and N,N-dimethylsulfamide through a procedure similar to that used for the synthesis of Example 5. $^1$H NMR (300 MHz, CD$_2$Cl$_2$) δ ppm 8.96 (br s, 1H), 7.73 (d, J=8.5 Hz, 1H), 7.16 (dd, J=2.4, 8.6 Hz, 1H), 7.08 (d, J=2.3 Hz, 1H), 6.99 (dd, J=2.0, 8.3 Hz, 1H), 6.86 (d, J=8.3 Hz, 1H), 6.48 (d, J=1.9 Hz, 1H), 6.46-6.34 (m, 1H), 5.75-5.63 (m, 1H), 4.06-3.96 (m, 2H), 3.95-3.80 (m, 2H), 3.75-3.46 (m, 7H), 3.32 (d, J=14.5 Hz, 1H), 3.27-3.03 (m, 6H), 2.96 (s, 3H), 2.87 (s, 6H), 2.81-2.61 (m, 3H), 2.50 (br d, J=16.8 Hz, 1H), 2.46-2.23 (m, 7H), 2.10-1.69 (m, 7H), 1.46-1.33 (m, 1H). LRMS: (ESI, +ve ion) m/z 848.2 (M+H)$^+$.

The title compound (71.6 mg, 71%) was synthesized from methyl (1S,3'R,6'R,7'S,8'E,15'R)-6-chloro-15'-hydroxy-7'-(2-bromoethoxy)-12'-methyl-13'-oxo-3,4-dihydro-2H-spiro[naphthalene-1,22'-[20]oxa[1,12]diazatetracyclo[14.7.2.0$^{3,6}$.0$^{19,24}$] pentacosa[8,16,18,24]tetraene]-15'-carboxylate (Example 173, Step 1) and 3-methoxyazetidine hydrochloride through a procedure similar to that used for the synthesis of Example 175, Step 1. $^1$H NMR (300 MHz, CDCl$_3$)

δ ppm 7.74 (d, J=8.5 Hz, 1H), 7.16 (dd, J=2.3, 8.5 Hz, 1H), 7.11 (dd, J=2.0, 8.3 Hz, 1H), 7.07 (d, J=2.2 Hz, 1H), 6.89 (d, J=8.3 Hz, 1H), 6.50 (d, J=1.9 Hz, 1H), 6.33-6.21 (m, 1H), 5.74-5.62 (m, 2H), 4.13-3.99 (m, 3H), 3.88-3.47 (m+s, 11H), 3.39-3.24 (m+s, 5H), 3.21-3.01 (m, 4H), 2.99 (s, 3H), 2.86-2.64 (m, 5H), 2.59 (br d, J=16.5 Hz, 1H), 2.51-2.22 (m, 3H), 2.09-1.65 (m, 7H), 1.46-1.32 (m, 1H). LRMS: (ESI, +ve ion) m/z 722.0 (M+H)⁺.

Step 2: (1S,3'R,6'R,7'S,8'E,15'R)-6-chloro-15'-hydroxy-7'-(2-(3-methoxy-1-azetidinyl)ethoxy)-12'-methyl-13'-oxo-3,4-dihydro-2H-spiro[naphthalene-1,22'-[20]oxa[1,12]diazatetracyclo[14.7.2.0~3,6~.019,24]pentacosa[8,16,18,24]tetraene]-15'-carboxylic acid

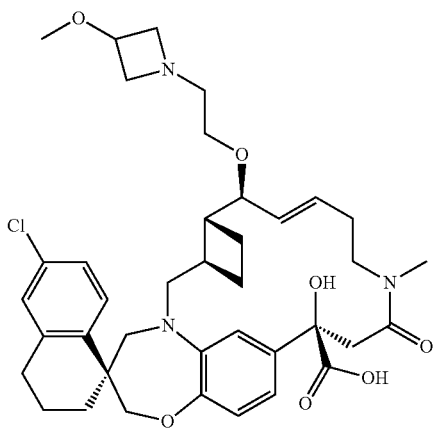 [SMILES: COC1CN(CCO[C@H]2/C=C/CCN(C)C(=O)C[C@](O)(C(=O)O)c3ccc4c(c3)N(C[C@@H]3CC[C@H]32)C[C@@]2(CCCc3cc(Cl)ccc32)CO4)C1]

The title compound (68 mg, 98%) was synthesized from methyl (1S,3'R,6'R,7'S,8'E,15'R)-6-chloro-15'-hydroxy-7'-(2-(3-methoxy-1-azetidinyl)ethoxy)-12'-methyl-13'-oxo-3,4-dihydro-2H-spiro[naphthalene-1,22'-[20]oxa[1,12]diazatetracyclo[14.7.2.0~3,6~.019,24] pentacosa[8,16,18,24] tetraene]-15'-carboxylate via saponification through a procedure similar to that used for the synthesis of Example 175, Step 2. ¹H NMR (300 MHz, CDCl₃) δ ppm 7.73 (d, J=8.5 Hz, 1H), 7.16 (dd, J=2.2, 8.5 Hz, 1H), 7.10-7.02 (m, 2H), 6.87 (d, J=8.3 Hz, 1H), 6.75-6.67 (m, 1H), 6.49-6.34 (m, 1H), 5.77-5.62 (m, 1H), 4.67-4.50 (m, 2H), 4.39-4.24 (m, 1H), 4.09-3.93 (m, 3H), 3.87-3.58 (m, 7H), 3.53 (br d, J=16.8 Hz, 1H), 3.38-3.21 (m+s, 6H), 3.20-3.01 (m, 2H), 2.99 (s, 3H), 2.88-2.65 (m, 3H), 2.57 (br d, J=16.4 Hz, 1H), 2.48-2.23 (m, 3H), 2.15-1.64 (m, 7H), 1.43-1.30 (m, 1H). LRMS: (ESI, +ve ion) m/z 708.0 (M+H)⁺.

Step 3: (1S,3'R,6'R,7'S,8'E,15'R)-6-chloro-N-(dimethylsulfamoyl)-15'-hydroxy-7'-(2-(3-methoxy-1-azetidinyl)ethoxy)-12'-methyl-13'-oxo-3,4-dihydro-2H-spiro[naphthalene-1,22'-[20]oxa[1,12]diazatetracyclo[14.7.2.0~3,6~.019,24]pentacosa[8,16,18,24]tetraene]-15'-carboxamide

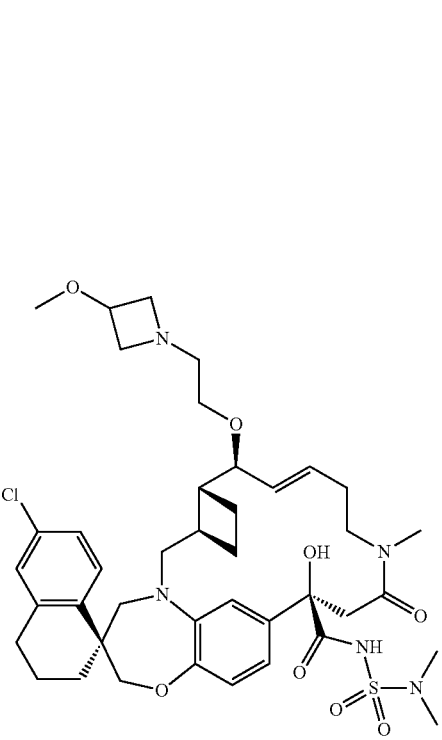 [SMILES: COC1CN(CCO[C@H]2/C=C/CCN(C)C(=O)C[C@](O)(C(=O)NS(=O)(=O)N(C)C)c3ccc4c(c3)N(C[C@@H]3CC[C@H]32)C[C@@]2(CCCc3cc(Cl)ccc32)CO4)C1]

The title compound (17.5 mg, 22%) was synthesized from (1S,3'R,6'R,7'S,8'E,15'R)-6-chloro-15'-hydroxy-7'-(2-(3-methoxy-1-azetidinyl)ethoxy)-12'-methyl-13'-oxo-3,4-dihydro-2H-spiro[naphthalene-1,22'-[20]oxa[1,12]diazatetracyclo[14.7.2.0~3,6~.019,24] pentacosa[8,16,18,24] tetraene]-15'-carboxylic acid and N,N-dimethylsulfamide through a procedure similar to that used for the synthesis of Example 5. ¹H NMR (300 MHz, CD₂Cl₂) δ ppm 7.72 (d, J=8.5 Hz, 1H), 7.15 (dd, J=2.3, 8.5 Hz, 1H), 7.08 (d, J=2.3 Hz, 1H), 6.98 (dd, J=2.0, 8.3 Hz, 1H), 6.85 (d, J=8.3 Hz, 1H), 6.54 (d, J=1.6 Hz, 1H), 6.40-6.26 (m, 1H), 5.65 (ddd, J=1.2, 9.5, 15.3 Hz, 1H), 4.08-3.93 (m, 3H), 3.82 (dd, J=1.1, 9.3 Hz, 1H), 3.71 (br d, J=14.3 Hz, 1H), 3.65-3.50 (m, 5H), 3.45-3.28 (m, 2H), 3.24-3.04 (m+s, 6H), 2.96 (s, 3H), 2.93-2.84 (m+s, 8H), 2.81-2.62 (m, 3H), 2.59-2.47 (m, 3H), 2.45-2.22 (m, 3H), 2.09-1.65 (m, 7H), 1.48-1.32 (m, 1H). LRMS: (ESI, +ve ion) m/z 814.2 (M+H)⁺.

Example 198

(1S,3'R,6'R,7'S,8'E,15'R)—N-(1-AZETIDI-NYLSULFONYL)-6-CHLORO-15'-HYDROXY-12'-METHYL-7'-(2-(4-MORPHOLINYL)ETHOXY)-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

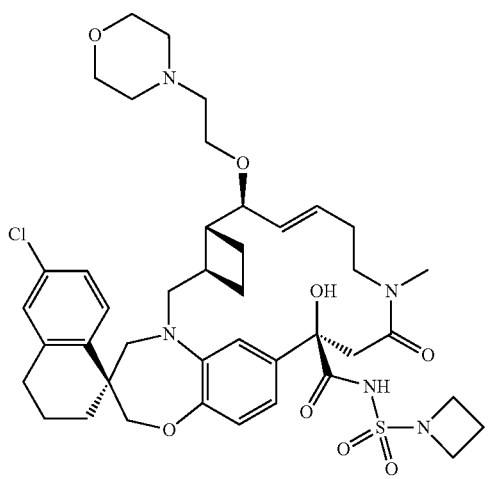 [SMILES: CN1CC/C=C/[C@H](OCCN2CCOCC2)[C@@H]2CC[C@H]2CN2C[C@@]3(CCCc4cc(Cl)ccc43)COc3ccc(cc32)[C@@](O)(C(=O)NS(=O)(=O)N2CCC2)CC1=O]

The title compound as TFA salt (29 mg, 46%) was synthesized from (1S,3'R,6'R,7'S,8'E,15'R)-6-chloro-15'-hydroxy-12'-methyl-7'-(2-(4-morpholinyl)ethoxy)-13'-oxo-3,4-dihydro-2H-spiro[naphthalene-1,22'-[20]oxa[1,12]diazatetracyclo[14.7.2.0$^{3,6}$.0$^{19,24}$] pentacosa[8,16,18,24]tetraene]-15'-carboxylic acid (Example 173, step 3) and azetidine-1-sulfonamide through a procedure similar to that used for the synthesis of Example 5. $^1$H NMR (300 MHz, CD$_2$Cl$_2$) δ ppm 9.05 (br s, 1H), 7.76 (d, J=8.5 Hz, 1H), 7.19 (dd, J=2.3, 8.5 Hz, 1H), 7.11 (d, J=2.2 Hz, 1H), 7.05 (dd, J=2.1, 8.3 Hz, 1H), 6.91 (d, J=8.2 Hz, 1H), 6.56 (d, J=2.0 Hz, 1H), 6.49-6.36 (m, 1H), 5.72 (ddd, J=1.5, 9.6, 15.2 Hz, 1H), 4.15-3.94 (m, 11H), 3.88 (ddd, J=3.7, 6.6, 12.0 Hz, 1H), 3.76 (br d, J=14.5 Hz, 1H), 3.70-3.47 (m, 6H), 3.35 (d, J=14.5 Hz, 1H), 3.28-3.02 (m, 6H), 3.01 (s, 3H), 2.85-2.65 (m, 3H), 2.60 (d, J=15.8 Hz, 1H), 2.50-2.29 (m, 3H), 2.18 (td, J=7.8, 15.6 Hz, 2H), 2.12-1.71 (m, 7H), 1.48-1.35 (m, 1H). LRMS: (ESI, +ve ion) m/z 826.3 (M+H)$^+$.

Example 199

(1S,3'R,6'R,7'S,8'E,15'R)-6-CHLORO-7'-(2-(3,3-DIFLUORO-1-AZETIDINYL)ETHOXY)-15'-HYDROXY-N-((3-METHOXY-1-AZETIDINYL)SULFONYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

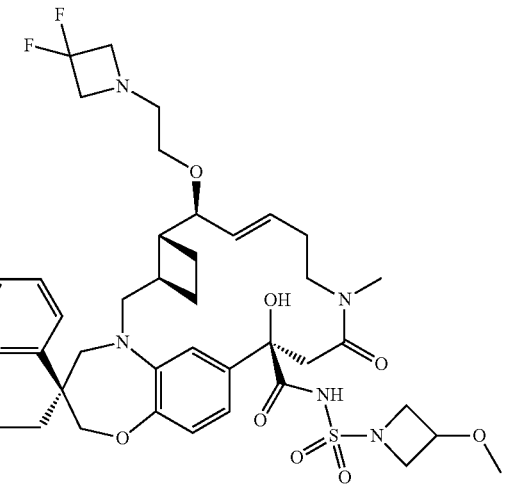

The title compound as TFA salt (18.4 mg, 34%) was synthesized from (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid (Example 175, step 2) and 3-methoxyazetidine-1-sulfonamide through a procedure similar to that used for the synthesis of Example 5. $^1$H NMR (300 MHz, CD$_2$Cl$_2$) δ ppm 9.03 (br s, 1H), 7.77 (d, J=8.5 Hz, 1H), 7.19 (dd, J=2.3, 8.5 Hz, 1H), 7.11 (d, J=2.2 Hz, 1H), 7.04 (dd, J=2.1, 8.3 Hz, 1H), 6.90 (d, J=8.2 Hz, 1H), 6.66 (s, 1H), 6.59 (d, J=1.9 Hz, 1H), 6.46-6.31 (m, 1H), 5.78-5.64 (m, 1H), 4.29-4.19 (m, 2H), 4.17-4.08 (m, 2H), 4.07-3.98 (m, 3H), 3.92-3.85 (m, 1H), 3.78-3.45 (m, 9H), 3.42-3.29 (m, 2H), 3.27 (s, 3H), 3.25-3.06 (m, 2H), 3.01 (s, 3H), 2.85-2.53 (m, 6H), 2.50-2.28 (m, 3H), 2.12-1.72 (m, 7H), 1.48-1.35 (m, 1H). LRMS: (ESI, +ve ion) m/z 862.0 (M+H)$^+$.

Example 200

(1S,3'R,6'R,7'S,8'E,15'R)-6-CHLORO-7'-(2-(3,3-DIFLUORO-1-AZETIDINYL)ETHOXY)-15'-HYDROXY-N-((2-HYDROXYETHYL)(METHYL)SULFAMOYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

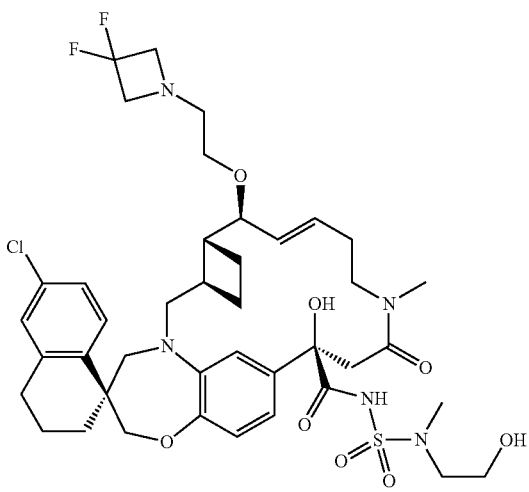 [SMILES: CN1CC/C=C/[C@H](OCCN2CC(F)(F)C2)[C@@H]2CC[C@H]2CN2C[C@@]3(CCCc4cc(Cl)ccc43)COc3ccc(cc32)[C@@](O)(C(=O)NS(=O)(=O)N(C)CCO)CC1=O]

Step 1: (1S,3'R,6'R,7'S,8'E,15'R)-6-chloro-7'-(2-(3,3-difluoro-1-azetidinyl)ethoxy)-15'-hydroxy-N-((2-((tert-butyldimethylsilyl)oxy)ethyl)(methyl)sulfamoyl)-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide

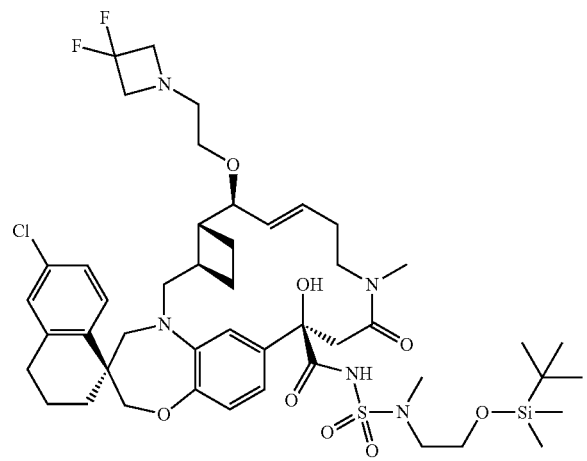 [SMILES: CN1CC/C=C/[C@H](OCCN2CC(F)(F)C2)[C@@H]2CC[C@H]2CN2C[C@@]3(CCCc4cc(Cl)ccc43)COc3ccc(cc32)[C@@](O)(C(=O)NS(=O)(=O)N(C)CCO[Si](C)(C)C(C)(C)C)CC1=O]

The title compound (45.7 mg, 68%) was synthesized from (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$] pentacosa[8,16,18,24]tetraene]-15'-carboxylic acid (Example 175, step 2) and N-(2-((tert-butyldimethylsilyl)oxy)ethyl)-N-methyl-1-sulfamide through a procedure similar to that used for the synthesis of Example 5. LRMS: (ESI, +ve ion) m/z 964.4 (M+H)$^+$.

Note: N-(2-(((tert-butyldimethylsilyl)oxy)ethyl)-N-methyl-1-sulfonamide was prepared from N-(2-hydroxyethyl)-N-methyl-1-sulfonamide: To a solution of N-(2-hydroxyethyl)-N-methyl-1-sulfonamide (0.157 g, 1.018 mmol) in DCM (2.04 mL) wad added triethylamine (0.156 ml, 1.120 mmol) and N,N-dimethylpyridin-4-amine (0.025 g, 0.204 mmol) followed by tert-butylchlorodimethylsilane (0.169 g, 1.120 mmol) under ice-cooling. The reaction mixture was then allowed to warm to RT and stirred overnight. Saturated aqueous ammonium chloride solution and ethyl acetate were added. The organic layer was washed with saturated aqueous sodium chloride solution and then dried over anhydrous sodium sulfate and the solvent was evaporated under reduced pressure. The crude material was absorbed onto a plug of silica gel and purified by chromatography through a Redi-Sep pre-packed silica gel column (12 g), eluting with a gradient of 0% to 40% EtOAc in hexane, to provide N-(2-((tert-butyldimethylsilyl)oxy)ethyl)-N-methyl-1-sulfonamide (0.14 g, 0.522 mmol, 51.2% yield) as white solid, $^1$H NMR (300 MHz, CDCl$_3$)) δ ppm 4.75 (br s, 2H), 3.81 (t, J=5.1 Hz, 2H), 3.39 (t, J=5.2 Hz, 2H), 2.92 (s, 3H), 0.96-0.80 (m, 9H), 0.16-0.01 (m, 6H).

Step 2: (1S,3'R,6'R,7'S,8'E,15'R)-6-chloro-7'-(2-(3,3-difluoro-1-azetidinyl)ethoxy)-15'-hydroxy-N-((2-hydroxyethyl)(methyl)sulfamoyl)-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide

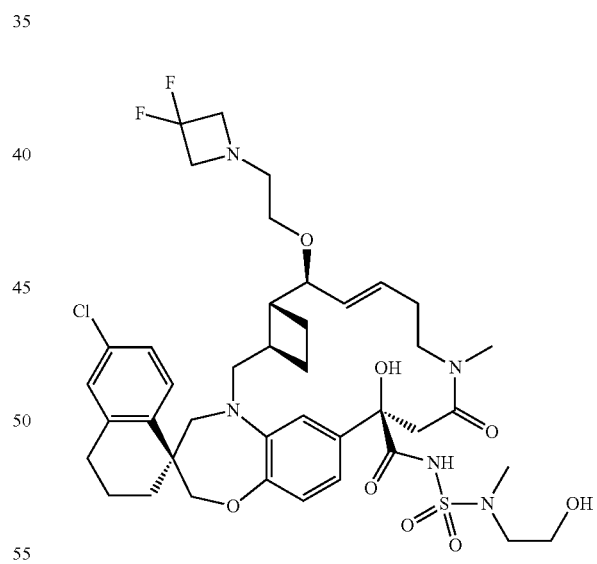

To (1S,3'R,6'R,7'S,8'E,15'R)-6-chloro-7'-(2-(3,3-difluoro-1-azetidinyl)ethoxy)-15'-hydroxy-n-((2-((tert- butyldimethylsilyl)oxy)ethyl)(methyl)sulfamoyl)-12'-methyl-13'-oxo-3, 4-dihydro-2H-spiro[naphthalene-1,22'-[20]oxa[1,12] diazatetracyclo[14.7.2.0$^{3,6}$.0$^{19,24}$]pentacosa[8,16,18,24] tetraene]-15'-carboxamide (0.025 g, 0.026 mmol) was added TBAF (1M in THF) (0.104 ml, 0.104 mmol) and the reaction mixture was stirred at room temperature overnight. 6 additional equivalents of TBAF (1M in THF) were added and the reaction mixture was stirred at RT for 42 hrs. A saturated solution of NH$_4$Cl was then added followed by water. The aqueous phase was extracted with EtOAc (×3). The layers were separated and the organic extract was washed with brine, dried over MgSO₄, filtered and concentrated in vacuo. The reaction was repeated a second time on the same scale. The crude material from each reaction was combined and absorbed onto a plug of silica gel and purified by chromatography through a Redi-Sep pre-packed silica gel column, eluting with a gradient of 0% to 50% acetone in heptanes, to provide the title product as white solid (m=20.4 mg, 46% yield, 2 batches). ¹H NMR (300 MHz, CD₂Cl₂) δ ppm 7.73 (d, J=8.5 Hz, 1H), 7.16 (dd, J=2.3, 8.6 Hz, 1H), 7.08 (d, J=2.2 Hz, 1H), 7.01-6.95 (m, 1H), 6.89-6.80 (m, 1H), 6.54-6.44 (m, 2H), 6.42-6.28 (m, 1H), 5.67 (ddd, J=1.2, 9.5, 15.1 Hz, 1H), 4.06-3.95 (m, 2H), 3.91-3.84 (m, 1H), 3.75-3.26 (m, 15H), 3.21-3.04 (m, 2H), 2.97 (s, 3H), 2.86 (s, 3H), 2.81-2.61 (m, 5H), 2.51 (d, J=16.8 Hz, 1H), 2.44-2.22 (m, 3H), 2.09-1.68 (m, 7H), 1.46-1.32 (m, 1H). LRMS. (ESI, +ve ion) m/z 850.0 (M+H)⁺.

Examples 201a and 201b (1S,3'R,6'R,7'S,8'E,11'S,17'R)-6-CHLORO-N-(DIMETHYLSULFAMOYL)-7',17'-DIHYDROXY-15'-OXO-3,4-DIHYDRO-2H-SPIRO[NAPHTHALENE-1,24'-[22]OXA[1,14]DIAZAPENTACYCLO[16.7.2.0~3,6~.0~11,14~.0~21,26~]HEPTACOSA[8,18,20,26]TETRAENE]-17'-CARBOXAMIDE OR (1S,3'R,6'R,7'S,8'E,11'S,17'S)-6-CHLORO-N-(DIMETHYLSULFAMOYL)-7',17'-DIHYDROXY-15'-OXO-3,4-DIHYDRO-2H-SPIRO[NAPHTHALENE-1,24'-[22]OXA[1,14]DIAZAPENTACYCLO[16.7.2.0~3,6~.0~11,14~.0~21,26~]HEPTACOSA[8,18,20,26]TETRAENE]-17'-CARBOXAMIDE

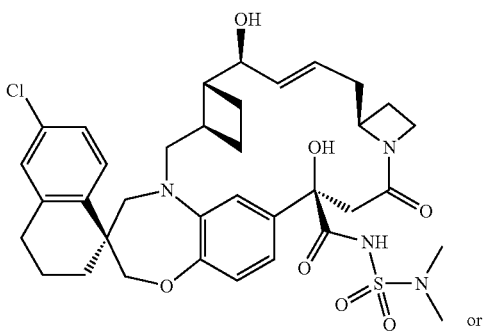

or

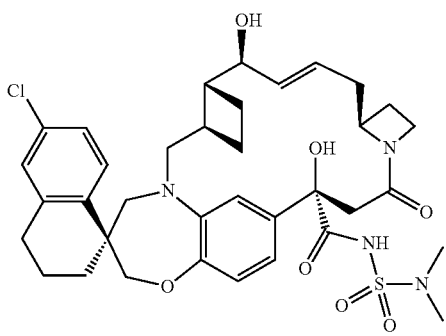

Step 1: Methyl (S)-4-((S)-2-allylazetidin-1-yl)-2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-4-oxobutanoate and methyl (R)-4-((S)-2-allylazetidin-1-yl)-2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-4-oxobutanoate

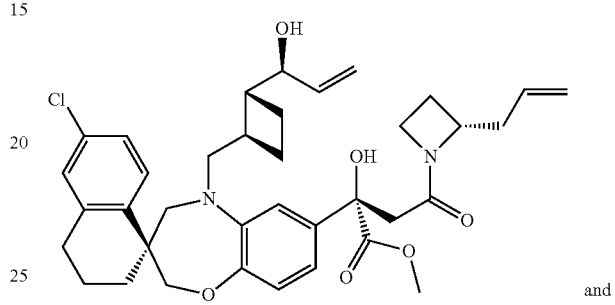

and

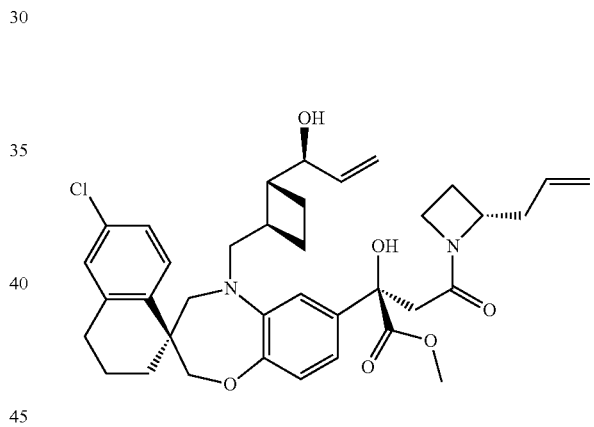

The title compounds were synthesized from 3-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-3-hydroxy-4-methoxy-4-oxobutanoic acid (Example 1, step 5) and (S)-2-allylpyrrolidine through a procedure similar to that used for the synthesis of Example 1, step 6. The crude material was absorbed onto a plug of silica gel and purified by chromatography through a Redi-Sep pre-packed silica gel column (24 g), eluting with a gradient of 0% to 50% EtOAc in hexane. The 1st eluting isomer (89.3 mg, 26%) came at about 44-47% EtOAc in hexanes and the 2nd eluting isomer (127 mg, 37%) came at about 48-51% EtOAc in hexanes. First eluting isomer (one of the title compound), LRMS: (ESI, +ve ion) m/z 649.2 (M+H)⁺; second eluting isomer (the other title compound), LRMS: (ESI, +ve ion) m/z 649.2 (M+H)⁺.

Step 2: Methyl (1S,3'R,6'R,7'S,8'E,11'S,17'R)-6-chloro-7',17'-dihydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-17'-carboxylate and Methyl (1S,3'R,6'R,7'S,8'E,11'S,17'S)-6-chloro-7',17'-dihydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-17'-carboxylate Step 3: Methyl (1S,3'R,6'R,7'S,8'E,11'S,17'R)-6-chloro-7'-((tert-butyldimethylsilyl)oxy)-17-hydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-17'-carboxylate and Methyl (1S,3'R,6'R,7'S,8'E,11'S,17'S)-6-chloro-7'-((tert-butyldimethylsilyl)oxy)-17'-hydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-17'-carboxylate

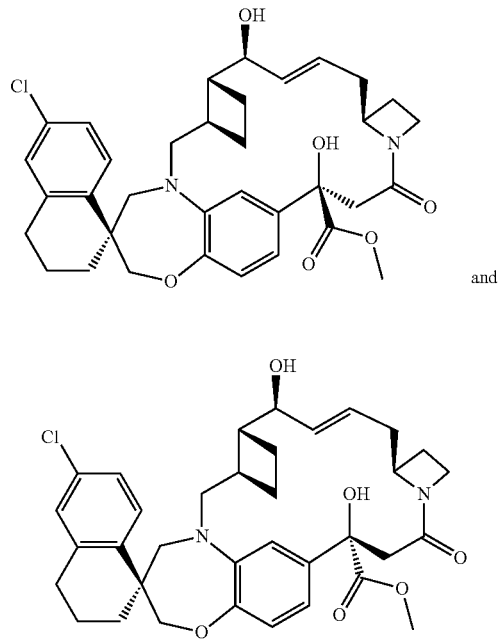

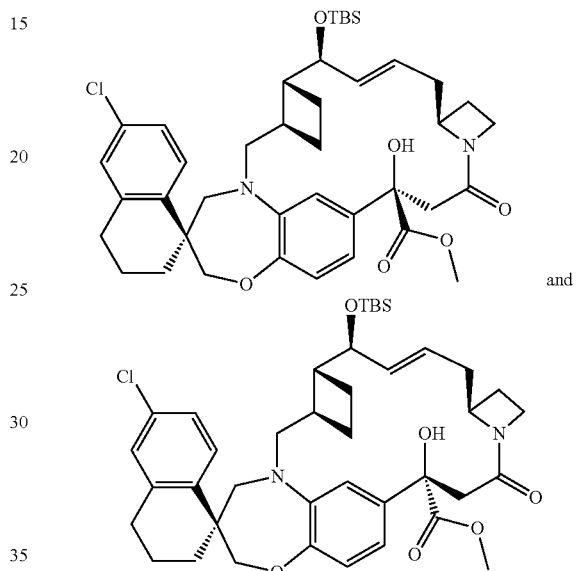

Step 2a: One of the title product (106.5 mg, 88%) was synthesized from the second eluting isomer obtained in Example 201, step 1 (methyl (S)-4-((S)-2-allylazetidin-1-yl)-2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-4-oxobutanoate or methyl (R)-4-((S)-2-allylazetidin-1-yl)-2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-4-oxobutanoate) via ring closing metathesis through a procedure similar to that used for the synthesis of Example 1, step 7. LRMS: (ESI, +ve ion) m/z 621.1 (M+H)+.

Step 2b: The other title product (78.5 mg, 92%) was synthesized from the first eluting isomer obtained in Example 201, step 1 (methyl (S)-4-((S)-2-allylazetidin-1-yl)-2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-4-oxobutanoate or methyl (R)-4-((S)-2-allylazetidin-1-yl)-2-((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-yl)-2-hydroxy-4-oxobutanoate) via ring closing metathesis through a procedure similar to that used for the synthesis of Example 1, step 7. LRMS: (ESI, +ve ion) m/z 621.1 (M+H)+.

Step 3a: To a solution of Example 201, step 2a (methyl (1S,3'R,6'R,7'S,8'E,11'S,17'R)-6-chloro-7',17'-dihydroxy-15'-oxo-3,4-dihydro-2H-spiro[naphthalene-1,24'-[22]oxa[1,14]diazapentacyclo [16.7.2.0~3,6~.011,14.021,26] heptacosa[8,18,20,26]tetraene]-7-carboxylate or methyl (1S,3'R,6'R,7'S,8'E,11'S,17'S)-6-chloro-7',17'-dihydroxy-15'-oxo-3,4-dihydro-2H-spiro[naphthalene-1,24'-[22]oxa[1,14] diazapentacyclo[16.7.2.0~3,6~.011,14.021,26]heptacosa[8,18,20,26]tetraene]-17'-carboxylate) (86 mg, 0.138 mmol) in a mixture of N, N-dimethylformamide (0.17 ml) and dichloromethane (0.52 ml) was added 1H-imidazole (0.019 g, 0.277 mmol) and tert-butylchlorodimethylsilane (0.042 g, 0.277 mmol). The reaction mixture was stirred at RT overnight and then quenched with water. A saturated solution of ammonium chloride was added and the reaction mixture was extracted with EtOAc (×3). The combined organic layer was dried over magnesium sulfate, filtered and concentrated under reduced pressure. The crude material was absorbed onto a plug of silica gel and purified by chromatography through a Redi-Sep pre-packed silica gel column (12 g), eluting with a gradient of 0% to 30% acetone in hexanes, to provide one of the title product (0.0731 g, 71.8% yield). The product came at around 19% acetone in hexanes. LRMS: (ESI, +ve ion) m/z 735.2 (M+H). Step 3b: The other title product (72.2 mg, 85% yield) was synthesized from Example 201, step 2b (methyl (1S,3'R,6'R,7'S,8'E,11'S,17'R)-6-chloro-7',17'-dihydroxy-15'-oxo-3,4-dihydro-2H-spiro[naphthalene-1,24'-[22]oxa[1,14]diazapentacyclo [16.7.2.0~3,6~.011,14.021,26]heptacosa[8,18,20,26]tetraene]-17'-carboxylate or methyl (1S,3'R,6'R,7'S,8'E, 11'S,17'S)-6-chloro-7',17'-dihydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-17'-carboxylate) through a procedure similar to that used for the synthesis of Example 201, step 3a. LRMS: (ESI, +ve ion) m/z 735.2 (M+H)+.

Step 4: (1S,3'R,6'R,7'S,8'E,11'S,17'R)-6-chloro-7'-((tert-butyldimethylsilyl)oxy)-17'-hydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-17'-carboxylic acid and (1S,3'R,6'R,7'S,8'E,11'S,17'S)-6-chloro-7'-((tert-butyldimethylsilyl)oxy)-17'-hydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-17'-carboxylic acid

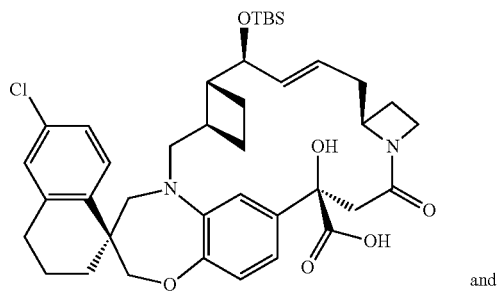

and

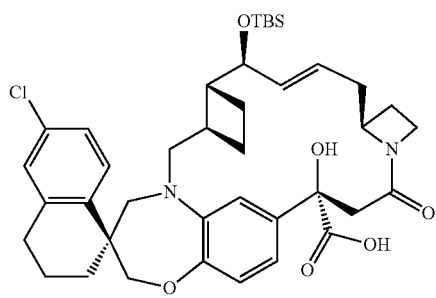

Step 4a: One of the title compound (71 mg, 99%) was synthesized from Example 201, step 3a (methyl (1S,3'R,6'R,7'S,8'E,11'S,17'R)-6-chloro-7'-((tert-butyldimethylsilyl)oxy)-17'-hydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-17'-carboxylate or Methyl (1S,3'R,6'R,7'S,8'E,11'S,17'S)-6-chloro-7'-((tert-butyldimethylsilyl)oxy)-17'-hydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-17'-carboxylate) via saponification through a procedure similar to that used for the synthesis of Example 173, Step 3. LRMS: (ESI, +ve ion) m/z 721.2 (M+H)+.

Step 4b: The other title compound (66 mg, 93% yield) was synthesized from Example 201, step 3b (methyl (1S,3'R,6'R,7'S,8'E,11'S,17'R)-6-chloro-7'-((tert-butyldimethylsilyl)oxy)-17'-hydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-17'-carboxylate or methyl (1S,3'R,6'R,7'S,8'E,11'S,17'S)-6-chloro-7'-((tert-butyldimethylsilyl)oxy)-17'-hydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-17'-carboxylate) via saponification through a procedure similar to that used for the synthesis of Example 173, Step 3. LRMS: (ESI, +ve ion) m/z 721.2 (M+H)+.

Step 5: (1S,3'R,6'R,7'S,8'E,11'S,17'R)-6-chloro-N-(dimethylsulfamoyl)-7'-((tert-butyldimethylsilyl)oxy)-17'-hydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-17'-carboxamide and (1S,3'R,6'R,7'S,8'E,11'S,17'S)-6-chloro-N-(dimethylsulfamoyl)-7'-((tert-butyldimethylsilyl)oxy)-17'-hydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-17'-carboxamide

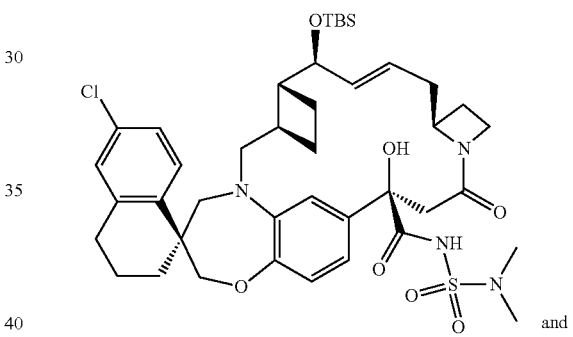

and

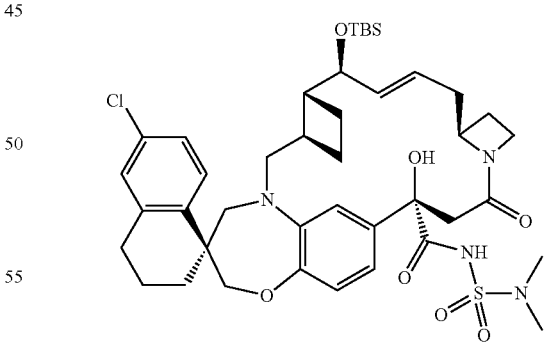

Step 5a: One of the title compound (51.7 mg, 63%) was synthesized from Example 201, step 4a ((1S,3'R,6'R,7'S,8'E,11'S,17'R)-6-chloro-7'-((tert-butyldimethylsilyl)oxy)-17'-hydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-17'-carboxylic acid or (1S,3'R,6'R,7'S,8'E,11'S,17'S)-6-chloro-7'-((tert-butyldimethylsilyl)oxy)-17'-hydroxy-15'-oxo-3,4-dihydro-2H-spiro[naphthalene-1,24'-[22]oxa[1,14]diazapentacyclo[16.7.2.0~3,6~.0¹¹,¹⁴.0²¹,²⁶]heptacosa[8,18,20,26]tetraene]-7-carboxylic acid) and N,N-dimethylsulfamide through a procedure similar to that used for the synthesis of Example 5.

Step 5b: The other title compound (16.7 mg, 22%) was synthesized from Example 201, step 4b ((1S,3'R,6'R,7'S,8'E,11'S,17'R)-6-chloro-7'-((tert-butyldimethylsilyl)oxy)-17'-hydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-7-carboxylic acid or (1S,3'R,6'R,7'S,8'E,11'S,17'S)-6-chloro-7'-((tert-butyldimethylsilyl)oxy)-17'-hydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-7-carboxylic acid) and N,N-dimethylsulfamide through a procedure similar to that used for the synthesis of Example 5.

Step 6: (1S,3'R,6'R,7'S,8'E,11'S,17'R)-6-chloro-N-(dimethylsulfamoyl)-7',17'-dihydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-17'-carboxamide and (1S,3'R,6'R,7'S,8'E,11'S,17'S)-6-chloro-N-(dimethylsulfamoyl)-7',17'-dihydroxy-15'-oxo-3,4-dihydro-2H-spiro[naphthalene-1,24'-[22]oxa[1,14]diazapentacyclo[16.7.2.0~3,6~.011,14.021,26]heptacosa[8,18,20,26]tetraene]-17'-carboxamide

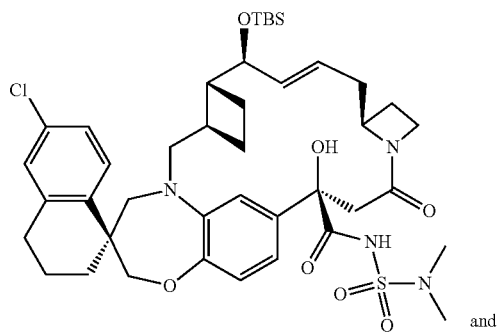

and

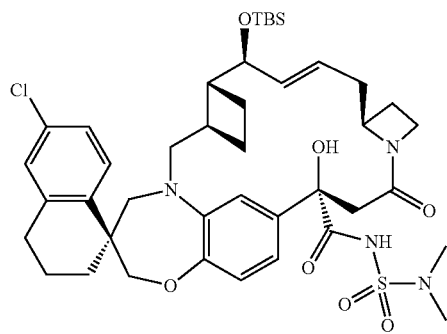

Step 6a: To Example 201, step 5a ((1S,3'R,6'R,7'S,8'E,11'S,17'R)-6-chloro-N-(dimethylsulfamoyl)-7'-((tert-butyldimethylsilyl)oxy)-17'-hydroxy-15'-oxo-3,4-dihydro-2H-spiro[naphthalene-1,24'-[22]oxa[1,14]diazapentacyclo[16.7.2.0~3,6~.011,14.021,26] heptacosa[8,18,20,26]tetraene]-17'-carboxamide or (1S,3'R,6'R,7'S,8'E,11'S,17'S)-6-chloro-N-(dimethylsulfamoyl)-7'-((tert-butyldimethylsilyl)oxy)-17'-hydroxy-15'-oxo-3,4-dihydro-2H-spiro[naphthalene-1,24'-[22]oxa[1,14]diazapentacyclo[16.7.2.0~3,6~.011,14.021,26] heptacosa[8,18,20,26]tetraene]-17'-carboxamide) (0.0435 g, 0.053 mmol) was added TBAF (1M in THF) (0.788 ml, 0.788 mmol) neat and the reaction mixture was stirred at room temperature overnight. 15 eq of TBAF were added and the reaction mixture was stirred at RT for 20 h. 0.4 ml of TBAF was added and the reaction mixture was stirred at RT for 24 h. The reaction mixture was diluted with a saturated solution of ammonium chloride, then water and extracted with EtOAc (×3). The organic extract was dried over MgSO4. The solution was filtered and concentrated in vacuo to give the crude material as a light-yellow oil. The crude material was absorbed onto a plug of silica gel and purified by chromatography through a Redi-Sep prepacked silica gel column (4 g), eluting with a gradient of 0% to 45% acetone in hexanes, to provide one of the title product 201b (0.036 g, 97% yield) as white solid. The compound came at around 40-45% acetone in hexanes. $^1$H NMR (600 MHz, CD$_2$Cl$_2$) δ ppm 7.73 (d, J=8.5 Hz, 1H), 7.20 (br s, 1H), 7.16 (br d, J=8.5 Hz, 1H), 7.09-7.07 (m, 1H), 7.01 (dd, J=1.8, 8.3 Hz, 1H), 6.86 (d, J=8.3 Hz, 1H), 6.56 (s, 1H), 6.32 (ddd, J=4.4, 9.9, 14.8 Hz, 1H), 5.80 (dd, J=8.0, 15.1 Hz, 1H), 4.32-4.25 (m, 1H), 4.23-4.16 (m, 1H), 4.07-3.96 (m, 4H), 3.71 (br d, J=14.6 Hz, 1H), 3.63 (br d, J=14.9 Hz, 1H), 3.38 (d, J=16.8 Hz, 1H), 3.33 (d, J=14.6 Hz, 1H), 3.09 (br dd, J=8.5, 15.4 Hz, 1H), 2.87-2.82 (s, 6H), 2.82-2.71 (m, 3H), 2.64-2.55 (m, 1H), 2.55-2.48 (m, 1H), 2.44-2.38 (m, 2H), 2.36-2.30 (m, 1H), 2.05-1.96 (m, 2H), 1.95-1.77 (m, 5H), 1.75-1.65 (m, 1H), 1.43-1.35 (m, 1H). LRMS: (ESI, +ve ion) m/z 713.2 (M+H)$^+$.

Step 6b: The other title product 201a (4.7 mg, 34%) was synthesized from Example 201, step 5b ((1S,3'R,6'R,7'S,8'E,11'S,17'R)-6-chloro-N-(dimethylsulfamoyl)-7'-((tert-butyldimethylsilyl)oxy)-17'-hydroxy-15'-oxo-3,4-dihydro-2H-spiro[naphthalene-1,24'-[22]oxa[1,14]diazapentacyclo[16.7.2.0~3,6~.011,14.021,26] heptacosa[8,18,20,26]tetraene]-17'-carboxamide or (1S,3'R,6'R,7'S,8'E,11'S,17'S)-6-chloro-N-(dimethylsulfamoyl)-7'-((tert-butyldimethylsilyl)oxy)-17'-hydroxy-15'-oxo-3,4-dihydro-2H-spiro[naphthalene-1,24'-[22]oxa[1,14]diazapentacyclo[16.7.2.0~3,6~.011,14.021,26] heptacosa[8,18,20,26]tetraene]-17'-carboxamide) through a procedure similar to that used for the synthesis of Example 201, step 6a. The compound came at around 42% acetone in hexanes. $^1$H NMR (500 MHz, CD$_2$Cl$_2$) δ ppm 7.73 (d, J=8.5 Hz, 1H), 7.26-7.21 (m, 1H), 7.19-7.14 (m, 2H), 7.08 (d, J=1.8 Hz, 1H), 6.91-6.87 (m, 1H), 6.86-6.81 (m, 1H), 6.49 (s, 1H), 6.03-5.95 (m, 1H), 5.73 (br d, J=15.6 Hz, 1H), 4.59-4.51 (m, 1H), 4.06-3.96 (m, 3H), 3.95-3.86 (m, 1H), 3.80-3.66 (m, 3H), 3.47 (br d, J=17.2 Hz, 1H), 3.27 (d, J=14.4 Hz, 1H), 3.02 (dd, J=9.4, 15.3 Hz, 1H), 2.83 (br d, J=17.4 Hz, 1H), 2.76 (m+s, 8H), 2.73-2.57 (m, 3H), 2.57-2.48 (m, 1H), 2.37 (br d, J=10.1 Hz, 1H), 2.32-2.24 (m, 1H), 2.06-2.00 (m, 1H), 1.96-1.76 (m, 6H), 1.66-1.60 (m, 1H), 1.43-1.35 (m, 1H). LRMS: (ESI, +ve ion) m/z 713.2 (M+H)$^+$.

Example 202

(1S,3'R,6'R,7'S,8'E,15'R)-6-CHLORO-7'-(2-((2,2-DIFLUORO-3-HYDROXYPROPYL)AMINO)ETHOXY)-N-(DIMETHYLSULFAMOYL)-15'-HYDROXY-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

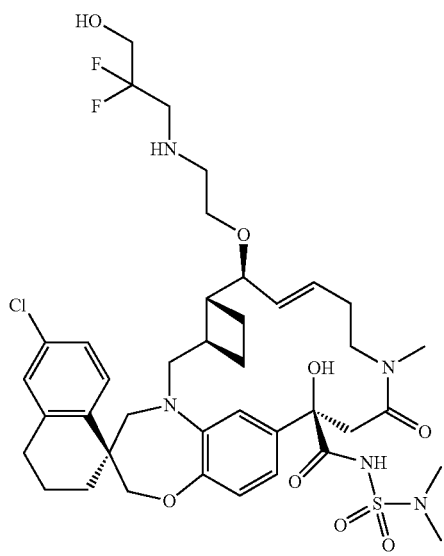 [SMILES: CN1CC/C=C/[C@H](OCCNCC(F)(F)CO)[C@@H]2CC[C@H]2CN2C[C@@]3(CCCc4cc(Cl)ccc43)COc3ccc(cc32)[C@@](O)(C(=O)NS(=O)(=O)N(C)C)CC1=O]

After being stored at RT for 2.5 months, the TFA salt of (1S,3'R,6'R,7'S,8'E,15'R)-6-chloro-7'-(2-(3,3-difluoro-1-azetidinyl)ethoxy)-N-(dimethylsulfamoyl)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$] pentacosa[8,16,18,24]tetraene]-15'-carboxamide (m=65 mg) was repurified by reverse-phase preparative HPLC using a Phenomenex Gemini column, 10 micron, C18, 100 Å, 150×30 mm, 0.1% TFA in CH$_3$CN/H$_2$O, gradient 35% to 90% over 30 min to provide (1S,3'R,6'R,7'S,8'E,15'R)-6-chloro-7'-(2-(3,3-difluoro-1-azetidinyl)ethoxy)-N-(dimethylsulfamoyl)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$] pentacosa[8,16,18,24]tetraene]-15'-carboxamide as TFA salt (56.6 mg) and the title product as TFA salt (5.1 mg) after lyophilization. $^1$H NMR (600 MHz, CD$_2$Cl$_2$) δ ppm 9.00 (br s, 1H), 7.72 (d, J=8.5 Hz, 1H), 7.16 (dd, J=1.7, 8.5 Hz, 1H), 7.08 (d, J=1.4 Hz, 1H), 6.98 (dd, J=1.7, 8.2 Hz, 1H), 6.86 (d, J=8.3 Hz, 1H), 6.47 (br s, 1H), 6.44-6.33 (m, 1H), 5.70 (br dd, J=9.6, 14.9 Hz, 1H), 4.06-3.92 (m, 5H), 3.77-3.67 (m, 2H), 3.62-3.47 (m, 6H), 3.34-3.23 (m, 3H), 3.19-3.14 (m, 1H), 3.10 (br dd, J=10.5, 15.1 Hz, 1H), 2.96 (s, 3H), 2.85 (s, 6H), 2.82-2.71 (m, 2H), 2.69-2.61 (m, 1H), 2.52 (br d, J=16.6 Hz, 1H), 2.48-2.35 (m, 2H), 2.34-2.25 (m, 1H), 2.09-1.81 (m, 6H), 1.79-1.68 (m, 1H), 1.43-1.35 (m, 1H). LRMS: (ESI, +ve ion) m/z 838.2 (M+H)$^+$.

Example 203

(1S,3'R,6'R,7'S,8'E,15'R)-6-CHLORO-7'-(2-(3,3-DIFLUORO-1-AZETIDINYL)ETHOXY)-15'-HYDROXY-N-((3-HYDROXY-1-AZETIDINYL)SULFONYL)-12'-METHYL-13'-OXO-3,4-DIHYDRO-2H-SPIRO[NAPHTHALENE-1,22'-[20]OXA[1,12]DIAZATETRACYCLO[14.7.2.0$^{3,6}$.0$^{19,24}$]PENTACOSA[8,16,18,24]TETRAENE]-15'-CARBOXAMIDE

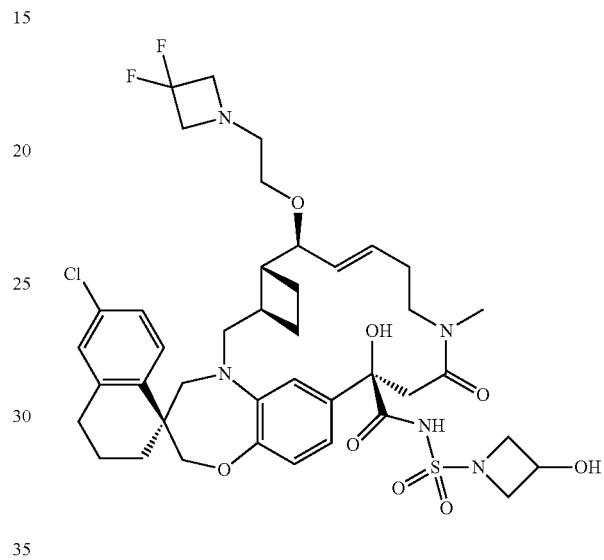

Step 1: (1S,3'R,6'R,7'S,8'E,15'R)-6-chloro-7'-(2-(3,3-difluoro-1-azetidinyl)ethoxy)-15'-hydroxy-n-((3-((tert-butyldimethylsilyl)oxy)azetidin-1-yl)-12'-methyl-13'-oxo-3,4-dihydro-2H-spiro[naphthalene-1,22'-[20]oxa[1,12]diazatetracyclo[14.7.2.0$^{3,6}$.0$^{19,24}$] pentacosa[8,16,18,24]tetraene]-15'-carboxamide

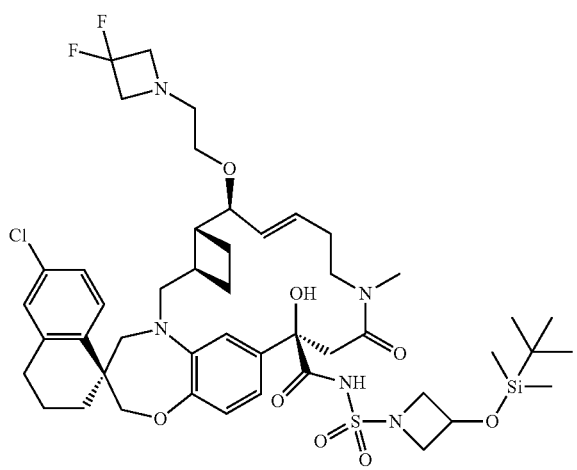 [SMILES: CN1CC/C=C/[C@H](OCCN2CC(F)(F)C2)[C@@H]2CC[C@H]2CN2C[C@@]3(CCCc4cc(Cl)ccc43)COc3ccc(cc32)[C@@](O)(C(=O)NS(=O)(=O)N2CC(O[Si](C)(C)C(C)(C)C)C2)CC1=O]

The title compound (38.9 mg, 58%) was synthesized from (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid (Example 175, step 2) and 3-((tert-butyldimethylsilyl)oxy)azetidine-1-sulfonamide through a procedure similar to that used for the synthesis of Example 5. LRMS: (ESI, +ve ion) m/z 962.2 (M+H)$^+$.

Note: 3-((tert-butyldimethylsilyl)oxy)azetidine-1-sulfonamide was synthesized following the procedure below: To a solution of 3-hydroxyazetidine-1-sulfonamide (0.1 g, 0.657 mmol) in dichloromethane (0.986 ml) and N, N-dimethylformamide (0.329 ml) was added triethylamine (0.101 ml, 0.723 mmol) and N,N-dimethylpyridin-4-amine (0.016 g, 0.131 mmol) followed by tert-butylchlorodimethylsilane (0.109 g, 0.723 mmol) under ice-cooling. The reaction mixture was then allowed to warm to RT and stirred overnight. 0.8 eq of triethylamine and 0.8 eq of TBDMSCl were added and the reaction mixture was stirred for 8 h (reaction complete on TLC). The reaction mixture was quenched with water. A saturated solution of ammonium chloride was then added and the reaction mixture was extracted with EtOAc (×3). The combined organic layer was dried over anhydrous magnesium sulfate and the solvent was evaporated under reduced pressure. The crude material was absorbed onto a plug of silica gel and purified by chromatography through a Redi-Sep pre-packed silica gel column (12 g), eluting with a gradient of 0% to 40% EtOAc in hexane, to provide 3-((tert-butyldimethylsilyl)oxy)azetidine-1-sulfonamide (0.0875 g, 0.328 mmol, 50.0% yield) as white solid. $^1$H NMR (300 MHz, CDCl$_3$) δ ppm 4.63-4.50 (m, 3H), 4.08-3.95 (m, 2H), 3.83-3.67 (m, 2H), 0.89 (s, 9H), 0.06 (s, 6H).

Step 2: (1S,3'R,6'R,7'S,8'E,15'R)-6-chloro-7'-(2-(3,3-difluoro-1-azetidinyl)ethoxy)-15'-hydroxy-n-((3-hydroxy-1-azetidinyl)sulfonyl)-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide To (1S,3'R,6'R,7'S,8'E,15'R)-6-chloro-7'-(2-(3,3-difluoro-1-azetidinyl)ethoxy)-15'-hydroxy-N-((3-((tert-butyldimethylsilyl)oxy)azetidin-1-yl)-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide (0.025 g, 0.026 mmol) was added TBAF (1M in THF) (0.156 ml, 0.156 mmol) and the reaction mixture was stirred at room temperature for 24 hrs. A saturated solution of NH$_4$Cl was then added followed by water. The aqueous phase was extracted with EtOAc (×3). The combined organic extract was washed with brine, dried over MgSO$_4$, filtered and concentrated in vacuo. The crude material was absorbed onto a plug of silica gel and purified by chromatography through a Redi-Sep pre-packed silica gel column, eluting with a gradient of 0% to 50% acetone in hexanes, to provide product (0.0104 g, 47.2% yield) as white solid. $^1$H NMR (300 MHz, CD$_2$Cl$_2$) δ ppm 7.73 (d, J=8.6 Hz, 1H), 7.16 (dd, J=2.3, 8.5 Hz, 1H), 7.08 (d, J=2.2 Hz, 1H), 6.99 (dd, J=2.0, 8.2 Hz, 1H), 6.86 (d, J=8.2 Hz, 1H), 6.49 (s, 1H), 6.29-6.14 (m, 1H), 5.80-5.64 (m, 2H), 4.50-4.38 (m, 1H), 4.37-4.14 (m, 3H), 4.09-4.00 (m, 3H), 3.85 (dd, J=1.5, 9.4 Hz, 1H), 3.78-3.53 (m, 8H), 3.52-3.41 (m, 1H), 3.39-3.28 (m, 2H), 3.26-3.16 (m, 1H), 3.15-3.00 (m, 1H), 2.98 (s, 3H), 2.84-2.58 (m, 6H), 2.47-2.27 (m, 3H), 2.11-1.66 (m, 7H), 1.45-1.31 (m, 1H). LRMS: (ESI, +ve ion) m/z 848.2 (M+H)$^+$.

Example 204

(1S,3'R,6'R,7'S,8'E,15'R)-6-CHLORO-N-(DIMETHYLSULFAMOYL)-15'-HYDROXY-12'-METHYL-7'-(2-((3R)-3-METHYL-4-MORPHOLINYL)ETHOXY)-13'-OXO-3,4-DIHYDRO-2H-SPIRO[NAPHTHALENE-1,22'-[20]OXA[1,12]DIAZATETRACYCLO [14.7.2.0$^{3,6}$.0$^{19,24}$]PENTACOSA[8,16,18,24]TETRAENE]-15'-CARBOXAMIDE

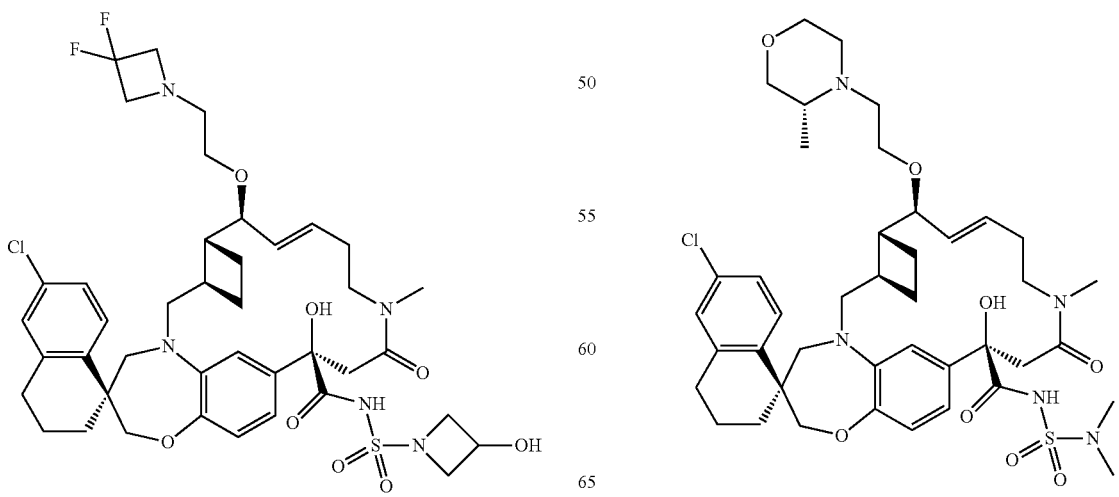

Step 1: Methyl (1S,3'R,6'R,7'S,8'E,15'R)-6-chloro-15'-hydroxy-12'-methyl-7'-(2-((3R)-3-methyl-4-morpholinyl)ethoxy)-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate Step 2: (1S,3'R,6'R,7'S,8'E,15'R)-6-chloro-15'-hydroxy-12'-methyl-7'-(2-((3R)-3-methyl-4-morpholinyl)ethoxy)-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid

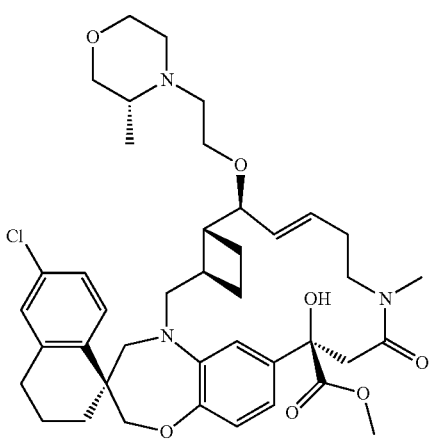 [SMILES: COC(=O)[C@@]1(O)CC(=O)N(C)CC/C=C/[C@H](OCCN2CCOC[C@H]2C)[C@@H]2CC[C@H]2CN2C[C@@]3(CCCc4cc(Cl)ccc43)COc3ccc1cc32]

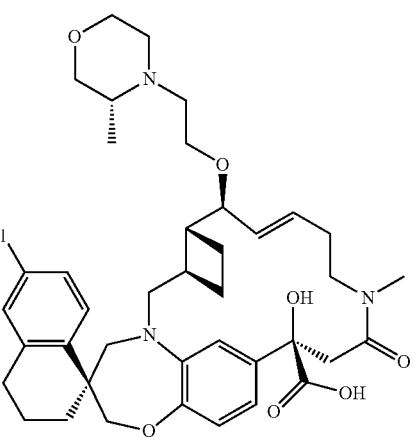

The title compound (14.7 mg, 43%) was synthesized from methyl (1S,3'R,6'R,7'S,8'E,15'R)-6-chloro-15'-hydroxy-7'-(2-bromoethoxy)-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate (Example 173, step 1) and (R)-3-methylmorpholine through a procedure similar to that used for the synthesis of Example 173, step 2. $^1$H NMR (300 MHz, CDCl$_3$) δ ppm 7.73 (d, J=8.5 Hz, 1H), 7.17 (dd, J=2.2, 8.5 Hz, 1H), 7.11 (dd, J=2.0, 8.3 Hz, 1H), 7.07 (d, J=2.2 Hz, 1H), 6.90 (d, J=8.3 Hz, 1H), 6.51 (d, J=2.0 Hz, 1H), 6.36-6.20 (m, 1H), 5.75-5.61 (m, 2H), 4.02 (s, 2H), 3.87 (dd, J=1.9, 9.5 Hz, 1H), 3.83-3.50 (m, 11H), 3.46-3.36 (m, 1H), 3.35-3.21 (m, 2H), 3.21-3.01 (m, 2H), 3.00 (s, 3H), 2.97-2.87 (m, 1H), 2.83-2.36 (m, 10H), 2.36-2.23 (m, 1H), 2.10-1.70 (m, 7H), 1.46-1.32 (m, 1H), 1.00 (d, J=6.3 Hz, 3H). LRMS: (ESI, +ve ion) m/z 736.1 (M+H)$^+$.

The title compound (12.3 mg, 96%) was synthesized from methyl (1S,3'R,6'R,7'S,8'E,15'R)-6-chloro-15'-hydroxy-12'-methyl-7'-(2-((3R)-3-methyl-4-morpholinyl)ethoxy)-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylate via saponification through a procedure similar to that used for the synthesis of Example 175, Step 2. $^1$H NMR (300 MHz, CDCl$_3$) δ ppm 7.73 (d, J=8.6 Hz, 1H), 7.16 (dd, J=2.2, 8.5 Hz, 1H), 7.10-7.03 (m, 2H), 6.88 (d, J=8.3 Hz, 1H), 6.63 (br s, 1H), 6.51-6.36 (m, 1H), 5.67 (br dd, J=9.7, 14.3 Hz, 1H), 4.11-3.85 (m, 7H), 3.78-3.47 (m, 6H), 3.40-3.03 (m, 8H), 3.01 (s, 3H), 2.82-2.66 (m, 3H), 2.63-2.53 (m, 1H), 2.46-2.24 (m, 3H), 2.14-1.67 (m, 7H), 1.44-1.32 (m+d, 4H). LRMS: (ESI, +ve ion) m/z 722.1 (M+H)$^+$.

483

Step 3: (1S,3'R,6'R,7'S,8'E,15'R)-6-chloro-N-(dimethylsulfamoyl)-15'-hydroxy-12'-methyl-7'-(2-((3R)-3-methyl-4-morpholinyl)ethoxy)-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide

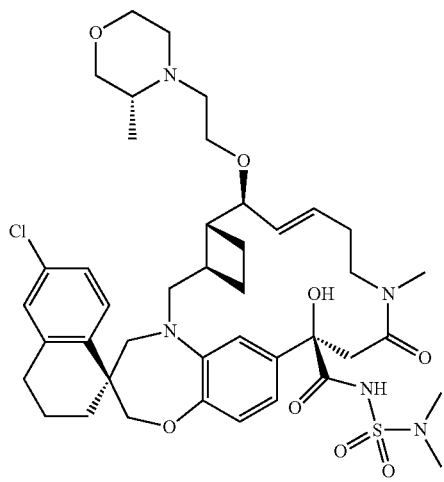 [SMILES: C[C@@H]1COCCN1CCO[C@H]1/C=C/CCN(C)C(=O)C[C@](O)(C(=O)NS(=O)(=O)N(C)C)c2ccc3c(c2)N(C[C@@H]2CC[C@H]21)C[C@@]1(CCCc2cc(Cl)ccc21)CO3]

The title compound as TFA salt (3.4 mg, 22%) was synthesized from (1S,3'R,6'R,7'S,8'E,15'R)-6-chloro-15'-hydroxy-12'-methyl-7'-(2-((3R)-3-methyl-4-morpholinyl)ethoxy)-13'-oxo-3,4-dihydro-2H-spiro[naphthalene-1,22'-[20]oxa[1,12] diazatetracyclo[14.7.2.0$^{3,6}$.0$^{19,24}$]pentacosa[8,16,18,24]tetraene]-15'-carboxylic acid and N,N-dimethylsulfamide through a procedure similar to that used for the synthesis of Example 5. $^1$H NMR (300 MHz, CD$_2$Cl$_2$) δ ppm 8.96 (s, 1H), 7.73 (d, J=8.5 Hz, 1H), 7.16 (dd, J=2.2, 8.5 Hz, 1H), 7.08 (d, J=2.2 Hz, 1H), 6.99 (dd, J=2.0, 8.3 Hz, 1H), 6.86 (d, J=8.2 Hz, 1H), 6.59 (s, 1H), 6.49 (d, J=1.9 Hz, 1H), 6.46-6.32 (m, 1H), 5.76-5.63 (m, 1H), 4.07-3.79 (m, 7H), 3.77-3.42 (m, 7H), 3.36-3.04 (m, 7H), 2.97 (s, 3H), 2.88 (s, 6H), 2.82-2.63 (m, 3H), 2.54-2.23 (m, 4H), 2.10-1.70 (m, 7H), 1.45-1.28 (m, 4H). LRMS: (ESI, +ve ion) m/z 828.3 (M+H)$^+$.

484

Example 205

(1S,3'R,6'R,7'S,8'E,15'R)-6-CHLORO-7'-(2-(3,3-DIFLUORO-1-AZETIDINYL)ETHOXY)-15'-HYDROXY-N-((2-METHOXYETHYL)SULFAMOYL)-12'-METHYL-13'-OXO-3,4-DIHYDRO-2H-SPIRO[NAPHTHALENE-1,22'-[20]OXA[1,12]DIAZATETRACYCLO[14.7.2.0~3,6~.019,24-]PENTACOSA[8,16,18,24]TETRAENE]-15'-CARBOXAMIDE

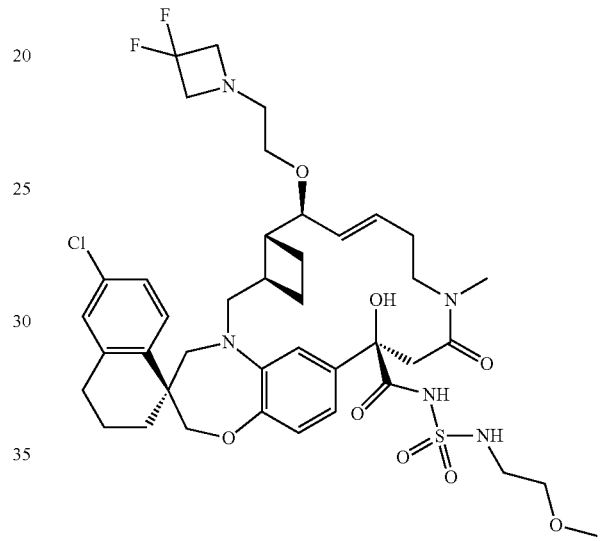

The title compound (15 mg, 21%) was synthesized from (1S,3'R,6'R,7'S,8'E,15'R)-6-chloro-7'-(2-(3,3-difluoro-1-azetidinyl)ethoxy)-15'-hydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxylic acid (Example 175, step 2) and potassium (N-(2-methoxyethyl)sulfamoyl)amide through a procedure similar to that used for the synthesis of Example 5. $^1$H NMR (500 MHz, CD$_2$Cl$_2$) δ ppm 9.11 (br s, 1H), 7.72 (d, J=8.6 Hz, 1H), 7.16 (dd, J=2.3, 8.4 Hz, 1H), 7.08 (d, J=2.2 Hz, 1H), 6.98 (dd, J=2.1, 8.2 Hz, 1H), 6.85 (d, J=8.2 Hz, 1H), 6.56 (br s, 1H), 6.51 (d, J=1.7 Hz, 1H), 6.40-6.25 (m, 1H), 5.74-5.61 (m, 2H), 4.05-3.93 (m, 2H), 3.86 (dd, J=1.2, 9.4 Hz, 1H), 3.74-3.54 (m, 8H), 3.52-3.45 (m, 1H), 3.45-3.40 (m, 2H), 3.38-3.28 (m+s, 5H), 3.19-3.10 (m, 2H), 3.09-3.01 (m, 1H), 2.95 (s, 3H), 2.88-2.59 (m, 6H), 2.52 (br d, J=16.8 Hz, 1H), 2.45-2.35 (m, 2H), 2.33-2.24 (m, 1H), 2.04-1.79 (m, 6H), 1.77-1.67 (m, 1H), 1.42-1.33 (m, 1H). LRMS: (ESI, +ve ion) m/z 850.0 (M+H)$^+$.

Note: potassium (N-(2-methoxyethyl)sulfamoyl)amide was synthesized from 2-methoxyethylamine using a procedure similar to that used in WO2004/50640 A1, 2004, p 29

Examples 206a and 206b (1S,3'R,6'R,7'S,8'E,15'R)-6-CHLORO-N-(DIMETH-YLSULFAMOYL)-15'-FLUORO-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0~3,6~.019,24-]PENTACOSA[8,16,18,24]TETRAENE]-15'-CARBOXAMIDE AND (1S,3'R,6'R,7'S,8'E,15'S)-6-CHLORO-N-(DIMETHYLSULFAMOYL)-15'-FLUORO-7'-METHOXY-12'-METHYL-13'-OXO-3,4-DIHYDRO-2H-SPIRO[NAPHTHALENE-1,22'-[20]OXA[1,12]DIAZATETRACYCLO[14.7.2.0~3,6~.0~19,24-]PENTACOSA [8,16,18,24]TETRAENE]-15'-CARBOXAMIDE (after Separation, the Relative Configuration of the Alkyl Fluoride Stereocenter was not Established)

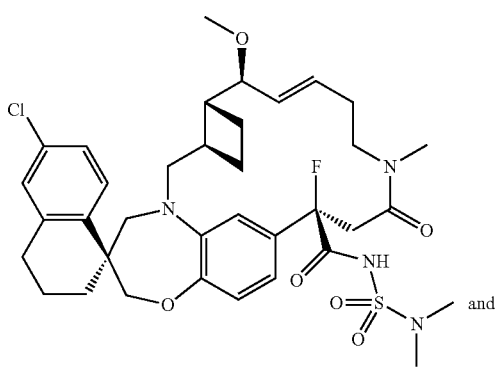

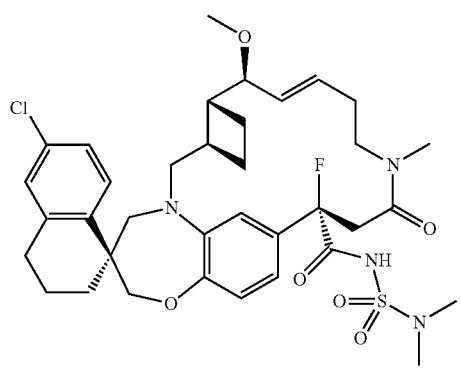

To a solution of (1S,3'R,6'R,7'S,8'E,15'R)-6-chloro-N-(dimethylsulfamoyl)-15'-hydroxy-7'-methoxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide (Example 5, 50 mg, 0.070 mmol) in dichloromethane (699 µl) cooled in an ice-water bath was added Deoxo-Fluor 50% solution in toluene (46.4 mg, 0.105 mmol). The reaction mixture was maintained in the chilled bath for 60 minutes. The reaction mixture was diluted with a saturated solution of ammonium chloride and extracted with EtOAc (2×). The organic extract was washed with a saturated solution of NaCl and dried over sodium sulfate. The solution was filtered and concentrated in vacuo. The crude material was absorbed onto a plug of silica gel and purified by chromatography through a Redi-Sep pre-packed silica gel column (12 g), eluting with a gradient of 0% to 80% acetone in hexanes, to provide the desired product as a mixture of isomers (4:1 dr; 121941-8-mixture). This mixture of isomers was combined with another batch that was obtained using the same procedure and performed on 12 mg of (1S,3'R,6'R,7'S,8'E,15'R)-6-chloro-N-(dimethylsulfamoyl)-15'-hydroxy-7'-methoxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide (Example 5). The combined mixture of isomers (40 mg) was submitted to chiral separation (Conditions: Thar 80 SFC with 250×21+150×21 mm IA columns with 25.0 mL/min methanol (neat)$^+$31.0 g/min CO$_2$, 45% co-solvent at 56 g/min. Temp.=29° C., Outlet pressure=100 bar, Wavelength=267 nm. Injected 0.3 mL of 40 mg sample dissolved in 6 mL of MeOH:DCM 2:1; c=6.67 mg/mL and 2.0 mg per injection.

Cycle time 8.0 min, run time 13.0 min.). Concentration under reduced pressure gave one of the title compounds as the first eluting isomer 206a (9 mg, 18%) and then the other title compound as the second eluting isomer 206b (18 mg, 36%). Minor isomer 206a (first eluting isomer): $^1$H NMR (300 MHz, CD$_2$Cl$_2$) δ ppm 7.73 (d, J=8.6 Hz, 1H), 7.16 (dd, J=2.0, 8.4 Hz, 1H), 7.11-7.05 (m, 1H), 6.87-6.81 (m, 1H), 6.81-6.72 (m, 1H), 6.54 (br s, 1H), 6.08-5.86 (m, 1H), 5.73-5.62 (m, 1H), 4.06-3.94 (m, 2H), 3.78-3.64 (m, 3H), 3.63-3.50 (m, 2H), 3.34 (d, J=14.4 Hz, 1H), 3.22-3.12 (m, 4H), 3.10-2.92 (m, 9H), 2.85-2.60 (m, 4H), 2.47-2.37 (m, 2H), 2.33-2.24 (m, 1H), 2.03 (t, J=13.4 Hz, 2H), 1.96-1.71 (m, 6H), 1.43-1.31 (m, 1H). LRMS: (ESI, +ve ion) m/z 717.2 (M+H)$^+$. Major isomer 206b (second eluting isomer): $^1$H NMR (500 MHz, CD$_2$Cl$_2$) δ ppm 7.72 (d, J=8.4 Hz, 1H), 7.16 (dd, J=1.9, 8.5 Hz, 1H), 7.08 (s, 1H), 6.80 (d, J=7.3 Hz, 1H), 6.73-6.62 (m, 1H), 6.54 (s, 1H), 5.86-5.77 (m, 1H), 5.67 (dd, J=1.8, 11.0 Hz, 1H), 4.10-3.92 (m, 2H), 3.74 (d, J=14.4 Hz, 2H), 3.67-3.49 (m, 2H), 3.45-3.21 (m, 3H), 3.21-3.13 (m, 4H), 3.12-2.98 (m, 6H), 2.96 (s, 3H), 2.83-2.60 (m, 3H), 2.49-2.36 (m, 2H), 2.36-2.23 (m, 1H), 2.09-1.99 (m, 2H), 1.97-1.69 (m, 6H), 1.38 (t, J=12.5 Hz, 1H). LRMS: (ESI, +ve ion) m/z 717.2 (M+H)$^+$.

487

Examples 207a and 207b (1S,3'R,6'R,7'S,8'E,15'R)-6-CHLORO-7'-(2-(DIMETHYLAMINO)-2-OXOETHYL)-N-(DIMETHYLSULFAMOYL)-7',15'-DIHYDROXY-12'-METHYL-13'-OXO-3,4-DIHYDRO-2H-SPIRO[NAPHTHALENE-1,22'-[20]OXA[1,12]DIAZATETRACYCLO [14.7.2.0~3,6~.0~19,24] PENTACOSA[8,16,18,24]TETRAENE]-15'-CARBOXAMIDE OR (1S,3'R,6'R,7'R,8'E,15'R)-6-CHLORO-7'-(2-(DIMETHYLAMINO)-2-OXOETHYL)-N-(DIMETHYLSULFAMOYL)-7',15'-DIHYDROXY-12'-METHYL-13'-OXO-3,4-DIHYDRO-2H-SPIRO[NAPHTHALENE-1,22'-[20]OXA[1,12]DIAZATETRACYCLO [14.7.2.0~3,6~.0~19,24-]PENTACOSA[8,16,18,24]TETRAENE]-15'-CARBOXAMIDE

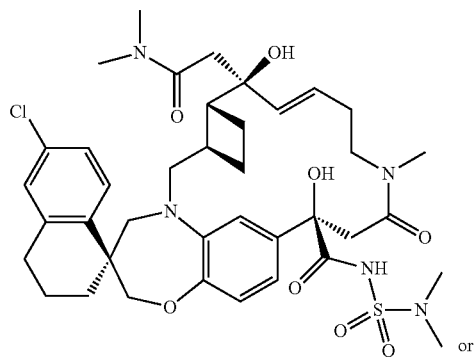

or

488

Step 1: (1S,3'R,6'R,8'E,15'R)-6-chloro-N-(dimethylsulfamoyl)-15'-hydroxy-12'-methyl-7',13'-dioxo-3,4-dihydro-2H-spiro[naphthalene-1,22'-[20]oxa[1,12]diazatetracyclo[14.7.2.0~3,6~.0 19,24]pentacosa[8,16,18,24]tetraene]-15'-carboxamide

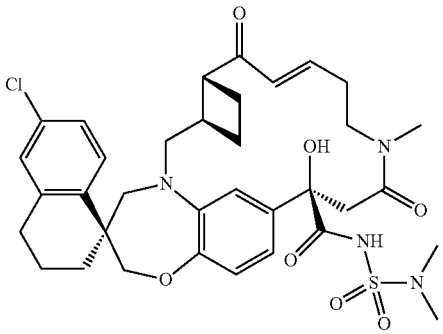 [SMILES: CN1CC/C=C/C(=O)[C@@H]2CC[C@H]2CN2C[C@@]3(CCCc4cc(Cl)ccc43)COc3ccc(cc32)[C@@](O)(C(=O)NS(=O)(=O)N(C)C)CC1=O]

To a solution of (1S,3'R,6'R,7'S,8'E,15'R)-6-chloro-N-(dimethylsulfamoyl)-7',15'-dihydroxy-12'-methyl-13'-oxo-3,4-dihydro-2H-spiro[naphthalene-1,22'-[20]oxa[1,12]diazatetracyclo[14.7.2.0$^{3,6}$.0$^{19,24}$]pentacosa[8,16,18,24]tetraene]-15'-carboxamide (Example 43, step 3, 31.0 mg, 0.044 mmol) in DCM (1105 µl) at RT was added manganese (IV) oxide (154 mg, 1.768 mmol) in a single portion. The reaction mixture was stirred at RT for 16 h. The reaction mixture was purified by chromatography through a Redi-Sep pre-packed silica gel column (40 g), eluting with a gradient of 10% to 100% acetone in hexanes, to give the title product (19.0 mg, 0.027 mmol, 61.5% yield). LRMS: (ESI, +ve ion) m/z 699.0 (M+H)⁺.

Step 2: (1S,3'R,6'R,7'S,8'E,15'R)-6-chloro-7'-(2-(dimethylamino)-2-oxoethyl)-N-(dimethylsulfamoyl)-7',15'-dihydroxy-12'-methyl-13'-oxo-3,4-dihydro-2H-spiro[naphthalene-1,22'-[20]oxa[1,12]diazatetracyclo[14.7.2.0~3,6~.019,24]pentacosa[8,16,18,24]tetraene]-15'-carboxamide and (1S,3'R,6'R,7'R,8'E,15'R)-6-chloro-7'-(2-(dimethylamino)-2-oxoethyl)-N-(dimethylsulfamoyl)-7',15'-dihydroxy-12'-methyl-13'-oxo-3,4-dihydro-2H-spiro[naphthalene-1,22'-[20]oxa[1,12]diazatetracyclo[14.7.2.0~3,6~.019,24]pentacosa[8,16,18,24]tetraene]-15'-carboxamide

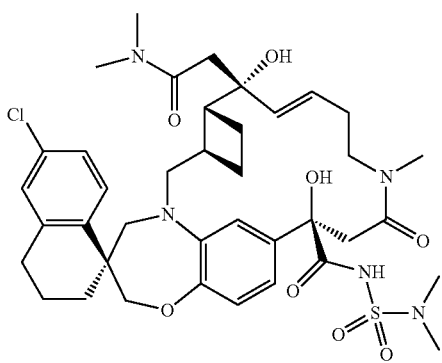

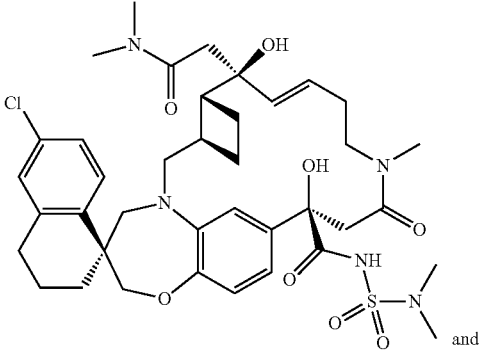

and

489
-continued

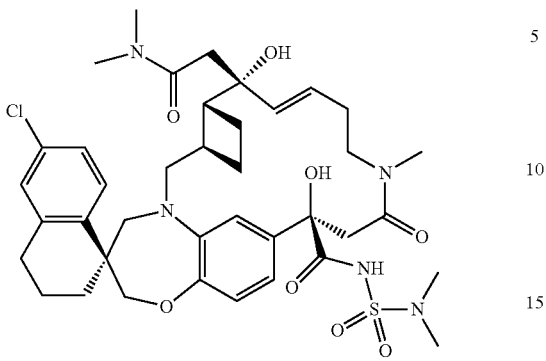

To a solution of lithium diisopropylamide (2.0 M in heptane/tetrahydrofuran/ethylbenzene) (0.429 ml, 0.858 mmol) in THF (0.2 ml) (ice bath) was added dimethyl acetamide (0.080 ml, 0.858 mmol). The reaction mixture was stirred at 0° C. for 7 min. Then a solution of (1S,3'R, 6'R,8'E,15'R)-6-chloro-N-(dimethylsulfamoyl)-15'-hydroxy-12'-methyl-7',13'-dioxo-3,4-dihydro-2H-spiro[naphthalene-1,22'-[20]oxa[1,12]diazatetracyclo[14.7.2.0~3, 6~.019,24]pentacosa[8,16,18,24]tetraene]-15'-carboxamide (30.0 mg, 0.043 mmol) in THF (1.0 ml) was added and the reaction mixture was stirred at 0° C. for 26 min. The reaction was quenched with a saturated solution of ammonium chloride (1 ml) and acidified with 1N HCl to pH 2-3 and extracted with EtOAc (80 ml). The organic phase was washed with brine, dried over anhydrous sodium sulfate and filtered. The solvent was removed by evaporation. The crude products were purified by chromatography through a Redi-Sep pre-packed silica gel column (4 g), eluting with a gradient of 10% to 100% acetone in hexanes, to give one of the tile compounds as the first eluting isomer 207a (21.0 mg, 0.027 mmol, 62.2% yield) and then the other title compound as the second isomer 207b (0.44 mg, 0.560 µmol, 1.304% yield). First eluting isomer 207a (major isomer): $^1$H NMR (400 MHz, CDCl$_3$) δ ppm 9.01 (br s, 1H), 7.74 (d, J=8.4 Hz, 1H), 7.16 (d, J=7.9 Hz, 1H), 7.08 (d, J=1.6 Hz, 1H), 7.01 (dd, J=1.7, 8.3 Hz, 1H), 6.89 (d, J=8.2 Hz, 1H), 6.51 (s, 1H), 6.47 (d, J=1.4 Hz, 1H), 6.11-6.00 (m, 1H), 5.96-5.87 (m, 1H), 5.84-5.80 (m, 1H), 4.08-3.99 (m, 2H), 3.81-3.73 (m, 1H), 3.68-3.46 (m, 3H), 3.35 (d, J=14.5 Hz, 1H), 3.20 (s, 3H), 3.04-2.91 (m+s, 14H), 2.87-2.83 (m, 1H), 2.80-2.73 (m, 2H), 2.71-2.55 (m, 3H), 2.53-2.28 (m, 3H), 2.07-1.65 (m, 7H), 1.43-1.35 (m, 1H). LRMS: (ESI, +ve ion) m/z 786.0 (M+H)$^+$. Second eluting isomer 207b (minor isomer): $^1$H NMR (400 MHz, CDCl$_3$) δ ppm 8.76 (s, 1H), 7.73 (d, J=8.2 Hz, 1H), 7.16 (d, J=9.0 Hz, 1H), 7.07 (s, 1H), 6.99 (d, J=6.1 Hz, 1H), 6.87 (d, J=8.4 Hz, 1H), 6.62 (s, 1H), 6.47 (s, 1H), 6.43-6.31 (m, 1H), 5.87 (d, J=14.7 Hz, 1H), 4.64 (s, 1H), 4.07-4.00 (m, 1H), 3.98-3.92 (m, 1H), 3.92-3.86 (m, 1H), 3.81-3.72 (m, 1H), 3.66-3.59 (m, 2H), 3.31 (br d, J=14.1 Hz, 1H), 3.21-3.10 (m, 1H), 3.01 (s, 3H), 2.96-2.89 (s+m, 4H), 2.93 (s, 3H), 2.87 (s, 6H), 2.80-2.72 (m, 2H), 2.65-2.62 (m, 1H), 2.55-2.26 (m, 6H), 2.06-1.63 (m, 7H), 1.42-1.33 (m, 1H). LRMS: (ESI, +ve ion) m/z 786.0 (M+H)$^+$.

Example 208

(1S,3'R,6'R,7'S,8'E,16'R)-6-CHLORO-N-(DIMETHYLSULFAMOYL)-7'-HYDROXY-16'-METHOXY-13'-METHYL-14'-OXO-3,4-DIHYDRO-2H-SPIRO[NAPHTHALENE-1,23'-[21]OXA[1,13]DIAZATETRACYCLO[15.7.2.0~3,6~.0~20,25]HEXACOSA[8,17,19,25]TETRAENE]-16'-CARBOXAMIDE OR (1S,3'R,6'R,7'S,8'E,16'S)-6-CHLORO-N-(DIMETHYLSULFAMOYL)-7'-HYDROXY-16'-METHOXY-13'-METHYL-14'-OXO-3,4-DIHYDRO-2H-SPIRO[NAPHTHALENE-1,23'-[21]OXA[1,13]DIAZATETRACYCLO[15.7.2.0~3,6~.020,25]HEXACOSA[8,17,19,25]TETRAENE]-16'-CARBOXAMIDE

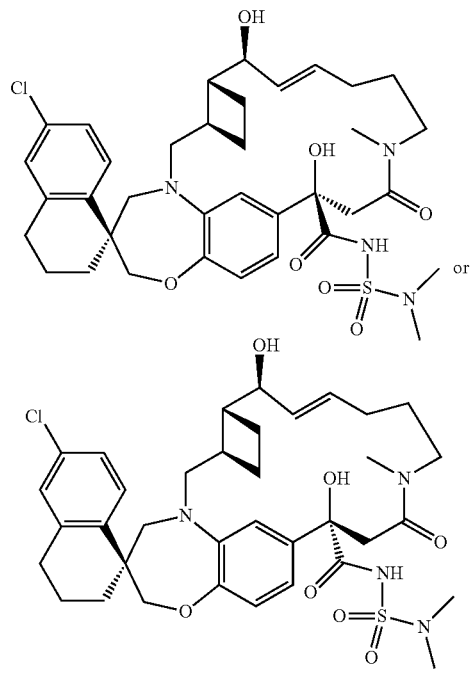

Step 1: Methyl(1S,3'R,6'R,7'S,8'E,16'R)-6-chloro-7'-hydroxy-16'-methoxy-13'-methyl-14'-oxo-3,4-dihydro-2H-spiro[naphthalene-1,23'-[21]oxa[1,13]diazatetracyclo[15.7.2.0~3,6~.020,25]hexacosa[8,17,19,25]tetraene]-16'-carboxylate or methyl (1S,3'R,6'R,7'S,8'E,16'S)-6-chloro-7'-hydroxy-16'-methoxy-13'-methyl-14'-oxo-3,4-dihydro-2H-spiro[naphthalene-1,23'-[21]oxa[1,13]diazatetracyclo[15.7.2.0~3,6~.020,25] hexacosa[8,17,19,25]tetraene]-16'-carboxylate

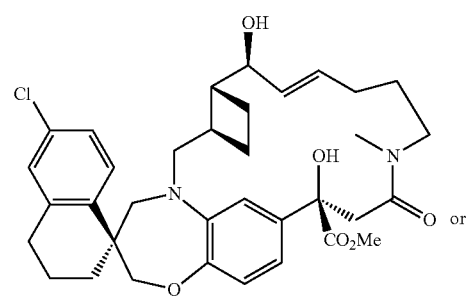

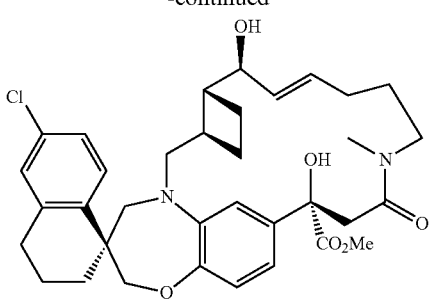

The title compound (30 mg, 45.1% yield) was synthesized from Example 83, step 1 through a procedure similar to that used for the synthesis of Example 3. LRMS: (ESI, +ve ion) m/z 637.1 (M+H)$^+$.

Step 2: (1S,3'R,6'R,7'S,8'E,16'R)-6-chloro-7'-hydroxy-16'-methoxy-13'-methyl-14'-oxo-3,4-dihydro-2H-spiro[naphthalene-1,23'-[21]oxa[1,13]diazatetracyclo[15.7.2.0~3,6~.020,25]hexacosa[8,17,19,25]tetraene]-16'-carboxylic Acid or (1S,3'R,6'R,7'S,8'E,16'S)-6-chloro-7'-hydroxy-16'-methoxy-13'-methyl-14'-oxo-3,4-dihydro-2H-spiro[naphthalene-1,23'-[21]oxa[1,13]diazatetracyclo[15.7.2.0~3,6~.020,25]hexacosa[8,17,19,25]tetraene]-16'-carboxylic acid

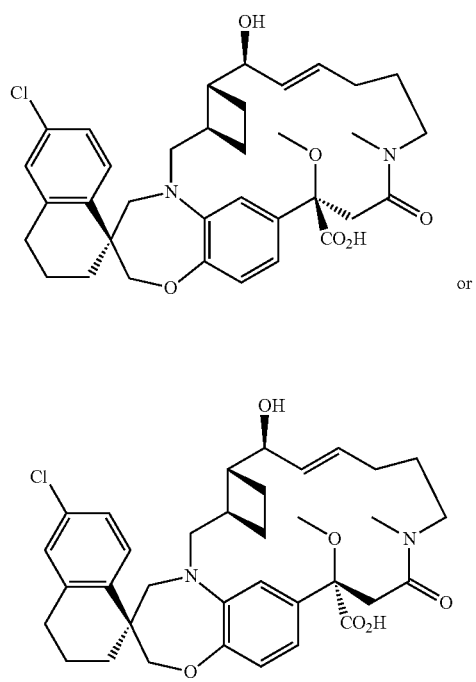

The title compound (29 mg, 100% yield) was synthesized from Example 208, Step 1 via saponification through a procedure similar to that used for the synthesis of Example 4. LRMS: (ESI, +ve ion) m/z 623.2 (M+H)$^+$.

Step 3: (1S,3'R,6'R,7'S,8'E,16'R)-6-chloro-N-(dimethylsulfamoyl)-7'-hydroxy-16'-methoxy-13'-methyl-14'-oxo-3,4-dihydro-2H-spiro[naphthalene-1,23'-[21]oxa[1,13]diazatetracyclo[15.7.2.0~3,6~.020,25] hexacosa[8,17,19,25]tetraene]-16'-carboxamide or (1S,3'R,6'R,7'S,8'E,16'S)-6-chloro-N-(dimethylsulfamoyl)-7'-hydroxy-16'-methoxy-13'-methyl-14'-oxo-3,4-dihydro-2H-spiro[naphthalene-1,23'-[21]oxa[1,13]diazatetracyclo[15.7.2.0~3,6~.020,25]hexacosa[8,17,19,25]tetraene]-16'-carboxamide

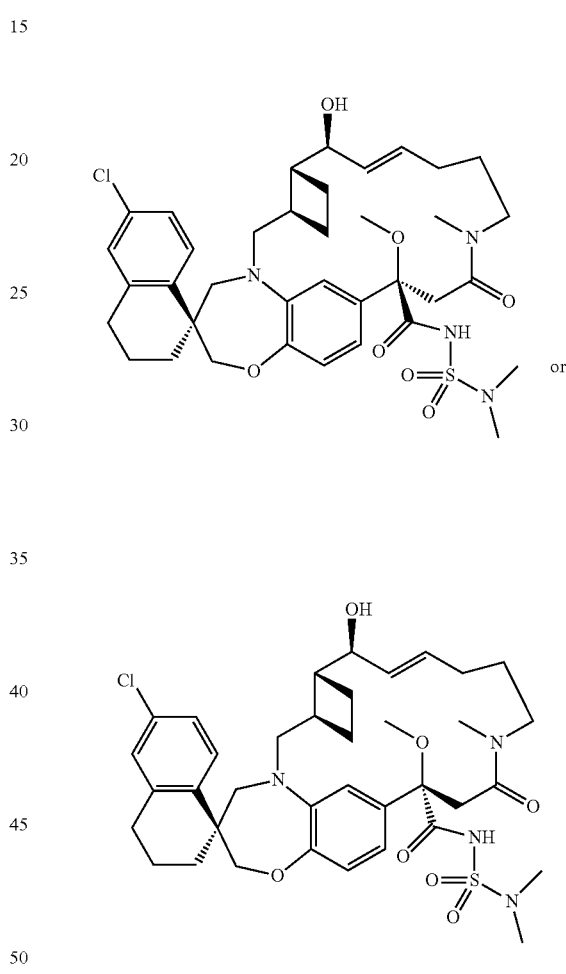

The title compound (6.3 mg, 17.94% yield) was synthesized from Example 298, Step 2 and dimethylsulfamide through a procedure similar to that used for the synthesis of Example 5. $^1$H NMR (300 MHz, CD$_2$Cl$_2$) δ ppm 9.37 (br s, 1H), 7.77 (d, J=8.5 Hz, 1H), 7.20 (dd, J=2.3, 8.5 Hz, 1H), 7.12 (d, J=2.0 Hz, 1H), 6.98-6.91 (m, 1H), 6.89-6.82 (m, 2H), 5.62 (br d, J=2.6 Hz, 2H), 4.17 (s, 2H), 4.02-3.89 (m, 1H), 3.79-3.42 (m, 7H), 3.19 (s, 3H), 2.99 (s, 6H), 2.96 (s, 3H), 2.86-2.77 (m, 2H), 2.76-2.66 (m, 1H), 2.64 (s, 2H), 2.40-2.22 (m, 2H), 2.12-1.85 (m, 7H), 1.80-1.65 (m, 2H), 1.46-1.34 (m, 1H). LRMS: (ESI, +ve ion) m/z 729.0 (M+H)$^+$.

Examples 209a and 209b (1S,3'R,6'R,7'S,8'E,15'S)-6-CHLORO-7',15'-DIHYDROXY-12'-METHYL-13'-OXO-3,4-DIHYDRO-2H-SPIRO[NAPHTHALENE-1,22'-[20]OXA[1,12,25]TRIAZATETRACYCLO[14.7.2.0~3,6~.019,24]PENTACOSA[8,16,18,24]TETRAENE]-15'-CARBOXYLIC ACID OR (1S,3'R,6'R,7'S,8'E,15'R)-6-CHLORO-7',15'-DIHYDROXY-12'-METHYL-13'-OXO-3,4-DIHYDRO-2H-SPIRO[NAPHTHALENE-1,22'-[20]OXA[1,12,25]TRIAZATETRACYCLO[14.7.2.0~3,6~.019,24]PENTACOSA[8,16,18,24]TETRAENE]-15'-CARBOXYLIC ACID

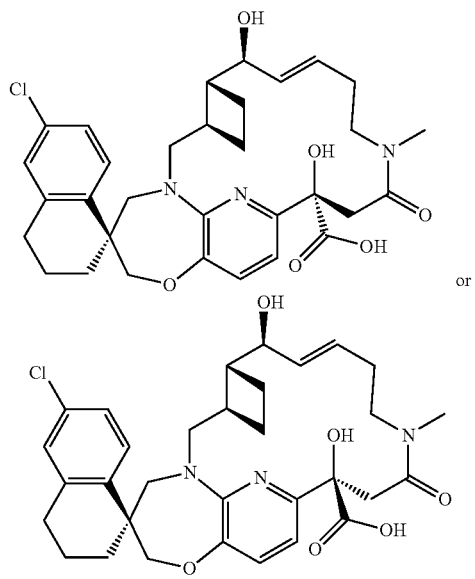

Step 1: (2S)-methyl 4-(but-3-en-1-yl(methyl)amino)-2-(6-chloro-5'-(((1R,2R)-2-((S)-1-hydroxyallyl)cyclobutyl)methyl)-3,4,4',5'-tetrahydro-2H,2'H-spiro[naphthalene-1,3'-pyrido[3,2-b][1,4]oxazepin]-7'-yl)-2-hydroxy-4-oxobutanoate and (2R)-methyl 4-(but-3-en-1-yl(methyl)amino)-2-(6-chloro-5'-(((1R,2R)-2-((S)-1-hydroxyallyl)cyclobutyl)methyl)-3,4,4',5'-tetrahydro-2H,2'H-spiro[naphthalene-1,3'-pyrido[3,2-b][1,4]oxazepin]-7'-yl)-2-hydroxy-4-oxobutanoate

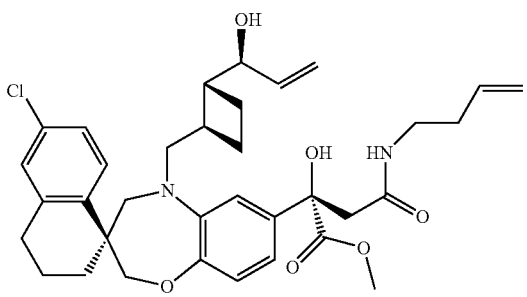

and

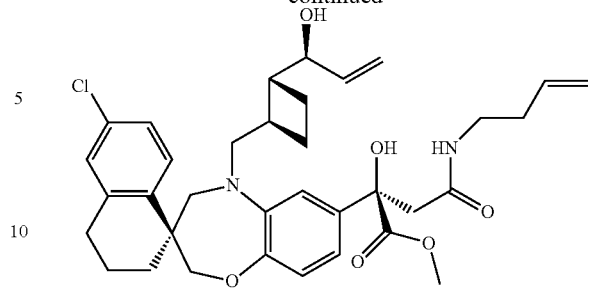

The title compounds were synthesized from Example 1, step 5 and N-methylbut-3-en-1-amine through a procedure similar to that used for the synthesis of Example 1, step 6. The crude material was purified by silica gel chromatography (eluting with 20%-70% EtOAc in heptanes to give the first eluting isomer (one of the title compounds, 70 mg, 48%) and then a 1 to 1 mixture of both title compounds (40 mg, 27.5% yield) both as white solids. The first eluting isomer (Rf=0.21) came with 50% EtOAc in heptanes. First eluting isomer: LRMS: (ESI, +ve ion) m/z 638.4 (M+H)$^+$.

Step 2: Methyl (1S,3'R,6'R,7'S,8'E,15'S)-6-chloro-7',15'-dihydroxy-12'-methyl-13'-oxo-3,4-dihydro-2H-spiro[naphthalene-1,22'-[20]oxa[1,12,25]triazatetracyclo[14.7.2.0~3,6~.019,24]pentacosa[8,16,18,24]tetraene]-15'-carboxylate or methyl (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12,25]triazatetracyclo[14.7.2.0~3,6~.019,24]pentacosa[8,16,18,24]tetraene]-15'-carboxylate

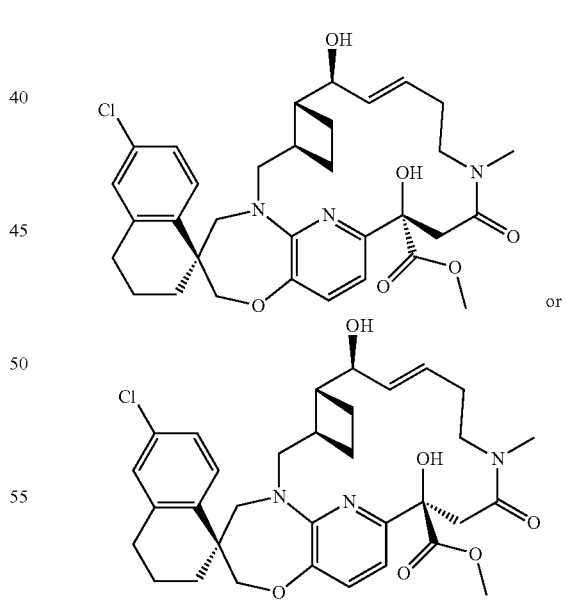

Step 2a: To a 100 ml flask was added the first eluting isomer obtained in Example 207, step 1 (65 mg, 0.102 mmol) and 1,2-dichloroethane (60 ml). The solution was sparged with argon for 15 minutes at which time Hoveyda-Grubbs 2nd generation (12.76 mg, 0.020 mmol) and 2,6-dichloro-1,4-benzoquinone (3.61 mg, 0.020 mmol) were added as a solution in 0.5 mL of the reaction mixture. The reaction was then stirred for 6 hours at 55° C. while sparging with argon. The reaction mixture was cooled while sparging with air, concentrated and the crude material was purified by silica gel chromatography (eluting with 0% to 50% EtOAc in Heptanes) to give one of the title products (30 mg, 48.3% yield) as a white solid. Rf=0.44 eluting with 50% EtOAc in heptanes. $^1$H NMR (400 MHz, CD$_2$Cl$_2$) δ=7.70 (d, J=8.4 Hz, 1H), 7.17 (dd, J=2.2, 8.5 Hz, 1H), 7.09 (d, J=2.3 Hz, 1H), 7.05 (d, J=7.8 Hz, 1H), 6.81 (d, J=8.0 Hz, 1H), 6.18-6.06 (m, 1H), 5.79 (br dd, J=7.4, 15.3 Hz, 1H), 4.24 (br dd, J=3.3, 13.9 Hz, 1H), 4.15-4.06 (m, 2H), 3.91 (d, J=12.1 Hz, 1H), 3.86 (br d, J=14.7 Hz, 1H), 3.73 (s, 3H), 3.54-3.39 (m, 3H), 3.28-3.20 (m, 1H), 2.94 (s, 3H), 2.84-2.74 (m, 3H), 2.65 (br d, J=16.6 Hz, 1H), 2.55-2.44 (m, 2H), 2.39-2.22 (m, 2H), 2.10-2.02 (m, 1H), 1.98-1.79 (m, 5H), 1.75-1.65 (m, 1H), 1.44-1.34 (m, 1H). LRMS: (ESI, +ve ion) m/z 610.4 (M+H)$^+$.

Step 2b: The other title compound was synthesized from the 1 to 1 mixture of diastereomers obtained in Example 207, step 1 through a procedure similar to that used for the synthesis of Example 207, Step 2a. The crude material was purified by silica gel chromatography (eluting with 0% to 50% EtOAc in Heptanes) to give the first eluting isomer (the other title compound) (20 mg, 52% yield) and the same isomer as in Example 207, Step 2a (19 mg, 50% yield) both as a white solid. First eluting isomer: LRMS: (ESI, +ve ion) m/z 609.8 (M+H)$^+$.

Step 3: (1S,3'R,6'R,7'S,8'E,15'S)-6-chloro-7',15'-dihydroxy-12'-methyl-13'-oxo-3,4-dihydro-2H-spiro[naphthalene-1,22'-[20]oxa[1,12,25]triazatetracyclo[14.7.2.0~3,6~.0 19,24]pentacosa[8,16,18,24]tetraene]-15'-carboxylic acid or (1S,3'R,6'R,7'S,8'E,15'R)-6-chloro-7',15'-dihydroxy-12'-methyl-13'-oxo-3,4-dihydro-2H-spiro[naphthalene-1,22'-[20]oxa[1,12,25]triazatetracyclo[14.7.2.0~3,6~.0 19,24]pentacosa[8,16,18,24]tetraene]-15'-carboxylic Acid

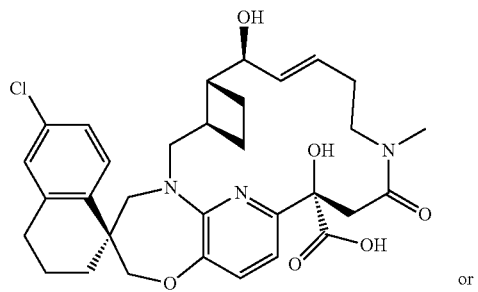

or

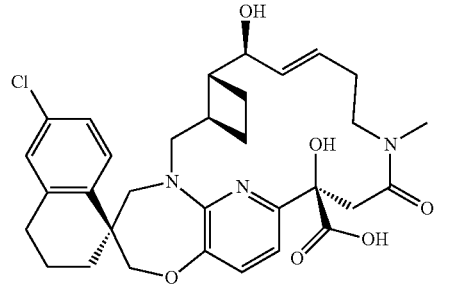

Step 3a: One of title compounds 209a (14 mg, 95%) was synthesized from Example 207, step 2a via saponification through a procedure similar to that used for the synthesis of Example 175, Step 2. $^1$H NMR (400 MHz, CD$_2$Cl$_2$) δ ppm 7.69 (d, J=8.4 Hz, 1H), 7.18 (dd, J=2.2, 8.5 Hz, 1H), 7.13-7.08 (m, 2H), 6.93 (d, J=7.8 Hz, 1H), 6.02 (ddd, J=4.4, 9.8, 14.7 Hz, 1H), 5.81 (dd, J=7.7, 15.4 Hz, 1H), 4.25-4.14 (m, 2H), 4.11 (d, J=12.3 Hz, 1H), 3.96-3.87 (m, 2H), 3.53-3.40 (m, 3H), 3.24 (td, J=4.3, 14.7 Hz, 1H), 3.00-2.86 (m+s, 4H), 2.86-2.63 (m, 3H), 2.57-2.42 (m, 2H), 2.41-2.22 (m, 2H), 2.10-2.02 (m, 1H), 1.99-1.80 (m, 5H), 1.79-1.68 (m, 1H), 1.47-1.35 (m, 1H). LRMS: (ESI, +ve ion) m/z 596.3 (M+H)$^+$.

Step 3b: The other title compound 209b (5 mg, 21%) was synthesized via saponification from Example 207, step 2b through a procedure similar to that used for the synthesis of Example 175, Step 2. LRMS: (ESI, +ve ion) m/z 595.8 (M+H)$^+$.

Examples 210a and 210b (1S,12'S)-6-chloro-9'-methyl-10'-oxo-3,4-dihydro-2H-spiro[naphthalene-1,19'-[17]oxa[1,9]diazatricyclo[11.7.2.0~16,21-]docosa[13,15,21]triene]-12'-carboxylic Acid and (1S,12'R)-6-chloro-9'-methyl-10'-oxo-3,4-dihydro-2H-spiro[naphthalene-1,19'-[17]oxa[1,9]diazatricyclo[11.7.2.0~16,21-]docosa[13,15,21]triene]-12'-carboxylic Acid

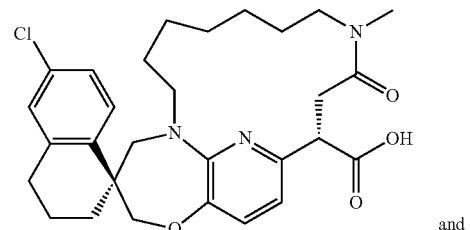

and

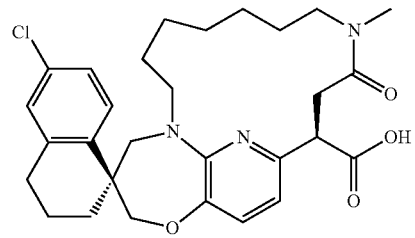

Step 1: (S)-methyl 6-chloro-1-(hydroxymethyl)-1,2,3,4-tetrahydronaphthalene-1-carboxylate and (R)-methyl 6-chloro-1-(hydroxymethyl)-1,2,3,4-tetrahydronaphthalene-1-carboxylate

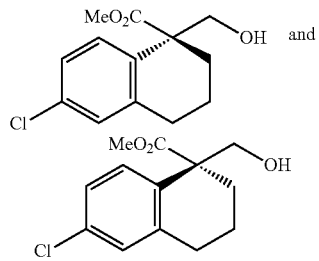

The title compounds (31 g) were separated by SFC (OJ-H column, 0.6 mL injections of 31 g/320 mL (96.9 mg/mL)

sample solution in methanol, i.e. 58 mg/injection. Run time=7.5 min.; Cycle time=2.35 min) and afforded first (S)-methyl 6-chloro-1-(hydroxymethyl)-1,2,3,4-tetrahydronaphthalene-1-carboxylate (13.78 g, ee>99%) and then (R)-methyl 6-chloro-1-(hydroxymethyl)-1,2,3,4-tetrahydronaphthalene-1-carboxylate (11.42 g, ee>99%)

Step 2: Methyl (S)-6-chloro-1-formyl-1,2,3,4-tetrahydronaphthalene-1-carboxylate

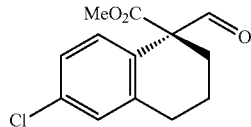

(S)-methyl 6-chloro-1-(hydroxymethyl)-1,2,3,4-tetrahydronaphthalene-1-carboxylate (3.80 g, 14.92 mmol) was dissolved in DCM (86 ml) and cooled to 0° C. Dessmartinperiodinane (9.49 g, 22.38 mmol) was added in 3.2 g portions and the white slurry was stirred at 0° C. for 30 minutes. The ice bath was removed and the reaction was stirred for an additional 1.5 hours (reaction complete by TLC). The reaction mixture was then diluted with ethyl acetate (1000 mL) and this mixture was extracted with 1:1 saturated sodium thiosulfate solution: water (2×250 mL), saturated sodium bicarbonate solution (1×250 mL) and brine (1×250 mL). The organic layer was dried over magnesium sulfate and concentrated to dryness to give (S)-methyl 6-chloro-1-formyl-1,2,3,4-tetrahydronaphthalene-1-carboxylate (3.60 g, 14.25 mmol, 95% yield) in 97% purity. The crude was used as such in the next reaction. LRMS: (ESI, +ve ion) m/z 253.0 (M+H).

Step 3: Methyl(S,E)-6-chloro-1-((hydroxyimino)methyl)-1,2,3,4-tetrahydronaphthalene-1-carboxylate

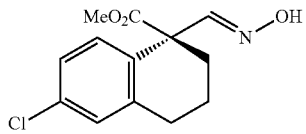 [SMILES: COC(=O)[C@@]1(/C=N/O)CCCc2cc(Cl)ccc21]

(S)-methyl 6-chloro-1-formyl-1,2,3,4-tetrahydronaphthalene-1-carboxylate (3.60 g, 14.25 mmol) was dissolved in ethanol (226 ml). Pyridine (4.61 ml, 57.0 mmol) and hydroxylamine hydrochloride (1.386 g, 19.95 mmol) were added and the clear solution was stirred at room temperature for one hour. The reaction mixture was concentrated under reduced pressure to 25% of original volume and water was added (500 mL). The white mixture was then extracted with ethyl acetate (1×1000 mL) and the organic layer was washed with water (1×500 mL) and brine (1×200 mL). The layers were separated and the organic layer was dried over magnesium sulfate. The filtrate was concentrated to give (S,E)-methyl 6-chloro-1-((hydroxyimino)methyl)-1,2,3,4-tetrahydronaphthalene-1-carboxylate (4.15 g, 15.50 mmol, 109% yield), which was used as such in the next step. LRMS: (ESI, +ve ion) m/z 268.1 (M+H)⁺.

Step 4: (S)-methyl 6-chloro-1-cyano-1,2,3,4-tetrahydronaphthalene-1-carboxylate

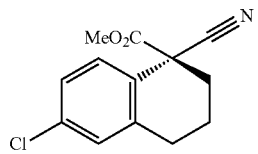 [SMILES: COC(=O)[C@@]1(C#N)CCCc2cc(Cl)ccc21]

The crude (S,E)-methyl 6-chloro-1-((hydroxyimino)methyl)-1,2,3,4-tetrahydronaphthalene-1-carboxylate (3.81 g, 14.23 mmol) was dissolved in dichloromethane (30.9 ml) and DMAP (0.174 g, 1.423 mmol) was added followed by acetic anhydride (30.9 ml, 327 mmol). The reaction mixture was stirred at room temperature overnight. The reaction was diluted with dichloromethane (250 mL) and washed with 0.6N HCl solution (1×250 mL), saturated sodium bicarbonate solution (1×250 mL) and brine (1×150 mL). The organic layer was dried over magnesium sulfate to give 4.33 g of the crude intermediate (S,E)-methyl 1-((acetoxyimino)methyl)-6-chloro-1,2,3,4-tetrahydronaphthalene-1-carboxylate (4.33 g, 13.98 mmol, 98% yield). The acetate intermediate was resubjected to acetic anhydride (80 mL) and heated at 140° C. for 3 hours. After using the same workup as above, the crude (S)-methyl 6-chloro-1-cyano-1,2,3,4-tetrahydronaphthalene-1-carboxylate (3.43 g, 13.74 mmol, 97% yield) was isolated and used as such in the next step.

Step 5: (S)-6-chloro-1-(hydroxymethyl)-1,2,3,4-tetrahydronaphthalene-1-carbonitrile

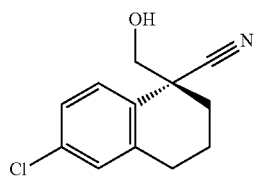 [SMILES: N#C[C@]1(CO)CCCc2cc(Cl)ccc21]

(S)-methyl 6-chloro-1-cyano-1,2,3,4-tetrahydronaphthalene-1-carboxylate (3.43 g, 13.74 mmol) was dissolved in 83.5 mL of a 20:4:3 mixture of THF: MeOH: H₂O. To the solution was added sodium borohydride (1.039 g, 27.5 mmol) in portions over a period of 10 minutes. The reaction was stirred for one hour. LCMS indicates 25% completion. Another aliquot of sodium borohydride (1.039 g, 27.5 mmol) was added portionwise at room temperature and the mixture was stirred for an additional 30 minutes. The reaction was then cooled to 0° C. and quenched with a approximately 3 mL of acetone followed by addition of 120 mL brine. This mixture was then extracted with ethyl acetate (2×400 mL). The combined organic layers were washed (1×150 mL) with saturated sodium bicarbonate, brine (1×150 mL) and dried over magnesium sulfate. The crude product was then purified by medium pressure chromatography (silica, 0 to 50% ethyl acetate: hexanes) to give (S)-6-chloro-1-(hydroxymethyl)-1,2,3,4-tetrahydronaphthalene-1-carbonitrile (780 mg, 3.52 mmol, 25.6% yield) and 6-chloro-1,2,3,4-tetrahydronaphthalene-1-carbonitrile (1.67 g, 8.71 mmol, 63.4% yield).

Step 6: (S)-methyl 2-(3-bromo-4-((7-chloro-1-cyano-1,2,3,4-tetrahydronaphthalen-1-yl)methoxy)phenyl)acetate

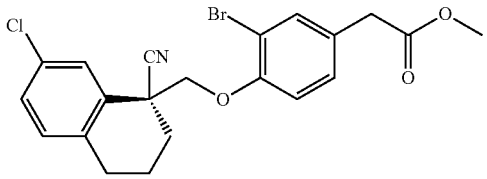 [SMILES: COC(=O)Cc1ccc(OC[C@@]2(C#N)CCCc3ccc(Cl)cc32)c(Br)c1]

To a 100 mL round bottom flask was added 446 mg of (S)-6-chloro-1-(hydroxymethyl)-1,2,3,4-tetrahydronaphthalene-1-carbonitrile, 792 mg of triphenylphosphine and 35 ml of THF. The reaction was cooled to 0° C., at which time was added 598 ul of (E)-diisopropyl diazene-1,2-dicarboxylate dropwise over 20 minutes. The cooling bath was removed and the mixture stirred for 15 minutes at ambient temperature and then refluxed for 16 hours. The mixture was diluted with 200 ml of EtOAc, washed twice with 50 ml of 1 N NaOH, once with 50 ml of brine and dried over sodium sulfate. The organic layer was filtered, concentrated and the residue purified by silica gel flash chromatography (slow 10-50% EtOAc/hexanes) to give 798 mg of (S)-methyl 2-(3-bromo-4-((7-chloro-1-cyano-1,2,3,4-tetrahydronaphthalen-1-yl)methoxy)phenyl)acetate as clear oil. Rf product=0.58 eluting with 50% EtOAc in Hexanes. Rf diisopropyl hydrazine-1,2-dicarboxylate=0.47 eluting with 50% EtOAc in Hexanes (stain with KMnO$_4$ no UV). LRMS: (ESI, +ve ion) m/z 472.0 (M+Na)$^+$.

Step 7: (S)-methyl 2-(3-bromo-4-((1-(((tert-butoxycarbonyl)amino)methyl)-7-chloro-1,2,3,4-tetrahydronaphthalen-1-yl)methoxy)phenyl)acetate

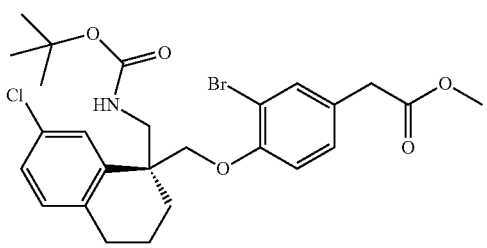 [SMILES: COC(=O)Cc1ccc(OC[C@@]2(CNC(=O)OC(C)(C)C)CCCc3ccc(Cl)cc32)c(Br)c1]

To a 100 ml Parr shaker flask was added 1596 mg of wet raney nickel (assumed 50% of mass is water), 60 ml of MeOH, 798 mg of (S)-methyl 2-(3-bromo-4-((7-chloro-1-cyano-1,2,3,4-tetrahydronaphthalen-1-yl)methoxy)phenyl)acetate, 776 mg of di-tert-butyl dicarbonate and 744 ul of triethylamine. The Parr flask was then placed on the Parr shaker and the reaction was run at 45 PSI for 4 hours. The reaction was then filtered over Celite® and was washed several times with MeOH and DCM. The solvent was then removed and the crude purified on a silica gel column (eluting with 10% to 50% EtOAc in Hexanes) to give 795 mg of (S)-methyl 2-(3-bromo-4-((1-(((tert-butoxycarbonyl)amino)methyl)-7-chloro-1,2,3,4-tetrahydronaphthalen-1-yl)methoxy)phenyl)acetate as a sticky white solid. Rf=0.76 eluting with 50% EtOAc in Hexanes. LRMS: (ESI, +ve ion) m/z 575.9 (M+Na)$^+$.

Step 8: (S)-tert-butyl 6'-chloro-7-(2-methoxy-2-oxoethyl)-3',4'-dihydro-2H,2'H-spiro[benzo[b][1,4]oxazepine-3,1'-naphthalene]-5(4H)-carboxylate

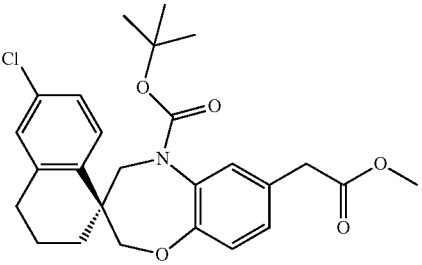 [SMILES: COC(=O)Cc1ccc2c(c1)N(C(=O)OC(C)(C)C)C[C@@]1(CCCc3cc(Cl)ccc31)CO2]

In a vial were added 62 mg of xantphos, 16 mg of palladium(ii) acetate, 937 mg of cesium carbonate, 759 mg of (S)-methyl 2-(3-bromo-4-((1-(((tert-butoxycarbonyl)amino)methyl)-7-chloro-1,2,3,4-tetrahydronaphthalen-1-yl)methoxy)phenyl)acetate and 15 ml of toluene. Argon was bubbled through the solution for 5 minutes at which time the vial was sealed and stirred at 105° C. for 16 hours The reaction mixture was diluted with 200 ml of EtOAc, washed with 50 ml of 1 N HCl and once with 50 ml of brine.

The organic solvent was dried over sodium sulfate, filtered and the solvent was removed by rotary evaporation. The crude was purified on silica gel eluting with 10-50% EtOAc in hexanes to give 352 mg of (S)-tert-butyl 6'-chloro-7-(2-methoxy-2-oxoethyl)-3',4'-dihydro-2H,2'H-spiro[benzo[b][1,4]oxazepine-3,1'-naphthalene]-5(4H)-carboxylate as white solids. Rf of=0.11 eluting in 10% EtOAc in hexanes. rf=0.76 eluting with 50% EtOAc in hexanes. LRMS: (ESI, +ve ion) m/z 494.0 (M+Na)$^+$.

Step 9: 4-tert-butyl 1-methyl 2-((S)-5-(tert-butoxycarbonyl)-6'-chloro-3',4,4',5-tetrahydro-2H,2'H-spiro[benzo[b][1,4]oxazepine-3,1'-naphthalen]-7-yl)succinate

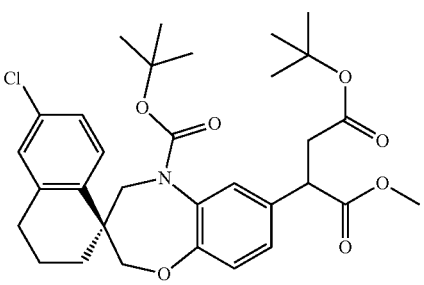 [SMILES: COC(=O)C(CC(=O)OC(C)(C)C)c1ccc2c(c1)N(C(=O)OC(C)(C)C)C[C@@]1(CCCc3cc(Cl)ccc31)CO2]

To a 100 ml flask was added 348 mg of (S)-tert-butyl 6'-chloro-7-(2-methoxy-2-oxoethyl)-3',4'-dihydro-2H,2'H-spiro[benzo[b][1,4]oxazepine-3,1'-naphthalene]-5(4H)-carboxylate (which was dried twice with 3 ml of toluene) and 5 ml of THF. The reaction was cooled to −78° C. at which time 811 ul of potassium tert-butoxide (1.0M solution in tetrahydrofuran) was added and immediately afterwards 136 ul of tert-butyl bromoacetate was added in 0.3 ml of THF. The reaction was stirred at −78° C. for 60 minutes at which time the reaction was quenched at −78 C with 50 ml of 1 N HCl. The reaction was then extracted with 300 ml of EtOAc and the organic layer was extracted once with 50 ml of brine.

The organic solvent was dried over sodium sulfate, filtered and the solvent removed by rotary evaporation to give 432 mg of 4-tert-butyl 1-methyl 2-((S)-5-(tert-butoxycarbonyl)-6'-chloro-3',4,4',5-tetrahydro-2H,2'H-spiro[benzo[b][1,4]oxazepine-3,1'-naphthalen]-7-yl)succinate, which was used in the next step with no further purification. LRMS: (ESI, +ve ion) m/z 608.1 (M+Na)⁺.

Step 10: 3-((S)-6'-chloro-3',4,4',5-tetrahydro-2H, 2'H-spiro[benzo[b][1,4]oxazepine-3,1'-naphthalen]-7-yl)-4-methoxy-4-oxobutanoic acid

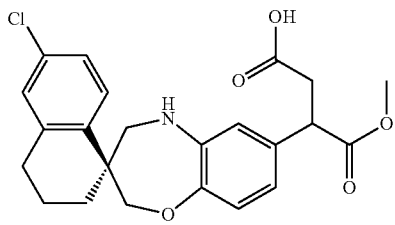 [SMILES: COC(=O)C(CC(=O)O)c1ccc2c(c1)NC[C@@]1(CCCc3cc(Cl)ccc31)CO2]

To a 100 ml flask was added 432 mg of 4-tert-butyl 1-methyl 2-((S)-5-(tert-butoxycarbonyl)-6'-chloro-3',4,4',5-tetrahydro-2H,2'H-spiro[benzo[b][1,4]oxazepine-3,1'-naphthalen]-7-yl)succinate, 9 ml of DCM and 3 ml of TFA. The reaction was stirred at room temperature for 3 hours under a stream of nitrogen. The crude was diluted with 200 ml of EtOAc and extracted once with 100 ml of brine. The organic layer was dried over sodium sulfate, filtered, and the solvent removed by rotary evaporation to give 438 mg of 3-((S)-6'-chloro-3',4,4',5-tetrahydro-2H,2'H-spiro[benzo[b][1,4]oxazepine-3,1'-naphthalen]-7-yl)-4-methoxy-4-oxobutanoic acid TFA salt as a light brown film. LRMS: (ESI, +ve ion) m/z 430.0 (M+H)⁺.

Step 11: 3-((S)-6'-chloro-5-(hex-5-en-1-yl)-3',4,4',5-tetrahydro-2H,2'H-spiro[benzo[b][1,4]oxazepine-3,1'-naphthalen]-7-yl)-4-methoxy-4-oxobutanoic Acid

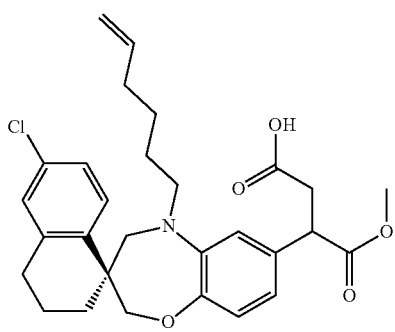 [SMILES: C=CCCCCN1C[C@@]2(CCCc3cc(Cl)ccc32)COc2ccc(C(CC(=O)O)C(=O)OC)cc21]

To a 100 ml flask was added 317 mg of 3-((S)-6'-chloro-3',4,4',5-tetrahydro-2H,2'H-spiro[benzo[b][1,4]oxazepine-3,1'-naphthalen]-7-yl)-4-methoxy-4-oxobutanoic acid, 10 ml of DCE, 1.386 ml of hex-5-enal (0.76 M in DCM), and 313 mg of sodium triacetoxyborohydride. The reaction was stirred at room temperature overnight at which time the reaction was quenched with brine, and extracted with 200 ml of EtOAc. The organic layer was dried over sodium sulfate, filtered and the solvent was removed by rotary evaporation. The crude was purified on a silica gel column (eluting with 2%-5% MeOH in DCM) to give 185.4 mg of 3-((S)-6'-chloro-5-(hex-5-en-1-yl)-3',4,4',5-tetrahydro-2H,2'H-spiro[benzo[b][1,4]oxazepine-3,1'-naphthalen]-7-yl)-4-methoxy-4-oxobutanoic acid as a light yellow oil. Rf=0.46 eluting with 50% EtOAc in hexanes. Note: 49.1% yield is for the combined last three steps. LRMS: (ESI, +ve ion) m/z 570.0 (M+H)⁺.

Step 12: Methyl 4-(allyl(methyl)amino)-2-((S)-6'-chloro-5-(hex-5-en-1-yl)-3',4,4',5-tetrahydro-2H,2'H-spiro[benzo[b][1,4]oxazepine-3,1'-naphthalen]-7-yl)-4-oxobutanoate

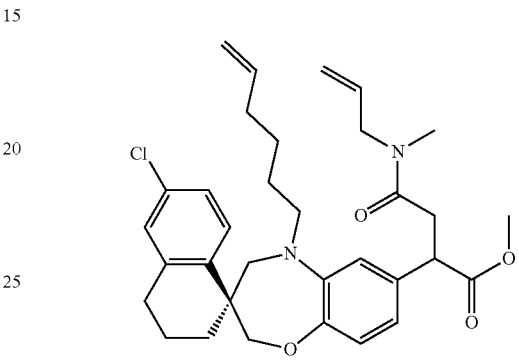

To a 100 ml flask was added 185 mg of 3-((S)-6'-chloro-5-(hex-5-en-1-yl)-3',4,4',5-tetrahydro-2H,2'H-spiro[benzo[b][1,4]oxazepine-3,1'-naphthalen]-7-yl)-4-methoxy-4-oxobutanoic acid, 5 ml of DMF, 275 mg of 2-(1H-benzo[d][1,2,3]triazol-1-yl)-1,1,3,3-tetramethylisouronium hexafluorophosphate(V), 49 ul of N-methylprop-2-en-1-amine and 180 ul of N,N-diisopropylethylamine. The reaction was stirred at 50 C for 4 hours at which time the reaction was diluted with 200 ml of diethyl ether and extracted twice with 50 ml of 1 N HCl. The organic layer was dried over sodium sulfate, filtered and the solvent was removed by rotary evaporation. The crude was purified on a silica gel column eluting with 10% to 50% EtOAc in hexanes to give 153 mg of the title compound a light yellow oil. Rf=0.55 eluting with 10% to 50% EtOAc. LRMS: (ESI, +ve ion) m/z 565.1 (M+H)⁺.

Step 13: Methyl (1S,6'E)-6-chloro-9'-methyl-10'-oxo-3,4-dihydro-2H-spiro[naphthalene-1,19'-[17]oxa[1,9]diazatricyclo[11.7.2.0~16,21~]docosa[6,13,15,21]tetraene]-12'-carboxylate

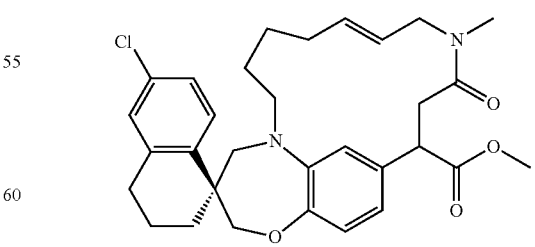

A 500 ml round bottom flask was charged with 152.7 mg of methyl 4-(allyl(methyl)amino)-2-((S)-6'-chloro-5-(hex-5-en-1-yl)-3',4,4',5-tetrahydro-2H,2'H-spiro[benzo[b][1,4]oxazepine-3,1'-naphthalen]-7-yl)-4-oxobutanoate in 150 ml of toluene. The reaction was stirred at room temperature for 10 min to dissolve the solid starting material and then subjected to three cycles of evacuation/back-filling with argon. To the homogeneous solution was added a solution of Hoveyda-Grubbs 11(33.9 mg in 1 ml of toluene) at room temperature. The mixture was stirred at 105° C. under nitrogen for 2.0 hrs at which time air was blown through the reaction vessel for 10 min to deactivate the catalyst, passed through a 0.45 m filter and then concentrated to give 145 mg of crude title compound as a dark brown film. The crude product was used in the next step with no further purification. LRMS: (ESI, +ve ion) m/z 537.1 (M+H)$^+$.

Step 14: Methyl (1S,6'E)-6-chloro-9'-methyl-10'-oxo-3,4-dihydro-2H-spiro[naphthalene-1,19'-[17]oxa[1,9]diazatricyclo[11.7.2.0~16,21~]docosa[6,13,15,21]tetraene]-12'-carboxylate

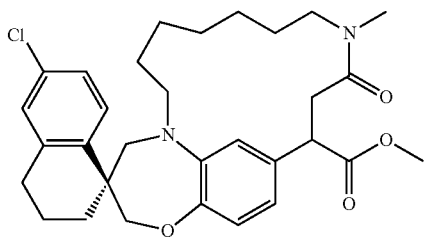 [SMILES: COC(=O)C1CC(=O)N(C)C/C=C/CCCCN2C[C@@]3(CCCc4cc(Cl)ccc43)COc3ccc1cc32]

A 100 ml flask was charged with 145 mg of methyl (S,6'E)-6-chloro-9'-methyl-10'-oxo-3,4-dihydro-2H-spiro[naphthalene-1,19'-[17]oxa[1,9]diazatricyclo[11.7.2.0~16,21~]docosa[6,13,15,21]tetraene]-12'-carboxylate, 20 ml of EtOAc, and 12.26 mg of platinum(IV) oxide. The mixture was degassed by $H_2$ three times at which time the reaction was stirred at room temperature under a hydrogen balloon for 3.0 hrs. The reaction was then filtered and the solvent was removed by rotary evaporation to give 146 mg of the title compound (100% yield) which was used in the next step without further purification. LRMS: (ESI, +ve ion) m/z 539.2 (M+H)$^+$.

Step 15: (1S)-6-chloro-9'-methyl-10'-oxo-3,4-dihydro-2H-spiro[naphthalene-1,19'-[17]oxa[1,9]diazatricyclo[11.7.2.0~16,21~]docosa[13,15,21]triene]-12'-carboxylic acid

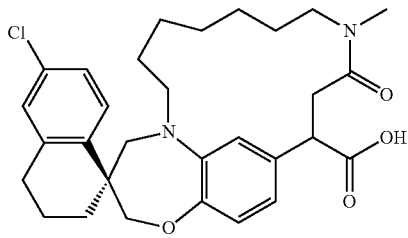 [SMILES: CN1CCCCCCCN2C[C@@]3(CCCc4cc(Cl)ccc43)COc3ccc(cc32)C(C(=O)O)CC1=O]

To a 25 ml flask was added 95 mg of ethyl (1S,6'E)-6-chloro-9'-methyl-10'-oxo-3,4-dihydro-2H-spiro[naphthalene-1,19'-[17]oxa[1,9]diazatricyclo[11.7.2.0~16,21~]docosa[6,13,15,21]tetraene]-12'-carboxylate, 3 ml of Dioxane/water (2 to 1) and 89 mg of LiOH. The reaction was stirred at 70 C for 3 hour at which time the reaction was quenched with 50 ml of 1 N HCl and extracted with 200 mL EtOAc. The organic phase was dried over anhydrous sodium sulfate, filtered and the solvent was removed by rotary evaporation. The crude was purified by reverse phase HPLC to give 104 mg (73% yield) of the title product. LRMS: (ESI, +ve ion) m/z 525.1 (M+H)$^+$.

Step 16: (1S,12'S)-6-chloro-9'-methyl-10'-oxo-3,4-dihydro-2H-spiro[naphthalene-1,19'-[17]oxa[1,9]diazatricyclo[11.7.2.0~16,21~]docosa[13,15,21]triene]-12'-carboxylic Acid and (1S,12'R)-6-chloro-9'-methyl-10'-oxo-3,4-dihydro-2H-spiro[naphthalene-1,19'-[17]oxa[1,9]diazatricyclo[11.7.2.0~16,21~]docosa[13,15,21]triene]-12'-carboxylic Acid

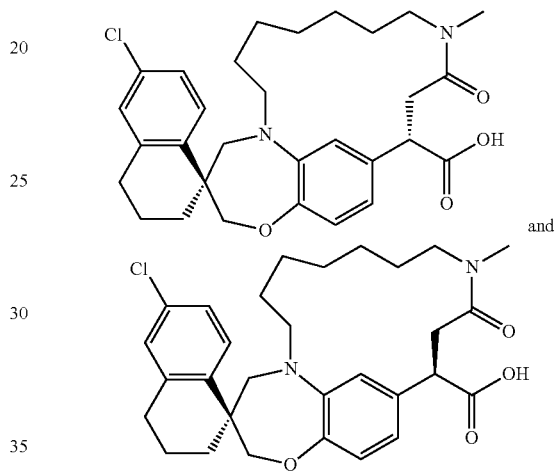

The title compounds were separated by chiral HPLC: 250×30 mm AD column with 50 g/min MeOH+(20 mM $NH_3$)$^+$60 g/min $CO_2$ on Thar 350 SFC. Outlet pressure=100 bar, Temp=21 C, wavelength=220 nm. Used 2.0 mL injections of 91 mg/30 mL (3.0 mg/mL) sample solution in Methanol: DCM (1:1), i.e. 60 mg/injection. Run time=14 min, cycle time=6.6 min. After chiral separation the solvent was removed by rotary evaporation to give 34.5 mg of the first eluting isomer 210a (one of the title compounds, LRMS: (ESI, +ve ion) m/z 525.0 (M+H)$^+$) and 33.1 mg of the second eluting isomer 210b (the other title compounds, LRMS: (ESI, +ve ion) m/z 525.0 (M+H)$^+$), both as off white solids.

Biological Assays

Table 1 Cell Free Mcl-1:Bim Binding Assays
(Mcl-1 TR-FRET Assays)

The inhibition of the Mcl-1/Bim interaction was measured using a time-resolved fluorescence resonance energy transfer (TR-FRET) assay. The recombinant human Mcl-1 (C-terminally 6xHis tagged Mcl-1 containing residues 171-327) was generated at Amgen Inc (Thousand Oaks, Calif.). A biotinylated peptide derived from human Bim (residues 51-76) was purchased from CPC Scientific (San Jose, Calif.). The TR-FRET assay was conducted in a 384-well white OptiPlate™ (PerkinElmer, Waltham, Mass.) in a total volume of 40 μL. The reaction mixture contained 0.1 nM Mcl-1 (171-327), 0.05 nM biotin-Bim(51-76), 0.05 nM LANCE® Eu-W1024 Anti-6×His (PerkinElmer), 0.072 nM Streptavidin-XLent (Cisbio, Bedford, Mass.), and serially diluted test compounds in the binding buffer of 20 mM HEPES, pH 7.5, 150 mM NaCl, 0.016 mM Brij®35, and 1 mM dithiothreitol. For Mcl-1 TR-FRET assay with 5% human serum, the same assay condition was used except for the addition of 5% human serum (Bioreclamation, Westbury, N.Y.) in the binding buffer and the increase of LANCE® Eu-W1024 Anti-6×His concentration to 0.075 nM. Test compounds were pre-incubated with Mcl-1 (171-327) and biotin-Bim (51-76) for 60 min before addition of the detection mixture (LANCE® Eu-W1024 Anti-6×His and Streptavidin-XLent). The reaction plates were further incubated overnight and then were read on an Envision® multimode reader (PerkinElmer). Fluorescence signals were measured at 620 nm (40-nm bandwidth) and 665 nm (7.5-nm bandwidth) with a 300 µs delay after excitation at 320 nm (75-nm bandwidth). The signal ratio at 665/620 nm corresponded to the Mcl-1/Bim interaction and was used in all data analyses. The $IC_{50}$ values of test compounds were determined from duplicate measurements by fitting concentration-response data of individual replicates with a four-parameter sigmoidal model in Genedata Screener® (Genedata, Basel, Switzerland).

Table 2 Cell Viability Assay (OPM-2 10 FBS)

The human multiple myeloma cell line, OPM-2, was cultured in complete growth medium containing RPMI 1640 and 10% fetal bovine serum (FBS). Cells were seeded into 384-well plates at 3000 cells/well density in complete growth medium containing 10% FBS, and incubated for 16 h with serially diluted test compounds in 37 incubator with 5% $CO_2$. Cell viability was tested using CellTiter-Glo® assay (Promega, Madison, Wis.) according to the manufacturer recommendations. Luminescence was determined using an EnVision® Multilabel plate reader 25 min after the addition of detection reagent. $IC_{50}$ values were then calculated with Xlfit using logistical 4-parameter fit model in GraphPad Prism (GraphPad Software, San Diego, Calif.) or in Genedata Screener® (Genedata, Basel, Switzerland). The OPM-2 with 000 and human serum (HS) were run under well known and accepted conditions to one skilled in the art.

Results for compounds tested in these biological assays are set forth below. "-", "NT", or "Undefined" means not tested or undefined. Examples 122, 123, 136, 137, 138, 139, 158, 159, 160 and 161 are intentionally omitted as they are intermediates.

TABLE 1

| Example number | Mcl-1 HTRF IC50 IP (µM) | Mcl-1 HTRF with 5% HS IC50 IP (µM) | Mcl-1 Ki (µM) |
| --- | --- | --- | --- |
| Example 1 | 0.01670 | 0.02813 | 0.003017 |
| Example 2 | No data | — | — |
| Example 3 | 0.03460 | 0.07320 | — |
| Example 4 | 0.00050 | 0.00503 | 0.000089 |
| Example 5 | 0.00028 | 0.00420 | 0.000097 |
| Example 6 | 0.00074 | 0.00311 | 0.000053 |
| Example 7 | 0.00273 | 0.07345 | 0.000894 |
| Example 8 | 0.00062 | 0.01895 | 0.000209 |
| Example 9 | 0.00068 | 0.01517 | 0.000216 |
| Example 10 | 0.00041 | 0.00913 | 0.000124 |
| Example 11 | 0.00063 | 0.00789 | 0.000150 |
| Example 12 | 0.00026 | 0.00391 | 0.000065 |
| Example 13 | 0.00023 | 0.00272 | 0.000054 |
| Example 14 | 0.00036 | 0.00577 | 0.000081 |
| Example 15 | 0.00037 | 0.00502 | 0.000093 |

TABLE 1-continued

| Example number | Mcl-1 HTRF IC50 IP (µM) | Mcl-1 HTRF with 5% HS IC50 IP (µM) | Mcl-1 Ki (µM) |
| --- | --- | --- | --- |
| Example 16 | 0.00340 | 0.04080 | 0.000779 |
| Example 17 | 0.00036 | 0.00416 | 0.000119 |
| Example 18 | 0.00163 | 0.04050 | 0.000861 |
| Example 19 | 0.00041 | 0.00633 | 0.000163 |
| Example 20 | 0.00050 | 0.00864 | 0.000108 |
| Example 21 | 0.00059 | 0.00951 | 0.000178 |
| Example 22 | 0.00155 | 0.02400 | 0.000634 |
| Example 23 | 0.00052 | 0.00906 | 0.000172 |
| Example 24 | 0.00052 | 0.01285 | 0.000185 |
| Example 25 | 0.00018 | 0.00404 | 0.000088 |
| Example 26 | 0.00029 | 0.00381 | 0.000104 |
| Example 27 | 0.03250 | 0.12500 | — |
| Example 28 | 0.00048 | 0.00450 | 0.000137 |
| Example 29 | 0.00090 | 0.01054 | 0.000276 |
| Example 30 | 0.00061 | 0.01305 | 0.000170 |
| Example 31 | 0.00036 | 0.00759 | 0.000127 |
| Example 32 | 0.00018 | 0.00216 | 0.000053 |
| Example 33 | 0.00029 | 0.00434 | 0.000105 |
| Example 34 | 0.00020 | 0.00514 | 0.000092 |
| Example 35 | 0.22700 | 0.39400 | — |
| Example 36 | 0.14965 | 0.60000 | — |
| Example 37 | 0.15300 | 0.40500 | — |
| Example 38 | 0.01020 | 0.10600 | 0.001588 |
| Example 39 | 0.00098 | 0.02470 | 0.000368 |
| Example 40 | 0.00059 | 0.00516 | 0.000099 |
| Example 41 | 0.00281 | 0.01645 | 0.000211 |
| Example 42 | 0.07325 | 1.06000 | — |
| Example 43 | 0.00022 | 0.00193 | 0.000068 |
| Example 44 | 0.00021 | 0.00422 | 0.000056 |
| Example 45 | 0.00015 | 0.00166 | 0.000043 |
| Example 46 | 0.00020 | 0.00425 | 0.000071 |
| Example 47 | 0.00028 | 0.00410 | 0.000093 |
| Example 48 | 0.00011 | 0.00110 | 0.000021 |
| Example 49 | 0.00010 | 0.00065 | 0.000014 |
| Example 50 | 0.00055 | 0.01065 | 0.000206 |
| Example 51 | 0.00030 | 0.00472 | 0.000107 |
| Example 53 | 0.01083 | 0.08125 | 0.001024 |
| Example 54 | 0.00496 | 0.02117 | 0.001004 |
| Example 55 | 0.02880 | 0.16000 | — |
| Example 56 | 0.00243 | 0.03430 | 0.000509 |
| Example 57 | 0.00162 | 0.03893 | 0.000344 |
| Example 58 | 0.02465 | 0.67850 | — |
| Example 59 | No data | — | — |
| Example 60 | No data | — | — |
| Example 61 | 0.00131 | 0.01665 | 0.000275 |
| Example 62 | 0.04745 | 0.57550 | 0.003110 |
| Example 63 | 0.00174 | 0.17767 | 0.000486 |
| Example 64 | 0.00219 | 0.29400 | 0.000960 |
| Example 65 | 0.25410 | 1.55000 | — |
| Example 66 | 0.00108 | 0.02088 | 0.000209 |
| Example 67 | 0.06090 | 2.29670 | — |
| Example 68 | 0.04245 | 1.13970 | — |
| Example 69 | 0.00043 | 0.00719 | 0.000066 |
| Example 70 | 0.00107 | 0.03190 | 0.000339 |
| Example 71 | 0.00046 | 0.01163 | 0.000116 |
| Example 72 | 0.00022 | 0.00435 | 0.000045 |
| Example 73 | 0.00050 | 0.01100 | 0.000132 |
| Example 74 | 0.00044 | 0.01195 | 0.000130 |
| Example 75 | 0.00451 | 0.11850 | 0.001305 |
| Example 76 | 0.00037 | 0.01340 | 0.000141 |
| Example 77 | 0.00040 | 0.01660 | 0.000132 |
| Example 78 | 0.00025 | 0.00733 | 0.000081 |
| Example 79 | 0.00030 | 0.00875 | 0.000092 |
| Example 80 | 0.00079 | 0.04360 | 0.000294 |
| Example 81 | 0.01510 | 0.65750 | 0.005903 |
| Example 82 | 0.00044 | 0.03155 | 0.000175 |
| Example 83 | 0.00049 | 0.00411 | 0.000111 |
| Example 84 | 0.00476 | 0.04790 | 0.001069 |
| Example 85 | 0.00061 | 0.01515 | 0.000187 |
| Example 86 | 0.00049 | 0.01280 | 0.000215 |
| Example 87 | 0.00110 | 0.03235 | 0.000428 |
| Example 88 | 0.00024 | 0.00328 | 0.000093 |
| Example 89 | 0.00037 | 0.00714 | 0.000141 |
| Example 90 | 0.28050 | 0.74300 | — |
| Example 91 | 0.06130 | 0.20600 | — |
| Example 92 | 0.01015 | 0.20600 | 0.002216 |

TABLE 1-continued

| Example number | Mcl-1 HTRF IC50 IP (μM) | Mcl-1 HTRF with 5% HS IC50 IP (μM) | Mcl-1 Ki (μM) |
|---|---|---|---|
| Example 93 | 0.00081 | 0.00392 | 0.000194 |
| Example 94 | 0.00073 | 0.01126 | 0.000130 |
| Example 95 | 0.00217 | 0.03140 | 0.000378 |
| Example 96 | 0.00112 | 0.01304 | 0.000160 |
| Example 97 | 0.05345 | 1.12500 | — |
| Example 98 | 0.00961 | 0.08700 | 0.001710 |
| Example 99 | 0.04440 | 0.98450 | — |
| Example 100 | 0.01313 | 0.29500 | 0.001976 |
| Example 101 | 1.00150 | 3.95000 | — |
| Example 102 | 0.05450 | 0.34100 | — |
| Example 103 | 0.00310 | 0.17862 | 0.000540 |
| Example 104 | 0.32400 | 3.65000 | — |
| Example 105 | 0.04695 | 4.32500 | — |
| Example 106 | 0.00407 | 1.53000 | 0.000460 |
| Example 107 | 0.02925 | >5.0 [2] | — |
| Example 108 | 0.00133 | 0.13650 | 0.000131 |
| Example 109 | 0.02625 | 1.07350 | — |
| Example 110 | 0.03390 | 1.15500 | — |
| Example 111 | 0.00553 | 1.36000 | 0.000886 |
| Example 112 | 0.00102 | 0.08305 | 0.000097 |
| Example 113 | 0.00992 | 2.88000 | 0.001314 |
| Example 114 | 0.00644 | 0.91700 | 0.000812 |
| Example 115 | 0.00067 | 0.09640 | 0.000113 |
| Example 116 | No data | — | — |
| Example 117 | 0.16000 | >5.0 [2] | — |
| Example 118 | 0.09245 | 4.70000 | — |
| Example 119 | 0.00571 | 0.19000 | 0.001014 |
| Example 120 | 0.16100 | 2.46500 | — |
| Example 121a | 0.03335 | 1.55500 | 0.002767 |
| Example 121b | 0.00308 | 0.16900 | 0.000916 |
| Example 124 | 0.01795 | 0.28800 | — |
| Example 125 | 0.45000 | 5.10000 | — |
| Example 126 | 0.03330 | 3.03000 | — |
| Example 127 | 0.00452 | 0.17150 | 0.000531 |
| Example 128 | 0.98550 | >5.0 [2] | — |
| Example 129 | 0.00023 | 0.00450 | 0.000075 |
| Example 130 | 0.00077 | 0.01195 | 0.000269 |
| Example 131 | 0.00031 | 0.00561 | 0.000121 |
| Example 132 | 0.00065 | 0.01115 | 0.000175 |
| Example 133 | 0.00041 | 0.00544 | 0.000135 |
| Example 134 | 0.00048 | 0.00726 | 0.000138 |
| Example 135 | 0.00079 | 0.01260 | 0.000290 |
| Example 140 | 0.02550 | 1.15500 | 0.005374 |
| Example 141 | 0.00131 | 0.04760 | 0.000359 |
| Example 142 | 0.00420 | 0.03960 | 0.001309 |
| Example 143 | 0.02290 | 2.37000 | — |
| Example 144 | 0.00666 | 0.14100 | 0.001167 |
| Example 145 | 0.01040 | 0.11300 | 0.001631 |
| Example 146 | 0.00294 | 0.01705 | 0.000579 |
| Example 147 | 0.00990 | 0.06345 | 0.002334 |
| Example 148 | 0.17900 | 0.41100 | — |
| Example 149 | 0.92400 | 1.75000 | — |
| Example 150 | 0.00446 | 0.03450 | 0.001158 |
| Example 151 | 0.01115 | 0.03290 | 0.003614 |
| Example 152 | 0.00061 | 0.00640 | 0.000090 |
| Example 153 | 0.00052 | 0.00672 | 0.000098 |
| Example 154 | 0.00117 | 0.01300 | 0.000276 |
| Example 155 | 0.06750 | 0.40300 | — |
| Example 156 | 0.00784 | 0.04320 | 0.001524 |
| Example 157 | 0.01257 | 0.03290 | 0.002161 |
| Example 162a | 0.08580 | 1.03850 | — |
| Example 162b | 0.01294 | 0.16250 | 0.002530 |
| Example 163 | 0.00039 | 0.00809 | 0.000128 |
| Example 164 | 0.00061 | 0.01400 | 0.000197 |
| Example 165 | 0.00042 | 0.02240 | 0.000321 |
| Example 166 | 0.00090 | 0.01235 | 0.000336 |
| Example 167 | 0.02995 | 0.04540 | 0.003351 |
| Example 168 | 0.00088 | 0.01498 | 0.000243 |
| Example 169 | 0.16500 | 0.82050 | — |
| Example 170 | 0.02705 | 0.20100 | — |
| Example 171 | 0.27700 | 0.45250 | — |
| Example 172 | 0.00136 | 0.00699 | 0.000163 |
| Example 173 | 0.00049 | 0.00248 | 0.000086 |
| Example 174 | 0.00084 | 0.00366 | 0.000139 |
| Example 175 | 0.00039 | 0.00371 | 0.000071 |
| Example 176 | 0.00042 | 0.00209 | 0.000067 |
| Example 177 | 0.00020 | 0.00243 | 0.000042 |
| Example 178 | 0.00018 | 0.00094 | 0.000035 |
| Example 179 | 0.00030 | 0.00324 | 0.000062 |
| Example 180 | 0.00133 | 0.00494 | 0.000066 |
| Example 181 | 0.00038 | 0.00303 | 0.000103 |
| Example 182 | 0.00023 | 0.00181 | 0.000056 |
| Example 183 | 0.00087 | 0.01580 | 0.000247 |
| Example 184 | 0.00054 | 0.00766 | 0.000131 |
| Example 185 | 0.00154 | 0.01293 | 0.000330 |
| Example 186 | 0.00040 | 0.00292 | 0.000073 |
| Example 187 | 0.00048 | 0.00609 | 0.000128 |
| Example 188 | 0.00017 | 0.00532 | 0.000045 |
| Example 189 | 0.00023 | 0.00313 | 0.000041 |
| Example 190 | 0.00037 | 0.00290 | 0.000042 |
| Example 191 | 0.00059 | 0.00727 | 0.000145 |
| Example 192 | 0.00060 | 0.00276 | 0.000050 |
| Example 193 | 0.00023 | 0.00151 | 0.000048 |
| Example 194 | 0.00068 | 0.00622 | 0.000183 |
| Example 195 | 0.00054 | 0.00451 | 0.000168 |
| Example 196 | 0.00113 | 0.00956 | 0.000229 |
| Example 197 | 0.00033 | 0.00215 | 0.000104 |
| Example 198 | 0.00036 | 0.00349 | 0.000111 |
| Example 199 | 0.00029 | 0.00292 | 0.000057 |
| Example 200 | 0.00031 | 0.00203 | 0.000051 |
| Example 201a | 0.00854 | 0.10063 | 0.002844 |
| Example 201b | 0.00057 | 0.00835 | 0.000214 |
| Example 202 | 0.00034 | 0.00197 | 0.000071 |
| Example 203 | 0.00023 | 0.00281 | 0.000047 |
| Example 204 | No data | — | — |
| Example 205 | 0.00032 | 0.00243 | 0.000047 |
| Example 206a | 0.02230 | 0.76850 | 0.004539 |
| Example 206b | 0.00033 | 0.01255 | 0.000110 |
| Example 207a | 0.00040 | 0.00455 | 0.000138 |
| Example 207b | 0.00089 | 0.01660 | 0.000380 |
| Example 208 | 0.00042 | 0.00393 | 0.000193 |
| Example 209a | 0.00065 | 0.00534 | 0.000096 |
| Example 209b | 0.00369 | 0.07105 | 0.000572 |
| Example 210a | 0.00232 | 0.25100 | 0.001259 |
| Example 210b | 0.01180 | 3.37500 | — |

TABLE 2

| | Cellular Assay | | | |
|---|---|---|---|---|
| Example number in patent draft | Split Luciferase IC50 IP (μM) | OPM-2 with 0% HS IC50 IP (μM) | OPM-2 with 10% FBS IC50 IP (μM) | OPM-2 with 5% HS IC50 IP (μM) |
| Example 1 | 0.3708 | 0.2214 | 0.5686 | 1.878 |
| Example 2 | No data | — | — | — |
| Example 3 | 0.43633 | 0.31233 | 0.87167 | 3.9233 |
| Example 4 | 0.10994 | 0.0576 | 0.23467 | 0.62029 |
| Example 5 | 0.05615 | 0.030338 | 0.17068 | 0.53862 |
| Example 6 | 0.035429 | 0.017533 | 0.1054 | 0.33971 |
| Example 7 | 0.184 | 0.09835 | 1.219 | 3.625 |
| Example 8 | 0.0919 | 0.0501 | 0.5175 | 1.635 |

TABLE 2-continued

| | Cellular Assay | | | |
|---|---|---|---|---|
| Example number in patent draft | Split Luciferase IC50 IP (μM) | OPM-2 with 0% HS IC50 IP (μM) | OPM-2 with 10% FBS IC50 IP (μM) | OPM-2 with 5% HS IC50 IP (μM) |
| Example 9 | 0.082 | 0.067 | 0.4195 | 1.0715 |
| Example 10 | 0.0722 | 0.0427 | 0.2945 | 0.894 |
| Example 11 | 0.07204 | 0.034525 | 0.21725 | 0.7498 |
| Example 12 | 0.0389 | 0.014925 | 0.1156 | 0.4015 |
| Example 13 | 0.0644 | 0.02524 | 0.1602 | 0.496 |
| Example 14 | 0.054833 | 0.028467 | 0.15967 | 0.399 |
| Example 15 | 0.04402 | 0.021875 | 0.15165 | 0.4036 |
| Example 16 | 0.10973 | 0.06035 | 0.75 | 2.15 |
| Example 17 | 0.056025 | 0.0388 | 0.219 | 0.69875 |
| Example 18 | 0.1835 | 0.1885 | 1.265 | 3.705 |
| Example 19 | 0.067367 | 0.0387 | 0.208 | 0.666 |
| Example 20 | 0.0387 | 0.0226 | 0.1785 | 0.5545 |
| Example 21 | 0.090367 | 0.0416 | 0.307 | 0.90567 |
| Example 22 | 0.1675 | 0.1615 | 0.807 | 2.33 |
| Example 23 | 0.11685 | 0.0521 | 0.271 | 1.093 |
| Example 24 | 0.1845 | 0.11945 | 0.6065 | 1.61 |
| Example 25 | 0.0471 | 0.02235 | 0.1201 | 0.4155 |
| Example 26 | 0.06535 | 0.0425 | 0.175 | 0.5195 |
| Example 27 | 1.04 | 0.695 | 1.88 | 8.6 |
| Example 28 | 0.085 | 0.0316 | 0.3085 | 0.973 |
| Example 29 | 0.10915 | 0.0479 | 0.874 | 2.24 |
| Example 30 | 0.08015 | 0.0345 | 0.308 | 0.967 |
| Example 31 | 0.03965 | 0.0243 | 0.184 | 0.521 |
| Example 32 | 0.03655 | 0.01545 | 0.07895 | 0.308 |
| Example 33 | 0.0731 | 0.03645 | 0.35367 | 1.43 |
| Example 34 | 0.0893 | 0.06135 | 0.465 | 1.27 |
| Example 35 | 1.128 | 0.8865 | 17.23 | >33.3 [2] |
| Example 36 | 3.94 | 2.97 | 11.4 | 36.1 |
| Example 37 | 1.46 | 0.969 | 5.125 | 18.6 |
| Example 38 | 2.32 | 2.245 | 13.74 | 7.32 |
| Example 39 | 0.14467 | 0.092 | 0.881 | 2.77 |
| Example 40 | 0.21943 | 0.19571 | 1.6117 | 4.0871 |
| Example 41 | 0.22 | 0.36 | 3.9 | 8.36 |
| Example 42 | 8.16 | 11.3 | >33.3 | >33.3 |
| Example 43 | 0.02805 | 0.0132 | 0.0784 | 0.25 |
| Example 44 | 0.0599 | 0.024667 | 0.179 | 0.462 |
| Example 45 | 0.03185 | 0.0133 | 0.08435 | 0.2595 |
| Example 46 | 0.0566 | 0.0311 | 0.178 | 0.4815 |
| Example 47 | 0.05665 | 0.0314 | 0.159 | 0.4415 |
| Example 48 | 0.519 | 0.127 | 1.625 | 4.17 |
| Example 49 | 0.1945 | 0.07555 | 0.6045 | 1.77 |
| Example 50 | 0.155 | 0.0776 | 0.581 | 1.405 |
| Example 51 | 0.0751 | 0.0335 | 0.223 | 0.5065 |
| Example 53 | 1.6 | 1.68 | 18.2 | Undefined |
| Example 54 | 1.6 | 2.595 | 22.25 | Undefined [2] |
| Example 55 | 3.77 | 3.94 | Undefined | >33.3 |
| Example 56 | 0.783 | 1.23 | 16.3 | 22.2 |
| Example 57 | 1.41 | 1.74 | 18.2 | >33.3, Undefined |
| Example 58 | 4.71 | 5.96 | >33.3 | >33.3 |
| Example 59 | No data | — | — | — |
| Example 60 | No data | — | — | — |
| Example 61 | 0.267 | 0.1725 | 0.6125 | 1.72 |
| Example 62 | 6.62 | 8.265 | >33.3, Undefined | >33.3 [2] |
| Example 63 | 0.866 | 0.709 | 7.875 | >33.3, Undefined |
| Example 64 | 0.648 | 0.418 | 3.2 | Undefined |
| Example 65 | 1.98 | 2.04 | >33.3 [2] | >33.3 [2] |
| Example 66 | 0.559 | 0.509 | 3.625 | 8.08 |
| Example 67 | 14.8 | 6.38 | >33.3 | >33.3 |
| Example 68 | 5.13 | 2.51 | >33.3 | >33.3 |
| Example 69 | 0.049233 | 0.020967 | 0.18333 | 0.60867 |
| Example 70 | 0.503 | 0.321 | 1.9 | 14.3 |
| Example 71 | 0.39425 | 0.2335 | 14.51 | >33.3 [4] |
| Example 72 | 0.024475 | 0.012625 | 0.1092 | 0.7125 |
| Example 73 | 0.273 | 0.128 | 1.52 | >33.3 |
| Example 74 | 0.11635 | 0.0535 | 0.389 | 1.2765 |
| Example 75 | 1.41 | 1.12 | 10.2 | 19.7 |
| Example 76 | 0.0744 | 0.0434 | 0.3595 | 2.635 |
| Example 77 | 0.05535 | 0.02865 | 0.316 | 3.175 |
| Example 78 | 0.03865 | 0.01685 | 0.189 | 1.1325 |
| Example 79 | 0.03985 | 0.0194 | 0.19 | 0.87 |
| Example 80 | 0.124 | 0.0796 | 1.28 | 4.84 |
| Example 81 | 0.953 | 0.282 | 17.9 | Undefined |
| Example 82 | 0.3445 | 0.1685 | 1.81 | 18.7 |
| Example 83 | 0.38725 | 0.21325 | 1.3005 | 2.16 |
| Example 84 | 1.81 | 1.42 | 15.2 | 24.2 |

TABLE 2-continued

| | Cellular Assay | | | |
|---|---|---|---|---|
| Example number in patent draft | Split Luciferase IC50 IP (μM) | OPM-2 with 0% HS IC50 IP (μM) | OPM-2 with 10% FBS IC50 IP (μM) | OPM-2 with 5% HS IC50 IP (μM) |
| Example 85 | 0.3815 | 0.2155 | 1.254 | 3.805 |
| Example 86 | 0.217 | 0.09655 | 0.8635 | 2.15 |
| Example 87 | 0.366 | 0.188 | 2.52 | 4.65 |
| Example 88 | 0.2215 | 0.109 | 0.8435 | 1.345 |
| Example 89 | 0.239 | 0.11255 | 0.809 | 1.44 |
| Example 90 | 3.3433 | 3.2 | 13.867 | 31.8 |
| Example 91 | 10.32 | 7.575 | 32.95 | > 33.3 [2] |
| Example 92 | 1.36 | 1.43 | 10.2 | Undefined |
| Example 93 | 0.182 | 0.0871 | 0.601 | 2.0067 |
| Example 94 | 0.39533 | 0.20833 | 2.2533 | 4.6967 |
| Example 95 | 0.616 | 0.717 | 6.43 | 18.5 |
| Example 96 | 0.11378 | 0.07118 | 0.329 | 0.9328 |
| Example 97 | 5.23 | 4.66 | Undefined | >33.3 |
| Example 98 | 5.41 | 4.71 | Undefined | >33.3 |
| Example 99 | 2.18 | 2.1 | >33.3 | >33.3 |
| Example 100 | 0.839 | 0.873 | 13.4 | 27.2 |
| Example 101 | 17.7 | 27 | >33.3 | >33.3 |
| Example 102 | 3.7 | 1.51 | Undefined | >33.3 |
| Example 103 | 1.0205 | 0.9435 | 6.97 | 19.4 |
| Example 104 | 14.8 | 15.5 | >33.3 | >33.3 |
| Example 105 | 1.55 | 6.69 | >33.3 | >33.3 |
| Example 106 | 0.581 | 0.589 | 11.2 | >33.3 |
| Example 107 | 5.51 | 12.1 | >33.3 | >33.3 |
| Example 108 | 0.22 | 0.322 | 3.06 | 23.3 |
| Example 109 | 4.18 | 3.61 | >33.3 | >33.3 |
| Example 110 | 3 | 3.78 | >33.3 | >33.3 |
| Example 111 | 1.98 | 1.67 | 31.3 | >33.3 |
| Example 112 | 0.132 | 0.229 | 2.46 | 23.9 |
| Example 113 | 2.67 | 2.83 | >33.3 | >33.3 |
| Example 114 | 1.39 | 1.12 | Undefined | >33.3 |
| Example 115 | 0.221 | 0.307 | 3.69 | Undefined |
| Example 116 | No data | — | — | — |
| Example 117 | 1.14 | 1.49 | 17.5 | >33.3 |
| Example 118 | 1.22 | 1.64 | 20.8 | >33.3 |
| Example 119 | 1.6 | 1.35 | 22.3 | >33.3 |
| Example 120 | 1.07 | 1.53 | >33.3 | >33.3 |
| Example 121a | 0.773 | 0.806 | 21.3 | >33.3 |
| Example 121b | 1.59 | 1.44 | 31.1 | >33.3 |
| Example 124 | 13.1 | 5 | >33.3 | >33.3 |
| Example 125 | Undefined | >33.3 | >33.3 | >33.3 |
| Example 126 | 3.82 | 2.6 | >33.3 | >33.3 |
| Example 127 | 0.696 | 0.397 | 4.28 | 19.9 |
| Example 128 | 3.665 | 4.285 | >33.3 [2] | >33.3 [2] |
| Example 129 | 0.05905 | 0.02835 | 0.1835 | 0.5335 |
| Example 130 | 0.112 | 0.08115 | 0.397 | 1.1915 |
| Example 131 | 0.09585 | 0.0393 | 0.164 | 0.4665 |
| Example 132 | 0.0828 | 0.04665 | 0.3725 | 1.0225 |
| Example 133 | 0.192 | 0.0595 | 0.457 | 1.285 |
| Example 134 | 0.0504 | 0.0283 | 0.189 | 0.58 |
| Example 135 | 0.1055 | 0.0497 | 0.3575 | 1.0875 |
| Example 140 | 1.94 | 2.48 | Undefined | >33.3 |
| Example 141 | 0.596 | 0.322 | 3.36 | 14 |
| Example 142 | 1.31 | 1.08 | 20.1 | Undefined |
| Example 143 | 2.24 | 2.24 | Undefined | >33.3 |
| Example 144 | 1.29 | 0.636 | 14.4 | Undefined |
| Example 145 | 0.742 | 0.296 | 6.38 | 17 |
| Example 146 | 0.691 | 0.589 | 3.24 | 6.27 |
| Example 147 | 2.56 | 1.47 | Undefined | >33.3 |
| Example 148 | 1.625 | 1.24 | 5.525 | 19.75 |
| Example 149 | 4.87 | 2.83 | 18.2 | >33.3, Undefined |
| Example 150 | 0.945 | 0.446 | 1.615 | 5.725 |
| Example 151 | 2.83 | 1.215 | 4.655 | 10.645 |
| Example 152 | 0.0469 | 0.0131 | 0.0961 | 0.253 |
| Example 153 | 0.05315 | 0.02295 | 0.142 | 0.426 |
| Example 154 | 0.0949 | 0.0618 | 0.299 | 0.9695 |
| Example 155 | 3.315 | 2.795 | 17.05 | >33.3 [2] |
| Example 156 | 0.8095 | 0.542 | 4.655 | 12.9 |
| Example 157 | 0.647 | 0.399 | 0.9775 | 3.06 |
| Example 162a | 3.11 | 1.79 | 15.1 | Undefined |
| Example 162b | 1.02 | 0.588 | 8.49 | 15.6 |
| Example 163 | 0.339 | 0.154 | 1.275 | 3.555 |
| Example 164 | 0.132 | 0.05395 | 0.2345 | 0.6085 |
| Example 165 | 1.34 | 0.337 | 2.1 | 9.7 |
| Example 166 | 0.339 | 0.1135 | 0.4885 | 0.8385 |
| Example 167 | 0.6605 | 0.423 | 1.193 | 4.3 |

TABLE 2-continued

Cellular Assay

| Example number in patent draft | Split Luciferase IC50 IP (μM) | OPM-2 with 0% HS IC50 IP (μM) | OPM-2 with 10% FBS IC50 IP (μM) | OPM-2 with 5% HS IC50 IP (μM) |
|---|---|---|---|---|
| Example 168 | 0.276 | 0.304 | 2.1 | 4.85 |
| Example 169 | 5.06 | 4.54 | 28.6 | >33.3 |
| Example 170 | 3.61 | 3.26 | 24.5 | >33.3 |
| Example 171 | 1.72 | 1.41 | 4.61 | 12.9 |
| Example 172 | 0.14567 | 0.0921 | 0.39467 | 0.76667 |
| Example 173 | 0.31033 | 0.21267 | 0.521 | 0.98067 |
| Example 174 | 1.105 | 0.9 | 4.73 | 4.895 |
| Example 175 | 0.13202 | 0.07195 | 0.3085 | 0.6112 |
| Example 176 | 0.040033 | 0.01195 | 0.0659 | 0.20567 |
| Example 177 | 0.036633 | 0.014333 | 0.18503 | 0.26667 |
| Example 178 | 0.0504 | 0.0328 | 0.0737 | 0.206 |
| Example 179 | 0.0435 | 0.018634 | 0.090225 | 0.218 |
| Example 180 | 0.0402 | 0.01525 | 0.0742 | 0.19 |
| Example 181 | 0.0986 | 0.04065 | 0.07235 | 0.183 |
| Example 182 | 0.07325 | 0.039775 | 0.080575 | 0.205 |
| Example 183 | 0.10225 | 0.05455 | 0.4245 | 0.9635 |
| Example 184 | 0.08605 | 0.0448 | 0.247 | 0.654 |
| Example 185 | 0.187 | 0.11665 | 0.321 | 0.84425 |
| Example 186 | 0.054483 | 0.02405 | 0.093417 | 0.26467 |
| Example 187 | 0.0569 | 0.03605 | 0.146 | 0.2865 |
| Example 188 | 0.0615 | 0.0237 | 0.103 | 0.259 |
| Example 189 | 0.0327 | 0.0163 | 0.0926 | 0.249 |
| Example 190 | 0.05485 | 0.0287 | 0.2075 | 0.5235 |
| Example 191 | 0.05435 | 0.04165 | 0.263 | 0.646 |
| Example 192 | 0.04845 | 0.01905 | 0.07695 | 0.201 |
| Example 193 | 0.0448 | 0.01855 | 0.043 | 0.12685 |
| Example 194 | 0.1485 | 0.08495 | 0.196 | 0.445 |
| Example 195 | 0.1366 | 0.08675 | 0.1985 | 0.5 |
| Example 196 | 0.1217 | 0.07575 | 0.336 | 0.8005 |
| Example 197 | 0.093525 | 0.053075 | 0.06415 | 0.1315 |
| Example 198 | 0.0906 | 0.04025 | 0.08145 | 0.2035 |
| Example 199 | 0.03245 | 0.0172 | 0.0778 | 0.184 |
| Example 200 | 0.022625 | 0.011538 | 0.05245 | 0.12615 |
| Example 201a | 0.973 | 0.671 | 8.67 | 15.3 |
| Example 201b | 0.246 | 0.0672 | 0.794 | 1.26 |
| Example 202 | 0.0333 | 0.0152 | 0.0492 | 0.1265 |
| Example 203 | 0.0508 | 0.01615 | 0.108 | 0.254 |
| Example 204 | No data | — | — | — |
| Example 205 | 0.032 | 0.0146 | 0.0676 | 0.191 |
| Example 206a | 1.78 | 0.811 | 21.2 | Undefined |
| Example 206b | 0.05435 | 0.0382 | 0.554 | 0.9785 |
| Example 207a | 0.115 | 0.04375 | 0.233 | 0.5485 |
| Example 207b | 0.3815 | 0.1995 | 0.6135 | 1.99 |
| Example 208 | 0.288 | 0.146 | 0.55083 | 1.715 |
| Example 209a | 0.45567 | 0.31067 | 2.0467 | 5.68 |
| Example 209b | 1.07 | 0.7 | 5.46 | 7.9 |
| Example 210a | 0.7324 | 0.508 | 15.7 | >33.3 |
| Example 210b | 2.14 | — | — | — |

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended Claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed:
1. A compound of Formula I:

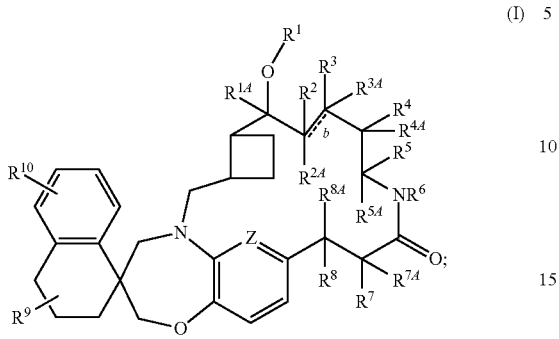

a stereoisomer thereof, a pharmaceutically acceptable salt thereof, or a pharmaceutically acceptable salt of the stereoisomer thereof,
wherein:
b, represented by the symbol ======, is a single or double chemical bond which may be cis or trans,
Z is selected from C or N;
$R^1$ is independently selected from H, —$C_{1-6}$haloalkyl, —$C_{1-6}$alkyl, —$C_{2-6}$alkenyl, —$C_{2-6}$alkynyl, —$(CH_2CH_2O)_nR^a$, —C(=O)$R^a$, —C(=O)O$R^a$, —C(=O)N$R^aR^b$, —$C_{1-6}$alkyl-O-$C_{1-6}$alkyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;
$R^{14}$ is H;
each of $R^6$, $R^8$, $R^{2A}$, $R^{3A}$, and $R^{8A}$ is independently selected from H, halo, —$C_{1-6}$haloalkyl, —$C_{1-6}$alkyl, —O—$C_{1-6}$alkyl, —$C_{2-6}$alkenyl, —$C_{1-6}$alkyl-O-$C_{1-6}$alkyl, —$(CH_2CH_2O)_nR^a$, —$SO_2R^a$, —C(=O)$R^a$, —C(=O)O$R^a$, —OC(=O)$R^a$, —C(=O)N$R^aR^b$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$ and further wherein $R^8$ and $R^{8A}$ may also be OH;
$R^2$ is H;
$R^3$ is H;
$R^4$ is H or $C_{1-6}$ alkyl;
$R^{4A}$ is H;
$R^5$ is H or $C_{1-6}$ alkyl;
$R^{5A}$ is H;
$R^7$ is H or $C_{1-6}$ alkyl;
$R^{7A}$ is H;
$R^9$ is H;
$R^{10}$ is halo;
when b is a double bond, $R^{2A}$ and $R^{3A}$ are absent;
wherein the aryl, heteroaryl, cycloalkyl, heterocycloalkyl, spirocycloalkyl and spiroheterocycloalkyl groups of the $R^1$ substituent can be unsubstituted or substituted with 1, 2, 3 or 4 $R^{11}$ substituents independently selected from OH, halo, —N$R^cR^d$, —$C_{1-6}$alkyl, —$C_2$-$C_6$ alkenyl, —$C_2$-$C_6$alkynyl, —O$C_{1-6}$alkyl, —$C_{1-6}$alkyl-OH, —$C_{1-6}$alkyl-O-$C_{1-6}$alkyl, $C_{1-6}$haloalkyl, —O-halo$C_{1-6}$alkyl, —$SO_2R^c$, —CN, —C(=O)N$R^cR^d$, —C(=O)$R^c$, —OC(=O)$R^a$, —C(=O)O$R^c$, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 0, 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;
wherein the —$C_{1-6}$alkyl of any of the $R^1$, $R^6$, $R^8$, $R^{11}$, $R^{2A}$, $R^{3A}$, and $R^{8A}$ substituents is unsubstituted or substituted by 1, 2 or 3 $R^{12}$ substituents independently selected from OH, —O$C_{1-6}$alkyl, —$C_{1-6}$alkyl-O-$C_{1-6}$alkyl, halo, —O-halo$C_{1-6}$alkyl, —CN, —N$R^aR^b$, —(N$R^aR^bR^c$)$_n$, —$SO_2R^a$, —(CH$_2$CH$_2$O)$_n$CH$_3$, (=O), —C(=O)$R^a$, —OC(=O)$R^a$, —C(=O)O$R^a$, —C(=O)N$R^aR^b$, —O—Si$R^aR^bR^c$, —O-(3- to 12-membered heterocycloalkyl), phenyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;
wherein the aryl, heteroaryl, cycloalkyl, heterocycloalkyl, spirocycloalkyl and spiroheterocycloalkyl groups of any of the $R^6$, $R^8$, $R^{11}$ and $R^{12}$ substituents can be unsubstituted or substituted with 1, 2, 3 or 4 $R^{13}$ substituents independently selected from OH, halo, —$C_{1-6}$alkyl, —O$C_{1-6}$alkyl, —$C_{1-6}$alkyl-OH, —$C_{1-6}$alkyl-O-$C_{1-6}$alkyl, $C_{1-6}$haloalkyl, —O-halo$C_{1-6}$alkyl, —$SO_2R^c$, —N$R^cR^d$, —CN, —C(=O)N$R^cR^d$, —C(=O)$R^c$, —OC(=O)$R^a$, —C(=O)O$R^c$, —B(OH)$_2$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein

517 the heteroaryl, spiroheterocycloalkyl, and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or SO$_2$;

wherein each R$^a$, R$^b$, R$^c$, and R$^d$ is independently H, OH, —C$_{1-6}$alkyl, —C$_{1-6}$alkenyl, —C$_{2-6}$alkynyl, —C$_{1-6}$alkyl-NR$^{14}$R$^{14}$, NR$^{14}$R$^{14}$, —SO$_2$R$^{14}$, —(CH$_2$CH$_2$O)$_n$CH$_3$, —C(=O)R$^{14}$, —OC(=O)R$^{14}$, —C(=O)OR$^{14}$, —C(=O)NR$^{14}$R$^{14}$, C$_{1-6}$haloalkyl, —O-haloC$_{1-6}$alkyl, —C$_{1-6}$alkyl-O-C$_{1-6}$alkyl, —C$_{1-6}$alkyl-OH, benzyl, phenyl, a —C$_{1-6}$alkyl-3- to 12-membered heterocycloalkyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups and the heterocycloalkyl group of the —C$_{1-6}$alkyl-heterocycloalkyl group have 1, 2, 3, or 4 heteroatoms independently selected from O, N or S, wherein the cycloalkyl, spirocycloalkyl, spiroheterocycloalkyl, heterocycloalkyl, and the heterocycloalkyl groups of the —C$_{1-6}$alkyl-heterocycloalkyl group may include a C=O group, and further wherein the spiroheterocycloalkyl and heterocycloalkyl groups may include a S=O or SO$_2$;

wherein R$^{14}$ substituents are independently selected from H, —OH, halo, —C$_{1-6}$alkyl, —OC$_{1-6}$alkyl, —C$_{1-6}$alkyl-OC$_{1-6}$alkyl, —C$_{1-6}$haloalkyl, —O-haloC$_{1-6}$alkyl, phenyl, tolyl, —C(O)C$_{1-6}$alkyl, —C(O)OCH$_3$, —SO$_2$-phenyl, —SO$_2$—N(CH$_3$)$_2$, —N=N=N, —NH$_2$, —N(C$_{1-6}$alkyl)$_2$, —NR$^{15}$C$_{1-6}$alkyl, —NR$^{15}$C$_{1-6}$alkyl-O-C$_{1-6}$alkyl, —N(C$_{1-6}$alkyl)C$_{1-6}$alkyl-O-C$_{1-6}$alkyl, —NR$^{15}$—C$_{1-6}$alkyl-3- to 12-membered heterocycloalkyl, a NR$^{15}$-6- to 12-membered aryl or heteroaryl, a NR$^{15}$-3- to 12-membered cycloalkenyl, a NR$^{15}$-3- to 12-membered monocyclic or bicyclic cycloalkyl, or a NR$^{15}$-3- to 12-membered monocyclic or bicyclic heterocycloalkyl group, a —C$_{1-6}$alkyl-3- to 12-membered heterocycloalkyl, a 6- to 12-membered aryl or heteroaryl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, and heterocycloalkyl groups and the heterocycloalkyl group of the —C$_{1-6}$alkyl-heterocycloalkyl group have 1, 2, 3, or 4 heteroatoms independently selected from O, N or S, wherein the cycloalkyl, heterocycloalkyl, and the heterocycloalkyl groups of the —C$_{1-6}$alkyl-heterocycloalkyl group may include a C=O group, and further wherein the heterocycloalkyl groups may include a S=O or SO$_2$;

the alkyl, aryl, heteroaryl, cycloalkyl, heterocycloalkyl and the heterocycloalkyl groups of the —C$_{1-6}$alkyl-heterocycloalkyl groups of R$^{14}$ can be unsubstituted or substituted with 1, 2, 3, or 4 R$^{15}$ substituents independently selected from H, —OH, —N=N=N, halo, —C$_{1-6}$alkyl, —OC$_{1-6}$alkyl, C$_{1-6}$haloalkyl,

518

—O-haloC$_{1-6}$alkyl, phenyl, tolyl, —C(O)C$_{1-6}$alkyl, —C(O)OCH$_3$, SO$_2$-phenyl, —SO$_2$—NH$_2$, or —SO$_2$—N(CH$_3$)$_2$; and n is independently, in each instance, an integer of 1, 2, 3 or 4.

2. The compound of claim 1, wherein the compound of Formula I is a compound of Formula Ia:

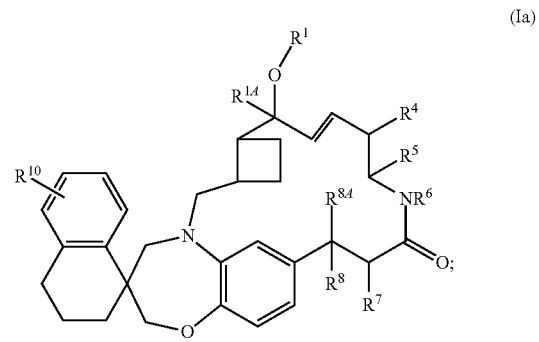

(Ia)

a stereoisomer thereof, a pharmaceutically acceptable salt thereof, or a pharmaceutically acceptable salt of the stereoisomer thereof, wherein:

R$^1$ is independently selected from H, —C$_{1-6}$haloalkyl, —C$_{1-6}$alkyl, —C$_{2-6}$alkenyl, —C$_{2-6}$alkynyl, —(CH$_2$CH$_2$O)$_n$R$^a$, —C(=O)R$^a$, —C(=O)OR$^a$, —C(=O)NR$^a$R$^b$, —C$_{1-6}$alkyl-O-C$_{1-6}$alkyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or SO$_2$;

R$^8$ is selected from —C$_{1-6}$haloalkyl, —C$_{1-6}$alkyl, —O—C$_{1-6}$alkyl, —C$_{2-6}$alkenyl, —C$_{1-6}$alkyl-O-C$_{1-6}$alkyl, —(CH$_2$CH$_2$O)$_n$R$^a$, —SO$_2$R$^a$, —C(=O)R$^a$, —C(=O)OR$^a$, —OC(=O)R$^a$, or —C(=O)NR$^a$R$^b$;

R$^{8A}$ is selected from H, OH, halo, —C$_{1-6}$haloalkyl, —C$_{1-6}$alkyl, —O-C$_{1-6}$alkyl, —C$_{2-6}$alkenyl, —C$_{1-6}$alkyl-O-C$_{1-6}$alkyl, —(CH$_2$CH$_2$O)$_n$R$^a$, —SO$_2$R$^a$, —C(=O)R$^a$, —C(=O)OR$^a$, —OC(=O)R$^a$, or —C(=O)NR$^a$R$^b$;

R$^{10}$ is halo;

wherein the aryl, heteroaryl, cycloalkyl, heterocycloalkyl, spirocycloalkyl and spiroheterocycloalkyl groups of the R$^1$ substituent can be unsubstituted or substituted with 1, 2, 3 or 4 R$^{11}$ substituents independently selected from OH, halo, —NR$^c$R$^d$, —C$_{1-6}$alkyl, —C$_2$-C$_6$ alkenyl, —C$_2$-C$_6$alkynyl, —OC$_{1-6}$alkyl, —C$_{1-6}$alkyl-OH, —C$_{1-6}$alkyl-O-C$_{1-6}$alkyl, C$_{1-6}$haloalkyl, —O-haloC$_{1-6}$alkyl, SO$_2$R$^c$, SO$_2$, —CN, —C(=O)NR$^c$R$^d$, —C(=O)R$^c$, —OC(=O)R$^a$, —C(=O)OR$^c$, a 6- to 12-membered aryl, a 6- to 12-membered heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 0, 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

wherein the —$C_{1-6}$alkyl of any of the $R^1$, $R^6$, $R^8$, $R^{11}$, and $R^{8A}$ substituents is unsubstituted or substituted by 1, 2 or 3 $R^{12}$ substituents independently selected from OH, —$OC_{1-6}$alkyl, —$C_{1-6}$alkyl-O-$C_{1-6}$alkyl, halo, —O-halo$C_{1-6}$alkyl, —CN, —$NR^aR^b$, —$(NR^aR^bR^c)_n$, —$SO_2R^a$, —$(CH_2CH_2O)_nCH_3$, (=O), —C(=O)$R^a$, —OC(=O)$R^a$, —C(=O)$OR^a$, —C(=O)$NR^aR^b$, —O—$SiR^aR^bR^c$, —O-(3- to 12-membered heterocycloakyl), phenyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

wherein the aryl, heteroaryl, cycloalkyl, heterocycloalkyl, spirocycloalkyl and spiroheterocycloalkyl groups of any of the $R^6$, $R^8$, $R^{11}$ and $R^{12}$ substituents can be unsubstituted or substituted with 1, 2, 3 or 4 $R^{13}$ substituents independently selected from OH, halo, —$C_{1-6}$alkyl, —$OC_{1-6}$alkyl, —$C_{1-6}$alkyl-OH, —$C_{1-6}$alkyl-O-$C_{1-6}$alkyl, $C_{1-6}$haloalkyl, —O-halo$C_{1-6}$alkyl, —$SO_2R^c$, —$NR^cR^d$, —CN, —C(=O)$NR^cR^d$, —C(=O)$R^c$, —OC(=O)$R^a$, —C(=O)$OR^c$, —B(OH)$_2$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups have 1, 2, 3, or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;

wherein each $R^a$, $R^b$, $R^c$, and $R^d$ is independently H, OH, —$C_{1-6}$alkyl, —$C_{1-6}$alkenyl, —$C_2$-6alkynyl, —$C_{1-6}$alkyl-$NR^{14}R^{14}$, $NR^{14}R^{14}$, —$SO_2R^{14}$, —$(CH_2CH_2O)_nCH_3$, —C(=O)$R^{14}$, —OC(=O)$R^{14}$, —C(=O)$OR^{14}$, —C(=O)$NR^{14}R^{14}$, —$C_{1-6}$haloalkyl, —O-halo$C_{1-6}$alkyl, —$C_{1-6}$alkyl-O-$C_{1-6}$alkyl, —$C_{1-6}$alkyl-OH, benzyl, phenyl, a —$C_{1-6}$alkyl-3- to 12-membered heterocycloalkyl, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl, and heterocycloalkyl groups and the heterocycloalkyl group of the —$C_{1-6}$alkyl-heterocycloalkyl group have 1, 2, 3, or 4 heteroatoms independently selected from O, N or S, wherein the cycloalkyl, spirocycloalkyl, spiroheterocycloalkyl, heterocycloalkyl, and the heterocycloalkyl groups of the —$C_{1-6}$alkyl-heterocycloalkyl group may include a C=O group, and further wherein the spiroheterocycloalkyl and heterocycloalkyl groups may include a S=O or $SO_2$;

wherein $R^{14}$ substituents are independently selected from H, —OH, halo, —$C_{1-6}$alkyl, —$OC_{1-6}$alkyl, —$C_{1-6}$alkyl-$OC_{1-6}$alkyl, —$C_{1-6}$haloalkyl, —O-halo$C_{1-6}$alkyl, phenyl, tolyl, —C(O)$C_{1-6}$alkyl, —C(O)$OCH_3$, $SO_2$-phenyl, —$SO_2$—N(CH$_3$)$_2$, —N=N=N, —NH$_2$, —N(C$_{1-6}$alkyl)$_2$, —$NR^{15}$ $C_{1-6}$alkyl, —$NR^{15}C_{1-6}$alkyl-O-$C_{1-6}$alkyl, —N(C$_{1-6}$alkyl)$C_{1-6}$alkyl-O-$C_{1-6}$alkyl, —$NR^{15}$—$C_{1-6}$alkyl-3- to 12-membered heterocycloalkyl, a $NR^{15}$-6- to 12-membered aryl or heteroaryl, a $NR^{15}$-3- to 12-membered cycloalkenyl, a $NR^{15}$-3- to 12-membered monocyclic or bicyclic cycloalkyl, or a $NR^{15}$-3- to 12-membered monocyclic or bicyclic heterocycloalkyl group, a —$C_{1-6}$alkyl-3- to 12-membered heterocycloalkyl, a 6- to 12-membered aryl or heteroaryl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, and heterocycloalkyl groups and the heterocycloalkyl group of the —$C_{1-6}$alkyl-heterocycloalkyl group have 1, 2, 3, or 4 heteroatoms independently selected from O, N or S, wherein the cycloalkyl, heterocycloalkyl, and the heterocycloalkyl groups of the —$C_{1-6}$alkyl-heterocycloalkyl group may include a C=O group, and further wherein the heterocycloalkyl groups may include a S=O or $SO_2$;

the alkyl, aryl, heteroaryl, cycloalkyl, heterocycloalkyl and the heterocycloalkyl groups of the —$C_{1-6}$alkyl-heterocycloalkyl groups of $R^{14}$ can be unsubstituted or substituted with 1, 2, 3, or 4 $R^{15}$ substituents independently selected from H, —OH, —N=N=N, halo, —$C_{1-6}$alkyl, —$OC_{1-6}$alkyl, $C_{1-6}$haloalkyl, —O-halo$C_{1-6}$alkyl, phenyl, tolyl, —C(O)$C_{1-6}$alkyl, —C(O)$OCH_3$, $SO_2$-phenyl, —$SO_2$—NH$_2$, or —$SO_2$—N(CH$_3$)$_2$; and n is independently, in each instance, an integer of 1, 2, 3 or 4.

3. The compound of claim 1, wherein $R^{10}$ is Cl.

4. The compound of claim 1, wherein $R^1$ is selected from H, —$C_1$-$C_6$ alkyl, or

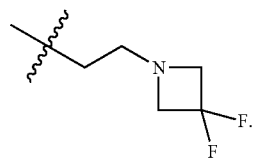

5. The compound of claim 4, wherein $R^1$ is H.

6. The compound of claim 1, wherein $R^4$ is H.

7. The compound of claim 1, wherein $R^5$ is H.

8. The compound of claim 1, wherein $R^6$ is H.

9. The compound of claim 1, wherein $R^7$ is H.

10. The compound of claim 1, wherein $R^8$ is independently selected from —OH, —COOH, or

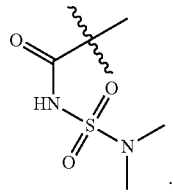 [SMILES: *C(=O)NS(=O)(=O)N(C)C]

11. The compound of claim 1, wherein $R^8$ is —COOH.

12. The compound of claim 1, wherein $R^8$ is —OH.

13. The compound of claim 1, wherein $R^{8A}$ is —OH.

14. The compound of claim 1, wherein the compound is selected from:

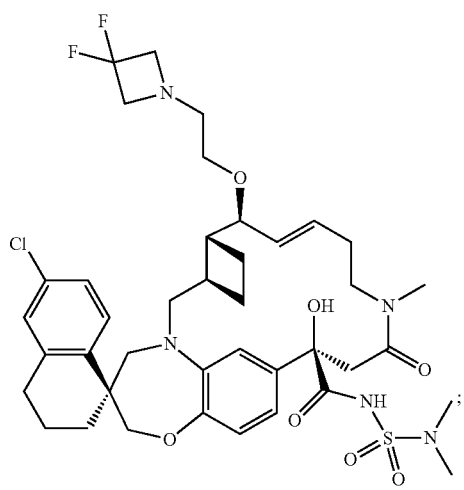

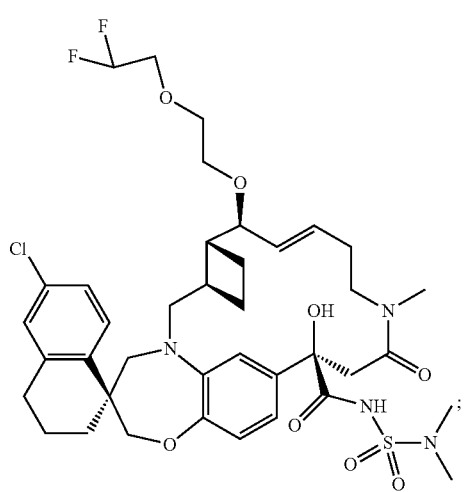

-continued

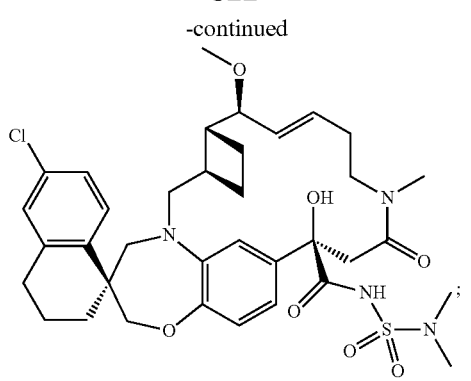

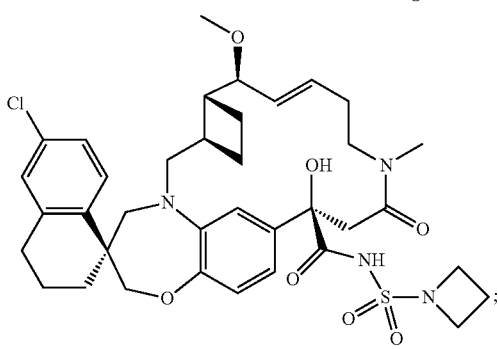

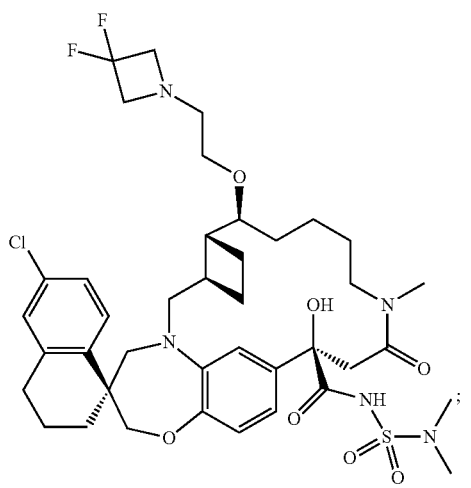

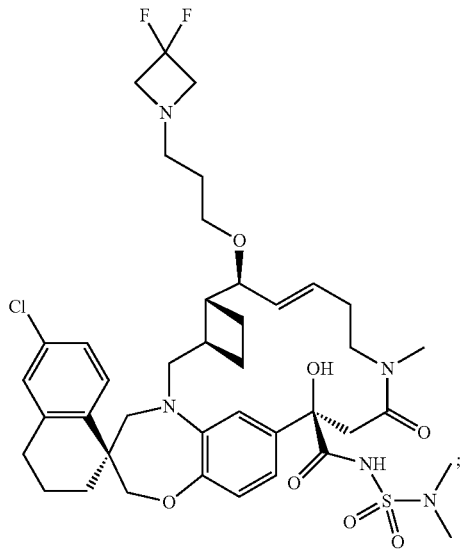

523
-continued
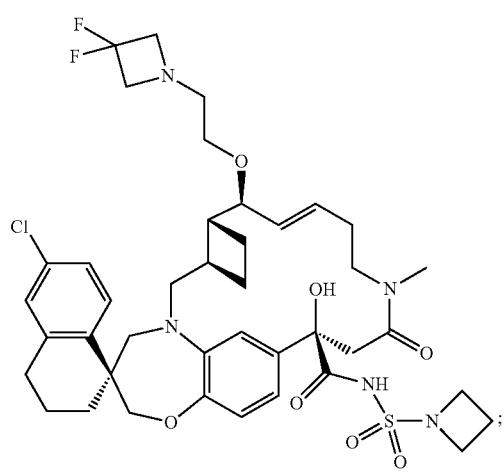
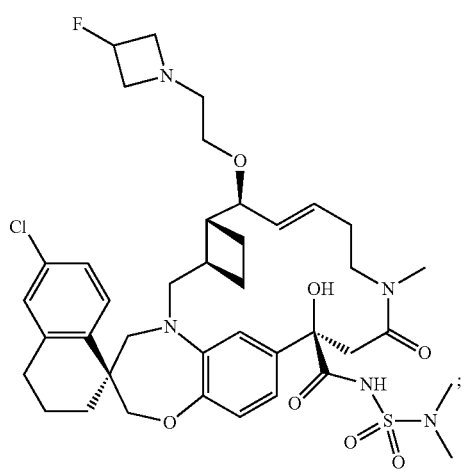
524
-continued
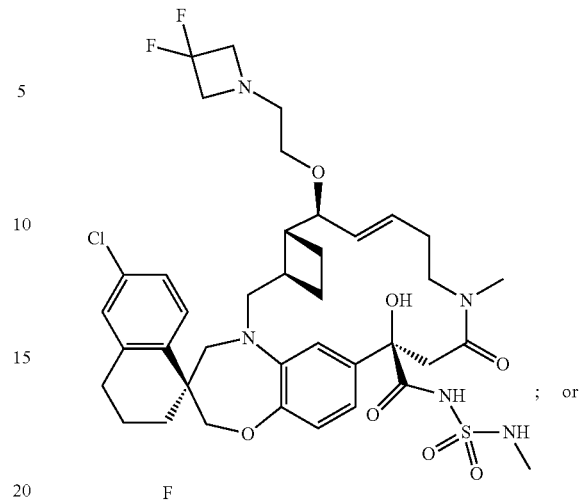
or a stereoisomer thereof, a pharmaceutically acceptable salt thereof, or a pharmaceutically acceptable salt of the stereoisomer thereof.
15. A pharmaceutical composition comprising the compound of claim 1, or the pharmaceutically acceptable salt thereof, and a pharmaceutically acceptable carrier or diluent.
* * * * *